US008211697B2

(12) United States Patent
Sakurada et al.

(10) Patent No.: US 8,211,697 B2
(45) Date of Patent: Jul. 3, 2012

(54) INDUCED PLURIPOTENT STEM CELLS PRODUCED USING REPROGRAMMING FACTORS AND A RHO KINASE INHIBITOR OR A HISTONE DEACETYLASE INHIBITOR

(75) Inventors: Kazuhiro Sakurada, Yokohama (JP); Hideki Masaki, Akita (JP); Tetsuya Ishikawa, Meguro-Ku (JP); Shunichi Takahashi, Kobe (JP)

(73) Assignee: Kyoto University, Kyoto (JP)

( * ) Notice: Subject to any disclaimer, the term of this patent is extended or adjusted under 35 U.S.C. 154(b) by 464 days.

(21) Appl. No.: 12/157,967

(22) Filed: Jun. 13, 2008
(Under 37 CFR 1.47)

(65) Prior Publication Data
US 2009/0191159 A1    Jul. 30, 2009

Related U.S. Application Data

(60) Provisional application No. 61/040,646, filed on Mar. 28, 2008.

(30) Foreign Application Priority Data

Jun. 15, 2007  (JP) .................................. 2007-159382
Nov. 20, 2007  (WO) .................. PCT/EP2007/010019

(51) Int. Cl.
*C12N 5/02*   (2006.01)
*C12N 15/00*  (2006.01)
(52) U.S. Cl. ..................... 435/377; 435/375; 435/455
(58) Field of Classification Search .................. None
See application file for complete search history.

(56) References Cited

U.S. PATENT DOCUMENTS

| | | | |
|---|---|---|---|
| 4,650,764 A | 3/1987 | Temin et al. |
| 4,861,719 A | 8/1989 | Miller |
| 4,937,190 A | 6/1990 | Palmenberg et al. |
| 5,225,348 A | 7/1993 | Nagata et al. |
| 5,266,491 A | 11/1993 | Nagata et al. |
| 5,268,290 A | 12/1993 | Hasegawa et al. |
| 5,288,514 A | 2/1994 | Ellman |
| 5,324,645 A | 6/1994 | Takahara et al. |
| 5,449,614 A | 9/1995 | Danos et al. |
| 5,519,134 A | 5/1996 | Acevedo et al. |
| 5,525,735 A | 6/1996 | Gallop et al. |
| 5,549,974 A | 8/1996 | Holmes |
| 5,591,624 A | 1/1997 | Barber et al. |
| 5,637,456 A | 6/1997 | Roth et al. |
| 5,652,122 A | 7/1997 | Frankel et al. |
| 5,674,980 A | 10/1997 | Frankel |
| 5,707,618 A | 1/1998 | Armentano et al. |
| 5,716,832 A | 2/1998 | Barber et al. |
| 5,744,320 A | 4/1998 | Sherf et al. |
| 5,817,491 A | 10/1998 | Yee et al. |
| 5,830,725 A | 11/1998 | Nolan et al. |
| 5,834,256 A | 11/1998 | Finer et al. |
| 5,858,740 A | 1/1999 | Finer et al. |
| 5,910,434 A | 6/1999 | Rigg et al. |
| 5,955,331 A | 9/1999 | Danos et al. |
| 6,013,517 A | 1/2000 | Respess et al. |
| 6,017,735 A | 1/2000 | O'Hare |
| 6,017,761 A | 1/2000 | Rigg et al. |
| 6,025,192 A | 2/2000 | Beach et al. |
| 6,140,111 A | 10/2000 | Riviere et al. |
| 6,146,874 A | 11/2000 | Zolotukhin et al. |
| 6,153,432 A | 11/2000 | Halvorsen et al. |
| 6,153,745 A | 11/2000 | Williams et al. |
| 6,203,975 B1 | 3/2001 | Wilson et al. |
| 6,251,398 B1 | 6/2001 | O'Hare et al. |
| 6,255,071 B1 | 7/2001 | Beach et al. |
| 6,312,948 B1 | 11/2001 | Cohen-Haguenauer |
| 6,312,949 B1 | 11/2001 | Sakurada et al. |
| 6,333,195 B1 | 12/2001 | Respess et al. |
| 6,365,352 B1 | 4/2002 | Yerramilli et al. |
| 6,395,546 B1 | 5/2002 | Zobel et al. |
| 6,451,595 B1 | 9/2002 | Kim et al. |
| 6,485,959 B1 | 11/2002 | Demetriou et al. |
| 6,521,453 B1 | 2/2003 | Crameri et al. |
| 6,521,455 B2 | 2/2003 | O'Hare et al. |
| 6,605,275 B1 | 8/2003 | Boyse et al. |
| 6,660,514 B1 | 12/2003 | Zolotukhin et al. |
| 6,773,920 B1 | 8/2004 | Dalby et al. |
| 6,833,269 B2 | 12/2004 | Carpenter |
| 6,841,535 B2 | 1/2005 | Divita et al. |
| 6,872,528 B2 | 3/2005 | Klatzmann et al. |
| 6,875,578 B2 | 4/2005 | Giuliano et al. |
| 6,881,825 B1 | 4/2005 | Robbins et al. |
| 6,910,434 B2 | 6/2005 | Lundgren et al. |
| 6,995,009 B1 | 2/2006 | Kitamura et al. |

(Continued)

FOREIGN PATENT DOCUMENTS

AU   2008201280 A1   4/2008

(Continued)

OTHER PUBLICATIONS

Xu et al. BMP4 Initiates Human Embryonic Stem Cell Differentiation to Trophoblast. Nature Biotech., 2002, vol. 20, 1261-1264.*
Stojvic et al. Derivation, Growth and Applications of Human Embryonic Stem Cells. Reproduction, 2004, vol. 128, pp. 259-267.*
Strelchencko et al. Embryonic Stem Cells for Morula, in Methods in Enzymology, vol. 418, 2006, Elsevier Inc., Lanza et al., eds. 93-108.*
A reprogramming rush. Editorial. Nature. Mar. 27, 2008. 452:388. Published online Mar. 26, 2008.
Adewumi, et al. Characterization of human embryonic stem cell lines by the International Stem Cell Initiative. Nat Biotechnol. 2007; 25, 803-816.
Adhikary, et al. Transcriptional regulation and transformation by Myc proteins. Nat Rev Mol Cell Biol. Aug. 2005;6(8):635-45.
Altschul, et al. Gapped BLAST and PSI-BLAST: a new generation of protein database search programs. Nucleic Acids Research. 1997;25(17): 3389-3402.

(Continued)

*Primary Examiner* — Deborah Crouch
(74) *Attorney, Agent, or Firm* — Knobbe Martens Olson & Bear LLP

(57) ABSTRACT

Described herein are multipotent stem cells, e.g., human and other mammalian pluripotent stem cells, and related methods.

3 Claims, 31 Drawing Sheets
(21 of 31 Drawing Sheet(s) Filed in Color)

U.S. PATENT DOCUMENTS

| | | | |
|---|---|---|---|
| 7,029,913 B2 | 4/2006 | Thomson | |
| 7,030,292 B2 | 4/2006 | Yan et al. | |
| 7,070,994 B2 | 7/2006 | Barber et al. | |
| 7,250,255 B2 | 7/2007 | Yamanaka | |
| 7,439,064 B2 | 10/2008 | Thomson et al. | |
| 2002/0090722 A1 | 7/2002 | Dominko et al. | |
| 2002/0174013 A1 | 11/2002 | Freeman et al. | |
| 2003/0003574 A1 | 1/2003 | Toma et al. | |
| 2003/0044976 A1 | 3/2003 | Dominko et al. | |
| 2003/0161817 A1 | 8/2003 | Young et al. | |
| 2004/0048297 A1 | 3/2004 | Scherf | |
| 2004/0137460 A1 | 7/2004 | Yamanaka et al. | |
| 2005/0019801 A1 | 1/2005 | Rubin et al. | |
| 2005/0026133 A1 | 2/2005 | Nakatsuji et al. | |
| 2005/0079606 A1 | 4/2005 | Tamaki et al. | |
| 2005/0130144 A1 | 6/2005 | Nakatsuji et al. | |
| 2006/0030041 A1 | 2/2006 | Furcht et al. | |
| 2006/0084172 A1 | 4/2006 | Muller et al. | |
| 2006/0088599 A1 | 4/2006 | Prasad et al. | |
| 2006/0095319 A1 | 5/2006 | Cardwell | |
| 2006/0110830 A1 | 5/2006 | Dominko et al. | |
| 2006/0292620 A1 | 12/2006 | Yamanaka et al. | |
| 2007/0033061 A1 | 2/2007 | Patten et al. | |
| 2007/0053884 A1 | 3/2007 | Suda et al. | |
| 2007/0155013 A1 | 7/2007 | Akaike et al. | |
| 2007/0202592 A1 | 8/2007 | Kitagawa et al. | |
| 2007/0254884 A1 | 11/2007 | Chen et al. | |
| 2007/0269790 A1 | 11/2007 | Amit et al. | |
| 2008/0003560 A1 | 1/2008 | Nakatsuji et al. | |
| 2008/0076176 A1 | 3/2008 | Dominko et al. | |
| 2008/0085555 A1 | 4/2008 | Asahara et al. | |
| 2008/0132803 A1 | 6/2008 | Friedlander | |
| 2008/0171358 A1 | 7/2008 | Perrault | |
| 2008/0171385 A1 | 7/2008 | Bergendahl et al. | |
| 2008/0206865 A1 | 8/2008 | Zhang et al. | |
| 2008/0233610 A1 | 9/2008 | Thomson et al. | |
| 2008/0274914 A1 | 11/2008 | Yamanaka | |
| 2008/0280362 A1 | 11/2008 | Jaenisch et al. | |
| 2008/0293143 A1 | 11/2008 | Lin et al. | |
| 2008/0299548 A1 | 12/2008 | Yamanaka | |
| 2009/0047263 A1 | 2/2009 | Yamanaka et al. | |
| 2009/0068742 A1 | 3/2009 | Yamanaka et al. | |
| 2009/0191159 A1 | 7/2009 | Sakurada et al. | |
| 2009/0191171 A1 | 7/2009 | Ma | |
| 2009/0227032 A1 | 9/2009 | Yamanaka | |
| 2009/0299763 A1 | 12/2009 | Sakurada et al. | |
| 2009/0304646 A1 | 12/2009 | Sakurada et al. | |
| 2009/0324559 A1 | 12/2009 | Sakurada et al. | |
| 2010/0003757 A1 | 1/2010 | Mack | |
| 2010/0021437 A1 | 1/2010 | Isacson | |
| 2010/0062533 A1 | 3/2010 | Yamanaka | |
| 2010/0062534 A1 | 3/2010 | Hochedlinger | |
| 2010/0075421 A1 | 3/2010 | Yamanaka | |
| 2010/0093090 A1 | 4/2010 | Deng | |
| 2010/0105100 A1 | 4/2010 | Sakurada et al. | |
| 2010/0120069 A1 | 5/2010 | Sakurada | |
| 2010/0144031 A1 | 6/2010 | Jaenisch | |
| 2010/0184051 A1 | 7/2010 | Hochedlinger | |
| 2010/0184227 A1 | 7/2010 | Thomson | |
| 2010/0210014 A1 | 8/2010 | Yamanaka | |
| 2010/0216236 A1 | 8/2010 | Yamanaka | |
| 2010/0221827 A1 | 9/2010 | Jaenisch | |
| 2010/0233804 A1 | 9/2010 | Zhou | |
| 2010/0240090 A1 | 9/2010 | Sakurada et al. | |
| 2010/0267135 A1 | 10/2010 | Sakurada | |
| 2010/0279404 A1 | 11/2010 | Yamanaka | |
| 2011/0039332 A1 | 2/2011 | Sakurada et al. | |

FOREIGN PATENT DOCUMENTS

| | | |
|---|---|---|
| CN | 101250502 A | 8/2008 |
| CN | 101550428 A | 10/2009 |
| EP | 1384775 | 1/2004 |
| EP | 1403366 A1 | 3/2004 |
| EP | 1970446 A1 | 9/2008 |
| EP | 2096169 A1 | 9/2009 |
| JP | 2-227075 | 9/1990 |
| JP | 2002-065261 | 3/2002 |
| JP | 2003-009854 | 1/2003 |
| JP | 2004-161682 A | 6/2004 |
| JP | 2005-095027 | 4/2005 |
| JP | 2005-359537 | 12/2005 |
| JP | 2008-283972 | 11/2008 |
| WO | WO 95/10619 A2 | 4/1995 |
| WO | WO 95/10619 A3 | 7/1995 |
| WO | WO 97/05265 A1 | 2/1997 |
| WO | WO 00/18885 A1 | 4/2000 |
| WO | WO 00/23567 A2 | 4/2000 |
| WO | WO 00/27995 A1 | 5/2000 |
| WO | WO 00/23567 A3 | 7/2000 |
| WO | WO 00/73423 A1 | 12/2000 |
| WO | WO 01/21767 A2 | 3/2001 |
| WO | WO 01/34776 A1 | 5/2001 |
| WO | WO 01/51616 A2 | 7/2001 |
| WO | WO 01/21767 A3 | 8/2001 |
| WO | WO 01/81549 A2 | 11/2001 |
| WO | WO 02/00871 A2 | 1/2002 |
| WO | WO 02/061033 A2 | 8/2002 |
| WO | WO 02/000871 A3 | 10/2002 |
| WO | WO 02/086129 A1 | 10/2002 |
| WO | WO 02/086134 A2 | 10/2002 |
| WO | WO 02/097090 A1 | 12/2002 |
| WO | WO 03/018780 A1 | 3/2003 |
| WO | WO 02/086134 A3 | 12/2003 |
| WO | WO 2004/081205 A1 | 9/2004 |
| WO | WO 2005/080598 A1 | 9/2005 |
| WO | WO 2005/090557 A1 | 9/2005 |
| WO | WO 2006/035741 A1 | 4/2006 |
| WO | WO 2006/084229 A2 | 8/2006 |
| WO | WO 2006/088867 A2 | 8/2006 |
| WO | WO 2007/026255 A2 | 3/2007 |
| WO | WO 2007/054720 A1 | 5/2007 |
| WO | WO 2007/069666 A1 | 6/2007 |
| WO | WO 2007/097494 A1 | 8/2007 |
| WO | WO 2008/030610 A2 | 3/2008 |
| WO | WO 2008/035110 A1 | 3/2008 |
| WO | WO 2008/038148 A2 | 4/2008 |
| WO | WO 2008/089351 A1 | 7/2008 |
| WO | WO 2008/105566 A1 | 9/2008 |
| WO | WO 2008/105630 A1 | 9/2008 |
| WO | WO 2008/116213 A1 | 9/2008 |
| WO | WO 2008/118820 A2 | 10/2008 |
| WO | WO 2008/124133 A1 | 10/2008 |
| WO | WO 2008/118820 A3 | 11/2008 |
| WO | WO 2008/150814 A2 | 12/2008 |
| WO | WO2008/151058 A2 | 12/2008 |
| WO | WO2008/151058 A3 | 1/2009 |
| WO | WO 2009/006930 A1 | 1/2009 |
| WO | WO 2009/006997 A1 | 1/2009 |
| WO | WO 2009/007852 A2 | 1/2009 |
| WO | WO 2008/150814 A3 | 2/2009 |
| WO | WO 2009/023161 A1 | 2/2009 |
| WO | WO 2009/032194 A1 | 3/2009 |
| WO | WO 2009/032456 A2 | 3/2009 |
| WO | WO 2009/032456 A3 | 4/2009 |
| WO | WO 2009/057831 A1 | 5/2009 |
| WO | WO 2009/061442 A1 | 5/2009 |
| WO | WO 2009/067563 A1 | 5/2009 |
| WO | WO 2009/096614 A1 | 6/2009 |
| WO | WO 2009/007852 A3 | 8/2009 |
| WO | WO 2009/102983 A2 | 8/2009 |
| WO | WO 2009/115295 A1 | 9/2009 |
| WO | WO 2009/133971 A1 | 11/2009 |
| WO | WO 2009/102983 A3 | 12/2009 |
| WO | WO 2009/144008 A1 | 12/2009 |
| WO | WO 2009/149233 A1 | 12/2009 |
| WO | WO 2010/013359 A1 | 2/2010 |
| WO | WO 2010/048567 A1 | 4/2010 |

OTHER PUBLICATIONS

Amit, et al. Clonally derived human embryonic stem cell lines maintain pluripotency and proliferative potential for prolonged periods of culture. Dev Biol. Nov. 15, 2000;227(2):271-8.

Anderson, et al. Transgenic enrichment of cardiomyocytes from human embryonic stem cells. Mol Ther. Nov. 2007;15(11):2027-36.

Aoi, et al. Generation of Pluripotent Stem Cells from Adult Mouse Liver and Stomach Cells. Science. Published Online Feb. 14, 2008. Science DOI: 10.1126/science.1154884.
Assady, et al. Insulin production by human embryonic stem cells. Diabetes. Aug. 2001;50(8):1691-7.
Assou, et al. A meta-analysis of human embryonic stem cells transcriptome integrated into a web-based expression atlas. Stem Cells. Apr. 2007;25(4):961-73.
Bader, et al. Leukemia inhibitory factor modulates cardiogenesis in embryoid bodies in opposite fashions. Circ Res. Apr. 14, 2000;86(7):787-94.
Bagutti, et al. Differentiation of embryonal stem cells into keratinocytes: comparison of wild-type and beta 1 integrin-deficient cells. Dev Biol. Oct. 10, 1996;179(1):184-96.
Barrett, et al. NCBI GEO: mining tens of millions of expression profiles—database and tools update. Nucleic Acids Res. Jan. 2007;35(Database issue):D760-5.
Bayani, et al. Multi-color FISH techniques. Curr. Protoc. Cell Biol. 2004; Chapter 22:Unit 22.5.
Bendall, et al. IGF and FGF cooperatively establish the regulatory stem cell niche of pluripotent human cells in vitro. Nature. Aug. 30, 2007;448(7157):1015-21.
Berg, et al. An argument against a role for Oct4 in somatic stem cells. Cell Stem Cell. Oct. 11, 2007;1(4):359-60.
Birnbaum, et al. Slicing across Kingdoms: Regeneration in Plants and Animals. Cell. Feb. 22, 2008; 132(4):697-710.
Blelloch, et al. Generation of Induced Pluripotent Stem Cells in the Absence of Drug Selection. Cell Stem Cell. 2007; 1, 245-247.
Blow, N. Stem cells: in search of common ground. Nature. Feb. 14, 2008;451(7180):855-8.
Bonetta, L. European Stem Cell Patents: Taking the moral High Road? Cell. Feb. 22, 2008; 132(4):514-516.
Boquest, et al. Epigenetic programming of mesenchymal stem cells from human adipose tissue. Stem Cell Rev. 2006;2(4):319-29.
Boyer, et al. Core Transcriptional Regulatory Circuitry in Human Embryonic Stem Cells. Cell. 2005;122(6):947-956.
Brambrink, et al. Sequential Expression of Pluripotency Markers during Direct Reprogramming of Mouse Somatic Cells. Cell Stem Cell. 2008; 2, 151-159.
Brena, et al. Quantitative assessment of DNA methylation: Potential applications for disease diagnosis, classification, and prognosis in clinical settings. J Mol Med. May 2006;84(5):365-77.
Brüstle, et al. Embryonic stem cell-derived glial precursors: a source of myelinating transplants. Science. Jul. 30, 1999;285(5428):754-6.
Burns, et al. Diabetes mellitus: a potential target for stem cell therapy. Curr Stem Cell Res Ther. May 2006;1(2):255-66.
Buttery, et al. Differentiation of osteoblasts and in vitro bone formation from murine embryonic stem cells. Tissue Eng. Feb. 2001;7(1):89-99.
Cai, et al. Directed differentiation of human embryonic stem cells into functional hepatic cells. Hepatology. May 2007;45(5):1229-39.
Campbell, et al. Phosphonate Ester Synthesis Using a Modified Mitsunobu Condensation. J. Org. Chem.1994;59: 658-660.
Cartright, et al. LIF/STAT3 controls ES cell self-renewal and pluripotency by a Myc-dependent mechanism. Development. Mar. 2005;132(5):885-96.
Chadwick, et al. Cytokines and BMP-4 promote hematopoietic differentiation of human embryonic stem cells. Blood. Aug. 1, 2003;102(3):906-15.
Chang, et al. The c-Myc transactivation domain is a direct modulator of apoptotic versus proliferative signals. Mol Cell Biol. Jun. 2000;20(12):4309-19.
Chen, et al. Analogous Organic-Synthesis of Small-Compound Libraries—Validation of Combinatorial Chemistry in Small-Molecule Synthesis. Journal of the American Chemical Society. 1994;116(6): 2661-2662.
Chen, et al. From stem cells to oligodendrocytes: prospects for brain therapy. Stem Cell Rev. Dec. 2007;3(4):280-8.
Childs, et al. Regression of metastatic renal-cell carcinoma after nonmyeloablative allogeneic peripheral-blood stem-cell transplantation. N Engl J Med. Sep. 14, 2000;343(11):750-8.
Cho, et al. An unnatural biopolymer. Science. Sep. 3, 1993;261(5126):1303-5.
Cinalli, et al. Germ Cells are Forever. Cell. Feb. 22, 2008; 132(4):559-562.
CIRM Public Release. $24 Million in New Stem Cell Research Funding Awarded to 25 California Institutions. California Institute for Regenerative Medicine (4 pages). Jun. 27, 2008.
CIRM: Summaries of Review for Applications to RFA 07-05. California Institute for Regenerative Medicine Web site. 2007. Available at: http://www.cirm.ca.gov/RFA/rfa_07-05/. Accessed Jul. 1, 2008.
Cline, et al. Randomize Gene Sequences with New PCR Mutagenesis Kit. Strategies Newsletter. 2000;13:157-161.
Coutts, et al. Stem cells for the treatment of spinal cord injury. Exp Neurol. Feb. 2008;209(2):368-77.
Cowling, et al. Mechanism of transcriptional activation by the Myc oncoproteins. Semin Cancer Biol. Aug. 2006;16(4):242-52.
Current claims for U.S. Appl. No. 10/861,040.
Cyranoski, D. Stem cells: 5 things to know before jumping on the iPS bandwagon. Nature. 2008;452(7186)406-408.
Cyranoski, et al. Simple switch turns cells embryonic. Nature. 2007; 447:618-619.
Cyranoski. Japan ramps up patent effort to keep iPS lead. Nature. 2008; 453(7198):962-3.
D'Amour, et al. Efficient differentiation of human embryonic stem cells to definitive endoderm. Nat Biotechnol. Dec. 2005;23(12):1534-41.
D'Amour, et al. Production of pancreatic hormone-expressing endocrine cells from human embryonic stem cells. Nat Biotechnol. Nov. 2006;24(11):1392-401.
Daley, et al. Prospects for Stem Cell Based Therapy. Cell. Feb. 22, 2008; 132(4):544-548.
Dani, et al. Differentiation of embryonic stem cells into adipocytes in vitro. J Cell Sci. Jun. 1997;110 ( Pt 11):1279-85.
Deb, et al. Embryonic Stem Cells: From Markers to Market. Feb. 2008;11(1):19-37.
Denker, H: W. Human embryonic stem cells: the real challenge for research as well as for bioethics is still ahead of us. Cells Tissues Organs. 2008;187(4):250-6.
Dewitt, et al. "Diversomers": an approach to nonpeptide, nonoligomeric chemical diversity. Proc Natl Acad Sci U S A. Aug. 1, 1993;90(15):6909-13.
D'Ippolito, et al. Marrow-isolated adult multilineage inducible (MIAMI) cells, a unique population of postnatal young and old human cells with extensive expansion and differentiation potential. J Cell Sci. Jun. 15, 2004;117(Pt 14):2971-81.
Ehrich, et al. Quantitative high-throughput analysis of DNA methylation patterns by base-specific cleavage and mass spectrometry. Proc Natl Acad Sci U S A. Nov. 1, 2005;102(44): 15785-90.
Eisen, et al. Cluster analysis and display of genome-wide expression patterns. Dec. 8, 1998;95(25): 14863-14868.
Elefanty, A. Ed. In this Issue . . . Stem Cell Research. 2008; 1:87.
Evans, et al. Krüppel-like factor 4 is acetylated by p300 and regulates gene transcription via modulation of histone acetylation. J Biol Chem. Nov. 23, 2007;282(47):33994-4002.
Felgner, et al. Lipofection: a highly efficient, lipid-mediated DNA-transfection procedure. Proc Natl Acad Sci U S A. Nov. 1987;84(21):7413-7.
Ferrer-Costa, et al. PMUT: a web-based tool for the annotation of pathological mutations on proteins. Bioinformatics. Jul. 15, 2005;21(14):3176-8.
Forsyth, et al. Human Embryonic Stem Cell Telomere Length Impacts Directly on Clonal Progenitor Isolation Frequency. Rejuvenation Research. Feb. 2008;11(1):5-17.
Gallop, et al. Applications of combinatorial technologies to drug discovery. 1. Background and peptide combinatorial libraries. J Med Chem. Apr. 29, 1994;37(9):1233-51.
Ghaleb, et al. Krüppel-like factors 4 and 5: the yin and yang regulators of cellular proliferation. Cell Res. Feb. 2005;15(2):92-6.
Goswami, et al. Embryonic stem cell therapy. IDrugs. Oct. 2007;10(10):713-9.
Gu, et al. Opposite regulation of gene transcription and cell proliferation by c-Myc and Max. Proc Natl Acad Sci U S A. Apr. 1, 1993;90(7):2935-9.

Ha, et al. Cryopreservation of human embryonic stem cells without the use of a programmable freezer. Hum Reprod. Jul. 2005;20(7):1779-85.

Hanna, et al. Direct Reprogramming of Terminally Differentiated Mature B Lymphocytes to Pluripotency. Cell. Apr. 18, 2008;133: 250-264. Erratum in: Cell. 2008; 134(2):365.

Hermann, et al. Efficient generation of neural stem cell-like cells from adult human bone marrow stromal cells. J Cell Sci. Sep. 1, 2004;117(Pt 19):4411-22.

Highfield, R. Dolly creator Prof Ian Wilmut shuns cloning. Available at http://www.telegraph.co.uk/earth/main.jhtml?xml=/earth/2007/11/16/scidolly116.xml. Accessed Nov. 12, 2008.

Huangfu, et al. Efficient Induction of Pluripotent Stem Cells Using Small Molecule Compounds. Companion manuscript to U.S. Appl. No. 61/029,287.

Itsykson, et al. Derivation of neural precursors from human embryonic stem cells in the presence of noggin. Mol Cell Neurosci. Sep. 2005;30(1):24-36.

Jaenisch, et al. Stem Cells, the Molecular Circuitry of Pluripotency and Nuclear Reprogramming. Cell. Feb. 22, 2008; 132(4):567-582.

Jahagirdar, et al. Multipotent adult progenitor cell and stem cell plasticity. Stem Cell Rev. 2005;1(1):53-9.

Janssens, et al. Autologous bone marrow-derived stem-cell transfer in patients with ST-segment elevation myocardial infarction: double-blind, randomised controlled trial. Lancet. Jan. 14, 2006;367(9505):113-21.

Jiang, et al. A core Klf circuitry regulates self-renewal of embryonic stem cells. Nat Cell Biol. Mar. 2008;10(3):353-60.

Jiang, et al. In vitro derivation of functional insulin-producing cells from human embryonic stem cells. Cell Res. Apr. 2007;17(4):333-44.

Jiang, et al. Pluripotency of mesenchymal stem cells derived from adult marrow. Nature. Jul. 4, 2002;418(6893):41-9.

Johnston, et al. Minimum requirements for efficient transduction of dividing and nondividing cells by feline immunodeficiency virus vectors. J Virol. Jun. 1999;73(6):4991-5000.

Kamachi, et al. Mechanism of regulatory target selection by the SOX high-mobility-group domain proteins as revealed by comparison of SOX1/2/3 and SOX9. Mol Cell Biol. Jan. 1999;19(1):107-20.

Kanegae, et al. Efficient gene activation in mammalian cells by using recombinant adenovirus expressing site-specific Cre recombinase. Nucleic Acids Res. Oct. 11, 1995;23(19):3816-21.

Kawasaki, et al. Induction of midbrain dopaminergic neurons from ES cells by stromal cell-derived inducing activity. Neuron. Oct. 2000;28(1):31-40.

Kehat, et al. Human embryonic stem cells can differentiate into myocytes with structural and functional properties of cardiomyocytes. J Clin Invest. Aug. 2001;108(3):407-14.

Kim, et al. Ex vivo characteristics of human amniotic membrane-derived stem cells. Cloning Stem Cells. 2007 Winter;9(4):581-94.

Kitamura, et al. Retrovirus-mediated gene transfer and expression cloning: powerful tools in functional genomics. Exp Hematol. Nov. 2003;31(11):1007-14.

Kitamura, T. New experimental approaches in retrovirus-mediated expression screening. Int J Hematol. Jun. 1998;67(4):351-9.

Klingemann, H. Discarded stem cells with a future? Expert Opin Biol Ther. Dec. 2006;6(12):1251-4.

Knoblich, J.A. Mechanisms of Asymmetric Stem Cell Division. Cell. Feb. 22, 2008; 132(4):583-597.

Koch, et al. Transduction of human embryonic stem cells by ecotropic retroviral vectors. Nucl Acids Res. 2006; 34, e120.

Kohge, et al. Promotion of antigen-specific antibody production in murine B cells by a moderate increase in histone acetylation. Biochem Pharmacol. Nov. 15, 1998;56(10):1359-64.

Kopsidas, et al. RNA mutagenesis yields highly diverse mRNA libraries for in vitro protein evolution. BMC Biotechnol. Apr. 11, 2007;7:18.

Kramer, et al. Embryonic stem cell-derived chondrogenic differentiation in vitro: activation by BMP-2 and BMP-4. Mech Dev. Apr. 2000;92(2):193-205.

Krausz, E. High-content siRNA screening. Mol Biosyst. Apr. 2007;3(4):232-40.

Kuroda, et al. Octamer and Sox Elements Are Required for Transcriptional cis Regulation of Nanog Gene Expression. Mol Cell Biol. Mar. 2005; 25(6): 2475-2485.

Laird, et al. Stem Cell Trafficking in Tissue Development, Growth, and Disease. Cell. Feb. 22, 2008; 132(4):612-630.

Lanza, et al. (Eds.) Essentials of Stem Cell Biology. Elsevier Academic Press. 2006. (Table of Contents only).

Lee, et al. Efficient generation of midbrain and hindbrain neurons from mouse embryonic stem cells. Nat Biotechnol. Jun. 2000;18(6):675-9.

Lemken, et al. Evidence for intercellular trafficking of VP22 in living cells. Mol Ther. Feb. 2007;15(2):310-9.

Lengner, et al. The pluripotency regulator Oct4: a role in somatic stem cells? Cell Cycle. Mar. 2008;7(6):725-8.

Li, et al. Small dsRNAs induce transcriptional activation in human cells. Proc Natl Acad Sci. 2006; 103, 17337-17342.

Lieschke, et al. Development of functional macrophages from embryonal stem cells in vitro. Exp Hematol. Apr. 1995;23(4):328-34.

Lin-Goerke, et al. PCR-based random mutagenesis using manganese and reduced dNTP concentration. Biotechniques. Sep. 1997;23(3):409-12.

Link, et al. Therapeutic protein transduction of mammalian cells and mice by nucleic acid-free lentiviral nanoparticles. Nucleic Acids Res. Jan. 30, 2006;34(2):e16.

Littlewood, et al. A modified oestrogen receptor ligand-binding domain as an improved switch for the regulation of heterologous proteins. Nucleic Acids Res. May 25, 1995;23(10):1686-90.

Liu, S. iPS Cells: a More Critical Review. Stem Cells Dev. Jun. 2008;17(3):391-7.

Loh, et al. The Oct4 and Nanog transcription network regulates pluripotency in mouse embryonic stem cells. Nat Genet. Apr. 2006;38(4):431-40.

Loudig, et al. Transcriptional co-operativity between distant retinoic acid response elements in regulation of Cyp26A1 inducibility. Biochem J. Nov. 15, 2005;392(Pt 1):241-8.

Lowry, et al. Generation of human induced pluripotent stem cells from dermal fibroblasts. Proc Natl Acad Sci U S A. Feb. 26, 2008;105(8):2883-8.

Ludwig, et al. Derivation of human embryonic stem cells in defined conditions. Nat Biotechnol. Feb. 2006;24(2):185-7.

Lumelsky, et al. Differentiation of embryonic stem cells to insulin-secreting structures similar to pancreatic islets. Science. May 18, 2001;292(5520):1389-94.

Lunde, et al. Zebrafish pou5fl/pou2, homolog of mammalian Oct4, functions in the endoderm specification cascade. Curr Biol. Jan. 6, 2004;14(1):48-55.

Lungwitz, et al. Polyethylenimine-based non-viral gene delivery systems. Eur J Pharm Biopharm. Jul. 2005;60(2):247-66.

Maherali, et al. Directly reprogrammed fibroblasts show global epigenetic remodeling and widespread tissue contribution. Cell Stem Cell. Jun. 7, 2007;1(1):55-70.

Masaki, et al. Heterogeneity of pluripotent marker gene expression in colonies generated in human iPS cell induction culture. Stem Cell Research. 2008; 1: 105-115.

Masaki, et al. Tendency of Pluripotential marker gene expression in colonies derived from human neonatal fibroblasts induced by the human iPS cell method. Stem Cell Researchr. 2008. doi: 10.1016/j.scr.2008.01.001 (Accepted Manuscript).

Mathe, et al. Computational approaches for predicting the biological effect of p53 missense mutations: a comparison of three sequence analysis based methods. Nucleic Acids Res. Mar. 6, 2006;34(5):1317-25.

Matsuda, et al. STAT3 activation is sufficient to maintain an undifferentiated state of mouse embryonic stem cells. EMBO J. Aug. 2, 1999;18(15):4261-9.

Meissner, et al. Direct reprogramming of genetically unmodified fibroblasts into pluripotent stem cells. Nat Biotech. 2007; 25, 1177-1181.

Mikkelsen, et al. Dissecting direct reprogramming through integrative genomic analysis. Nature. Jul. 3, 2008;454(7200):49-55. Erratum in: Nature. 2008;454(7205):794.

Miyagishi, et al. Strategies for generation of an siRNA expression library directed against the human genome. Oligonucleotides. 2003;13(5):325-33.

Miyoshi, et al. Development of a self-inactivating lentivirus vector. J Virol. Oct. 1998;72(10):8150-7.

More California Dough—$23 Million—Rolls Out the Door for Stem Cell Research. California Stem Cell Report Web Site. 2005. Available at: http://californiastemcellreport.blogspot.com/2008/06/more-dough-25-million-rolls-out-door-in.html. Accessed Jul. 1, 2008.

Morgenstern, et al. Advanced mammalian gene transfer: high titre retroviral vectors with multiple drug selection markers and a complementary helper-free packaging cell line. Nucleic Acids Res. Jun. 25, 1990; 18(12): 3587-3596.

Morita, et al. Plat-E: an efficient and stable system for transient packaging of retroviruses. Gene Ther. Jun. 2000;7(12):1063-6.

Morizane, et al. From bench to bed: the potential of stem cells for the treatment of Parkinson's disease. Cell Tissue Res. Jan. 2008;331(1):323-36.

Morling, et al. Enhanced transduction efficiency of retroviral vectors coprecipitated with calcium phosphate. Gene Ther. Sep. 1995;2(7):504-8.

Morrison, S.J. Stem Cells and Niches: Mechanisms that Promote Stem Cell Maintencance throughout Life. Cell. Feb. 22, 2008; 132(4):598-611.

Mummery, et al. Differentiation of human embryonic stem cells to cardiomyocytes: role of coculture with visceral endoderm-like cells. Circulation. Jun. 3, 2003;107(21):2733-40.

Murry, et al. Differentiation of Embryonic Stem Cells to Clinically Relevant Populations: Lessons from Embryonic Development. Cell. Feb. 22, 2008; 132(4):661-680.

Nagy, et al. Embryonic stem cells alone are able to support fetal development in the mouse. Development. Nov. 1990;110(3):815-21.

Nakagawa, et al. Generation of induced pluripotent stem cells without Myc from mouse and human fibroblasts. Nat Biotechnol. Jan. 2008;26(1):101-6.

Nakatake, et al. Klf4 cooperates with Oct3/4 and Sox2 to activate the Lefty1 core promoter in embryonic stem cells. Mol Cell Biol. Oct. 2006;26(20):7772-82.

Naldini, et al. In vivo gene delivery and stable transduction of nondividing cells by a lentiviral vector. Science. Apr. 12, 1996;272(5259):263-7.

Needleman, et al. A general method applicable to the search for similarities in the amino acid sequence of two proteins. J Mol Biol. Mar. 1970;48(3):443-53.

Négre, et al. Lentiviral vectors derived from simian immunodeficiency virus. Curr Top Microbiol Immunol. 2002;261:53-74.

Ng, et al. Predicting the effects of amino acid substitutions on protein function. Annu Rev Genomics Hum Genet. 2006;7:61-80.

Niwa, et al. Self-renewal of pluripotent embryonic stem cells is mediated via activation of STAT3. Genes Dev. Jul. 1, 1998;12(13):2048-60.

Office Action dated Jun. 20, 2007 concerning U.S. Appl. No. 10/861,040, entitled, "Stem Cell-Based Methods for Identifying and Characterizing Agents.".

Okita, et al. Generation of germline-competent induced pluripotent stem cells. Nature Jul. 19, 2007 448(7151) 313-17.

Okita, et al. Intracellular Signaling Pathways Regulating Pluripotency of Embryonic Stem Cells. Current Stem Cell Research & Therapy. 2006;1: 103-111.

Onishi, et al. Applications of retrovirus-mediated expression cloning. Exp Hematol. Feb. 1996;24(2):324-9.

Orkin, et al. Hematopoiesis: An Evolving Paradigm for Stem Cell Biology. Cell. Feb. 22, 2008; 132(4):631-644.

Osuna, et al. Protein evolution by codon-based random deletions. Nucleic Acids Res. Sep. 30, 2004;32(17):e136.

Padmanabhan, et al. Visualization of telomerase reverse transcriptase (hTERT) promoter activity using a trimodality fusion reporter construct. J Nucl Med. Feb. 2006;47(2):270-7.

Park, et al. Reprogramming of human somatic cells to pluripotency with defined factors. Nature. 2008;451(7175):141-146.

Parson, A.B. Stem Cell Biotech: Seeking a Piece of the Action. Cell. Feb. 22, 2008; 132(4):511-513.

PCT Application Claims from: Yamanaka et al. PCT/JP2006/324881.

Pearson, et al. Improved tools for biological sequence comparison. Proc Natl Acad Sci U S A. Apr. 1988;85(8):2444-8.

Pearson, W.R. Rapid and sensitive sequence comparison with FASTP and FASTA. Methods Enzymol. 1990;183:63-98.

Pera, M. On the Road to Reprogramming. Stem Cell Research. 2008; 1:103-104.

Pomp, et al. Generation of peripheral sensory and sympathetic neurons and neural crest cells from human embryonic stem cells. Stem Cells. Aug. 2005;23(7):923-30.

Pralong, et al. Cell fusion for reprogramming pluripotency: toward elimination of the pluripotent genome. Stem Cell Rev. 2006;2(4):331-40.

Prelle, et al. Overexpression of insulin-like growth factor-II in mouse embryonic stem cells promotes myogenic differentiation. Biochem Biophys Res Commun. Nov. 2, 2000;277(3):631-8.

Rambhatla, et al. Generation of hepatocyte-like cells from human embryonic stem cells. Cell Transplant. 2003;12(1):1-11.

Rao, M. Conserved and divergent paths that regulate self-renewal in mouse and human embryonic stem cells. Dev Biol. Nov. 15, 2004;275(2):269-86.

Ratajczak, et al. Bone-marrow-derived stem cells—our key to longevity? J. Appl. Genet. 2007;48(4): 307-319.

Reubinoff, et al. Neural progenitors from human embryonic stem cells. Nat Biotechnol. Dec. 2001;19(12):1134-40.

Riviére, et al. Effects of retroviral vector design on expression of human adenosine deaminase in murine bone marrow transplant recipients engrafted with genetically modified cells. Proc Natl Acad Sci U S A. Jul. 18, 1995;92(15):6733-7.

Rodda, et al. Transcriptional regulation of nanog by OCT4 and SOX2. J Biol Chem. Jul. 1, 2005;280(26):24731-7.

Root, et al. Genome-scale loss-of-function screening with a lentiviral RNAi library. Nat Methods. Sep. 2006;3(9):715-9.

Rosenfeld, et al. Adenovirus-mediated transfer of a recombinant alpha 1-antitrypsin gene to the lung epithelium in vivo. Science. Apr. 19, 1991;252(5004):431-4.

Rossant, J. Stem Cell and Early Lineage Development. Cell. Feb. 22, 2008; 132(4):527-531.

Rossant, J. Stem Cells: The Magic Brew. Nature. Jul. 19, 2007;448, 260-262.

Rossi, et al. Stem Cells and the Pathways to Aging and Cancer. Cell. Feb. 22, 2008; 132(4):681-696.

Rubin, L. Stem Cell and Drug Discovery: The Beginning of a New Era? Cell. Feb. 22, 2008; 132(4):549-552.

Sadowski, et al. GAL4-VP16 is an unusually potent transcriptional activator. Nature. Oct. 6, 1988;335(6190):563-4.

Saldanha, et al. Assessment of telomere length and factors that contribute to its stability. Eur J Biochem. Feb. 2003 ;270(3):389-403.

Scherr, et al. Gene silencing by small regulatory RNAs in mammalian cells. Cell Cycle. Feb. 1, 2007;6(4):444-9.

Schuldiner, et al. Induced neuronal differentiation of human embryonic stem cells. Brain Res. Sep. 21, 2001;913(2):201-5.

Schwenk, et al. Hybrid embryonic stem cell-derived tetraploid mice show apparently normal morphological, physiological, and neurological characteristics. Mol Cell Biol. Jun. 2003;23(11):3982-9.

Shah, R. Pharmacogenetics in drug regulation: promise, potential and pitfalls. Philos Trans R Soc Lond B Biol Sci. Aug. 29, 2005; 360(1460): 1617-1638.

Silva, et al. Capturing Pluripotency. Cell. Feb. 22, 2008; 132(4):532-536.

Silva, et al. Profiling essential genes in human mammary cells by multiplex RNAi screening. Science. Feb. 1, 2008;319(5863):617-20.

Skottman, et al. Culture conditions for human embryonic stem cells. Reproduction. Nov. 2006;132(5):691-8.

Sottile, et al. In vitro osteogenic differentiation of human ES cells. Cloning Stem Cells. 2003;5(2):149-55.

Stadler, et al. Small RNAs: Keeping Stem Cells in Line. Cell. Feb. 22, 2008; 132(4):563-566.

Stadtfeld, M. Defining molecular cornerstones during fibroblast to iPS cell reprogramming in mouse. Cell Stem Cell. Mar. 6, 2008;2(3):230-40.

Stewart, et al. Mechanisms of self-renewal in human embryonic stem cells. Eur J Cancer. Jun. 2006;42(9):1257-72.

Sumi, et al. Apoptosis and differentiation of human embryonic stem cells induced by sustained activation of c-Myc. Oncogene. Aug. 16, 2007;26(38):5564-76.

Takahashi, et al. Induction of pluripotent stem cells from adult human fibroblasts by defined factors. Cell. Nov. 30, 2007 30;131(5):861-72.

Takahashi, et al. Induction of pluripotent stem cells from fibroblast cultures. Nat Protoc. 2007;2(12):3081-9.

Takahashi, et al. Induction of pluripotent stem cells from mouse embryonic and adult fibroblasts by defined factors. Cell. Aug. 25, 2006; 126(4):663-676.

Tan, et al. Changing viral tropism using immunoliposomes alters the stability of gene expression: implications for viral vector design. Mol Med. Mar.-Apr. 2007;13(3-4):216-26.

Tantin, et al. High-throughput biochemical analysis of in vivo location data reveals novel distinct classes of POU5F1(Oct4)/DNA complexes. Genome Res. Apr. 2008;18(4):631-9.

Thomson, et al. Embryonic Stem Cell Lines Derived from Human Blastocysts. Science. Nov. 1998;282(5391): 1145.

Time. The Top 10 Everything of 2008—1. First Neurons Created from ALS Patients. Available at http://www.time.com/time/specials/2008/top10/article/0,30583,1855948_1863993,00.html. Accessed Dec. 15, 2008.

Tokuzawa, et al. Utilization of Digital Differential Display to Identify Novel Targets of Oct3/4. In: Turksen, K., ed. Embryonic Stem Cell Protocols: vol. I: Isolation and Characterization. Humana Press; 2nd ed. Edition. Feb. 15, 2006: 223-231.

Trompeter, et al. Rapid and highly efficient gene transfer into natural killer cells by nucleofection. J Immunol Methods. Mar. 1, 2003;274(1-2):245-56.

Troyanskaya, et al. Nonparametric methods for identifying differentially expressed genes in microarray data. Bioinformatics. 2002;18(11): 1454-1461.

Tsai, et al. In vivo immunological function of mast cells derived from embryonic stem cells: an approach for the rapid analysis of even embryonic lethal mutations in adult mice in vivo. Proc Natl Acad Sci U S A. Aug. 1, 2000;97(16):9186-90.

Tzukerman, et al. Identification of a novel transcription factor binding element involved in the regulation by differentiation of the human telomerase (hTERT) promoter. Mol Biol Cell. Dec. 2000;11(12):4381-91.

Ulloa-Montoya, et al. Comparative transcriptome analysis of embryonic and adult stem cells with extended and limited differentiation capacity. Genome Biol. 2007;8(8):R163.

Vermeesch, et al. Guidelines for molecular karyotyping in constitutional genetic diagnosis. Eur J Hum Genet. Nov. 2007;15(11):1105-14.

Wagner, et al. Mesenchymal stem cell preparations—comparing apples and oranges. Stem Cell Rev. Dec. 2007;3(4):239-48.

Watanabe, et al. A ROCK inhibitor permits survival of dissociated human embryonic stem cells. Nat Biotechnol. 2007; 25, 681-686.

Watson, et al. Identifying Genes Regulated in a Myc-dependent Manner. J Biol Chem. Oct. 4, 2002;277(40):36921-30.

Wernig, et al. c-Myc is dispensable for direct reprogramming of mouse fibroblast. Cell Stem Cell. 2008; 2, 10-12.

Wernig, et al. In vitro reprogramming of fibroblasts into a pluripotent ES-cell-like state. Nature. Jul. 19, 2007;448: 318-324.

Wernig, et al. Neurons derived from reprogrammed fibroblasts functionally integrate into the fetal brain and improve symptoms of rats with Parkinson's disease. Proc Natl Acad Sci U S A. Apr. 15, 2008;105(15):5856-61.

What are adult stem Cells? Stem Cell Information. The National Institutes of Health resource for stem cell research. 2007. Available at: http://stemcells.nih.gov/info/basics/basics4.asp. Accessed Jun. 4, 2007.

Wu, et al. Origins and Fates of Cardiovascular Progenitor Cells. Cell. Feb. 22, 2008; 132(4):537-543.

Xu, et al. Random mutagenesis libraries: optimization and simplification by PCR. Biotechniques. Dec. 1999;27(6):1102, 1104, 1106, 1108.

Yamanaka, S. Induction of Pluripotent stem cells from mouse fibroblasts by four transcription factors. Cell Prolif. 2008;41(Suppl. 1): 51-56.

Yamanaka, S. Strategies and new developments in the generation of patient-specific pluripotent stem cells. Cell Stem Cell. Jun. 7, 2007;1(1):39-49.

Yamane, et al. Derivation of melanocytes from embryonic stem cells in culture. Dev. Dyn. 1999;216: 450-458.

Yamashita, et al. Flk1-positive cells derived from embryonic stem cells serve as vascular progenitors. Nature. Nov. 2, 2000;408(6808):92-6.

Yee, et al. Generation of high-titer pseudotyped retroviral vectors with very broad host range. Methods Cell Biol. 1994;43 Pt A:99-112.

Yu, et al. Induced pluripotent stem cell lines derived from human somatic cells. Science. Dec. 21, 2007;318(5858):1917-20.

Yuasa, et al. Transient inhibition of BMP signaling by Noggin induces cardiomyocyte differentiation of mouse embryonic stem cells. Nat Biotechnol. May 2005;23(5):607-11.

Zhan, et al. Conservation and variation of gene regulation in embryonic stem cells assessed by comparative genomics. Cell Biochem Biophys. 2005;43(3):379-405.

Zhang, et al. In vitro differentiation of transplantable neural precursors from human embryonic stem cells. Nat Biotechnol. Dec. 2001;19(12):1129-33.

Zhao, et al. Mechanisms and Functional Implications of Adult Neurogenesis. Cell. Feb. 22, 2008; 132(4):645-660.

Ebert, L. Yamanaka scooped on iPS (stem cell) patent?!. TMCNews reports on Jan. 4, 2009. Available at http://ipbiz.blogspot.com/2009/01/yamanaka-scooped-on-ips-stem-cell.html. Accessed May 19, 2009.

Hyun, et al. New advances in iPS cell research do not obviate the need for human embryonic stem cells. Cell Stem Cell. Oct. 11, 2007;1(4):367-8.

Park, A. Stem-cell research: The quest resumes.Time Magazine. Feb. 9, 2009. Available at http://www.time.com/time/health/article/0,8599,1874717,00.html. Accessed Jun. 3, 2009.

Science magazine names top 10 breakthroughs of 2008. Available at http://arstechnica.com/old/content/2008/12/is ciencei-names-top-10-scientific-breakthroughs-of-2008.ars. Accessed May 19, 2009.

The Japan Times. Bayer team makes stem cells from skin. Apr. 12, 2008. Available at http://search.japantimes.co.jp/cgi-bin/nn20080412a5.html. Accessed May 19, 2009.

Vogel, G. Breakthrough of the year. Reprogramming Cells. Science. Dec. 19, 2008;322(5909):1766-7.

U.S. Appl. No. 12/465,633, filed May 13, 2009, Sakurada et al.
U.S. Appl. No. 12/484,152, filed Jun. 12, 2009, Sakurada et al.
U.S. Appl. No. 12/484,163, filed Jun. 12, 2009, Sakurada et al.
U.S. Appl. No. 12/564,836, filed Sep. 22, 2009, Sakurada et al.
U.S. Appl. No. 12/580,216, filed Oct. 15, 2009, Sakurada et al.

Chin, et al. Induced pluripotent stem cells and embryonic stem cells are distinguished by gene expression signatures. Cell Stem Cell. Jul. 2, 2009;5(1):111-23.

Kunath, et al. FGF stimulation of the Erk1/2 signalling cascade triggers transition of pluripotent embryonic stem cells from self-renewal to lineage commitment. Development. Aug. 2007;134(16):2895-902.

Mali, et al. Improved efficiency and pace of generating induced pluripotent stem cells from human adult and fetal fibroblasts. Stem Cells. Aug. 2008;26(8):1998-2005.

Marchetto, et al. Transcriptional signature and memory retention of human-induced pluripotent stem cells. PLoS One. Sep. 18, 2009;4(9):e7076.

Vallier, et al. Activin/Nodal and FGF pathways cooperate to maintain pluripotency of human embryonic stem cells. J Cell Sci. Oct. 1, 2005;118(Pt 19):4495-509.

Wang, et al Inhibition of caspase-mediated anoikis is critical for bFGF-sustained culture of human pluripotent stem cells. J Biol Chem. Oct. 16, 2009. [Epub ahead of print].

Werbowetski-Ogilvie, et al. Characterization of human embryonic stem cells with features of neoplastic progression. Nat Biotechnol. Jan. 2009;27(1):91-7.

U.S. Appl. No. 12/663,840, filed Dec. 9, 2009, Sakurada et al.
U.S. Appl. No. 12/685,569, filed Jan. 11, 2010, Sakurada et al.

Becker-Hapak, et al. Protein transduction: generation of full-length transducible proteins using the TAT system. Curr Protoc Cell Biol. May 2003;Chapter 20:Unit 20.2.

Durcova-Hills, et al. Induced reprogramming of human somatic cells into pluripotency: a new way how to generate pluripotent stem cells. Differentiation. Apr. 2008;76(4):323-5.

Heng, et al. Incorporating protein transduction domains (PTD) within intracellular proteins associated with the 'sternness' phenotype. Novel use of such recombinant 'fusion' proteins to overcome current limitations of applying autologous adult stem cells in regenerative medicine? Med Hypotheses. 2005;64(5):992-6.

Adachi et al. Role of SOX2 in maintaining pluripotency of human embryonic stem cells. Genes Cells. May 2010; 15(5):455-70.

Akimov et al., Bypass of Senescence, Immortalization, and Transformation of Human Hematopoietic Progenitor Cells, Stem Cells 23:1423-33, 2005.

Allergucci et al. Differences between human embryonic stem cell lines. Hum Reprod Update. Mar.-Apr. 2007;13(2):103-20.

Amsellem et al., Ex vivo Expansion of Human Hematopoietic Stem Cells by Direct Delivery of the HOXB4 Homeoprotein, Nat. Med. 9(11):1423-27, 2003.

Asahi Shimbun Weekly AERA, The Novel Pluripotent Cells Established by Professor Yamanaka of Kyoto University May change Medical Care, pp. 72-73, Dec. 24, 2009, along with a partial English language translation thereof.

Avilion et al., Multipotent Cell Lineages in Early Mouse Development Depend on SOX2 Function, Genes Dev. 17:126-40, 2003.

Bang et al., Deconstructing Pluripotency, Science 320:58-59, 2008.

Barrett et al., Activation Domains of L-Myc and c-Myc Determine Their Transforming Potencies in Rat Embryo Cells, Mol. Cell. Biol. 12(7):3130-37, 1992.

Belmonte et al. "Induced pluripotent stem cells and reprogramming: seeing the science through the hype." Nat Rev Genet. Dec. 2009;10(12):878-83.

Benetti et al., A Mammalian microRNA Cluster Controls DNA Methylation and Telomere Recombination Via RbI2-Dependent Regulation of DNA Methyltransferases, Nat. Struct. Mol. Biol. 15(3):268-79, published online Mar. 2, 2008.

Ben-Shushan et al., Rex-1, A Gene Encoding a Transcription Factor Expressed in the Early Embryo, Is Regulated via Oct-3/4 and Oct-6 Binding to an Octomer Site and a Novel Protein, Rox-1, Binding to an Adjacent Site, Mol. Cell Biol. 18(4):1866-78, 1998.

Bibel et al., "Differentiation of mouse embryonic stem cells into a defined neuronal lineage," Nature Neuroscience, 2004, vol. 7, pp. 1003-1009.

Bigdeli et al., Adaptation of Human Embryonic Stem Cells to Feeder-Free and Matrix-Free Culture Conditions Directly on Plastic Surfaces. J. Biotec., 2008, vol. 133, pp. 146-153.

BioPorter™ Gene Therapy System, Inc., Wako Bio Window 40:7, 2002.

BioPorter™ Protein Delivery Reagent From www.biocarta.com.

Birrer et al., L-myc Cooperates With ras to Transform Primary Rat Embryo Fibroblasts, Mol. Cell. Biol. 8(6):2668-73, 1988.

Blackwood et al., Max: A Helix-Loop-Helix Zipper Protein That Forms a Sequence-Specific DNA-Binding Complex With Myc, Science 251(499*):1211-17, 1991.

Block et al., Population Expansion, Clonal Growth, and Specific Differentiation Patterns in Primary Cultures of Hepatocytes Induced by HGF/SF, EGF and TGFα in a Chemically Defined (HGM) Medium, J. Cell Biol. 132(6):1133-49, 1996.

Bortvin et al., Incomplete Reactivation of Oct4-Related Genes in Mouse Embryos Cloned From Somatic Nuclei, Development 130:1673-80, 2003.

Brough et al., An Essential Domain of the c-Myc Protein Interacts With a Nuclear Factor That Is Also Required for E1A-Mediated Transformation, Mol. Cell. Biol. 15(3):1536-44, 1995.

Carey et al., "Reprogramming of murine and human somatic cells using a single polycistronic vector," Proc. Natl. Acad. Sci. USA, Jan. 6, 2009, vol. 106(1), pp. 157-62, Epub. Dec. 24, 2008. Erratum in: Proc. Natl. Acad. Sci. USA, Mar. 31, 2009, Vol.

Chambers et al., Functional Expression Cloning of Nanog, A Pluripotency Sustaining Factor in Embryonic Stem Cells, Cell 113:643-55, 2003.

Chang et al., Embryonic Stem Cells/Induced Pluripotent Stem Cells, Stem Cells, 2009, vol. 27, pp. 1042-1049.

Check, E., Simple Recipe Gives Adult Cells Embryonic Powers, Nature 442:11, Jul. 6, 2006.

Cheng et al., Mammalian Grb2 Regulates Multiple Steps in Embryonic Development and Malignant Transformation, Cell 95:793-803, 1998.

Chin et al. Induced pluripotent stem cells and embryonic stem cells are distinguished by gene expression signatures. Cell Stem Cell. Jul. 2, 2009;5(1): 111-23.

Cohen et al., "Ooplasmic Transfer in Mature Human Oocytes," Molecular Human Reproduction, 1998, vol. 4, pp. 269-280.

Correction printed in Nature 447:897, Jun. 21, 2007.

Cosmo Bio News 49:5, 2005 (catalog of Es cell culture medium).

Cowan et al. Nuclear Reprogramming of Somatic Cells After Fusion with Human Embryonic Stem Cells. Science, 2005, vol. 309, pp. 1369-1374.

Cowan et al., Derivation of Embryonic Stem-Cell Lines From Human Blastocysts, N. Engl. J. Med. 350:1353-56, 2004.

Daley, et al., "Broader implications of defining standards for the pluripotency of iPSCs." Cell Stem Cell. Mar. 6, 2009;4(3):200-1; author reply 202.

Dang et al., The Biology of the Mammalian Kruppel-Like Family of Transcription Factors, Int. J. Biochem. Cell Biol. 32:1103-21, 2000.

Dimos et al. Induced pluripotent stem cells generated from patients with ALS can be differentiated into motor neurons. Science. Aug. 29, 2008;321(5893):1218-21.

Do et al., "Nuclei of Embryonic Stem Cells Reprogram Somatic Cells," Stem Cells, 2004, vol. 22, pp. 941-949.

Essentials of Stem Cell Biology, R. Lanza et al. Ed., 2006, Elsevier Academic Press, pp. 266-267.

Evans et al., Establishment in Culture of Pluripotential Cells From Mouse Embryos, Nature 292:154-56, 1981.

Examination Report issued in Australian Patent Application No. 2006325975, Apr. 18, 2011.

Extended European Search Report issued in connection with European Patent Application No. 10154819.6, Jun. 10, 2010.

Extended European Search Report issued in connection with European Patent Application No. EP 06834636.0, Mar. 11, 2009.

Extended European Search Report issued in connection with European Patent Application No. EP 10154817.0, Jun. 10, 2010.

Extended European Search Report issued in connection with European Patent Application No. EP 10154821.2, Jun. 10, 2010.

Feng et al., Reprogramming of Fibroblasts Into Induced Pluripotent Stem Cells With Orphan Nuclear Receptor Esrrb, Nature Cell Biology 11:197-203, 2009.

Griffiths-Jones et al., miRBase: Tools for microRNA Genomics, Nucleic Acids Research 36:D154-D158, published online Nov. 8, 2007.

Hakelien et al. Reprogramming Fibroblasts to Express T-Cell Functions Using Cell Extracts. Nature Biotechnology, May 2002, vol. 20, pp. 460-466.

Hanna et al., Direct Reprogramming of Terminally Differentiated Mature B Lymphocytes to Pluripotency, Cell 133:250-264, Apr. 17, 2008.

Hanna et al., Treatment of Sickle Cell Anemia Mouse Model With iPS Cells Generated From Autologous Skin, Science4 318(5858):1920-23, published online Dec. 6, 2007.

Hasegawa et al., Efficient Multicistronic Expression of a Transgene in Human Embryonic Stem Cells, Stem Cells 25:1707-12,. 2007.

Hatfield et al., Stem Cell Division is Regulated by the microRNA Pathway, Nature 435(7044):974-978, 2005.

Herold et al., Negative Regulation of the Mammalian UV Response by Myc Through Association with Miz-1, Mol. Cell 10(3):509-21, 2002.

Hockemeyer et al. A drug-inducible system for direct reprogramming of human somatic cells to pluripotency. Cell Stem Cell. Sep. 11, 2008;3(3):346-53.

Hong et al., "Suppression of induced pluripotent stem cell generation by the p53-p21 pathway." Nature. Aug. 27, 2009;460(7259):1132-5.

Horikawa et al., Differential Cis-Regulation of Human Versus Mouse TERT Gene Expression in vivo: Identification of a Human-Specific Repressive Element, proc. Natl. Acad. Sci. U.S.A. 102(51):1843742, 2005.

Houbaviy et al., Embryonic Stem Cell-Specific MicroRNAs, Developmental Cell 5(2):351-58, 2003.

Hsiao et al., Marking Embryonic Stem Cells With a 2A Self-Cleaving Peptide: a NKX2-5 Emerald GFP BAC Reporter, PLoS One 3(7):e2532, 2008.

Huangfu et al., Induction of Pluripotent Stem Cells by Defined Factors is Greatly Improved by Small-Molecule Compounds, Nature Biotechnology 26(7):795-97, 2008.

Huangfu et al., Induction of Pluripotent Stem Cells From Primary Human Fibroblasts With Only Oct4 and Sox 2, Nature Biotechnology 26:1269-1275, 2008.

Humphries, C., Reprogrammed Stem Cells Work on Parkinson's: A Study in Rodents Suggests that Skin Cells Can Be Transformed into Neurons to Treat Neurodegeneration, Technology Review, published by MIT, Apr. 8, 2008: http://www.technologyreview.com/printer.

Hwang et al., Evidence of Pluripotent Human Embryonic Stem Cell Line Derived From a Cloned Blastocyst, Science 303:1669-74, 2004.

Hwang et al., Patient-Specific Embryonic Stem Cells Derived From Human SCNT Blastocysts, Science 308:1777-83, 2005.

International search report dated Jan. 20, 2010 for PCT Application No. US2009/047291.

International Search Report issued with respect to PCT/JP2009/058873, mailed Jul. 7, 2009.

Itskovitz-Eldor et al., Differentiation of Human Embryonic Stem Cells Into Embryoid Bodies Comprising the Three Embryonic Germ Layers, Mol. Med. 6(2):88-95, 2000.

Jikken Igaku (Experimental Medicine) 24:814-19, 2006, along with an English language translation thereof.

Kaji et al., Virus-Free Induction of Pluripotency and Subsequent Excision of Reprogramming Factors, Nature, Mar. 1, 2009, vol. 458, Issue 7239, pp. 771-775.

Kanellopoulou et al., Dicer-Deficient Mouse Embryonic Stem Cells Are Defective in Differentiation and Centromeric Silencing, Genes & Development 19:489-501, 2005.

Kim et al., Generation of Human Induced Pluripotent Stem Cells by Direct Delivery of Reprogramming Proteins, Cell Stem Cell 4:472-476, 2009.

Kim et al., Oct4-Induced Pluripotency in Adult Neural Stem Cells, Cell 136:411-419, 2009.

Kim et al., Pluripotent Stem Cells Induced From Adult Neural Stem Cells by Reprogramming with Two Factors, Nature 454:656-650, 2008.

Kohlhase et al., Cloning and Expression Analysis of Sall4, The Murine Homologue of the Gene Mutated in Okihiro Syndrome, Cytogenet. Genome Res. 98:274-77, 2002.

Koyanagi et al., Screening and Functional Analysis of microRNAs which involve in Reprogramming, of Murine Somatic Cells, The Journal of Biochemistry, vol. 79, No. 11, Abstract 1T-7-7 From the 80$^{th}$ Annual Meeting of the Japanese Biochemical Society, Novemb.

Krosl et al., In vitro Expansion of Hematopoietic Stem Cells by Recombinant TAT-HOXB4 Protein, Nat. Med 9(11):1428-32, 2003.

Kubicek et al., Reversal of H3K9me2 by a Small-Molecule Inhibitor for the G9a Histone Methyltransferase, Molecular Cell 25:473-81, 2007.

Kunath et al. FGF stimulation of the Erk1/2 signalling cascade triggers transition of pluripotent embryonic stem cells from self-renewal to lineage commitment. Development. Aug. 2007;134(16):2895-902.

Kyoto Shimbun (Japanese Newspaper) article of Apr. 16, 2008, columns 1-3, along with a partial English language translation thereof.

Laflamme et al, Cardiomyocytes Derived From Human Embryonic Stem Cells in Pro-Survival Factors Enhance Function of Infarcted Rat Hearts, Nat. Biotechnol. 25(9):1015-24, 2007.

Lewitzky et al., "Reprogramming somatic cells towards pluripotency by defined factors." Curr Opin Biotechnol. Oct. 2007;18(5):467-73.

Li et al., Leukaemia Disease Genes: Large-Scale Cloning and Pathway Predictions, Nat. Genet. 23(3):348-353, 1999.

Liao et al., Enhanced Efficiency of Generating Induced Pluripotent Stem (iPS) Cells From Human Somatic Cells by a Combination of Six Transcription Factors, Cell Research 18:600-603, doi: 10.1038/cr.2008.51, published online Apr. 15, 2008.

Lin et al., Mir-302 Reprograms Human Skin Cancer Cells into a Pluripotent ES-Cell-Like State, RNA 14:1-10, 2008.

Loriot et al., Five New Human Cancer-Germline Genes Identified Among 12 Genes Expressed in Spermatogonia, Int. J. Cancer 105:371-76, 2003.

Maherali et al. A high-efficiency system for the generation and study of human induced pluripotent stem cells. Cell Stem Cell. Sep. 11, 2008;3(3):340-5.

Mali et al. Improved efficiency and pace of generating induced pluripotent stem cells from human adult and fetal fibroblasts. Stem Cells. Aug. 2008;26(8):1998-2005.

Marchetto et al. Transcriptional signature and memory retention of human-induced pluripotent stem cells. PLoS One. Sep. 18, 2009;4(9):e7076.

Marson et al., Wnt Signaling Promotes Reprogramming of Somatic Cells to Pluripotency, Cell Stem Cell 3:132-35, 2008.

Martin, Isolation of a Pluripotent Cell Line From Early Mouse Embryos Cultured in Medium Conditioned by Teratocarcinoma Stem Cells, Proc. Natl. Acad. Sci. U.S.A. 78(12):7634-38, 1981.

Maruyama et al., Differential Roles for Sox15 and Sox2 in Transcriptional Control in Mouse Embryonic Stem Cells, J. Biol., Chem. 280(26):24371-79, 2005.

McMahon et al., The Wnt-1 (int-1) Proto-Oncogene Is Required for Development of a Large Region of the Mouse Brain, Cell 62:1073-85, 1990.

Meiner et al, Disruption of the Acyl-CoA: Cholesterol Acyltransferase Gene in Mice: Evidence Suggesting Multiple Cholesterol Esterification Enzymes in Mammals, Proc. Natl. Acad. Sci. U.S.A. 93:14041-46, 1996.

microRNA Jikken Purotokoru (microRNA Experimental Protocol), pp. 20-35, 2008, Yodosha Co., Ltd.

Mitsui et al., The Homeoprotein Nanog is Required for Maintenance of Pluripotency in Mouse Epiblast and ES Cells, Cell 113:631-42, 2003.

Miura et al. "Variation in the safety of induced pluripotent stem cell lines." Nat Biotechnol. Aug. 2009;27(8):743-5.

Nagano et al., "Large-Scale Identification of Proteins Expressed in Mouse Embryonic Stem Cells," Proteomics 5:1346-1361, 2005.

Nakagawa et al., "Promotion of direct reprogramming by transformation-deficient Myc." Proc Natl Acad Sci U S A. Aug. 10, 2010;107(32):14152-7.

Newton, Attracting World's Attention. Pluripotent Cells Are Generated From Human Skin. What is the 'iPS Cell' That Can Be Used Not Only in the Regeneration Therapy but Also in the Tailor-Made Therapy, pp. 70-75, Feb. 2008, along with a partial Engli.

Nichols et al., Formation of Pluripotent Stem Cells in the Mammalian Embryo Depends on the POU Transcription Factor Oct4, Cell 95:379-91, 1998.

Nienhuis et al., Genotoxicity of Retroviral Integration in Hematopoietic Cells, Mol. Ther. 13(6):1031-49, 2006.

Niwa et al., Efficient Selection for High-Expression Transfectants With a Novel Eukaryotic Vector, Gene 108(2):193-99,1991.

Nolta et al., Transduction of Pluripotent Human Hematopoietic Stem Cells Demonstrated by Clonal Analysis After Engraftment in Immune-Deficient Mice, Proc. Natl. Acad. Sci. USA 93(6):2414-19, 1996.

Office Action issued in connection with Chinese Patent Application No. 200680048227.7, Sep. 9, 2010.

Office Action issued in connection with European Patent Application No. EP 06834636.0, Apr. 30, 2010.

Office Action issued in connection with European Patent Application No. EP 06834636.0, Oct. 25, 2010.

Office Action issued in connection with Israeli Patent Application No. 191903, Aug. 19, 2010.

Office Action issued in connection with Japanese Patent Application No. JP 2009-056747, mailed Jun. 2, 2009.

Office Action issued in connection with Japanese Patent Application No. JP 2009-056748, mailed Jun. 2, 2009.

Office Action issued in connection with Japanese Patent Application No. JP 2009-056749, mailed Jun. 4, 2009.

Office Action issued in connection with Japanese Patent Application No. JP 2009-056750, mailed Jun. 2, 2009.

Office Action issued in connection with New Zealand Patent Application No. 569530, Apr. 20, 2010.

Office Action issued in connection with Singapore Patent Application No. 200804231-9, Apr. 13, 2010.
Office Action issued in connection with Singapore Patent Application No. 200901803-7, Jan. 22, 2010.
Official Action issued in connection with Eurasian Patent Application No. 200870046, Nov. 9, 2009.
Official Action issued in connection with Eurasian Patent Application No. 201000858, Jul. 14, 2010.
Official Action issued in connection with Japanese Patent Application No. JP 2009-056748, mailed Nov. 4, 2009.
Official Rejection issued in connection with Japanese Patent Application No. JP 2009-056748, mailed Feb. 23, 2010.
Official Rejection issued in connection with Japanese Patent Application No. JP 2009-056749, mailed Nov. 4, 2009.
Ohnuki et al., "Generation and characterization of human induced pluripotent stem cells." Curr Protoc Stem Cell Biol. Jun. 2009;Chapter 4:Unit 4A.2.
Okabe et al., Green Mice' as a Source of Ubiquitous Green Cells, FEBS Letters, 1997, vol. 407, pp. 313-319.
Okamoto et al., A Novel Octamer Binding Transportation Factor is Differentially Expressed in Mouse Embryonic Cells, Cell 60:461-72, 1990.
Okita et al., "Generation of mouse-induced pluripotent stem cells with plasmid vectors." Nat Protoc. 2010;5(3):418-28.
Okita et al., "Induction of pluripotency by defined factors." Exp Cell Res. Oct. 1, 2010;316(16):2565-70. Epub Apr. 24, 2010.
Okita et al., Generation of Mouse Induced Pluripotent Stem Cells Without Viral Vectors, Science 322(5903):949-53, published online Oct. 9, 2008.
Okuda et al., UTF1, A Novel Transcriptional Coactivator Expressed in Pluripotent Embryonic Stem Cells and Extra-Embryonic Cells, EMBO J. 17(7):2019-32, 1998.
Okumura-Nakanishi et al., "Oct-3/4 and Sox2 Regulate Oct-3/4 Gene in Embryonic Stem Cells," The Journal of Biological Chemistry 280(7):5307-5317, Feb. 18, 2006.
Park et al. Disease-specific induced pluripotent stem cells. Cell. Sep. 5, 2008; 134(5):877-86.
Peister et al., Gene Ther, Jan. 2004, vol. 11, Issue 2, pp. 224-228.
Postic et al., Dual Roles for Glucokinase in Glucose Homeostasis as Determined by Liver and Pancreatic β Cell-Specific Gene Knockouts Using Cre Recombinase, J. Biol. Chem 274(1):305-15.
Qin et al., Direct Generation of ESLike Cells From Unmodified Mouse Embryonic Fibroblasts by Oct4/Sox2/Myc/Klf4, Cell Res. 17(11):959-62, 2007.
Quenneville et al., Mol. Ther., Oct. 2004, vol. 10, Issue 4, pp. 679-687.
Rodriguez et al. Manipulation of OCT4 levels in human embryonic stem cells results in induction of differential cell types. Exp Biol Med (Maywood). Nov. 2007;232(10):1368-80.
Ryan et al., POU Domain Family Values: Flexibility, Partnerships, and Developmental Codes, Genes Dev. 11:1207-25, 1997.
Sakai et al., A Transgenic Mouse Line That Retains Cre Recombinase Activity in Mature Oocytes Irrespective of the cre Transgene Transmission, Biochem. Biophys. Res. Commun. 237(2):318-24, 1997.
Salmon et al., Reversible Immortalization of Human Primary Cells by Lentivector-Mediated Transfer of Specific Genes, Mol. Ther. 2(4):404-14, 2000.
Sato et al., Maintenance of Pluripotency in Human and Mouse Embryonic Stem Cells Through Activation of Wnt Signaling by a Pharmacological GSK-3-Specific Inhibitor, Nat. Med. 10(1):55-63, 2004.
Schepers et al., Twenty Pairs of Sox: Extent, Homology, and Nomenclature of the Mouse and Human Sox Transcription Factor Gene Families, Dev. Cell 3:167-70, 2002.
Shao et al., Generation of iPS Cells Using Defined Factors Linked Via the Self-Cleaving 2A Sequences in a Single Open Reading Frame, Cell Res., Mar. 2009, vol. 19, Issue 3, pp. 296-312.
Shi et al., A Combined Chemical and Genetic Approach for the Generation of Induced Pluripotent Stem Cells, Cell Stem Cell 2:525-28, 2008.
Shi et al., Induction of Pluripotent Stem Cells From Mouse Embryonic Fibroblasts by Oct4 and Klf4 With Small-Molecule Compounds, Cell Stem Cell 3:568-74, 2008.

Silva et al., Promotion of Reprogramming to ground State Pluripotency by Signal Inhibition, PLoS Biology 6910):2237-47, 2008.
Sinkkonen et al., MicroRNAs Control de novo DNA Methylation Through Regulation of Transcriptional Repressors in Mouse Embryonic Stem Cells, Nat. Struct. Mol. Biol. 15(3):259-267, published online Mar. 2, 2008.
Soldner et al., Parkinson's Disease Patient-Derived Induced Pluripotent Stem Cells Free of Viral Reprogramming Factors, Cell, Mar. 6, 2009, vol. 136, Issue 5, pp. 964-977.
Spencer et al., E-Cadherin Inhibits Cell Surface Localization of the Pro-Migratory 5T4 Oncofetal Antigen in Mouse Embryonic Stem Cells, Mol. Biol. Cell 18:2838-51, 2007.
Spivakov et al., Epigenetic Signatures of Stem-Cell Identify, Nat. Rev. Genet. 8(4):263-271, 2007.
Stadtfeld et al., Induced Pluripotent Stem Cells Generated Without Viral Integration, Science 322(5903):945-49, published online Sep. 25, 2008.
Stem Cells Made to Mimic Disease, BBC News, http://newsvote.bbc.co.uk/mpapps/pagetools/print/news.bbc.co.uk/2/hi/health/7334365.stm, Apr. 7, 2008.
Suh et al., Human Embryonic Stem Cells Express a Unique Set of microRNAs, Developmental Biology 270:488-498, 2004.
Surani et al., A New Route to Rejuvenation, nature 443:284-285, Sep. 21, 2006.
Tada et al., Nuclear Reprogramming of Somatic Cells by in vitro Hybridization With ES Cells, Current Biology 11(19):1553-58, 2001.
Takahashi et al., Induced Pluripotent Stem Cells, Jikken Igaku (Experimental Medicine) 26(5):35-40, 2008.
Takahashi et al., Role of ERas in Promoting Tumour-Like Properties in Mouse Embryonic Stem Cells, Nature 423:541-45, 2003.
Takahashi, K. et al. "Human induced pluripotent stem cells on autologous feeders." PLoS One. Dec. 2, 2009;4(12):e8067.
Takeda et al., Characterization of Dental Pulp Stem Cells of Human Tooth Germs, Journal of Dental Research, 2008, vol. 87, pp. 676-681.
Takeda et al., Human Oct3 Gene Family: cDNA Sequences, Alternative Splicing, Gene Organization, Chromosomal Location, and Expression at Low Levels in Adult Tissues, Nucleic Acids Research 20(17):4613-4620, 1992.
Taranger et al., Induction of Dedifferentiation, Genomewide Transcriptional Programming, and Epigenetic reprogramming by Extracts of Carcinoma and Embryonic Stem Cells, Mol. Biol. Cell 16:5719-35, 2005.
Tateno et al., Heterogeneity of Growth Potential of Adult Rat Hepatocytes in vitro, Hepatology 31(1):65-74, 2000.
Tokuzawa et al., Fbx15 Is a Novel Target of Oct3/4 but is Dispensible for Embryonic Stem Cell Self-Renewal and Mouse Development, Mol. Cell Biol. 23(8):2699-718, 2003.
Tsubooka et al. "Roles of Sall4 in the generation of pluripotent stem cells from blastocysts and fibroblasts." Genes Cells. Jun. 2009;14(6):683-94.
Tsunoda, Y., et al., The Recent Progress on Nuclear Transfer in Mammals, Zoological Science 17:1177-1184, 2000.
Verrey et al., CATs and HATs: The SLC7 Family of Amino Acid Transporters, Pflugers Archive-European Journal of Physiology, DOI 10.1007/s00424-003-1086-Z, pp. 1-23, published online Jun. 11, 2003.
Vintersten et al., Mouse in Red: Red Fluorescent Protein Expression in Mouse ES Cells, Embryos, and Adult Animals, Genesis 4041-46, 2004.
Viswanathan et al., Selective Blockade of MicroRNA Processing by Lin28, Science 320:97-100, 2008.
Wadia et al., Protein Transduction Technology, Curr. Opin. Biotechnol. 13:52-56, 200.
Wakao et al., "Multilineage-Differentiating Stress-Enduring (Muse) Cells Are a Primary Source of Induced Pluripotent Stem Cells in Human Fibroblasts," PNAS Early Edition, pp. 1-6, May 31, 2011, available at www.pnas.org/cgi/content/short/1100816108.
Wakayama et al., Differentiation of Embryonic Stem Cell Lines Generated From Adult Somatic Cells by Nuclear Transfer, Science 292:740-43, 2001.

Wakayama et al., Full-Term Development of Mice From Enucleated Oocytes Injected With Cumulus Cell Nuclei, Nature 394:369-74, 1998.

Wang et al. Inhibition of caspase-mediated anoikis is critical for bFGF-sustained culture of human pluripotent stem cells. J Biol Chem. Oct. 16, 2009. [Epub ahead of print].

Wang et al., A Protein Interaction Network for Pluripotency of Embryonic Stem Cells, Nature 444:364-68, 2006.

Werbowetski-Ogilvie et al. Characterization of human embryonic stem cells with features of neoplastic progression. Nat Biotechnol. Jan. 2009;27(1):91-7.

Wernig et al., Neurons Derived From Reprogrammed Fibroblasts Functionally Integrate Into the Fetal Brain and Improve Symptoms of Rats With Parkinson's Disease, Proc. Natl. Acad. Sci. U.S.A. 105(15):5856-5861, 2008.

Wilmut et al., Viable Offspring Derived From Fetal and Adult Mammalian Cells, Nature 385:810-13, 1997.

Woltjen et al., PiggyBac Transposition Reprograms Fibroblasts to Induced Pluripotent Stem Cells, Nature, Mar. 1, 2009, vol. 458, Issue 7239, pp. 766-770.

Wu et al., Sall4 Interacts With Nanog and Co-Occupies Nanog Genomic Sites in Embryonic Stem Cells, J. Biol., Chem., 281(34):24090-24094, 2000.

Xu et al., Basic FGF and Suppression of BMP Signaling Sustain Undifferentiated Proliferation of Human ES Cells, Nat. Methods 2(3):185-90, 2005.

Yamanaka et al., "Nuclear reprogramming to a pluripotent state by three approaches." Nature. Jun. 10, 2010;465(7299):704-12.

Yamanaka et al., Mouse Sen'iga Saibo Kara Yudo Tansosei Kansaibo o Tsukuru (Induction of Pluripotent Stem Cells From Mouse Fibroblast Cultures) Tanpakushitsu Kakusan Koso (Protein, Nucleic Acid and Enzyme) 51(15):2346-51, 2006.

Yamanaka S., "An interview with . . . Shinya Yamanaka. Interview by Mary Muers." Nat Rev Genet. Jun. 2010;11(6):390.

Yamanaka S., "Patient-specific pluripotent stem cells become even more accessible" Cell Stem Cell. Jul. 2, 2010;7(1):1-2.

Yamanaka S., "Pluripotency and nuclear reprogramming." Philos Trans R Soc Lond B Biol Sci. Jun. 27, 2008;363(1500):2079-87.

Yamanaka S., "Symposium: Nuclear reprogramming and the control of differentiation in mammalian embryos. Introduction." Reprod Biomed Online. Jan. 2008;16(1):11-2.

Yamanaka, Pluripotency of Differentiation and miRNA, The Journal of Biochemistry, vol. 79, No. 11, Abstract 3BT17 From the 80th Annual Meeting of the Japanese Biochemical Society, Nov. 25, 2007, along with an English language translation thereof.

Yamanaka, S., "A fresh look at iPS cells." Cell. Apr. 3, 2009;137(1):13-7.

Yamanaka, S., "Ekiden to iPS Cells." Nat Med. Oct. 2009;15(10):1145-8.

Yamanaka, S., "Elite and stochastic models for induced pluripotent stem cell generation." Nature. Jul. 2, 2009;460(7251):49-52.

Yamanaka, S., "Induction of Pluripotency by Defined Factors—The History of iPS Cells", Gairdner Award acceptance speech, presented on or about Oct. 29, 2009.

Yamanaka, S., "Induction of Pluripotency by Defined Factors", lecture presented on or about Oct. 29, 2009.

Yang et al., Nuclear Reprogramming of Cloned Embryos and Its Implications for Therapeutic Cloning, Nat. Genet. 39(3):295-302, 2007.

Ying et al., BMP Induction of ID Proteins Suppresses Differentiation and Sustains Embryonic Stem Cell Self-Renewal in Collaboration With STAT3, Cell 115:281-92, 2003.

Ying et al., The MicroRNA: Overview of the RNA Gene That Modulates Gene Functions, Methods in Molecular Biology, MicroRNA Protocols, vol. 342, pp. 1-18, Humana Press, 2006.

Yoshida et al. "Hypoxia enhances the generation of induced pluripotent stem cells." Cell Stem Cell. Sep. 4, 2009;5(3):237-41. Epub Aug. 27, 2009.

Yoshida et al., "Recent stem cell advances: induced pluripotent stem cells for disease modeling and stem cell-based regeneration." Circulation. Jul. 6, 2010;122(1):80-7.

Yu et al., Human Induced Pluripotent Stem Cells Free of Vector and Transgene Sequences, Science 324:797-801, 2009.

Zhang et al., MicroRNA: A New Player in Stem Cells, Journal of Cellular Physiology 209:266-269, 2006.

Zhao et al., "Two Supporting Factors Greatly Improve the Efficiency of Human iPSC Generation" Cell Stem Cell 3:475-79, 2008.

Zhou et al., Generation of Induced Pluripotent Stem Cells Using Recombinant Proteins, Cell Stem Cell 4:381-384, 2009.

Ziegler et al., The Cationic Cell-Penetrating Peptide $CPP^{TAT}$ Derived From the HIV-1 Protein TAT is Rapidly Transported into Living Fibroblasts: Optical, Biophysical, and Metabolic Evidence, Biochemistry 44:138-148, published online Dec. 14, 2004.

Bongso, A., et al., Isolation and Culture of Inner Cell Mass Cells From Human Blastocysts, Human Reproduction 9(11):2110-2117, 1994.

European Examination Report on EP 07 856 194.1, issued Sep. 29, 2011.

Crouch, D.H., et al., Multiple Phenotypes Associated With Myc-Induced Transformation of Chick Embryo Fibroblasts Can Be Dissociated by a Basic Region Mutation, Nucleic Acids Research 24(16):3216-3221, 1996.

Nakagawa, M., et al., Promotion of Direct Reprogramming by Transformation-Deficient Myc., Proc. Natl. Acad. Sci. USA 107(32):14152-14157, Aug. 2010.

Sarid, J., et al., Evolutionarily Conserved Regions of the Human c-Myc Protein Can Be Uncoupled From Transforming Activity, Proc. Natl. Acad. Sci. USA 84(1):170-173, 1987.

* cited by examiner

Amount of Nanog expressed after 3 gene introduction and HDAC inhibitor treatment in mouse adult bone marrow derived cells Morphology and expansion culture of human iPS clone 1-8

Surface antigen and gene expression analysis of clone 1-8

Gene expression analysis by RT-PCR in clone 1-8

Global gene expression analysis – scatter plot

Global gene expression analysis – gene tree (1)

Global gene expression analysis – gene tree (2)

Methylation analysis of promoter regions in human IPS 1-8

Teratoma formation (1)

(T1, 56 d.p.i)

Teratoma formation (2)

Teratoma formation (3)

Southern blot analysis hES marker gene expression in ALP positive colonies

Morphologies of analyzed ALP positive colonies (1)

Group #1 (8 gene positive)

Group #2 (7 gene positive)

Group #3 (7 gene positive)

Group #4 (7 gene positive)

Morphologies of analyzed ALP positive colonies (2)

Morphologies of analyzed ALP positive colonies (3)

Morphologies of analyzed ALP positive colonies (4)

Group #14 (5 gene positive)

Group #15 (5 gene positive)

Group #16 (5 gene positive)    Group #17 (5 gene positive)

Group #18 (5 gene positive)    Group #19 (5 gene positive)

Group #20 (4 gene positive)

Morphologies of analyzed ALP positive colonies (5)

Morphologies of analyzed ALP positive colonies (6)

Group #29 (3 gene positive)

Group #36 (2 gene positive)

Group #37 (2 gene positive)

Group #38 (2 gene positive)

Group #39 (1 gene positive)

Group #40 (0 gene positive)

Morphologies of analyzed ALP negative colonies

Human Oct 3/4 Predicted Mutation Tolerance Map

Human Sox2 Predicted Mutation Tolerance Map

Human Klf4 Predicted Mutation Tolerance Map

Human c-Myc Predicted Mutation Tolerance Map

Analysis of ALP Positive Colonies
Mouse Embryonic Fibroblasts

Analysis of ALP Positive Colonies
Adult Neural Stem Cells

**Analysis of ALP Positive Colonies
Bone Marrow Derived Cells**

**Analysis of ALP Positive Colonies
Bone Marrow Derived Cells**

INDUCED PLURIPOTENT STEM CELLS PRODUCED USING REPROGRAMMING FACTORS AND A RHO KINASE INHIBITOR OR A HISTONE DEACETYLASE INHIBITOR

CROSS-REFERENCE

This application claims the benefit of Japanese Patent Application, JPO 2007-159382, filed Jun. 15, 2007, PCT/EP2007/010019, filed Nov. 20, 2007, and U.S. Provisional Application 61/040,646, filed Mar. 28, 2008, the contents of all three of which are incorporated by reference herein in their entirety.

BACKGROUND OF THE INVENTION

The field of regenerative medicine encompasses therapies designed to aid the repair, replacement, or regeneration of damaged cells, tissues, or organs. One branch of regenerative medicine includes cell therapies that rely on embryonic stem cells (ES), which have the potential to give rise to a diverse range of cell types. ES-based cell therapies have the promise of treating a variety of health conditions including Alzheimer's Disease, Parkinson's Disease, stroke, spinal injuries, heart attack, renal failure, osteoporosis, type I diabetes, multiple sclerosis, rheumatoid arthritis, burns, and wounds. However, the progress of such therapies has been hindered by a range of factors including the possibility of immune rejection of ES cells derived from a donor who is immunologically incompatible with the recipient.

SUMMARY OF THE INVENTION

This disclosure encompasses human stem cells that in some cases are pluripotent and in some cases are multipotent. The disclosure further encompasses methods for generating such human stem cells, methods for using such stem cells, and related compositions.

Accordingly, in one aspect provided herein are human stem cells that are pluripotent, somatic, non-embryonic, and have the property of long-term self renewal. In some embodiments, such human stem cells comprise exogenous genes including a first exogenous gene encoding an Oct3/4 polypeptide, a second exogenous gene encoding a Sox2 polypeptide, and a third exogenous gene encoding a Klf4 polypeptide. In one embodiment, the human stem cells comprising exogenous genes comprise three and only three exogenous genes, where a first exogenous gene encodes an Oct3/4 polypeptide, a second exogenous gene encodes a Sox2 polypeptide, and a third exogenous gene encodes a Klf4 polypeptide. In a further embodiment, the exogenous genes consist essentially of the just-mentioned first, second, and third exogenous genes. In another embodiment, the exogenous genes comprise a first exogenous gene encoding an Oct3/4 polypeptide, a second exogenous gene encoding a Sox2 polypeptide, a third exogenous gene encoding a Klf4 polypeptide, and a fourth exogenous gene encoding the amino acid sequence of the mouse-derived cationic amino acid transporter (mCAT) (e.g. mCAT1). In another embodiment, the human stem cells comprising exogenous genes comprise four and only four exogenous genes, where a first exogenous gene encodes an Oct3/4 polypeptide, a second exogenous gene encodes a Sox2 polypeptide, a third exogenous gene encodes a Klf4 polypeptide, and a fourth exogenous gene encodes a c-Myc polypeptide. In a further embodiment, the exogenous genes consist essentially of the just-mentioned first, second, third, and fourth exogenous genes. In some embodiments, the exogenous genes do not include a gene encoding a c-Myc polypeptide. In further embodiments, the human stem cell comprising the exogenous genes, does not comprise an exogenous c-Myc polypeptide. In other embodiments, the exogenous genes include a gene encoding a c-Myc polypeptide. In one embodiment, where the exogenous genes include a gene encoding the c-Myc polypeptide, the exogenous genes include a fifth exogenous gene encoding the amino acid sequence of the mouse-derived cationic amino acid transporter (mCAT). In some embodiments, the exogenous genes do not include a gene encoding a TERT polypeptide. In some embodiments, the exogenous genes do not include a gene encoding an HPV16 E6 polypeptide or an HPV16E7 polypeptide. In further embodiments, the exogenous genes do not include a gene encoding any of a TERT polypeptide, an SV40 Large T antigen polypeptide, an HPV16 E6 polypeptide, or a Bmi 1 polypeptide. In yet other embodiments, the human stem cells comprising the exogenous genes do not comprise an exogenous gene capable of inducing cancer. In yet other embodiments, the human stem cells comprise exogenous genes encoding three or more of the following: an Oct3/4 polypeptide, a Sox2 polypeptide, a Klf4 polypeptide, and a c-Myc polypeptide.

In another aspect provided herein are stem cells that are somatic, non-embryonic, positive for alkaline phosphatase, and express two or more of the genes TDGF 1, Dnmt3b, FoxD3, GDF3, Cyp26a1, TERT, Zfp42, Sox2, Oct3/4, and Nanog. In some embodiments, such stem cells are pluripotent.

In a related aspect provided herein are human stem cells that, compared to human embryonic stem cells have a higher level of gene expression in 1 to 1000 genes (e.g., in 1 to 700 genes, 1 to 500 genes, 1 to 300 genes, 1 to 200 genes, 1 to 100 genes, 1 to 50 genes, 3 to 20 genes, 5 to 20 genes, 5 to 50 genes, 10 to 50 genes, 20 to 50 genes, 30 to 100 genes, or 50 to 100 genes). In some embodiments, such human stems cells are alkaline phosphatase positive, and express two or more (e.g., 3, 4, 5, 6, 7, 8, 9, or 10) genes selected from TDGF1, Dnmt3b, FoxD3, GDF3, Cyp26a1, Tert, Zfp42, Sox2, Oct3/4, and Nanog.

In another aspect provided herein are human stem cells that compared to human embryonic stem cells have a higher level of gene expression in two or more (e.g., 3 or more, 4 or more, 5 or more, 10 or more, 15 or more, 25 or more, 50 or more, 75 or more, 100 or more, or 200 or more) of the genes listed in Tables 13, 15, or 16 provided herein. In some embodiments, such human stems cells are alkaline phosphatase positive, and express two or more (e.g., 3, 4, 5, 6, 7, 8, 9, or 10) genes selected from TDGF1, Dnmt3b, FoxD3, GDF3, Cyp26a1, Tert, Zfp42, Sox2, Oct3/4, and Nanog.

In a further aspect provided herein are human stem cells that compared to human embryonic stem cells have a lower level of gene expression in two or more (e.g., 3 or more, 4 or more, 5 or more, 10 or more, 15 or more, 25 or more, 50 or more, 75 or more, 100 or more, or 200 or more) of the genes listed in Table 14 provided herein. In some embodiments, such human stems cells are alkaline phosphatase positive, and express two or more genes (e.g., 3, 4, 5, 6, 7, 8, 9, or 10) selected from TDGF1, Dnmt3b, FoxD3, GDF3, Cyp26a1, Tert, Zfp42, Sox2, Oct3/4, and Nanog.

In another aspect provided herein are human stem cells that compared to human embryonic stem cells have a lower level of gene expression in 1 to 1000 genes (e.g., in 1 to 300 genes, or 1 to 50 genes). In some embodiments, such human stems cells are alkaline phosphatase positive, and express two or more genes (e.g., 3, 4, 5, 6, 7, 8, 9, or 10) selected from TDGF1, Dnmt3b, FoxD3, GDF3, Cyp26a1, Tert, zfp42, Sox2, Oct3/4, and Nanog.

In a further aspect provided herein are human stem cells in which the expression levels of 1 to 100 genes is closer to the expression levels in human fibroblasts than in human embryonic stem cells. In some embodiments, such human stems cells are alkaline phosphatase positive, and express two or more genes (e.g., 3, 4, 5, 6, 7, 8, 9, or 10) selected from TDGF1, Dnmt3b, FoxD3, GDF3, Cyp26a1, Tert, zfp42, Sox2, Oct3/4, and Nanog.

In yet another aspect provided herein is a method for generating an autologous stem cell by forcing expression of an Oct3/4 polypeptide, a Sox2 polypeptide, and a Klf4 polypeptide in a cultured population of non-embryonic postnatal cells from the human subject. In some embodiments, the autologous stem cells generated by this method are capable of forming a teratoma. In one embodiment, the autologous stem cells so generated are pluripotent.

In a further aspect provided herein are human stem cells generated by a method comprising forcing the expression of an Oct3/4 polypeptide, a Sox2 polypeptide, and a Klf4 polypeptide in human postnatal cells to obtain one or more colonies of cells that have a high nucleus to cytoplasm ratio and are smaller in size than cells surrounding the one or more colonies, and isolating at least one of the one or more colonies. In some embodiments, the human stem cells generated by the just-mentioned method are pluripotent human stem cells. In some embodiments, forced expression of the Oct3/4, Sox2, and Klf4 polypeptides is achieved by introducing into the human postnatal cells one or more expression vectors, e.g., retroviral expression vectors, lentiviral expression vectors, adeno-associated viral expression vectors, adenoviral expression vectors, recombinant retroviruses, or nucleic acid expression vectors such as plasmid expression vectors. In one embodiment, the above-mentioned method does not include forcing expression of a c-Myc polypeptide in the human postnatal cells. In another embodiment, the method does not include forcing expression of an exogenous gene encoding a c-Myc polypeptide in the human postnatal cells. In a further embodiment, the method further includes forcing expression of a c-Myc polypeptide in the human postnatal cells. In some embodiments, where the method further includes forcing expression of the c-Myc polypeptide, the method comprises forcing expression of four and only four exogenous genes encoding induction factors, where the exogenous genes encode an Oct3/4 polypeptide, a Sox2 polypeptide, a Klf4 polypeptide, and a c-Myc polypeptide. In one embodiment, the method comprises forcing expression of four exogenous genes encoding induction factors, where the four exogenous genes encode an Oct3/4 polypeptide, a Sox2 polypeptide, a Klf4 polypeptide, and a c-Myc polypeptide. In yet another embodiment, the method includes forcing the expression of a set of polypeptides consisting essentially of an Oct3/4 polypeptide, a Sox2 polypeptide, a Klf4 polypeptide, and a c-Myc polypeptide. In another embodiment, the method includes forcing the expression of three and only three exogenous genes encoding induction factors, where the exogenous genes encode an Oct3/4 polypeptide, a Sox2 polypeptide, and a Klf4 polypeptide. In another embodiment, the method includes forcing the expression of a set of polypeptides consisting essentially of an Oct3/4 polypeptide, a Sox2 polypeptide, and a Klf4 polypeptide. In yet another embodiment, the above-mentioned method for generating the human stem cells also includes contacting the human postnatal cells with a histone deacetylase inhibitor. In other embodiments, the above-mentioned method comprises forcing expression of the Oct3/4, Sox2, and Klf4 polypeptides by introducing into the human postnatal cells: (i) a first purified polypeptide comprising the amino acid sequence of the Oct3/4 polypeptide; (ii) a second purified polypeptide comprising the amino acid sequence of the Sox2 polypeptide; and (iii) a third purified polypeptide comprising the amino acid sequence of the Klf4 polypeptide. In some embodiments, at least one of the first, second, and third purified polypeptides, further comprises a protein transduction domain.

In some embodiments, the human stem cells disclosed herein have one or more of the following properties: pluripotency; multipotency; capability to form a teratoma; a normal diploid karyotype; progeny that can be passaged at least about 30 times to at least about 100 times; shorter telomeres than human embryonic stem cells; ability to proliferate with an undifferentiated phenotype under atmospheric oxygen conditions (e.g. greater than 5% oxygen to about 21% oxygen); proliferation in colonies; induction from human somatic or postnatal cells that have been passaged four or fewer times after preparation from a biological sample; induction from fetal human somatic cells; induction from adult human somatic cells; induction from a population of cells comprising any of: adult human skin fibroblasts, adult peripheral blood mononuclear cells, adult human bone marrow-derived mononuclear cells, neonatal human skin fibroblasts, human umbilical vein endothelial cells, human umbilical artery smooth muscle cells, human postnatal skeletal muscle cells, human postnatal adipose cells, human postnatal peripheral blood mononuclear cells, or human cord blood mononuclear cells; induction from the foregoing population of cells, where the population was prepared from a composition of cells that had been stored frozen and was then thawed before the preparation.

A number of aspects provided herein relate to any of the above-described human stem cells. Such aspects include: a purified population of the human stem cells; and cells differentiated from the human stem cells (e.g., purified populations of differentiated cells). Such differentiated stem cells include, but are not limited to, pancreatic beta cells, neural stem cells, cortical neurons, dopaminergic neurons, oligodendrocytes or oligodendrocyte progenitor cells, hepatocytes or hepatocyte stem cells, or cardiac muscle cells. Other related aspects include the following methods: a method for storing the human stem cells by suspending them in a cryopreservation medium and freezing the resulting suspension; a method for generating differentiated cells (including any of the foregoing differentiated cells) by differentiating the human stem cells; a method for introducing differentiated cells (e.g., differentiated cells substantially free of other cell types) into a human subject, where the differentiated cells share the same genome as the subject or are immunocompatible with the subject. Further related aspects include: a composition comprising the human stem cells and a cryopreservation medium; a composition comprising the human stem cells and a medium comprising a purified growth factor (e.g., at a concentration of about 4 ng/ml to about 100 ng/ml). In various embodiments, such growth factors may include one or more of bFGF, FGF-2, PDGF, EGF, IGF, insulin, TGFb-1, activin A, Noggin, BDNF, NGF, NT-1, NT-2, or NT-3, IGF, IGFI, IGFII, or a member of the FGF family of growth factors.

In yet another aspect provided herein is a composition comprising at least one of the following components:
 i. a purified polypeptide comprising the amino acid sequence of a protein transduction domain and an Oct3/4 polypeptide;
 ii. a carrier reagent and a purified Oct3/4 polypeptide;

iii. a purified polypeptide comprising the amino acid sequence of a protein transduction and a Sox2 polypeptide;
iv. a carrier reagent and a purified Sox2 polypeptide;
v. a purified polypeptide comprising the amino acid sequence of a protein transduction domain and a Klf4 polypeptide;
vi. a carrier reagent and a purified Klf4 polypeptide;
vii. a purified polypeptide comprising the amino acid sequence of a protein transduction domain and a c-Myc polypeptide;
viii. a carrier reagent and a purified c-Myc; or
any combination of (i) to (viii).

In some embodiments, the above-mentioned composition contains at least two, three, or four of components (i) to (viii). In a further aspect provided herein is a method for generating human stem cells by forcing expression of polypeptides in human postnatal cells, wherein the polypeptides comprise an Oct3/4 polypeptide, a Sox2 polypeptide, and a Klf4 polypeptide. In some embodiments, the human postnatal cells used in the method were passaged four or fewer times after preparation from a biological sample. In some embodiments, the human postnatal cells were prepared from a composition comprising human postnatal cells that had been stored frozen and were then thawed. In one embodiment, the human postnatal cells are from an adult. In some embodiments, the human postnatal cells to be used in the method comprise adult human bone marrow-derived mononuclear cells, neonatal human skin fibroblasts, umbilical vein endothelial cells, umbilical artery smooth muscle cells, postnatal skeletal muscle cells, postnatal adipose cells, postnatal peripheral blood mononuclear cells, cord blood mononuclear cells, or placental cells. In some embodiments, the human postnatal cells used in this method have been passaged four or fewer times after preparation from a biological sample. In some embodiments, the postnatal human cells are cultured at a density of about $10^3$ cells/cm$^2$ to about $10^4$ cells/cm$^2$ prior to the forced expression. In some embodiments, the human postnatal cells are cultured in the presence of a serum concentration of 5% or less (e.g., 2% or less). In some embodiments, the human postnatal cells are cultured in the presence of one or more of bFGF, FGF-2, PDGF, EGF, IGF, insulin, TGFb-1, activin A, Noggin, BDNF, NGF, NT-1, NT-2, NT-3, or an FGF-growth factor family member prior to the forced expression.

In some embodiments, forcing expression of the Oct3/4, Sox2, and Klf4 polypeptides is carried out by introducing into the human postnatal cells one or more expression vectors encoding the Oct3/4, Sox2, and Klf4 polypeptides. Such vectors include, e.g., recombinant retroviruses, lentiviruses, or adenoviruses; retroviral expression vectors, lentiviral expression vectors, nucleic acid expression vectors, or plasmid expression vectors. In other embodiments, where recombinant retroviruses are used for forced expression, the method includes introducing into the population of cultured human cells an expression vector for expression of a mouse-derived cationic amino acid transporter (mCAT) polypeptide prior to introducing the one or more retroviral vectors encoding the Oct 3/4, Sox2, and Klf4 polypeptides.

In some embodiments, this method does not include forcing the expression of a c-Myc polypeptide. In other embodiments, the method includes forcing expression of a c-Myc polypeptide. In one embodiment, the method does not include forcing expression of a TERT polypeptide.

In some embodiments, this method also includes contacting the postnatal human cells with a histone deacetylase inhibitor.

In some embodiments, forcing expression of the Oct3/4, Sox2, and Klf4 polypeptides, comprises introducing into the human postnatal cells one or more expression vectors In some embodiments, the above method for generating human stem cells also includes isolating, after the forced expression, one or more colonies of cells smaller in size than surrounding cells, and identifying at least one of the one or more colonies that expresses alkaline phosphatase, nanog, TDGF1, Dnmt3b, FoxD3, GDF3, CYP26A1, TERT, and Zfp42.

In some embodiments, the method comprises forcing expression of the Oct 3/4, Sox2, and Klf4 polypeptides, by introducing into a culture of the human postnatal cells: (i) a first purified polypeptide comprising the amino acid sequence of the Oct3/4 polypeptide; (ii) a second purified polypeptide comprising the amino acid sequence of the Sox2 polypeptide, and (iii) a third purified polypeptide comprising the amino acid sequence of the Klf4 polypeptide. In one embodiment, at least one of the just-mentioned polypeptides further comprises a protein transduction domain.

In other embodiments, forcing expression of the Oct 3/4, Sox2, and Klf4 polypeptides in the human postnatal cells is done by contacting them with at least one of:
i. a purified polypeptide comprising the amino acid sequence of a protein transduction domain and an Oct3/4 polypeptide;
ii. a carrier reagent and a purified Oct3/4 polypeptide;
iii. a purified polypeptide comprising the amino acid sequence of a protein transduction and a Sox2 polypeptide;
iv. a carrier reagent and a purified Sox2 polypeptide;
v. a purified polypeptide comprising the amino acid sequence of a protein transduction domain and a Klf4 polypeptide;
vi. a carrier reagent and a purified Klf4 polypeptide;
vii. a purified polypeptide comprising the amino acid sequence of a protein transduction domain and a c-Myc polypeptide; or
any combination of (i) to (vii).

In some embodiments, the human stem cells generated by this method are capable of forming a teratoma. In some embodiments, the human stem cells generated by this method are pluripotency, and thus capable of generating ectoderm, mesoderm, and endoderm.

In another aspect provided herein is a method for identifying an agent that stimulates pluripotency or multipotency in human somatic cells (e.g., postnatal human somatic cells) comprising:
(i) providing first and second cultured human somatic cells;
(ii) contacting the first cultured human somatic cell with a test agent;
(iii) contacting the second cultured human somatic cell with a negative control agent;
(iv) determining expression levels of an embryonic stem cell marker gene in the contacted first and second cultured cells; and
(v) comparing the expression levels determined in step (iii) and indicating that the test agent stimulates pluripotency or multipotency if the embryonic stem cell marker gene expression level in the contacted first cultured cell is greater than that determined in the contacted second cultured cell, and indicating that the test agent fails to stimulate multipotency or pluripotency if the expression level of the embryonic stem cell marker gene in the contacted first cultured cell is the same or less than that determined in the contacted second cultured cell, wherein determining the expression levels of the embryonic stem cell marker gene comprises determining the expression levels of Tert or Cyp26A1.

In a further aspect provided herein is a method for performing cell transplantation in a subject in need thereof, comprising:

(i) identifying a donor that is immunocompatible with the subject;

(ii) generating an induced pluripotent stem cell line from postnatal cells of the donor; and (iii) transplanting one or more cells differentiated from the induced pluripotent stem cell line into the subject. In some embodiments, the donor is identified as immunocompatible if the HLA genotype matches the HLA genotype of the recipient. In one embodiment, the immunocompatible donor is identified by genotyping a blood sample from the immunocompatible donor. In some embodiments, the induced pluripotent stem cell line is induced from a mononuclear blood cell.

In some embodiments of the human stem cells, compositions, and methods described herein, an Oct3/4 polypeptide comprises an amino acid sequence at least 70% identical (e.g., 75%, 80%, 85%, 90%, 95%, or 100%) identical to SEQ ID NO:7, the Sox2 polypeptide comprises an amino acid sequence least 70% identical (e.g., 75%, 80%, 85%, 90%, 95%, or 100%) to SEQ ID NO:9, the Klf4 polypeptide comprises an amino acid at least 70% (e.g., 75%, 80%, 85%, 90%, 95%, or 100%) identical to SEQ ID NO:11, or a c-Myc polypeptide at least 70% (e.g., 75%, 80%, 85%, 90%, 95%, or 100%) identical to SEQ ID NO: 13. In other embodiments, an Oct3/4 polypeptide comprises an amino acid sequence at least 70% identical (e.g., 75%, 80%, 85%, 90%, 95%, or 100%) identical to SEQ ID NO:6, the Sox2 polypeptide comprises an amino acid sequence least 70% identical (e.g., 75%, 80%, 85%, 90%, 95%, or 100%) to SEQ ID NO:8, the Klf4 polypeptide comprises an amino acid at least 70% (e.g., 75%, 80%, 85%, 90%, 95%, or 100%) identical to SEQ ID NO: 10, or a c-Myc polypeptide at least 70% (e.g., 75%, 80%, 85%, 90%, 95%, or 100%) identical to SEQ ID NO:12. In some embodiments, the Oct3/4 polypeptide comprises the amino acid sequence of human Oct3/4 or mouse Oct3/4 polypeptide, the Sox2 polypeptide comprises the amino acid sequence of human Sox2 or mouse Sox2; and the Klf4 polypeptide comprises the amino acid sequence of human Klf4 or mouse Klf4. In some embodiments, the Oct3/4 polypeptide is an Oct family member other than Oct3/4, the Sox2 polypeptide is a Sox family member other than Sox2, the Klf4 polypeptide is a Klf family member other than Klf4, and the c-Myc polypeptide is a c-Myc family member other than c-Myc. In some embodiments, the c-Myc polypeptide has inducible activity. In one embodiment, the c-Myc polypeptide is a c-Myc-estrogen receptor (c-Myc-ER) fusion polypeptide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION
Table of Contents

| | |
|---|---|
| I. Overview | 15 |
| II. Preparation of Cells | 16 |
|   A. Description of cells that can be induced | 16 |
|   B. Collection of Cells | 17 |
| III. Induction | 20 |
|   A. Overview | 20 |
|   B. Cell Culture | 21 |
|   C. Induction Factors | 25 |
|   D. HDAC Inhibitor | 26 |
|   E. IF Expression Vectors | 28 |
|     1. Recombinant Viruses | 29 |
|     2. Nucleic Acid Vectors | 35 |
|     3. Protein Transduction | 36 |
|   F. Induction Factor Sequences | 37 |
|   G. Subcloning Induced Cell Colonies | 47 |
|   H. Passaging and Maintaining Induced Cells | 48 |
| IV. Analysis of Induced Cells | 48 |
|   A. Methylation Analysis | 50 |
|   B. Self-renewal Assay | 50 |
|   C. Karyotype Analysis | 50 |
|   D. Teratoma Analysis | 51 |
|   E. Global Gene Expression | 51 |
| V. Description of Induced Cells | 52 |
| VI. Cell Differentiation | 58 |
| VII. Cell Therapies | 59 |
| VIII. Analytical Methods | 61 |
| IX. Storage of Cells | 64 |
| X. Examples | 64 |
| XI. Tables | 64 |

I. OVERVIEW

The present disclosure features induced multipotent and pluripotent stem cells and related methods and compositions. Pluripotent stem cells have the ability to differentiate into cells of all three germ layers (ectoderm, mesoderm and endoderm); in contrast, multipotent stem cells can give rise to one or more cell-types of a particular germ layer(s), but not necessarily all three.

Figure 1:
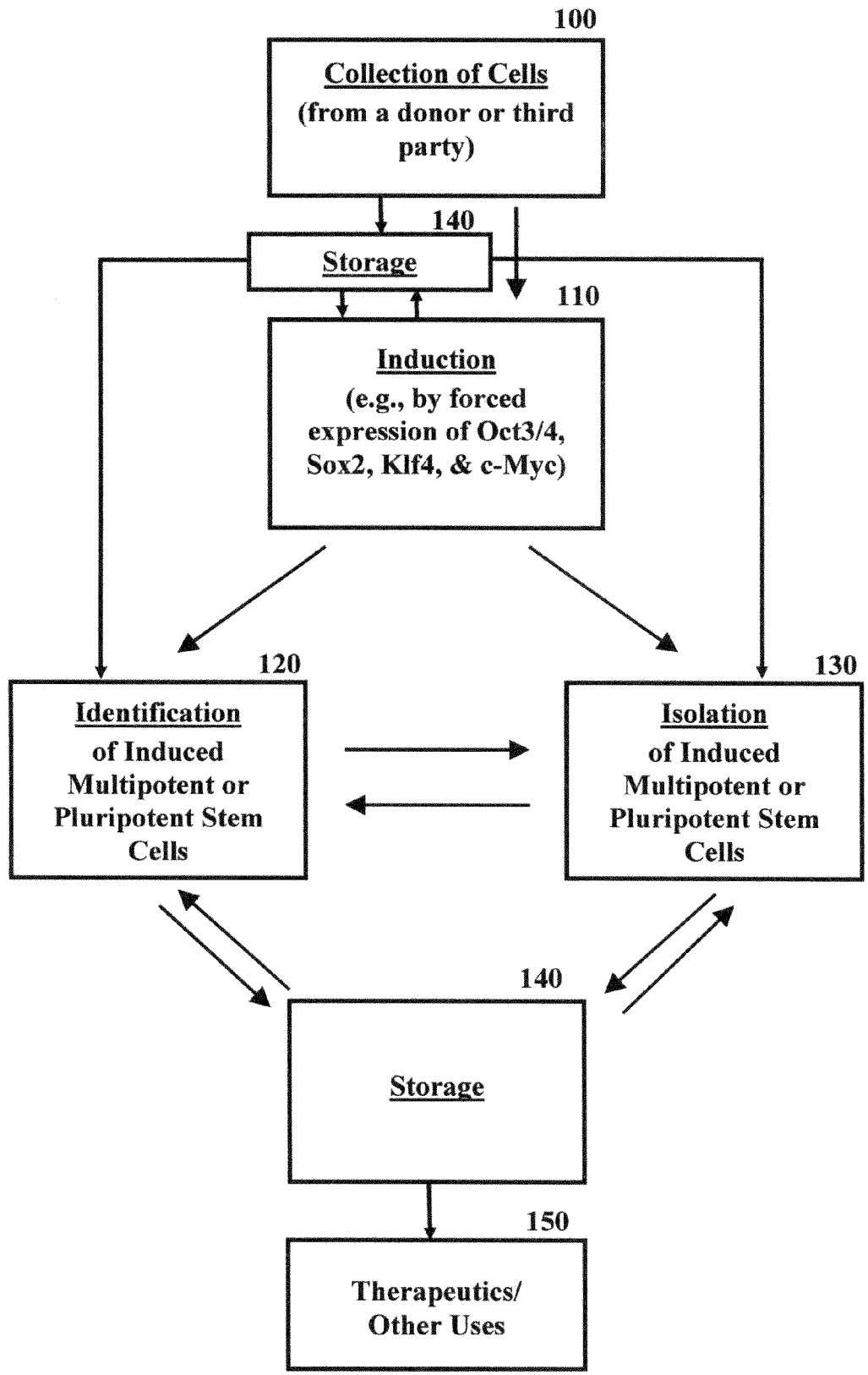
FIG. 1 is an overview of an approach to the induction process and uses of cells.

The process of inducing cells to become multipotent or pluripotent is based on forcing the expression of polypeptides, particularly proteins that play a role in maintaining or regulating self-renewal and/or pluripotency of ES cells. Examples of such proteins are the Oct3/4, Sox2, Klf4, and c-Myc transcription factors, all of which are highly expressed in ES cells. Forced expression may include introducing expression vectors encoding polypeptides of interest into cells, transduction of cells with recombinant viruses, introducing exogenous purified polypeptides of interest into cells, contacting cells with a non-naturally occurring reagent that induces expression of an endogenous gene encoding a polypeptide of interest (e.g., Oct3/4, Sox2, Klf4, or c-Myc), or any other biological, chemical, or physical means to induce expression of a gene encoding a polypeptide of interest (e.g., an endogenous gene Oct3/4, Sox2, Klf4, or c-Myc). Some basic steps to induce the cells are shown in FIG. 1. These steps may involve: collection of cells from a donor, e.g., a human donor, or a third party (100); induction of the cells, e.g., by forcing expression of polypeptides such as Oct3/4, Sox2, Klf4, and c-Myc (110); identifying multipotent or pluripotent stem cells (120); isolating colonies (130); and optionally, storing the cells (140). Interspersed between all of these steps are steps to maintain the cells, including culturing or expanding the cells. In addition, storage of the cells can occur after many steps in the process. Cells may later be used in many contexts, such as therapeutics or other uses (150).

Embryonic stem (ES) cells are both self-renewing and pluripotent. The induced cells may also be self-renewing and pluripotent. However, in contrast to ES cells, the induced cells can be derived from a wide range of cells and tissue, including non-embryonic tissue.

The induced cells (e.g., induced multipotent or pluripotent stem cells) have many uses. They may be subjected to conditions that enable them to generate differentiated cells, e.g., neurons, hepatocytes, or cardiomyocytes. They may also give rise to other types of stem cells, e.g., neural stem cells, hepatic stem cells, or cardiac stem cells, that have the ability differentiate into other cells of a specific lineage. The induced cells, and cells differentiated from them, are also useful for medical therapies such as cell replacement therapies. Since the induced cells can be induced from non-embryonic cells, a cell therapy can involve providing a subject with cells derived from his or her own tissue, thereby lessening the possibility of immune rejection.

This disclosure describes induced multipotent and pluripotent stem cells, their preparation, and their storage. The disclosure further describes cells differentiated from the induced multipotent and pluripotent stem cells, their preparation, and their storage. Also described is the use of the induced cells, or of cells differentiated from them, for cell therapies. Analytical methods and methods of cell banking are also provided.

II. PREPARATION OF CELLS

A. Description of Cells that can be Induced

The multipotent or pluripotent cells may be induced from a wide variety of mammalian cells. Examples of suitable populations of mammalian cells include those that include, but are not limited to: fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, gastric epithelial cells, lung epithelial cells, synovial cells, kidney cells, skin epithelial cells or osteoblasts.

The cells can also originate from many different types of tissue, e.g., bone marrow, skin (e.g., dermis, epidermis), muscle, adipose tissue, peripheral blood, foreskin, skeletal muscle, or smooth muscle. The cells can also be derived from neonatal tissue, including, but not limited to: umbilical cord tissues (e.g., the umbilical cord, cord blood, cord blood vessels), the amnion, the placenta, or other various neonatal tissues (e.g., bone marrow fluid, muscle, adipose tissue, peripheral blood, skin, skeletal muscle etc.).

The cells can be derived from neonatal or post-natal tissue collected from a subject within the period from birth, including cesarean birth, to death. For example, the tissue may be from a subject who is >10 minutes old, >1 hour old, >1 day old, >1 month old, >2 months old, >6 months old, >1 year old, >2 years old, >5 years old, >10 years old, >15 years old, >18 years old, >25 years old, >35 years old, >45 years old, >55 years old, >65 years old, >80 years old, <80 years old, <70 years old, <60 years old, <50 years old, <40 years old, <30 years old, <20 years old or <10 years old. The subject may be a neonatal infant. In some cases, the subject is a child or an adult. In some examples, the tissue is from a human of age 2, 5, 10 or 20 hours. In other examples, the tissue is from a human of age 1 month, 2 months, 3 months, 4 months, 5 months, 6 months, 9 months or 12 months. In some cases, the tissue is from a human of age 1 year, 2 years, 3 years, 4 years, 5 years, 18 years, 20 years, 21 years, 23 years, 24 years, 25 years, 28 years, 29 years, 31 years, 33 years, 34 years, 35 years, 37 years, 38 years, 40 years, 41 years, 42 years, 43 years, 44 years, 47 years, 51 years, 55 years, 61 years, 63 years, 65 years, 70 years, 77 years, or 85 years old.

The cells may be from non-embryonic tissue, e.g., at a stage of development later than the embryonic stage. In other cases, the cells may be derived from an embryo. In some cases, the cells may be from tissue at a stage of development later than the fetal stage. In other cases, the cells may be derived from a fetus.

The cells are preferably from a human subject but can also be derived from non-human subjects, e.g., non-human mammals. Examples of non-human mammals include, but are not limited to, non-human primates (e.g., apes, monkeys, gorillas), rodents (e.g., mice, rats), cows, pigs, sheep, horses, dogs, cats, or rabbits.

The cells may be collected from subjects with a variety of disease statuses. The cells can be collected from a subject who is free of an adverse health condition. In other cases, the subject is suffering from, or at high risk of suffering from, a disease or disorder, e.g., a chronic health condition such as cardiovascular disease, eye disease (e.g., macular degeneration), auditory disease, (e.g., deafness), diabetes, cognitive impairment, schizophrenia, depression, bipolar disorder, dementia, neurodegenerative disease, Alzheimer's Disease, Parkinson's Disease, multiple sclerosis, osteoporosis, liver disease, kidney disease, autoimmune disease, arthritis, or a proliferative disorder (e.g., a cancer). In other cases, the subject is suffering from, or at high risk of suffering from, an acute health condition, e.g., stroke, spinal cord injury, burn, or a wound. In certain cases, a subject provides cells for his or her future use (e.g., an autologous therapy), or for the use of another subject who may need treatment or therapy (e.g., an allogeneic therapy). In some cases, the donor and the recipient are immunohistologically compatible or HLA-matched.

The cells to be induced can be obtained from a single cell or a population of cells. The population may be homogeneous or heterogeneous. The cells may be a population of cells found in a human cellular sample, e.g., a biopsy or blood sample. Often, the cells are somatic cells. The cells may be a cell line. In some cases, the cells are derived from cells fused to other cells. In some cases, the cells are not derived from cells fused to other cells. In some cases, the cells are not derived from cells artificially fused to other cells. In some cases, the cells are not a cell that has undergone the procedure known as somatic cell nuclear transfer (SCNT) or a cell descended from a cell that underwent SCNT.

The cellular population may include both differentiated and undifferentiated cells. In some cases, the population primarily contains differentiated cells. In other cases, the population primarily contains undifferentiated cells, e.g., undifferentiated stem cells. The undifferentiated cells within the population may be induced to become pluripotent or multipotent. In some cases, differentiated cells within the cellular population are induced to become pluripotent or multipotent.

The cellular population may include undifferentiated stem cells or naïve stem cells. In some cases, the undifferentiated stem cells are stem cells that have not undergone epigenetic inactivating modification by heterochromatin formation due to DNA methylation or histone modification of at least four genes, at least three genes, at least two genes, at least one gene, or none of the following: Nanog, Oct3/4, Sox2 and Tert. Activation, or expression of such genes, e.g., Tert, Nanog, Oct3/4 or Sox2, may occur when human pluripotent stem cells are induced from undifferentiated stem cells present in a human postnatal tissue.

B. Collection of Cells

Methods for obtaining human somatic cells are well established, as described in, e.g., Schantz and Ng (2004), *A Manual for Primary Human Cell Culture*, World Scientific Publishing Co., Pte, Ltd. In some cases, the methods include obtaining a cellular sample, e.g., by a biopsy (e.g., a skin sample), blood draw, or alveolar or other pulmonary lavage. It is to be understood that initial plating densities of cells prepared from a tissue may be varied based on such variables as expected viability or adherence of cells from that particular tissue. Methods for obtaining various types of human somatic cells include, but are not limited to, the following exemplary methods:

1. Bone Marrow

The donor is given a general anesthetic and placed in a prone position. From the posterior border of the ilium, a collection needle is inserted directly into the skin and through the iliac surface to the bone marrow, and liquid from the bone marrow is aspirated into a syringe. The somatic stem cells are enriched by isolating bone marrow cells from an osteogenic zone of bone marrow. A mononuclear cell fraction is then prepared from the aspirate by density gradient centrifugation. The collected crude mononuclear cell fraction is then cultured prior to use in the methods described herein for induction.

2. Postnatal Skin

Skin tissue containing the dermis is harvested, for example, from the back of a knee or buttock. The skin tissue is then incubated for 30 minutes at 37° C. in 0.6% trypsin/Dulbecco's Modified Eagle's Medium (DMEM)/F-12 with 1% antibiotics/antimycotics, with the inner side of the skin facing downward.

After the skin tissue is turned over, tweezers are used to lightly scrub the inner side of the skin. The skin tissue is finely cut into 1 mm² sections using scissors and is then centrifuged at 1200 rpm and room temperature for 10 minutes. The supernatant is removed, and 25 ml of 0.1% trypsin/DMEM/F-12/1% antibiotics, antimycotics, is added to the tissue precipitate. The mixture is stirred at 200-300 rpm using a stirrer at 37° C. for 40 minutes. After confirming that the tissue precipitate is fully digested, 3 ml fetal bovine serum (FBS) (manufactured by JRH) is added, and the mixture is filtered sequentially with gauze (Type I manufactured by PIP), a 100 µm nylon filter (manufactured by FALCON) and a 40 µm nylon filter (manufactured by FALCON). After centrifuging the resulting filtrate at 1200 rpm and room temperature for 10 minutes to remove the supernatant, DMEM/F-12/1% antibiotics, antimycotics is added to wash the precipitate, and then centrifuged at 1200 rpm and room temperature for 10 minutes. The cell fraction thus obtained is then cultured prior to induction.

Dermal stem cells can be enriched by isolating dermal papilla from scalp tissue. Human scalp tissues (0.5-2 cm² or less) are rinsed, trimmed to remove excess adipose tissues, and cut into small pieces. These tissue pieces are enzymatically digested in 12.5 mg/ml dispase (Invitrogen, Carlsbad, Calif.) in DMEM for 24 hours at 4° C. After the enzymatic treatment, the epidermis is peeled off from the dermis; and hair follicles are pulled out from the dermis. Hair follicles are washed with phosphate-buffered saline (PBS); and the epidermis and dermis are removed. A microscope may be used for this procedure. Single dermal papilla derived cells are generated by culturing the explanted papilla on a plastic tissue culture dish in the medium containing DMEM and 10% FCS for 1 week. When single dermal papilla cells are generated, these cells are removed and cultured in fibroblast basal medium (FBM) supplemented with fibroblast growth medium-2 (FGM-2) SingleQuots (Lonza) or cultured in the presence of 20 ng/ml EGF, 40 ng/ml FGF-2, and B27 without serum.

Epidermal stem cells can be also enriched from human scalp tissues (0.5-2 cm² or less). Human scalp tissues are rinsed, trimmed to remove excess adipose tissues, and cut into small pieces. These tissue pieces are enzymatically digested in 12.5 mg/ml dispase (Invitrogen, Carlsbad, Calif.) in Dulbecco's modified Eagle's medium (DMEM) for 24 hours at 4° C. After the enzymatic treatment, the epidermis is peeled off from the dermis; and hair follicles are pulled out from the dermis. The bulb and intact outer root sheath (ORS) are dissected under the microscope. After the wash, the follicles are transferred into a plastic dish. Then the bulge region is dissected from the upper follicle using a fine needle. After the wash, the bulge is transferred into a new dish and cultured in medium containing DMEM/F12 and 10% FBS. After the cells are identified, culture medium is changed to the EpiLife™ Extended-Lifespan Serum-FreeMedium (Sigma).

3. Postnatal Skeletal Muscle

After the epidermis of a connective tissue containing muscle such as the lateral head of the biceps brachii muscle or the sartorius muscle of the leg is cut and the muscle tissue is excised, it is sutured. The whole muscle obtained is minced with scissors or a scalpel, and then suspended in DMEM (high glucose) containing 0.06% collagenase type IA and 10% FBS, and incubated at 37° C. for 2 hours.

Cells are collected by centrifugation from the minced muscle, and suspended in DMEM (high glucose) containing 10% FBS. After passing the suspension through a microfilter with a pore size of 40 µm and then a microfilter with a pore size of 20 µm, the cell fraction obtained may be cultured as crude purified cells containing undifferentiated stem cells, and used for the induction of human pluripotent stem cells as described herein.

4. Postnatal Adipose Tissue

Cells derived from adipose tissue for use in the present invention may be isolated by various methods known to a person skilled in the art. For example, such a method is described in U.S. Pat. No. 6,153,432, which is incorporated herein in its entirety. A preferred source of adipose tissue is omental adipose tissue. In humans, adipose cells are typically isolated by fat aspiration.

In one method of isolating cells derived from adipose cells, adipose tissue is treated with 0.01% to 0.5%, e.g., 0.04% to 0.2%, 0.1% collagenase; 0.01% to 0.5%, e.g., 0.04%, or 0.2% trypsin; and/or 0.5 ng/ml to 10 ng/ml dispase, or an effective amount of hyaluronidase or DNase (DNA digesting enzyme), and about 0.01 to about 2.0 mM, e.g., about 0.1 to about 1.0 mM, or 0.53 mM ethylenediaminetetraacetic acid (EDTA) at 25 to 50° C., e.g., 33 to 40° C., or 37° C. for 10 minutes to 3 hours, e.g., 30 minutes to 1 hour, or 45 minutes.

Cells are passed through nylon or a cheese cloth mesh filter of 20 microns to 800 microns, more preferably 40 microns to 400 microns, and most preferably 70 microns. Then the cells in the culture medium are subjected to differential centrifugation directly or using Ficoll or Percoll or another particle gradient. The cells are centrifuged at 100 to 3000×g, more preferably 200 to 1500×g, most preferably 500×g for 1 minute to 1 hours, more preferably 2 to 15 minutes and most preferably 5 minutes, at 4 to 50° C., preferably 20 to 40° C. and more preferably about 25° C.

The adipose tissue-derived cell fraction thus obtained may be cultured according to the method described herein as crude purified cells containing undifferentiated stem cells, and used for the induction of human pluripotent or multipotent stem cells.

5. Blood

About 50 ml to about 500 ml vein blood or cord blood is collected, and a mononuclear cell fraction is obtained by the Ficoll-Hypaque method, as described in, e.g., Kanof et al., (1993), *Current Protocols in Immunology* (J. E. Coligan, A. M. Kruisbeek, D. H. Margulies, E. M. Shevack, and W. Strober, eds.), ch. 7.1.1.-7.1.5, John Wiley & Sons, New York).

After isolation of the mononuclear cell fraction, approximately $1\times10^7$ to $1\times10^8$ human peripheral blood mononuclear cells are suspended in a RPMI 1640 medium containing 10% fetal bovine serum, 100 µg/ml streptomycin and 100 units/ml penicillin, and after washing twice, the cells are recovered. The recovered cells are resuspended in RPMI 1640 medium and then plated in a 100 mm plastic petri dish at a density of about $1\times10^7$ cells/dish, and incubated in a 37° C. incubator at 8% $CO_2$. After 10 minutes, cells remaining in suspension are removed and adherent cells are harvested by pipetting. The resulting adherent mononuclear cell fraction is then cultured prior to the induction period as described herein. In some cases, the peripheral blood-derived or cord blood-derived adherent cell fraction thus obtained may be cultured according to the method described herein as crude purified cells containing undifferentiated stem cells, and used for the induction of human pluripotent or multipotent stem cells.

Macrophages in the peripheral blood can be enriched by culturing the mononuclear cell fraction in low-glucose DMEM supplemented with 10% heat-inactivated fetal bovine serum (FBS; JRH Biosciences, Lenexa, Kans.), 2 mM L-glutamine, 50 U/ml penicillin, and 50 µg/ml streptomycin. In order to expand macrophages, peripheral blood mononuclear cells are spread at a density of $2\times10^6$/ml on plastic plates that have been treated with 10 µg/ml FN (Sigma, St. Louis, Mo.) overnight at 4° C. The cells are then cultured without any additional growth factors at 37° C. and 5% $CO_2$ in a humidified atmosphere. The medium containing floating cells is changed every 3 days. Macrophages with observable fibroblastic features may be used for the induction experiments.

In some cases, a cell fraction from peripheral blood, cord blood, or bone marrow is expanded, as described in U.S. patent application Ser. No. 11/885,112, and then used in the induction methods described herein.

III. INDUCTION

A. Overview

During the induction process, forced expression of certain polypeptides is carried out in cultured cells for a period of time, after which the induced cells are screened for a number of properties that characterize multipotent and pluripotent stem cells (e.g., morphological, gene expression). Induced cells that meet these screening criteria may then be subcloned and expanded. In some cases, the cells to be induced may be cultured for a period of time prior to the induction procedure. Alternatively, the cells to be induced may be used directly in the induction process without a prior culture period. In some cases, different cell culture media are used at different points prior to, during, and after the induction process. For example, one type of culture medium may be used after collection of tissue and/or directly before the induction process, while a second type of media is used during and/or after the induction process. At times, a third type of culture medium is used during and/or after the induction process.

B. Cell Culture

After collection, tissue or cellular samples can be cultured in any medium suitable for the specific cells or tissue collected. Some representative media that the tissue or cells can be cultured in include but are not limited to: multipotent adult progenitor cell (MAPC) medium; FBM (manufactured by Lonza); Embryonic Stem cell (ES) ES medium; Mesenchymal Stem Cell Growth Medium (MSCGM) (manufactured by Lonza); MCDB202 modified medium; Endothelial Cell Medium kit-2 (EBM2) (manufactured by Lonza); Iscove's Modified Dulbecco's Medium (IMDM) (Sigma); Dulbecco's Modified Eagle Medium (DMEM); MEF-conditioned ES (MC-ES); and mTeSR™ (available, e.g., from StemCell Technologies, Vancouver, Canada), See, e.g., Ludwig et al., (2006), *Nat. Biotechnol.*, 24(2):185-187. In other cases, alternative culture conditions for growth of human ES cells are used, as described in, e.g., Skottman et al., (2006), *Reproduction*, 132(5):691-698.

MAPC (2% FBS) medium may comprise: 60% Dulbecco's Modified Eagle's Medium-low glucose, 40% MCDB 201, Insulin Transferrin Selenium supplement, (0.01 mg/ml insulin; 0.0055 mg/ml transferrin; 0.005 µg/ml sodium selenite), 1× linolenic acid albumin (1 mg/mL albumin; 2 moles linoneic acid/mole albumin), 1 nM dexamethasone, 2% fetal bovine serum, 1 nM dexamethasone, $10^{-4}$ M ascorbic acid, and 10 µg/ml gentamycin FBM (2% FBS) medium may comprise: MCDB202 modified medium, 2% fetal bovine serum, 5 µg/ml insulin, 50 µg/ml gentamycin, and 50 ng/ml amphotericin-B.

ES medium may comprise: 40% Dulbecco's Modified Eagle's Medium (DMEM) 40% F12 medium, 2 mM L-glutamine, 1× non-essential amino acids (Sigma, Inc., St. Louis, Mo.), 20% Knockout Serum Replacement™ (Invitrogen, Inc., Carlsbad, Calif.), and 10 µg/ml gentamycin.

MC-ES medium may be prepared as follows. ES medium is conditioned on mitomycin C-treated murine embryonic fibroblasts (MEFs), for 20 to 24 hours, harvested, filtered through a 0.45-1M filter, and supplemented with about 0.1 mM β-mercaptoethanol, about 10 ng/ml bFGF or FGF-2, and, optionally, about 10 ng/ml activin A. In some cases, irradiated MEFs are used in place of the mitomycin C-treated MEFs. In other cases, STO (ATCC) or human fibroblast cells are used in place of the MEFs.

Cells may be cultured in medium supplemented with a particular serum. In some embodiments, the serum is fetal bovine serum (FBS). The serum can also be fetal calf serum (FCS). In some cases, the serum may be human serum (e.g., human AB serum). Mixtures of serum may also be used, e.g. mixture of FBS and Human AB, FBS and FCS, or FCS and Human AB.

After collection of tissue and preparation of cells, it may be useful to promote the expansion of tissue stem cells or progenitor cells that may be present among the prepared cells by use of suitable culture conditions. In some cases, a low-serum culture or serum-free medium (as described herein) may facilitate the expansion of tissue stem cells or progenitor cells. Suitable culture media include, but are not limited to, MAPC, FBM, or MSCGM.

Primary culture ordinarily occurs immediately after the cells are isolated from a donor, e.g., human. The cells can also be sub-cultured after the primary culture. A "second" subculture describes primary culture cells subcultured once, a "third" subculture describes primary cultures subcultured twice, a "fourth" subculture describes primary cells subcultured three times, etc. In some cases, the primary cells are subjected to a second subculture, a third subculture, or a fourth subculture. In some cases, the primary cells are subjected to less than four subcultures. The culture techniques described herein may generally include culturing from the period between the primary culture and the fourth subculture, but other culture periods may also be employed. Preferably, cells are cultured from the primary culture to the second subculture. In some cases, the cells may be cultured for about 1 to about 12 days e.g., 2 days, 3 days, 4.5 days, 5 days, 6.5 days, 7 days, 8 days, 9 days, 10 days, or any other number of days from about 1 day to about 12 days prior to undergoing the induction methods described herein. In other cases, the cells may be cultured for more than 12 days, e.g. from about 12 days to about 20 days; from about 12 days to about 30 days; or from about 12 days to about 40 days. In some embodiments, the cells to be induced are passaged four or fewer times (e.g., 3, 2, 1, or 0 times) prior to induction.

In some cases, prior to induction cells are cultured at a low density, e.g., from about $1\times10^3$ cells/cm² to about $1\times10^4$ cells/cm². In other cases, prior to induction (e.g., just prior to induction), cells are cultured at a density of about $1\times10^3$ cells/cm² to about $3\times10^4$ cells/cm²; or from about $1\times10^4$ cells/cm² to about $3\times10^4$ cells/cm².

Often the cells and/or tissue are cultured in a first medium, as described above, prior to and/or during the introduction of induction factors to the cells; and then the cells are cultured in a second or third medium during and/or after the introduction of the induction factors to the cells. The second or third medium may be MEF-Conditioned (MC)-ES, mTeSR1 medium, or other ES cell medium, as described in, e.g., Skottman et al., (2006), *Reproduction*, 132(5):691-698.

In many examples, the cells are cultured in MAPC, FBM or MSCGM medium prior to the initiation of forced expression of genes or polypeptides in the cells (e.g., immediately after a retroviral infection period); and then, following the initiation of the forced expression, the cells are cultured in MC-ES medium, mTeSR1™ medium, or other ES cell medium as described herein.

Culture of cells may be carried out under low serum culture conditions prior to, during, or following the introduction of induction factors. A "low serum culture condition" refers to the use of a cell culture medium containing a concentration of serum ranging from 0% (v/v) (i.e., serum-free) to about 5% (v/v), e.g., 0% to 2%, 0% to 2.5%, 0% to 3%, 0% to 4%, 0% to 5%, 0.1% to 2%, 0.1% to 5%, 0%, 0.1%, 0.5%, 1%, 1.2%, 1.5%, 2%, 2.5%, 3%, 3.5%, 4%, or 5%. In some embodiments, a low serum concentration is from about 0% (v/v) to about 2% (v/v). In some cases, the serum concentration is about 2%. In other embodiments, cells are cultured under a "high serum condition," i.e., greater than 5% (v/v) serum to about 20% (v/v) serum, e.g., 6%, 7%, 8%, 10%, 12%, 15%, or 20%. Culturing under high serum conditions may occur prior to, during, and/or after the introduction of induction factors. Media with low concentrations of serum may be particularly useful to enrich undifferentiated stem cells. For example, MSCs are often obtained by isolating the non-hematopoietic cells (e.g., interstitial cells) adhering to a plastic culture dish when tissue, e.g., bone marrow, fat, muscle, or skin etc., is cultured in a culture medium containing a high-concentration serum (5% or more). However, even under these culture conditions, a very small number of undifferentiated cells can be maintained, especially if the cells were passaged under certain culture conditions (e.g., low passage number, low-density culturing or low oxygen).

When either low or high serum conditions are used for culturing the cells, one or more growth factors such as fibroblast growth factor (FGF)-2; basic FGF (bFGF); platelet-derived growth factor (PDGF), epidermal growth factor (EGF); insulin-like growth factor (IGF); IGF II; or insulin can be included in the culture medium. Other growth factors that can be used to supplement cell culture media include, but are not limited to one or more: Transforming Growth Factor β-1 (TGF β-1), Activin A, Noggin, Brain-derived Neurotrophic Factor (BDNF), Nerve Growth Factor (NGF), Neurotrophin (NT)-1, NT-2, or NT-3. In some cases, one or more of such factors is used in place of the bFGF or FGF-2 in the MC-ES medium or other cell culture medium.

The concentration of growth factor(s) (e.g., FGF-2, bFGF, PDGF, EGF, IGF, insulin, IGF II, TGF β-1, Activin A, Noggin, BDNF, NGF, NT-1, NT-2, NT-3) in the culture media described herein (e.g., MAPC, FBM, MC-ES, MSCGM, IMDM, mTeSR1™) may be from about 4 ng/ml to about 50 ng/ml, e.g., about 2 ng/ml, 3 ng/ml, 4 ng/ml, 5 ng/ml, 6 ng/ml, 7 ng/ml, 8 ng/ml, 10 ng/ml, 12 ng/ml, 14 ng/ml, 15 ng/ml, 17 ng/ml, 20 ng/ml, 25 ng/ml, 30 ng/ml, 35 ng/ml, 40 ng/ml, 45 ng/ml, or 50 ng/ml. The concentration of growth factors may also be from about 4 ng/ml to about 10 ng/ml; from about 4 ng/ml to about 20 ng/ml; from about 10 ng/ml to about 30 ng/ml; from about 5 ng/ml to about 40 ng/ml; or from about 10 ng/ml to about 50 ng/ml. In other cases, higher concentrations of growth factors may be used, e.g., from about 50 ng/ml to about 100 ng/ml; or from about 50 ng/ml to about 75 ng/ml.

The growth factors may be used alone or in combination. For example, FGF-2 may be added alone to the medium; in another example, both PDGF and EGF are added to the culture medium. Often, growth factors appropriate for a particular cell type may be used. For example, dermal cells may be cultured in the presence of about 20 ng/ml EGF and/or about 40 ng/ml FGF-2, while epidermal cells may be cultured in the presence of about 50 ng/ml EGF and/or 5 μg/ml Insulin.

The induced cells may be maintained in the presence of a rho, or rho-associated, protein kinase (ROCK) inhibitor to reduce apoptosis. A ROCK inhibitor may be particularly useful when the cells are subjected to a harsh treatment, such as an enzymatic treatment. For example, the addition of Y-27632 (Calbiochem; water soluble) or Fasudil (HA1077: Calbiochem), an inhibitor of Rho associated kinase (Rho associated coiled coil-containing protein kinase) may be used to culture the human pluripotent and multipotent stem cells of the present invention. In some cases the concentration of Y-27632 or Fasudil, is from about 2.5 μM to about 20 μM, e.g., about 2.5 μM, 5 μM, 10 μM, 15 μM, or 20 μM.

The induced cells may be cultured in a maintenance culture medium in a 37° C., 5% $CO_2$ incubator (e.g., under an atmospheric oxygen level), with medium changes preferably every day. In some embodiments, in order to culture and grow human pluripotent stem cells induced from the undifferentiated stem cells of the present invention present in a human postnatal tissue, it is preferred that the cells are subcultured every 5 to 7 days in a culture medium containing the additives described herein on a MEF-covered plastic culture dish or a matrigel-coated plastic culture dish. Examples of maintenance culture media for induced cells include any and all complete ES cell media (e.g., MC-ES). The maintenance culture medium may be supplemented with b-FGF or FGF2. In some cases, the maintenance culture medium is supplemented with other factors, e.g., IGF-II, Activin A or other growth factor described herein, see, e.g., Bendall et al., (2007), *Nature*, 30:448(7157):1015-21. In some embodiments, the induced cells are cultured and observed for about 14 days to about 40 days, e.g., 15, 16, 17, 18, 19, 20, 23, 24, 27, 28, 29, 30, 31, 33, 34, 35, 36, 37, 38 days, or other period from about 14 days to about 40 days, prior to identifying and selecting candidate multipotent or pluripotent stem cell colonies based on morphological characteristics.

Morphological characteristics for identifying candidate multipotent or pluripotent stem cell colonies include, but are not limited to, a rounder, smaller cell size relative to surrounding cells and a high nucleus-to-cytoplasm ratio. The size of the candidate induced cell may be from about 5 μm to about 10 μm; from about 5 μm to about 15 μm; from about 5 μm to about 30 μm; from about 10 μm to about 30 μm; or from about 20 μm to about 30 μm. A high nucleus-to-cytoplasm ratio may be from about 1.5:1 to about 10:1, e.g., about 1.5:1; about 2:1; about 3:1; about 4:1; about 5:1; about 7:1; about 8:1; about 9.5:1; or about 10:1. In some cases, the induced cell clones display a flattened morphology relative to mouse ES cells. For example, candidate induced cells derived from peripheral blood cells or from cells cultured in feeder-free media may exhibit a flattened morphology compared to surrounding cells. Another morphological characteristic for identifying induced cell clones is the formation of small monolayer colonies within the space between parental cells (e.g., between fibroblasts).

The induced cells can be plated and cultured directly on tissue culture-grade plastic. Alternatively, cells are plated and cultured on a coated substrate, e.g., a substrate coated with fibronectin, gelatin, Matrigel™ (BD Bioscience), collagen, or laminin. In some cases, untreated petri-dishes may be used. Suitable cell culture vessels include, e.g., 35 mm, 60 mm, 100 mm, and 150 mm cell culture dishes, 6-well cell culture plates, and other size-equivalent cell culture vessels. In some cases, the cells are cultured with feeder cells. For example, the cells may be cultured on a layer, or carpet, of MEFs (e.g., irradiated or mitomycin-treated MEFs).

Typically, the induced cells may be plated (or cultured) at a low density, which may be accomplished by splitting the cells from about 1:8 to about 1:3, e.g., about 1:8; about 1:6; about 1:5; about 1:4; or about 1:3. Cells may be plated at a density of from about $10^3$ cells/cm$^2$ to about $10^4$ cells/cm$^2$. In some examples, the cells may be plated at a density of from about $1.5 \times 10^3$ cells/cm$^2$ to about $10^4$ cells/cm$^2$; from about $2 \times 10^3$ cells/cm$^2$ to about $10^4$ cells/cm$^2$; from about $3 \times 10^3$ cells/cm$^2$ to about $10^4$ cells/cm$^2$; from about $4 \times 10^3$ cells/cm$^2$ to about $10^4$ cells/cm$^2$; or from about $10^3$ cells/cm$^2$ to about $9 \times 10^3$ cells/cm$^2$. In some embodiments, the cells may be plated at a density greater than $10^4$ cells/cm$^2$, e.g., from about $1.25 \times 10^4$ cells/cm$^2$ to about $3 \times 10^4$ cells/cm$^2$.

C. Induction Factors

Inducing a cell to become multipotent or pluripotent can be accomplished in a number of ways. In some embodiments, the methods for induction of pluripotency or multipotency in one or more cells include forcing expression of a set of induction factors (IFs). Forced expression may include introducing expression vectors encoding polypeptides of interest into cells, introducing exogenous purified polypeptides of interest into cells, or contacting cells with a non-naturally occurring reagent that induces expression of an endogenous gene encoding a polypeptide of interest.

In some cases, the set of IFs includes one or more: an Oct3/4 polypeptide, a Sox2 polypeptide, a Klf4 polypeptide, or a c-Myc polypeptide. In some cases, the set does not include a c-Myc polypeptide. For example, the set of IFs can include one or more of: an Oct3/4 polypeptide, a Sox2 polypeptide, and a Klf4 polypeptide, but not a c-Myc polypeptide. In some cases, the set of IFs does not include polypeptides that might increase the risk of cell transformation or the risk of inducing cancer. The ability of c-Myc to induce cell transformation has been described, see, e.g., Adhikary et al., (2005), *Nat. Rev. Mol. Cell. Biol.*, 6(8):635-645.

In some cases, the set includes a c-Myc polypeptide. In certain cases, the c-Myc polypeptide is a constitutively active variant of c-Myc. In some instances, the set includes a c-Myc polypeptide capable of inducible activity, e.g., a c-Myc-ER polypeptide, see, e.g., Littlewood, et al., (1995), *Nucleic Acid Res.*, 23(10): 1686-90.

In other cases, the set of IFs includes: an Oct3/4 polypeptide, a Sox2 polypeptide, and a Klf4 polypeptide, but not a TERT polypeptide, a SV40 Large T antigen polypeptide, HPV16 E6 polypeptide, a HPV16 E7 polypeptide, or a Bmi1 polypeptide. In some cases, the set of IFs does not include a TERT polypeptide. In some cases, the set of IFs does not include a SV40 Large T antigen. In other cases, the set of IFS does not include a HPV16 E6 polypeptide or a HPV16 E7 polypeptide.

In some cases, the set of IFs includes three IFs, wherein two of the three IFs are an Oct3/4 polypeptide and a Sox2 polypeptide. In other cases, the set of IFs includes two IFs, e.g., a c-Myc polypeptide and a Sox2 polypeptide or an Oct3/4 and a Klf4 polypeptide. In some cases, the set of IFs is limited to Oct 3/4, Sox2, and Klf4 polypeptides. In other cases, the set of IFs may be limited to a set of four IFs: an Oct3/4 polypeptide, a Sox2 polypeptide, a Klf4 polypeptide, and a c-Myc polypeptide.

A set of IFs may include IFs in addition to an Oct 3/4, a Sox2, and a Klf4 polypeptide. Such additional IFs include, but are not limited to Nanog, TERT, LIN28, CYP26A1, GDF3, FoxD3, Zfp42, Dnmt3b, Ecat1, and Tcl1 polypeptides. In some cases, the set of additional IFs does not include a c-Myc polypeptide. In some cases, the set of additional IFs does not include polypeptides that might increase the risk of cell transformation or of inducing cancer.

Forced expression of IFs may be maintained for a period of at least about 7 days to at least about 40 days, e.g., 8 days, 9 days, 10 days, 11 days, 12 days, 13 days, 14 days, 15 days, 16 days, 17 days, 18 days, 19 days, 20 days, 21 days, 25 days, 30 days, 33 days, or 37 days.

The efficiency of inducing pluripotency in cells of a human population of cells is from at least about 0.001% to at least about 0.1% of the total number of parental cells cultured initially, e.g., 0.002%, 0.0034%, 0.004%, 0.005%, 0.0065%, 0.007%, 0.008%, 0.01%, 0.04%, 0.06%, 0.08%, or 0.09%. At times, depending on the age of the donor, the origin of the tissue, or the culture conditions, higher efficiencies may be achieved.

D. HDAC Inhibitor

Induction of the cells may be accomplished by combining histone deacetylase (HDAC) inhibitor treatment with forced expression of sets of IFs. The cells to be induced may be undifferentiated stem cells present in a human postnatal tissue. In other cases, the cells to be induced are differentiated cells or are a mixture of differentiated and undifferentiated cells.

The HDAC may be combined with the forced expression of a specific set of IFs, e.g., Oct3/4, Sox2, and Klf4. For example, a human somatic cell is induced to become pluripotent after HDAC inhibitor treatment is combined with forced expression of Oct3/4, Sox2 and Klf4 or forced expression of Oct3/4, Sox2, Klf4, and c-Myc. In some cases, human pluripotent stem cells can be induced by introducing three genes (e.g., Oct3/4, Sox2 and Klf4) or three genes (e.g., Oct3/4, Sox2 and Klf4) plus the c-Myc gene or a HDAC inhibitor into undifferentiated stem cells present in a human postnatal tissue in which each gene of Tert, Nanog, Oct3/4 and Sox2 has not undergone epigenetic inactivation. In still other cases, human pluripotent stem cells are induced by introducing three genes (e.g., Oct3/4, Sox2 and Klf4) or three genes (e.g., Oct3/4, Sox2 and Klf4) plus the c-Myc gene or a histone deacetylase inhibitor into undifferentiated stem cells after the undifferentiated stem cells were amplified by a primary culture or a second subculture, or a subculture in a low density and subculturing in a culture medium comprising a low-concentration serum.

Cells may be treated with one or more HDACs for about 2 hours to about 5 days, e.g., 3 hours, 6 hours, 12 hours, 14 hours, 18 hours, 1 day, 2 days, 3 days, or 4 days. Treatment with HDAC inhibitor may be initiated prior to beginning forced expression of IFs in the cells. In some cases, HDAC inhibitor treatment begins during or after forced expression of IFs in the cells. In other cases, HDAC inhibitor treatment begins prior to forced expression and is maintained during forced expression.

Suitable concentrations of an HDAC inhibitor range from about 0.001 nM to about 10 mM, depending on the particular HDAC inhibitor to be used, but are selected so as to not significantly decrease cell survival in the treated cells. The HDAC concentration may range from 0.01 nM, to 1000 nM. In some embodiments, the HDAC concentration ranges from about 0.01 nM to about 1000 nM, e.g., about 0.05 nM, 0.1 nM, 0.5 nM, 0.75 nM, 1.0 nM, 1.5 nM, 10 nM, 20 nM, 40 nM, 50 nM, 100 nM, 200 nM, 300 nM, 500 nM, 600 nM, 700 nM, 800 nM, or other concentration from about 0.01 nM to about 1000 nM. Cells are exposed for 1 to 5 days or 1 to 3 days. For example, cells are exposed 1 day, 2 days, 3 days, 4 days or 5 days.

Multiple varieties of HDAC inhibitors can be used for the induction experiments. In a preferred embodiment, the HDAC inhibitor MS-275 is used. Examples of suitable HDAC inhibitors include, but are not limited to, any the following:

A. Trichostatin A and its analogs, for example: trichostatin A (TSA); and trichostatin C (Koghe et al., (1998), *Biochem. Pharmacol.*, 56:1359-1364).

B. Peptides, for example: oxamflatin [(2E)-5[3-[(phenyl-sulfonyl)aminophenyl]-pent-2-ene-4-ynohydroxamic acid (Kim et al., (1999), *Oncogene*, 18:2461-2470); Trapoxin A (cyclo-(L-phenylalanyl-L-phenylalanyl-D-pipecolinyl-L-2-amino-8-oxo-9,10-epoxy-decanoyl) (Kijima et al., (1993), *J. Biol. Chem.*, 268:22429-22435); FR901228, depsipeptide (Nakajima et al., (1998). *Ex. Cell Res.*, 241:126-133); FR225497, cyclic tetrapeptide (H. Mori et al., (2000), PCT International Patent Publication WO 00/08048); apicidin, cyclic tetrapeptide [cyclo-(N—O-methyl-L-tryptophanyl-L-isoleucinyl-D-pipecolinyl-L-2-amino-8-oxodecanoyl)] (Darkin-Rattray et al., (1996), *Proc. Natl. Acad. Sci. U.S.A.*, 93:13143-13147; apicidin Ia, apicidin Ib, apicidin Ic, apicidin IIa, and apicidin IIb (P. Dulski et al., PCT International Patent Publication WO 97/11366); HC-toxin, cyclic tetrapeptide (Bosch et al., (1995), *Plant Cell*, 7:1941-1950); WF27082, cyclic tetrapeptide (PCT International Patent Publication WO 98/48825); and chlamydocin (Bosch et al., supra).

C. Hybrid polar compounds (HPC) based on hydroxamic acid, for example: salicyl hydroxamic acid (SBHA) (Andrews et al., (2000), *International J. Parasitology*, 30:761-8); suberoylanilide hydroxamic acid (SAHA) (Richon et al., (1998), *Proc. Natl. Acad. Sci. U.S.A.*, 95: 3003-7); azelaic bishydroxamic acid (ABHA) (Andrews et al., supra); azelaic-1-hydroxamate-9-anilide (AAHA) (Qiu et al., (2000), *Mol. Biol. Cell*, 11:2069-83); M-carboxy cinnamic acid bishydroxamide (CBHA) (Ricon et al., supra); 6-(3-chlorophenylureido) carpoic hydroxamic acid, 3-Cl-UCHA) (Richon et al., supra); MW2796 (Andrews et al., supra); and MW2996 (Andrews et al., supra).

D. Short chain fatty acid (SCFA) compounds, for example: sodium butyrate (Cousens et al., (1979), *J. Biol. Chem.*, 254: 1716-23); isovalerate (McBain et al., (1997), *Biochem. Pharm.*, 53:1357-68); valproic acid; valerate (McBain et al., supra); 4-phenyl butyric acid (4-PBA) (Lea and Tulsyan, (1995), *Anticancer Research*, 15:879-3); phenyl butyric acid (PB) (Wang et al., (1999), Cancer Research 59: 2766-99); propinate (McBain et al., supra); butylamide (Lea and Tulsyan, supra); isobutylamide (Lea and Tulsyan, supra); phenyl acetate (Lea and Tulsyan, supra); 3-bromopropionate (Lea and Tulsyan, supra); tributyrin (Guan et al., (2000), *Cancer Research*, 60:749-55); arginine butyrate; isobutyl amide; and valproate.

E. Benzamide derivatives, for example: MS-275 [N-(2-aminophenyl)-4-[N-(pyridine-3-yl-methoxycarbonyl)aminomethyl]benzamide] (Saito et al., (1999), *Proc. Natl. Acad. Sci. U.S.A.*, 96:4592-7); and a 3'-amino derivative of MS-275 (Saito et al., supra); and CI-994.

A histone deacetylase inhibitor treatment may be carried out, for example, as follows. The concentration of the HDAC inhibitor may depend on a particular inhibitor, but is preferably 0.001 nM to about 10 mM, and more preferably about 0.01 nM to about 1000 nM. The effective amount or the dosage of a histone deacetylase inhibitor is defined as the amount of the histone deacetylase inhibitor that does not significantly decrease the survival rate of cells, specifically undifferentiated stem cells. Cells are exposed for 1 to 5 days or 1 to 3 days. The exposure period may be less than one day. In a specific embodiment, cells are cultured for about 1 to 5 days, and then exposed to an effective amount of a histone deacetylase inhibitor. However, the histone deacetylase inhibitor may be added at the start of culturing. Within such a time frame, a gene-carrying vehicle such as a vector containing a nucleic acid encoding three genes (Oct3/4, Sox2 and Klf4) is introduced into cultured cells by a known method.

E. IF Expression Vectors

Forced expression of the IFs may comprise introducing one or more mammalian expression vectors encoding an Oct3/4, a Sox2, and a Klf4 polypeptide to a population of cells. The IFs may be introduced into the cells as exogenous genes. In some cases, the exogenous genes are integrated into the genome of a host cell and its progeny. In other cases, the exogenous genes persist in an episomal state in the host cell and its progeny. Exogenous genes are genes that are introduced to the cell from an external source. A gene as used herein is a nucleic acid that normally includes an open reading frame encoding a polypeptide of interest, e.g., an IF. The gene preferably includes a promoter operably linked to an open reading frame. In some cases, a natural version of the gene may already exist in the cell but an additional "exogenous gene" is added to the cell to induce polypeptide expression.

The one or more mammalian expression vectors may be introduced into greater than 20% of the total population of cells, e.g., 25%, 30%, 35%, 40%, 44%, 50%, 57%, 62%, 70%, 74%, 75%, 80%, 90%, or other percent of cells greater than 20%. A single mammalian expression vector may contain two or more of the just-mentioned IFs. In other cases, one or more expression vectors encoding an Oct 3/4, Sox2, Klf4, and c-Myc polypeptide are used. In some embodiments, each of the IFs to be expressed is encoded on a separate mammalian expression vector.

In some cases, the IFs are genetically fused in frame with a transport protein amino acid sequence, e.g., that of a VP22 polypeptide as described in, e.g., U.S. Pat. Nos. 6,773,920, 6,521,455, 6,251,398, and 6,017,735. In particular, VP22 polypeptide encompasses polypeptides corresponding to amino acids 60-301 and 159-301 of the full HSV1 VP22 sequence (1-301), whose sequence is disclosed in FIG. 4 in WO 97/05265. Homologous proteins and fragments based on sequences of VP22 protein homologues from other herpes viruses are described in U.S. Pat. No. 6,017,735. Such VP22 sequences confer intercellular transport of VP22 fusion polypeptides from cells that have been transfected with a VP22 fusion polypeptide expression vector to neighboring cells that have not been transfected or transduced. See, e.g., Lemken et al., (2007), *Mol. Ther.*, 15(2):310-319. Accordingly, the use of vectors encoding IF-VP22 fusion polypeptides can significantly increase the functional efficiency of transfected mammalian expression vectors in the induction methods described herein.

Examples of suitable mammalian expression vectors include, but are not limited to: recombinant viruses, nucleic acid vectors, such as plasmids, bacterial artificial chromosomes, yeast artificial chromosomes, human artificial chromosomes, cDNA, cRNA, and PCR product expression cassettes. Examples of suitable promoters for driving expression of IFs include, but are not limited to, retroviral LTR elements; constitutive promoters such as CMV, HSV1-TK, SV40, EF-1α, β-actin; PGK, and inducible promoters, such as those containing Tet-operator elements. In some cases, one or more of the mammalian expression vectors encodes, in addition to an IF, a marker gene that facilitates identification or selection of cells that have been transfected or infected. Examples of marker genes include, but are not limited to, genes encoding fluorescent proteins, e.g., EGFP, DS-Red, YFP, and CFP; genes encoding proteins conferring resistance to a selection agent, e.g., the $neo^R$ gene, and the blasticidin resistance gene.

1. Recombinant Viruses

Forced expression of an IF may be accomplished by introducing a recombinant virus carrying DNA or RNA encoding an IF to one or more cells. For ease of reference, at times a virus will be referred to herein by the IF it is encoding. For example, a virus encoding an Oct3/4 polypeptide, may be described as an "Oct3/4 virus." In certain cases, a virus may encode more than one copy of an IF or may encode more than one IF, e.g., two IFs, at a time.

Combinations or sets of recombinant viruses may be introduced to the cells for forced expression of various sets of IFs. In some cases, the set of IFs expressed by the recombinant viruses includes one or more: an Oct314 polypeptide, a Sox2 polypeptide, a Klf4 polypeptide, or a c-Myc polypeptide. In some cases, the set does not include a c-Myc polypeptide. For example, the set of IFs can include: an Oct3/4 polypeptide, a Sox2 polypeptide, and a Klf4 polypeptide, but not a c-Myc polypeptide. In some cases, the set of IFs does not include polypeptides that might increase the risk of cell transformation or the risk of inducing cancer. The ability of c-Myc to induce cell transformation has been described, see, e.g., Adhikary et al., (2005), *Nat. Rev. Mal. Cell Biol.*, 6(8):635-645.

In some cases, the set of IFs to be expressed includes a c-Myc polypeptide. In certain cases, the c-Myc polypeptide is a constitutively active variant of c-Myc. In some instances, the set includes a c-Myc polypeptide capable of inducible activity, e.g., a c-Myc-ER polypeptide, see, e.g., Littlewood, et al., (1995), *Nucleic Acid Res.*, 23(10):1686-90.

In other cases, the set of IFs to be expressed includes: an Oct314 polypeptide, a Sox2 polypeptide, and a Klf4 polypeptide, but not a TERT polypeptide, a SV40 Large T antigen polypeptide, HPV16 E6 polypeptide, a HPV16 E7 polypeptide, or a Bmi1 polypeptide. In some cases, the set of IFs does not include a TERT polypeptide. In some cases, the set of IFs does not include a SV40 Large T antigen. In other cases, the set of IFs does not include a HPV16 E6 polypeptide or a HPV16 E7 polypeptide.

In some cases, the set of IFs includes three IFs, wherein two of the three IFs are an Oct3/4 polypeptide and a Sox2 polypeptide. In other cases, the set of IFs includes two IFs, wherein the two polypeptides are a c-Myc polypeptide and a Sox2 polypeptide. In some cases, the set of IFs is limited to Oct 3/4, Sox2, and Klf4 polypeptides. In other cases, the set of IFs may be limited to a set of four IFs: an Oct3/4 polypeptide, a Sox2 polypeptide, a Klf4 polypeptide, and a c-Myc polypeptide.

A set of IFs may include IFs in addition to an Oct 3/4, a Sox2, and a Klf4 polypeptide. Such additional IFs include, but are not limited to Nanog, TERT, LIN28, CYP26A1, GDF3, FoxD3, Zfp42, Dnmt3b, Ecat1, and Tcl1 polypeptides. In some cases, the set of additional IFs does not include a c-Myc polypeptide. In some cases, the set of additional IFs does not include polypeptides that might increase the risk of cell transformation or of inducing cancer.

Individual viruses may be added to the cells sequentially in time or simultaneously. In some cases, at least one virus, e.g., an Oct3/4 virus, a Sox2 virus, a Klf4 virus, or a c-Myc virus, is added to the cells at a time different from the time when one or more other viruses are added. In some examples, the Oct3/4 virus, Sox2 virus and Klf4 virus are added to the cells simultaneously, or very close in time, and the c-Myc virus is added at a time different from the time when the other viruses are added.

At least two recombinant viruses may be added to the cells simultaneously or very close in time. In some examples, Oct3/4 virus and Sox2 virus are added simultaneously, or very close in time, and the Klf4 virus or c-Myc virus is added at a different time. In some examples, Oct3/4 virus and Sox2 virus; Oct3/4 virus and Klf4 virus; Oct3/4 virus and c-Myc virus; Sox2 virus and Klf4 virus; Sox2 virus and c-Myc virus; or Klf4 and c-Myc virus are added simultaneously or very close in time.

In some cases, at least three viruses, e.g., an Oct3/4 virus, a Sox2 virus, and a Klf4 virus, are added to the cells simultaneously or very close in time. In other instances, at least four viruses, e.g., Oct3/4 virus, Sox2 virus, Klf4 virus, and c-Myc virus are added to the cells simultaneously or very close in time.

At times, the efficiency of viral infection can be improved by repetitive treatment with the same virus. In some cases, one or more Oct3/4 virus, Sox2 virus, Klf4 virus, or c-Myc virus is added to the cells at least two, at least three, or at least four separate times.

Examples of recombinant viruses include, but are not limited to, retroviruses (including lentiviruses); adenoviruses; and adeno-associated viruses. Often, the recombinant retrovirus is murine moloney leukemia virus (MMLV), but other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Ape Leukemia Virus, Mason Pfizer Monkey Virus, or Rous Sarcoma Virus, see, e.g., U.S. Pat. No. 6,333,195.

In other cases, the recombinant retrovirus is a lentivirus (e.g., Human Immunodeficiency Virus-1 (HIV-1); Simian Immunodeficiency Virus (SIV); or Feline Immunodeficiency Virus (FIV)), See, e.g., Johnston et al., (1999), *Journal of Virology*, 73(6):4991-5000 (FIV); Nègre D et al., (2002), *Current Topics in Microbiology and Immunology*, 261:53-74 (SIV); Naldini et al., (1996), *Science*, 272:263-267 (HIV).

The recombinant retrovirus may comprise a viral polypeptide (e.g., retroviral env) to aid entry into the target cell. Such viral polypeptides are well-established in the art, see, e.g., U.S. Pat. No. 5,449,614. The viral polypeptide may be an amphotropic viral polypeptide, e.g., amphotropic env, that aids entry into cells derived from multiple species, including cells outside of the original host species. See, e.g., id. The viral polypeptide may be a xenotropic viral polypeptide that aids entry into cells outside of the original host species. See, e.g., id. In some embodiments, the viral polypeptide is an ecotropic viral polypeptide, e.g., ecotropic env, that aids entry into cells of the original host species. See, e.g., id.

Examples of viral polypeptides capable of aiding entry of retroviruses into cells include but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. See e.g., Yee et al., (1994), *Methods Cell Biol., Pt A*:99-112 (VSV-G); U.S. Pat. No. 5,449,614. In some cases, the viral polypeptide is genetically modified to promote expression or enhanced binding to a receptor.

In general, a recombinant virus is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. The retroviral packaging cell may comprise a gene encoding a viral polypeptide, e.g., VSV-g that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as E1A or E1B or other adenoviral proteins. For example, proteins supplied by packaging cells may be retrovirus-derived proteins such as gag, pol, and env; lentivirus-derived proteins such as gag, pol, env, vpr, vpu, vpx, vif, tat, rev, and nef; and adenovirus-derived proteins such as E1A and E1B. In many examples, the packaging cells supply proteins derived from a virus that differs from the virus from which the viral vector derives.

Packaging cell lines include but are not limited to any easily-transfectable cell line. Packaging cell lines can be based on 293T cells, NIH3T3, COS or HeLa cell lines. Packaging cells are often used to package virus vector plasmids deficient in at least one gene encoding a protein required for virus packaging. Any cells that can supply a protein or polypeptide lacking from the proteins encoded by such virus vector plasmid may be used as packaging cells. Examples of packaging cell lines include but are not limited to: Platinum-E (Plat-E); Platinum-A (Plat-A); BOSC 23 (ATCC CRL 11554); and Bing (ATCC CRL 11270), see, e.g., Morita et al., (2000), *Gene Therapy*, 7:1063-1066; Onishi et al., (1996), *Experimental Hematology*, 24:324-329; U.S. Pat. No. 6,995,009. Commercial packaging lines are also useful, e.g., Ampho-Pak 293 cell line, Eco-Pak 2-293 cell line, RetroPack PT67 cell line, and Retro-X Universal Packaging System (all available from Clontech).

The retroviral construct may be derived from a range of retroviruses, e.g., MMLV, HIV-1, SIV, FIV, or other retrovirus described herein. The retroviral construct may encode all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides can help facilitate viral entry. In an exemplary embodiment, the recombinant retrovirus is HIV-1 virus comprising a VSV-g polypeptide but not comprising a HIV-1 env polypeptide.

The retroviral construct may comprise: a promoter, a multicloning site, and/or a resistance gene. Examples of promoters include but are not limited to CMV, SV40, EF1α, β-actin; retroviral LTR promoters, and inducible promoters. The retroviral construct may also comprise a packaging signal (e.g., a packaging signal derived from the MFG vector; a psi packaging signal). Examples of some retroviral constructs known in the art include but are not limited to: pMX, pBabeX or derivatives thereof. See e.g., Onishi et al., (1996), *Experimental Hematology*, 24:324-329. In some cases, the retroviral construct is a self-inactivating lentiviral vector (SIN) vector, see, e.g., Miyoshi et al., (1998), *J. Virol.*, 72(10):8150-8157. In some cases, the retroviral construct is LL-CG, LS-CG, CL-CG, CS-CG, CLG or MFG. Miyoshi et al., (1998), *J. Virol.*, 72(10):8150-8157; Onishi et al., (1996), *Experimental Hematology*, 24:324-329; Riviere et al., (1995), *PNAS*, 92:6733-6737. Virus vector plasmids (or constructs), include: pMXs, pMxs-IB, pMXs-puro, pMXs-neo (pMXs-IB is a vector carrying the blasticidin-resistant gene in stead of the puromycin-resistant gene of pMXs-puro) Kimatura et al., (2003), *Experimental Hematology*, 31: 1007-1014; MFG Riviere et al., (1995), *Proc. Natl. Acad. Sci. U.S.A.*, 92:6733-6737; pBabePuro; Morgenstern et al., (1990), *Nucleic Acids Research*, 18:3587-3596; LL-CG, CL-CG, CS-CG, CLG Miyoshi et al., (1998), *Journal of Virology*, 72:8150-8157 and the like as the retrovirus system, and pAdex1 Kanegae et al., (1995), *Nucleic Acids Research*, 23:3816-3821 and the like as the adenovirus system. In exemplary embodiments, the retroviral construct comprises blasticidin (e.g., pMXs-IB), puromycin (e.g., pMXs-puro, pBabePuro); or neomycin (e.g., pMXs-neo). See, e.g., Morgenstern et al., (1990), *Nucleic Acids Research*, 18:3587-3596.

The retroviral construct may encode one or more IFs. In an exemplary embodiment, pMX vectors encoding Oct3/4, Sox2, Klf4, or c-Myc polypeptides, or variants thereof, are generated or obtained. For example, Oct3/4 is inserted into pMXs-puro to create pMX-Oct3/4; Sox2 is inserted into pMXs-neo to create pMX-Sox2; Klf4 is inserted into pMXs-IB to create pMX-Klf4; and c-Myc is inserted into pMXs-IB to create pMX-c-Myc.

Methods of producing recombinant viruses from packaging cells and their uses are well-established, see, e.g., U.S. Pat. Nos. 5,834,256; 6,910,434; 5,591,624; 5,817,491; 7,070,994; and 6,995,009, incorporated herein by reference. Many methods begin with the introduction of a viral construct into a packaging cell line. The viral construct may be introduced by any method known in the art, including but not limited to: the calcium phosphate method (see, e.g., Kokai, Japanese Unexamined Patent Publication No. 2-227075, the lipofection method Felgner et al., (1987), *Proc. Natl. Acad. Sci. U.S.A.*, 84:7413-7417, the electroporation method, microinjection, Fugene transfection, and the like, and any method described herein.

In one example, pMX-Oct3/4, pMX-Sox2, pMX-Klf4 or pMX-c-Myc is introduced into PlatE cells by Fugene HD (Roche) transfection. The cell culture medium may be replaced with fresh medium comprising FBM (Lonza) supplemented with FGM-2 Single Quots (Lonza). In some embodiments, the medium is replaced from about 12 to about 60 hours following the introduction of the viral construct, e.g., from about 12 to about 18 hours; about 18 to about 24; about 24 to about 30; about 30 to about 36; about 36 to about 42; about 42 to about 48; about 48 to about 54; or about 54 to about 60 hours following introduction of the viral construct to the producer cells. The medium may be replaced from about 24 to about 48 hours after introduction of the viral construct to the producer cells. The supernatant can be recovered from about 4 to about 24 hours following the addition of fresh media, e.g., about 4 hours. In some cases, the supernatant may be recovered about every 4 hours following the addition of fresh media. The recovered supernatant may be passed through a 0.45 uM filter (Millipore). In some cases, the recovered supernatant comprises retrovirus derived from one or more: pMX-Oct3/4, pMX-Sox2, pMX-Klf4 or pMX-c-Myc.

Adenoviral transduction may be used to force expression of the sets of IFs. Methods for generating adenoviruses and their use are well established as described in, e.g., Straus, The Adenovirus, Plenum Press (NY 1984), 451 496; Rosenfeld, et al., (1991), *Science*, 252:431-434; U.S. Pat. Nos. 6,203,975, 5,707,618, and 5,637,456. In other cases, adenoviral-associated viral transduction is used to force expression of the sets of IFs. Methods for preparing adeno-associated viruses and their use are well established as described in, e.g., U.S. Pat. Nos. 6,660,514 and 6,146,874.

In an exemplary embodiment, an adenoviral construct is obtained or generated, wherein the adenoviral construct, e.g., Adeno-X, comprises DNA encoding Oct3/4, Sox2, Klf4, or c-Myc. An adenoviral construct may be introduced by any method known in the art, e.g., Lipofectamine 2000 (Invitrogen) or Fugene HD (Roche), into HEK 293 cells. In some cases, the method further comprises (1) collecting the cells when they exhibit a cytopathic effect (CPE), such effect occurring from about 10 to about 20 days, e.g., about 11, 13, 14, 15, 18, or 20 days after transfection (2) subjecting the cells to from about 2 to about 5 freeze-thaw cycles, e.g., about 3, (3) collecting the resulting virus-containing liquid; (4) purifying the virus using an adenovirus purification kit (Clontech) and (5) storing the virus at −80° C. In some cases, the titer, or plaque-forming unit (PFU), of the adenoviral stocks is determined using an Adeno-X rapid titer kit (Clontech), as described herein.

The cells may be infected with a recombinant retrovirus that naturally targets a different cell type or cells originating from a different host. To aid infection efficiency, an exogenous receptor may be first introduced into the human cells. For example, an exogenous mouse receptor may be added to human cells, e.g., postnatal dermal fibroblasts, in order help entry of murine moloney leukemia virus (MMLV). The exogenous receptor may improve infection efficiency by facilitating viral entry, especially if the receptor recognizes a viral polypeptide, e.g., MMLV env, or HIV env. Examples of exogenous receptors include but are not limited to any receptor recognized by a specific retrovirus or lentivirus known in the art. For example, a murine receptor, mCAT1, GenBank Accession No NM_007513 protein is used in order to aid MMLV infection of a human target cell.

The exogenous receptor may be introduced by methods described herein. Methods of introducing the exogenous receptor include but are not limited to: calcium phosphate transfection, Lipofectamine transfection, Fugene transfection, microinjection, or electroporation. In exemplary embodiments, a virus, e.g., recombinant adenovirus or retrovirus (including lentivirus), is used to introduce the exogenous receptor to the target cell. In a further exemplary embodiment, a recombinant adenovirus is used to introduce mCAT1 to human cells and then a recombinant retrovirus, e.g., MMLV, is used to introduce the IF genes, e.g., Oct 3/4, a Sox2, a Klf4, or c-Myc, to the cells.

In some cases, a solution of adenovirus comprising DNA encoding the mCAT1 protein, e.g., an adenovirus generated by using a pADEX-mCAT1 construct, is generated or obtained. The adenovirus solution can comprise Hanks' balanced salt solution. In exemplary embodiments, infection of cells is accomplished by: (1) contacting the p-ADEX-mCAT1 adenovirus solution with cells, e.g., human, non-embryonic fibroblasts, at a multiplicity of infection (m.o.i.) (virus to cell ratio) from about 1 m.o.i. to about 50 m.o.i., e.g., about 1 m.o.i., about 5 m.o.i., about 7.5; m.o.i., about 10 m.o.i., about 15 m.o.i., about 20 m.o.i., about 30 m.o.i., about 40 m.o.i., or about 50 m.o.i.; (2) incubating the cells with the adenovirus solution at room temperature from about 15 minutes to about 2 hours, e.g., about 15 minutes, about 30 minutes, about 45 minutes, about 1 hour, about 1.25 hours, about 1.5 hours, about 1.75 hours, or about 2 hours; and (3) culturing the somatic cell population in culture medium from about 24 hours to about 60 hours, e.g., about 24 hours, about 30 hours, about 36 hours, about 42 hours, about 48 hours, about 54 hours, or about 60 hours.

The cells can be infected using a wide variety of methods. In some cases, the infection of cells occurs by (1) combining one or more, two or more, three or more, or all four: pMX-Oct3/4 retrovirus, pMX-Sox2 retrovirus, pMX-Klf4, or pMX-c-Myc to obtain a retrovirus solution (2) supplementing the retrovirus solution with from about 2 µg/ml to about 15 µg/ml Polybrene, e.g., about 2 µg/ml, about 3 µg/ml, about 5 µg/ml, about 7 µg/ml, about 10 about 12 µg/ml, or about 15 µg/ml Polybrene; (3) contacting the retroviral solution with the somatic cells, at a m.o.i. (virus-to-cell ratio) of from about 0.5 m.o.i. to about 10 m.o.i., e.g., about 0.5 m.o.i., about 1 m.o.i., about 2 m.o.i., about 5 m.o.i., about 7.5 m.o.i., or about 10 m.o.i.; (4) allowing the contacting of step (3) to continue at 37° C. from about 2 hours to about 24 hours, e.g., about 2 hours, about 3 hours, about 4 hours, about 5 hours, about 6 hours, about 7 hours, about 9 hours, about 10 hours, about 11 hours, about 12 hours, about 14 hours, about 15 hours, about 16 hours, about 17 hours, about 18 hours, about 19 hours, about 20 hours, about 21 hours, about 22 hours, about 23 hours, or about 24 hours; (5) soon after the contacting of step (4), changing the medium to MC-ES medium, as described herein; and (6) changing the MC-ES medium with fresh medium every 1 to 2 days. In some cases, infection of somatic cells occurs by following steps (1) through (6) described herein, with the added step of pre-incubating the somatic cells for a length of time, e.g., about 48 hours, prior to contacting the cells with the retroviral solution. Such pre-incubation may be necessary when the somatic cell expresses an exogenous receptor that was introduced by viral transduction, transfection, or other method. Thus, in some embodiments, if an adenovirus or lentivirus is used to introduce an exogenous receptor, e.g., mCAT1, to the somatic cell; such cells may need to be cultured for a length of time from at least about 30 hours to at least about 60 hours, e.g., about 30, about 35, about 40, about 48, about 52, about 55, or about 60 hours.

The infection of cells may be accomplished by any method known in the art. e.g., Palsson, B., et al., (1995), WO95/10619; Morling, F. J. et al., (1995), *Gene Therapy,* 2:504-508; Gopp et al., (2006), *Methods Enzymol,* 420:64-81. For example, the infection may be accomplished by spin-infection or "spinoculation" methods that involve subjecting the cells to centrifugation during the period closely following the addition of virus to the cells. In some cases, virus may be concentrated prior to the infection, e.g., by ultracentrifugation. In some cases, other technologies may be used to aid or improve entry of retroviruses into the target cell. For example, the retrovirus may be contacted with a liposome or immunoliposome to aid or direct entry into a specific cell type. See, e.g., Tan et al., (2007), *Mol. Med.* 13(34):216-226.

The methods of infecting cells described herein may be used to infect cells expressing an exogenous receptor, e.g., mCAT1 or other exogenous receptor described herein. Depending on how the exogenous receptor was introduced, the preincubation period of the cells prior to infection may need to be varied. In some cases, cells that do not express an exogenous receptor are used. Some recombinant retroviruses, e.g., VSV-G pseudotyped recombinant retroviruses, may not need the aid of an exogenous receptor in order to efficiently enter cells. In some examples, VSV-G pseudotyped recombinant retrovirus is introduced to cells following the method described herein, except that the timing of the preculturing of the cells may vary.

2. Nucleic Acid Vectors

Nucleic acid vector transfection (e.g., transient transfection) methods may be used to introduce IFs into human cells. Methods for preparation of transfection-grade nucleic acid expression vectors and transfection methods are well established. See, e.g., Sambrook and Russell (2001), "Molecular Cloning: A Laboratory Manual," $3^{rd}$ ed, (CSHL Press); and *Current Protocols in Molecular Biology*, John Wiley & Sons, N.Y. (2005), 9.1-9.14. Examples of high efficiency transfection efficiency methods include "nucleofection," as described in, e.g., Trompeter (2003), *J Immunol. Methods,* 274(1-2): 245-256, and in international patent application publications WO2002086134, WO200200871, and WO2002086129, transfection with lipid-based transfection reagents such as Fugene® 6 and Fugene® HD(Roche), DOTAP, and Lipofectamine™ LTX in combination with the PLUS™ (Invitrogen, Carlsbad, Calif.), Dreamfect™ (OZ Biosciences, Marseille, France), GeneJuice™ (Novagen, Madison, Wis.), polyethylenimine (see, e.g., Lungwitz et al., (2005), *Eur. J*

Pharm. Biopharm., 60(2):247-266), and GeneJammer™ (Stratagene, La Jolla, Calif.), and nanoparticle transfection reagents as described in, e.g., U.S. patent application Ser. No. 11/195,066.

3. Protein Transduction

The induction methods may use protein transduction to introduce at least one of the IFs directly into cells. In some cases, protein transduction method includes contacting cells with a composition containing a carrier agent and at least one purified polypeptide comprising the amino acid sequence of one of the above-mentioned IFs. Examples of suitable carrier agents and methods for their use include, but are not limited to, commercially available reagents such as Chariot™ (Active Motif, Inc., Carlsbad, Calif.) described in U.S. Pat. No. 6,841,535; Bioport® (Gene Therapy Systems, Inc., San Diego, Calif.), GenomeONE (Cosmo Bio Co., Ltd., Tokyo, Japan), and ProteoJuice™ (Novagen, Madison, Wis.), or nanoparticle protein transduction reagents as described in, e.g., in U.S. patent application Ser. No. 10/138,593.

The protein transduction method may comprise contacting a cells with at least one purified polypeptide comprising the amino acid sequence of one of the above-mentioned IFs fused to a protein transduction domain (PTD) sequence (IF-PTD fusion polypeptide). The PTD domain may be fused to the amino terminal of an IF sequence; or, the PTD domain may be fused to the carboxy terminal of an IF sequence. In some cases, the iF-PTD fusion polypeptide is added to cells as a denatured polypeptide, which may facilitate its transport into cells where it is then renatured. Generation of PTD fusion proteins and methods for their use are established in the art as described in, e.g., U.S. Pat. Nos. 5,674,980, 5,652,122, and 6,881,825. See also, Becker-Hapak et al., (2003), *Curr Protocols in Cell Biol*, John Wiley & Sons, Inc. Exemplary PTD domain amino acid sequences include, but are not limited to, any of the following: YGRKKRRQRRR (SEQ ID NO:1); RKKRRQRR (SEQ ID NO:2); YARAAARQARA (SEQ ID NO:3); THRLPRRRRRR (SEQ ID NO:4); and GGRRAR-RRRRR (SEQ ID NO:5).

In some cases, individual purified IF polypeptides are added to cells sequentially at different times. In other embodiments, a set of at least three purified IF polypeptides, but not a purified c-Myc polypeptide, e.g., an Oct3/4 polypeptide, a Sox2 polypeptide, and a Klf4 polypeptide are added to cells. In some embodiments, a set of four purified IF polypeptides, e.g., purified Oct3/4, Sox2, Klf4, and c-Myc polypeptides are added to cells. In some embodiments, the purified IF polypeptides are added to cells as one composition (i.e., a composition containing a mixture of the IF polypeptides). In some embodiments, cells are incubated in the presence of a purified IF polypeptide for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours. In some embodiments, protein transduction of cells is repeated with a frequency of about every day to about every 4 days, e.g., every 1.5 days, every 2 days, every 3 days, or any other frequency from about every day to about every four days with the same or different IF polypeptides.

In some cases, the methods described herein utilize protein transduction and expression vector transduction/transfection in any combination to force expression of a set of IFs as described herein. In some embodiments, retroviral expression vectors are used to force expression of Oct 3/4, a Sox2, and a Klf4 polypeptides in cells, and purified c-Myc purified polypeptide is introduced into cells by protein transduction as described herein. HDAC inhibitor treatment can be used in addition to the purified IF polypeptide. In some cases, a set of at least three purified IF polypeptides, but not a purified c-Myc polypeptide, e.g., an 3/4Oct3/4 polypeptide, a Sox2 polypeptide, and a Klf4 polypeptide are added to cells which are also subjected to HDAC inhibitor treatment.

F. Induction Factor Sequences

Described herein are polypeptides comprising the amino acid sequences of IFs used in the induction methods described herein, and exogenous genes encoding such polypeptides. In some embodiments, an IF amino acid sequence is a naturally occurring amino acid sequence, e.g., that of: human or mouse Oct 3/4, human or mouse Sox2, human or mouse Klf4, or human or mouse c-Myc polypeptides. In other embodiments, the amino acid sequence of an IF is a non-naturally occurring amino acid sequence variant of an IF that is, nevertheless, functionally or structurally homologous to an IF amino acid sequence, as described herein.

Evaluating the structural and functional homology of two or polypeptides generally includes determining the percent identity of their amino acid sequences to each other. Sequence identity between two or more amino acid sequences is determined by conventional methods. See, for example, Altschul et al., (1997), *Nucleic Acids Research*, 25(17):3389-3402; and Henikoff and Henikoff (1982), *Proc. Natl. Acad. Sci. USA*, 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Those skilled in the art will appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman (1988), *Proc. Nat'l Acad. Sci. USA*, 85:2444, and by Pearson (1990), *Meth. Enzymol.*, 183:63. Briefly, FASTA first characterizes sequence similarity by identifying regions shared by the query sequence (e.g., any of SEQ ID NOs:6-13) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch (1970), *J. Mol. Biol.*, 48:444-453; Sellers (1974), *SIAM J. Appl. Math.*, 26:787), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson (1990), *Meth. Enzymol.*, 183:63.

Also described herein are nucleic acids (e.g., exogenous genes) encoding Oct3/4, Sox2, Klf4, or c-Myc polypeptides, as described herein, that hybridize specifically under low, medium, or high stringency conditions to a probe of at least 100 nucleotides from a nucleic acid encoding the amino acid sequence any of SEQ ID NOs:6-13. Low stringency hybridization conditions include, e.g., hybridization with a 100 nucleotide probe of about 40% to about 70% GC content; at 42° C. in 2×SSC and 0.1% SDS. Medium stringency hybridization conditions include, e.g., at 50° C. in 0.5×SSC and 0.1% SDS. High stringency hybridization conditions include, e.g., hybridization with the above-mentioned probe at 65° C. in 0.2×SSC and 0.1% SDS. Under these conditions, as the hybridization temperature is elevated, a nucleic acid with a higher homology can be obtained. Such nucleic acids encoding Oct 3/4, Sox2, Klf4, or c-Myc polypeptides are useful in the forced expression of these IFs as described herein.

A number of considerations are useful to the skilled artisan in determining if a particular amino acid sequence variant of an IF is suitable for use in the methods described herein. These considerations include, but are not limited to: (1) known structure-function relationships for the IF, e.g., the presence of modular domains such as a DNA binding domain or a transactivation domain, which, in many cases, have been shown to be functionally discrete and capable of independent function; (2) the presence of amino acid sequence conservation among naturally occurring homologs (e.g., in paralogs and orthologs) of the IF, as revealed by sequence alignment algorithms as described herein. Notably, a number of bioinformatic algorithms are known in the art that successfully predict the functional effect, i.e., "tolerance" of particular amino substitutions in the amino acid sequence of a protein on its function. Such algorithms include, e.g., pMUT, SIFT, PolyPhen, and SNPs3D. For a review see, e.g., Ng and Henikoff (2006), *Ann Rev Genomics Hum Genet.*, 7:61-80. For example, pMUT predicts with a high degree of accuracy (about 84% overall) whether a particular amino acid substitution at a given sequence position affects a protein's function based on sequence homology. See Ferrer-Costa et al., (2005), *Bioinformatics*, 21(14):3176-3178; Ferrer-Costa et al., (2004), *Proteins*, 57(4):811-819; and Ferrer-Costa et al., (2002), *J Mol Biol*, 315:771-786. The PMUT algorithm server is publicly available on the world wide web at: //mmb2.pcb.ub.es:8080/PMut/. Thus, for any IF polypeptide amino acid sequence, an "amino acid substitution matrix" can be generated that provides the predicted neutrality or deleteriousness of any given amino acid substitution on IF polypeptide function.

Non-naturally occurring sequence variants can be generated by a number of known methods. Such methods include, but are not limited to, "Gene Shuffling," as described in U.S. Pat. No. 6,521,453; "RNA mutagenesis," as described in Kopsidas et al., (2007), *BMC Biotechnology*, 7:18-29; and "error-prone PCR methods." Error prone PCR methods can be divided into (a) methods that reduce the fidelity of the polymerase by unbalancing nucleotides concentrations and/ or adding of chemical compounds such as manganese chloride (see, e.g., Lin-Goerke et al., (1997), *Biotechniques*, 23:409-412), (b) methods that employ nucleotide analogs (see, e.g., U.S. Pat. No. 6,153,745), (c) methods that utilize 'mutagenic' polymerases (see, e.g., Cline, J. and Hogrefe, H. H. (2000), *Strategies* (Stratagene Newsletter), 13:157-161 and (d) combined methods (see, e.g., Xu et al., (1999), *Biotechniques*, 27:1102-1108. Other PCR-based mutagenesis methods include those, e.g., described by Osuna et al., (2004), *Nucleic Acids Res.*, 32(17):e136 and Wong et al., (2004), *Nucleic Acids Res.*, 10; 32(3):e26), and others known in the art.

Confirmation of the retention, loss, or gain of function of the amino acid sequence variants of an IF can be determined in various types of assays according to the protein function being assessed. For example, where the IF is a transcriptional activator, e.g., an Oct3/4, function is readily assessed using cell-based, promoter-reporter assays, where the reporter construct comprises one or more cognate target elements for the transactivator polypeptide to be assayed. Methods for generating promoter-reporter constructs, introducing them into cells, and assaying various reporter polypeptide activities, can be found in detail in, e.g., *Current Protocols in Molecular Biology*, John Wiley & Sons, N.Y. (2005), 3.16-3.17 and 9.1-9.14, respectively). Promoter activity can be quantified by measuring a property of the reporter polypeptide (e.g., enzymatic activity or fluorescence), reporter polypeptide expression (e.g., by an ELISA assay), or reporter mRNA expression (e.g., by a fluorescent hybridization technique). Suitable reporter polypeptides include, e.g., firefly luciferase, *Renilla* luciferase, fluorescent proteins (e.g., enhanced green fluorescent protein), β-galactosidase, β lactamase, ALP, and horseradish peroxidase.

For example, luciferase activity can be detected by providing an appropriate luminogenic substrate, e.g., firefly luciferin for firefly luciferase or coelenterazine for *Renilla* luciferase. Luciferase activity in the presence of an appropriate substrate can be quantified by a number of standard techniques, e.g., luminometry. See, e.g., U.S. Pat. No. 5,744,320. Fluorescent polypeptides (e.g., EGFP) can be detected and quantified in live cells by a number of detection methods known in the art (e.g., fluorimetry or fluorescence microscopy). Details of reporter assay screens in live cells using fluorescent polypeptides, including high-throughput screening methods, can be found, e.g., in U.S. Pat. No. 6,875,578.

Described herein are a number of IFs that are transcriptional activators, i.e., polypeptides that transactivate promoters containing specific target elements to which the transcriptional activator binds as a monomer, a multimer, or in a heteromeric complex with other polypeptides. Naturally occurring transcriptional activators, e.g., Klf4, are modular proteins minimally composed of two domains as follows: a DNA binding domain that dictates the genes to be targeted and an activation domain that governs the nature and the extent of the transcriptional response through interactions with the transcriptional machinery. The two domains typically operate in an independent fashion such that the DNA binding domain of one transcriptional activator, e.g., the DNA binding domain Sox2, can be attached to the transactivation domain of another transcriptional activator, e.g., Herpes VP16, to generate a fully functional, "chimeric" transcriptional activator, e.g., a chimeric Sox2 transcriptional activator as described in, e.g., Kamachi et al., (1999), *Mol Cell Biol.*, 19(1): 107-120.

In view of the guidance provided herein, a broad range of IF sequence variants (e.g., Oct3/4, Sox2, Klf4, or c-Myc sequence variants), operable in the methods described herein, can readily be identified by those of ordinary skill in the art without undue effort.

Oct3/4 Polypeptide

As referred to herein, an "Oct3/4 polypeptide" includes human Oct 3/4, mouse Oct 3/4, or any polypeptide that:

(i) includes a DNA binding domain (DBD) that binds to the human nanog gene Octamer element:

5'-TTTTGCAT-3'; and (ii) is capable of transactivating a promoter comprising one or more nanog Octamer elements. See, e.g., Kuroda et al., (2005), *Mol and Cell Biol.*, 25(6):2475-2485.

In some embodiments, an Oct3/4 is a polypeptide having the above-mentioned functional properties, and comprising an amino acid sequence at least 70% identical to SEQ ID NO:6 corresponding to the amino acid sequence of human Oct 3/4, also known as *Homo sapiens* POU class 5 homeobox 1 (POU5F1; GenBank Accession No. NP_002692), e.g., 75%, 80%, 85%, 90%, 91%, 92%, 95%, 97%, 99%, or any other percent identical from at least 70% to 100% identical to SEQ ID NO:6. In some embodiments, an Oct3/4 is a polypeptide having the above-mentioned functional properties, and comprising an amino acid sequence from at least 70% to less than 100% identical (e.g., 75%, 80%, 85%, 90%, 91%, 92%, 95%, 97%, 99% identical) to SEQ ID NO:6, e.g., SEQ ID NO: 6 with at least one amin amino acid substitution, deletion, or insertion. In other embodiments, an Oct-3/4 is a polypeptide having the above-mentioned functional properties comprising the amino acid sequence of SEQ ID NO:6 with up to a total of 30 amino acid substitutions, deletions, insertions, or any combination thereof, e.g., SEQ ID NO:6 with 0, 1, 2, 3, 4, 5, 6, 7, 8, 9, 10, 11, 15, 20, 25, or any other number of amino acid substitutions, deletions, insertions, or any combination thereof, from 0 to 30.

```
SEQ ID NO:6 (Human Oct 3/4):
MAGHLASDFAFSPPPGGGGDGPGGPEPGWVDPRTWLSFQGPPGGPGIGPG

VGPGSEVWGIPPCPPPYEFCGGMAYCGPQVGVGLVPQGGLETSQPEGEAG

VGVESNSDGASPEPCTVTPGAVKLEKEKLEQNPEESQDIKALQKELEQFA

KLLKQKRITLGYTQADVGLTLGVLFGKVFSQTTICRFEALQLSFKNMCKL

RPLLQKWVEEADNNENLQEICKAETLVQARKRKRTSIENRVRGNLENLFL

QCPKPTLQQISHIAQQLGLEKDVVRVWFCNRRQKGKRSSSDYAQREDFEA

AGSPFSGGPVSFPLAPGPHFGTPGYGSPHFTALYSSVPFPEGEAFPPVSV

TTLGSPMHSN
```

In some embodiments, an Oct3/4 is a polypeptide having the above-mentioned functional properties, and comprising an amino acid sequence at least 70% identical to SEQ ID NO:7, e.g., 75%, 80%, 85%, 90%, 91%, 92%, 95%, 97%, 99%, or any other percent identical from at least 70% to 100% identical to SEQ ID NO:7, corresponding to amino acids 138-290 of Human Oct3/4 comprising the highly conserved POU DNA binding domain. In some embodiments, an Oct3/4 is a polypeptide having the above-mentioned functional properties, and comprising an amino acid sequence from at least 70% to less than 100% identical (e.g., 75%, 80%, 85%, 90%, 91%, 92%, 95%, 97%, 99% identical) to SEQ ID NO:7, e.g., SEQ ID NO: 7 with at least one amino acid substitution, deletion, or insertion (e.g., 1 to 10 amino acid substitutions, deletions, or insertions).

```
(POU/DNA BindinG Domain of Human Oct 3/4)
                                       SEQ ID NO:7
DIKALQKELEQFAKLLKQKRITLGYTQADVGLTLGVLFGKVFSQTTICRF

EALQLSFKNMCKLRPLLQKWVEEADNNENLQEICKAETLVQARKRKRTSI

ENRVRGNLENLFLQCPKPTLQQISHIAQQLGLEKDVVRVWFCNRRQKGKR

SSS
```

Oct3/4 polypeptides, as described herein, may include naturally occurring or non-naturally occurring homologs of human Oct 3/4. Examples of naturally occurring homologs of human Oct3/4 include, but are not limited to, those listed under GenBank Accession Nos: NP_002692; NP_001108427; NP_001093427; NP_001009178; and NP_038661, or any other Oct family members that meet the above-mentioned structural and functional criteria.

Examples of non-naturally occurring homologs of human Oct 3/4, include, but are not limited to those described in, e.g., Niwa et al., (2002), *Mol Cell Biol.*, 22(5):1526-1536; and Lunde et al., (2004), *Curr. Biol.*, 14(1):48-55.

pMUT analysis of the human Oct3/4 amino acid sequence (SEQ ID NO:6) based on a PSI-BLAST multiple alignment encompassing 250 sequences yields an amino acid substitution matrix (ASM) as shown in Table 17. For each wild-type amino acid position in the human Oct3/4 amino acid sequence, Table 17 shows which amino acid substitutions (of 20 possible amino acids) are predicted to be deleterious (bold and underlined) or neutral (plain text) to the protein's function. Functional assays for the ability of Oct3/4 polypeptides to bind to the cognate nanog gene octamer element (described above) and to transactivate a promoter containing one or more nanog target elements are known in the art as described in, e.g., Kuroda et al., (supra); and Loh et al., (2006), *Nat. Genet.*, 39(4):431-440.

Sox2 Polypeptide

As referred to herein, a "Sox2 polypeptide" includes human Sox2, mouse Sox2, or any polypeptide that:
(i) includes a DNA binding domain (DBD) that binds to the human nanog gene Sox element:

5'-TACAATG-3'; and (ii) is capable of transactivating a promoter comprising one or more nanog gene promoter Sox elements. See, e.g., Kuroda et al., (2005), *Mol and Cell Biol.*, 25(6):2475-2485.

In some embodiments, a Sox2 polypeptide is a polypeptide having the above-mentioned functional properties, and comprising the amino acid sequence at least 70% identical to SEQ ID NO:8 corresponding to the amino acid sequence of human Sox2, i.e., sex-determining region Y-box 2 protein (GenBank Accession No. NP_003097), e.g., 75%, 80%, 85%, 90%, 91%, 92%, 95%, 97%, 99%, or any other percent identical from at least 70% to 100% identical to SEQ ID NO:8. In some embodiments, a Sox2 polypeptide is a polypeptide having the above-mentioned functional properties, and comprising an amino acid sequence from at least 70% to less than 100% identical (e.g., 75%, 80%, 85%, 90%, 91%, 92%, 95%, 97%, 99% identical) to SEQ ID NO:8, e.g., SEQ ID NO: 8 with at least one amino acid substitution, deletion, or insertion (e.g., 1 to 10 amino acid substitutions, deletions, or insertions).

In other embodiments, a Sox2 polypeptide is a polypeptide having the above-mentioned functional properties, and comprising the amino acid sequence of SEQ ID NO:8 with up to a total of 30 amino acid substitutions, deletions, insertions, or any combination thereof, e.g., SEQ ID NO:8 with 0, 1, 2, 3, 4, 5, 6, 7, 8, 9, 10, 11, 15, 20, 25, or any other number of amino acid substitutions, deletions, insertions, or any combination thereof, from 0 to 30.

SEQ ID NO:8 (Human Sox2):
MYNMMETELKPPGPQQTSGGGGGNSTAAAAGGNQKNSPDRVKRPMNAFMV

WSRGQRRKMAQENPKMHNSEISKRLGAEWKLLSETEKRPFIDEAKRLRAL

HMKEHPDYKYRPRRKTKTLMKKDKYTLPGGLLAPGGNSMASGVGVGAGLG

AGVNQRMDSYAHMNGWSNGSYSMMQDQLGYPQHPGLNAHGAAQMQPMHRY

DVSALQYNSMTSSQTYMNGSPTYSMSYSQQGTPGMALGSMGSVVKSEASS

SPPVVTSSSHSRAPCQAGDLRDMISMYLPGAEVPEPAAPSRLHMSQHYQS

GPVPGTAINGTLPLSHM

In some embodiments, a Sox2 polypeptide is a polypeptide having the above-mentioned functional properties, and comprising an amino acid sequence at least 70% identical to SEQ ID NO:9, e.g., 75%, 80%, 85%, 90%, 91%, 92%, 95%, 97%, 99%, or any other percent identical from at least 70% to 100% identical to SEQ ID NO:9, amino acids 40-115 of Human Sox2 comprising the highly conserved High Mobility Group-Sox-TCF (HMG-Sox-TCF) motif DNA binding domain (DBD). In some embodiments, a Sox2 polypeptide is a polypeptide having the above-mentioned functional properties, and comprising an amino acid sequence from at least 70% to less than 100% identical (e.g., 75%, 80%, 85%, 90%, 91%, 92%, 95%, 97%, 99% identical) to SEQ ID NO:9, e.g., SEQ ID NO: 9 with at least one amino acid substitution, deletion, or insertion (e.g., 1 to 5 amino acid substitutions, deletions, or insertions).

SEQ ID NO:9 (HMG-Sox2-TCF DBD)
RVKRPMNAFMVWSRGQRRKMAQENPKMHNSEISKRLGAEWKLLSETEKRP

FDEAKRLRALHMKEHPDYKYRPRRK

Sox2 polypeptides, as described herein, may include naturally occurring or non-naturally occurring homologs of human Sox2. Examples of naturally occurring homologs of human Sox2 include, but are not limited to, those listed under GenBank Accession Nos: NP_001098933; NP_035573, ACA58281; BAA09168; NP_001032751; and NP_648694, or any other Sox family members that meet the above-mentioned structural and functional criteria.

Examples of non-naturally occurring homologs of human Sox2, include, but are not limited to those described in, e.g., Kamachi et al., (1999), *Mol Cell Biol.*, 19(1):107-120.

pMUT analysis (described above) of the human Sox2 amino acid sequence (SEQ ID NO:8) based on a PSI-BLAST multiple alignment encompassing 250 sequences yields an ASM (Table 18) showing amino acid substitutions predicted to be deleterious or neutral to the protein's function. Functional assays for the ability of Sox2 polypeptides to bind to the nanog gene Sox element and to transactivate a promoter containing one or more nanog Sox elements are known in the art as described in, e.g., Kuroda et al., (supra).

Klf4 Polypeptide

As referred to herein, a "Klf4 polypeptide" includes human Klf4, mouse Klf4, or any polypeptide that:
(i) includes a zinc-finger DNA binding domain (DBD) that binds to a Klf target element, e.g., 5'-GAGGTCC-3' OR 5'-GGGGTGT-3'; and (ii) is capable of transactivating a promoter comprising one or more of the above-mentioned target elements. See, e.g., Nakatake et al., (2006), *Mol Cell Biol.*, 24(20):7772-7782.

In some embodiments, a Klf4 polypeptide is a polypeptide having the above-mentioned functional properties, and comprising the amino acid sequence at least 70% identical to SEQ ID NO:10 corresponding to the amino acid sequence of human Klf4, i.e., Kruppel-Like Factor 4 (GenBank Accession No. NP_004226), e.g., 75%, 80%, 85%, 90%, 91%, 92%, 95%, 97%, 99%, or any other percent identical from at least 70% to 100% identical to SEQ ID NO:10. In some embodiments, a Klf4 polypeptide is a polypeptide having the above-mentioned functional properties, and comprising an amino acid sequence from at least 70% to less than 100% identical (e.g., 75%, 80%, 85%, 90%, 91%, 92%, 95%, 97%, 99% identical) to SEQ ID NO:10, e.g., SEQ ID NO:10 with at least one amino acid substitution, deletion, or insertion (e.g., 1 to 10 amino acid substitutions, deletions, or insertions).

In other embodiments, a Klf polypeptide is a polypeptide having the above-mentioned functional properties, and comprising the amino acid sequence of SEQ ID NO:10 with up to a total of 30 amino acid substitutions, deletions, insertions, or any combination thereof, e.g., SEQ ID NO:10 with 0, 1, 2, 3, 4, 5, 6, 7, 8, 9, 10, 11, 15, 20, 25, or any other number of amino acid substitutions, deletions, insertions, or any combination thereof, from 0 to 30.

SEQ ID NO:10 (Human Klf4):
MAVSDALLPSFSTFASGPAGREKTLRQAGAPNNRWREELSHMKRLPPVLP

GRPYDLAAATVATDLESGGAGAACGGSNLAPLPRRETEEFNDLLDLDFIL

SNSLTHYPESVAATVSSSASASSSSSPSSSGPASAPSTCSFTYPIRAGND

PGVAPGGTGGGLLYGRESAPPPTAPFNLADINDVSPSGGFVAELLRPELD

PVYWPPQQPQPPGGGLMGKFVLKASLSAPGSEYGSPSVISVSKGSPDGSH

PVVVAPYNGGPPRTCPKIKQEAVSSCTHLGAGPPLSNGHRPAAHDFPLGR

QLPSRTTPTLGLEEVLSSRDCHPALPLPPGFHPHPGPNYPSFLPDQMQPQ

VPPLHYQELMPPGSCMPEEPKPKRGRRSWPRKRTATHTCDYAGCGKTYTK

SSHLKAHLRTHTGEKPYHCDWDGCGWKFARSDELTRHYRKHTGHRPFQGQ

KGDRAFSRSDHLALHMKRHF

In some embodiments, a Klf4 polypeptide is a polypeptide having the above-mentioned functional properties, and comprising an amino acid sequence at least 70% identical to SEQ ID NO:11, e.g., 75%, 80%, 85%, 90%, 91%, 92%, 95%, 97%, 99%, or any other percent identical from at least 70% to 100% identical to SEQ ID NO:11, amino acids 382-469 of Human Klf4 comprising the highly conserved Zinc Finger motif DNA binding domain (ZF-DBD). In some embodiments, a Klf4 polypeptide is a polypeptide having the above-mentioned functional properties, and comprising an amino acid sequence from at least 70% to less than 100% identical (e.g., 75%, 80%, 85%, 90%, 91%, 92%, 95%, 97%, 99% identical) to SEQ ID NO:11, e.g., SEQ ID NO:11 with at least one amino acid substitution, deletion, or insertion (e.g., 1 to 5 amino acid substitutions, deletions, or insertions).

SEQ ID NO:11 (Human Klf4-ZF-DBD)
KRTAHTHTCDYAGCGKTYTKSSHLKAHLRTHTGEKPYHCDWDGCGWKFARS

DELTRHYRKHTGHRPFQCQKGDRAFSRSDHLALHMKRH

Klf4 polypeptides, as described herein, may include naturally occurring or non-naturally occurring homologs of human Klf4. Examples of naturally occurring homologs of human Klf4 include, but are not limited to, those listed under listed under GenBank Accession Nos: NP_001017280, NP_057354 (Klf2); AAP36222 (Klf5); NP_034767; and NP_446165, or any other Klf family members that meet the above-mentioned structural and functional criteria. Examples of non-naturally occurring Klf4 polypeptides include, but are not limited to, those having the above-mentioned functional properties and comprising an amino acid sequence at least 70%, e.g., 75%, 80%, 85%, 90%, or a percent from 70% to 100% identical to SEQ ID NO:10 or SEQ ID NO:11.

In some embodiments, a Klf4 polypeptide is a non-naturally occurring polypeptide having the above-mentioned functional properties.

pMUT analysis (described above) of the human Klf4 amino acid sequence (SEQ ID NO:10) based on a PSI-BLAST multiple alignment encompassing 136 sequences yields an ASM (Table 19) showing amino acid substitutions predicted to be deleterious or neutral to the protein's function. Functional assays for the ability of Klf4 polypeptides to bind to any of the above-mentioned target elements and to transactivate a promoter containing one or more of the target elements are known in the art as described in, e.g., Nakatake et al., (supra).

c-Myc Polypeptide

As referred to herein, a "c-Myc polypeptide" includes human c-Myc, mouse c-Myc, or any polypeptide that:
(i) includes a basic helix-loop-helix leucine zipper domain and binds to a target element comprising the sequence: 5'-CACGTG-3'; or 5'-C/GACCACGTGGTG/C-3' (SEQ ID NO: 18) and
(ii) is capable of transactivating a promoter comprising one or more of the above-mentioned target elements. See, e.g., Cowling et al., (2006), Seminars in Canc. Biol., 16:242-252.

In some embodiments, a c-Myc polypeptide is a polypeptide having the above-mentioned functional properties, and comprising an amino acid sequence at least 70% identical to SEQ ID NO:12 corresponding to the amino acid sequence of human c-Myc, i.e., myelocytomatosis viral oncogene homolog (GenBank Accession No. NP_002458), e.g., 75%, 80%, 85%, 90%, 91%, 92%, 95%, 97%, 99%, or any other percent identical from at least 70% to 100% identical to SEQ ID NO:12. In some embodiments, a c-Myc polypeptide is a polypeptide having the above-mentioned functional properties, and comprising an amino acid sequence from at least 70% to less than 100% identical (e.g., 75%, 80%, 85%, 90%, 91%, 92%, 95%, 97%, 99% identical) to SEQ ID NO:12, e.g., SEQ ID NO:12 with at least one amino acid substitution, deletion, or insertion (e.g., 1 to 10 amino acid substitutions, deletions, or insertions).

In other embodiments, a c-Myc polypeptide is a polypeptide having the above-mentioned functional properties, and comprising the amino acid sequence of SEQ ID NO:12 with up to a total of 30 amino acid substitutions, deletions, insertions, or any combination thereof, e.g., SEQ ID NO:12 with 0, 1, 2, 3, 4, 5, 6, 7, 8, 9, 10, 11, 15, 20, 25, or any other number of amino acid substitutions, deletions, insertions, or any combination thereof, from 0 to 30.

SEQ ID NO:12 (Human c-Myc):
MDFFRVVENQQPPATMPLNVSFTNRNYDLDYDSVQPYFYCDEEENFYQQ

QQQSELQPPAPSEDIWKKFELLPTPPLSPSRRSGLCSPSYVAVTPFSLR

GDNDGGGGSFSTADQLEMVTELLGGDMVNQSFICDPDDETFIKNIIIQD

CMWSGFSAAAKLVSEKLASYQAARKDSGSPNPARGHSVCSTSSLYLQDL

SAAASECIDPSVVFPYPLNDSSSPKSCASQDSSAFSPSSDSLLSSTESS

PQGSPEPLVLHEETPPTTSSDSEEEQEDEEEIDVVSVEKRQAPGKRSES

GSPSAGGHSKPPHSPLVLKRCHVSTHQHNYAAPPSTRKDYPAAKRVKLD

SVRVLRQISNNRKCTSPRSSDTEENVKRRTHNVLERQRRNELKRSFFAL

RDQIPELENNEKAPKVVILKKATAYILSVQAEEQKLISEEDLLRKRREQ

LKHKLEQLRNSCA

In some embodiments, a c-Myc polypeptide is a polypeptide having the above-mentioned functional properties, and comprising an amino acid sequence at least 70% identical to SEQ ID NO:13, e.g., 75%, 80%, 85%, 90%, 91%, 92%, 95%, 97%, 99%, or any other percent identical from at least 70% to 100% identical to SEQ ID NO:13, amino acids 370-454 of Human c-Myc comprising the highly conserved basic helix-loop-helix (bHLH)-leucine zipper (LZ) DNA binding domain. In some embodiments, a Klf4 polypeptide is a polypeptide having the above-mentioned functional properties, and comprising an amino acid sequence from at least 70% to less than 100% identical (e.g., 75%, 80%, 85%, 90%, 91%, 92%, 95%, 97%, 99% identical) to SEQ ID NO:13, e.g., SEQ ID NO:13 with at least one amino acid substitution, deletion, or insertion (e.g., 1 to 5 amino acid substitutions, deletions, or insertions).

SEQ ID NO:13 (Human c-Myc bHLH-LZ domain)
KRRTHNVLERQRRNELKRSFFALRDQIPELENNEKAPKVVILKKATAYI

LSVQAEEQKLISEEDLLRKRREQLKHKLEQLRNSCA c-Myc polypeptides, as described herein, may include naturally occurring or non-naturally occurring homologs of human c-Myc. Examples of naturally occurring homologs of human c-Myc include, but are not limited to, those listed under listed under GenBank Accession Nos: NP_001005154, NP_036735, NP_034979, P0C0N9, and NP_001026123, or any other c-Myc family members that meet the above-mentioned structural and functional criteria. Examples of non-naturally occurring homologs of human c-Myc include, but are not limited to, those described in, e.g., Chang et al., (2000), Mol Cell Biol., 20:4309-4319.

pMUT analysis (described above) of the human c-Myc amino acid sequence (SEQ ID NO:12) based on a PSI-BLAST multiple alignment encompassing 250 sequences yields an ASM (Table 20) showing amino acid substitutions predicted to be deleterious or neutral to the protein's function. Functional assays for the ability of c-Myc polypeptides to bind to any of the above-mentioned target elements and to transactivate a promoter containing one or more of the target elements are known in the art as described in, e.g., Gu et al., (1993), Proc. Natl. Acad. Sci. USA, 90:2935-2939.

In some cases, any of the Oct3/4, Sox2, Klf4, or c-Myc polypeptide DNA binding domains are fused to the Herpes VP16 transactivation domain to generate chimeric fusion proteins that can be used as induction factors in the induction methods described herein. In one embodiment the Herpes VP16 transactivation domain comprises the following amino acid sequence:

```
                                          (SEQ ID NO: 19)
TKTLMKKDKYTLPGGLLAPGGNSMASGVGVGAGLGAGVNQRMDSYAHMN

GWSNGSYSMMQDQLGYPQHSTTAPITDVSLGDELRLDGEEVDMTPADAL

DDFDLEMLGDVESPSPGMTHDPVSYGALDVDDFEFEQMFTDALGIDDF

GG
```

In some embodiments, any of the Oct 3/4, Sox2, Klf4, or c-Myc polypeptides, or combinations thereof are provided as polypeptide transduction compositions for use in the induction methods described herein. Such compositions contain at least one of the following:
(i) a purified 3/4Oct3/4 polypeptide comprising a protein transduction domain at the amino or carboxy terminus;
(ii) a carrier reagent and a purified 3/4Oct3/4 polypeptide;
(iii) a purified Sox2 polypeptide comprising a protein transduction domain and the amino acid sequence of a Sox2 polypeptide;
(iv) a carrier reagent and a purified Sox2 polypeptide;
(v) a purified Klf4 polypeptide comprising a protein transduction domain;
(vi) a carrier reagent and a purified Klf4 polypeptide;
(vii) a purified c-Myc polypeptide comprising a protein transduction domain
(viii) a carrier reagent and a purified c-Myc-polypeptide
(ix) any combination of (i) to (vi) where the composition is substantially free of a purified polypeptide comprising the amino acid of a c-Myc polypeptide.

In some embodiments, the protein transduction domain is fused to the amino terminal of an IF sequence. In other embodiments, the PTD domain is fused to the carboxy terminal of an IF sequence. In some embodiments, the IF-PTD fusion polypeptide is added to cells as a denatured polypeptide, which may facilitate its transport into cells where it is then renatured. The generation of PTD fusion proteins and methods for their use are known the art as described in, e.g., U.S. Pat. Nos. 5,674,980, 5,652,122, 6,881,825. See also, Becker-Hapak et al., (2003), *Curr. Protocols in Cell Biol.*, John Wiley & Sons, Inc. Exemplary PTD domain amino acid sequences include, but are not limited to, any of the following:

```
    YGRKKRRQRRR;        (SEQ ID NO:1)

RKKRRQRR;           (SEQ ID NO:2)

YARAAARQARA;        (SEQ ID NO:3)

THRLPRRRRRR;        (SEQ ID NO:4)
    and

GGRRARRRRRR.        (SEQ ID NO:5)
```

Examples of suitable carrier agents and methods for their use include, but are not limited to those described in U.S. Pat. No. 6,841,535.

G. Subcloning Induced Cell Colonies

Cell colonies may be subcloned, by any method known in the art, to obtain a pure population of human stem cells, which contains a higher proportion of the generated human stem cells relative to the total cell population than that found in the total cell population before purification. In some cases, the induced cells are cultured and observed for about 14 days to about 40 days, e.g., 15 days, 16 days, 17 days, 18 days, 19 days, 20 days, 23 days, 24 days, 27 days, 28 days, 29 days, 30 days, 31 days, 33 days, 34 days, 35 days, 36 days, 37 days, 38 days, or other period from about 14 days to about 40 days prior to identifying and selecting clones comprising "induced cells" based on morphological characteristics, as described herein. The induced cells may be cultured in a maintenance culture medium in a 37° C., 5% $CO_2$ incubator, with medium changes about every 1 to 2 days, preferably every day. Examples of maintenance culture media include any and all complete ES media (e.g., MC-ES). The maintenance culture medium may be supplemented with b-FGF or FGF2. In some cases, the maintenance culture medium is supplemented with other factors, e.g., IGF-II or Activin A.

After washing cell cultures with a physiological buffer, e.g., Hank's balanced salt solution, colonies displaying the morphological characteristics of interest are surrounded by a cloning ring coated with silicone grease on the bottom side. About 100 µl (or 50 µl to 150 µl) of "Detachment Medium For Primate ES Cells" (manufactured by ReproCELL, Tokyo Japan) may be then added to the cloning ring and incubated at 37° C. for about 20 minutes to form a cell suspension. The cell suspension in the ring containing the detached colonies may be added to about 2 ml of MC-ES medium (or other medium described herein), and plated in one well of a MEF-coated 24-well plate or other cell culture vessel of equivalent surface area. After culturing the colony-derived cells in a 5% $CO_2$ (atmospheric $O_2$) cell culture incubator at 37° C. for about 14 hours, the medium is replaced. Subsequently, the medium is replaced about every two days until about 8 days later when a second subculture is carried out.

In some embodiments, in the first subculture, the medium is removed, the cells are washed with Hank's balanced salt solution, and Detachment Medium For Primate ES Cells (ReproCell, Tokyo, Japan) is then added to the cells and incubated at 37° C. for 10 minutes. After the incubation, MC-ES medium (2 ml) is added to the resulting cell suspension to quench the activity of the Detachment Medium. The cell suspension is then transferred to a centrifuge tube, and centrifuged at 200×g at 4° C. for 5 minutes. The supernatant is removed, the cell pellet is resuspended in MC-ES medium, and the resuspended cells are plated on four wells of a MEF-coated 24-well plate and cultured for about seven days until a second subculture is prepared.

In the second subculture, prepared by the method described above, cells are plated on a 60 mm cell culture dish coated with Matrigel™ at a concentration of 20 µg/cm2. About eight days later (approximately 5 weeks after initiating forced expression of IFs), a third subculture is prepared in which cells are plated on two Matrigel™-coated 60 mm cell culture dishes, one of which can subsequently be used for gene expression analysis and the other for continued passaging as described below. One of the subcultures is used for gene expression analysis, as described herein, and the other is passaged as needed to maintain a cell line derived from the induced cell clone.

H. Passaging and Maintaining Induced Cells

After subcloning, the induced cells may be subcultured about every 5 to 7 days. In some cases, the cells are washed with Hank's balanced salt solution, and dispase or Detachment Medium For Primate ES Cells is added, and incubated at 37° C. for 5 to 10 minutes. When approximately more than half of the colonies are detached, MC-ES medium is added to quench enzymatic activity of the detachment medium, and the resulting cell/colony suspension is transferred to a centrifuge tube. Colonies in the suspension are allowed to settle on the bottom of the tube, the supernatant is carefully removed, and MC-ES medium is then added to resuspend the colonies. After examining the size of the colonies, any extremely large ones are broken up into smaller sizes by slow up and down pipetting. Appropriately sized colonies are plated on a matrigel-coated plastic culture dish with a base area of about 3 to 6 times that before subculture. For example, the cells may be split from about 1:6 to about 1:3, e.g., about 1:6, 1:5, 1:4, or 1:3.

Examples of culture media useful for culturing human pluripotent stem cells induced from undifferentiated stem cells present in a human postnatal tissue of the present invention include, but are not limited to, the ES medium, and a culture medium suitable for culturing human ES cells such as MEF-conditioned ES medium (MC-ES) or other medium described herein, e.g., mTeSR1™. In some examples, the cells are maintained in the presence of a ROCK inhibitor, as described herein.

IV. ANALYSIS OF INDUCED CELLS

Cell colonies subcultured from those initially identified on the basis of morphological characteristics may be assayed for any of a number of properties associated with pluripotent stem cells, including, but not limited to, expression of ALP activity, expression of ES cell marker genes, expression of protein markers, hypomethylation of Oct3/4 and Nanog promoters relative to a parental cells, long term self-renewal, normal diploid karyotype, and the ability to form a teratoma comprising ectodermal, mesodermal, and endodermal tissues.

A number of assays and reagents for detecting ALP activity in cells (e.g., in fixed cells or in living cells) are known in the art. In an exemplary embodiment, colonies to be analyzed are fixed with a 10% formalin neutral buffer solution at room temperature for about 5 minutes, e.g., for 2 to 5 minutes, and then washed with PBS. A chromogenic substrate of ALP, 1 step BCIP (5-Bromo-4-Chloro-3'-Indolyphosphate p-Toluidine Salt) and NBT (Nitro-Blue Tetrazolium Chloride) manufactured by Pierce (Rockford, Ill.) is then added and reacted at room temperature for 20 to 30 minutes. Cells having ALP activity are stained blue-violet.

Putative iPS cell colonies tested for ALP activity may then be assayed for expression of a series of human embryonic stem cell marker (ESCM) genes including, but not limited to, Nanog, TDGF1, Dnmt3b, Zfp42, FoxD3, GDF3, CYP26A1, TERT, Oct 3/4, Sox2, Sall4, and HPRT. See, e.g., Assou et al., (2007), *Stem Cells,* 25:961-973. Many methods for gene expression analysis are known in the art. See, e.g., Lorkowski et al., (2003), *Analysing Gene Expression, A Handbook of Methods: Possibilities and Pitfalls,* Wiley-VCH. Examples of suitable nucleic acid-based gene expression assays include, but are not limited to, quantitative RT-PCR (qRT-PCR), microarray hybridization, dot blotting, RNA blotting, RNAse protection, and SAGE.

In some embodiments, levels of ESCM gene mRNA expression levels in putative iPS cell colonies are determined by qRT-PCR. Putative iPS cell colonies are harvested, and total RNA is extracted using the "Recoverall total nucleic acid isolation kit for formaldehyde- or paraformaldehyde-fixed, paraffin-embedded (FFPE) tissues" (manufactured by Ambion, Austin, Tex.). In some instances, the colonies used for RNA extraction are fixed colonies, e.g., colonies that have been tested for ALP activity. The colonies can be used directly for RNA extraction, i.e., without prior fixation. In an exemplary embodiment, after synthesizing cDNA from the extracted RNA, the target gene is amplified using the TaqMan® PreAmp mastermix (manufactured by Applied Biosystems, Foster City, Calif.). Real-time quantitative PCR is performed using an ABI Prism 7900HT using the following PCR primer sets (from Applied Biosystems) for detecting mRNA of the above-mentioned ESCM genes: Nanog, Hs02387400_g1, Dnmt3b, Hs00171876_m1, FoxD3, Hs00255287_s1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1).

Putative iPS cell colonies may be assayed by an immunocytochemistry method for expression of protein markers including, but not limited to, SSEA-3, SSEA4, TRA-1-60, TRA-1-81, CD9, CD24, Thy-1, and Nanog. A wide range of immunocytochemistry assays, e.g., fluorescence immunocytochemistry assays, are known as described in, e.g., Harlow et al., (1988), *Antibodies: A Laboratory Manual* 353-355, Cold Spring Harbor Laboratory, Cold Spring Harbor, N.Y., and see also, *The Handbook—A Guide to Fluorescent Probes and Labeling Technologies* (2004), Molecular Probes, Inc., Eugene, Oreg.

In an exemplary embodiment, expression of one or more of the above-mentioned protein markers in putative iPS cell colonies is assayed as follows. Cultured cells are fixed with 10% formaldehyde for 10 min and blocked with 0.1% gelatin/PBS at room temperature for about an hour. The cells are incubated overnight at 4° C. with primary antibodies against SSEA-3 (MC-631; Chemicon), SSEA-4 (MC813-70; Chemicon), TRA-1-60 (ab16288; abcam), TRA-1-81 (ab16289; abcam), CD9 (M-L13; R&D systems), CD24 (ALB9; abcam), Thy1 (5E10; BD Bioscience), or Nanog (MAB1997; R&D Systems). For Nanog staining, cells are permeabilized with 0.1% Triton X-100/PBS before blocking. The cell colonies are washed with PBS three times, then incubated with AlexaFluor 488-conjugated secondary antibodies (Molecular Probes) and Hoechst 33258 (Nacalai) at room temperature for 1 h. After further washing, fluorescence is detected with a fluorescence microscope, e.g., Axiovert 200M microscope (Carl Zeiss).

A. Methylation Analysis

In some embodiments, a characteristic of the induced cells is reduced methylation of the genomic promoters of Oct3/4 and Nanog relative to those of their parental cells. Suitable Oct3/4 promoter regions to be analyzed include, but are not limited to, the Oct3/4 proximal promoter including conserved region 1 (CR1) and the Oct3/4 promoter distal enhancer including CR4. Suitable Nanog promoter regions to be analyzed include, but are not limited to, the Nanog proximal promoter including the Oct3/4 and Sox2 binding sites. See, e.g., Rodda et al., (2005), *J. Biol. Chem.,* 280:24731-24737 and Yang et al., (2005), *J Cell Biochem.,* 96:821-830. A number of methods for the quantitative analysis of genomic DNA are known as described in, e.g., Brena et al., (2006), *J Mol. Med.,* 84(5):365-377. In an exemplary embodiment, genomic DNA isolated from putative induced cells and cells used for a comparison is isolated and treated with bisulfite. Bisulfite-treated genomic DNA is then PCR-amplified with primers containing a T7 promoter sequence. Afterwards, RNA transcripts are generated using T7 polymerase and then treated with RNAse A to generate methylation-specific cleavage products. Methylation of individual CpG sites is assessed by MALDI-TOF mass spectrometry of the cleavage products. A detailed description of the method is provided in, e.g., Ehich et al., (2005), *Proc. Natl. Acad. Sci. USA,* 102:15785-15790.

B. Self-Renewal Assay

One of the characteristics of stem cells is their ability to proliferate continuously without undergoing senescence. Accordingly, induced cells are assessed for their ability to be passaged continuously in vitro. In some cases, the induced cells are assayed for their ability to be passaged for at least about 30 to at least about 100 times in vitro, e.g., about 33, 35, 40, 45, 51, 56, 60, 68, 75, 80, 90, 93, 100, or any other number of passages from at least about 30 to at least about 100 passages.

In another evaluation, induced cells are assayed for their ability to proliferate for a period of about 30 days to about 500 days from initiation of forced expression of IFs in parental cells, e.g., 40 days, 50 days, 60 days, 70 days, 80 days, 100 days, 150 days, 180 days, 200 days, 250 days, 300 days, 400 days, 450 days or any other period from about 30 days to about 500 days from initiation of forced expression of IFs in the parental cells. In some embodiments, long-term self-renewal of induced cells is determined when the cells are passaged in a defined medium (e.g., mTeSR1 medium) and in the absence of feeder cells, e.g., mTeSR1 medium as described herein. In other embodiments, cells are passaged in MC-ES medium as described herein.

C. Karyotype Analysis

As another possible analysis, induced cells are assessed for diploidy and a normal, stable karyotype, e.g., stable after the cells of have been passaged for at least one year in vitro. A number of karotype analysis methods are known in the art. In some embodiments, the karyotype analysis method is multi-color FISH as described in, e.g., Bayani et al., (2004), *Curr. Protoc. Cell Biol.*, Chapter 22:Unit 22.5. In other embodiments, the karyotype analysis includes a molecular karyotype analysis as described in, e.g., Vermeesch et al., (2007), *Eur. J. Hum. Genet.*, 15(11):1105-1114. In an exemplary embodiment, induced cells are pretreated with 0.02 µg/ml colecemid for about 2 to about 3 hours, incubated with about 0.06 to about 0.075M KCl for about 20 minutes, and then fixed with Carnoy's fixative. Afterwards, for multicolor FISH analysis, cells are hybridized with multicolor FISH probes, e.g., those in the Star*FISH® Human Multicolour FISH (M-FISH) Kit from Cambio, Ltd (Cambridge, UK).

D. Teratoma Analysis

It is generally believed that pluripotent stem cells have the ability to form a teratoma, comprising ectodermal, mesodermal, and endodermal tissues, when injected into an immunocompromised animal. Induced cells or induced pluripotent stem cells (iPS) or ES cell-like pluripotent stem cells may refer to cells having an in vitro long-term self-renewal ability and the pluripotency of differentiating into three germ layers, and said pluripotent stem cells may form a teratoma when transplanted into a test animal such as mouse.

The induced cells may be assessed for pluripotency in a teratoma formation assay in an immunocompromised animal model. The immunocompromised animal may be a rodent that is administered an immunosuppressive agent, e.g., cyclosporin or FK-506. For example, the immunocompromised animal model may be a SCID mouse. About $0.5 \times 10^6$ to about $2.0 \times 10^6$, e.g., $0.6 \times 10^6$, $0.8 \times 10^6$, $1.0 \times 10^6$, $1.2 \times 10^6$, $1.5 \times 10^6$, $1.7 \times 10^6$, or other number of induced cells from about $0.5 \times 10^6$ to about $2.0 \times 10^6$ induced cells/mouse may be injected into the medulla of a testis of a 7- to 8-week-old immunocompromised animal. After about 6 to about 8 weeks, the teratomas are excised after perfusing the animal with PBS followed by 10% buffered formalin. The excised teratomas are then subjected to immunohistological analysis. One method of distinguishing human teratoma tissue from host (e.g., rodent) tissue includes immunostaining for the human-specific nuclear marker HuNu. Immunohistological analysis includes determining the presence of ectodermal (e.g., neuroectodermal), mesodermal, and endodermal tissues. Protein markers for ectodermal tissue include, but are not limited to, nestin, GFAP, and integrin β1. Protein markers for mesodermal tissue include, but are not limited to, collagen II, Brachyury, and osteocalcin. Protein markers for endodermal tissue include, but are not limited to, α-fetoprotein (α-FP) and HNF3beta.

E. Gene Expression

In some embodiments, gene expression analysis is performed on putative iPS cell colonies. Such gene expression analysis may include a comparison of gene expression profiles from a putative iPS cell colony with those of one or more cell types, including but not limited to, (i) parental cells, i.e., one or more cells from which the putative iPS cell colony was induced; (ii) a human ES cell line; or (iii) an established iPS cell line. As known in the art, gene expression data for human ES cell lines are available through public sources, e.g., on the world wide web in the NCBI "Gene Expression Omnibus" database. See, e.g., Barrett et al., (2007), *Nuc. Acids Research*, D760-D765. Thus, in some embodiments, comparison of gene expression profiles from a putative iPS colony to those of an ES cell line entails comparison experimentally obtained data from a putative iPS cell colony with gene expression data available through public databases. Examples of human ES cell lines for which gene expression data are publicly available include, but are not limited to, hE14 (GEO data set accession numbers GSM151739 and GSM151741), Sheff4 (GEO Accession Nos GSM194307, GSM194308, and GSM193409), h_ES 01 (GEO Accession No. GSM194390), h_ES H9 (GEO Accession No. GSM194392), and h_ES BG03 (GEO Accession No. GSM194391).

It is also possible to accomplish gene expression by analyzing the total RNA isolated from one or more iPS cell lines by a nucleic acid microarray hybridization assay. Examples of suitable microarray platforms for global gene expression analysis include, but are not limited to, the Human Genome U133 plus 2.0 microarray (Affymetrix) and the Whole Human Genome Oligo Micoarray (Agilent). A number of analytical methods for comparison of gene expression profiles are known as described in, e.g., Suarez-Farinas et al., (2007), *Methods Mol. Biol.*, 377:139-152, Hardin et al., (2007), *BMC Bioinformatics*, 8:220-232, Troyanskaya et al., (2002), *Bioinformatics*, 18(11): 1454-1461, and Knudsen (2002), *A Biologist's Guide to Analysis of DNA Microarray Data*, John Wiley & Sons. In some embodiments, gene expression data from cells produced by the methods described herein are compared to those obtained from other cell types including, but not limited to, human ES cell lines, parental cells, and multipotent stem cell lines. Suitable statistical analytical metrics and methods include, but are not limited to, the Pearson Correlation, Euclidean Distance, Hierarchical Clustering (See, e.g., Eisen et al., (1998), *Proc. Natl. Acad. Sci. USA,* 95(25):14863-14868), and Self Organizing Maps (See, e.g., Tamayo et al., (1999), *Proc. Natl. Acad. Sci. USA,* 96(6):2907-2912.

V. DESCRIPTION OF INDUCED CELLS

The induced cells may share certain properties associated with pluripotent or multipotent stem cells, including, but not limited to: expression of ALP activity, expression of ES cell marker genes, expression of protein markers, higher or lower expression of genetic markers compared to ES cells or parental cells, hypomethylation of certain promoters (e.g., Oct3/4 and Nanog) relative to parental cells, long-term self-renewal ability, normal diploid karyotype, morphological characteristics and the ability to form a teratoma comprising ectodermal, mesodermal, and endodermal tissue. The compositions of induced cells may include the cells and another component such as a supplement to culture medium.

The induced cells may be positive for alkaline phosphatase (ALP) activity. They may express ALP and express from 2 to 10 (e.g., 3, 4, 5, 6, 7, 8, 9, or 10) of the following ES cell marker genes: TDGF1, Dnmt3b, FoxD3, GDF3, Cyp26a1, TERT, Zfp42, Sox2, Oct 3/4, and Nanog. In some cases, the induced cells express Tert or Cyp26a1. In some cases, the induced cells express both Tert and Cyp26a1. In some cases, the induced cells are positive for ALP activity, and express all of the foregoing ES-cell marker genes. In some cases, the induced cells are positive for ALP activity and express Nanog. In some cases, the induced cells are positive for ALP activity and express one or more: TERT, CYP26A1, or GDF3. In some cases, the induced cells are positive for ALP activity and express one or more: Nanog, TDGF, and Dnmt3b.

The induced cells may express two or more of the following marker proteins: SSEA-3, SSEA4, TRA-1-60, TRA-1-81, CD9, CD24, or Thy-1. In some cases, the induced cells express all of the foregoing marker proteins. In exemplary embodiments, the human pluripotent stem cells express cell surface antigens SSEA-3, SSEA-4, TRA-1-60, TRA-1-81, CD9, CD24, and CD90, and ES cell marker genes Nanog, Oct3/4, TDGF1, Dnmt3b, GABRB3, GDF3, Zfp42, ALP, CD9, and Thy-1.

The induced cells may exhibit a difference in the expression level, e.g., a higher or lower expression level, of one or more genes (e.g., endogenous genes), compared to the expression levels of those genes in one or more embryonic stem cells, e.g., a human embryonic stem cell. Preferably, differences in gene expression are statistically significant by one or more statistical tests (e.g., Student's t-test or other parametric or non-parametric tests). For example, the difference in expression may have a p value of less than or equal to 0.05, less than or equal to 0.01, or less or equal to 0.001.

The number of genes exhibiting different expression levels in the induced cells and embryonic stem cells, can be, e.g., 1 to 1000 genes, 1 to 700 genes, 1 to 500 genes, 1 to 300 genes, 1 to 200 genes, 1 to 100 genes, 1 to 50 genes, 3 to 20 genes, 5 to 20 genes, 5 to 50 genes, 10 to 50 genes, 20 to 50 genes, 30 to 100 genes, or 50 to 100 genes, 1 or more genes, 2 or more genes, 3 or more genes, 5 or more genes, 10 or more genes, 15 or more genes, 20 or more genes, 50 or more genes, 70 or more genes, or 100 or more genes, 500 or more genes, 1000 or more genes, 9 genes, 12 genes, 42 genes, 70 genes, or 100 genes. The differences in gene expression levels may be at least 2 fold, e.g., at least 3 fold, 4 fold, 5 fold, 6 fold, 7 fold, 10 fold, 2 to 50 fold, 2 to 30 fold, 2 to 20 fold, 2 to 10 fold, or 2 to 5 fold.

In some cases, the genes exhibiting different expression levels in the induced cells and embryonic stem cells exhibit a higher level of expression in the induced cells than in human embryonic stem cells. In some cases, the genes expressing the higher level of expression in the induced cells are 1 or more, 2 or more, 3 or more, 4 or more, 5 or more, 10 or more, 15 or more, 25 or more, 50 or more, 75 or more, 100 or more, or 200 or more of the genes listed in Tables 13, 15, or 16. In some cases, the genes exhibiting a different expression level from in the induced cells compared to the embryonic stem cells are expressed at a higher level in human embryonic stem cells compared to the induced cells. In some cases, the genes expressed at a higher level in human embryonic stem cells are a 1 or more, 2 or more, 3 or more, 4 or more, 5 or more, 10 or more, 15 or more, 25 or more, 50 or more, 75 or more, 100 or more, or 200 or more of the genes listed in Table 14.

In certain cases, a gene or a set of genes exhibits a higher expression level in the induced cells when compared to embryonic stem cells and when compared to the parental cells, e.g., fibroblasts. For example, the genes exhibiting higher expression in the induced cells than in both embryonic stem cells and parental cells are 1 or more, 2 or more, 3 or more, 4 or more, 5 or more, 10 or more, 15 or more, 25 or more, 50 or more, 75 or more, 100 or more, or 200 or more of the genes listed in Table 15.

A gene or set of genes may be expressed in the induced cells at a level that is closer to the expression level in parental cells (e.g., fibroblasts) than its expression level in embryonic stem cells. A gene or set of genes may, for example, exhibit a higher expression level in the induced cells when compared to embryonic stem cells but not when compared to parental cells, e.g., fibroblasts. Genes. exhibiting higher expression level in the induced cells than in embryonic cells but not the parental cells may be 1 or more, 2 or more, 3 or more, 4 or more, 5 or more, 10 or more, 15 or more, 25 or more, 50 or more, 75 or more, 100 or more, or 200 or more of the genes listed in Table 16.

The lengths of the telomeres within the induced cells may be shorter than that of telomeres at the ends of chromosomes within embryonic stem cells. In some cases, the telomeres in the induced cells are at least 0.1 kB, at least 0.25 kB, at least 0.5 kB, at least 1 kB, at least 2 kB, at least 3 kB, at least 4 kB, or at least 5 kB shorter than telomeres within embryonic stem cell lines. In certain instances, the induced cells have telomeres that are shorter than at least 1, at least 2, at least 3, at least 4, at least 5, at least 6, at least 8, at least 10, or at least 15 embryonic stem cell lines.

The induced cells may comprise exogenous genes (or transgenes) encoding IFs. The induced cells may comprise exogenous genes encoding any set of IFs described herein. For example, the induced cells may comprise four exogenous genes encoding Oct 3/4, Sox2, Klf4, and c-Myc polypeptides. In some cases, the induced cells comprise four exogenous genes encoding Oct 3/4, Sox2, Klf4, and c-Myc polypeptides, but not other exogenous genes encoding induction factors. In other cases, the induced cells may comprise exogenous genes encoding Oct 3/4, Sox2, and Klf4 polypeptides, but not an exogenous gene encoding a c-Myc polypeptide. In some cases, the induced cells contain exogenous genes consisting essentially of three genes encoding Oct 3/4, Sox2, and Klf4 polypeptides. In some cases, the human pluripotent stem cells carry at least a single copy of exogenous genes encoding Oct3/4, Sox2, Klf4, and c-Myc. In some cases, any of the induced cells containing exogenous genes also contain an exogenous gene encoding a polypeptide comprising the amino acid sequence of mouse-derived cationic transporter 1 (mCAT-1), a receptor for ecotropic retroviruses.

At some point after introduction of exogenous genes, one or more of the exogenous genes may be silenced. In some cases, the Oct3/4 exogenous gene is silenced; the Klf4 exogenous gene is silenced; the Sox2 exogenous gene is silenced; or the c-Myc transgene is silenced. In some cases, all four exogenous genes (e.g., Oct3/4; Sox2; Klf4; and c-Myc) are silenced. In some cases, all three exogenous genes (e.g., Oct3/4; Sox2; and Klf4) are silenced.

The induced cells may share all of the identifying characteristics of induced pluripotent stem (iPS) cell lines: 1-8; 24; or 3-2, described herein. Cell line iPS 1-8 is deposited with the International Patent Organism Depositary (IPOD) in compliance with the terms of the Budapest Treaty. The certificate number for the deposit is FERM BP-10956. The address of IPOD is as follows:
International Patent Organism Depositary (IPOD)
AIST Tsukuba Central 6
1-1, Higashi 1-chome
Tsukuba-shi, Ibaraki-Ken 305-8566
Japan In some cases, human pluripotent or multipotent stem cells are induced from undifferentiated stem cells present in a human postnatal tissue in which the Tert, Nanog, Oct3/4 and Sox2 genes have not undergone epigenetic inactivation. In some cases, the cells are induced from differentiated cells present in tissue or from a combination of differentiated and undifferentiated cells present in tissue.

The promoter regions of Nanog and Oct3/4 in the induced cells may be hypo- or de-methylated compared to the parental fibroblasts. The induced cells may be stem cells that have long-term self-renewal ability when cultured under human ES cell-culture conditions.

One of the characteristics of stem cells is their ability to proliferate continuously without undergoing senescence. Accordingly, induced cells may be passaged continuously in vitro. In some cases, the induced cells are able to be passaged for at least about 30 to at least about 100 times in vitro, e.g., about 33, 35, 40, 45, 51, 56, 60, 68, 75, 80, 90, 93, 100, or other number of passages from at least about 30 to at least about 100 passages. The induced cells may be able to proliferate for a period of about 30 days to about 500 days from initiation of forced expression of IFs in parental cells, e.g., 40 days, 50 days, 60 days, 70 days, 80 days, 100 days, 150 days, 180 days, 200 days, 250 days, 300 days, 400 days, 450 days, or other number of days from about 30 to about 500 days. In some embodiments, the induced cells proliferate for greater than 500 days.

Typically, the induced cells are able to proliferate with an undifferentiated phenotype under atmospheric oxygen conditions, (e.g., about 21% oxygen). In other cases, the induced cells proliferate as undifferentiated cells under oxygen conditions ranging from greater than 5% oxygen to about 21% oxygen. Generally, the induced cells proliferate in colonies.

The induced cells may have in vitro pluripotency capabilities, such as the ability to differentiate into ectoderm, mesoderm and endoderm under conditions for inducing in vitro differentiation of human ES cells; and such cells may further have a potential of differentiating into primordial germ cells (e.g., sperm, oocytes).

In some cases, the induced human pluripotent stem cells and the parental cells (e.g., undifferentiated stem cells present in a human postnatal tissue) have identical or almost identical SNP genotypes. In some cases, the induced cells and the parental cells have the same HLA type (e.g., HLA-A, B, Cw, DR, DQ, DP, and Bw).

The compositions provided herein may include other components in addition to the induced cells, or in addition to the cells differentiated from the induced cells. In some cases, the composition comprises such cells and a cryopreservative agent, e.g., a cryopreservation medium described in, U.S. patent application Ser. Nos. 10/902,571; 11/142,651; or in Ha et al., (2005), *Hum. Reprod.,* 20(7):1779-1785.

The composition may comprise such cells and a culture medium, e.g., human ES culture medium. In some cases, the culture medium is a medium comprised of one or more growth factors, for example: FGF-2, bFGF, PDGF, EGF, IGF, or derivatives thereof. In some examples, the composition comprises human induced pluripotent or multipotent stem cells and a medium comprising FGF-2 or bFGF or derivatives thereof. In other instances, the composition comprises human induced pluripotent or multipotent stem cells and a medium comprising human ES culture medium and FGF-2 or bFGF, or derivatives thereof. In still another example, the composition comprises human induced pluripotent or multipotent stem cells and MC-ES medium described herein.

In some cases, the concentration of bFGF or FGF2 in the culture medium is from 2 ng/ml to about 50 ng/ml, e.g., about 2 ng/ml, 3 ng/ml, 4 ng/ml, 5 ng/ml, 6 ng/ml, 7 ng/ml, 8 ng/ml, 10 ng/ml, 12 ng/ml, 14 ng/ml, 15 ng/ml, 17 ng/ml, 20 ng/ml, 25 ng/ml, 30 ng/ml, 35 ng/ml, 40 ng/ml, 45 ng/ml, 50 ng/ml. The concentration of bFGF or FGF2 may also be from about 4 ng/ml to about 10 ng/ml; from about 4 ng/ml to about 20 ng/ml; from about 10 ng/ml to about 30 ng/ml; from about 5 ng/ml to about 40 ng/ml; or from about 10 ng/ml to about 50 ng/ml. In other cases, higher concentrations of bFGF or FGF2 may be used, e.g., from about 50 ng/ml to about 100 ng/ml; from about 50 ng/ml to about 75 ng/ml. Similarly, the culture medium can contain growth factors other than bFGF or FGF2 that are concentrations from about 2 ng/ml to about 100 ng/ml, as described herein.

VI. CELL DIFFERENTIATION

The induced cells may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

The differentiated cells derived from the induced cells may be terminally differentiated cells, or they may be capable of giving rise to cells of a specific lineage. For example, induced cells can be differentiated into a variety of multipotent cell types, e.g., neural stem cells, cardiac stem cells, or hepatic stem cells. The stem cells may then be further differentiated into new cell types, e.g., neural stem cells may be differentiated into neurons; cardiac stem cells may be differentiated into cardiomyocytes; and hepatic stem cells may be differentiated into hepatocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

Any known method of generating neural stem cells from ES cells may be used to generate neural stem cells from induced cells, See, e.g., Reubinoff et al., (2001), *Nat, Biotechnol.,* 19(12): 1134-40. For example, neural stem cells may be generated by culturing the induced cells as floating aggregates in the presence of noggin, or other bone morphogenetic protein antagonist, see e.g., Itsykson et al., (2005), *Mol, Cell Neurosci.,* 30(1):24-36. In another example, neural stem cells may be generated by culturing the induced cells in suspension to form aggregates in the presence of growth factors, e.g., FGF-2, Zhang et al., (2001), *Nat. Biotech.,* (19): 1129-1133. In some cases, the aggregates are cultured in serum-free medium containing FGF-2. In another example, the induced cells are co-cultured with a mouse stromal cell line, e.g., PA6 in the presence of serum-free medium comprising FGF-2. In yet another example, the induced cells are directly transferred to serum-free medium containing FGF-2 to directly induce differentiation.

Neural stems derived from the induced cells may be differentiated into neurons, oligodendrocytes, or astrocytes. Often, the conditions used to generate neural stem cells can also be used to generate neurons, oligodendrocytes, or astrocytes.

Dopaminergic neurons play a central role in Parkinson's Disease and other neurodegenerative diseases and are thus of particular interest. In order to promote differentiation into dopaminergic neurons, induced cells may be co-cultured with a PA6 mouse stromal cell line under serum-free conditions, see, e.g., Kawasaki et al., (2000) *Neuron*, 28(1):3140. Other methods have also been described, see, e.g., Pomp et al., (2005), *Stem Cells* 23(7):923-30; U.S. Pat. No. 6,395,546, e.g., Lee et al., (2000), *Nature Biotechnol.*, 18:675-679

Oligodendrocytes may also be generated from the induced cells. Differentiation of the induced cells into oligodendrocytes may be accomplished by known methods for differentiating ES cells or neural stem cells into oligodendrocytes. For example, oligodendrocytes may be generated by co-culturing induced cells or neural stem cells with stromal cells, e.g., Hermann et al. (2004), *J Cell Sci.* 117(Pt 19):4411-22. In another example, oligodendrocytes may be generated by culturing the induced cells or neural stem cells in the presence of a fusion protein, in which the Interleukin (IL)-6 receptor, or derivative, is linked to the IL-6 cytokine, or derivative thereof. Oligodendrocytes can also be generated from the induced cells by other methods known in the art, see, e.g. Kang et al., (2007) *Stem Cells* 25, 419-424.

Astrocytes may also be produced from the induced cells. Astrocytes may be generated by culturing induced cells or neural stem cells in the presence of neurogenic medium with bFGF and EGF, see e.g., Brustle et al., (1999), *Science*, 285:754-756.

Induced cells may be differentiated into pancreatic beta cells by methods known in the art, e.g., Lumelsky et al., (2001) *Science*, 292:1389-1394; Assady et al., (2001), *Diabetes*, 50:1691-1697; D'Amour et al., (2006), *Nat. Biotechnol.*, 24:1392-1401; D'Amour et al., (2005), *Nat. Biotechnol.* 23:1534-1541. The method may comprise culturing the induced cells in serum-free medium supplemented with Activin A, followed by culturing in the presence of serum-free medium supplemented with all-trans retinoic acid, followed by culturing in the presence of serum-free medium supplemented with bFGF and nicotinamide, e.g., Jiang et al., (2007), *Cell Res.*, 4:333-444. In other examples, the method comprises culturing the induced cells in the presence of serum-free medium, activin A, and Wnt protein from about 0.5 to about 6 days, e.g., about 0.5, 1, 2, 3, 4, 5, 6, days; followed by culturing in the presence of from about 0.1% to about 2%, e.g., 0.2%, FBS and activin A from about 1 to about 4 days, e.g., about 1, 2, 3, or 4 days; followed by culturing in the presence of 2% FBS, FGF-10, and KAAD-cyclopamine (keto-N-aminoethylaminocaproyl dihydro cinnamoylcyclopamine) and retinoic acid from about 1 to about 5 days, e.g., 1, 2, 3, 4, or 5 days; followed by culturing with 1% B27, gamma secretase inhibitor and extendin-4 from about 1 to about 4 days, e.g., 1, 2, 3, or 4 days; and finally culturing in the presence of 1% B27, extendin-4, IGF-1, and HGF for from about 1 to about 4 days, e.g., 1, 2, 3, or 4 days.

Hepatic cells or hepatic stem cells may be differentiated from the induced cells. For example, culturing the induced cells in the presence of sodium butyrate may generate hepatocytes, see e.g., Rambhatla et al., (2003), *Cell Transplant*, 12:1-11. In another example, hepatocytes may be produced by culturing the induced cells in serum-free medium in the presence of Activin A, followed by culturing the cells in fibroblast growth factor-4 and bone morphogenetic protein-2, e.g., Cai et al., (2007), *Hepatology*, 45(5): 1229-39. In an exemplary embodiment, the induced cells are differentiated into hepatic cells or hepatic stem cells by culturing the induced cells in the presence of Activin A from about 2 to about 6 days, e.g., about 2, about 3, about 4, about 5, or about 6 days, and then culturing the induced cells in the presence of hepatocyte growth factor (HGF) for from about 5 days to about 10 days, e.g., about 5, about 6, about 7, about 8, about 9, or about 10 days.

The induced cells may also be differentiated into cardiac muscle cells. Inhibition of bone morphogenetic protein (BMP) signaling may result in the generation of cardiac muscle cells (or cardiomyocytes), see, e.g., Yuasa et al., (2005), *Nat. Biotechnol.*, 23(5):607-11. Thus, in an exemplary embodiment, the induced cells are cultured in the presence of noggin for from about two to about six days, e.g., about 2, about 3, about 4, about 5, or about 6 days, prior to allowing formation of an embryoid body, and culturing the embryoid body for from about 1 week to about 4 weeks, e.g., about 1, about 2, about 3, or about 4 weeks.

In other examples, cardiomyocytes may be generated by culturing the induced cells in the presence of leukemia inhibitory factor (LIF), or by subjecting them to other methods known in the art to generate cardiomyocytes from ES cells, e.g., Bader et al., (2000), *Circ. Res.*, 86:787-794, Kehat et al., (2001), *J. Clin. Invest.*, 108:407-414; Mummery et al., (2003), *Circulation*, 107:2733-2740.

Examples of methods to generate other cell-types from induced cells include: (1) culturing induced cells in the presence of retinoic acid, leukemia inhibitory factor (LIF), thyroid hormone (T3), and insulin in order to generate adipocytes, e.g., Dani et al., (1997), *J. Cell Sci.*, 110:1279-1285; (2) culturing induced cells in the presence of BMP-2 or BMP4 to generate chondrocytes, e.g., Kramer et al., (2000), *Mech. Dev.*, 92:193-205; (3) culturing the induced cells under conditions to generate smooth muscle, e.g., Yamashita et al., (2000), *Nature*, 408:92-96; (4) culturing the induced cells in the presence of beta-1 integrin to generate keratinocytes, e.g., Bagutti et al., (1996), *Dev. Biol.*, 179:184-196; (5) culturing the induced cells in the presence of Interleukin-3 (IL-3) and macrophage colony stimulating factor to generate macrophages, e.g., Lieschke and Dunn (1995), *Exp. Hemat.*, 23:328-334; (6) culturing the induced cells in the presence of IL-3 and stem cell factor to generate mast cells, e.g., Tsai et al., (2000), *Proc. Natl. Acad. Sci. USA*, 97:9186-9190; (7) culturing the induced cells in the presence of dexamethasone and stromal cell layer, steel factor to generate melanocytes, e.g., Yamane et al., (1999), *Dev. Dyn.*, 216:450-458; (8) co-culturing the induced cells with fetal mouse osteoblasts in the presence of dexamethasone, retinoic acid, ascorbic acid, beta-glycerophosphate to generate osteoblasts, e.g., Buttery et al., (2001), *Tissue Eng.*, 7:89-99; (9) culturing the induced cells in the presence of osteogenic factors to generate osteoblasts, e.g., Sottile et al., (2003), *Cloning Stem Cells*, 5:149-155; (10) overexpressing insulin-like growth factor-2 in the induced cells and culturing the cells in the presence of dimethyl sulfoxide to generate skeletal muscle cells, e.g., Prelle et al., (2000), *Biochem. Biophys. Res. Commun.*, 277:631-638; (11) subjecting the induced cells to conditions for generating white blood cells; or (12) culturing the induced cells in the presence of BMP4 and one or more: SCF, FLT3, IL-3, IL-6, and GCSF to generate hematopoietic progenitor cells, e.g., Chadwick et al., (2003), *Blood*, 102:906-915.

In some cases, sub-populations of differentiated cells may be purified or isolated. In some cases, one or more monoclonal antibodies specific to the desired cell type are incubated with the cell population and those bound cells are isolated. In other cases, the desired subpopulation of cells expresses a reporter gene that is under the control of a cell type specific promoter.

In a specific embodiment, the hygromycin B phosphotransferase-EGFP fusion protein is expressed in a cell type specific manner. The method of purifying comprises sorting the cells to select green fluorescent cells and reiterating the sorting as necessary, in order to obtain a population of cells enriched for cells expressing the construct (e.g., hygromycin B phosphotransferase-EGFP) in a cell-type-dependent manner. Selection of desired sub-populations of cells may also be accomplished by negative selection of proliferating cells with the herpes simplex virus thymidine kinase/ganciclovir (HSVtk/GCV) suicide gene system or by positive selection of cells expressing a bicistronic reporter, e.g., Anderson et al. (2007) *Mol. Ther.* (11):2027-2036.

VII. CELL THERAPIES

The induced cells, or cells differentiated from the induced cells, may be used as a therapy to treat disease (e.g., a genetic defect). The therapy may be directed at treating the cause of the disease; or alternatively, the therapy may be to treat the effects of the disease or condition. The induced cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from induced cells. The transferred cells also may be multipotent stem cells differentiated from the induced cells. In some cases, the transferred cells may be induced cells that have not been differentiated.

The number of administrations of treatment to a subject may vary. Introducing the induced and/or differentiated cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease and parameters of the individual subject being treated.

The cells may be introduced to the subject via any of the following routes: parenteral, intravenous, intraarterial, intramuscular, subcutaneous, transdermal, intratracheal, intraperitoneal, or into spinal fluid.

The induced cells may be differentiated into cells and then transferred to subjects suffering from a wide range of diseases or disorders. Subjects suffering from neurological diseases or disorders could especially benefit from stem cell therapies. In some approaches, the induced cells may be differentiated into neural stem cells or neural cells and then transplanted to an injured site to treat a neurological condition, e.g., Alzheimer's disease, Parkinson's disease, multiple sclerosis, cerebral infarction, spinal cord injury, or other central nervous system disorder, see, e.g., Morizane et al., (2008), *Cell Tissue Res.*, 331(1):323-326; Coutts and Keirstead (2008), *Exp. Neurol.*, 209(2):368-377; Goswami and Rao (2007), *Drugs*, 10(10):713-719.

For the treatment of Parkinson's disease, the induced cells may be differentiated into dopamine-acting neurons and then transplanted into the striate body of a subject with Parkinson's disease. For the treatment of multiple sclerosis, neural stem cells may be differentiated into oligodendrocytes or progenitors of oligodendrocytes, which are then transferred to a subject suffering from MS.

For the treatment of any neurologic disease or disorder, a successful approach may be to introduce neural stem cells to the subject. For example, in order to treat Alzheimer's disease, cerebral infarction or a spinal injury, the induced cells may be differentiated into neural stem cells followed by transplantation into the injured site. The induced cells may also be engineered to respond to cues that can target their migration into lesions for brain and spinal cord repair, e.g., Chen et al., (2007), *Stem Cell Rev.*, 3(4):280-288.

Diseases other then neurological disorders may also be treated by a stem cell therapy that uses cells differentiated from induced cells, e.g., induced multipotent or pluripotent stem cells. Degenerative heart diseases such as ischemic cardiomyopathy, conduction disease, and congenital defects could benefit from stem cell therapies, see, e.g. Janssens et al., (2006), *Lancet*, 367:113-121.

Pancreatic islet cells (or primary cells of the islets of Langerhans) may be transplanted into a subject suffering from diabetes (e.g., diabetes mellitus, type 1), see e.g., Burns et al., (2006) *Curr. Stem Cell Res. Ther.*, 2:255-266. In some embodiments, pancreatic beta cells derived from induced cells may be transplanted into a subject suffering from diabetes (e.g., diabetes mellitus, type 1).

In other examples, hepatic cells or hepatic stem cells derived from induced cells are transplanted into a subject suffering from a liver disease, e.g., hepatitis, cirrhosis, or liver failure.

Hematopoietic cells or hematopoietic stem cells (HSCs) derived from induced cells may be transplanted into a subject suffering from cancer of the blood, or other blood or immune disorder. Examples of cancers of the blood that are potentially treated by hematopoietic cells or HSCs include: acute lymphoblastic leukemia, acute myeloblastic leukemia, chronic myelogenous leukemia (CML), Hodgkin's disease, multiple myeloma, and non-Hodgkin's lymphoma. Often, a subject suffering from such disease must undergo radiation and/or chemotherapeutic treatment in order to kill rapidly dividing blood cells. Introducing HSCs derived from induced cells to these subjects may help to repopulate depleted reservoirs of cells.

In some cases, hematopoietic cells or HSCs derived from induced cells may also be used to directly fight cancer. For example, transplantation of allogeneic HSCs has shown promise in the treatment of kidney cancer, see, e.g., Childs et al., (2000), *N. Engl. J. Med.*, 343:750-758. In some embodiments, allogeneic, or even autologous, HSCs derived from induced cells may be introduced into a subject in order to treat kidney or other cancers.

Hematopoietic cells or HSCs derived from induced cells may also be introduced into a subject in order to generate or repair cells or tissue other than blood cells, e.g., muscle, blood vessels, or bone. Such treatments may be useful for a multitude of disorders.

In some cases, the induced cells are transferred into an immunocompromised animal, e.g., SCID mouse, and allowed to differentiate. The transplanted cells may form a mixture of differentiated cell types and tumor cells. The specific differentiated cell types of interest can be selected and purified away from the tumor cells by use of lineage specific markers, e.g., by fluorescent activated cell sorting (FACS) or other sorting method, e.g., magnetic activated cell sorting (MACS). The differentiated cells may then be transplanted into a subject (e.g., an autologous subject, HLA-matched subject) to treat a disease or condition. The disease or condition may be a hematopoietic disorder, an endocrine deficiency, degenerative neurologic disorder, hair loss, or other disease or condition described herein.

VIII. ANALYTICAL METHODS

Also described herein are assay methods for identifying an agent capable of inducing pluripotency alone or in combination with other agents, such as the induction factors described herein, in primary somatic cells (e.g., skin cells, mononuclear blood cells, or bone marrow cells) or a cell line (e.g., HEK293 cells, Hela cells, a multipotent stem cell line, or an adult stem cell line). The methods may also include methods for identifying agents that increase the ability of induction factors to induce pluripotency (e.g., the efficiency of inducing pluripotency). In some embodiments, cells to be used in the assay methods have not undergone epigenetic inactivation of Tert, Nanog, Oct3/4 or Sox2.

In some embodiments, the ability of a test agent to induce pluripotency or multipotency is assessed in a primary screen endpoint by determining the test agent's ability to induce the expression of one or more of: alkaline phosphatase (ALP), ES marker genes, or protein markers. In some cases, such determination is made by comparing the test agent's inducing ability with that of a negative control agent (e.g., an agent with limited or non-existent ability to induce the subject gene or protein markers). In most instances, prior to and during incubation with a test agent or control agent, cells are cultivated in a cell culture medium suited to the particular cell type being cultured, e.g., any of the cell culture media for culturing cells as described herein, although it is possible to take a sample and utilize it directly in an assay without prior culturing steps. In some cases, after a test agent incubation period, cells are cultured in MC-ES medium as described herein.

Examples of ES marker genes suitable for a screening assay include, but are not limited to, Tert, Cyp26A1, Nanog, Oct3/4, or Sox2. The expression of a marker may be determined by detecting or quantifying mRNA levels or protein levels by a standard method, e.g., any of the methods mentioned herein, such as qPCR. In other embodiments, a reporter construct containing one or more elements from an ES marker gene promoter is introduced into the cells to be assayed prior to contacting the cells with a test agent. Methods for generating promoter-reporter constructs, introducing them into cells, and assaying various reporter polypeptide activities, can be found in detail in, e.g., *Current Protocols in Molecular Biology*, John Wiley & Sons, N.Y. (2005), 3.16-3.17 and 9.1-9.14, respectively). Where a particular cell type is difficult to transfect by conventional methods, viral transduction can be used, e.g., as described herein, to introduce a viral promoter-reporter construct. Promoter activity can be quantified by measuring a property of the reporter polypeptide (e.g., enzymatic activity or fluorescence), reporter polypeptide expression (e.g., by an ELISA assay), or reporter mRNA expression (e.g., by a fluorescent hybridization technique). Suitable reporter polypeptides include, e.g., firefly luciferase, *Renilla* luciferase, fluorescent proteins (e.g., enhanced green fluorescent protein), β-galactosidase, β lactamase, and horseradish peroxidase. Exemplary promoter-reporter constructs for detecting induction of Nanog, Sox2, Oct 3/4, TERT, or Cyp26A1 promoter activation are described in Kuroda et al., (2005), *Mol. Cell. Biol.*, 25(6): 2475-2485 (for Nanog); Zhan et al., (2005), *Cell Biochem. Biophys.*, 43(3):379-405 (for Oct3/4 and Sox2); and Tzukerman et al., (2000), *Mol. Biol. Cell*, 11(12):4381-4391 (for hTert), and Loudig et al., (2005), *Biochem. J.*, 392(Pt 1):241-248. In some embodiments, the presence of ALP activity in assayed cells is used as a preliminary test for inducing activity of a test agent. A positive result in any of the foregoing assays, such as a significantly higher level of activity for a test agent than for a control agent, is taken as a preliminary indication that a test agent has inducing activity. Such candidate inducing agents may be further screened by testing the cells contacted with the test agent in the primary screen in any of the assays described herein for determining pluripotency or multipotency, including, but not limited, determining the expression of a panel of ES marker genes, protein markers, long term self renewal, hypomethylation of Oct3/4, Sox2, and Nanog promoters, ability to form teratomas, and the ability to differentiate into cell types of ectodermal, mesodermal, or endodermal lineage ex vivo.

The conditions for the assays may vary and depend upon the nature of the assay protocol being utilized and the cells and agent being employed. For such assays, the cell culture period prior to an endpoint assay may vary from at least about 3 days to at least about 40 days, e.g., 5, 6, 9, 10, 12, 14, 20, 21, 25, 26, 27, 30, 32, 34, 36, 38, or other period from at least about 3 days to at least about 40 days. Additionally, in most cases the time for the test agent incubation ranges from at least about 30 minutes to about 40 days, e.g., 1 hour, 2 hours, 12 hours, 18 hours, 1 day, 3 days, 5 days, 7 days, 14 days, 21 days, 25 days, 30 days, 34 days, or any other period from at least about 30 minutes to at least about 40 days.

In some embodiments, the agent to be tested is an siRNA, including, but not limited to, a double stranded RNA that comprises about 19 base pairs of a target gene sequence and is capable of inhibiting target gene expression by RNA interference. See, e.g., Scherr et al., (2007), *Cell Cycle*, 6(4):444-449. In some embodiments, the siRNAs to be assayed include, but are not limited to, whole-genome siRNA libraries, as described in, e.g., Miyagishi et al., (2003), Oligonucleotides, 13(5):325-333; and Huesken et al., (2005), *Nat. Biotechnol.*, 8:995-1001. Suitable whole genome siRNA libraries, e.g., arrayed siRNA libraries that are commercially available include, the "Human Whole Genome siRNA Set V4.0" from Qiagen (Valencia, Calif.); the "Human siGENOME siRNA Library—Genome" from Dharmacon, Inc. (Lafayette, Colo.); and the Silencer® Human Genome siRNA Library from Ambion (Austin, Tex.). Methods and reagents for introducing siRNAs include, but are not limited to, commercial reagents such as Lipofectamine™ RNAiMAX (Invitrogen, Carlsbad, Calif.), TransMessenger Transfection Reagent (Qiagen, Valencia, Calif.), or Dharma FECT® (Dharmacon, Lafayette, Colo.). See, e.g., Krausz (2007), *Mol. Biosyst.*, 3(4):232-240. In some embodiments, a viral RNAi library is used as described in, e.g., Root et al., (2006), *Nat. Methods*, 3(9):715-719.

Optionally, the induction test agents to be screened are small molecules. The test molecules may be individual small molecules of choice or in some cases, the small molecule test agents to be screened come from a combinatorial library, i.e., a collection of diverse chemical compounds generated by either chemical synthesis or biological synthesis by combining a number of chemical "building blocks." For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al., (1994), *J. Med. Chem.*, 37(9), 1233-1251. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al., (1993), *Proc. Natl. Acad. Sci. U.S.A.*, 90:6909-6913; analogous organic syntheses of small compound libraries, as described in Chen et al., (1994), *J. Amer.*

Chem. Soc., 116:2661-2662; Oligocarbamates, as described in Cho, et al., (1993), Science, 261:1303-1305; peptidyl phosphonates, as described in Campbell et al., (1994), J. Org. Chem., 59: 658-660; and small organic molecule libraries containing, e.g., thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514).

Numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.)/

In some cases, test agents to be screened for inducing activity may be used in combination with one or more induction factors (e.g., Oct3/4, Sox2, Klf4, or c-Myc) described herein, e.g., 1, 2, 3, or 4 of the induction factors described herein. In some cases, a test agent is screened in combination with one induction factor, e.g., with Oct3/4, Sox2, Klf4, or c-Myc. In other cases, the test agent is screened in combination with two induction factors, e.g., Oct3/4 and Sox2; Oct3/4 and Klf4; Oct3/4 and c-Myc; Sox2 and Klf4; Sox2 and c-Myc; or Klf4- and c-Myc. In some embodiments, the test agent is screened in combination with three induction factors, e.g., Oct3/4, Sox2, and Klf4; Oct3/4, Klf4, and c-Myc; Oct3/4, Sox2, and c-Myc; or Sox2, Klf4, and c-Myc. Test agents may also be assayed for their ability to increase the efficiency of pluripotency induction by a set of induction factors, e.g., a combination of Oct3/4, Sox2, Klf4, and c-Myc.

IX. STORAGE OF CELLS

The harvested tissue, the cells, the induced cells, the induced pluripotent cells, the induced multipotent cells, cells differentiated from the harvested tissue, or other cells described herein may be stored. Thus, cells or materials from any point during the processes may be stored for future completion of the process or modification for use.

The methods of storage may be any method including the methods described herein, e.g., using cryopreservation medium. Some exemplary cryopreservation media include the "Cryopreservation Medium For Primate ES Cells" (ReproCELL, Tokyo, Japan) or mFreSR™ (StemCell Technologies, Vancouver, Calif.). The cells preferably are rapidly frozen in liquid nitrogen, and stored in a liquid nitrogen storage vessel. Other suitable cryopreservation media and methods for cryopreservation/thawing of cells generated by the methods described herein are provided in, e.g., U.S. patent application Ser. Nos. 10/902,571 and 11/142,651. See also, Ha et al., (2005), Hum. Reprod., 20(7):1779-1785.

X. EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1

Preparation of Retrovirus Vector

Retrovirus vector plasmids for four genes (Oct3/4-pMx, Sox2-pMx, Klf4-pMx and c-Myc-pMx) constructed as in Table 1 were introduced into the packaging cell line Plat-E [Experimental Hematology, 2003, 31 (11): 1007-1014], using Fugene HD (manufactured by Roche). About 24 to 48 hours after introduction of the retroviral vector plasmids, the medium was replaced with a medium suitable for the cell to which the gene is to be introduced. After culturing the Plat-E cells to which retrovirus vector was introduced for more than 4 hours, the supernatant was recovered and passed through a filter of 45 µm in diameter (manufactured by Millipore). Retrovirus vector solutions of the four genes (Oct3/4, Sox2, Klf4 and c-Myc) were prepared by the above procedure.

Retrovirus vector plasmids for three genes (Oct3/4-pMx, Sox2-pMx, and Klf4-pMx) were introduced into the packaging cell, the Plat-E cell, using Fugene HD (manufactured by Roche). During 24 to 48 hours after retrovirus vector introduction, the medium was replaced with a medium suitable for the cell to which gene is to be introduced. After culturing the Plat-E cell to which retrovirus vector was introduced for more than 4 hours, the supernatant was recovered and passed through a filter of 45 µm in diameter (manufactured by Millipore). Retrovirus vector solutions of the three genes (Oct3/4, Sox2 and Klf4) were prepared by the above procedure.

Example 2

Preparation of Adenovirus Vector

The use of amphotropic retroviruses presents a significant risk of infection to experimenters. This risk is of particular concern where a retrovirus encodes an oncogenic protein (e.g., c-myc). Accordingly, we utilized an ecotropic retrovirus vector that selectively recognizes a mouse receptor, mouse-derived cationic amino acid transporter 1 (mCAT1). We infected human cells with an adenovirus vector carrying the gene encoding mCAT 1, thus allowing ecotropic retroviruses to selectively infect human cells expressing the mCAT 1 receptor.

First, an adenovirus vector carrying cDNA having the sequence of coding region of the mouse-derived cationic amino acid transporter (mCAT1) gene was constructed. Specifically, Adeno-X Expression System 1 kit (manufactured by TakaraBio Clontech) was used. In Adeno-X Expression System 1 kit, based on the experimental method attached to the kit by TakaraBio, the mCAT1 gene was subcloned into the multi-cloning site of a vector called pShuttle.

Subsequently, an expression cassette was excised by the PI-Sce I site and the I-Ceu I site, cleavage sites on both ends of the expression cassette of pShuttle, and a DNA fragment containing the desired gene was inserted in between the PI-Sce I site and the I-Ceu I site in the Adeno-X Viral DNA in the above kit, which was then treated with a restriction enzyme Swa I to remove adenovirus DNA for which integration was unsuccessful. After the plasmid was transformed into an E. coli DH5 strain, whether the desired gene was correctly introduced into adenovirus DNA was confirmed by restriction enzyme treatment, PCR etc. The plasmid was prepared in large quantities, and cleaved with the Pac I restriction enzyme. Using the recombinant adenovirus DNA thus obtained, the gene was introduced into the HEK293 cells (MicroBix) and plated in six wells using Lipofectamin 2000 (manufactured by Invitrogen), and two weeks later when the cell exhibited a cytopathic effect (CPE), the cells were collected as they are in the medium.

Subsequently, after the cell suspension was subjected to freezing and thawing three times, the cells were disrupted, and virus particles present in the cells were allowed to release into the liquid. The virus suspension thus prepared was added to one 100 mm plastic culture dish equivalent of HEK293 cells ($5 \times 10^6$ cells) to infect the cells, the virus was propagated. Furthermore, after virus was prepared in large quantities using four 150 mm plate equivalent of HEK293 cells, virus was purified using the Adenovirus Purification kit (manufactured by Clontech), and stored frozen at $-80°$ C.

The titer (plaque forming units, PFU) of the mCAT1 adenovirus vector was determined using the Adeno-X Rapid Titer kit. On a 24-well plate, HEK293 cells were plated at a concentration of $5 \times 10^4$ cells/500 µl per well. Fifty µl of serially diluted (from $10^{-2}$ to $10^{-7}$) virus vector was mixed with 500 µl of the medium, and then used to infect the cells. After culturing at 5% $CO_2$ and 37° C. for 48 hours, the medium was aspirated off, the cells were dried for 5 minutes, and then using 500 µl of cold 100% methanol the cells were fixed by allowing to stand at $-20°$ C. for 10 minutes. After aspirating off methanol, the wells were washed three times with 500 µl of phosphate buffer containing 1% bovine serum albumin. A mouse anti-Hexon antibody was diluted 1000-fold with phosphate buffer containing 1% bovine serum albumin, and 250 µl each of it was added to wells.

After allowing to stand at 37° C. for 1 hour, the antibody solution was removed, and the wells were washed three times with 500 µl phosphate buffer containing 1% bovine serum albumin. Horseradish peroxidase-labelled rat anti-mouse immunoglobulin antibody was diluted 500-fold with phosphate buffer containing 1% bovine serum albumin, and 250 µl was added to wells. After allowing to stand at 37° C. for 1 hour, the antibody solution was removed, and washed three times with 500 µl of phosphate buffer containing 1% bovine serum albumin. 250 µl of the DAB (diaminobenzidine) solution (10-fold DAB concentrate was diluted with a stable peroxidase buffer) was added to wells, and was allowed to stand at room temperature for 10 minutes. After aspirating off DAB, 500 µl of phosphate buffer was added. Using a 20× objective lens, the number of brown positive cells in six viewing fields was counted.

Radius of a standard 20× objective lens: 0.5 mm
Area in one viewing field: $7.853 \times 10^{-3}$ cm$^2$
Area of a well: 2 cm$^2$
Viewing field of a well: 2 cm$^2$/$7.853 \times 10^3$ cm$^2$=254.7 viewing fields
$(32/6) \times 254.7/(0.55 \times 10^{-5}) = 2.5 \times 10^8$ ifu (infection unit)/ml

Example 3

Alkaline Phosphatase Staining

Staining for confirming alkaline phosphatase activity which is a characteristic of pluripotent stem cells was conducted in the following manner. After removing the culture medium, a 10% formalin neutral buffer solution was added to wells, and cells were fixed at room temperature for 5 minutes. After washing with a phosphate buffer etc., a chromogenic substrate of alkaline phosphatase, I step NBT/BCIP (manufactured by Pierce) was added and reacted at room temperature for 20 to 30 minutes. Cells having alkaline phosphatase activity were all stained blue violet.

Example 4

Determination Gene Expression of a Colony by Quantitative PCR

The expression of target genes in each colony including ALP-positive colonies was determined using quantitative PCR in the following manner. Colonies developed by the induction of pluripotent or multipotent stem cells were harvested, and RNA was extracted using the Recoverall total nucleic acid isolation kit for FFPE (manufactured by Ambion). After synthesizing cDNA from the extracted RNA, the target gene was amplified using the Taqman Preamp mastermix (manufactured by Applied Biosystems).

As the primers for quantitative PCR, the Taqman gene exprESsion assay (manufactured by Applied Biosystems) was used. The following shows the name of the target gene and the product code of each primer. Human Hprt: Hs99999909_m1, human Nanog: Hs02387400_g1, human Tert: Hs00162669_m1, Mouse Hprt: Mm01545399_m1, mouse Nanog: Ma02019550_s1.

As the positive control for quantitative PCR, cDNA extracted from mesenchymal stem cells established by the following manner was used.

One vial ($2.5 \times 10^7$ cells) of human bone marrow-derived mononuclear cells (hBMMNCs (manufactured by Lonza), Lot 060175A: female, 21 years old, black) was thawed in a 37° C. water bath, and suspended in 10 ml of the MSCGM medium (a growth medium for mesenchymal cells) (manufactured by Lonza). In order to remove DMSO in the frozen solution, this was centrifuged at 300 g and 4° C. for seven minutes and the supernatant was removed. The cell mass thus obtained was resuspended in 10 ml of MSCGM medium, and plated on a 100 mm plate at a density of $10^5$ cells/cm$^2$ and cultured at 37° C. Seven days later, the medium was changed. At this time, the suspended cells in the old medium were collected by centrifuging at 300 g and 4° C. for five minutes, and were returned to the cells together with the fresh medium. On day 13 when the adherent cells became confluent, the supernatant was removed, non-adherent cells were washed off with a phosphate buffer, and adherent cells were collected by detaching with a 0.05% trypsin-EDTA solution and plated at a density of 3000 cells/cm$^2$. RNA was collected from the cells of the third subculture, and cDNA was synthesized.

Example 5

Induction of Human Pluripotent Stem Cells from Undifferentiated Stem Cells Present in a Postnatal Human Adult Bone Marrow Tissue From human adult bone marrow-derived cells (trade name: Human Bone Marrow-Derived Mononuclear Cell) containing undifferentiated stem cells present in a postnatal human adult bone marrow tissue, the cells were established under low serum (2%) and high serum (10%) culture conditions, and were used in the experiment for inducing pluripotent stem cells. Thus, one vial each ($2.5 \times 10^7$ cells) of frozen human bone marrow-derived mononuclear cells (hBMMNCs (manufactured by Lonza), Lot 060809B: female, 20 years old, white/ and hBMMNCs (manufactured by Lonza), Lot 060470B: female, 20 years old, black) was thawed in a 37° C. water bath, and suspended in 10 ml of the MAPC medium for use in the low serum culture. In order to remove DMSO in the frozen solution, this was centrifuged at 300 g and 4° C. for seven minutes and the supernatant was removed.

The cell mass thus obtained was resuspended, and plated at a density of $10^5$ cells/cm$^2$ on a 100 mm plate coated with 10 ng/ml fibronectin. Growth factors [10 ng/ml PDGF-BB (manufactured by Peprotech), 10 ng/ml EGF (manufactured by Peprotech), 10 ng/ml IGF-II (manufactured by Peprotech)] were added. Three days later, growth factors were only added. Seven days later, the suspended cells and the medium were collected except the adherent cells, and centrifuged at 300 g and 4° C. for five minutes. After the supernatant was removed, the cells were resuspended in a fresh medium. The cell suspension was returned to the original 10 cm dish, and growth factors were added thereto. On day 10 when the adherent cells became confluent, the supernatant was removed, non-adherent cells were washed off with a phosphate buffer, and adherent cells were collected by detaching with a 0.05% trypsin-EDTA solution, and using a cell banker (manufactured by Juji Field), the primary culture was stored frozen.

Using the human bone marrow-derived mononuclear cell of the same lot, the cells were established using a MSCGM medium (manufactured by Lonza) containing 10% FBS under the high serum condition. The Human Bone Marrow-Derived Mononuclear Cells were plated at a density of $10^5$ cells/cm$^2$ in a 100 mm plate to which 10 ml of the MSCGM medium had been added, and cultured at 37° C. Seven days later, the suspended cells and the medium were collected except the adherent cells, and centrifuged at 300 g and 4° C. for five minutes, and after the supernatant was removed, the cells were resuspended in a fresh medium. The cell suspension was returned to the original 10 cm dish, and culturing was continued. On day 13 when the adherent cells became confluent, the supernatant was removed, non-adherent cells were washed off with a phosphate buffer. Adherent cells were collected by detaching with a 0.05% trypsin-EDTA solution, and using a cell banker (manufactured by Juji Field), the primary culture was stored frozen.

One vial each of the human bone marrow-derived primary culture cells that were established under the high serum and the low serum conditions and stored frozen was thawed in a 37° C. incubator. Two ml of the medium used for the establishment was added to the cells respectively, and the cells were plated at a density of $10^4$ cells/cm$^2$ on a 6-well plastic culture dish the wells of which had been coated with matrigel (manufactured by BD Bioscience) at a concentration of 20 μg/cm$^2$ and cultured for 14 hours (a second subculture cells). Fourteen hours later, the medium was removed, and the mCAT1 adenovirus vector prepared in Example 2 at an amount equivalent to a m.o.i. of 10 in 500 μl of the Hank's balanced salt solution per well was added, and were infected at room temperature for 30 minutes.

Two ml each of the medium used for establishment was added to each well, and cultured at 37° C. Forty eight hours after the introduction of the mCAT-1 adenovirus vector, the medium of each well was replaced with 2 ml of the retrovirus vector solution (polybrene at a final concentration of 4 μg/ml was added) of four genes(Oct3/4, Sox2, Klf4, c-Myc) which were prepared in Example 1, and cultured at 37° C. for 14 hours. The virus supernatant was removed and replaced with the MEF-conditioned ES medium. Then medium change with the MEF-conditioned ES medium was continued every two days. On examining fourteen days after the introduction of the four genes, one typical colony was found in the low serum condition group of Lot 060809B that exhibits a characteristics of the induced pluripotent stem cells. Said colony was composed of markedly smaller cells than the surrounding cells. In addition to the pluripotent stem cell-like colony, a plurality of colonies were observed in both the low serum group and the high serum group, but they were not stained with alkaline phosphatase.

In order to isolate the pluripotent stem cell-like colonies, the wells were washed with the Hank's balanced salt solution, and then colonies were surrounded by a cloning ring (manufactured by Iwaki) to the bottom of which silicone grease had been applied. One hundred μl of the Detachment Medium For Primate ES Cells (manufactured by ReproCELL) was added in the ring and cultured at 37° C. for 10 to 20 minutes. The cell suspension in the ring containing the detached colony was added to 2 ml of the MEF-conditioned ES medium, and plated in one well of a MEF-coated 24-well plate. After culturing at 37° C. for 8 to 14 hours, the medium was changed, and subsequently medium change was continued every two days, and 8 days later a second subculture was carried out.

The medium was removed, washed with the Hank's balanced salt solution, the Detachment Medium For Primate ES Cells (manufactured by ReproCELL) was added, cultured at 37° C. for 10 minutes, and 2 ml of the medium was added to stop the reaction. The cell suspension was transferred to a centrifuge tube, and centrifuged at 4° C. and 200 g for 5 minutes to remove the supernatant. The cells were resuspended in the MEF-conditioned ES medium, and plated in 4 wells of MEF-coated 24-well plate. Medium change was continued every 2 days, and seven days after the second subculture, the cells were subjected to alkaline phosphatase staining, and the cloned colony-derived cells were stained blue violet.

Figure 2:
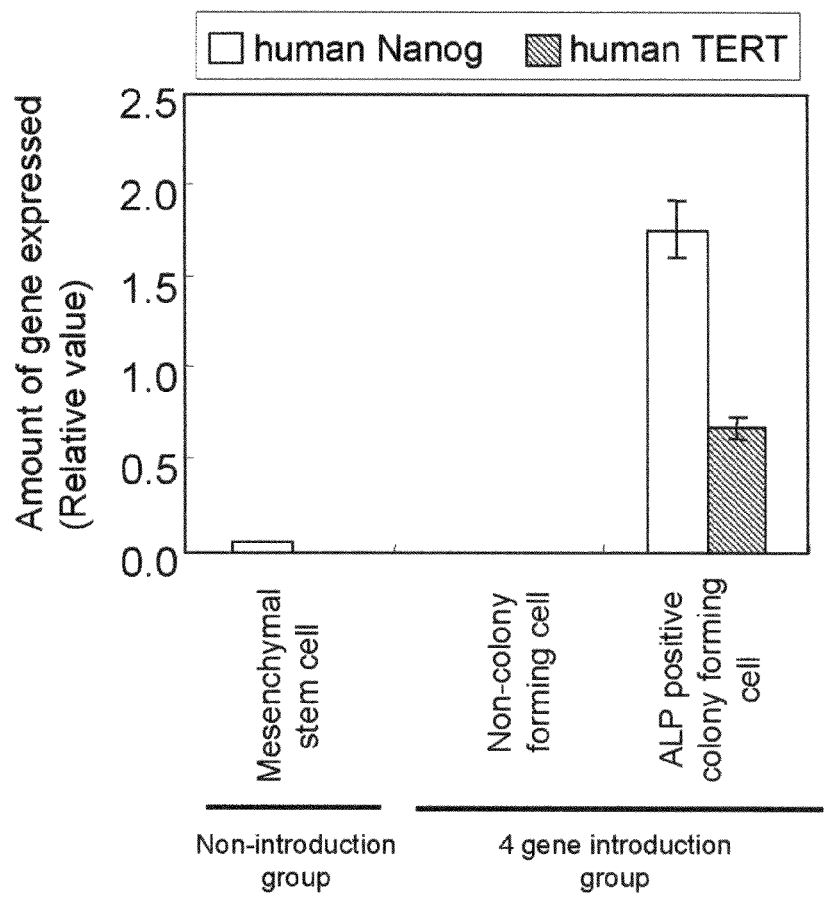
FIG. 2 shows the relative expression of Nanog and Tert genes in human adult bone-marrow derived cells following introduction of four genes. Oct3/4, Sox2, Klf4 and c-Myc were introduced into cells established from mononuclear cells derived from human adult bone marrow under low serum conditions. RNA was extracted from the colonies obtained, and the expression of human Nanog and human Tert genes was demonstrated by quantitative PCR. Fibroblasts and mesenchymal stem cells in which the four genes were not introduced were used as controls in the experiment. The amount of gene expression is provided as a relative value in which the amount of expression was normalized by the amount of expression of the human hypoxanthine phosphoribosyltransferase (HPRT) gene, and by setting as one the amount of HPRT gene expression in Alkaline Phosphatase (ALP)-positive colonies induced from a neonatal skin fibroblast. It was confirmed that the expression of Nanog and Tert was significantly higher in colonies in which four genes (Oct3/4, Sox2, Klf4 and c-Myc) were introduced and which were positive for ALP.

Furthermore, by quantitative PCR, it was confirmed that Nanog and Tert were expressed by the colony of alkaline phosphatase activity-positive pluripotent stem cells. When compared to the mesenchymal stem cells established in Example 4, the amount expressed of Nanog was as much as 30-fold higher. The expression of Tert was noted only in said pluripotent stem cells, and not in the mesenchymal stem cells. FIG. 2 shows the relative expression of Nanog and Tert genes in human adult bone-marrow derived cells following introduction of four genes. Oct3/4, Sox2, Klf4 and c-Myc, were introduced into cells established from mononuclear cells derived from human adult bone marrow under low serum conditions. RNA was extracted from the colonies obtained, and the expression of human Nanog and human Tert genes was demonstrated by quantitative PCR. Fibroblasts and mesenchymal stem cells in which the four genes were not introduced were used as controls in the experiment. The amount of gene expression is provided as a relative value in which the amount of expression was normalized by the amount of expression of the human hypoxanthine phosphoribosyltransferase (HPRT) gene, and by setting as one the amount of HPRT gene expression in Alkaline Phosphatase (ALP)-positive colonies induced from a neonatal skin fibroblast. It was confirmed that the expression of Nanog and Tert was significantly high in colonies in which four genes (Oct3/4, Sox2, Klf4 and c-Myc) were introduced and which were positive for ALP. As shown in FIG. 2, Nanog and Tert were not expressed in the cells that did not form colonies, despite the introduction of the four genes.

From the foregoing, when human adult bone marrow-derived cells were used, the pluripotent stem cells were obtained from the low serum culture group but not at all from the high serum culture group (Lot 060809B and Lot 060470B) (Table 2). Also, culturing under the low serum condition was suitable for the maintenance of the undifferentiated cells.

Example 6

Induction of Human Pluripotent Stem Cells from Undifferentiated Stem Cells Present in Human Neonatal Skin Using cells (trade name: Neonatal Normal Human Skin Fibroblasts, primary culture) derived from a human neonatal tissue, a human tissue immediately after birth, the induction of human pluripotent stem cells from undifferentiated stem cells present in the skin of a human neonate was attempted.

One vial of the frozen Neonatal Normal Human Skin Fibroblasts (primary culture, manufactured by Lonza, Lot 5F0438) was thawed in a 37° C. incubator, and was suspended in the MCDB202 modified medium, a medium containing 2% fetal bovine serum, 5 µg/ml insulin, 50 µg/ml gentamycin, 50 ng/ml amphotericin-B (FBM medium, manufactured by Lonza) to obtain 12 ml of a cell suspension. Two ml each of the cell suspension was plated on a 6-well plastic culture dish of which bottom had been coated with matrigel (BD Biosciences) at a concentration of 20 µg/cm$^2$ (second subculture cells).

Fourteen hours later, the medium was removed, and the mCAT1 adenovirus vector prepared in Example 2 at an amount equivalent to a m.o.i. of 5 in 500 µl of the Hank's balanced salt solution per well was added, and was infected at room temperature for 30 minutes. To each well, 2 ml of the FBM medium was added respectively, and cultured at 37° C. Forty eight hours after the introduction of the mCAT-1 adenovirus vector, the medium of each well was replaced with 2 ml of the retrovirus vector solution (polybrene at a final concentration of 4 µg/ml was added) of the four genes (Oct3/4, Sox2, Klf4 and c-Myc) prepared in Example 1, and cultured at 37° C. for 4 hours.

The virus supernatant was removed and replaced with MEF-conditioned ES medium. Then medium change with MEF-conditioned ES medium was continued every two days, and fourteen days after the introduction of the four genes, one well of the 6-well plate was subjected to alkaline phosphatase staining. As a result, six pluripotent stem cell-like alkaline phosphatase-positive colonies were obtained. Alkaline phosphatase-positive colonies were composed of markedly smaller cells than the neonatal normal human skin fibroblasts.

Figure 3:
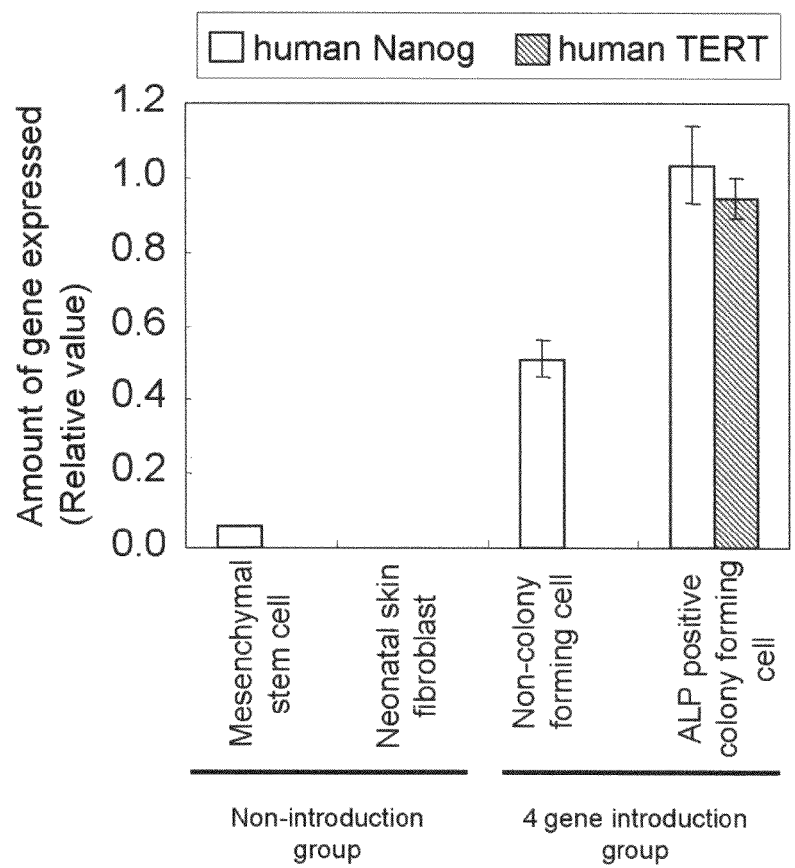
FIG. 3 shows the relative expression of Nanog and Tert genes in neonatal fibroblasts following introduction of four genes. Oct3/4, Sox2, Klf4 and c-Myc, were introduced into primary culture fibroblasts derived from neonatal skin; RNA was extracted from the colonies obtained; and the amount expressed of the human Nanog and human Tert genes was determined by quantitative PCR. Parental fibroblasts and mesenchymal stem cells in which four genes were not introduced were used as controls in the experiment. Gene expression was normalized using the same procedure outlined in FIG. 2. It was confirmed that the expression of Nanog and Tert was significantly higher in colonies in which four genes were introduced and which were positive for ALP.

Subsequently, by quantitative PCR, it was confirmed that Nanog and Tert were expressed by the colonies of alkaline phosphatase activity-positive pluripotent stem cells. FIG. 3 shows the relative expression of Nanog and Tert genes in neonatal fibroblasts following introduction of four genes. Oct3/4, Sox2, Klf4 and c-Myc, were introduced into primary culture fibroblasts derived from neonatal skin; RNA was extracted from the colonies obtained; and the amount expressed of the human Nanog and human Tert genes was determined by quantitative PCR. Parental fibroblasts and mesenchymal stem cells in which four genes were not introduced were used as controls in the experiment. Gene expression was normalized using the same procedure outlined in FIG. 2. It was confirmed that the expression of Nanog and Tert was significantly high in colonies in which four genes were introduced and which were positive for ALP. As shown in FIG. 3, when compared to the mesenchymal stem cells established under the high serum (10%) culture condition in Example 5, the neonatal normal human skin fibroblasts before the introduction of the four genes did not express Nanog, whereas in the case of the cells after the introduction of the four genes, 9-fold as much in the cells that are not forming colonies and 18-fold as much expression of Nanog in the alkaline phosphatase activity-positive colonies were observed (FIG. 3). On the other hand, the expression of Tert was only noted in the alkaline phosphatase activity-positive colonies. From this, the pluripotent stem cells may be defined by the characteristics of alkaline phosphatase activity-positive and Nanog-positive and Tert-positive. Also, the neonatal normal human skin fibroblasts were confirmed to be the cells that have a relatively high efficiency of inducing the pluripotent stem cells and that can express Nanog by the introduction of the four genes.

Colonies of the pluripotent stem cells were isolated in the following manner. On day 17 after gene introduction, six colonies with a characteristic shape were selected from the remaining wells. After washing the wells with the Hank's balanced salt solution, colonies were surrounded by a cloning ring (manufactured by Iwaki) to the bottom of which silicone grease had been applied. One hundred µl of the Detachment Medium For Primate ES Cells (manufactured by Repro-CELL) was added in the ring and cultured at 37° C. for 20 minutes. The cell suspension in the ring containing the detached colonies was added to 2 ml of MEF-conditioned ES medium, and plated in one well of a MEF-coated 24-well plate. After culturing at 37° C. for 14 hours, the medium was changed, and subsequently medium change was continued every two days, and 8 days later a second subculture was carried out. The medium was removed, the cells were washed with the Hank's balanced salt solution, the Detachment Medium For Primate ES Cells was added and cultured at 37° C. for 10 minutes, and 2 ml of the medium was added to stop the reaction.

The cell suspension was transferred to a centrifuge tube, and centrifuged at 4° C. and 200 g for 5 minutes, and the supernatant was removed. The cells were resuspended in MEF-conditioned ES medium, and plated on four wells of a MEF-coated 24-well plate. Seven days after the second subculture, in a subculturing method described below, the cells were plated on a 60 mm plastic culture dish of which bottom had been coated with matrigel at a concentration of 20 µg/cm$^2$. Further eight days later (37 days after the introduction of the four genes), a third subculture was conducted, and plated on two matrigel-coated 60 mm plastic culture dishes, and part of it was used in alkaline phosphatase staining and RNA extraction. The result confirmed that the cells derived from the cloned colonies are alkaline phosphatase activity-positive and are expressing Nanog and Tert at high rate, thereby endorsing that they are pluripotent stem cells.

The induced pluripotent stem cells were subcultured every 5 to 7 days for maintenance and growth. From the plastic culture dish on which subculturing is to be conducted, the medium was removed, the cells were washed with the Hank's balanced salt solution, dispase or the Detachment Medium For Primate ES Cells was added, and cultured at 37° C. for 5 to 10 minutes. When more than half of the colonies were detached, the ES medium was added to stop the reaction, and the cell suspension was transferred to a centrifuge tube. When colonies precipitated on the bottom of the tube, the supernatant was removed, and the ES medium was added again for suspension. After examining the size of the colonies, any extremely large ones were divided into appropriate sizes by slowly pipetting. Appropriately sized colonies were plated on a matrigel-coated plastic culture dish with a base area of about 3 to 6 times that before subculture.

As shown in Table 2, the Neonatal Normal Human Skin Fibroblasts in the lot (Lot 5F0474) other than the above lot 5F0438 exhibited a favorable induction of pluripotent stem cells. From comparison to Example 5, cells derived from young individuals or cells of which culturing time is short were thought to be suitable for the induction of the pluripotent stem cells.

From the above results, when cells derived from human neonatal tissue that is a human postnatal tissue containing undifferentiated cells were subjected to a second subculture in a culture medium containing 2% serum, it was possible to induce the pluripotent stem cells.

Example 7

Induction of Human Pluripotent Stem Cells from Undifferentiated Stem Cells Present in a Human Adult Skin Then, using human adult tissue-derived cells (trade name: Adult Normal Human Skin Fibroblasts, primary culture) containing undifferentiated stem cells present in a human adult skin, the induction of pluripotent stem cells of the present invention was carried out.

One vial each of the frozen Adult Normal Human Skin Fibroblasts (primary culture, manufactured by Lonza, Lot 6F3535: 28 years old, female, white, Lot 6F4026: 39 year old, female, white) was thawed in a 37° C. incubator, suspended in the FBM medium, and 12 ml of the cell suspension was obtained, respectively. Two ml each of the cell suspensions was plated on a 6-well plastic culture dish of which bottom had been coated with matrigel at a concentration of 20 μg/cm$^2$ (second subculture cells).

Fourteen hours later, the medium was removed, and the mCAT1 adenovirus vector prepared in Example 2 at an amount equivalent to a m.o.i. of 5 in 500 μl of the Hank's balanced salt solution per well was added, and was infected at room temperature for 30 minutes. To each well, 2 ml of the FBM medium was added, and cultured at 37° C. Forty eight hours after the introduction of the mCAT-1 adenovirus vector, the medium of each well was replaced with 2 ml of the retrovirus vector solution (polybrene at a final concentration of 4 μg/ml was added) of the four genes (Oct3/4, Sox2, Klf4 and c-Myc) prepared in Example 1, and cultured at 37° C. for 4 hours. The virus supernatant was removed and replaced with the MEF-conditioned ES medium. Then medium change with the MEF-conditioned ES medium was continued every two days, and thirteen days after the introduction of the four genes, alkaline phosphatase staining was carried out. As a result, two pluripotent stem cell-like alkaline phosphatase-positive colonies per well were obtained from the Lot 6F3535, whereas no alkaline phosphatase-positive colonies were obtained from the Lot 6F4242 (Table 2).

From comparison to Example 6, the neonate-derived cells among the skin fibroblasts had a higher efficiency of inducing the pluripotent stem cells. Also, among the Adult Normal Human Skin Fibroblasts, cells derived from younger donors had a higher transformation efficiency. From the foregoing, it was demonstrated that the efficiency of inducing the pluripotent stem cells decreases in an age-dependent manner.

Example 8

Examination Using Neonatal Normal Human Skin Fibroblasts of the Third Subculture One vial of frozen Neonatal Normal Human Skin Fibroblasts (primary culture, manufactured by Lonza, Lot 5F0439) was thawed in a 37° C. incubator, suspended in the FBM medium, and plated on two 100 mm plastic culture dishes (a second subculture). After culturing for six days until a 70 to 90% confluence could be obtained, the cells were detached using a 0.025% trypsin-EDTA solution (manufactured by Lonza), centrifuged at 4° C. and 200 g for 5 minutes, and the supernatant was removed. The second subcultured cells collected were stored frozen using the cell banker.

The frozen second subculture cells were thawed in a 37° C. incubator, suspended in 12 ml of the FBM medium, centrifuged at 4° C. and 200 g for 5 minutes, and the supernatant was removed. The cells were suspended, and plated at a density of 10$^4$ cell/cm$^2$ on a 100 mm plastic culture dish of which bottom had been coated with matrigel at a concentration of 20 μg/cm$^2$ (a third subculture). Fourteen hours later, the medium was removed, and the mCAT1 adenovirus vector prepared in Example 2 at an amount equivalent to a m.o.i. of 5 in 2 ml of the Hank's balanced salt solution was added, and was infected at room temperature for 30 minutes. To each well, 10 ml of the FBM medium was added, and cultured at 37° C.

Forty eight hours after the introduction of the mCAT-1 adenovirus vector, the medium was removed, and replaced with 10 ml of the retrovirus vector solution (polybrene at a final concentration of 4 μg/ml was added) of the four genes (Oct3/4, Sox2, Klf4 and c-Myc) prepared in Example 1, and cultured at 37° C. for 4 hours. The virus supernatant was removed and replaced with the MEF-conditioned ES medium. Then medium change with the MEF-conditioned ES medium was continued every two days, and fourteen days after the introduction of the four genes, alkaline phosphatase staining was carried out. As a result, five pluripotent stem cell-like alkaline phosphatase-positive colonies were obtained. By calculating based on the area of the bottom, this indicates that 0.83 colony per well of the 6-well plate was obtained (Table 2).

From comparison to Example 6, it was demonstrated that the efficiency of inducing the pluripotent stem cells decreases with the prolonged culture period.

Example 9

Induction of Human Pluripotent Stem Cells from Undifferentiated Stem Cells Present in the Umbilical Cord (1)

Using the cells (trade name: Normal Human Umbilical Vein Endothelial Cells, primary culture) derived from a human umbilical cord, a human tissue immediately after birth, the induction of the human pluripotent stem cells of the present invention from undifferentiated stem cells present in the umbilical cord was attempted.

One vial of the frozen Normal Human Umbilical Vein Endothelial Cells (primary culture, manufactured by Lonza) was thawed in a 37° C. incubator, and suspended in the Endothelial Cell Medium kit-2 manufactured by Lonza (2% serum) (hereinafter referred to as EBM-2) to obtain 12 ml of the cell suspension. About 10$^5$/2 ml/well each of the cell suspension was plated to a 6-well plastic culture dish the bottom of which had been coated with matrigel at a concentration of 20 μg/cm$^2$ (second subculture). Six hours later, the medium was removed, and the mCAT1 adenovirus vector prepared in Example 2 at an amount equivalent to a m.o.i. of 5 in 500 μl of the Hank's balanced salt solution per well was added, and infected at room temperature for 30 minutes.

2.5 ml each of the EBM-2 medium was added to each well, and cultured at 37° C. Forty eight hours after the introduction of the mCAT-1 adenovirus vector, the medium of each well was replaced with 2 ml each of the retrovirus vector solutions (polybrene at a final concentration of 5 μg/ml was added) of the four genes (Oct3/4, Sox2, Klf4 and c-Myc) prepared in Example 1, and cultured at 37° C. for 4 hours. The virus supernatant was removed and replaced with the MEF-conditioned ES medium. Then medium change with the MEF-conditioned ES medium was continued every two days. Twelve days after the introduction of the four genes, colonies were confirmed.

Thirteen days after the introduction of the four genes, the induced colonies were stained with alkaline phosphatase activity.

From the above results, when cells derived from human umbilical cord that is a human tissue immediately after birth containing undifferentiated cells were subjected to a second subculture in a culture medium containing 2% serum, it was possible to induce the pluripotent stem cells.

Example 10

Induction of Human Pluripotent Stem Cells from Undifferentiated Stem Cells Present in the Umbilical Cord (2)

As described below, using the cells (trade name: Normal Human Umbilical Artery Smooth Muscle Cells, the third subculture) derived from a human umbilical cord, a human tissue immediately after birth, the induction of the human pluripotent stem cells of the present invention from undifferentiated stem cells present in the umbilical cord was attempted.

One vial of the frozen Normal Human Umbilical Artery Smooth Muscle Cells (the third culture, manufactured by Lonza) was thawed in a 37° C. incubator, and suspended in the Smooth Muscle Cell Medium kit-2 manufactured by Lonza (5% serum) (hereinafter referred to as SmGM-2) to obtain 12 ml of the cell suspension. About $10^5/2$ ml/well each of the cell suspension was plated to a 6-well plastic culture dish (manufactured by Becton Dickinson) of which bottom had been coated with matrigel (manufactured by Becton Dickinson) at a concentration of 20 µg/cm² (the fourth subculture). One day later, the medium was removed, and the mCAT1 adenovirus vector at an amount equivalent to a m.o.i. of 1.25 to 5 in 500 µl of the Hank's balanced salt solution per well was added, and infected at room temperature for 30 minutes. 2.5 ml each of the SmGM-2 medium was added to each well, and cultured at 37° C.

Forty eight hours after the introduction of the mCAT-1 adenovirus vector, the medium of each well was replaced with 2 ml each of the retrovirus vector solutions (polybrene at a final concentration of 5 µg/ml was added) of the four genes (Oct3/4, Sox2, Klf4 and c-Myc) prepared in Example 1, and cultured at 37° C. for 4 hours. The virus supernatant was removed and replaced with the MEF-conditioned ES medium. Then medium change with the MEF-conditioned ES medium was continued every two days. Thirteen days after the introduction of the four genes, colonies were confirmed. However, the induced colonies were not stained with alkaline phosphatase activity.

From the above results, it was revealed that though the cells derived from human umbilical cord which is a human tissue immediately after birth contains undifferentiated cells present in the umbilical cord, when the cells were subjected to a fourth subculture in a culture medium containing 5% serum, the induction of the pluripotent stem cells is more challenging.

Example 11

Induction of Mouse Pluripotent Stem Cells from Undifferentiated Stem Cells Present in a Mouse Postnatal Tissue Using mouse bone marrow-derived cells, a mouse postnatal tissue, the induction of pluripotent stem cells of the present invention from undifferentiated stem cells present in a mouse postnatal tissue was attempted.

Femurs and tibias were extracted from 4 to 6 week-old mice (c57BL/6N lineage, 4-week-old, female) taking utmost care not to bring in any other tissue. By soaking the collected bone in 70% ethanol for a short period of time, the cells that attached to the outside of the bone were killed to prevent the contamination of cells other than the bone marrow. After ethanol treatment, the bone was immediately transferred to Iscove's Modified Dulbecco's Medium (IMDM) (SIGMA) to prevent the effect of the cells inside of the bone marrow. The outside of each bone was wiped with Kimwipe to remove the connective tissue. All of the treated bone was transferred to a mortar containing IMDM, and was smashed with a pestle. After washing several times with IMDM, the bone was cut into pieces with scissors. After further washing with IMDM several times, bone fragments were transferred to centrifuge tubes.

After removing IMDM, 10 ml of IMDM containing 0.2% collagenase I (manufactured by SIGMA) per bone fragments of five mice was added, and shaken at 37° C. for 1 hour. After shaking, the suspension was stirred several times using a Pipetman, and then the supernatant was transferred to another tube, to which an equal amount of cold 10% FBS-containing IMDM was added to stop the enzyme reaction. The bone fragments after enzyme treatment were transferred to a mortar containing cold 10% FBS-containing IMDM, and smashed again with a pestle, and after stirring several times, the supernatant was collected. The cell suspension thus collected was filtered by sequentially passing through a Nylon mesh of 70 µm and 40 µm in diameter. The cell suspension was centrifuged at 4° C. and 600 g for 7 minutes, and cells derived from the mouse deep bone marrow were collected.

The cells derived from mouse deep bone marrow were suspended in the MAPC medium, and plated at a density of $10^5$ cells/cm². For plating of cells, a dish previously coated with a phosphate buffer containing 10 ng/ml fibronectin (Becton Dickinson) was used. To the medium, growth factors [10 ng/ml PDGF-BB (manufactured by Peprotech), 10 ng/ml EGF (manufactured by Peprotech), 1000 units/ml LIF (manufactured by Chemicon)] were added at the time of use. Three days after plating, growth factors were only added without changing the medium. Six days later, non-adherent cells were washed off with the phosphate buffer, and adherent cells were collected by detaching with a 0.05% trypsin-EDTA solution (manufactured by Invitrogen), and using a cell banker (manufactured by Juji Field), the cells were stored frozen as the primary culture.

The primary culture cells that had been stored frozen were thawed in a 37° C. water bath, and suspended in 10 ml of the MAPC medium that is a medium containing 2% FBS. In order to remove DMSO in the frozen solution, it was centrifuged at 4° C. and 300 g for 7 minutes, and the supernatant was removed. The cell mass obtained was resuspended, and plated at a density of $2.5 \times 10^3$ cells/cm² on a 12-well plastic plate having the bottom which had been gelatin-coated with 0.1% gelatin/phosphate buffer, and 2 ml each of the MAPC medium was added (the second subculture).

Eight to 14 hours later, the medium was removed, and 2 ml each of the four gene retrovirus vector solution prepared as in Example 1 was added thereto and cultured at 37° C. for 4 to 14 hours. Then the virus solution was removed, and replaced with the mouse ES medium [the ES medium to which a final concentration of 0.3% FBS (manufactured by Invitrogen), 1000 units/ml LIF (manufactured by Chemicon), and 0.1 mM 2-mercaptoethanol were added]. Then medium change with the mouse ES medium was continued every three days, and 5 to 7 days after the introduction of the four genes, said pluripotent stem cells formed colonies comprising mouse ES cell-like small cells. The colonies of the induced pluripotent stem cells were stained blue violet by alkaline phosphatase activity.

From the remaining wells of the 12-well plate, the mouse pluripotent stem cells were subcultured, and subculture was continued to a gelatin-coated 100 mm plate. From the seventh subculture cells, RNA was extracted using the RNeasy mini kit (manufactured by QIAGEN) and cDNA was synthesized. Using the cDNA, quantitative PCR was conducted to confirm the expression of Nanog.

The mouse pluripotent stem cells of the seventh subculture were subcutaneously transplanted to the back of three syngeneic C57BL/6N mice at $3\times10^5$ cells/mouse, and 38 days later the teratoma that formed was extracted. Teratoma was formed in all three mice. From the extracted teratoma, slices were prepared, and differentiation potential into three germ layers was analyzed by immunological staining and histological staining (HE stain, alcian blue stain). As a result, MAP2-positive cells (the nervous system) and GFAP-positive cells (the nervous system) as the ectodermic system, skeletal muscle cells (myocytes) and cartilage tissues as the mesodermic system, and intestinal tract tissues as the endodermic system were observed.

In order to maintain and grow the mouse pluripotent stem cells, they were subcultured every 3 to 4 days. The medium was removed from the plastic culture dish in which subculture is carried out, washed with phosphate buffer, a 0.05% trypsin-EDTA solution was added, and cultured at 37° C. for 5 minutes. When the cells detached, the ES medium was added to stop the reaction, and the cell suspension was transferred to a centrifuge tube. By centrifuging at 200 g for 5 minutes, the supernatant was removed, and after suspending the precipitate in the mouse ES medium, the cells were plated in a gelatin-coated plate at a density of $10^4$ cells/cm$^2$. The pluripotent stem cells induced from the cells derived from the mouse bone marrow cultured in low serum in the same subculture method could be cultured for a long time.

As described above, pluripotent stem cells were induced from the postnatal mouse bone marrow-derived cells established under the low serum condition.

Example 12

Induction of Mouse Pluripotent Stem Cells by the Introduction of Three Genes and Histone Deacetylase Inhibitor Treatment Using cells derived from mouse bone marrow that is a mouse postnatal tissue, the induction of pluripotent stem cells was carried out with the introduction of three genes and histone deacetylase inhibitor treatment.

The primary culture cells derived from mouse bone marrow containing undifferentiated stem cells that had been stored frozen after preparing in a manner similar to Example 11 were plated at a density of $5\times10^3$ cells/cm$^2$ on a 24-well plastic plate (manufactured by Becton Dickinson) having the bottom which had been gelatin-coated with a 0.1% gelatin/phosphate buffer, and 2 ml each of the MAPC medium was added.

Eight hours later, the medium was removed, 2 ml each of the three gene (human Oct3/4, Sox2 and Klf4) retrovirus vector solution prepared as in Example 1 were added, and after further adding MS-275, a histone deacetylase inhibitor, at a final concentration of 1 or 0.1 μM, they were cultured at 37° C. for 14 hours. Then after removing the virus solution, 2 ml each of the MAPC medium containing MS-275, a histone deacetylase inhibitor, at a final concentration of 1 or 0.1 μM was added. Three days later, the medium was replaced with the mouse ES medium [a final concentration of 0.3% FBS (manufactured by Invitrogen), 1000 units/ml LIF (manufactured by Chemicon) and 0.1 mM 2-mercaptoethanol were added to the ES medium at the time of use].

Medium change with the mouse ES medium was continued every 2 to 3 days. Twelve days after the introduction of three genes (human Oct3/4, Sox2 and Klf4) retrovirus vector, the cells were subcultured from each well of the 24-well plastic plate to each well of a 6-well plastic plate. A portion of it was also cultured in a 24-well plastic plate. Fifteen days after said three gene introduction and MS-275 treatment, the pluripotent stem cells formed colonies composed of mouse ES cell-like small cells. The colonies of said pluripotent stem cells were stained blue violet by alkaline phosphatase activity.

Figure 4:
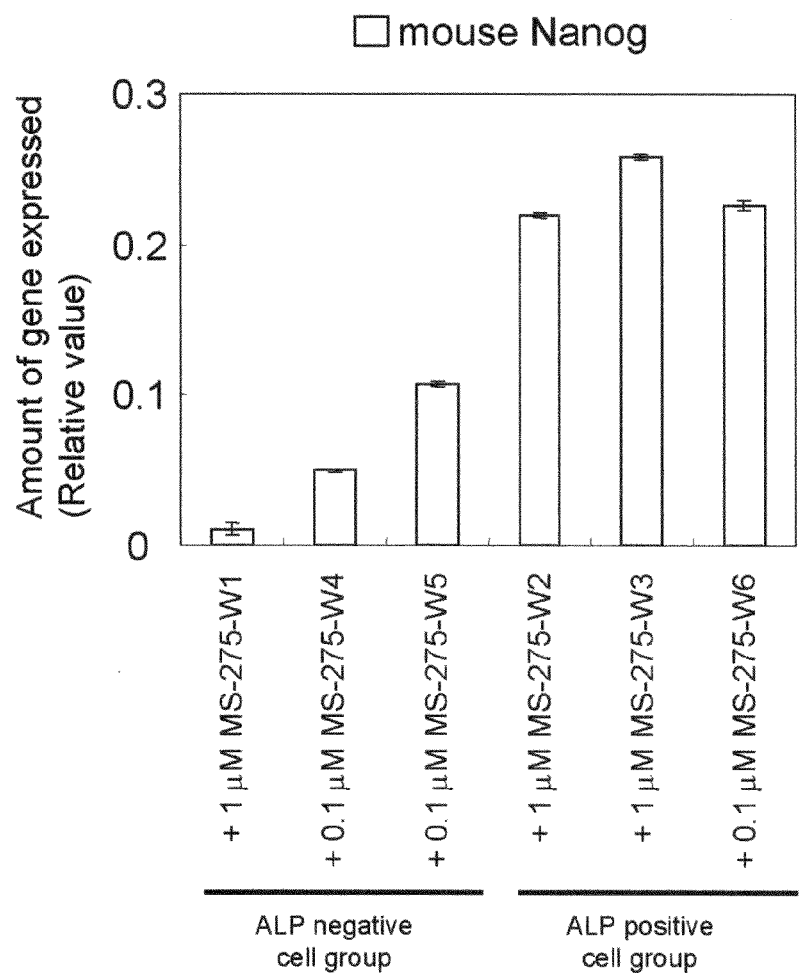
FIG. 4 shows the relative expression of Nanog and Tert genes in mouse adult bone-marrow-derived cells following introduction of three genes and treatment with histone deacetylase (HDAC) inhibitor. Three genes (Oct3/4, Sox2, and Klf4) were introduced into mouse bone marrow-derived cells established under low serum conditions. The cells were also treated with MS-275 (0.1 or 1.0 μM), an HDAC inhibitor. RNA was extracted from the colonies obtained, and the amount of Nanog expression was determined by quantitative PCR. From the cells in which three genes were introduced and which were treated with a histone deacetylase inhibitor, ALP-positive cell group (colonies) were formed, and it was confirmed that the expression of Nanog in these colonies was significantly higher than the ALP-negative colonies. In the figure, W1, W2, W3, W4, W5 and W6 represent the designation of each well of the 6-well plate used in Example 12.

Then, the amount expressed of the Nanog gene was confirmed by quantitative PCR, and the expression of mouse Nanog of colonies of pluripotent stem cells having alkaline phosphatase activity was confirmed (FIG. 4). FIG. 4 shows the relative expression of Nanog and Tert genes in mouse adult bone-marrow-derived cells following introduction of three genes and treatment with histone deacetylase (HDAC) inhibitor. Three genes (Oct3/4, Sox2, and Klf4) were introduced into mouse bone marrow-derived cells established under low serum conditions. The cells were also treated with MS-275 (0.1 or 1.0 μM), an HDAC inhibitor. RNA was extracted from the colonies obtained, and the amount of Nanog expression was determined by quantitative PCR. From the cells in which three genes were introduced and which were treated with a histone deacetylase inhibitor, ALP-positive cell group (colonies) were formed, and it was confirmed that the expression of Nanog in these colonies was significantly higher than the ALP-negative colonies. In the figure, W1, W2, W3, W4, W5 and W6 represent the designation of each well of the 6-well plate used in Example 12.

Eighteen days after said three gene introduction and MS-275 treatment, the pluripotent stem cells were subcultured from each well of the 6-well plate to a gelatin-coated 100 mm plate. Subculture was continued similarly.

Twenty nine days after said three gene introduction and MS-275 treatment, the mouse pluripotent stem cells were subcutaneously transplanted to the back of syngeneic C57BL/6N mice at $2\times10^7$ cells/mouse, and 34 days later the teratoma that formed was extracted. From the extracted teratoma, slices were prepared, and differentiation potential into three germ layers was analyzed by immunological and histological staining (HE stain, alcian blue stain). As a result, GFAP-positive cells (the nervous system) and keratin producing cells (skin cells) as the ectodermic system, smooth muscle actin-positive cells (smooth muscle cells), bone tissues and cartilage tissues as the mesodermic system, and intestinal tract tissues (endodermal epithelium positive for MUC-1) as the endodermic system were observed.

Example 13

Induction of Mouse Pluripotent Stem Cells by the Introduction of Three Genes Then, using cells derived from mouse bone marrow that is a mouse postnatal tissue, the induction of mouse pluripotent stem cells was carried out with the introduction of three genes.

The primary culture cells derived from mouse bone marrow containing undifferentiated stem cells that had been stored frozen after preparing in Example 11 were plated at a density of $1 \times 10^4$ cells/cm$^2$ on a 24-well plastic plate (manufactured by Becton Dickinson) having the bottom which had been gelatin-coated with a 0.1% gelatin/phosphate buffer solution, and 2 ml each of the MAPC medium was added.

Two days later, the medium was removed, 2 ml each of the three gene (human Oct3/4, Sox2 and Klf4) retrovirus vector solution prepared as in Example 1 were added, and after culturing at 37° C. for 1 day, the virus solution was removed, and 2 ml each of the MAPC medium was added. Three days later, the medium was replaced with the mouse ES medium [a final concentration of 0.3% FBS (manufactured by Invitrogen), 1000 units/ml LIF (manufactured by Chemicon) and 0.1 mM 2-mercaptoethanol were added to the ES medium at the time of use]. Then medium change with the mouse ES medium was continued every 2 to 3 days. Eleven days after the introduction of three gene (human Oct3/4, Sox2 and Klf4) retrovirus vector, the cells were subcultured from each well of the 24-well plastic plate to each well of a 6-well plastic plate.

Then medium change with the mouse ES medium was continued every 2 to 3 days. Nineteen days after said three gene introduction, the pluripotent stem cells formed colonies composed of mouse ES cell-like small cells. In order to confirm the alkaline phosphatase activity, the medium was removed and then a 10% formalin neutral buffer solution was added to wells, and fixed at room temperature for 5 minutes. After washing with a phosphate buffer etc., the I step NBT/BCIP solution (manufactured by Pierce) comprising a chromogenic substrate of alkaline phosphatase was added and reacted at room temperature for 20 to 30 minutes. The colonies of said pluripotent stem cells were stained blue violet by alkaline phosphatase activity.

Then, the amount expressed of the Nanog gene was confirmed by quantitative PCR, and the expression of mouse Nanog of colonies of pluripotent stem cells having alkaline phosphatase activity was confirmed.

Using cells derived from mouse bone marrow that is a mouse postnatal tissue, the induction of pluripotent stem cells was carried out with the introduction of three genes.

The primary culture cells derived from mouse bone marrow containing undifferentiated stem cells that had been stored frozen after preparing in Example 11 were plated at a density of $1 \times 10^4$ cells/cm$^2$ on a 6-well plastic plate (manufactured by Becton Dickinson) the bottom of which had been gelatin-coated with a 0.1% gelatin/phosphate buffer solution, and the MAPC medium was added in 2 ml portions.

Two days later, the medium was removed, the three gene (human Oct3/4, Sox2 and Klf4) retrovirus vector solution prepared as in Example 1 were added in 2 ml portions, and after culturing at 37° C. for 1 day, the virus solution was removed, and the MAPC medium was added in 2 ml portions. Three days later, the medium was replaced with the mouse ES medium [a final concentration of 0.3% FBS (manufactured by Invitrogen), 1000 units/ml LIF (manufactured by Chemicon) and 0.1 mM 2-mercaptoethanol were added to the ES medium at the time of use]. Medium change with the mouse ES medium was continued every 2 to 3 days. Nine days after the introduction of three gene (human Oct3/4, Sox2 and Klf4) retrovirus vector, the cells were subcultured from each well of the 6-well plastic plate to each well of a 10 cm plastic dish.

Medium change with the mouse ES medium was continued every 2 to 3 days. Seven days after said three gene introduction, the pluripotent stem cells formed colonies composed of mouse ES cell-like small cells. In order to confirm the alkaline phosphatase activity, the medium was removed and then a 10% formalin neutral buffer solution was added to wells, and fixed at room temperature for 5 minutes. After washing with a phosphate buffer etc., the 1 step NBT/BCIP (manufactured by Pierce), a chromogenic substrate of alkaline phosphatase, was added and reacted at room temperature for 20 to 30 minutes. The colonies of said pluripotent stem cells were stained blue violet by alkaline phosphatase activity.

Then, the amount expressed of the Nanog gene was confirmed by quantitative PCR, and the expression of mouse Nanog of colonies of pluripotent stem cells having alkaline phosphatase activity was confirmed.

Forty nine days after said three gene introduction, the mouse pluripotent stem cells were subcutaneously transplanted on the back of syngeneic C57BL/6N mice at $2 \times 10^7$ cells/mouse, and 13 and 17 days later the teratoma that formed was extracted. Slices were prepared from the extracted teratoma, and differentiation potential into three germ layers was analyzed by immunological and histological staining (HE stain, alcian blue stain). As a result, GFAP-positive cells (the nervous system) and keratin producing cells as the ectodermic system, smooth muscle actin-positive cells (smooth muscle cells), bone tissues and cartilage tissues as the mesodermic system, and intestinal tract tissues (endodermal epithelium positive for MUC-1) as the endodermic system were observed.

Likewise, after said three gene introduction, the mouse pluripotent stem cells which were single-sorted based on GFP and SSEA-1 positive with FACSAria, were subcutaneously transplanted on the back of syngeneic C57BL/6N mice at $2 \times 10^7$ cells/mouse, and 13 and 14 days later the teratoma that formed was extracted. Slices were prepared from the extracted teratoma, and differentiation potential into three germ layers was analyzed by immunological and histological staining (HE stain, alcian blue stain). As a result, neural tube derived cells positive for GFAP, Nestin or Neurofilament as ectodermic system and cartilage tissues as the mesodermic system, and intestinal tract tissues (endodermal epithelium positive for MUC-1 and alpha-fetoprotein) as the endodermic system were observed.

From the above results, pluripotent stem cell were obtained by the forced expression of each of three genes of Oct3/4, Sox2, and Klf4 in undifferentiated stem cell present in a postnatal tissue. The pluripotent stem cells showed an in vitro long-term self-renewal ability, and were expressed ES cell marker, Nanog expression and alkaline phosphatase activity, and the ability of differentiation of tissues derivative from all three germ layers (ectoderm; mesoderm and endoderm).

Example 14

Long Term Expansion and Characterization of Human Induced Pluripotent Stem Cells Human induced pluripotent stem (iPS) cell line generated from neonatal human skin fibroblasts (lot #5F0438) in Example 6 which was termed iPS-1-8 was further sub-cloned with cloning cylinder and 0.25% trypsin-EDTA as described in Example 6. Nine sub-clones which were termed human iPS-1-1, 1-2, 1-3, 1-4, 1-5, 1-6, 1-7, 1-8 and 1-9 were obtained. One of nine sub clones, termed human iPS-1-8 clone, was successfully expanded on MEF feeder cells in human ES medium supplemented with 0.1 mM 2-mercaptoethanol and 10 ng/ml bFGF or in mTeSR1 defined medium (Stem cell Technologies) on matrigel (BD Biosciences)-coated culture dishes. Medium was changed for human iPS-1-8 clone culture everyday and usually treated with 5 to 20 µM of Y-27632 (Calbiochem) to avoid cell apoptosis triggered by the passaging procedures. For the passage to continue the culture, human induced pluripotent stem cells were washed with Hanks's balanced solution, incubated in 0.25% trypsin-EDTA (Gibco) at 37° C. for 3 minutes, and then added the culture medium to terminate the trypsin activity. Human induced pluripotent stem cells were centrifuged at 300×g at room temperature or 4° C. for 5 minutes and the supernatant was removed. Precipitated human induced pluripotent stem cells were re-suspended into culture medium. The pluripotent stem cells were usually split into new culture dishes using 1:4 to 1:6 splits. Human iPS-1-8 clone was frozen using Cell freezing solution for ES cells (Reprocell) according to the manufacture's manual.

Figure 5:
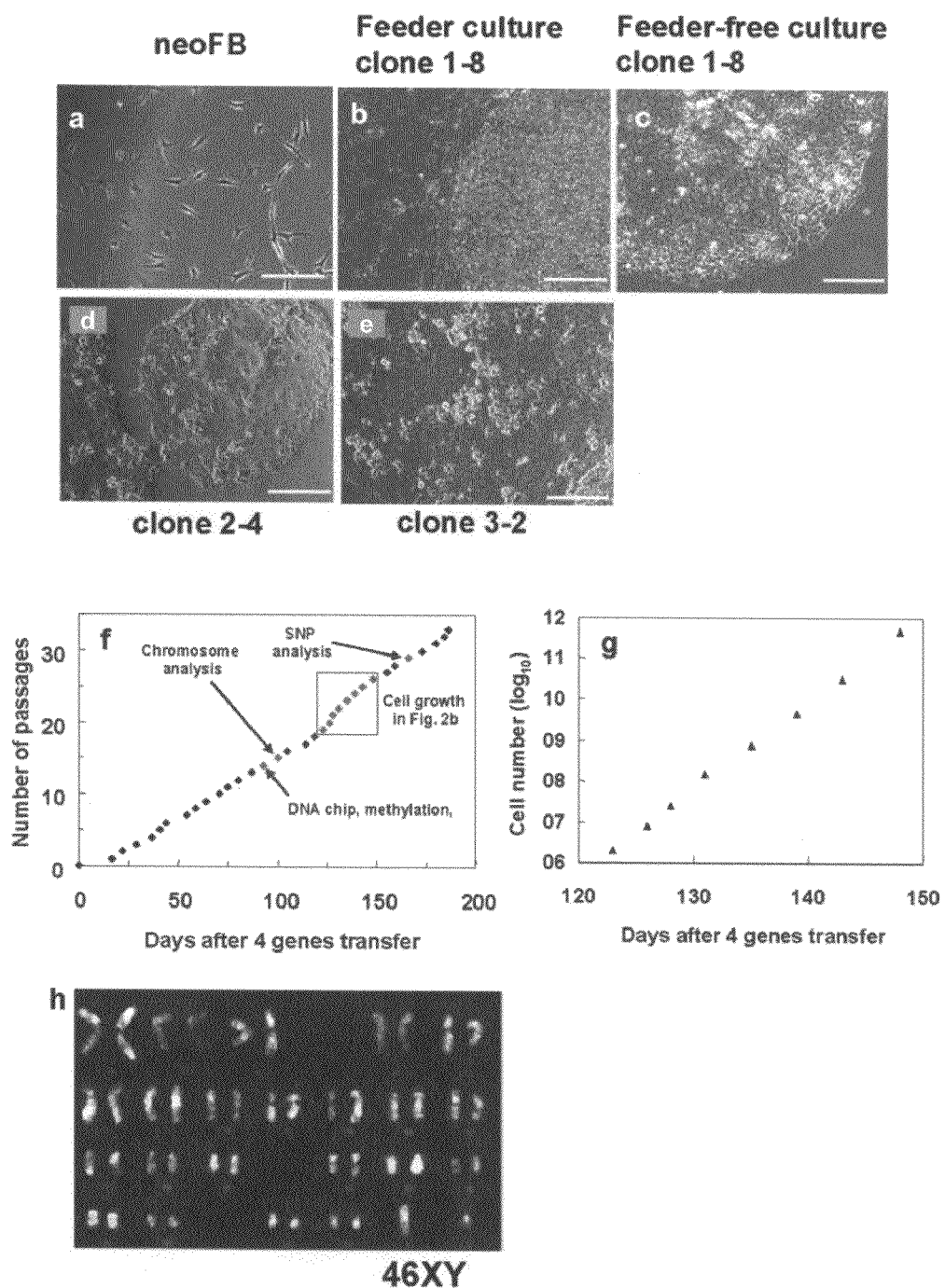
FIG. 5 shows the characterization of human iPS clone 1-8. The morphology of its parental fibroblast (lot. 5F0438) is shown in Panel a; the morphology of human iPS clone 1-8 cells cultured on murine embryonic fibroblast (MEF) feeder cells is shown in Panel b; the morphology of human iPS clone 1-8 cells in mTeSR1 medium is shown in Panel c; clone 2-4 cells in mTeSR1 medium are shown in Panel d; and clone 3-2 cells in mTeSR1 medium are shown in Panel e. The growth curve of clone 1-8 is shown in Panels f and g. Arrows indicate the dates of examinations. The square indicates the period for counting cell numbers to estimate cell proliferation rate. Panel h is a multicolor karyogram image indicating a normal karyotype of iPS clone 1-8 derived cell at day 101.

Human iPS-1-8 clone was morphologically indistinguishable from typical human ES cell colonies with defined edges that consist of small, round, and compact cells when cultured on mitomycin-C treated mouse embryonic fibroblasts (MEFs) (FIG. 5). FIG. 5 shows the characterization of human iPS clone 1-8. The morphology of its parental fibroblast (lot. 5F0438) is shown in Panel a; the morphology human iPS clone 1-8 cells cultured on murine embryonic fibroblast (MEF) feeder cells is shown in Panel b; the morphology of human iPS clone 1-8 cells in mTeSR1 medium is shown in Panel c; clone 24 cells in mTeSR1 medium are shown in Panel d; and clone 3-2 cells in mTeSR1 medium are shown in Panel e. The growth curve of clone 1-8 is shown in Panels f and g. Arrows indicate the dates of examinations. The square indicates the period for counting cell numbers to estimate cell proliferation rate. Panel h is a multicolor karyogram image indicating a normal karyotype of iPS clone 1-8 derived cell at day 101.

Human iPS-1-8 clone actively proliferated in mTeSR1 medium. Human iPS-1-8 clone derived cells cultured in mTeSR1 medium was termed human iPS-1-8 mTeSR cells. Human iPS-1-8 clone was able to be passaged more than 30 times, and cultured for more than half year after four factor infections (FIG. 5f, g). Human iPS-1-8 mTeSR cells were able to be stored in liquid nitrogen and re-cultured in mTeSR medium in the presence of 5 to 20 µM of Y-27632. Population doubling time of human iPS-1-8 mTeSR cells was approximately 48.5 hours when analyzed between passages 19 to 26 which correspond to days 123 to 148 after four factor infection.

Karyotype analysis of long-term cultured human iPS-1-8 clone (1-8 mTeSR) was performed using giemsa stain and multicolor-FISH analysis. Human iPS cells were pretreated with 0.02 µg/ml colecemid for 2 hours, followed by incubation with 0.075 M KCl for 20 minutes, and then fixed with Carnoy's fixative. For multicolor-FISH analysis, cells were hybridized with the multicolor FISH probe (Cambio) and analyzed under DMRA2 fluorescent microscope (Leica). Human iPS-1-8 mTeSR cells mainly maintained a normal karyotype (46XY) after long-term culture in mTeSR (68%) without any chromosomal translocation or deletion (FIG. 5h, Table 3).

For alkaline phosphatase staining, cells were fixed with 10% formalin neutral buffer solution (Wako) at room temperature for 5 minutes, washed with PBS, and incubated with alkaline phosphatase substrate I step NBT/BCIP (Pierce) at room temperature for 20-30 minutes. Cells having alkaline phosphatase activity were stained in blue violet. For immunocytochemistry, cultured cells were fixed with 10% formaldehyde for 10 minutes and blocked with 0.1% gelatin/PBS at room temperature for 1 hour. The cells were incubated overnight at 4° C. with primary antibodies against SSEA-3 (MC-631; Chemicon), SSEA4 (MC813-70; Chemicon) TRA-1-60 (abcam), TRA-1-81 (abcam), CD9 (M-L13; R&D systems), CD24 (ALB9; abcam), CD90 (5E10; BD bioscience), or Nanog (R&D systems). For Nanog staining, cells were permeabilized with 0.1% Triton X-100/PBS before blocking. The cells were washed with PBS for three times, and then incubated with AlexaFluor 488-conjugated secondary antibodies. (Molecular Probes) and Hoechst 33258 at room temperature for 1 hour. After further washing, fluorescence was detected with an Axiovert 200M microscope (Carl Zeiss).

Figure 6:
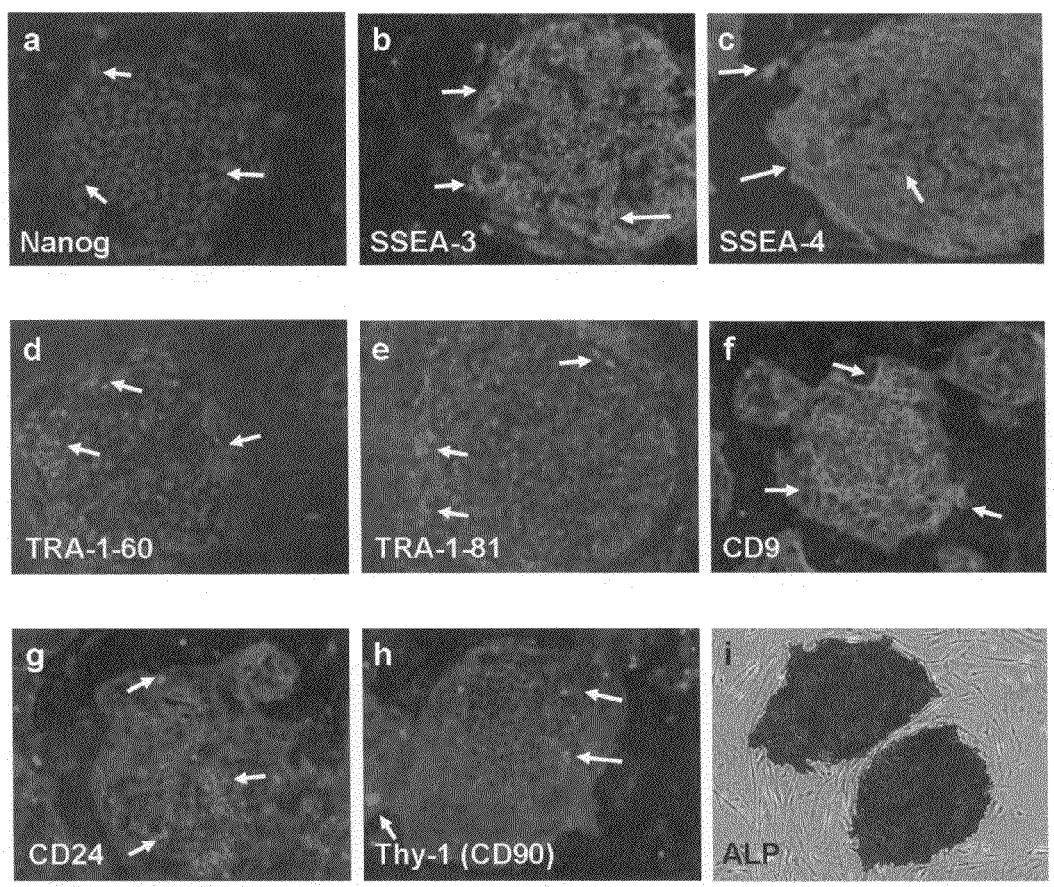
FIG. 6 shows the characterization of transcription factors, cell surface antigens and ALP activity in human iPS clone 1-8. Human iPS cells (clone 1-8) were stained for Nanog (Panel a), SSEA-3 (Panel b), SSEA4 (Panel c), TRA-1-60 (Panel d), TRA-1-81 (Panel e), CD9 (Panel f), CD24 (Panel g), Thy-1 (also called CD90) (Panel h). Green fluorescent staining indicates that human iPS clone 1-8 expresses all of these surface antigens. ALP staining indicates that iPS clone 1-8 is ALP positive. Arrows illustrate regions of green fluorescent staining.

Human iPS-1-8 mTeSR cells were positive for alkaline phosphatase (hereinafter referred to as "ALP") activity and the carbohydrate antigens SSEA-3 and SSEA4, the keratin sulfate antigens TRA-1-60 and TRA-1-81, and the protein antigens CD9, CD24, Thy-1 (CD90) staining (FIG. 6). FIG. 6 shows the characterization of transcription factors, cell surface antigens and ALP activity in human iPS clone 1-8. Human iPS cells (clone 1-8) were stained for Nanog (Panel a), SSEA-3 (Panel b), SSEA4 (Panel c), TRA-1-60 (Panel d), TRA-1-81 (Panel e), CD9 (Panel f), CD24 (Panel g), Thy-1 (also called CD90) (Panel h). Green fluorescent staining indicates that human iPS clone 1-8 expresses all of these surface antigens. ALP staining indicates that iPS clone 1-8 is ALP positive. Arrows illustrate regions of green fluorescent staining.

Figure 7:
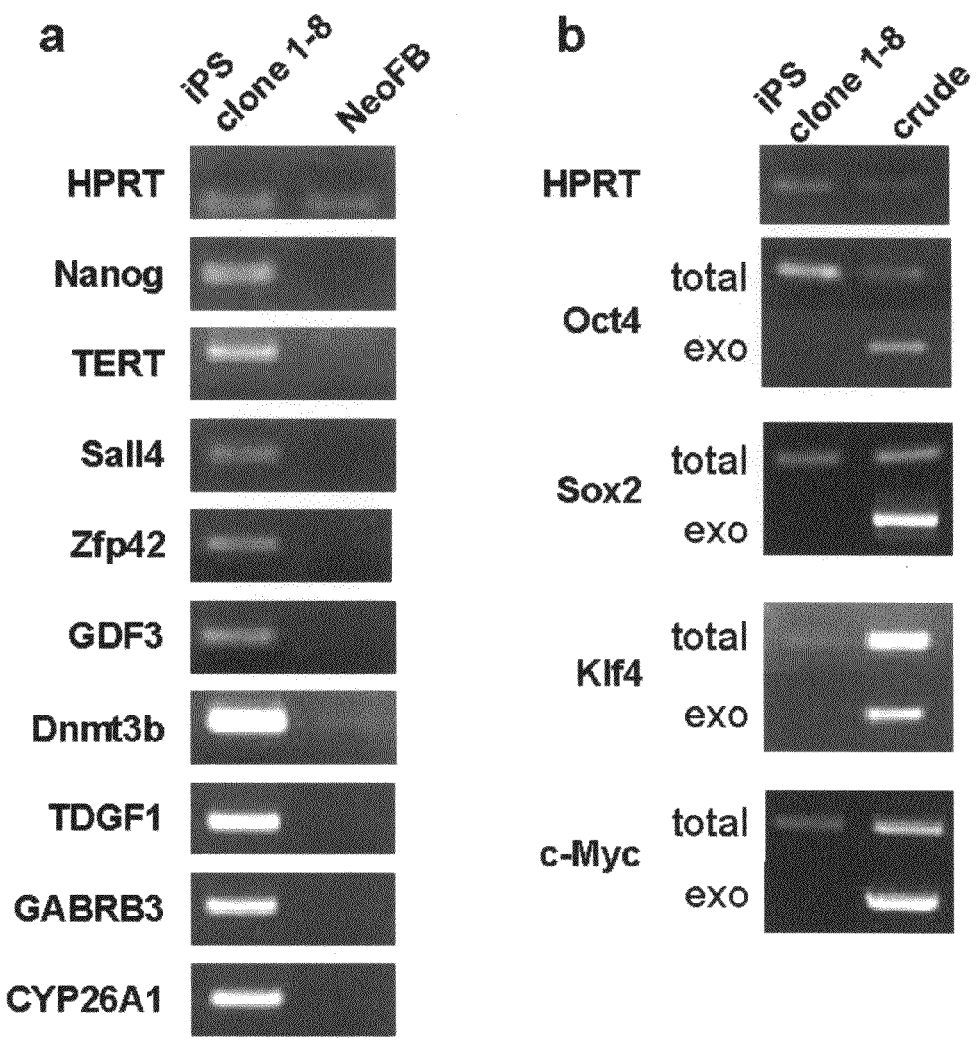
FIG. 7 shows the RT-PCR analysis of gene expression of human iPS clone 1-8 cells. Panel a depicts a RT-PCR analysis of hES marker gene expression in clone 1-8 and its parental fibroblast (NeoFB). Genes were detected at 30 cycles except for CYP26A1 (35 cycles). Panel b depicts the silencing of four transgenes in clone 1-8. Crude fibroblasts obtained 17 days after gene transduction were used as control. "Exo" primer sets selectively detected the expression of the exogenous genes; and "total" primer sets detected both endogenous and exogenous gene expression.

Total RNA was isolated from human iPS-1-8 clone, its parental fibroblasts, and crude fibroblasts obtained on 17 days after gene transduction by using RNeasy (Qiagen). cDNA was synthesized by SuperScript III (Invitrogen). Gene expressions were detected by PCR using Extaq (Takara). Sequences of the primers were described in Table 4. "Exo" primer sets selectively detected exogenous expression and "total" primer sets i endogenous expression Human iPS-1-8 clone expressed human ES marker genes Nanog, TERT, Sal14, Zfp42, GDF3, Dnmt3b, TDGF1, GABRB3, and CYP26A1 though the parental fibroblasts expressed none of those marker genes (FIG. 7a). In contrast to crude fibroblasts, the human iPS-1-8 clone down-regulated forced expression of four genes, Oct4, Sox2, Klf4, and c-Myc (FIG. 7b). FIG. 7 shows the RT-PCR analysis of gene expression of human iPS clone 1-8 cells. Panel a depicts a RT-PCR analysis of hES marker gene expression in clone 1-8 and its parental fibroblast (NeoFB). Genes were detected at 30 cycles except for CYP26 µl (35 cycles). Panel b depicts the silencing of four transgenes in clone 1-8. Crude fibroblasts obtained 17 days after gene transduction were used as control. "Exo" primer sets selectively detected the expression of the exogenous genes; and "total" primer sets detected both endogenous and exogenous gene expression.

Human iPS cells cultured in both mTeSR1 on matrigel (1-8 mTeSR) and MEF-conditioned medium on matrigel (1-8CM) and its parental fibroblasts (5F0438) were analyzed for global gene expression. The microarray study was carried out using the Affymetrix Human Genome U133 Plus 2.0 gene expression arrays (Affymetrix, Santa Clara, Calif.). The Gene-Chip® Human Genome U133 Plus 2.0 Array provides comprehensive coverage of the transcribed human genome on a single array and analyzes the expression level of over 47,000 transcripts and variants, including 38,500 well-characterized human genes. Briefly, total RNA was extracted from cells with RNAeasy (Qiagen). Biotin-labelled cRNA was reverse transcribed from 1 μg of total RNA according to Affymetrix technical protocols. Fifteen micrograms of cRNA was fragmented and hybridized to a Affymetrix U133 plus 2 Gene-Chip arrays at 45° C. for 16 hours and then washed and stained using the Affimetrix Fluidics (Affymetrix). The assays were scanned in the Affimetrix GCS3000 scanner, and the images obtained were analyzed using the GCOS software. Data from this experiment and GEO were investigated with the GeneSpring 7.3.1. software.

Figure 8:
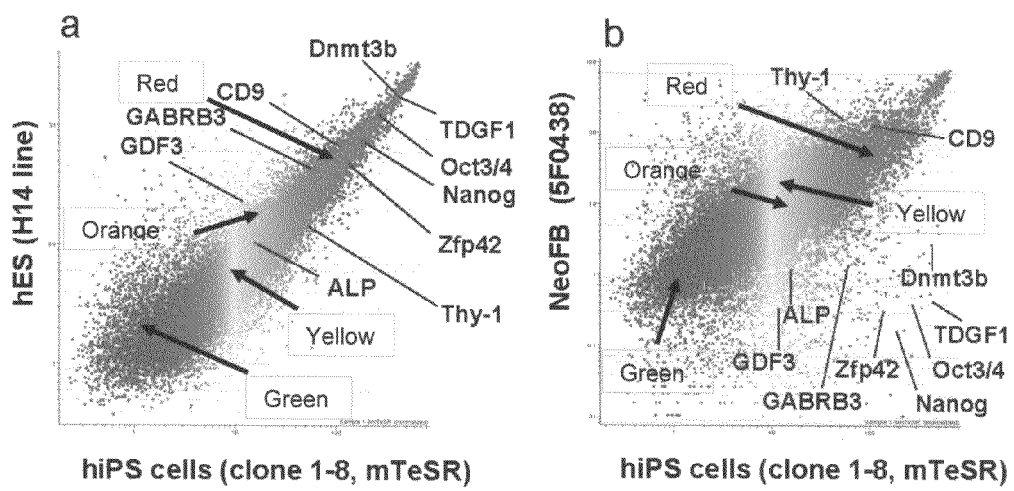
FIG. 8 shows a scatter plot analysis of the global gene expression of human iPS clone 1-8 cells. The scatter plots show a comparison of global gene expression between human iPS clone-1-8 cells cultured in mTeSR1 and H14 hES cells cultured with MEFs (GSM151741 from public database GEO)(Panel a), or between clones 1-8 and their parental fibroblasts (Panel b). Symbols of ES cell specific genes were pointed with lines in both scatter plots. Expression intensity was shown in colorimetric order from red (high) to green (low). Arrows indicate representative regions of color.

For scatter plot analyses, human induced pluripotent stem cell clone-1-8, cultured in mTeSR1 on matrigel (1-8 mTeSR) and its parental fibroblasts (5F0438) were analyzed based on a set of 21,080 genes with present flag call (P<0.04) or marginal flag call (0.04≦P<0.06) for both clone 1-8 and H14 hES line which is data from GEO (GSM151741), were used as a representative of human ES cells for comparison purposes. FIG. 8 shows a scatter plot analysis of the global gene expression of human iPS clone 1-8 cells. Scatter plots show a comparison of global gene expression between human iPS clone-1-8 cells cultured in mTeSR1 and H14 hES cells with MEFs (GSM151741 from public database GEO) (Panel a), or between clone 1-8 and its parental fibroblasts (Panel b). Symbols of ES cell specific genes were pointed with lines in both scatter plots. Expression intensity was shown in colorimetric order from red (high) to green (low). Arrows indicate representative regions of color.

For cluster analysis, DNA microarray data for clone-1-8 cultured in mTeSR1 (1-8 mTeSR), clone 1-8 cultured in MEF-conditioned medium (1-8CM) and its parental fibroblasts (5F0438) were compared with DNA microarray data for Sheff 4 line cultured on MEF (hES1:GSM194307, hES2: GSM194308, hES3: GSM194309), Sheff4 line cultured on matrigel (hES4: GSM194313, hES5: GSM194314), H14 line cultured on MEF (hES6: GSM151739, hES7: GSM151741), and three fibroblasts (GSM96262 for Fibroblasts1, GSM96263 for Fibroblasts2 and GSM96264 for Fibroblasts3).

Figure 9:
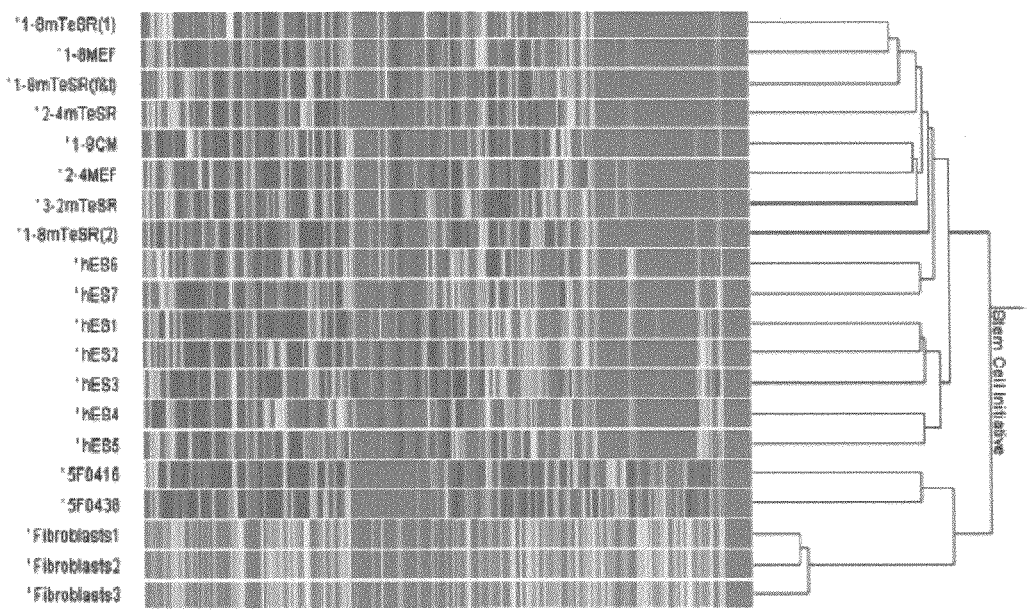
FIG. 9 shows global gene expression of different cell lines and gene trees based on global gene expression analysis. Cells were clustered in the gene tree based on a set of genes identified by the International Stem Cell Initiative (see Table 21). Samples were designated "1-8 mTeSR" for clone-1-8 cultured in mTeSR; "1-8CM" for clone 1-8 cultured in MEF-conditioned medium; "I-8 mTeSR(f&t)" for clone 1-8 cultured in mTeSR after freeze-thaw treatment; "1-8MEF" for clone 1-8 cultured on MEF; "24 mTeSr" for clone 24 cultured in mTeSR medium; "24MEF" for clone 24 cultured on MEF; "3-2 mTeSR" for clone 3-2 cultured in mTeSR medium; "5F0438" or "5F0416" for the parental fibroblasts; "hES1," "hES2," "hES3" (GSM194307, GSM194308, GSM194309, respectively) for Sheff 4 line cultured on MEF; "hES4," or "hES5" (GSM194313, GSM194314, respectively) for Sheff 4 line cultured on matrigel; "hES6," or "hES7" (GSM151739, GSM151741) for H14 line cultured on MEF; "Fibroblasts1" for GSM96262; "Fibroblasts2" for GSM96263, and "Fibroblasts3" for GSM96264, respectively. Expression intensity was shown in colorimetric order from red (high) to green (low).

The global gene expression profiles of the human iPS lines (1-8, 2-4, and 3-2) and their parental fibroblasts were analyzed using microarray technology. Hierarchical cluster analysis using the gene set defined by the International Stem Cell Initiative (see Table 21) revealed that the human iPS lines (1-8, 24, and 3-2) clustered with human ES cell lines but separated from their parental skin-derived cells (FIG. 9). FIG. 9 shows global gene expression of different cell lines and gene trees based on global gene expression analysis. Cells were clustered in the gene tree based on a set of genes identified by the International Stem Cell Initiative (see Table 21). Samples were designated "1-8 mTeSR" for clone-1-8 cultured in mTeSR; "1-8CM" for clone 1-8 cultured in MEF-conditioned medium; "1-8 mTeSR(f&t)" for clone 1-8 cultured in mTeSR after freeze-thaw treatment; "1-8MEF" for clone 1-8 cultured on MEF; "2-4 mTeSr" for clone 24 cultured in mTeSR medium; "24MEF" for clone 24 cultured on MEF; "3-2 mTeSR" for clone 3-2 cultured in mTeSR medium; "5F0438" or "5F0416" for the parental fibroblasts; "hES1," "hES2," "hES3" (GSM194307, GSM194308, GSM194309, respectively) for Sheff4 line cultured on MEF; "hES4," or "hES5" (GSM194313, GSM194314, respectively) for Sheff4 line cultured on matrigel; "hES6," or "hES7" (GSM151739, GSM151741) for H14 line cultured on MEF; "Fibroblasts1" for GSM96262; "Fibroblasts2" for GSM96263, and "Fibroblasts3" for GSM96264, respectively. Expression intensity was shown in colorimetric order from red (high) to green (low).

The Pearson correlation coefficient was 0.675 between human ES cell lines sheff4 and H14, and 0.835 between human iPS cell line 1-8 and human ES cell line H14 (FIG. 9). Similar Pearson correlation efficients were observed between the global gene expression profiles of iPS lines 1-8, 2-4, and 3-2 and the hES cell lines This analysis indicates that human iPS cell line 1-8 had a similar gene expression pattern to the human ES cell lines H14.

Figure 10:
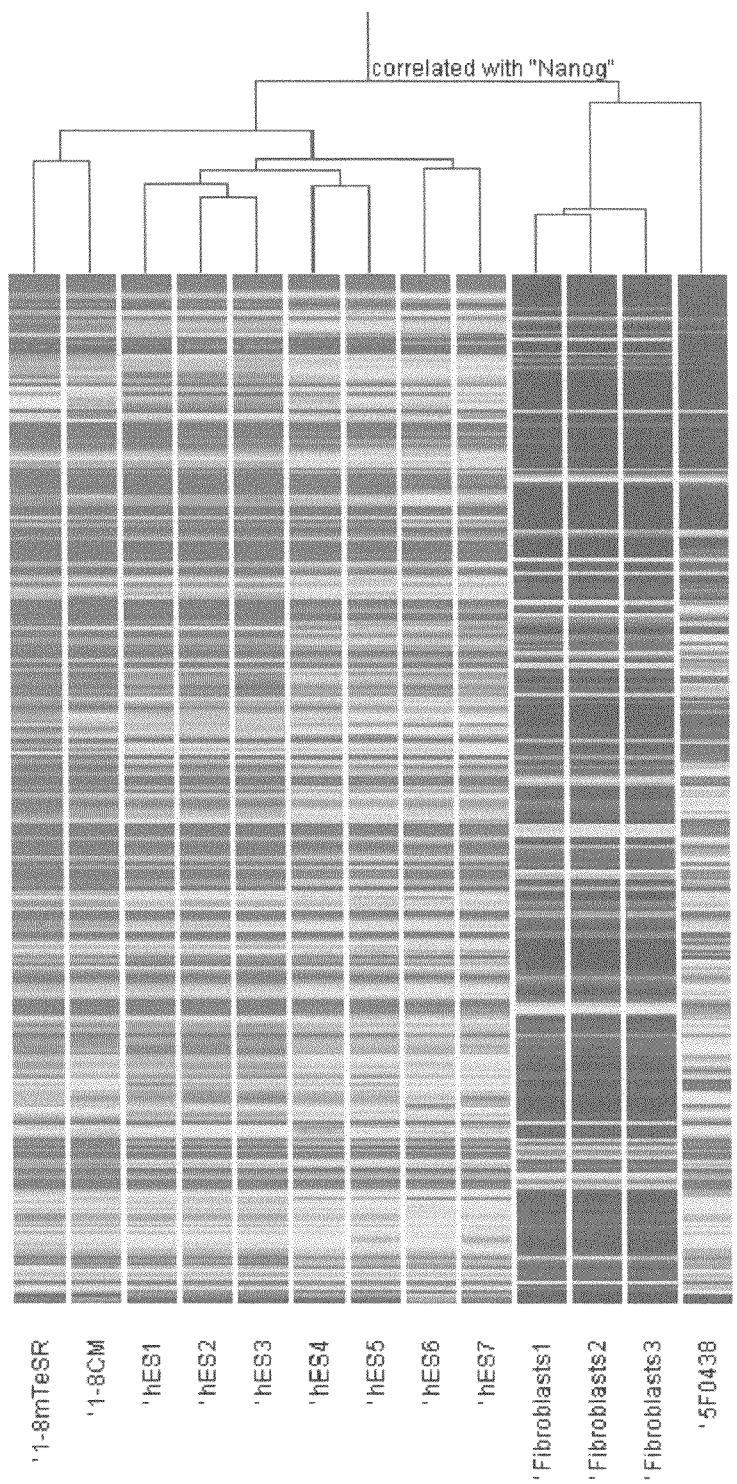
FIG. 10 shows global gene expression of different cell lines and gene trees based on the global gene expression analysis. Cells were clustered in the gene tree based on a set of genes correlated with Nanog gene expression in human ES cells (seven GEO data) between the ratio of 0.99 and 1 when compared with fibroblasts (three GEO data). Samples were designated "1-8 mTeSR" for clone-1-8 cultured in mTeSR; "1-8CM" for clone 1-8 cultured in MEF-conditioned medium, "5F0438" for the parental fibroblasts, "hES1," "hES2," "hES3" (GSM194307, GSM194308, GSM194309, respectively) for Sheff 4 line cultured on MEF; "hES4," "hES5" (GSM194313, GSM194314, respectively) for Sheff4 line cultured on matrigel" "hES6," "hES7" (GSM151739, GSM151741, respectively) for H14 line cultured on MEF; "Fibroblasts1" for GSM96262, "Fibroblasts2" for GSM96263, and "Fibroblasts3" for GSM96264, respectively. Expression intensity was shown in colorimetric order from red (high) to green (low).

Scatter plot analysis between human iPS cell line (clone 1-8) and human ES cell line H14 indicates that the human ES cell marker genes, Nanog, Oct3/4, TDGF1, Dnmt3b, GABRB3, GDF3, Zfp42, ALP, CD9, and Thy-1 showed high correlation between human iPS cell line and human ES cell line H14 (FIG. 8a). In contrast, clone 1-8 was different from the parental neonatal fibroblasts (FIG. 8b). This was confirmed by the cluster analysis using the Nanog-related genes. Pearson correlation coefficient was 0.908 between human iPS cell line 1-8 and human ES cell line H14 and 0.100 between human iPS cell line 1-8 and its parental fibroblasts (FIG. 10). FIG. 10 shows global gene expression of different cell lines and gene trees based on the global gene expression analysis. Cells were clustered in the gene tree based on a set of genes correlated with Nanog gene expression in human ES cells (seven GEO data) between the ratio of 0.99 and 1 when compared with fibroblasts (three GEO data). Samples were designated "1-8 mTeSR" for clone-1-8 cultured in mTeSR; "1-8CM" for clone 1-8 cultured in MEF-conditioned medium, "5F0438" for the parental fibroblasts, "hES1," "hES2," "hES3" (GSM194307, GSM194308, GSM194309, respectively) for Sheff 4 line cultured on MEF; "hES4," "hES5" (GSM194313, GSM194314, respectively) for Sheff4 line cultured on matrigel" "hES6," "hES7" (GSM151739, GSM151741, respectively) for H14 line cultured on MEF; "Fibroblasts1" for GSM96262, "Fibroblasts2" for GSM96263, and "Fibroblasts3" for GSM96264, respectively. Expression intensity was shown in colorimetric order from red (high) to green (low). Global gene expression data for the 1-8, 2-4, and 3-2 cell lines and their parental fibroblasts were deposited in the Gene Expression Omnibus (GEO) database under accession number GSE9709. These analyses reveal that human iPS cell line is very similar to human ES cell lines in terms of gene expression.

The promoter regions of Nanog and Oct3/4 in clones 1-8 and 24 were analyzed for methylation of individual CpG sites. Ten nanograms of bisulfite-treated genomic DNA was PCR-amplified with primers containing a T7-promoter and transcripts treated with RNase A. As fragments originating from a methylated CpG sequence contained a G instead of an A-base, they had a 16 Da higher molecular weight than those resulting from the corresponding non-methylated CpG. This mass difference was detected using a MALDI-TOF mass spectrometer (Autoflex, Bruker Daltonics). The spectra produced by the mass spectrometer were analyzed using the EpiTYPER (Sequenom). The percentage methylation of individual CpG sites was calculated using the area under the peak of the signal from the unmethylated and methylated fragments. The percentage methylation of individual CpG sites was calculated using the area under the peak of the signal from the unmethylated and methylated fragments. Table 9 lists up locations and sizes in genome corresponding to the amplicons used for the methylation analyses. Table 10 lists up the primer sets using for methylation analyses.

Figure 11:
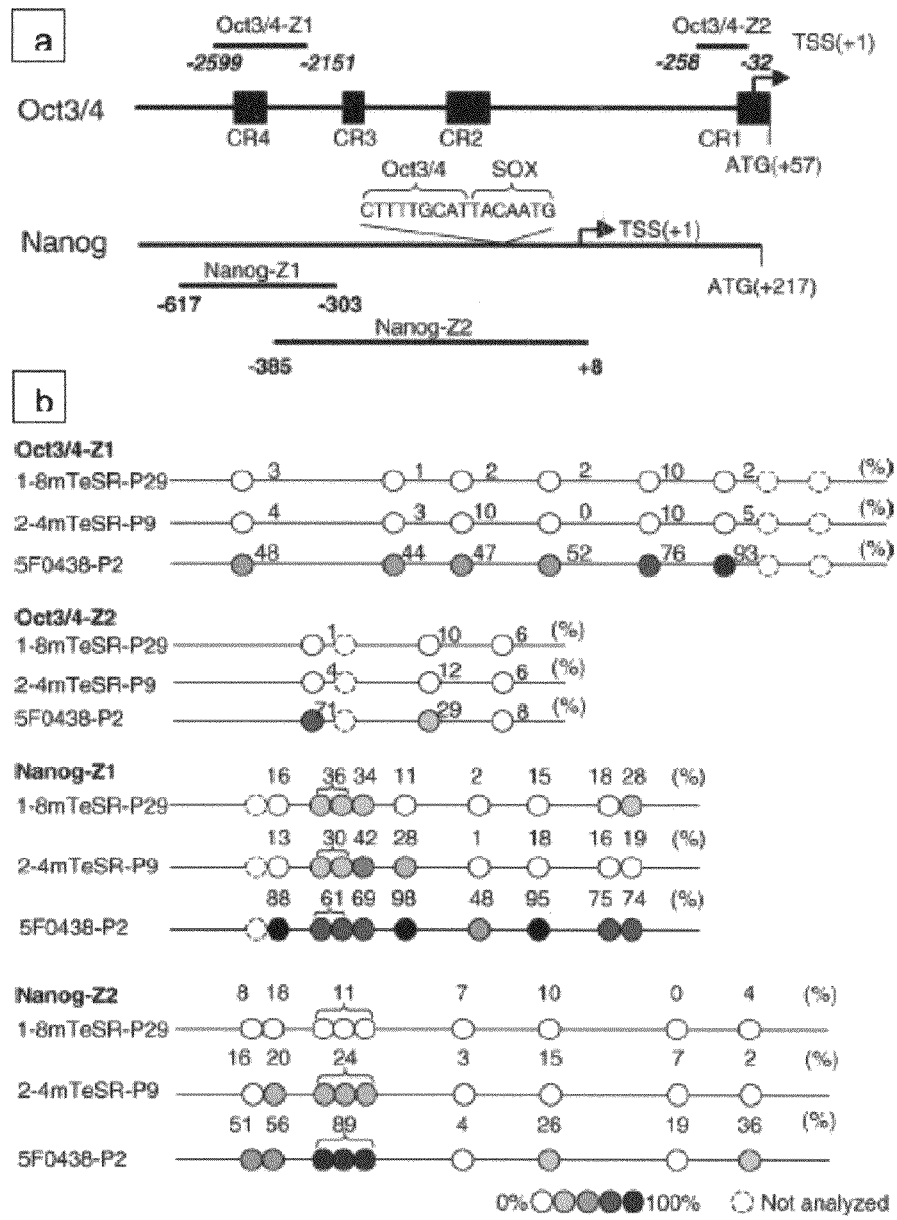
FIG. 11 shows the methylation analysis of promoters in human iPS 1-8. The Oct3/4 promoter (including the distal enhancer (Oct3/4-Z1) and the proximal promoter region (Oct3/4-Z2)) and parts of the Nanog promoter (including the proximal promoter region (Nanog-Z1, -Z2)), were analyzed for the methylation of CpG (Panel a). Panel b depicts the ratio of methylation on CpG shown by circles, as indicated by the percentage.

The Oct3/4 proximal promoter including conserved region 1 (CR1), the Oct3/4 promoter distal enhancer including CR4 and the Nanog proximal promoter including Oct3/4 and Sox2 binding sites were examined (FIG. 11a). As shown in FIG. 11b, cytosine-phosphate-guanosine (CpG) dinucleotides in these regions were demethylated in clones 1-8 and 24 derived cells compared to the parental fibroblasts.

Human iPS-1-8 mTeSR cell-suspension (0.5 to 2×10$^6$ cells/mouse) was injected into the medulla of left testis of 7 to 8 week old SCID mice (CB17, Oriental Yeast) using a Hamilton syringe. After 6 to 8 weeks, the teratomas were excised under perfusion with PBS followed with 10% buffered formalin, and subjected to the histological analysis. Human iPS-1-8 mTeSR cells gave rise to teratomas 4 to 8 weeks after transplantation into testes of SCID mice.

Teratomas were embedded in the mounting medium, and sectioned at 10 μm on a cryostat. Serial sections were stained with hematoxylin-eosin (HE) to visualize the general morphology. For the detection of cartilage, alcian blue staining was employed or combined with HE.

For immunostaining, sections were treated with Immunoblock (Dainippon-Sumitomo) for 30 minutes to block non-specific binding. Slides were incubated with the following primary antibodies: anti Nestin polyclonal antibody (PRB-570C, COVANCE, 1:300), anti Type II collagen polyclonal antibody (LB-1297, LSL, 1:200), anti Smooth muscle actin polyclonal antibody (RB-9010-R7, LAB VISION, 1:1), anti α-Fetoprotein polyclonal antibody (A0008, DAKO, 1:500), anti MUC-1 polyclonal antibody (RB-9222-P0, LAB VISION, 1:100), and anti Human nuclei monoclonal antibody (HuNu) (MAB1281, CHEMICON, 1:300). For Type II collagen, before the treatment with primary antibody a section was incubated with Hyaluronidase (25 mg/mL) for 30 minutes. Localization of antigens was visualized by using appropriate secondary antibodies (Alexa fluor 594 and 688, Molecular Probes, 1:600). Nuclei were stained with DAPI. Immunostained teratoma sections were analyzed under a fluorescence microscope (Axio Imager Z1, Zeiss).

Figure 12:
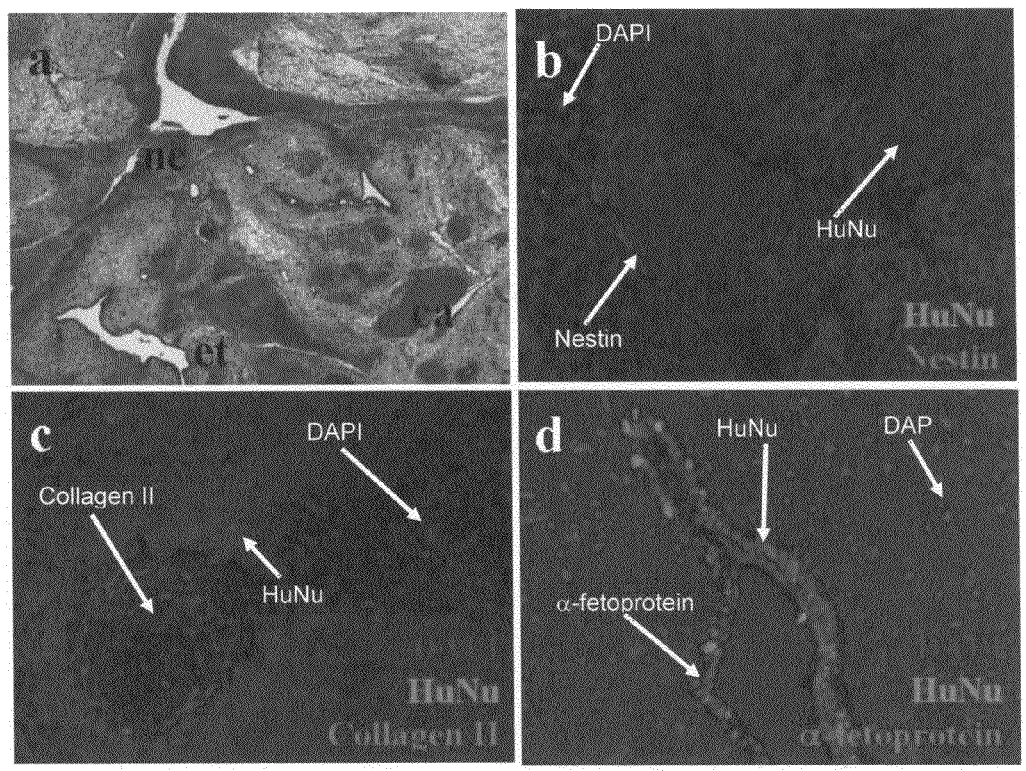
FIG. 12 shows the teratoma-formation ability of cells derived from human iPS-1-8 mTeSR cells cultured for 94 days. Human iPS-1-8 mTeSR cells were injected into SCID mouse testes and analyzed 56 days after injection. Panel a depicts HE and alcian blue staining of formaldehyde-fixed teratoma tissues. The teratomas contained tissues representative of the three germ layers; ne: neural epithelium, ca: cartilage, et: endodermal tract. Tissues originated from transplant were distinguished from host tissues by HuNu staining (Panels b-d). Nestin-expressing neural epithelium is depicted in Panel b; Collagen II expressing chondrocyte is depicted in Panel c; alpha-fetoprotein expressing endodermal tract is depicted in Panel d. Arrows indicate representative regions of staining.
Figure 13:
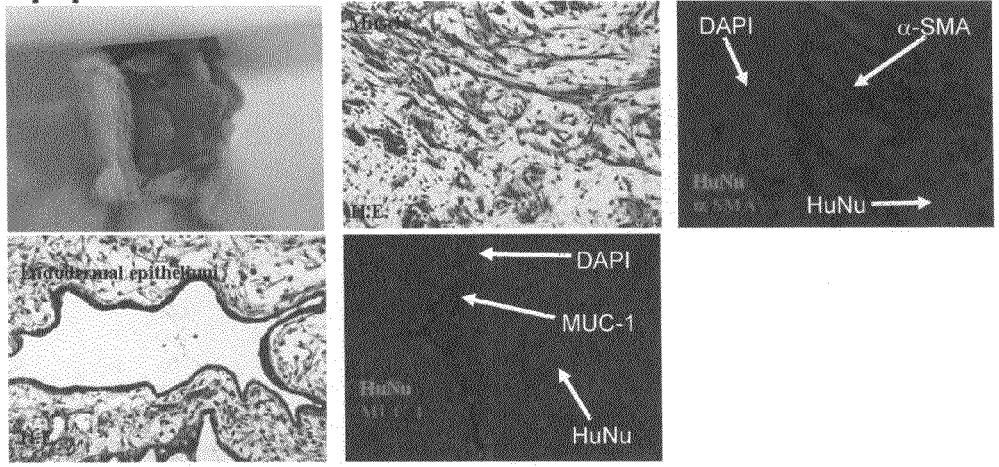
FIG. 13 shows the teratoma-formation ability of cells that had been cultured under varying conditions. Teratoma 1 (Panel T-1) was derived from human iPS-1-8 mTeSR cells cultured for 94 days. The human iPS-1-8 mTeSR cells were injected into SCID mouse testes and analyzed 56 days after injection. Teratoma 2 (Panel T-2) was derived from human iPS-1-8 mTeSR cells cultured for 102 days. The human iPS-1-8 mTeSR cells were injected into SCID mouse testes and analyzed 48 days after injection. In teratoma-1 (Panel T-1), smooth muscle cells (positive for α-SMA) and secretary epithelium (positive for MUC-1) were observed in addition to three germ layers observed in FIG. 12. Arrows indicate representative regions of staining.
Figure 13:
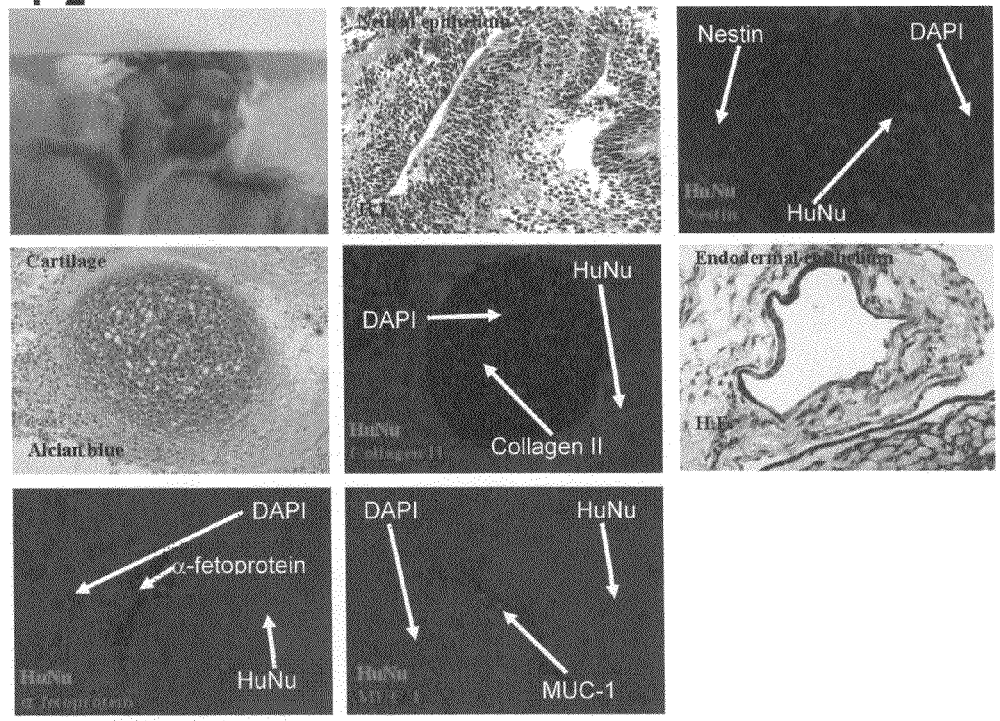
Figure 14:
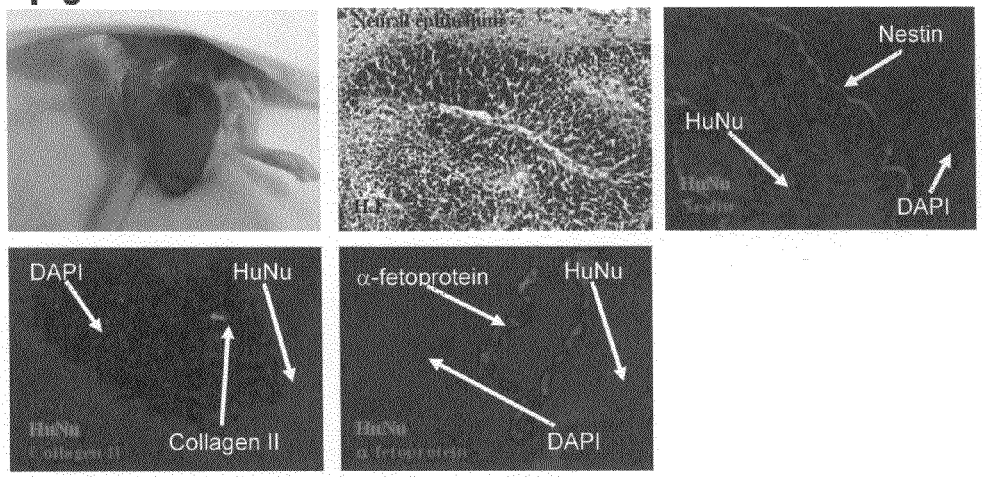
FIG. 14 shows the teratoma-formation ability of cells that had been cultured under varying conditions. Teratoma 3 (Panel T3) was derived from human iPS-1-8 mTeSR cells cultured for 114 days. Human iPS-1-8 mTeSR cells were injected into SCID mouse testis and analyzed 42 days after injection. Three germ layers similar to FIGS. 12 and 13 were observed. T-F1 and F2 figure shows teratoma that were derived from freeze-thawed iPS-1-8 mTeSR cells cultured for 134 days (passage 19). Human iPS-1-8 mTeSR cells were injected into SCID mouse testes and analyzed 46 days (Panel T-F1) and 48 days (Panel T-F2) after injection. Tissues consisting of three germ layers were observed. Melanocytes were also observed in T-F2 experiment. Pluripotency was maintained even after freezing and thawing. Arrows indicate representative regions of staining.
Figure 14:
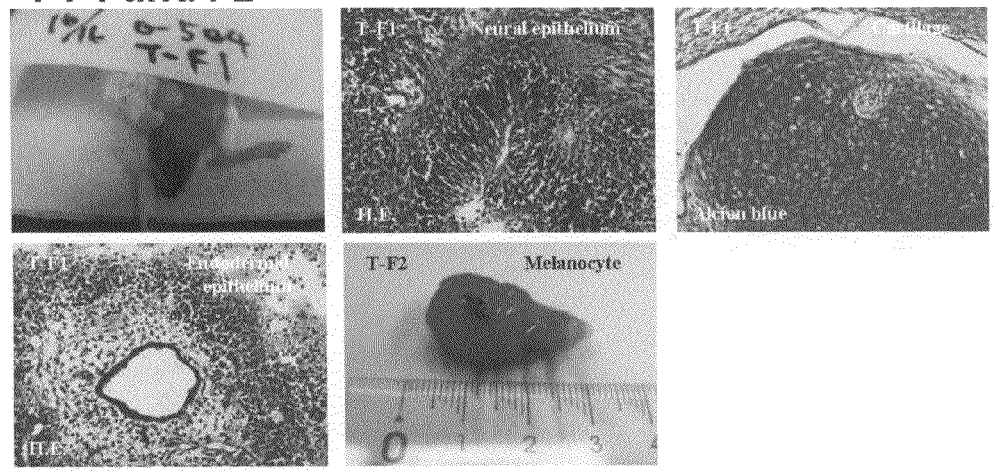

Teratomas of human iPS-1-8 mTeSR cells contained tissues representative of three germ layers, neuroectoderm, mesoderm, and endoderm. FIG. 12 shows teratoma that was derived from human iPS-1-8 mTeSR cells cultured for 94 days (T1). Human iPS-1-8 mTeSR cells were injected into SCID mouse testes and analyzed 56 days after injection. HE and alcian blue staining of teratoma tissues reveled that teratomas contained neural epithelium (positive for nestin) cartilage (positive for collagen II), endodermal tract(alpha-fetoprotein). Human iPS-1-8 mTeSR cell derived tissues were distinguished from host tissues by HuNu staining. In T1 teratoma, smooth muscle cells (positive for alpha-SMA) and secretary epithelium (positive for MUC-1) were also observed (FIG. 13). Human iPS-1-8 mTeSR cells which were cultured for 102 days and 114 days, were injected into SCID mouse testes and analyzed 48 days and 42 days(T3) after injection, respectively (T2, FIG. 13, T3, FIG. 14). Tissues representative of three germ layers, neuroectoderm, mesoderm and endoderm, were observed. To confirm whether human iPS can be cryopreserved, human iPS-1-8 mTeSR cells were frozen down, stored in liquid nitrogen and recultured. These cells were injected into SCID mouse testes and analyzed 46 days(T-F1) and 48 days (T-F2) after injection. Tissues representative of three germ layers, neuroectoderm, mesoderm and endoderm, were observed. Melanocytes were also observed in the T-F2 teratoma (FIG. 14). Thus, pluripotency was maintained via freezing and thawing.

Figure 15:
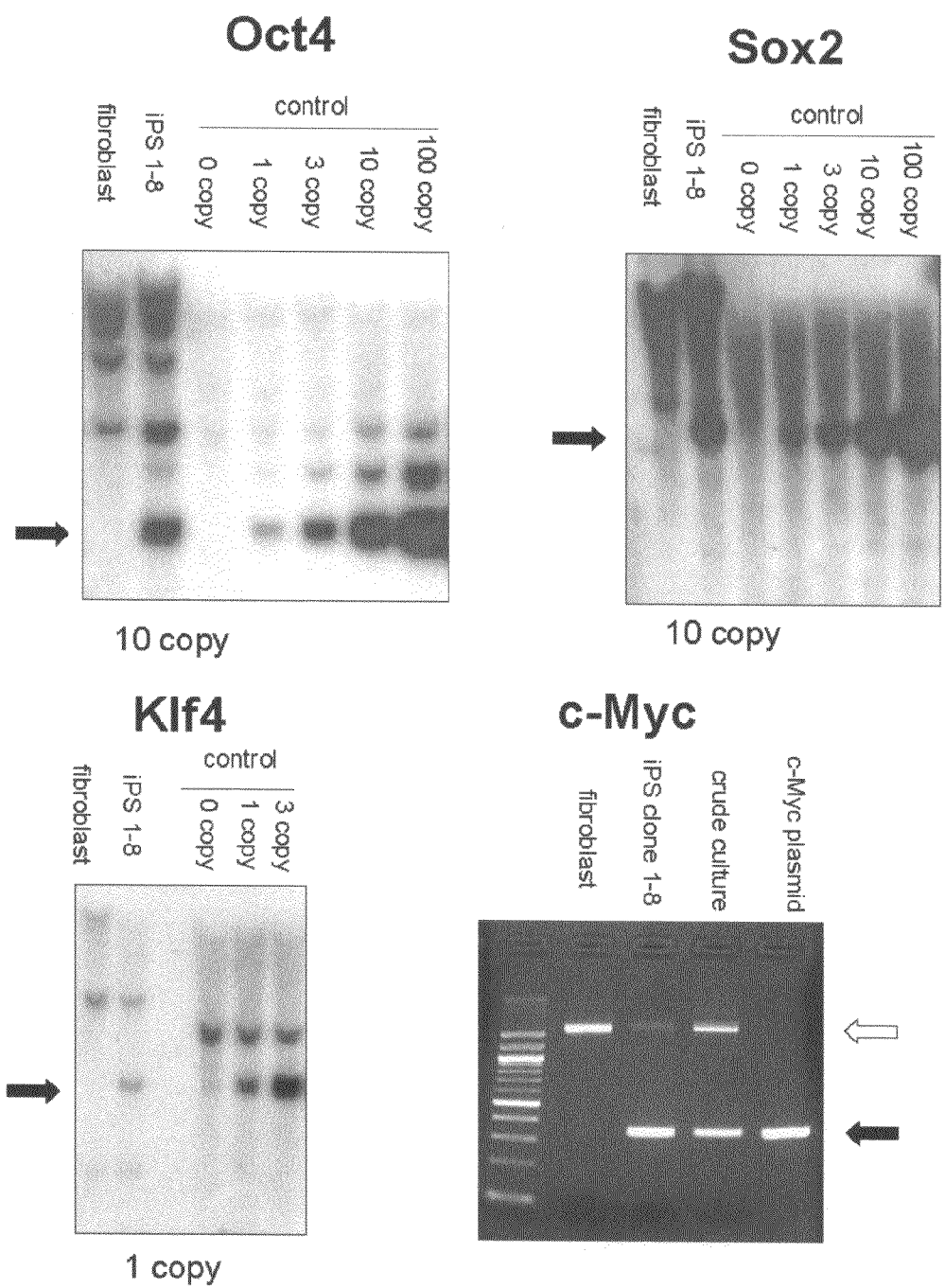
FIG. 15 shows Southern blot and PCR analyses of transgenes detected in human iPS clone 1-8. Oct3/4, Sox2, and Klf4 transgenes were detected by Southern blot analysis. Human iPS clone-1-8 was estimated to have approximately ten copies of both Oct3/4 transgenes and Sox2 transgenes, and a single copy of Klf4 transgene. For the c-Myc transgene, genomic PCR analysis was performed. The primer set was designed to include the entire second intron. Black arrows indicate the position of the transgene of interest. The white arrow indicates the position of endogenous c-Myc.

Both southern blot analysis and genomic PCR analysis indicated human iPS-1-8 clone carried four transgenes. In southern blot analysis cDNA fragments were prepared by restriction enzyme digestion (XhoI for POU5F1, NotI for Sox2, PstI for KIF4) from the corresponding pMX vector plasmids. These fragments were purified as [32P]-labeled probes with agarose gel electrophoresis and a QIAquick gel extraction kit (QIAGEN). Genomic DNA was prepared from the human iPS clone 1-8 and its parental fibroblasts. Five μg of each genomic DNA was digested with KpnI (POU5F1, Sox2, and Klf4). Fragments were separated on a 0.8% agarose gel, blotted onto HybondXL membrane (GE Healthcare), and hybridized with [32P]-labeled probes. Human iPS clone-1-8 was shown to carry approximately ten copies of both Oct3/4 transgenes and Sox2 transgenes, and a single copy of Klf4 transgene (FIG. 15). In genomic PCR analysis, primer set indicated as c-Myc-total in Table 4 was designed so that the amplicon included whole second intron of c-Myc. Thus, amplicon size of the transgene (338 bp) was smaller than amplicon of endogene (1814 bp). Vector plasmid and the parental fibroblast genome, crude cultured fibroblast genome obtained from 17 days culture post infection were used as a control template. The genomic PCR confirmed clone-1-8 cells carries c-Myc transgene (FIG. 15).

SNP genotyping was performed with the use of the GeneChip Human Mapping 500K Array Set (Affymetrix) according to the manufacture's protocol. Human iPS-1-8 mTeSR cells cultured in mTeSR1 on matrigel, its parental fibroblasts (5F0438), and fibroblast (5F0416) derived from a different donor were analyzed for this assay. The array set includes a StyI and a NspI chip. Two aliquots of 250 ng of DNA each were digested with NspI and StyI, respectively. Each enzyme preparation was hybridized to the corresponding SNP array (262,000 and 238,000 on the NspI and StyI array respectively). The 93% call rate threshold at P=0.33 (dynamic Model algorithm confidence threshold) with the Dynamic Model algorithm 138 was used in individual assays.

To confirm whether human iPS-1-8 mTeSR cells were generated from fibroblasts (5F0438), we compared SNP genotyping between human iPS-1-8 mTeSR cells and the employed fibroblasts (Table 5). SNPs of human iPS-1-8 mTeSR cells were consistent to that of parental cells in 464,069 (99.17%) of 467,946 of called SNPs and different from that of parental cells in 3,877 (0.83%) of them. In contrast, SNPs of human iPS-1-8 mTeSR cells were consistent to that of unrelated donor cells (5F0416) only in 284,950 (60.50%) of 470,960 of called SNPs and different from that of the unrelated cells in 186,010 (39.50%) of them. Thus, human iPS-1-8 clone (1-8 mTeSR) and parental cells had almost the same SNP genotype to each other, strongly suggesting that both cells originated from a single donor.

HLA DNA typing was performed by utilizing hybridization of PCR-amplified DNA with sequence specific oligonucleotide probes (SSOP) (Luminex). To investigate the DNA mutation ratio associated with the process of pluripotent stem cell induction, genome-wide single-nucleotide polymorphism array analysis was performed for human iPS clone 1-8 (n=2), its parental skin-derived cells (n=2), and skin cells derived from another donor (n=1). No marked differences were observed between human iPS clone 1-8 and the parental cells (Table 5). Consistent with these observations, HLA genotypes of human iPS cell lines 1-8, 2-4, and 3-2 were identical to those of their respective parental cells. Assays were performed to determine the HLA-A, HLA-B, HLA-Cw, HLA-DR, HLA-DQ, HLA-DP and Bw loci according to manufacturer's instructions. Human iPS cells are promising materials in cell transplantation therapies, they would overcome immune rejection, because human iPS cells can be directly generated from subjects' cells and must be the identical HLA type. We carried out HLA typing of human iPS-1-8 clone (1-8 mTeSR), parental cells (5F0438), and unrelated fibroblasts (5F0416). As expected, HLA type of iPS-1-8 clone was completely identical to that of 5F0438 but not 5F0416 (Table 6).

From the foregoing, human pluripotent stem cell were obtained by the forced expression of each of four genes of Oct3/4, Sox2, Klf4, and c-Myc in undifferentiated stem cell present in a human postnatal tissue. The human pluripotent stem cells showed an in vitro long-term self-renewal ability and the pluripotency of differentiation into ectoderm, mesoderm and endoderm. The human pluripotent stem cells were expressed cell surface antigens SSEA-3, SSEA4, TRA-1-60, TRA-1-81, CD9, CD24, and CD90, and ES cell marker genes Nanog, Oct3/4, TDGF1, Dnmt3b, GABRB3, GDF3, Zfp42, ALP, CD9, and Thy-1. The promoter regions of Nanog and Oct3/4 in the human pluripotent stem cells were demethylated compared to the parental fibroblasts. The human pluripotent stem cells carries at least a single copy of Oct3/4, Sox2, Klf4, and c-Myc transgene. The induced human pluripotent stem cells and the parental cells (undifferentiated stem cell present in a human postnatal tissue) had almost the same SNP genotype each other, and HLA type of the induced human pluripotent stem cell was completely identical to that of the parental cell (undifferentiated stem cell present in a human postnatal tissue).

Example 15

Gene Expression Profile of Primary Culture of 4 Genes Introduced Neonatal Fibroblast Two lots of neonatal fibroblasts (5F0416 and 5F0474) were seeded at $10^3$ cells/cm$^2$ or $10^4$ cells/cm$^2$ into 35 mm diameter wells of 6 well plates and cultured in FBM supplemented with FGM-2 SingleQuots (manufactured by Lonza) before the four genes transduction. Cells were infected with mCAT1-adenovirus vectors at $2\times10^5$ ifu/well and then infected with the retroviral vectors carrying four genes as described in Example 6. Eight wells were prepared for this study (2 different lot and 2 different densities in duplicate).

Seventeen days post 4-gene infection, cells were fixed and stained for alkaline phosphatase (ALP) as described in Example 3. In total, 163 ALP positive(+) colonies were observed in four independent experiments. All 163 ALP(+) colonies and 18 ALP-negative (ALP(−)) colonies were dissected, and total RNA from these colonies were extracted using a Recover All Total Nucleic Acid Isolation kit (manufactured by Ambion). After the cDNA preparation, genes of interest were amplified using Taqman preamp (manufactured by Applied Biosystems). Real-time quantitative PCR was performed with ABI PRISM 7900HT (manufactured by Applied Biosystems) using PCR primer sets (manufactured by Applied Biosystems, Nanog, Hs02387400_g1, Dnmt3b, Hs00171876 ml, FoxD3, Hs00255287_s1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1) to determine gene expression of human ES cell markers in colonies. Eight genes (Nanog, TDGF1, Dnmt3b Zfp42 FoxD3, GDF3, CYP26A1 and TERT genes) which were reported to express in human ES cells were selected as a pluripotent stem cell marker genes. A standard curves was generated for each primer pair. All expression values were normalized against GAPDH.

Figure 16:
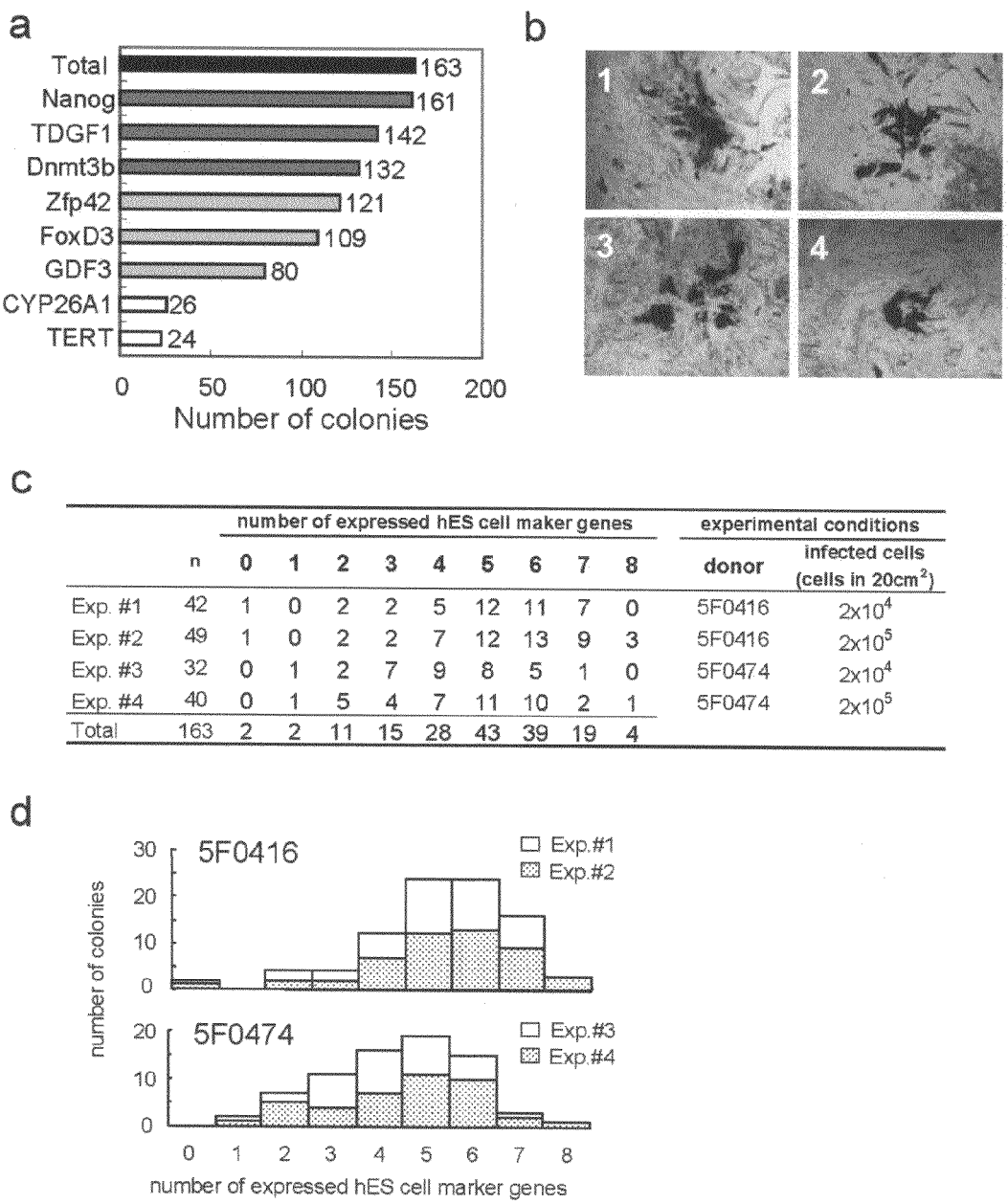
FIG. 16 shows hES maker gene expression profile in ALP positive colonies induced by four genes (Oct4, Sox2, Klf4 and c-Myc). Colonies were stained for ALP at 17 days after 4 gene transduction. All ALP(+) colonies were dissected and evaluated for hES marker gene expression. Panel a shows the number of colonies expressing Nanog, TDGF1, Dnmt3b, Zfp42, FoxD3, TERT, CYP26A1, and GDF3. Panel b shows the morphologies of octa-positive colonies. Panels c-d show the number of hES cell marker genes categorized by individual experiments.
Figure 17:
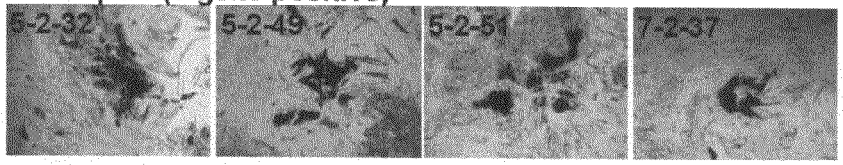
FIG. 17-FIG. 23 show morphologies of four gene (Oct4, Sox2, Klf4 and c-Myc) induced colonies categorized by gene expression profile of ES cell related 8 genes (Nanog, TDGF1, Dnmt3b, Zfp42, FoxD3, TERT, CYP26A1, and GDF3) as well as ALP activity. Circles indicate the picked-up colony.
Figure 17:
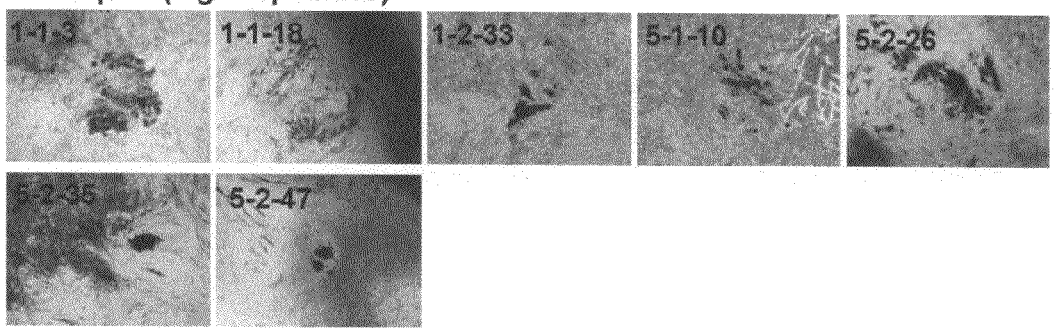
Figure 17:
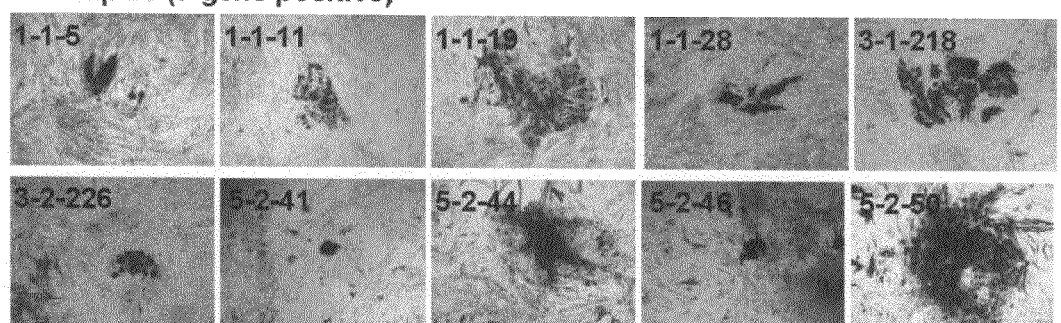
Figure 17:
Figure 18:
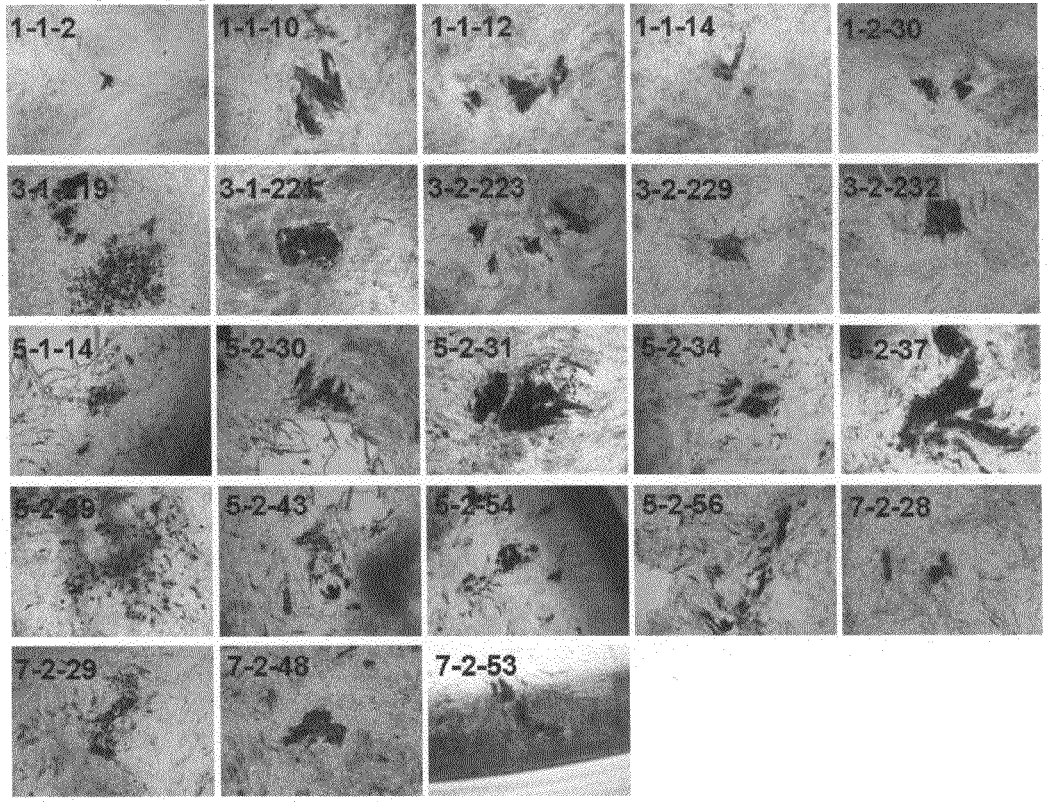
Figure 18:
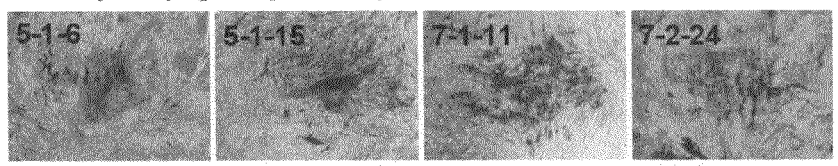
Figure 18:
Figure 18:
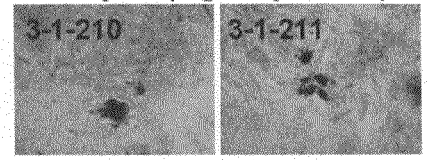
Figure 19:
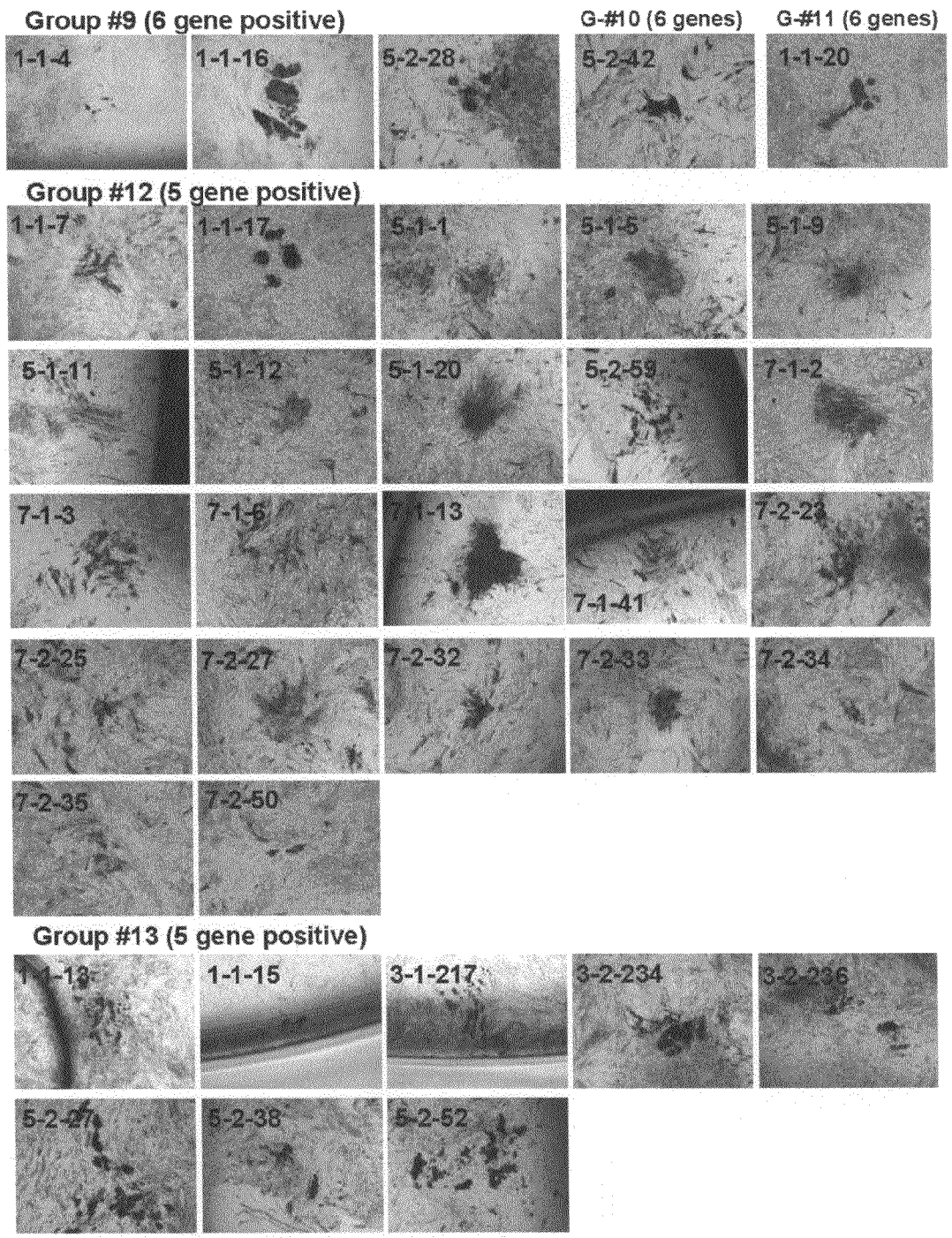
Figure 20:
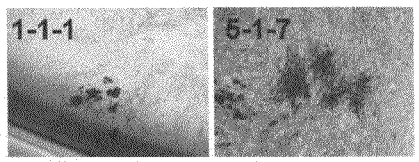
Figure 20:
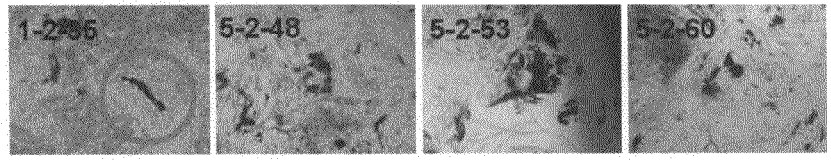
Figure 20:
Figure 20:
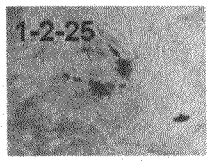
Figure 20:
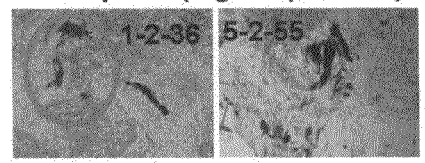
Figure 20:
Figure 20:
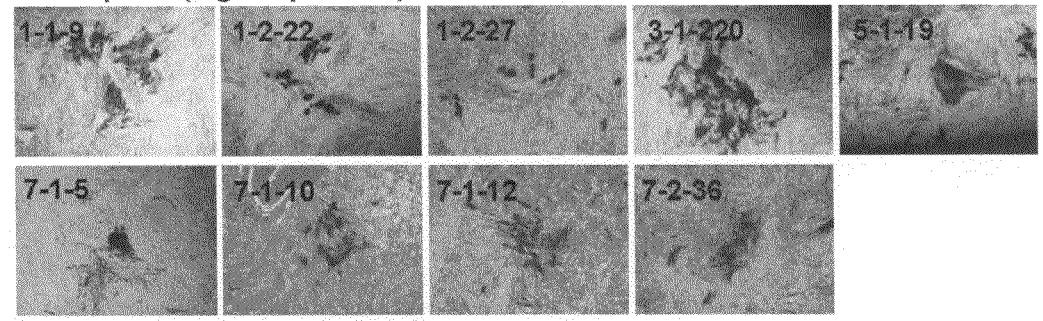
Figure 21:
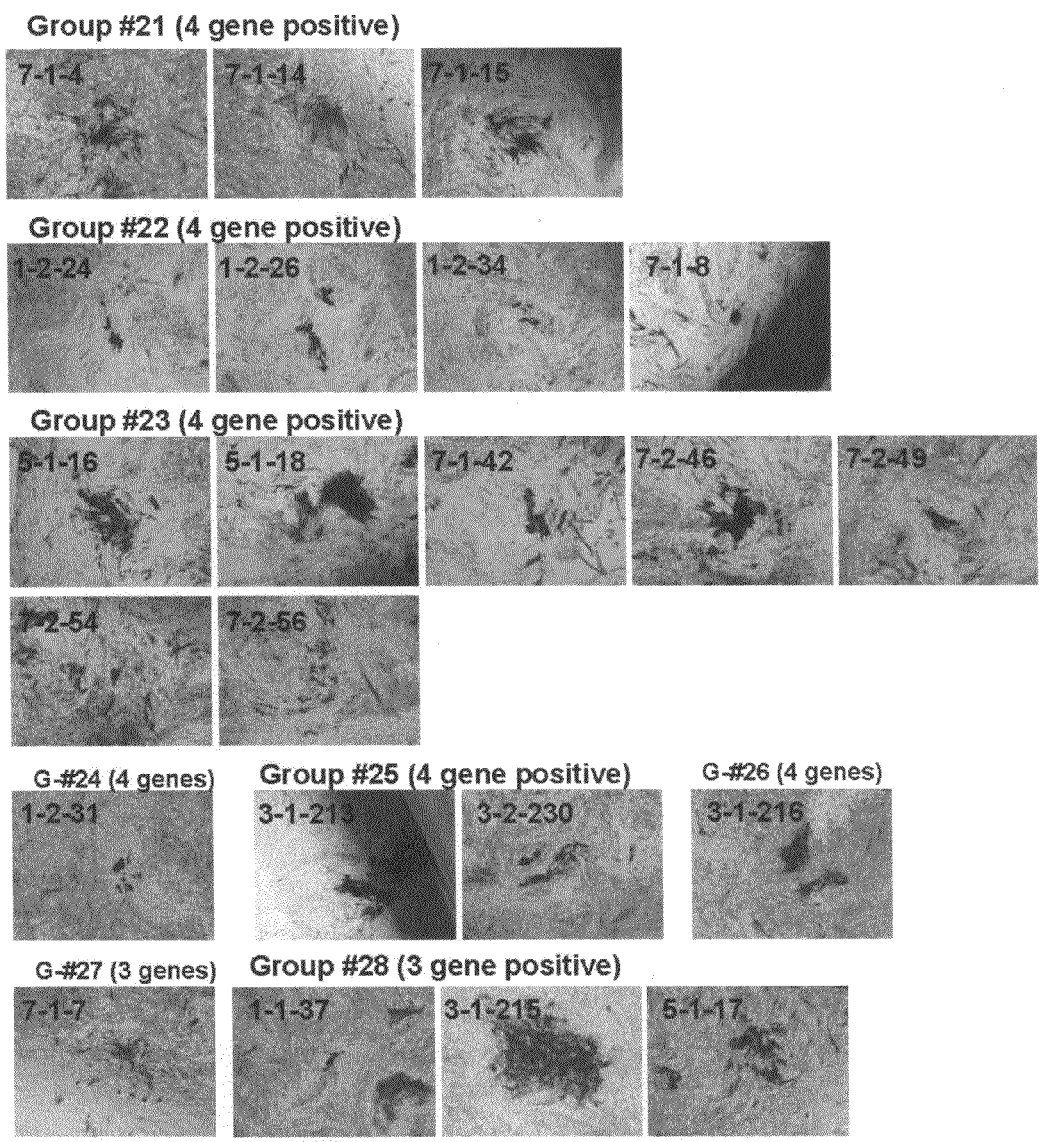
Figure 22:
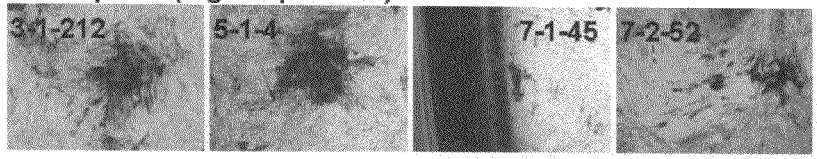
Figure 22:
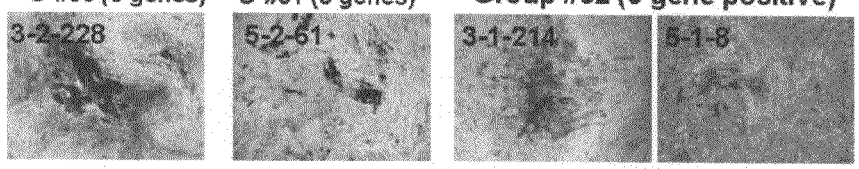
Figure 22:
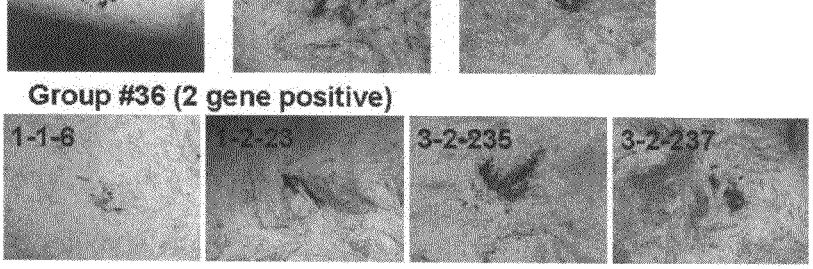
Figure 22:
Figure 22:
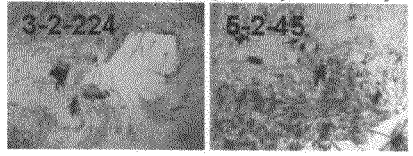
Figure 22:
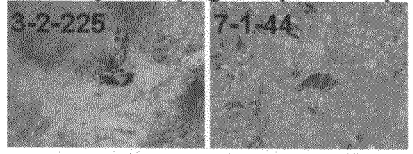
Figure 22:
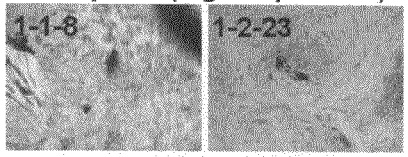

It is known that mouse ES cells and mouse iPS cells form multilayered/aggregated colonies. Thus we first analyzed the mouse ES cell like aggregated colonies which were induced by ectopic expression of four gene in human fibroblasts (e.g., colony #1-2-F and #1-2-B in FIG. 23). However, these colonies are all ALP(−). Next we analyzed the Nanog gene expression in colonies. Nanog gene expression was observed in 161 out of 163 ALP positive colonies and 16 out of 18 ALP negative colonies. On the other hand expression of TERT and CYP26A1 genes were observed only in 26 and 24 colonies out of 163 ALP positive colonies respectively (FIG. 16a). Genes such as Nanog, TDGF, and Dnmt3b which are well know to be close association with the pluripotent state in human ES cells, and to be strongly downregulated upon their differentiation had higher tendency to be induced by the four gene transduction.

ALP positive colonies can be categorized into 40 groups based on the gene expression pattern of the eight human marker genes (Table 7). When colonies are categorized by the total number of eight marker genes expression, the distribution of colony number followed a normal distribution suggesting the presence of a stochastic process in the colony induction (FIG. 16c,d). In addition the efficiency of human ES cell marker gene expression in human fibroblasts was affected by the donor difference.

Figure 23:
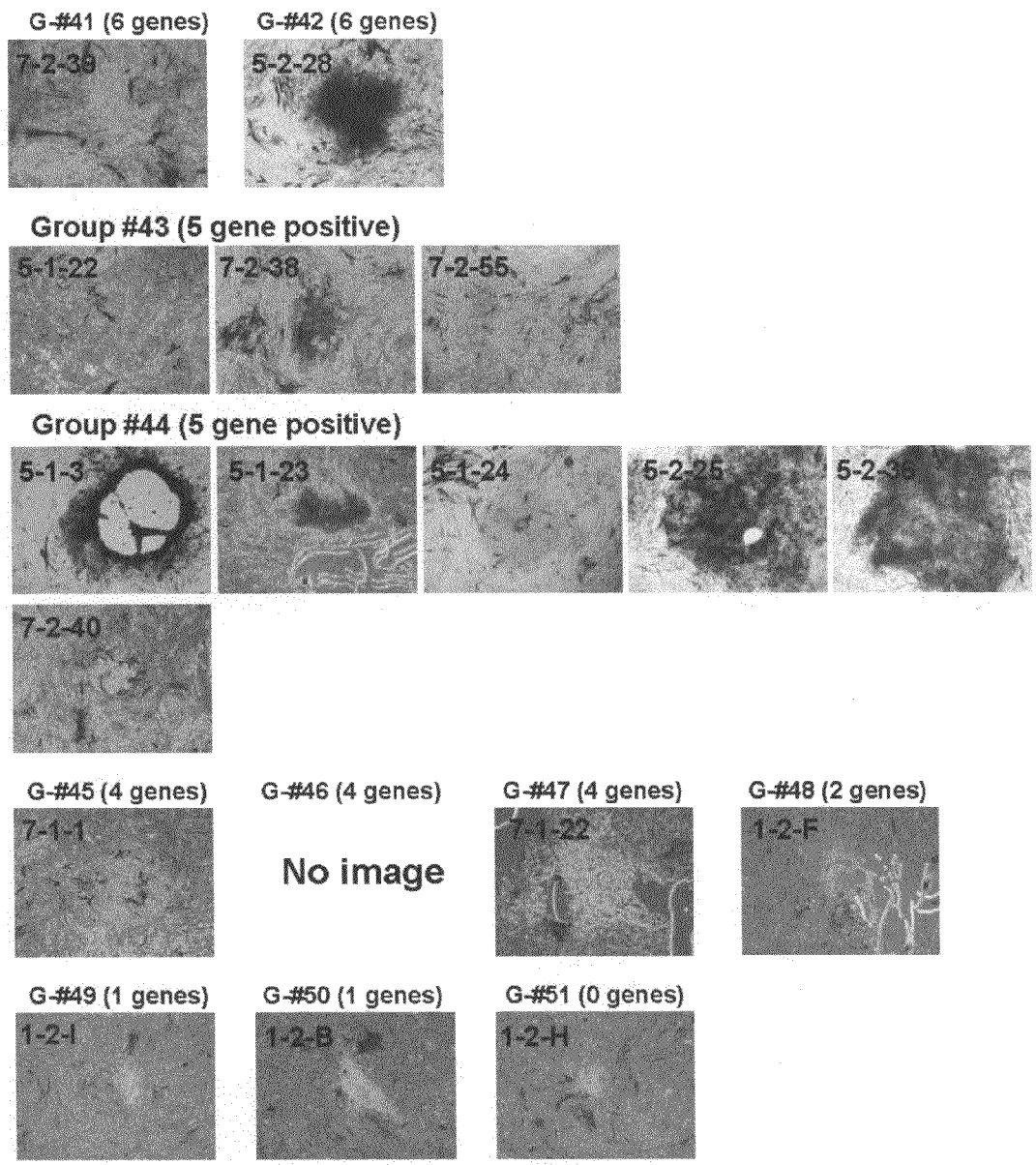
Figure 24:
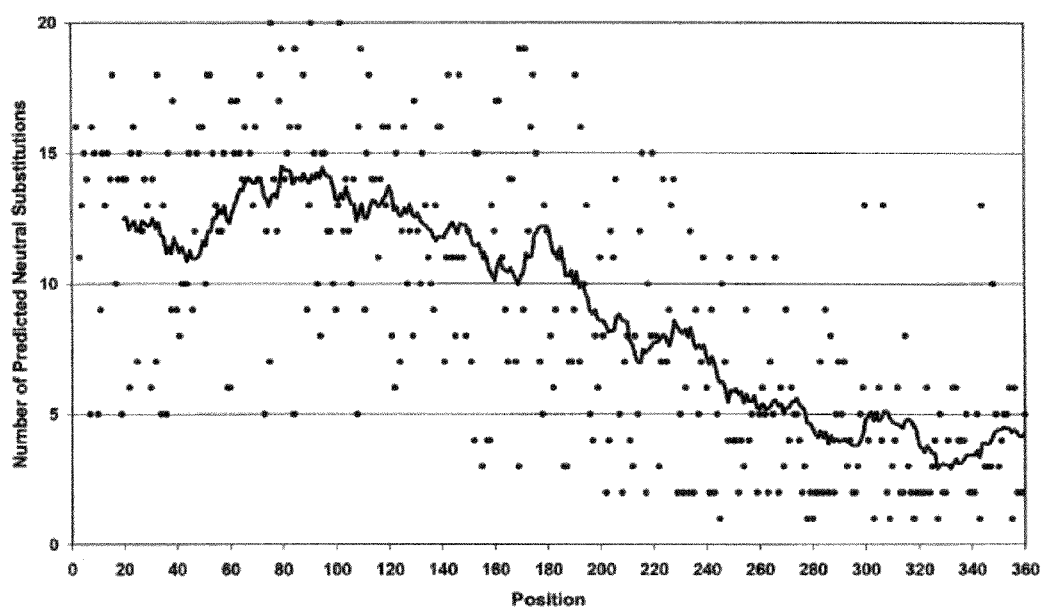
FIG. 24 is a graphic representation of the human Oct3/4 predicted mutation tolerance map.
Figure 25:
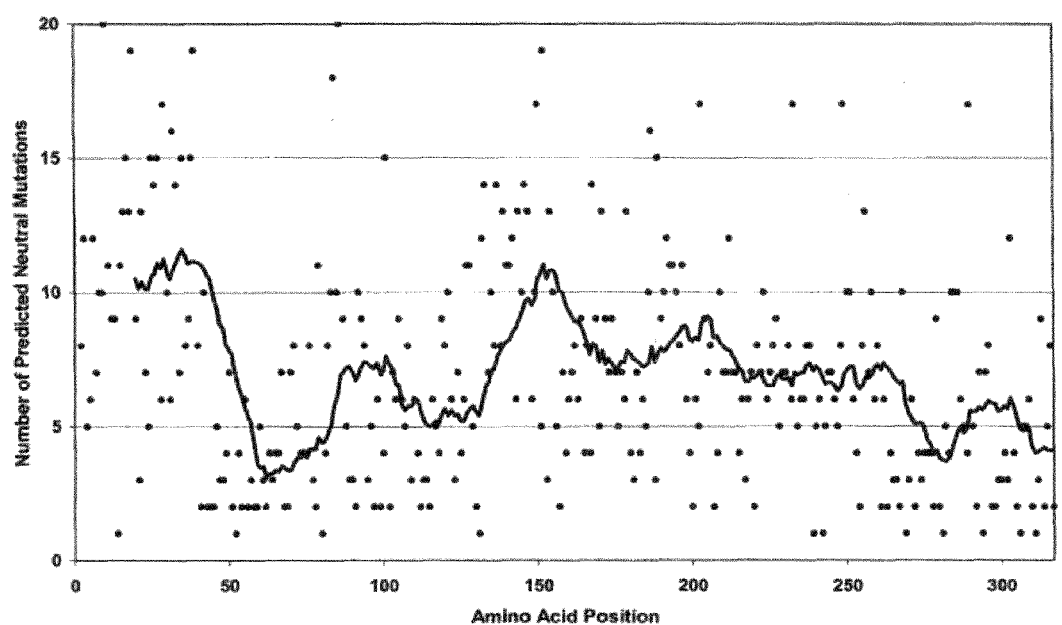
FIG. 25 is a graphic representation of the human Sox2 predicted mutation tolerance map.
Figure 26:
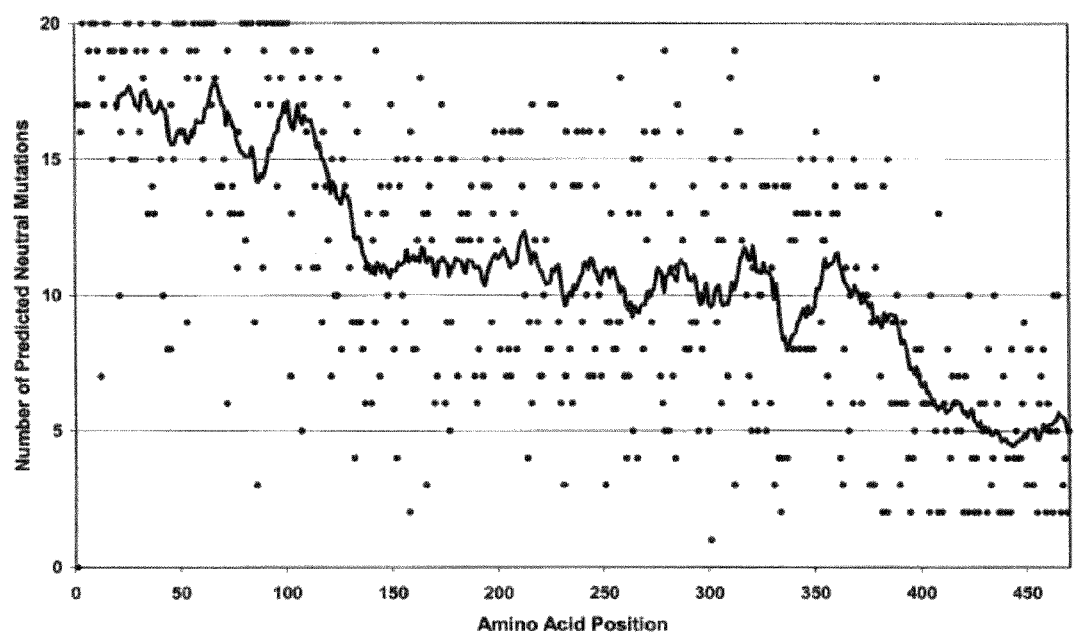
FIG. 26 is a graphic representation of the human Klf4 predicted mutation tolerance map.
Figure 27:
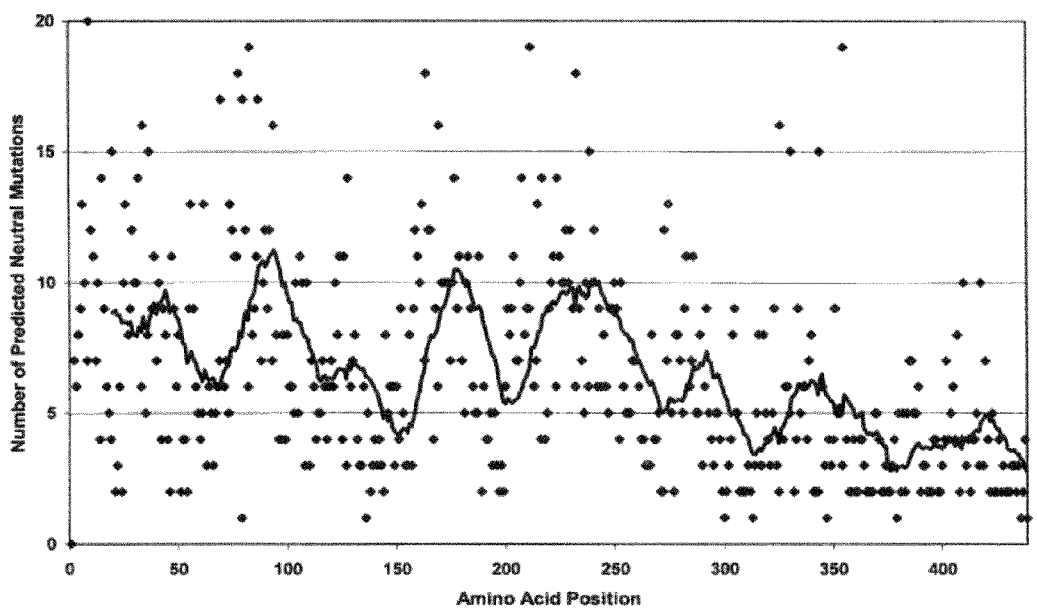
FIG. 27 is a graphic representation of the human c-Myc predicted mutation tolerance map.

Quantitative gene expression analysis of colonies formed 17 days after infection indicated that the transgenes c-Myc and Oct4 showed high expression in all the analyzed colonies (Table 11). In addition endogenous Nanog expression was very high in most of the ALP positive colonies, including cells lacking expression of one or more of the eight human ES cell marker genes (Table 11). These results indicate that the process of pluripotent stem cell induction from human skin fibroblasts is slower than that described for mouse iPS cell generation. Only 4 out of 163 ALP positive colonies were positive for Nanog, TDGF1, Dnmt3b, Zfp42, FoxD3, GDF3, Cyp26a1 and TERT (octa-positive colony). Cells in these octa-positive colonies showed common features: 1) small size with the high nucleus to cytoplasm ratio and 2) formation of small monolayer colonies within the space between fibroblasts (FIG. 16c). These features are consistent to the feature of human ES cells. However, these three features were also observed in some of ALP(+) colonies which lacked one or more ES cell marker expression. In addition, the large colony with these three features lack ALP expression (FIG. 23 colony #7-1-1). ALP (+) colonies with fibroblastic feature (colony #5-1-7, #3-1-214, #3-2-233, #3-1-212, #3-1-215, #5-1-4 in FIG. 17-23 and Table 7, 11) usually lacked one or more ES cell marker gene expressions.

These results indicate that induced pluripotent stem cells can be isolated from small monolayer colonies comprising small cells with high nucleus to cytoplasm ratio not from fibroblastic colonies, defused colonies or multilayered colonies. Table 8 summarizes all of experiments and results on the ALP positive colony number using human neonatal fibroblasts.

Example 16

Generation of Human iPS-2-4 Clone from Human Neonatal Skin Fibroblasts

Adenovirus vector plasmids for mCAT1 were transfected into 293 cells. The mCAT1-adenoviruses were isolated from these cells by three freeze-thaw cycles, purified using Adenovirus purification kit (Clontech) and stored at −80° C. The titer of the vector stocks was determined by Adeno-X rapid titer kit (Clontech).

The replication deficient MMLV derived retrovirus vector pMx was used for the ectopic expression of human Oct3/4, Sox-2, c-Myc and Klf4. Recombinant retroviruses were generated by transfecting vectors to the Plat-E packaging system (Morita et al., (2000), *Gene Therapy*, 7:1063-1066) followed by incubation in FBM (Lonza) supplemented with FGM-2

SingleQuots (Lonza). Between 24 and 48 hours after the transfection, supernatant from the Plat-E culture was collected several times at intervals of at least 4 hours and passed through a 0.45 μm filter.

For MEF-conditioned medium (MEF-CM) preparation, human ES medium (DMEM/F12 (Gibco) supplemented with 20% Knockout Serum Replacement (KSR, Invitrogen), 2 mM L-glutamine (Sigma), 1× nonessential amino acids (Sigma), 10 μg/ml gentamycin), 10 ng/ml bFGF was conditioned on mitomycin-C treated MEF (Reprocell) for 20-24 hours, harvested, filtered through a 0.45 μm filter and supplemented with 0.1 mM 2-mercaptoethanol (Sigma) and 10 ng/ml bFGF before use.

Using cells (trade name: Neonatal Normal Human Skin Fibroblasts, primary culture) derived from a human neonatal tissue, a human tissue immediately after birth, the induction of human pluripotent stem cells from undifferentiated stem cells present in the skin of a human neonate was attempted.

Human neonatal dermal fibroblasts (Lonza; lot 5F0416) were cultured in FBM supplemented with FGM-2 SingleQuots. Three days before the 4 gene introduction, fibroblasts were seeded at $10^3$ cells/cm$^2$ into 6 well plates. Eighteen hours later, the cells were mixed with the mCAT1 adenovirus vector solution in 500 μl Hanks' balanced salt solution, and incubated at room temperature for 30 min. The cells were then added to 2 ml of medium and cultured for 48 hrs. Subsequently, the cells were incubated in 2 ml of the retrovirus/polybrene solution (mixture of equal volumes of the retrovirus vector suspension for each of the four genes (Oct3/4, Sox2, Klf4 and c-Myc) prepared in Example 1, supplemented with 5 μg/ml of polybrene) at 37° C. for 4 hrs to overnight. The virus supernatant was replaced with MEF-conditioned ES medium. Then medium was changed every days.

On day 33 after gene introduction, a colony with a characteristic shape was picked with forceps from a well. The picked colony was transferred into a matrigel-coated well in a 24-well plate and maintained in mTeSR1 defined medium supplemented with 10 μM Y-27632. Fourteen hours later the medium was changed. Medium change was continued every days. At day 54 after the infection a second culture was carried out. At day 67, human iPS-24 clone was sub-cloned and designated as human iPS-2-4 sub-clone.

For passaging, medium was removed, and the cells were washed with the Hank's balanced salt solution followed by the treatment with 0.25% trysin-EDTA at 37° C. for 3 minutes. Fresh medium was added to stop the reaction. The cell suspension was centrifuged at 4° C. and 200×g for 5 minutes, and the supernatant was removed. The cells were resuspended in mTeSR1 defined medium supplemented with 10 μM Y-27632 and plated.

Human iPS-24 sub-clone was successfully expanded in mTeSR1 defined medium (Stem cell Technologies) on matrigel (BD Biosciences)-coated culture dishes. We termed cells derived from the sub-clone iPS-2-4 and cultured in mTeSR1 medium as human iPS-2-4 mTeSR cells. Medium was changed for human iPS-2-4 mTeSR cell culture everyday and usually treated with Y-27632 (Calbiochem) to avoid cell apoptosis after passaging. For passaging, cells were washed with Hanks's balanced solution, incubated in 0.25% trypsin-EDTA (Gibco) at 37° C. for 3 minutes, and then added the culture medium. Cells were centrifuged at 300×g at room temperature or 4° C. for 5 minutes and the supernatant was removed. The cells were re-suspended into culture medium. Human iPS-2-4 mTeSR cells were morphologically indistinguishable from typical human ES cells and human iPS-1-8 mTeSR cells, which grown in colonies with defined edges consisting of small, round cells with a high nucleus to cytoplasm ratio.

Fifty nine days post 4-gene infection, a part of cells were fixed and stained for alkaline phosphatase (ALP) as described in Example 3. Colonies consisting of cells were positive for ALP and Total RNA from colonies was extracted using a Recover All Total Nucleic Acid Isolation kit (manufactured by Ambion). After the cDNA preparation, genes of interest were amplified using Taqman preamp (manufactured by Applied Biosystems). Real-time quantitative PCR was performed with ABI PRISM 7900HT (manufactured by Applied Biosystems) using PCR primer sets (manufactured by Applied Biosystems, Nanog, Hs02387400_g1, Dnmt3b, Hs00171876_m1, FoxD3, Hs00255287_s1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1) to determine gene expression of human ES cell markers in colonies. Clone-2-4 showed expression of ES cell marker genes (Table 12). As observed for the iPS 1-8 line, both southern blot analysis and genomic PCR analysis indicated the 24 line contained integrated Oct 3/4, Sox2, Klf4, and c-Myc transgenes. Likewise, the 24 iPS line expressed the cell surface markers CD24, CD90, TRA 1-60, TRA-1-81, SSEA3, and SSEA4; had a normal karyotype; HLA genotypes identical to its parental cells, a global gene expression pattern similar to that of the 1-8 line; and an Oct 3/4 and Nanog promoter hypomethylation as observed in the 1-8 line.

From the above results, human pluripotent stem cell were obtained by the forced expression of each of four genes of Oct3/4, Sox2, Klf4, and c-Myc in undifferentiated stem cell present in a human postnatal tissue. The human pluripotent stem cells showed an in vitro long-term self-renewal ability, and expressed the ES cell marker genes Nanog, Oct3/4, TDGF1, Dnmt3b, GABRB3, GDF3, Zfp42, ALP, CD9, and Thy-1.

Example 17

Generation of Human iPS-3-2 Clone from Human Neonatal Skin Fibroblasts

According to Example 16, human neonatal dermal fibroblasts (Lonza; lot 5F0438) were cultured in FBM supplemented with FGM-2 SingleQuots. Three days before the 4 gene introduction, fibroblasts were seeded at $10^3$ cells/cm$^2$ into 6 well plates. Eighteen hours later, the cells were mixed with the mCAT1 adenovirus vector solution in 500 μl Hanks' balanced salt solution, and incubated at room temperature for 30 min. The cells were then added to 2 ml of medium and cultured for 48 hrs. Subsequently, the cells were incubated in 2 ml of the retrovirus/polybrene solution (mixture of equal volumes of the retrovirus vector suspension for each of the four genes (Oct3/4, Sox2, Klf4 and c-Myc) prepared in Example 1, supplemented with 5 μg/ml of polybrene) at 37° C. for 4 hrs to overnight. The virus supernatant was replaced with MEF-conditioned ES medium. Then medium was changed every days.

On day 21 after gene introduction, a colony with a characteristic shape was directly picked with forceps from one of dishes. The picked colony was transferred into a matrigel-coated well in a 24-well plate and maintained in mTeSR1 defined medium supplemented with 10 μM Y-27632.

Fourteen hours later the medium was changed. Medium change was continued every days. 40 days after the infection, a second subcloning was carried out, and cells were successfully expanded in mTeSR1 defined medium (Stem cell Technologies) on matrigel-coated culture dishes. Medium was changed everyday and usually treated with Y-27632 (Calbiochem) to avoid cell apoptosis after passaging. For passaging, cells were washed with Hanks's balanced solution, incubated in 0.25% trypsin-EDTA (Gibco) at 37° C. for 5 minutes, and then added the culture medium. Cells were centrifuged at 300×g at room temperature for 5 minutes and the supernatant was removed. The cells were re-suspended into culture medium.

Cells were morphologically indistinguishable from typical human ES cells, human iPS-1-8 mTeSR cells, and human iPS-2-4 mTeSR cells, which grow in colonies with well defined edges and consist of small, round cells with a high nucleus to cytoplasm ratio. Thus we termed this clone as human iPS-3-2 clone. Human iPS-3-2 clone actively proliferated in mTeSR1 medium. We termed these cells derived from human iPS-3-2 clone which culture in mTeSR1 medium as human iPS-3-2 mTeSR cells.

Forty eight days post 4-gene infection, cells were fixed and stained for alkaline phosphatase (ALP) as described in Example 3. Total RNA from colonies were extracted using a RecoverAll Total Nucleic Acid Isolation kit (manufactured by Ambion). After the cDNA preparation, genes of interest were amplified using Taqman preamp (manufactured by Applied Biosystems). Real-time quantitative PCR was performed with ABI PRISM 7900HT (manufactured by Applied Biosystems) using PCR primer sets (manufactured by Applied Biosystems, Nanog, Hs02387400_g1, Dnmt3b, Hs00171876_m1, FoxD3, Hs00255287_s1, Zfp42, Hs01938187_s1, TDGF1, Hs02339499_g1, TERT, Hs00162669_m1, GDF3, Hs00220998_m1, CYP26A1, Hs00175627_m1, GAPDH, Hs99999905_m1) to determine gene expression of human ES cell markers in colonies. Clone 3-2 showed expression of ES cell marker genes (Table 12). Genomic PCR analysis indicated the 3-2 line contained integrated Oct 3/4, Sox2, Klf4, and c-Myc transgenes. Likewise, the 3-2 iPS line had HLA genotypes identical to its parental cells and a global gene expression pattern similar to that of the 1-8 line.

From the above results, human pluripotent stem cell were obtained by the forced expression of each of four genes of Oct3/4, Sox2, Klf4, and c-Myc in undifferentiated stem cell present in a human postnatal tissue. The human pluripotent stem cells showed an in vitro long-term self-renewal ability, and were expressed ES cell marker genes Nanog, Oct3/4, TDGF1, Dnmt3b, GABRB3, GDF3, Zfp42, ALP, CD9, and Thy-1.

Example 18

Induction of Human Pluripotent Stem Cells by Forced Expression of Oct3/4, Sox2, and Klf4 by Retroviral Transduction Plus HDAC Inhibitor Treatment (Prophetic Example)

Human postnatal dermal fibroblasts are cultured in FBM supplemented with FGM-2 SingleQuots. Three days before retroviral transduction and histone deacetylase inhibitor treatment, the fibroblasts are seeded at $10^3$ cells/cm$^2$ into 6 well cell culture plates. Eighteen hours later, the cells are incubated for 30 minutes at room temperature, with occasional shaking, in 500 µl Hanks' balanced salt solution containing the mCAT1 adenovirus vector (described in Example 2) at an MOI of 5. Afterwards, 2 ml of FBM medium are added to each well and the cells are cultured for 48 hrs. Subsequently, the cells are incubated in 2 ml of the retrovirus/polybrene solution (a mixture of equal volumes of the retrovirus vectors encoding Oct3/4, Sox2, and Klf4 as described in Examples 1 and 5) at an m.o.i. of approximately 10 for each virus prepared, supplemented with 5 µg/ml of polybrene) at 37° C. for 4 hrs to overnight. The virus supernatant is then replaced with MC-ES medium supplemented with the histone deacetylase inhibitor MS-275 at a final concentration of 1 µM. On the following day, the medium is replaced with MC-ES medium, and is replaced daily afterwards.

Between days 17-33 after viral transduction plus MS-275 treatment, a colony with a characteristic shape (e.g., small, round, and having a high nucleus to cytoplasm ratio) is picked from a well with forceps. The picked colony is then transferred into a matrigel-coated well in a 24-well plate and maintained in mTeSR1 defined medium supplemented with 10 µM Y-27632. Fourteen hours later the medium is replaced. Afterwards, the medium is changed daily. At days 38-54 after viral transduction plus MS-275 treatment, a second subculture is carried out. For passaging, the medium is removed, and the cells are washed with the Hank's balanced salt solution followed by the treatment with 0.25% trysin-EDTA at 37° C. for 3-5 minutes. Fresh medium is added to stop the reaction. The cell suspension is centrifuged at 4° C. and 200×g for 5 minutes, and the supernatant is then removed. The cells are resuspended in mTeSR1 defined medium supplemented with 10 µM Y-27632 and plated in a matrigel-coated well of a 6-well culture dish.

The resulting human iPS clones are expanded in mTeSR1 defined medium on matrigel (BD Bioscience)-coated culture dishes. The culture medium is changed daily for human iPS cell culture. For passaging human iPS cell lines, cells are washed with Hanks's balanced solution, incubated in 0.25% trypsin-EDTA (Gibco) at 37° C. for 3-5 minutes, and then added the culture medium. The resulting cell suspension is then centrifuged at 300×g at room temperature or 4° C. for 5 minutes and the supernatant is removed. The cells are re-suspended into culture medium and plated as described above. After passaging, the medium is supplemented with 10 µM Y-27632 (Calbiochem) to avoid cell apoptosis. The resulting human iPS cells are morphologically indistinguishable from typical human ES cells and human iPS-1-8 mTeSRcells grow in colonies with defined edges and consisting of small, round cells with a high nucleus to cytoplasm ratio. According to all analyses described as in Examples 14-15, the resulting human iPS cells show an in vitro long-term self-renewal ability and are very similar to typical human ES cells in many characteristics.

Example 19

Induction of Human Pluripotent Stem Cells by Forced Expression of Oct3/4, Sox2, and Klf4 by Retroviral Transduction (Prophetic Example)

Human postnatal dermal fibroblasts are cultured in FBM supplemented with FGM-2 SingleQuots. Three days before retroviral transduction, the fibroblasts are seeded at $10^3$ cells/cm$^2$ into 6 well cell culture plates. Eighteen hours later, the cells are incubated for 30 minutes at room temperature, with occasional shaking, in 500 µl Hanks' balanced salt solution containing the mCAT1 adenovirus vector (described in Example 2) at an MOI of 5. Afterwards, 2 ml of FBM medium are added to each well and the cells are cultured for 48 hrs. Subsequently, the cells are incubated in 2 ml of the retrovirus/polybrene solution (a mixture of equal volumes of the retrovirus vectors encoding Oct3/4, Sox2, and Klf4 as described in Examples 1 and 5) at an m.o.i. of approximately 10 for each virus prepared, supplemented with 5 µg/ml of polybrene) at 37° C. for 4 hrs to overnight. The virus supernatant is then replaced with MC-ES medium. On the following day, the medium is replaced with MC-ES medium, and is replaced daily afterwards.

Between days 17-33 after viral transduction, a colony with a characteristic shape (e.g., small, round, and having a high nucleus to cytoplasm ratio) is picked from a well with forceps. The picked colony is then transferred into a matrigel-coated well in a 24-well plate and maintained in mTeSR1 defined medium supplemented with 10 µM Y-27632. Fourteen hours later the medium is replaced. Afterwards, the medium is replaced daily. At days 38-54 after viral transduction, a second subculture is carried out. For passaging, the medium is removed, and the cells are washed with the Hank's balanced salt solution followed by the treatment with 0.25% trysin-EDTA at 37° C. for 3-5 minutes. Fresh medium is added to stop the reaction. The cell suspension is centrifuged at 4° C. and 200×g for 5 minutes, and the supernatant is then removed. The cells are resuspended in mTeSR1 defined medium supplemented with 10 µM Y-27632 and plated in four matrigel-coated wells of a 6-well culture dish.

The resulting human iPS clones is expanded in mTeSR1 defined medium on matrigel (BD Bioscience)-coated culture dishes. The culture medium is changed daily for human iPS cell culture. For passaging human iPS cell lines, cells are washed with Hanks's balanced solution, incubated in 0.25% trypsin-EDTA (Gibco) at 37° C. for 3-5 minutes, and then added the culture medium. The resulting cell suspension is then centrifuged at 300×g at room temperature or 4° C. for 5 minutes and the supernatant is removed. The cells are re-suspended in culture medium and plated as described above. After passaging, the medium is supplemented with 10 µM Y-27632 (Calbiochem) to avoid cell apoptosis. The resulting human iPS cells are morphologically indistinguishable from typical human ES cells and human iPS-1-8 mTeSRcells, which grow in colonies with defined edges and consisting of small, round cells with a high nucleus to cytoplasm ratio. According to all analyses described as in Examples 14-15, the resulting human iPS cells show an in vitro long-term self-renewal ability and are very similar to typical human ES cells in many characteristics.

Example 20

Assay for Identifying siRNAs that Induce Pluripotency ("inducing siRNAs") in Combination with a Subset of Induction Factors Using a Tert Reporter Construct (Prophetic Example)

A whole human genome siRNA library is used in a primary screen to identify siRNAs having the ability to induce pluripotency or increase the induction of pluripotency in a human adult fibroblast population when used in combination with a subset of three induction factors selected from Oct 3/4, Sox2, Klf4, and c-Myc. The screen utilizes a reporter assay for activation of the iPS-marker gene Tert to identify candidate siRNAs capable of complementing the inducing activity of a subset of three induction factors selected from Oct 3/4, Sox2, Klf4, and c-Myc. For example, a test siRNA may be used in combination with Oct 3/4, Klf4, and c-Myc to identify siRNAs that complement the missing Sox2 activity. In a secondary screen, the candidate inducing siRNAs are tested again in the same assay, and the expression of another, iPS-marker gene Cyp26A1, is also assayed in the tested cells.

Generation of a Tert Promoter Reporter Retrovirus:

A 0.5 kb fragment of the human tert promoter is PCR amplified from human genomic DNA with using an upstream primer hTERT-475F:

5'-GCAGCCCTGGGTCTCCAGATCTGGCCAGC-3'  (SEQ ID NO:14)

and a downstream primer hTERT+49R:

5'GGTGGCCGGGGCCAGGGCTAGCCACGTGC-3'  (SEQ ID NO:15)

Primers are numbered by the number of bases upstream (+) or downstream (−) of the start of hTERT exon 1 (chromosome 5, base 1306027 on human July 2003 genome assembly on the world wide web at genome.ucsc.edu). See, e.g., Padmanabhan et al., (2006), *Journal of Nuclear Medicine*, 47(2) 270-277.

The amplified fragment is then subcloned 5' to the luc2P ORF in the promoterless pGL4.11[luc2P] vector (Promega, Madison, Wis.). The entire tert-luc2 reporter cassette is then PCR amplified, subcloned into the pMX retroviral vector, validated by sequencing, and packaged in Plat-A cells (see Morita et al., (2000), *Gene Therapy*, 7(12): 1063-1066) to generate a Tert-luc reporter ("TLR") ecotropic retrovirus, as described in Example 1.

Cell Culture, Viral Infection, and siRNA Transfection

Adult or neonatal normal Human Skin Fibroblasts (Lonza) of $6 \times 10^5$ cells in 10 ml of medium are plated with FBM medium in a dish with 10 cm diameter cell culture plates at a density of $10^4$ cells/cm$^2$. Adult or neonatal normal Human Skin Fibroblasts (Lonza) are plated with FBM medium in a dish with 10 cm diameter cell culture plates at a density of $10^4$ cells/cm$^2$ in 10 ml of medium per a dish. Human postnatal dermal fibroblasts are cultured in FBM supplemented with FGM-2 SingleQuots. Eighteen hours later, the cells are incubated at room temperature, with occasional shaking, for 30 minutes with 3 ml of FBM medium or Hanks' balanced salt solution containing the mCAT1 adenovirus vector (described in Example 2) at an MOI of 1 to 5. Afterwards, 12 ml of complete FBM medium are added to each dish and the cells are cultured for 48 hrs. Forty eight hours later, the medium is removed, and a mixture of the TLR retrovirus, and retroviruses encoding any three of Oct 3/4, Sox2, Klf4, and c-Myc prepared as described above is added, each virus at an m.o.i. of about 10-50 in 3 ml of the medium per a dish is added, and the infection is continued at room temperature for 30 minutes. Afterwards 12 ml of the FBM medium was added, and the plates are incubated at 37 C. Twenty four hours after the addition of the TLR retrovirus and retroviruses encoding any three of Oct 3/4, Sox2, Klf4, and c-Myc, cells are plated with FBM medium in 384 or 96-well cell culture plates coated with matrigel (20 g/cm$^2$) at a density of $10^4$ cells/cm$^2$ in 25 or 100 µl of medium per well. The resulting cells are cultured in FBM supplemented with FGM-2 SingleQuots. Twenty four hours later, the medium of each well is replaced with 50 or 200 µl (for 384 or 96-well, respectively) of a mixture containing antibiotic-free Opti-MEM® I Reduced Serum medium (Invitrogen), Lipofectamine™-RNAiMax transfection reagent (Invitrogen), mixed according to the manufacturer's protocol with 4 siRNAs to a human gene target, with a final concentration of 50 nM for each siRNA ("test siRNA wells"). Thus, siRNAs against a total of approximately 25,000 target human genes (i.e. most, if not all, expressed sequences) are tested in the assay. As a "negative control" in the assay, 20 wells ("negative control wells") of cells transduced as described above are transfected with 20 sets of scrambled siRNAs (checked for lack of homology to vector or mammalian sequences).

Luciferase Assay of TLR Plus siRNA-Treated Human Fibroblasts

After 48 hours, cell lysates are prepared from each well, and luciferase activity is measured in the presence of luciferin and ATP (Sigma, St. Louis, Mo.), as a measure of nanog promoter activity in Ad-nanog-luc-infected cells, using a Berthold-Lumat B9501 luminometer (Berthold-Lumat, St Albans, Herts, UK). Luciferase activity from each of the test siRNA wells is compared to the mean luciferase activity determined for the negative control wells. Where siRNA wells are determined to have significantly higher luciferase activity than the mean negative control well value, the corresponding siRNA sequences ("candidate inducing siRNAs") are tested in a secondary screen.

Secondary Screens

In one secondary screen, cells are plated in a 48 well format using the same cell culture conditions as described above. After 24 hours, wells are transfected with the candidate inducing siRNAs (n=10 per target gene) identified in the primary screen, but adjusting the volumes for a 48 well culture format. Cells are then cultured for a further 72 hours. Afterwards, medium is removed, cells are washed with Hanks Buffered Saline solution and the level of Cyp26a1 mRNA is determined by qRT-PCR.

Example 21

Assay for Identifying siRNAs that Induce Pluripotency ("Inducing siRNAs") in Combination with a Subset of Induction Factors Using qRT-PCR (Prophetic Example)

A whole human genome siRNA library is used in a primary screen to identify siRNAs having the ability to induce pluripotency or increase the induction of pluripotency in a human adult fibroblast population when used in combination with a subset of three induction factors selected from Oct 3/4, Sox2, Klf4, and c-Myc. The screen utilizes a qRT-PCR assay for detecting expression of the iPS marker gene Tert to identify candidate siRNAs capable of complementing the inducing activity of a subset of three induction factors selected from Oct 3/4, Sox2, Klf4, and c-Myc. For example, a test siRNA may be used in combination with Oct 3/4, Klf4, and c-Myc to identify siRNAs that complement the missing Sox2 activity. In a secondary screen, the candidate inducing siRNAs are tested again in the same assay, and the expression of another, iPS-marker gene Cyp26A1, is also assayed in the tested cells.

Cell Culture, Viral Infection, and siRNA Transfection

Adult or neonatal normal Human Skin Fibroblasts (Lonza) are plated with FBM medium in a dish with 10 cm diameter cell culture plates at a density of $10^4$ cells/cm$^2$ in 10 ml of medium per a dish. Human postnatal dermal fibroblasts are cultured in FBM supplemented with FGM-2 SingleQuots. Eighteen hours later, the cells are incubated, with occasional shaking, for 30 minutes at room temperature with 3 ml of FBM medium or Hanks' balanced salt-solution containing the mCAT1 adenovirus vector (described in Example 2) at an MOI of 1 to 5. Afterwards, 12 ml of complete FBM medium are added to each dish and the cells are cultured for 48 hrs. Forty eight hours later, the medium is removed, and a mixture of the TLR retrovirus, and retroviruses encoding any three of Oct 3/4, Sox2, Klf4, and c-Myc prepared as described above is added, each virus at an m.o.i. of about 10-50 in 3 ml of the medium per a dish is added, and the infection is continued at room temperature for 30 minutes. Afterwards 12 ml of the FBM medium was added, and the plates are incubated at 37 C. Twenty four hours after the addition of the TLR retrovirus and retroviruses encoding any three of Oct 3/4, Sox2, Klf4, and c-Myc, cells are plated with FBM medium in 384 or 96-well cell culture plates coated with matrigel (20 g/cm$^2$) at a density of $10^4$ cells/cm$^2$ in 25 or 100 µl of medium per well. The resulting cells are cultured in FBM supplemented with FGM-2 SingleQuots. Twenty four hours later, the medium of each well is replaced with 50 or 200 µl (for 384 or 96-well, respectively) of a mixture containing antibiotic-free Opti-MEM® I Reduced Serum medium (Invitrogen), Lipofectamine™-RNAiMax transfection reagent (Invitrogen), mixed according to the manufacturer's protocol with 4 siRNAs to a human gene target, with a final concentration of 50 nM for each siRNA ("test siRNA wells"). Thus, siRNAs against a total of approximately 25,000 target human genes (i.e. most, if not all, expressed sequences) are tested in the assay. As a "negative control" in the assay, 20 wells ("negative control wells") of cells transduced as described above are transfected with 20 sets of scrambled siRNAs (checked for lack of homology to vector or mammalian sequences).

Total RNA from colonies is extracted using the RecoverAll Total Nucleic Acid Isolation kit (manufactured by Ambion). After reverse transcription, Tert or CYP26A1 are amplified using the Taqman preamp (manufactured by Applied Biosystems). Real-time quantitative PCR is then performed with an ABI PRISM 7900HT device (manufactured by Applied Biosystems) using PCR primer sets TERT, Hs00162669_m1 and CYP26A1, Hs00175627_m1 (available from Applied Biosystems).

Where siRNA wells are determined to induce a higher level of Tert mRNA expression relative to the negative control level, the corresponding siRNA sequences ("candidate inducing siRNAs") are tested in a secondary screen.

Secondary Screens

In one secondary screen, cells are plated in a 48 well format using the same cell culture conditions as described above. After 24 hours, wells are transfected with the candidate inducing siRNAs (n=10 per target gene) identified in the primary screen, but adjusting the volumes for a 48 well culture format. Cells are then cultured for a further 72 hours. Afterwards, medium is removed, cells are washed with Hanks Buffered Saline solution and the level of Cyp26A1 mRNA is determined by qRT-PCR as described above. Candidate inducing siRNAs identified as inducing expression of both Tert and Cyp26A1 when used in combination with other induction factors are then further tested to determine if they are indeed capable of inducing pluripotency when used in combination with the corresponding subset of induction factors used in the primary screen.

Example 22

Induction of Human Pluripotent Stem Cells from Fibroblasts Including at Least One Chimeric IF-VP16 Polypeptide (Prophetic Example)

The induction protocol and assays are carried out as described in Example 7, but a retrovirus expressing a chimeric human Sox2-VP16 fusion polypeptide is used, instead of full length human Sox2 retrovirus, as one of the four IFs. The Sox2-VP16 fusion polypeptide comprises amino acids 1-183 of human Sox2, which includes the Sox2 DNA binding domain, and amino acids 411-490 of the herpes VP16 protein (GenBank Accession No. AAA45864), a strong transactivator domain (see, e.g., Sadowski et al (1988), *Nature*, 6; 335

(6190):563-564) fused to the C-terminal of the human Sox2 fragment. The sequence of the Sox2-VP16 fusion protein is:

```
                                              (SEQ ID NO:16)
MYNMMETELKPPGPQQTSGGGGGNSTAAAAGGNQKNSPDRVKRPMNAFMV

WSRGQRRKMAQENPKMHNSEISKRLGAEWKLLSETEKRPFIDEAKRLRAL

HMKEHPDYKYRPRRKTKTLMKKDKYTLPGGLLAPGGNSMASGVGVGAGLG

AGVNQRMDSYAHMNGWSNGSYSMMQDQLGYPQHSTTAPITDVSLGDELRL

DGEEVDMTPADALDDFDLEMLGDVESPSPGMTHDPVSYGALDVDDFEFEQ

MFTDALGIDDFGG
```

Example 23

Induction of Human Pluripotent Stem Cells from Fibroblasts Using a Combination of Viral Expression of Oct 3/4, Sox2, and Klf4, and Protein Transduction of c-Myc (Prophetic Example)

Cell culture and infection with Oct 3/4, Sox2, and Klf4 retroviruses are performed as described in Example 7, but after the four hour viral infection incubation, the three virus-containing polybrene solution is replaced with MC-medium containing a purified human c-Myc-PTD fusion polypeptide comprising the amino acid sequence of human c-Myc:

```
SEQ ID NO:12 (Human c-Myc):
MDFFRVVENQQPPATMPLNVSFTNRNYDLDYDSVQPYFYCDEEENFYQQQ

QQSELQPPAPSEDIWKKFELLPTPPLSPSRRSGLCSPSYVAVTPFSLRGD

NDGGGGSFSTADQLEMVTELLGGDMVNQSFICDPDDETFIKNIIQDCMW

SGFSAAAKLVSEKLASYQAARKDSGSPNPARGHSVCSTSSLYLQDLSAAA

SECIDPSVVFPYPLNDSSSPKSCASQDSSAFSPSSDSLLSSTESSPQGSP

EPLVLHEETPPTTSSDSEEEQEDEEEIDVVSVEKRQAPGKRSESGSPSAG

GHSKPPHSPLVLKRCHVSTHQHNYAAPPSTRKDYPAAKRVKLDSVRVLRQ

ISNNRKCTSPRSSDTEENVKRRTHNVLERQRRNELKRSFFALRDQIPELE

NNEKAPKVVILKKATAYILSVQAEEQKLISEEDLLRKRREQLKHKLEQLR

NSCA fused at its N-terminus with a protein trans-
duction domain having the amino acid sequence:
YGRKKRRQRRR;              (SEQ ID NO:1)

RKKRRQRR;                 (SEQ ID NO:2)

YARAAARQARA;              (SEQ ID NO:3)

THRLPRRRRRR;              (SEQ ID NO:4)

GGRRARRRRRR;              (SEQ ID NO:5)
or

KKKKKKKK                  (SEQ ID NO:17)
```

Subcloning and purification of the c-Myc-PTD fusion protein are performed essentially as described in Becker-Hapak et al., (2003), *Curr. Protocols Cell Biol.*, Unit 20.2, John Wiley & Sons. After the retroviral infection period (with Oct 3/4, Sox2, and Klf4 retroviruses), the polybrene-viral solution is removed and replaced with 2 ml of MC-ES medium containing purified c-Myc-PTD fusion polypeptide at a concentration of 100 nM, and the cultured is incubated for about three hours at 37° C. Afterwards, the medium is replaced with MC-ES medium, and the induction protocol and assays are continued as described in Example 7. Forced expression of c-Myc by protein transduction, avoids potential long term undesirable effects (e.g., cell transformation or risk of inducing cancer) of introducing an exogenous c-Myc gene, especially where the exogenous gene is integrated into the genome, e.g., following retroviral transduction.

Example 24

Induction of Human Pluripotent Stem Cells from Fibroblasts Using Protein Transduction of Oct 3/4, Sox2, Klf4, and c-Myc (Prophetic Example)

Human postnatal dermal fibroblasts are cultured in FBM supplemented with FGM-2 SingleQuots. Three days before protein transduction, the fibroblasts are seeded at $10^3$ cells/$cm^2$ into 6 well cell culture plates.

Subcloning and purification of the Oct 3/4, Sox2, Klf4, and c-Myc fusion proteins are performed essentially as described in Becker-Hapak et al., (2003), *Curr. Protocols Cell Biol.*, Unit 20.2, John Wiley & Sons. Induction is initiated by replacing the culture medium with 2 ml of MC-ES medium containing purified fusion proteins (100 nM each) of Oct 3/4 (SEQ ID NO:6), Sox2 (SEQ ID NO:8), Klf4 (SEQ ID NO:10), and c-Myc (SEQ ID NO: 12) fused at their N-termini with a protein transduction domain having the amino acid sequence:

YGRKKRRQRRR (SEQ ID NO: 1); RKKRRQRR (SEQ ID NO:2); YARAAARQARA (SEQ ID NO:3); THRLPRRRRRR (SEQ ID NO:4); GGRRARRRRR (SEQ ID NO:5); or KKKKKKKK (SEQ ID NO:17). The cells are then incubated with the fusion proteins for about three hours at 37° C. Afterwards, the medium is replaced with MC-ES medium supplemented with 10 µM Y-27632. During the induction period the medium is replaced daily with MC-ES medium containing 100 nM of each of the fusion proteins for one hour, and the medium is then replaced with MC-ES medium free of fusion proteins until the following day. After the induction period, assays are performed as described in Example 7 to identify induced pluripotent stem cell candidates.

Example 25

Induction of Human Pluripotent Stem Cells from Fibroblasts Using Protein Transduction of Oct 3/4, Sox2, and Klf4 Plus HDAC Inhibitor Treatment (Prophetic Example)

Human postnatal dermal fibroblasts are cultured in FBM supplemented with FGM-2 SingleQuots. Three days before protein transduction, the fibroblasts are seeded at $10^3$ cells/$cm^2$ into 6 well cell culture plates.

Subcloning and purification of the Oct 3/4, Sox2, Klf4, and c-Myc fusion proteins are performed essentially as described in Becker-Hapak et al., (2003), *Curr. Protocols Cell Biol.*, Unit 20.2, John Wiley & Sons. Induction is initiated by replacing the culture medium with 2 ml of MC-ES medium containing purified fusion proteins (100 nM each) of Oct 3/4 (SEQ ID NO:6), Sox2 (SEQ ID NO:8), and Klf4 (SEQ ID NO:10 fused at their N-termini with a protein transduction domain having the amino acid sequence:

```
YGRKKRRQRRR;      (SEQ ID NO:1)
RKKRRQRR;         (SEQ ID NO:2)
YARAAARQARA;      (SEQ ID NO:3)
THRLPRRRRRR;      (SEQ ID NO:4)
GGRRARRRRRR;      (SEQ ID NO:5)
or
KKKKKKKK.         (SEQ ID NO:17)
```

The cells are then incubated with the fusion proteins for about three hours at 37° C. Afterwards, the medium is replaced with MC-ES medium supplemented with the is then replaced with MC-ES medium supplemented with the histone deacetylase inhibitor MS-275 at a final concentration of 1 µM, and the Rho kinase inhibitor 10 µM Y-27632. During the subsequent induction period the medium is replaced daily with MC-ES medium containing 100 nM of each of the fusion proteins for one hour, and the medium is then replaced with fusion protein-free MC-ES medium containing 10 µM Y-27632 on subsequent days until the end of the induction period (about 14 days after the beginning of induction). After the induction period, assays are performed as described in Example 7 to identify induced pluripotent stem cell candidates.

Example 26

Induction of Mouse Pluripotent Stem Cells by Forced Expression of Three or Four Exogenous Genes by Retroviral Transduction Murine embryonic Fibroblasts (MEFs) were plated into 12-well plates, seeded at a density of 5000 cells/cm² in MEF medium (DMEM supplemented with 10% FBS and gentamycin) and cultured overnight (approximately 16 hours). The cells were then incubated in a 1 ml retrovirus/polybrene solution. The retrovirus/polybrene solution included a mixture of 0.25 ml of each retrovirus vectors encoding either four factors (Oct3/4, Sox2, Klf4 and c-Myc); three factors (the four factors minus either Oct3/4, Sox2, Klf4 or c-Myc); or two factors (Oct3/4 and Sox2) supplemented with 5 µg/ml of polybrene. For two or three genes transduction, culture media was added to virus carrying solution up to 1 ml. Cells were infected with each virus prepared, at 37° C. The "Oct4a" is equivalent to "Oct3/4." The virus supernatant was then replaced with mouse ES_medium on the following day. Media was changed every 2-3 days.

Figure 28:
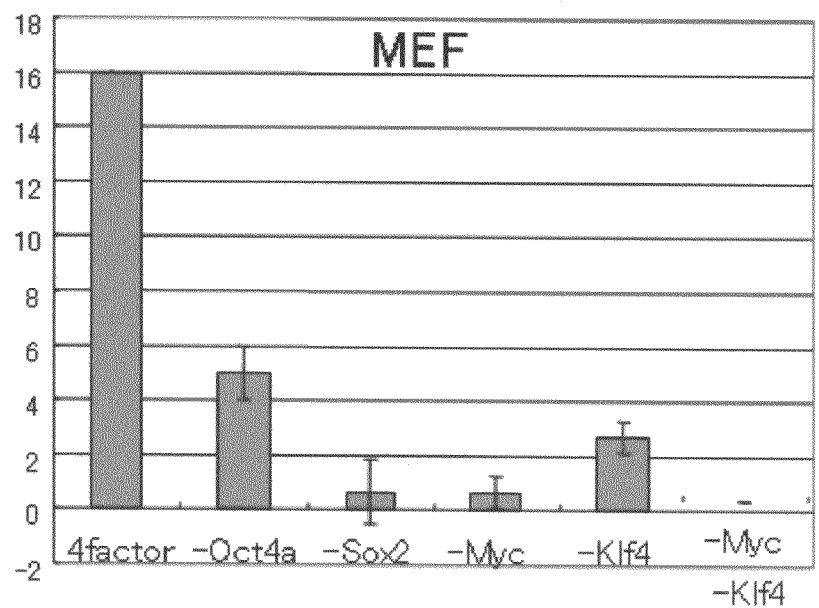
FIG. 28 shows the use of transgenes to induce ALP positive colonies from mouse embryonic fibroblasts. The gene combination of (Sox2, c-Myc, and Klf4), and (Oct4, Sox2 and c-Myc) can induce ALP colonies on day 12.

Approximately 12 days after viral transduction, colonies were subjected to alkaline phosphatase (ALP) staining, and the cloned colony-derived cells were stained blue violet. The number ALP positive colonies were recorded, as indicated by FIG. 28. ALP-positive colonies were observed in the samples that had received the four factors (Oct3/4, Sox2, Klf4 and c-Myc); and any combination of three factors.

Example 27

Induction of Mouse Pluripotent Stem Cells by Forced Expression of Two Three, or Four Exogenous Genes by Retroviral Transduction into Mouse-Derived Neural Stem Cells Adult mouse-derived neural stem cells (NSC) were isolated from the subventricular zones of 9-week-old C57BL/6 mice (Oriental Yeast, Tokyo, Japan) as previously described (Reynolds et al., 1992). In brief, adult mouse brains were dissociated into single cells by trypsin digestion, and the cells were suspended in Dulbecco's modified Eagle's medium/Ham's F-12 medium (DMEM/F12; Invitrogen) containing 100 1 g/mL human transferrin (Sigma), 20 nM progesterone (Sigma), 100 lM putrescine (Sigma), 30 nM sodium selenite (Sigma), and 5 lg/mL insulin (Sigma). The suspended cells were plated in tissue culture dishes. The cells were maintained in an undifferentiated proliferative state by culturing them as free-floating neurospheres in NSC medium (DMEM/F12 containing 100 lg/mL human transferrin, 20 nM progesterone, 100 lM putrescine, 30 nM sodium selenite, 5 lg/mL insulin, 20 ng/mL human basic fibroblast growth factor (bFGF; Sigma), and 20 ng/mL epidermal growth factor (EGF; Sigma)). The NSCs were seeded at 10⁴ cells/cm2 as a monolayer on Omitin/Lamin coated 12-well cell culture plates one day before infection, and cultured in 1 ml of NSC medium. After over night, the cells were incubated in 1 ml of the retrovirus/polybrene solution. The retrovirus/polybrene solution included a mixture of 0.25 ml of each retrovirus vectors encoding either four factors (Oct3/4, Sox2, Klf4 and c-Myc); three factors (the four factors minus either Sox2 or c-Myc); or two factors (Oct3/4 and Klf4) supplemented with 5 µg/ml of polybrene). For two or three genes transduction, culture media was added to virus carrying solution up to 1 ml. Cells were infected at 37° C. The virus supernatant was then replaced with mouse ES_medium on the following day. Media was changed every 2-3 days.

Figure 29:
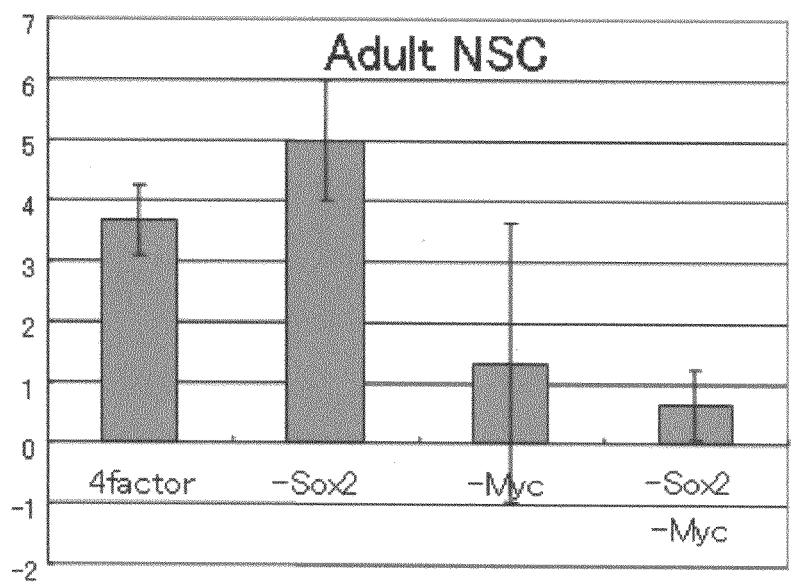
FIG. 29 shows the use of transgenes to induce ALP positive colonies from Mouse adult neural stem cells. In comparison to MEF cells, adult neural stem cells do not require expression of exogenous Sox2 to induce ALP colonies.

Approximately 12 days after viral transduction, colonies were subjected to alkaline phosphatase (ALP) staining, and the cloned colony-derived cells were stained blue violet. The number of ALP positive colonies was recorded. ALP-positive colonies were observed in the samples that had received the four factors (Oct3/4, Sox2, Klf4 and c-Myc); both combinations of three factors; and two factors (Oct3/4 and Klf4) (as shown in FIG. 29).

Example 28

Induction of Mouse Pluripotent Stem Cells by Forced Expression of Three or Four Exogenous Genes by Retroviral Transduction Adult mouse-derived bone marrow cells (Losac) were obtained using the same procedure described in Example 11. One day before retroviral transduction, the cells were seeded at 10⁴ cells/cm² into 6-well cell culture plates and cultured in 2 ml of low serum medium. Over night later, the cells were incubated in 2 ml of the retrovirus/polybrene solution (a mixture of 0.5 ml of each retrovirus vectors encoding either four factors (Oct3/4, Sox2, Klf4 and c-Myc); three factors (the four factors minus either Sox2, Oct3/4, Klf4 or c-Myc) supplemented with 5 µg/ml of polybrene). The virus supernatant was replaced the next day with mouse ES_medium. At this time, some samples also were treated with either 10 ng/ml FGF or 0.1 µM MS-275 for three days. On the following day, the medium was replaced with mouse ES_medium and was replaced every 2-3 days afterwards.

Figure 30:
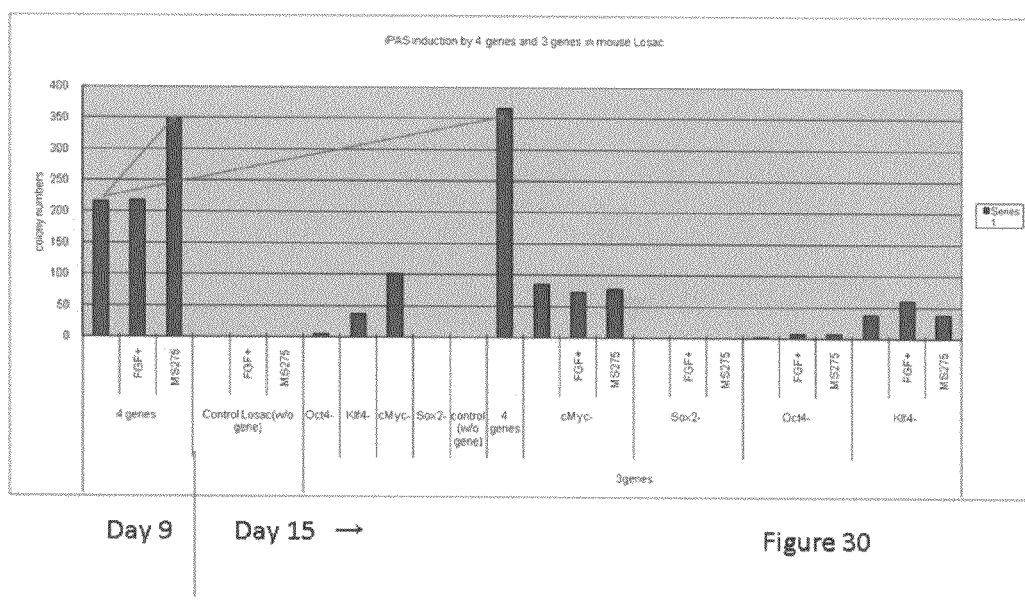
FIG. 30 shows the use of three or four transgenes to induce ALP positive colonies from mouse bone marrow derived cells. ALP colonies can be induced without c-Myc or Klf4.

Approximately 9 or 15 days after viral transduction, colonies were subjected to alkaline phosphatase (ALP) staining, and the cloned colony-derived cells were stained blue violet. The number of ALP-positive colonies was recorded, as indicated in FIG. 30. Of the samples analyzed on Day 15, ALP-positive colonies were observed in the samples that had received the four factors (Oct314, Sox2, Klf4 and c-Myc) and samples that received four factors minus either c-Myc, Oct3/4, or Klf4 (FIG. 30).

ALP-positive colonies were also observed in the four-gene transduction samples analyzed on Day 9 after the viral transduction, but this number was less than the number of colonies observed in the four-gene transduction samples from Day 15. On Day 9, in the four-gene transduction samples, more colonies were observed in samples that were exposed to MS-275 compared to samples that were not exposed to MS-275.

Example 29

Figure 31:
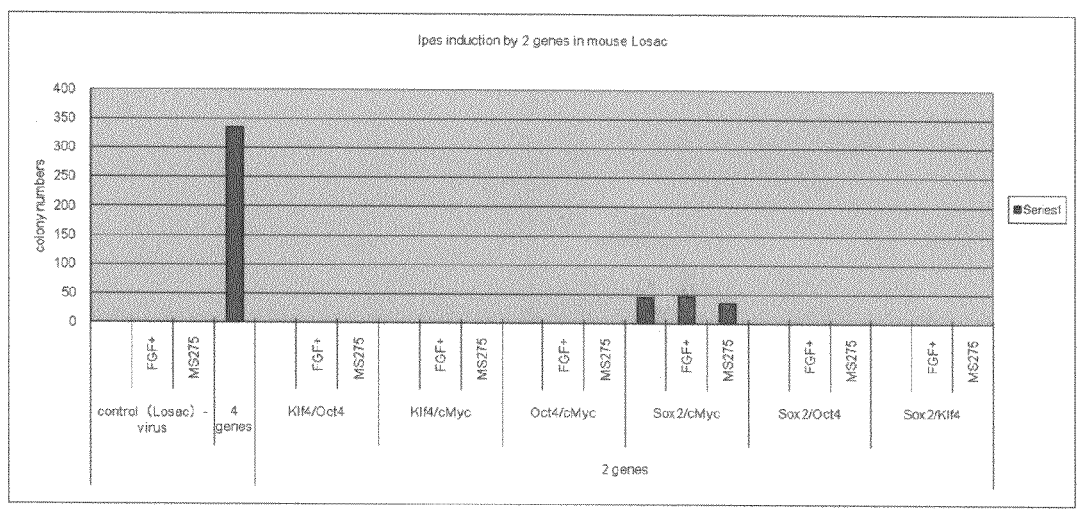
FIG. 31 shows the use of two or four transgenes to induce ALP positive colonies from mouse bone marrow derived cells. The combination of Sox2 and cMyc can induce ALP colonies.

Induction of Mouse Pluripotent Stem Cells by Forced Expression of Two or Four Exogenous Genes by Retroviral Transduction Adult mouse-derived bone marrow cells (Losac) were obtained using the same procedure described in Example 11. Retroviral transduction was performed following the methods described in Example 28. However, in this experiment, retrovirus/polybrene solution included a mixture of equal volumes of the retrovirus vectors encoding either four factors (Oct3/4, Sox2, Klf4 and c-Myc); or different combinations of two factors (as shown in FIG. 31).

Approximately 15 days after viral transduction, colonies were subjected to alkaline phosphatase (ALP) staining, and the cloned colony-derived cells were stained blue violet. The number of ALP-positive colonies was recorded, as indicated in FIG. 31. ALP-positive colonies were observed in the samples that had received the four factors (Oct3/4, Sox2, Klf4 and c-Myc) and samples that received the combination of Sox2 and c-Myc (FIG. 31)

Example 30

Analysis of Global Gene Expression Differences in iPS cells versus human ES cell lines and Parental Fibroblasts The global gene expression data obtained for iPS cell lines, 1-8, 2-4, and 3-2, as described in Examples 14, 16, and 17, respectively (GEO accession number GSE9709) were compared to global gene expression data for human ES cell (hES cell) lines: Sheff4 cultured on MEF; Sheff4 cultured on matrigel, and the H14 line cultured on MEF; and the iPS line parental fibroblasts. The gene expression data were compared to identify genes that were: (1) expressed at a significantly higher level in the iPS cell lines than in the hES cell lines; (2) expressed at a significantly higher level in the hES cell lines than in the iPS cell lines; (3) expressed at a significantly higher level in the iPS cell lines than in the hES cell lines and the parental fibroblasts; and (4) expressed at a significantly higher level in the iPS cell lines than in the hES cell lines, but not expressed at a significantly higher level than in the parental fibroblasts. Data were compared by Student's t-test with a cut-off of $p \leq 0.01$. The results are shown in Tables 13-16.

Table 13 shows a list of genes expressed at a five fold or higher level in the iPS cell lines than in the hES cell lines ($p \leq 0.01$). Table 14 shows a list of genes expressed at a two fold or higher level in the hES cell lines than in the iPS cell lines ($p \leq 0.01$). Table 15 shows a list of genes expressed at a five fold or higher level in the iPS cell lines than in both the hES cell lines and in the parental fibroblasts ($p \leq 0.01$). Table 16 shows a list of genes expressed at a five fold or higher level in the iPS cell lines than in the hES cell lines, but not expressed at a significantly higher level than in the parental fibroblasts ($p \geq 0.05$).

These results indicated that notwithstanding the overall similarity in global gene expression between the iPS cell lines and the hES cell lines as described in Example 14, iPS lines do exhibit significant gene expression differences with respect to hES cell lines.

Example 31

Oct3/4 polypeptide amino acid sequence variants (prophetic example)

Based on Table 17 (PMUT analysis of Human Oct3/4), any of the following Oct3/4 amino acid sequence variants are generated by site-directed mutagenesis and used in conjunction with a Sox2 polypeptide and a Klf4 polypeptide; or with Sox2, Klf4, and c-Myc polypeptides to induce multipotent or pluripotent stem cells as described in previous examples.

The amino acid sequence of SEQ ID NO:6 with any of the following pairs of amino acid substitutions: Oct3/4 variant$^{2AA-1}$ (H4→N and F9→I); Oct3/4 variant$^{2AA-2}$ (P15→M and G18→L); and Oct3/4 variant$^{2AA-3}$ (I60→F and L84→V).

The amino acid sequence of SEQ ID NO:6 with the following set of 10 amino acid substitutions (Oct3/4 variant$^{10AA}$): H4→N, F9→I, P15→M, G18→L, I60→F, L84→V, P62→S, V101→I, G109→I, and P112→I.

The amino acid sequence of SEQ ID NO:6 with the following set of 20 amino acid substitutions (Oct3/4 variant$^{20AA}$): H4→N, F9→I, P15→M, G18→L, I60→F, P62→S, Q79→D, L84→V, V101→I, G109→I, P112→I, G161→L, D166→E, L169→I, V173→F, F175→A, E215→D, E219→D, A223→M, V227→F.

The amino acid sequence of SEQ ID NO:6 with the following set of 25 amino acid substitutions (Oct3/4 variant$^{25AA}$): H4→N, F9→I, P15→M, G18→L, V51→I, I6→F, P62→S, C63→S, Y67→F, Q79→D, L84→V, L900M, Q94→D, V101→I, G109→I, P112→I, G161→L, D166→E, L169→I, V173→F, F175→A, E215→D, E219→D, A223→M, V227→F.

Table I shows the name of gene, the NCBI number, the virus vector in which said gene was inserted, insert size, the restriction site at the 5'-end, the restriction site at the 3'-end, the length of the translated region, the length of the 3'-untranslated region, clone ID, and the supplier of the four genes or the three genes and the receptor of mouse ecotropic retrovirus vector (mCAT: mouse-derived cationic amino acid transporter) used in Examples.

TABLE 1

Construction data

| Name of gene | NCBI No. | Gene-inserted virus vector | Insert size | 5'-end restriction site | 3'-end restriction site | Length of translated region | 3'-untranslated region | Clone ID | Supplier |
|---|---|---|---|---|---|---|---|---|---|
| human Oct3/4 | NM_002701 | pMXs-puro | 1411 | EcoRI | Xho1 | 1083 | 274 | 6578897 | Open Biosystems |
| human Sox2 | BC013923 | pMXs-neo | 1172 | EcoRI | Xho1 | 954 | 143 | 2823424 | Open Biosystems |
| human c-Myc | BC058901 | pMXs-IB | 1876 | EcoRI | Xho1 | 1365 | 473 | 6012670 | Open Biosystems |
| human Klf4 | BC029923 | pMXs-IB | 1591 | EcoRI | EcoRI | 1413 | 38 | 5111134 | Open Biosystems |
| mCAT1 | NM_007513 | Adeno-X | 2032 | BssS1 | BssS1 | 1869 | 132 | A830015N05 | RIKEN FANTOM clone |

Table 2 summarizes the number of alkaline phosphatase-positive colonies of Examples 4 to 7. For cell type, the number of subculture is attached. The day of four gene introduction is a day when a retrovirus vector was infected. Lot No. is that of Lonza products. Age of donors is based on the donor information of Lonza products. The number of colonies is the number of colonies composed of alkaline phosphatase-positive small cells per 10 cm$^2$.

TABLE 2

Examples 5 to 8 and 10, Number of alkaline phosphatase (ALP)-positive colonies formed by gene introduction

| Example | Cell type | Donor age | Lot No. | Serum concentration (%) | No. of passages at the time of gene introduction | Colony count* |
|---|---|---|---|---|---|---|
| 8 | Neonatal skin fibroblast | Neonate | 5F0439 | 2 | 3 | 0.8 |
| 6 | Neonatal skin fibroblast | Neonate | 5F0438 | 2 | 2 | 6.0 |
| 6 | Neonatal skin fibroblast | Neonate | 5F0438 | 2 | 2 | 6.0 |
| 6 | Neonatal skin fibroblast | Neonate | 5F0474 | 2 | 2 | 4.0 |
| 6 | Neonatal skin fibroblast | Neonate | 5F0438 | 2 | 2 | 7.0 |
| 6 | Neonatal skin fibroblast | Neonate | 5F0474 | 2 | 2 | 9.5 |
| 7 | Adult skin fibroblast | 28 | 6F3535 | 2 | 2 | 2.0 |
| 7 | Adult skin fibroblast | 39 | 6F4026 | 2 | 2 | 0.0 |
| 5 | Adult BM-derived cell (low serum) | 20 | 060470B | 2 | 2 | 0.0 |
| 5 | Adult BM-derived cell (low serum) | 20 | 060809B | 2 | 2 | 0.0 |
| 5 | Adult BM-derived cell (low serum) | 20 | 060809B | 2 | 2 | 0.2 |
| 5 | Adult BM-derived cell (low serum) | 20 | 060809B | 2 | 2 | 0.0 |
| 5 | Adult BM-derived mesenchymal stem cell (high serum) | 20 | 060809B | 10 | 2 | 0.0 |
| 5 | Adult BM-derived mesenchymal stem cell (high serum) | 20 | 060470B | 10 | 2 | 0.0 |
| 10 | Neonatal umbilical cord artery smooth muscle cell | Neonate | 5F0442 | 5 | 4 | 0.0 |

*The number of colonies composed of alkaline phosphatase-positive small cells per 10 cm$^2$.
"BM" in Table 2 means "Bone Marrow".

Table 3 summarizes the distribution of the karyotype of clone 1-8 at day 101. After the Giemsa stain, chromosome numbers were counted. 67 of 100 cells showed normal karyotype.

TABLE 3

Karyotype Analysis

| Chromosome no. | Cell no |
|---|---|
| 44 | 1 |
| 45 | 22 |
| 46 | 67 |
| 47 | 7 |
| 48 | 1 |
| 89 | 1 |
| 136 | 1 |

One hundred cells were analyzed in human iPS cells (clone 1-8mTeSR)

Table 4 shows primer sequences used in FIG. 7 and FIG. 15.

TABLE 4

Primer Sequences for RT-PCR

| | Forward primer sequence | Reverse primer sequence |
|---|---|---|
| HPRT | AGTCTGGCTTATATCCAACACTTCG (SEQ ID NO: 20) | GACTTTGCTTTCCTTGGTCAGG (SEQ ID NO: 21) |
| Nanog | TACCTCAGCCTCCAGCAGAT (SEQ ID NO: 22) | TGCGTCACACCATTGCTATT (SEQ ID NO: 23) |
| TERT | AGCCAGTCTCACCTTCAACCGC (SEQ ID NO: 24) | GGAGTAGCAGAGGGAGGCCG (SEQ ID NO: 25) |
| Sall4 | AAACCCCAGCACATCAACTC (SEQ ID NO: 26) | GTCATTCCCTGGGTGGTTC (SEQ ID NO: 27) |
| Zfp42 | TTGGAGTGCAATGGTGTGAT (SEQ ID NO: 28) | TCTGTTCACACAGGCTCCAG (SEQ ID NO: 29) |
| GDF3 | GGCGTCCGCGGGAATGTACTTC (SEQ ID NO: 30) | TGGCTTAGGGGTGGTCTGGCC (SEQ ID NO: 31) |
| Dnmt3b | GCAGCGACCAGTCCTCCGACT (SEQ ID NO: 32) | AACGTGGGGAAGGCCTGTGC (SEQ ID NO: 33) |
| TDGF1 | ACAGAACCTGCTGCCTGAAT (SEQ ID NO: 34) | AGAAATGCCTGAGGAAAGCA (SEQ ID NO: 35) |
| GABRB3 | CTTGACAATCGAGTGGCTGA (SEQ ID NO: 36) | TCATCCGTGGTGTAGCCATA (SEQ ID NO: 37) |
| CYP26A1 | AACCTGCACGACTCCTCGCACA (SEQ ID NO: 38) | AGGATGCGCATGGCGATTCG (SEQ ID NO: 39) |
| Oct4-total | GAGAAGGAGAAGCTGGAGCA (SEQ ID NO: 40) | AATAGAACCCCCAGGGTGAG (SEQ ID NO: 41) |
| Oct4-exo | AGTAGACGGCATCGCAGCTTGG (SEQ ID NO: 42) | GGAAGCTTAGCCAGGTCCGAGG (SEQ ID NO: 43) |
| Sox2-total | CAGGAGAACCCCAAGATGC (SEQ ID NO: 44) | GCAGCCGCTTAGCCTCG (SEQ ID NO: 45) |
| Sox2-exo | ACACTGCCCCTCTCACACAT (SEQ ID NO: 46) | CGGGACTATGGTTGCTGAGT (SEQ ID NO: 47) |
| Klf4-total | ACCCTGGGTCTTGAGGAAGT (SEQ ID NO: 48) | ACGATCGTCTTCCCCTCTTT (SEQ ID NO: 49) |
| Klf4-exo | CTCACCCTTACCGAGTCGGCG (SEQ ID NO: 50) | GCAGCTGGGGCACCTGAACC (SEQ ID NO: 51) |
| c-Myc-total | TCCAGCTTGTACCTGCAGGATCTGA (SEQ ID NO: 52) | CCTCCAGCAGAAGGTGATCCAGACT (SEQ ID NO: 53) |
| c-Myc-exo | AGTAGACGGCATCGCAGCTTGG (SEQ ID NO: 54) | CCTCCAGCAGAAGGTGATCCAGACT (SEQ ID NO: 55) |

Table 5 summarizes SNP genotyping of human iPS clone 1-8 and fibroblasts (5F0438 and 5F04156) which were analyzed using the GeneChip Human Mapping 500K Array Set. SNPs of clone 1-8 were consistent to that of parental cells in 464,069 (99.17%) of 467,946 of called SNPs and different from that of parental cells in 3,877 (0.83%) of them. In contrast, SNPs of clone 1-8 mTeSR were consistent to that of unrelated donor cells (5F0416) only in 284,950 (60.50%) of 470,960 of called SNPs and different from that of the unrelated cells in 186,010 (39.50%) of them.

TABLE 5

SNP genotyping
Consistent SNP (%) between human iPS clone 1-8,
its parental skin-derived cells (5F0438), and skin
cells derived from a different donor (5F0416)

| | iPS 1-8_01 | iPS 1-8_02 | 5F0438_01 | 5F0438_02 |
|---|---|---|---|---|
| iPS 1-8_02 | 99.41 | | | |
| 5F0438_01 | 99.17 | 99.26 | | |
| 5F0438_02 | 99.44 | 99.44 | 99.32 | |
| 5F0416 | 60.50 | 60.75 | 60.72 | 60.47 |

Table 6 The HLA-A, HLA-B, HLA-Cw and HLA-DR types of human iPS1-8 (1-8 mTeSR), iPS 24 (mTeSR), and iPS 3-2 9 mTeSR); and fibroblasts (5F0438 and 5F0416) were classified using hybridization of PCR-amplified DNA with sequence specific oligonucleotide probes (SSOP) (Luminex).

TABLE 6

| ID | A allele | | B allele | | Cw allele | | DRB1 allele | | DQB1 allele | | DPB1 allele | |
|---|---|---|---|---|---|---|---|---|---|---|---|---|
| 5F0438 | *0101/ | *0206/ | *3801/09 | *3905 | *0602/ | *0702/ | *0802 | *1104/43/ | *0301/ | *0402 | *0402/ | *0501 |
| 5F0416 | *0201/ | — | *1501/ | *5101/ | *0303/ | *0401/ | *0401/33/38 | *0801/26 | *0302/ | *0402 | *0201 | *0301/ |
| iPS 1-8 | *0101/ | *0206/ | *3801/09 | *3905 | *0602/ | *0702/ | *0802 | *1104/43/ | *0301/ | *0402 | *0402/ | *0501/ |
| iPS 2-4 | *0201/ | — | *1501/ | *5101/ | *0303/ | *0401/ | *0401/33/38 | *0801/26 | *0302/ | *0402 | *0201 | *0301/ |
| iPS 3-2 | *0101/ | *0206/ | *3801/09 | *3905 | *0802/ | *0702/ | *0802 | *1104/43/ | *0301/ | *0402 | *0402/ | *0501 |

| ID | HLA-A | | HLA-B | | HLA-Cw | | HLA-DR | | HLA-DQ | | HLA-DP | | Bw |
|---|---|---|---|---|---|---|---|---|---|---|---|---|---|
| 5F0438 | A1 | A2 | B38 | B39 | Cw6 | Cw7 | DR8.2 | DR11 | DQ7 | DQ4 | DP4 | DP5 | 4/6 |
| 5F0416 | A2 | — | B62 | B51 | Cw9 | Cw4 | DR4.1 | DR8.1 | DQ8 | DQ4 | DP2 | DP3 | 4/6 |
| iPS 1-8 | A1 | A2 | B38 | B39 | Cw6 | Cw7 | DR8.2 | DR11 | DQ7 | DQ4 | DP4 | DP5 | 4/6 |
| iPS 2-4 | A2 | — | B62 | B51 | Cw9 | Cw4 | DR4.1 | DR8.1 | DQ8 | DQ4 | DP2 | DP2 | 4/6 |
| iPS 3-2 | A1 | A2 | B38 | B39 | Cw6 | Cw7 | DR8.2 | DR11 | DQ7 | DQ4 | DP4 | DP5 | 4/6 |

Table 7 summarized hES cell marker gene expression patterns in colonies. Colonies were stained for alkaline phosphatase at 17 days post 4 genes transduction. All ALP(+) colonies and 18 ALP(−) colonies were dissected and determined their hES marker gene expression by RT-PCR. Each colony was categorized and counted the number. "+" represents gene expression, and "−" represents no detection by a 40 cycle RT-PCR using amplified cDNA samples.

TABLE 7

Gene expression patterns in ALP(+) and ALP(−) colonies
Gene expression patterns in ALP(+) colonies

| Group No. | No. of gene expressed | Nanog | TDGF1 | Dnmt3b | Zfp42 | FoxD3 | GDF3 | CYP26A1 | TERT | No. of colony |
|---|---|---|---|---|---|---|---|---|---|---|
| 1 | 8 | + | + | + | + | + | + | + | + | 4 |
| 2 | 7 | + | + | + | + | + | + | + | − | 7 |
| 3 | 7 | + | + | + | + | + | + | − | + | 11 |
| 4 | 7 | + | + | + | + | + | − | + | + | 1 |
| 5 | 6 | + | + | + | + | + | + | − | − | 25 |
| 6 | 6 | + | + | + | + | + | − | + | − | 4 |
| 7 | 6 | + | + | + | + | + | − | − | + | 3 |
| 8 | 6 | + | + | + | + | − | + | − | + | 2 |
| 9 | 6 | + | + | + | + | − | + | + | − | 3 |
| 10 | 6 | + | + | + | − | + | + | + | − | 1 |
| 11 | 6 | + | + | + | − | − | + | + | + | 1 |
| 12 | 5 | + | + | + | + | + | − | − | − | 22 |
| 13 | 5 | + | + | + | + | − | + | − | − | 9 |
| 14 | 5 | + | + | + | + | − | − | + | − | 2 |
| 15 | 5 | + | + | + | − | + | + | − | − | 4 |
| 16 | 5 | + | + | + | − | + | − | + | − | 2 |
| 17 | 5 | + | + | + | − | − | + | + | − | 1 |
| 18 | 5 | + | + | − | + | + | + | − | − | 2 |
| 19 | 5 | + | + | − | + | + | − | − | + | 1 |
| 20 | 4 | + | + | + | + | − | − | − | − | 9 |
| 21 | 4 | + | + | + | − | + | − | − | − | 3 |
| 22 | 4 | + | + | + | − | − | + | − | − | 5 |
| 23 | 4 | + | + | − | + | + | − | − | − | 7 |
| 24 | 4 | + | − | + | + | + | − | − | − | 1 |
| 25 | 4 | + | − | + | − | + | + | − | − | 2 |
| 26 | 4 | + | − | − | + | + | + | − | − | 1 |
| 27 | 3 | + | + | + | − | − | − | − | − | 1 |
| 28 | 3 | + | + | − | + | − | − | − | − | 3 |
| 29 | 3 | + | + | − | − | + | − | − | − | 4 |
| 30 | 3 | + | + | − | − | − | − | + | − | 1 |
| 31 | 3 | + | − | + | + | − | − | − | − | 1 |
| 32 | 3 | + | − | + | − | + | − | − | − | 2 |
| 33 | 3 | + | − | + | − | − | + | − | − | 1 |
| 34 | 3 | + | − | − | + | + | − | − | − | 1 |

TABLE 7-continued

Gene expression patterns in ALP(+) and ALP(−) colonies
Gene expression patterns in ALP(+) colonies

| Group No. | No. of gene expressed | Nanog | TDGF1 | Dnmt3b | Zfp42 | FoxD3 | GDF3 | CYP26A1 | TERT | No. of colony |
|---|---|---|---|---|---|---|---|---|---|---|
| 35 | 3 | + | − | − | − | + | + | − | − | 1 |
| 36 | 2 | + | + | − | − | − | − | − | − | 4 |
| 37 | 2 | + | − | + | − | − | − | − | − | 5 |
| 38 | 2 | + | − | − | + | − | − | − | − | 2 |
| 39 | 1 | + | − | − | − | − | − | − | − | 2 |
| 40 | 0 | − | − | − | − | − | − | − | − | 2 |
| 41 | 6 | + | + | + | + | + | − | + | − | 1 |
| 42 | 6 | + | + | − | + | + | + | − | + | 1 |
| 43 | 5 | + | + | + | + | + | − | − | − | 3 |
| 44 | 5 | + | + | − | + | + | − | − | + | 6 |
| 45 | 4 | + | + | + | − | + | − | − | − | 1 |
| 46 | 4 | + | + | − | + | + | − | − | − | 1 |
| 47 | 4 | + | + | + | − | − | − | − | + | 1 |
| 48 | 2 | + | − | − | − | − | − | − | + | 1 |
| 49 | 1 | + | − | − | − | − | − | − | − | 1 |
| 50 | 1 | − | + | − | − | − | − | − | − | 1 |
| 51 | 0 | − | − | − | − | − | − | − | − | 1 |

Table 8 summarizes the number of alkaline phosphatase-positive colonies of the experiments using neonatal fibroblasts. The date of four gene introduction is a day when a retrovirus vector was infected. The donor indicates lot number of Lonza products. The number of colonies is the number of colonies composed of alkaline phosphatase-positive small cells per 10 cm². ND: not determined.

TABLE 8

List of experiments

| experimental conditions | | | |
|---|---|---|---|
| donor | cell density (cells/cm²) | ALP staining number of colony (/10 cm²) | notes |
| 5F0439 | 1 × 10⁴ | 0.8 | |
| 5F0438 | 1 × 10⁴ | 6.0 | iPS clone#1-8 |
| 5F0438 | 1 × 10⁴ | 6.0 | |
| 5F0474 | 1 × 10⁴ | 4.0 | |
| 5F0438 | 1 × 10⁴ | 7.0 | |
| 5F0474 | 1 × 10⁴ | 9.5 | |
| 5F0474 | 1 × 10⁴ | 13.3 | |
| 5F0416 | 1 × 10³ | 19.0 | |
| 5F0416 | 1 × 10⁴ | 17.5 | |
| 5F0474 | 1 × 10⁴ | 14.0 | |
| 5F0416 | 1 × 10³ | 3.0 | |
| 5F0416 | 1 × 10⁴ | 9.0 | |
| 5F0416 | 1 × 10³ | 21.0 | ALP(+) |
| 5F0416 | 1 × 10⁴ | 21.5 | colony |
| 5F0474 | 1 × 10³ | 17.0 | classification |
| 5F0474 | 1 × 10⁴ | 19.5 | |
| 5F0416 | 1 × 10³ | ND | iPS clone #2-4 |
| 5F0416 | 1 × 10⁴ | ND | |
| 5F0474 | 1 × 10³ | ND | |
| 5F0474 | 1 × 10⁴ | ND | |
| 5F1195 | 1 × 10³ | ND | |
| 5F0438 | 1 × 10³ | ND | iPS clone #3-2 |

Table 9 lists up locations and sizes in genome corresponding to amplicons using for methylation analyses of the promoter regions of Nanog and Oct3/4. Columns A, B and C indicate amplicon name, locations and sizes in genome corresponding to amplicons, respectively.

TABLE 9

Promoter regions in methylation analysis

| amplicon name | location in genome corresponding to amplicon | size of amplicon |
|---|---|---|
| Nanog-z1 | chr12:7832645-7832959 | 315 |
| Nanog-z2 | chr12:7832877-7833269 | 393 |
| Oct3/4-z1 | chr6:31248581-31249029 | 449 |
| Oct3/4-z2 | chr6_qb1_hap2:2388299-2388525 | 227 |

Table 10 lists up the primer sets using for methylation analyses of the promoter regions of Nanog and Oct3/4. Columns A and B indicate names of primers and sequences of primers (capital for gene-specific sequences, lower case for tag sequences), respectively.

TABLE 10

Primer sequences for methylation analyses

| names of primers | sequences of primers (capital for gene-specific sequences, lower case for tag sequences) |
|---|---|
| Nanog-z1-L | aggaagagagGGAATTTAAGGTGTATGTATTTTTATTT T (SEQ ID NO: 56) |
| Nanog-z1-R | cagtaatacgactcactatagggagaaggctATAACCCA CCCCTATAATCCCAATA (SEQ ID NO: 57) |
| Nanog-z2-L | aggaagagagGTTAGGTTGGTTTTAAATTTTTGAT (SEQ ID NO: 58) |
| Nanog-z2-R | cagtaatacgactcactatagggagaaggctTTTATAAT AAAAACTCTATCACCTTAAACC (SEQ ID NO: 59) |
| Oct3/4-z1-L | aggaagagagTAGTAGGGATTTTTTGGATTGGTTT (SEQ ID NO: 60) |
| Oct3/4-z1-R | cagtaatacgactcactatagggagaaggctAAAACTTT TCCCCCACTCTTATATTAC (SEQ ID NO: 61) |
| Oct3/4-z2-L | aggaagagagGGTAATAAAGTGAGATTTTGTTTTAAAAA (SEQ ID NO: 62) |
| Oct3/4-z2-R | cagtaatacgactcactatagggagaaggctCCACCCAC TAACCTTAACCTCTAA (SEQ ID NO: 63) |

Table 11 summarizes relative mRNA expression in ALP positive colonies of Examples 15. Numbers of colonies are corresponding to FIG. 16-23. Colony #5-2-32, #5-249, #5-2-51, #7-2-37 expressed all analyzed human ES cell markers. In contrast, fibroblastic colonies #3-1-212, #3-1-215, #5-1-4 expressed only Nanog though it highly expressed transgenes.

TABLE 11

Relative mRNA expression of ES cell markers in ALP positive colonies

| no. of genes | ALP | Nanog mean SD | GDF3 mean SD | CYP26A1 mean SD | TERT mean SD | c-Myc mean SD | Oct3/4 mean SD |
|---|---|---|---|---|---|---|---|
| 8 | ALP(+) | 9.3 ± 1.5 | 4.8 ± 0.3 | 27.2 ± 12.5 | 0.2 ± 0.0 | 1121.1 ± 25.3 | 39.3 ± 1.5 |
| 8 | ALP(+) | 15.9 ± 5.7 | 242.9 ± 78.8 | 3.0 ± 0.3 | 3.7 ± 0.5 | 1106.3 ± 51.8 | 770.6 ± 9.3 |
| 8 | ALP(+) | 27.1 ± 2.2 | 419.2 ± 24.7 | 73.5 ± 8.2 | 2.5 ± 0.1 | 1329.4 ± 272.1 | 101.6 ± 5.1 |
| 8 | ALP(+) | 36.9 ± 7.8 | 171.3 ± 20.0 | 110.1 ± 15.4 | 6.2 ± 1.1 | 566.9 ± 22.1 | 30.9 ± 2.4 |
| 7 | ALP(+) | 21.0 ± 2.4 | 59.2 ± 10.2 | 0.0 ± 0.0 | 0.12 ± 0.09 | 436 ± 12 | 25.0 ± 1.2 |
| 7 | ALP(+) | 127.6 ± 6.0 | 259.7 ± 3.9 | 0.0 ± 0.0 | 0.6 ± 0.3 | 59.2 ± 1.2 | 9.1 ± 0.1 |
| 7 | ALP(+) | 32.6 ± 8.4 | 34.0 ± 5.0 | 0.0 ± 0.0 | 1.1 | 446.9 ± 15.8 | 14.9 ± 0.1 |
| 7 | ALP(+) | 9.5 ± 1.0 | 3.4 ± 0.9 | 0.0 ± 0.0 | 1.6 ± 0.1 | 1052.8 ± 129.5 | 17.1 ± 0.3 |
| 7 | ALP(+) | 141.5 ± 64.3 | 328.8 ± 54.1 | 0.0 ± 0.0 | 7.0 ± 0.7 | 9796.2 ± 275.5 | 324.2 ± 29.8 |
| 7 | ALP(+) | 78.0 ± 16.6 | 188.2 ± 3.8 | 0.0 ± 0.0 | 67.6 ± 7.1 | 9714.4 ± 15.7 | 258.7 ± 13.3 |
| 7 | ALP(+) | 55.5 ± 12.2 | 151.3 ± 21.2 | 0.0 ± 0.0 | 5.2 ± 0.1 | 285.3 ± 49.6 | 24.8 ± 3.2 |
| 7 | ALP(+) | 0.1 ± 0.1 | 0.1 ± 0.1 | 0.0 ± 0.0 | 1.1 ± 0.0 | 13065.1 ± 769.8 | 241.8 ± 0.7 |
| 7 | ALP(+) | 10.9 ± 2.6 | 67.9 ± 12.3 | 0.0 ± 0.0 | 4.4 ± 0.8 | 171.5 ± 2.3 | 578.7 ± 13.4 |
| 7 | ALP(+) | 0.1 ± 0.0 | 0.4 ± 0.1 | 0.0 ± 0.0 | 0.7 ± 0.5 | 3176.2 ± 751.2 | 233.4 ± 17.7 |
| 7 | ALP(+) | 51.5 ± 14.4 | 126.4 ± 1.1 | 0.0 ± 0.0 | 2.5 ± 0.3 | 1446.0 ± 421.7 | 33.8 ± 2.6 |
| 7 | ALP(+) | 0.7 ± 0.1 | 0.0 ± 0.0 | 5.0 | 0.5 ± 0.2 | 6049.2 ± 396.9 | 3.8 ± 0.3 |
| 6 | ALP(+) | 14.6 ± 1.1 | 0.0 ± 0.0 | 0.0 ± 0.0 | 40.0 ± 5.7 | 27086.4 ± 3870.8 | 530.6 ± 84.1 |
| 6 | ALP(+) | 20.1 ± 5.9 | 0.0 ± 0.0 | 0.0 ± 0.0 | 1.9 ± 1.0 | 9125.8 ± 883.7 | 7.5 ± 0.7 |
| 6 | ALP(+) | 1.1 ± 0.4 | 0.0 ± 0.0 | 0.0 ± 0.0 | 20.6 ± 0.6 | 8344.9 ± 2054.5 | 6.7 ± 0.5 |
| 6 | ALP(+) | 103.4 ± 11.7 | 195.3 ± 17.7 | 0.0 ± 0.0 | 18.1 ± 1.8 | 95692.9 ± 5109.8 | 2843.9 ± 113.9 |
| 6 | ALP(+) | 50.8 ± 3.6 | 291.3 ± 43.9 | 0.0 ± 0.0 | 20.2 ± 2.9 | 29701.1 ± 4821.3 | 483.1 ± 13.9 |
| 6 | ALP(+) | 50.3 ± 14.5 | 34.3 ± 3.6 | 10.4 ± 2.0 | 1.3 ± 0.1 | 533.8 ± 24.8 | 30.2 ± 1.2 |
| 5 | ALP(+) | 9.3 ± 0.5 | 0.0 ± 0.0 | 0.0 ± 0.0 | 0.0 ± 0.0 | 16848.2 ± 1742.0 | 4.7 ± 0.2 |
| 5 | ALP(+) | 126.4 ± 65.3 | 0.0 ± 0.0 | 0.0 ± 0.0 | 28.7 ± 4.9 | 23614.4 ± 388.9 | 310.9 ± 19.2 |
| 4 | ALP(+) | 3.7 ± 1.3 | 0.0 ± 0.0 | 0.0 ± 0.0 | 0.0 ± 0.0 | 2927.9 ± 412.5 | 130.3 ± 10.1 |
| 4 | ALP(+) | 1.9 ± 0.3 | 0.0 ± 0.0 | 0.0 ± 0.0 | 0.0 ± 0.0 | 19433.2 ± 297.0 | 4.2 ± 0.5 |
| 4 | ALP(+) | 17.4 ± 5.1 | 0.0 ± 0.0 | 0.0 ± 0.0 | 0.0 ± 0.0 | 1959.8 ± 379.9 | 8.5 ± 0.7 |
| 3 | ALP(+) | 2.2 ± 0.3 | 0.0 ± 0.0 | 0.0 ± 0.0 | 0.0 ± 0.0 | 6065.6 ± 704.9 | 3.4 ± 0.3 |
| 3 | ALP(+) | 1.9 ± 0.3 | 0.0 ± 0.0 | 0.0 ± 0.0 | 0.0 ± 0.0 | 4572.6 ± 303.7 | 7.4 ± 0.1 |
| 3 | ALP(+) | 1.4 ± 0.2 | 0.0 ± 0.0 | 0.0 ± 0.0 | 0.0 ± 0.0 | 53755.3 ± 10897.7 | 22.9 ± 3.0 |
| 3 | ALP(+) | 5.6 ± 2.9 | 0.0 ± 0.0 | 0.0 ± 0.0 | 807.1 ± 13.4 | 25595.8 ± 2002.8 | 414.9 ± 22.6 |
| 6 | ALP(−) | 0.5 ± 0.1 | 0.07 | 0.0 ± 0.0 | 0.01 ± 0.01 | 5873.2 ± 156.2 | 226.3 ± 12.9 |
| 5 | ALP(−) | 0.8 ± 0.2 | 0.0 ± 0.0 | 0.0 ± 0.0 | 0.5 ± 0.2 | 8698.4 ± 492.3 | 58.7 ± 2.6 |
| 5 | ALP(−) | 6.9 ± 1.1 | 0.0 ± 0.0 | 0.0 ± 0.0 | 0.7 ± 0.1 | 9350.1 ± 201.0 | 2.1 ± 0.1 |
| 5 | ALP(−) | 7.2 ± 2.0 | 0.0 ± 0.0 | 0.0 ± 0.0 | 7.3 ± 1.8 | 26133.6 ± 3528.5 | 8.0 ± 0.1 |
| 5 | ALP(−) | 0.2 ± 0.1 | 0.0 ± 0.0 | 0.0 ± 0.0 | 0.5 ± 0.1 | 5211.8 ± 618.7 | 370.7 ± 7.8 |
| 5 | ALP(−) | 2.5 ± 0.5 | 0.0 ± 0.0 | 0.0 ± 0.0 | 0.5 ± 0.1 | 8971.8 ± 110.3 | 266.6 ± 21.4 |
| 5 | ALP(−) | 3.4 ± 0.9 | 0.0 ± 0.0 | 0.0 ± 0.0 | 11.8 ± 3.4 | 9748.3 ± 530.0 | 7.3 ± 0.1 |
| 4 | ALP(−) | 0.2 ± 0.1 | 0.0 ± 0.0 | 0.0 ± 0.0 | 14.6 ± 1.9 | 7681.0 ± 286.9 | 261.0 ± 26.0 |
| 2 | ALP(−) | 0.6 ± 0.3 | 0.0 ± 0.0 | 0.0 ± 0.0 | 8.2 ± 0.6 | 53887.9 ± 1343.2 | 13.3 ± 1.2 |
| 1 | ALP(−) | 3.4 ± 0.5 | 0.0 ± 0.0 | 0.0 ± 0.0 | 0.0 ± 0.0 | 7721.3 ± 437.0 | 52.1 ± 2.3 |
| 1 | ALP(−) | 0.0 ± 0.0 | 0.0 ± 0.0 | 0.0 ± 0.0 | 0.0 ± 0.0 | 96049.6 ± 2394.1 | 23.7 ± 2.1 |
| 0 | ALP(−) | 0.0 ± 0.0 | 0.0 ± 0.0 | 0.0 ± 0.0 | 0.0 ± 0.0 | 1454.7 ± 371.7 | 11.6 ± 0.3 |
| clone1-8 (Std) | | 1.0 | 1.0 | 1.0 | 1.0 | 1.0 | 1.0 |

Table 12 summarizes relative mRNA expression in clone-24 and 3-2. Total RNA was extracted from clones 24 and 3-2. Expression of ES cell marker genes were determined by qRT-PCR as described in Example 16 and 17. Both clone-24 and -3-2 showed ES cell marker gene expression. All expression values were normalized against human iPS clone-1-8 (day 94).

TABLE 12 relative mRNA expression in clone-2-4 and 3-2.

| | #3-2_day48 | #2-4_day59 | #1-8_day82 | #1-8_day94 |
|---|---|---|---|---|
| Nanog | 4.21 ± 1.11 | 2.88 ± 0.43 | 2.41 | 1.00 ± 0.24 |
| TERT | 1.52 ± 0.50 | 1.94 ± 0.14 | 0.69 | 1.00 ± 0.70 |
| GDF3 | 6.42 ± 0.16 | 6.65 ± 0.05 | 0.92 | 1.00 ± 0.49 |
| CYP26A1 | 72.45 ± 14.92 | 49.12 ± 0.06 | 62.50 | 1.00 ± 0.01 |
| TDGF1 | 2.55 ± 0.10 | 3.53 ± 0.05 | 3.53 | 1.00 ± 0.01 |
| Dnmt3b | 2.66 ± 0.04 | 0.96 ± 0.02 | 0.91 | 1.00 ± 0.01 |
| Foxd3 | 1.16 ± 0.08 | 0.59 ± 0.17 | 1.14 | 1.00 ± 0.18 |
| Zfp42 | 0.98 ± 0.15 | 0.76 ± 0.01 | 2.44 | 1.00 ± 0.02 |
| Myc | 6.14 ± 0.58 | 4.58 ± 0.16 | 3.82 | 1.00 ± 0.05 |
| Oct3/4 | 2.00 ± 0.07 | 1.08 ± 0.01 | 1.33 | 1.00 ± 0.00 |

TABLE 13

(DEAH peptide disclosed as SEQ ID NO: 64; DEAD peptide disclosed as SEQ ID NO: 65)

| Systematic Name | Genbank | Description |
| --- | --- | --- |
| 235940_at | AW983691 | chromosome 9 open reading frame 64 |
| 239206_at | BE552138 | complement component (3b/4b) receptor 1-like |
| 239205_s_at | BE552138 | complement component (3b/4b) receptor 1 (Knops blood group) /// complement component (3b/4b) receptor 1-like /// similar to complement component (3b/4b) receptor 1 isoform F precursor |
| 215101_s_at | BG166705 | chemokine (C—X—C motif) ligand 5 |
| AFFX-r2-Ec-bioD-3_at | AFFX-ThrX-M | — |
| AFFX-M27830_5_at | AFFX-M27830_3 | — |
| 210697_at | AF070651 | zinc finger protein 257 |
| 213122_at | AI096375 | TSPY-like 5 |
| 223551_at | AF225513 | protein kinase (cAMP-dependent, catalytic) inhibitor beta |
| 214974_x_at | AK026546 | chemokine (C—X—C motif) ligand 5 |
| 237552_at | BF056473 | CDNA clone IMAGE: 4667929 |
| 212575_at | BF966155 | chromosome 19 open reading frame 6 |
| 229328_at | T90358 | Zinc finger protein 540 |
| 231120_x_at | AL569326 | protein kinase (cAMP-dependent, catalytic) inhibitor beta |
| 235075_at | AI813438 | desmoglein 3 (pemphigus vulgaris antigen) |
| 211906_s_at | AB046400 | serpin peptidase inhibitor, clade B (ovalbumin), member 4 |
| 225061_at | N45231 | DnaJ (Hsp40) homolog, subfamily A, member 4 |
| 217230_at | AF199015 | villin 2 (ezrin) |
| 225908_at | AI829927 | isoamyl acetate-hydrolyzing esterase 1 homolog (S. cerevisiae) |
| 232881_at | AI500353 | GNAS1 antisense |
| 239951_at | AI734093 | Transcribed locus |
| 1554333_at | BC031044 | DnaJ (Hsp40) homolog, subfamily A, member 4 |
| 1553276_at | NM_152476 | zinc finger protein 560 |
| 1553970_s_at | BC042510 | carboxyl ester lipase (bile salt-stimulated lipase) |
| 219837_s_at | NM_018659 | cytokine-like 1 |
| 228063_s_at | AW025330 | nucleosome assembly protein 1-like 5 |
| 208542_x_at | NM_007153 | zinc finger protein 208 |
| 243110_x_at | AI868441 | neuropeptide W |
| 239319_at | BE542563 | Hypothetical protein LOC728342 |
| 215826_x_at | AK023017 | hypothetical BC37295_3 |
| 1555229_a_at | BC007010 | complement component 1, s subcomponent |
| 235779_at | AW467077 | Hypothetical protein LOC284408 |
| 220638_s_at | NM_012116 | Cas-Br-M (murine) ecotropic retroviral transforming sequence c |
| 232315_at | AU149712 | Zinc finger-like |
| 222546_s_at | AW204755 | EPS8-like 2 |
| 235913_at | AI285722 | zinc finger-like |
| 215019_x_at | AW474158 | zinc finger protein 528 |
| 210362_x_at | AF230409 | promyelocytic leukemia |
| 231299_at | AI494590 | centaurin, gamma 3 |
| 214336_s_at | AI621079 | coatomer protein complex, subunit alpha |
| 210171_s_at | S68134 | cAMP responsive element modulator |
| 219807_x_at | NM_016154 | RAB4B, member RAS oncogene family |
| 205827_at | NM_000729 | cholecystokinin |
| 1559503_a_at | AA350425 | Similar to zinc finger protein 91 |
| 228062_at | AW025330 | nucleosome assembly protein 1-like 5 |
| 223789_s_at | AF116627 | GTP binding protein 2 |
| 215634_at | AF007137 | Clone 23618 mRNA sequence |
| 201679_at | BE646076 | ARS2 protein |
| 213695_at | L48516 | paraoxonase 3 |
| 1553219_a_at | NM_015365 | Alport syndrome, mental retardation, midface hypoplasia and elliptocytosis chromosomal region, gene 1 |
| 1552470_a_at | NM_148914 | abhydrolase domain containing 11 |
| 216884_at | S69182 | protein tyrosine phosphatase, non-receptor type 12 |
| 237215_s_at | N76327 | transferrin receptor (p90, CD71) |
| 209040_s_at | U17496 | proteasome (prosome, macropain) subunit, beta type, 8 (large multifunctional peptidase 7) |
| 214090_at | BF732462 | PRKC, apoptosis, WT1, regulator |
| 223629_at | BC001186 | protocadherin beta 5 |
| 216971_s_at | Z54367 | plectin 1, intermediate filament binding protein 500 kDa |
| 201008_s_at | AA812232 | thioredoxin interacting protein |
| 233754_x_at | AC007228 | zinc finger protein 71 |
| 200621_at | NM_004078 | cysteine and glycine-rich protein 1 |
| 208978_at | U36190 | cysteine-rich protein 2 |
| 1552914_a_at | NM_025240 | CD276 molecule |
| 1559051_s_at | AK097148 | chromosome 6 open reading frame 150 |
| 212105_s_at | BF313832 | DEAH (Asp-Glu-Ala-His) box polypeptide 9 |
| 222814_s_at | AI916361 | zinc finger, HIT type 2 |
| 236562_at | N29327 | zinc finger protein 439 |
| 1562245_a_at | AL833487 | MRNA; cDNA DKFZp686H1629 (from clone DKFZp686H1629) |
| 203782_at | NM_001100 | actin, alpha 1, skeletal muscle |
| 222935_x_at | AW139759 | solute carrier family 39 (zinc transporter), member 8 |
| 1555695_a_at | AF388368 | clarin 1 |
| 207080_s_at | NM_004160 | peptide YY |
| 243195_s_at | BF438407 | zinc finger protein 551 |
| 220179_at | NM_022357 | dipeptidase 3 |

TABLE 13-continued (DEAH peptide disclosed as SEQ ID NO: 64; DEAD peptide disclosed as SEQ ID NO: 65)

| Systematic Name | Genbank | Description |
|---|---|---|
| 207099_s_at | NM_000390 | choroideremia (Rab escort protein 1) |
| 222898_s_at | BE350882 | delta-like 3 (*Drosophila*) |
| 226539_s_at | BF436337 | — |
| 229332_at | AI653050 | 4-hydroxyphenylpyruvate dioxygenase-like |
| 207852_at | NM_002994 | chemokine (C—X—C motif) ligand 5 |
| 1554334_a_at | BC031044 | DnaJ (Hsp40) homolog, subfamily A, member 4 |
| 1555731_a_at | AF393369 | adaptor-related protein complex 1, sigma 3 subunit |
| AFFX-r2-Ec-bioC-5_at | AFFX-ThrX-5 | — |
| 215337_at | AK022508 | mediator complex subunit 24 |
| 211124_s_at | AF119835 | KIT ligand |
| 1553873_at | NM_153270 | kelch-like 34 (*Drosophila*) |
| 201796_s_at | BE790854 | valyl-tRNA synthetase |
| 235942_at | AI272059 | LOC401629 /// LOC401630 |
| 202873_at | BF034973 | ATPase, H+ transporting, lysosomal 42 kDa, V1 subunit C1 |
| 244178_at | AW451792 | COMM domain containing 7 |
| 215172_at | AL050040 | protein tyrosine phosphatase, non-receptor type 20B /// protein tyrosine phosphatase, non-receptor type 20A |
| 228251_at | BE467577 | UBX domain containing 1 |
| 224463_s_at | BC006128 | chromosome 11 open reading frame 70 |
| 206797_at | NM_000015 | N-acetyltransferase 2 (arylamine N-acetyltransferase) |
| 212278_x_at | BF588511 | ubiquitin protein ligase E3A (human papilloma virus E6-associated protein, Angelman syndrome) |
| 1555766_a_at | AF493870 | guanine nucleotide binding protein (G protein), gamma 2 |
| 211107_s_at | AB017332 | aurora kinase C |
| 214519_s_at | NM_005059 | relaxin 2 |
| 226504_at | AA522720 | family with sequence similarity 109, member B |
| 216469_at | AL163202 | similar to zinc finger protein 43 (HTF6) |
| 221123_x_at | NM_018660 | zinc finger protein 395 |
| 1568574_x_at | AB019562 | Secreted phosphoprotein 1 (osteopontin, bone sialoprotein I, early T-lymphocyte activation 1) |
| 215989_at | BE258133 | chromobox homolog 2 (Pc class homolog, *Drosophila*) |
| 205195_at | NM_001283 | adaptor-related protein complex 1, sigma 1 subunit |
| 223994_s_at | BC000154 | solute carrier family 12 (potassium/chloride transporters), member 9 |
| 205095_s_at | NM_005177 | ATPase, H+ transporting, lysosomal V0 subunit a1 |
| 1554777_at | BI092935 | zinc finger protein 42 homolog (mouse) |
| 217494_s_at | AF023139 | phosphatase and tensin homolog (mutated in multiple advanced cancers 1), pseudogene 1 |
| 201169_s_at | BG326045 | basic helix-loop-helix domain containing, class B, 2 |
| 214123_s_at | AI126492 | chromosome 4 open reading frame 10 |
| 229896_at | H41907 | CDNA clone IMAGE: 6106200 |
| 211214_s_at | BC003614 | death-associated protein kinase 1 |
| 203402_at | AL520102 | potassium voltage-gated channel, shaker-related subfamily, beta member 2 |
| 205920_at | NM_003043 | solute carrier family 6 (neurotransmitter transporter, taurine), member 6 |
| 212937_s_at | M20776 | collagen, type VI, alpha 1 |
| 200796_s_at | BF594446 | myeloid cell leukemia sequence 1 (BCL2-related) |
| 1558697_a_at | BI600341 | KIAA0430 |
| 232771_at | Z83850 | Nik related kinase |
| 1559501_at | BC037580 | CDNA clone IMAGE: 5262521 |
| 238750_at | AW083576 | chemokine (C-C motif) ligand 28 |
| 239818_x_at | AA576947 | tribbles homolog 1 (*Drosophila*) |
| 1555765_a_at | AF493872 | guanine nucleotide binding protein (G protein), gamma 4 |
| 233573_s_at | AK001080 | WD repeat domain 6 |
| 206220_s_at | NM_007368 | RAS p21 protein activator 3 |
| 212113_at | AI927479 | hypothetical LOC552889 |
| 205577_at | NM_005609 | phosphorylase, glycogen; muscle (McArdle syndrome, glycogen storage disease type V) |
| 201130_s_at | L08599 | cadherin 1, type 1, E-cadherin (epithelial) |
| 219911_s_at | NM_016354 | solute carrier organic anion transporter family, member 4A1 |
| 227598_at | AI762857 | chromosome 7 open reading frame 29 |
| 226654_at | AF147790 | mucin 12, cell surface associated |
| 205461_at | NM_006861 | RAB35, member RAS oncogene family |
| 221285_at | NM_006011 | ST8 alpha-N-acetyl-neuraminide alpha-2,8-sialyltransferase 2 |
| 203027_s_at | AI189359 | mevalonate (diphospho) decarboxylase |
| 243639_at | R51605 | Transcribed locus |
| 211162_x_at | AF116616 | stearoyl-CoA desaturase (delta-9-desaturase) |
| 213667_at | AB002307 | Snf2-related CBP activator protein |
| 1559361_at | AF086401 | Full length insert cDNA clone ZD75H06 |
| 218000_s_at | NM_007350 | pleckstrin homology-like domain, family A, member 1 |
| 209260_at | BC000329 | stratifin |
| 211530_x_at | M90686 | HLA-G histocompatibility antigen, class I, G |
| AFFX-r2-Bs-dap-M_at | AFFX-r2-Bs-phe-M | — |
| 239947_at | AI969304 | Transcribed locus |
| 215955_x_at | Y10388 | Rho GTPase activating protein 26 |
| 227806_at | BG285710 | chromosome 16 open reading frame 74 |
| 220259_at | NM_024927 | pleckstrin homology domain containing, family H (with MyTH4 domain) member 3 |
| 1560154_a_at | AK026500 | CDNA: FLJ22847 fis, clone KAIA686 |

TABLE 13-continued (DEAH peptide disclosed as SEQ ID NO: 64; DEAD peptide disclosed as SEQ ID NO: 65)

| Systematic Name | Genbank | Description |
| --- | --- | --- |
| AFFX-r2-Bs-dap-5_at | AFFX-r2-Bs-phe-5 | — |
| 223708_at | AF329838 | C1q and tumor necrosis factor related protein 4 |
| 215581_s_at | AK022303 | minichromosome maintenance complex component 3 associated protein |
| 1552399_a_at | NM_145696 | BRF1 homolog, subunit of RNA polymerase III transcription initiation factor IIIB (S. cerevisiae) |
| 221310_at | NM_004115 | fibroblast growth factor 14 |
| 234939_s_at | AL161953 | PHD finger protein 12 |
| 218944_at | NM_023078 | pyrroline-5-carboxylate reductase-like |
| 206673_at | NM_007223 | G protein-coupled receptor 176 |
| 205910_s_at | NM_001807 | carboxyl ester lipase (bile salt-stimulated lipase) |
| 206232_s_at | NM_004775 | UDP-Gal:betaGlcNAc beta 1,4-galactosyltransferase, polypeptide 6 |
| 212009_s_at | AL553320 | stress-induced-phosphoprotein 1 (Hsp70/Hsp90-organizing protein) |
| 204815_s_at | AI924903 | DEAH (Asp-Glu-Ala-His) box polypeptide 34 |
| 234237_s_at | AL137611 | hypothetical protein FLJ20294 |
| 229502_at | AW242403 | choline dehydrogenase |
| 1554776_at | AF450454 | zinc finger protein 42 homolog (mouse) |
| 242070_at | AI014470 | hypothetical protein LOC728485 |
| 1554508_at | BC029917 | phosphoinositide-3-kinase adaptor protein 1 |
| 210935_s_at | AF274954 | WD repeat domain 1 |
| 236741_at | AW299463 | WD repeat domain 72 |
| 205081_at | NM_001311 | cysteine-rich protein 1 (intestinal) |
| 1555040_s_at | AF493879 | guanine nucleotide binding protein (G protein), gamma 12 |
| 205824_at | NM_001541 | heat shock 27 kDa protein 2 |
| 230033_at | BF436398 | chromosome 19 open reading frame 51 |
| 206832_s_at | NM_004186 | sema domain, immunoglobulin domain (Ig), short basic domain, secreted, (semaphorin) 3F |
| 223083_s_at | AW057545 | egl nine homolog 2 (C. elegans) |
| 235234_at | AA359612 | FLJ36874 protein |
| 206604_at | NM_004561 | ovo-like 1 (Drosophila) |
| 1555829_at | BC001224 | family with sequence similarity 62 (C2 domain containing) member B |
| 1555434_a_at | BC015770 | solute carrier family 39 (zinc transporter), member 14 |
| 205196_s_at | NM_001283 | adaptor-related protein complex 1, sigma 1 subunit |
| 1564706_s_at | AF110329 | glutaminase 2 (liver, mitochondrial) |
| 242519_at | BF432331 | Selenoprotein P, plasma, 1 |
| 205344_at | NM_006574 | chondroitin sulfate proteoglycan 5 (neuroglycan C) |
| 201123_s_at | NM_001970 | eukaryotic translation initiation factor 5A |
| 220825_s_at | NM_018240 | kin of IRRE like (Drosophila) |
| 224805_s_at | BF508824 | chromosome 15 open reading frame 17 |
| 224033_at | AF130083 | — |
| 1564339_a_at | AF279779 | cholinergic receptor, muscarinic 3 /// similar to cholinergic receptor, muscarinic 3 |
| 216031_x_at | T53900 | hematological and neurological expressed 1-like |
| 202627_s_at | AL574210 | serpin peptidase inhibitor, clade E (nexin, plasminogen activator inhibitor type 1), member 1 |
| 221628_s_at | AF326966 | cytokine-like nuclear factor n-pac |
| 201432_at | NM_001752 | catalase |
| 223285_s_at | AW044319 | ST6 (alpha-N-acetyl-neuraminyl-2,3-beta-galactosyl-1,3)-N-acetylgalactosaminide alpha-2,6-sialyltransferase 4 |
| 1555800_at | BC038422 | zinc finger protein 533 |
| 209261_s_at | BF000629 | nuclear receptor subfamily 2, group F, member 6 |
| 1553055_a_at | NM_144975 | schlafen family member 5 |
| 233492_s_at | AC005587 | olfactory receptor, family 2, subfamily A, member 4 /// olfactory receptor, family 2, subfamily A, member 7 /// similar to rho guanine nucleotide exchange factor 5 |
| 205867_at | NM_002834 | protein tyrosine phosphatase, non-receptor type 11 (Noonan syndrome 1) |
| 1554417_s_at | AY113699 | anterior pharynx defective 1 homolog A (C. elegans) |
| 223799_at | AF253976 | KIAA1826 |
| 214040_s_at | BE675337 | gelsolin (amyloidosis, Finnish type) |
| 201045_s_at | BF513857 | RAB6A, member RAS oncogene family /// RAB6C-like |
| 1557910_at | BG612458 | heat shock protein 90 kDa alpha (cytosolic), class B member 1 |
| 204823_at | NM_014903 | neuron navigator 3 |
| 1553852_at | NM_152564 | vacuolar protein sorting 13 homolog B (yeast) |
| 1557924_s_at | S76738 | alkaline phosphatase, liver/bone/kidney |
| 221807_s_at | BG399562 | TraB domain containing |
| 1552995_at | NM_145659 | interleukin 27 |
| 1567013_at | AF323119 | nuclear factor (erythroid-derived 2)-like 2 |
| 216360_x_at | AK000238 | ribosomal RNA processing 12 homolog (S. cerevisiae) |
| 242676_at | AA401733 | Transcribed locus |
| 205925_s_at | NM_002867 | RAB3B, member RAS oncogene family |
| 232751_at | AL121893 | retinoblastoma binding protein 9 |
| 1555680_a_at | AY033891 | spermine oxidase |
| 231452_at | AW510925 | HRAS-like suppressor family, member 5 |
| 210068_s_at | U63622 | aquaporin 4 |
| 205884_at | NM_005031 | FXYD domain containing ion transport regulator 1 (phospholemman) |
| 213171_s_at | AL121753 | matrix metallopeptidase 24 (membrane-inserted) |
| 210732_s_at | AF342816 | lectin, galactoside-binding, soluble, 8 (galectin 8) |
| 203890_s_at | BF686824 | death-associated protein kinase 3 |
| 209756_s_at | AI871354 | v-myc myelocytomatosis viral related oncogene, neuroblastoma derived (avian) |
| 232506_s_at | AK026504 | chromosome 15 open reading frame 41 |

TABLE 13-continued (DEAH peptide disclosed as SEQ ID NO: 64; DEAD peptide disclosed as SEQ ID NO: 65)

| Systematic Name | Genbank | Description |
| --- | --- | --- |
| 211708_s_at | BC005807 | stearoyl-CoA desaturase (delta-9-desaturase) |
| 1556670_at | AK098715 | CDNA FLJ25849 fis, clone TST08968 |
| 1558214_s_at | BG330076 | catenin (cadherin-associated protein), alpha 1, 102 kDa |
| 1555559_s_at | AF419247 | ubiquitin specific peptidase 25 |
| 209458_x_at | AF105974 | hemoglobin, alpha 1 /// hemoglobin, alpha 2 |
| 222385_x_at | AF346602 | Sec61 alpha 1 subunit (*S. cerevisiae*) |
| 228102_at | AA127691 | Neuropilin 2 |
| 229284_at | R60683 | Methionine adenosyltransferase II, beta |
| 227759_at | W92036 | proprotein convertase subtilisin/kexin type 9 |
| 208621_s_at | BF663141 | villin 2 (ezrin) |
| 211538_s_at | U56725 | heat shock 70 kDa protein 2 |
| 218832_x_at | NM_004041 | arrestin, beta 1 |
| 229289_at | AL517395 | hypothetical protein BC004941 |
| 1553698_a_at | NM_145257 | chromosome 1 open reading frame 96 |
| 209427_at | AF064238 | smoothelin |
| 214971_s_at | AV695711 | ST6 beta-galactosamide alpha-2,6-sialyltranferase 1 |
| 235854_x_at | AA167669 | Rho-associated, coiled-coil containing protein kinase 1 |
| 217601_at | AL523184 | nucleoporin 188 kDa |
| 205715_at | NM_004334 | bone marrow stromal cell antigen 1 |
| 207532_at | NM_006891 | crystallin, gamma D |
| 239852_at | AL532029 | methylmalonic aciduria (cobalamin deficiency) cb1A type |
| 206997_s_at | NM_004807 | heparan sulfate 6-O-sulfotransferase 1 /// similar to Heparan-sulfate 6-O-sulfotransferase 1 (HS6ST-1) |
| 219424_at | NM_005755 | Epstein-Barr virus induced gene 3 |
| 225322_s_at | AL514147 | chromosome 17 open reading frame 70 |
| 221414_s_at | NM_030931 | defensin, beta 126 |
| 214154_s_at | AA888057 | plakophilin 2 |
| 1562527_at | AF519622 | hypothetical protein LOC283027 |
| 221213_s_at | NM_017661 | suppressor of hairy wing homolog 4 (*Drosophila*) |
| 214007_s_at | AW665024 | twinfilin, actin-binding protein, homolog 1 (*Drosophila*) |
| 1556834_at | BC042986 | CDNA clone IMAGE: 5296106 |
| 227757_at | AL563297 | cullin 4A |
| 236340_at | AI769947 | Transcribed locus, strongly similar to XP_001146557.1 hypothetical protein [Pantroglodytes] |
| 204698_at | NM_002201 | interferon stimulated exonuclease gene 20 kDa |
| 1554383_a_at | BC028121 | translocation associated membrane protein 2 |
| 210978_s_at | BC002616 | transgelin 2 |
| 234773_x_at | AL442080 | MRNA; cDNA DKFZp434A0226 (from clone DKFZp434A0226) |
| 208504_x_at | NM_018931 | protocadherin beta 11 |
| 214008_at | N25562 | Twinfilin, actin-binding protein, homolog 1 (*Drosophila*) |
| 209875_s_at | M83248 | secreted phosphoprotein 1 (osteopontin, bone sialoprotein I, early T-lymphocyte activation 1) |
| 1555821_a_at | BC016043 | AKT1 substrate 1 (proline-rich) |
| 216915_s_at | S69182 | protein tyrosine phosphatase, non-receptor type 12 |
| 1568905_at | BC030750 | CDNA clone IMAGE: 4795773 |
| 233421_s_at | AU146738 | nucleoporin 133 kDa |
| 232490_s_at | U67085 | prune homolog (*Drosophila*) |
| 227419_x_at | AW964972 | placenta-specific 9 |
| 242948_x_at | T97602 | Transcribed locus |
| 227175_at | AI806486 | Myeloid cell leukemia sequence 1 (BCL2-related) |
| 209213_at | BC002511 | carbonyl reductase 1 |
| 208262_x_at | NM_000243 | Mediterranean fever |
| 227486_at | AI086864 | 5'-nucleotidase, ecto (CD73) |
| 239239_at | W58601 | Transcribed locus |
| 236574_at | AI304870 | Hypothetical protein LOC284373 |
| 219360_s_at | NM_017636 | transient receptor potential cation channel, subfamily M, member 4 |
| 1558423_at | BE715671 | hypothetical LOC349114 |
| 221408_x_at | NM_018932 | protocadherin beta 12 |
| 1562234_a_at | AF397731 | neuron navigator 3 /// similar to neuron navigator 3 |
| 226632_at | AL513673 | cytoglobin |
| 216831_s_at | AF018283 | runt-related transcription factor 1; translocated to, 1 (cyclin D-related) |
| 206932_at | NM_003956 | cholesterol 25-hydroxylase |
| 213210_at | AI005317 | TAF6-like RNA polymerase II, p300/CBP-associated factor (PCAF)-associated factor, 65 kDa |
| 201167_x_at | D13989 | Rho GDP dissociation inhibitor (GDI) alpha |
| 212016_s_at | AA679988 | polypyrimidine tract binding protein 1 |
| 203324_s_at | NM_001233 | caveolin 2 |
| 214828_s_at | AL157851 | CGI-96 protein /// similar to CGI-96 |
| 219298_at | NM_024693 | enoyl Coenzyme A hydratase domain containing 3 |
| 233305_at | AF193756 | EF-hand calcium binding protein 1 |
| 216985_s_at | AJ002077 | syntaxin 3 |
| 214738_s_at | BE792298 | NIMA (never in mitosis gene a)-related kinase 9 |
| 231789_at | AV722990 | protocadherin beta 15 |
| 200841_s_at | AI142677 | glutamyl-prolyl-tRNA synthetase |
| 204570_at | NM_001864 | cytochrome c oxidase subunit VIIa polypeptide 1 (muscle) |
| 226983_at | AA626717 | zinc finger protein 777 |
| 212938_at | M20776 | collagen, type VI, alpha 1 |

TABLE 13-continued (DEAH peptide disclosed as SEQ ID NO: 64; DEAD peptide disclosed as SEQ ID NO: 65)

| Systematic Name | Genbank | Description |
|---|---|---|
| 230255_at | AI936907 | gamma-aminobutyric acid (GABA) A receptor, delta |
| 211363_s_at | AF109294 | methylthioadenosine phosphorylase |
| 219430_at | NM_020155 | G protein-coupled receptor 137 |
| 210990_s_at | U77706 | laminin, alpha 4 |
| 205259_at | NM_000901 | nuclear receptor subfamily 3, group C, member 2 |
| 217294_s_at | U88968 | enolase 1, (alpha) |
| 211922_s_at | AY028632 | catalase |
| 204018_x_at | NM_000558 | hemoglobin, alpha 1 /// hemoglobin, alpha 2 |
| 211823_s_at | D86862 | paxillin |
| 219593_at | NM_016582 | solute carrier family 15, member 3 |
| 223143_s_at | AI742378 | chromosome 6 open reading frame 166 |
| 243347_at | AW003107 | — |
| 222896_at | AA196034 | transmembrane protein 38A |
| 213767_at | U43586 | kinase suppressor of ras 1 |
| 206595_at | NM_001323 | cystatin E/M |
| 203508_at | NM_001066 | tumor necrosis factor receptor superfamily, member 1B |
| 238125_at | AI740544 | ADAM metallopeptidase with thrombospondin type 1 motif, 16 |
| 209958_s_at | AF095771 | Bardet-Biedl syndrome 9 |
| 225800_at | AI990891 | JAZF zinc finger 1 |
| 233900_at | U46120 | Expressed unknown mRNA |
| 238692_at | AL040935 | BTB (POZ) domain containing 11 |
| 201048_x_at | NM_002869 | RAB6A, member RAS oncogene family |
| 206390_x_at | NM_002619 | platelet factor 4 (chemokine (C—X—C motif) ligand 4) |
| 210572_at | BC003126 | protocadherin alpha 2 |
| 231881_at | AU145225 | caldesmon 1 |
| 1567274_at | Z36814 | — |
| 1555034_at | AF482697 | clarin 1 |
| 210587_at | BC005161 | inhibin, beta E |
| 210298_x_at | AF098518 | four and a half LIM domains 1 |
| 209727_at | M76477 | GM2 ganglioside activator |
| 213550_s_at | AA993683 | transmembrane and coiled-coil domains 6 |
| 231013_at | W80446 | — |
| 213807_x_at | BE870509 | met proto-oncogene (hepatocyte growth factor receptor) |
| 206665_s_at | NM_001191 | BCL2-like 1 |
| 206882_at | NM_005071 | solute carrier family 1 (high affinity aspartate/glutamate transporter), member 6 |
| 1555716_a_at | AY072911 | coxsackie virus and adenovirus receptor |
| 244852_at | AU119545 | dermatan sulfate epimerase-like |
| 211082_x_at | Z25427 | MAP/microtubule affinity-regulating kinase 2 |
| 203726_s_at | NM_000227 | laminin, alpha 3 |
| 213928_s_at | AI742626 | HIV-1 Rev binding protein |
| 217051_s_at | AF257501 | synovial sarcoma translocation, chromosome 18 |
| 206488_s_at | NM_000072 | CD36 molecule (thrombospondin receptor) |
| 222508_s_at | AU135021 | hypothetical protein FLJ10154 |
| 211529_x_at | M90684 | HLA-G histocompatibility antigen, class I, G |
| 220108_at | NM_004297 | guanine nucleotide binding protein (G protein), alpha 14 |
| 203676_at | NM_002076 | glucosamine (N-acetyl)-6-sulfatase (Sanfilippo disease IIID) |
| 1558775_s_at | AU142380 | neutral sphingomyelinase (N-SMase) activation associated factor |
| 209555_s_at | M98399 | CD36 molecule (thrombospondin receptor) |
| 1561367_a_at | BC035104 | CDNA clone IMAGE: 5262438 |
| 211272_s_at | AF064771 | diacylglycerol kinase, alpha 80 kDa |
| 217248_s_at | AL365343 | solute carrier family 7 (cationic amino acid transporter, y+ system), member 8 |
| 201156_s_at | AF141304 | RAB5C, member RAS oncogene family |
| 211022_s_at | BC002521 | alpha thalassemia/mental retardation syndrome X-linked (RAD54 homolog, S. cerevisiae) |
| AFFX-HSAC07/X00351_5_at | AFFX-HSAC07/X00351_5 | actin, beta |
| 218931_at | NM_022449 | RAB17, member RAS oncogene family |
| 240407_at | AW450035 | Homo sapiens, clone IMAGE: 5171705, mRNA |
| 214505_s_at | AF220153 | four and a half LIM domains 1 |
| 213363_at | AW170549 | Homo sapiens, clone IMAGE: 5244869, mRNA |
| 1555724_s_at | BC010946 | transgelin |
| 230112_at | AB037820 | membrane-associated ring finger (C3HC4) 4 |
| 209136_s_at | BG390445 | ubiquitin specific peptidase 10 |
| 203047_at | NM_005990 | serine/threonine kinase 10 |
| 227137_at | N25937 | Chromosome 10 open reading frame 46 |
| 212125_at | NM_002883 | Ran GTPase activating protein 1 |
| 243409_at | AI005407 | forkhead box L1 |
| 1568646_x_at | BC038199 | zinc finger protein 208 |
| 217370_x_at | S75762 | fusion (involved in t(12; 16) in malignant liposarcoma) |
| 87100_at | AI832249 | abhydrolase domain containing 2 |
| 211016_x_at | BC002526 | heat shock 70 kDa protein 4 |
| 241661_at | AA001021 | jumonji domain containing 1C |
| 222611_s_at | AA969958 | paraspeckle component 1 |
| 210930_s_at | AF177761 | v-erb-b2 erythroblastic leukemia viral oncogene homolog 2, neuro/glioblastoma derived oncogene homolog (avian) |
| 213722_at | AW007161 | SRY (sex determining region Y)-box 2 |
| 228901_at | AI040910 | Cyclin-dependent kinase 9 (CDC2-related kinase) |

TABLE 13-continued (DEAH peptide disclosed as SEQ ID NO: 64; DEAD peptide disclosed as SEQ ID NO: 65)

| Systematic Name | Genbank | Description |
| --- | --- | --- |
| 208850_s_at | AL558479 | Thy-1 cell surface antigen |
| 212574_x_at | AC004528 | chromosome 19 open reading frame 6 |
| 204952_at | NM_014400 | LY6/PLAUR domain containing 3 |
| 204876_at | NM_014699 | zinc finger protein 646 |
| 213014_at | BG222394 | mitogen-activated protein kinase 8 interacting protein 1 |
| 219928_s_at | NM_012189 | calcium binding tyrosine-(Y)-phosphorylation regulated (fibrousheathin 2) |
| 204895_x_at | NM_004532 | mucin 4, cell surface associated |
| 208275_x_at | NM_003577 | undifferentiated embryonic cell transcription factor 1 |
| 200917_s_at | BG474541 | signal recognition particle receptor ('docking protein') |
| 213643_s_at | AK022846 | inositol polyphosphate-5-phosphatase, 75 kDa |
| 232001_at | AW193600 | hypothetical gene supported by AY007155 |
| 223828_s_at | AF222694 | lectin, galactoside-binding, soluble, 12 (galectin 12) |
| 210654_at | AF021233 | tumor necrosis factor receptor superfamily, member 10d, decoy with truncated death domain |
| 208721_s_at | BF967271 | anaphase promoting complex subunit 5 |
| 206208_at | NM_000717 | carbonic anhydrase IV |
| 1553535_a_at | NM_002883 | Ran GTPase activating protein 1 |
| 206531_at | NM_004647 | D4, zinc and double PHD fingers family 1 |
| 1563719_a_at | AK024924 | CDNA: FLJ21271 fis, clone COL01751 |
| 236731_at | BF223086 | leucine zipper protein pseudogene 1 |
| 1555337_a_at | AF307097 | zinc finger protein 317 |
| 222936_s_at | AF151904 | chromosome 1 open reading frame 121 |
| 209999_x_at | AI056051 | suppressor of cytokine signaling 1 |
| 1555730_a_at | D00682 | cofilin 1 (non-muscle) |
| 1566764_at | AL359055 | MRNA full length insert cDNA clone EUROIMAGE 2344436 |
| 215315_at | AC003682 | zinc finger protein 549 |
| 211019_s_at | D63807 | lanosterol synthase (2,3-oxidosqualene-lanosterol cyclase) |
| 226913_s_at | BF527050 | SRY (sex determining region Y)-box 8 |
| 217569_x_at | AA017093 | — |
| 231146_at | AI300541 | family with sequence similarity 24, member B |
| 208478_s_at | NM_004324 | BCL2-associated X protein |
| 210892_s_at | BC004472 | general transcription factor II, i |
| 206100_at | NM_001874 | carboxypeptidase M |
| 216926_s_at | AC003030 | KIAA0892 |
| 222511_x_at | AW140098 | Fas (TNFRSF6) associated factor 1 |
| 202662_s_at | NM_002223 | inositol 1,4,5-triphosphate receptor, type 2 |
| 1552667_a_at | NM_005489 | SH2 domain containing 3C |
| 228851_s_at | AV726322 | endosulfine alpha |
| AFFX-r2-Bs-dap-3_at | AFFX-r2-Bs-phe-3 | — |
| 206552_s_at | NM_003182 | tachykinin, precursor 1 (substance K, substance P, neurokinin 1, neurokinin 2, neuromedin L, neurokinin alpha, neuropeptide K, neuropeptide gamma) |
| 233757_x_at | AK026906 | CDNA: FLJ23253 fis, clone COL04706 |
| 213943_at | X99268 | twist homolog 1 (acrocephalosyndactyly 3; Saethre-Chotzen syndrome) (*Drosophila*) |
| 209198_s_at | BC004291 | synaptotagmin XI |
| 1553138_a_at | NM_152363 | ankyrin repeat domain 41 |
| 232915_at | AW571715 | DEAD (Asp-Glu-Ala-Asp) box polypeptide 49 |
| 1560224_at | BF327463 | AT hook containing transcription factor 1 |
| 239959_x_at | AI147520 | — |
| 211699_x_at | AF349571 | hemoglobin, alpha 1 /// hemoglobin, alpha 2 |
| 228261_at | BE045549 | mindbomb homolog 2 (*Drosophila*) |
| 206617_s_at | NM_002910 | renin binding protein |
| 207402_at | NM_003433 | zinc finger protein 132 |
| 224539_s_at | AF152474 | protocadherin alpha subfamily C, 2 |
| 240397_x_at | AI801626 | Transcribed locus |
| 208894_at | M60334 | major histocompatibility complex, class II, DR alpha |
| 229566_at | AA149250 | similar to WDNM1-like protein |
| 238742_x_at | AW302207 | Transcribed locus |
| 215236_s_at | AV721177 | phosphatidylinositol binding clathrin assembly protein |
| 210256_s_at | U78576 | phosphatidylinositol-4-phosphate 5-kinase, type I, alpha |
| 1555639_a_at | AF315633 | RNA binding motif protein 14 |
| 1566666_at | AK074225 | CDNA FLJ23645 fis, clone COL02691 |
| 211899_s_at | AF082185 | TNF receptor-associated factor 4 |
| 222387_s_at | BG476669 | vacuolar protein sorting 35 homolog (*S. cerevisiae*) |
| 1553694_a_at | NM_002645 | phosphoinositide-3-kinase, class 2, alpha polypeptide |
| 203348_s_at | BF060791 | ets variant gene 5 (ets-related molecule) |
| 213548_s_at | BG257762 | CDV3 homolog (mouse) |
| 219656_at | NM_016580 | protocadherin 12 |
| 241198_s_at | BE645435 | chromosome 11 open reading frame 70 |
| 219878_s_at | NM_015995 | Kruppel-like factor 13 |
| 1556748_x_at | AI476341 | CDNA FLJ39784 fis, clone SPLEN2002314 |
| 1554988_at | BC042592 | solute carrier family 9, member 11 |
| 227071_at | AI762558 | zinc finger protein 414 |
| 213926_s_at | AI742626 | HIV-1 Rev binding protein |
| 234971_x_at | AI521584 | phospholipase C, delta 3 |
| 219899_x_at | NM_014434 | NADPH dependent diflavin oxidoreductase 1 |
| 215774_s_at | AV650470 | — |

TABLE 13-continued (DEAH peptide disclosed as SEQ ID NO: 64; DEAD peptide disclosed as SEQ ID NO: 65)

| Systematic Name | Genbank | Description |
| --- | --- | --- |
| 229339_at | AI093327 | Transcribed locus |
| 238013_at | BF347859 | pleckstrin homology domain containing, family A (phosphoinositide binding specific) member 2 |
| 214000_s_at | AI744627 | Regulator of G-protein signalling 10 |
| 203729_at | NM_001425 | epithelial membrane protein 3 |
| 203085_s_at | BC000125 | transforming growth factor, beta 1 |
| 1558689_a_at | BG701300 | hypothetical gene supported by BC030123 |
| 211668_s_at | K03226 | plasminogen activator, urokinase |
| 205457_at | NM_024294 | chromosome 6 open reading frame 106 |
| 202639_s_at | AI689052 | RAN binding protein 3 |
| 211527_x_at | M27281 | vascular endothelial growth factor A |
| 207118_s_at | NM_004659 | matrix metallopeptidase 23B /// matrix metallopeptidase 23A (pseudogene) |
| 204560_at | NM_004117 | FK506 binding protein 5 |
| 232591_s_at | AK022883 | transmembrane protein 30A |
| 236158_at | R42281 | Similar to KIAA1875 protein |
| 230257_s_at | AI264325 | chromosome 1 open reading frame 19 |
| 230629_s_at | AI809582 | E1A binding protein p400 |
| 238969_at | BF512162 | chromosome 3 open reading frame 55 |
| 1569895_at | BC016994 | Homo sapiens, clone IMAGE: 4401848, mRNA |
| 1554544_a_at | L18865 | myelin basic protein |
| 229901_at | AI056483 | zinc finger protein 488 |
| 211051_s_at | BC006363 | exostoses (multiple)-like 3 |
| 236657_at | AW014647 | Full length insert cDNA YI37C01 |
| 202017_at | NM_000120 | epoxide hydrolase 1, microsomal (xenobiotic) |
| 229746_x_at | BF439451 | Homo sapiens, clone IMAGE: 3885733, mRNA |
| 205382_s_at | NM_001928 | complement factor D (adipsin) |
| 222458_s_at | AI205764 | chromosome 1 open reading frame 108 |
| 1553565_s_at | NM_012137 | dimethylarginine dimethylaminohydrolase 1 |
| 230809_at | R45446 | Transcribed locus |
| 222363_at | AW979018 | Transcribed locus |
| 217767_at | NM_000064 | similar to Complement C3 precursor |
| 221279_at | NM_018972 | ganglioside-induced differentiation-associated protein 1 |
| 211087_x_at | Z25432 | mitogen-activated protein kinase 14 |
| 204904_at | NM_002463 | myxovirus (influenza virus) resistance 2 (mouse) |
| 225245_x_at | BG386566 | H2A histone family, member J |
| 243319_at | AI274981 | Transcribed locus |
| 216252_x_at | Z70519 | Fas (TNF receptor superfamily, member 6) |
| 215891_s_at | X61094 | GM2 ganglioside activator |
| 238493_at | AI559570 | zinc finger protein 506 |
| 224169_at | AF257210 | neuropeptide FF receptor 2 |
| 232343_at | AK022200 | CDNA FLJ12138 fis, clone MAMMA1000331 |
| 1569039_s_at | BC029855 | zinc finger protein 677 |
| 201971_s_at | NM_001690 | ATPase, H+ transporting, lysosomal 70 kDa, V1 subunit A |
| 211564_s_at | BC003096 | PDZ and LIM domain 4 |
| 200869_at | NM_000980 | ribosomal protein L18a /// similar to ribosomal protein L18a; 60S ribosomal protein L18a |
| 233297_s_at | AL139377 | hypothetical protein LOC728591 |
| 219058_x_at | NM_022164 | tubulointerstitial nephritis antigen-like 1 |
| 242762_s_at | AA372349 | KIAA1946 |
| 1552611_a_at | AL555086 | Janus kinase 1 (a protein tyrosine kinase) |
| 1554660_a_at | BC036200 | chromosome 1 open reading frame 71 |
| 236771_at | AW511485 | chromosome 6 open reading frame 159 |
| 221943_x_at | AW303136 | Ribosomal protein L38 |
| 221665_s_at | BC004907 | EPS8-like 1 |
| 205391_x_at | M28880 | ankyrin 1, erythrocytic |
| 207678_s_at | NM_007017 | SRY (sex determining region Y)-box 30 |
| 215728_s_at | AL031848 | acyl-CoA thioesterase 7 |
| 224346_at | AF116671 | — |
| 205822_s_at | NM_002130 | 3-hydroxy-3-methylglutaryl-Coenzyme A synthase 1 (soluble) |
| 241084_x_at | BF062339 | dynein, cytoplasmic 1, heavy chain 1 |
| 1554757_a_at | AF273055 | inositol polyphosphate-5-phosphatase, 40 kDa |
| 222542_x_at | BF724826 | chaperone, ABC1 activity of bc1 complex homolog (S. pombe) |
| 206749_at | NM_001764 | CD1b molecule |
| 219558_at | NM_024524 | ATPase type 13A3 |
| 240703_s_at | AW591969 | hect (homologous to the E6-AP (UBE3A) carboxyl terminus) domain and RCC1 (CHC1)-like domain (RLD) 1 |
| 231805_at | AL563031 | prolactin releasing hormone receptor |
| 232566_at | AK026258 | nucleolar protein family 6 (RNA-associated) |
| 228683_s_at | AI925361 | potassium channel tetramerisation domain containing 15 |
| 235271_s_at | BG027325 | zinc finger protein 397 |
| 214300_s_at | AI676092 | topoisomerase (DNA) III alpha |
| 220472_at | NM_014150 | zinc finger, CCHC domain containing 4 |
| 214992_s_at | AD000092 | deoxyribonuclease II, lysosomal |
| 236491_at | AI813346 | BCL2-like 10 (apoptosis facilitator) |
| 208474_at | NM_021195 | claudin 6 |
| 76897_s_at | AA628140 | FK506 binding protein 15, 133 kDa |

TABLE 13-continued (DEAH peptide disclosed as SEQ ID NO: 64; DEAD peptide disclosed as SEQ ID NO: 65)

| Systematic Name | Genbank | Description |
| --- | --- | --- |
| 238461_at | AA228031 | eukaryotic translation initiation factor 4E family member 3 |
| 223567_at | AB022433 | sema domain, transmembrane domain (TM), and cytoplasmic domain, (semaphorin) 6B |
| 214975_s_at | AK001816 | myotubularin related protein 1 |
| 217399_s_at | AF032887 | forkhead box O3 |
| 208879_x_at | BG469030 | PRP6 pre-mRNA processing factor 6 homolog (S. cerevisiae) |
| 1558662_s_at | BG200452 | B-cell scaffold protein with ankyrin repeats 1 |
| 1552367_a_at | AF276507 | scinderin |
| 201367_s_at | AI356398 | zinc finger protein 36, C3H type-like 2 |
| 215719_x_at | X83493 | Fas (TNF receptor superfamily, member 6) |
| 200601_at | U48734 | actinin, alpha 4 |
| 210620_s_at | BC000212 | general transcription factor IIIC, polypeptide 2, beta 110 kDa |
| 1554321_a_at | BC018471 | NFS1 nitrogen fixation 1 homolog (S. cerevisiae) |
| 210932_s_at | AF293342 | ring finger protein (C3H2C3 type) 6 |
| 211020_at | L19659 | glucosaminyl (N-acetyl) transferase 2, I-branching enzyme (I blood group) |
| 231698_at | AV661152 | hypothetical LOC647115 |
| 216205_s_at | AK021947 | mitofusin 2 |
| 227316_at | AI761798 | CSRP2 binding protein |
| 1555814_a_at | AF498970 | ras homolog gene family, member A |
| 235728_at | AA845646 | zinc finger protein 3 homolog (mouse) |
| 238542_at | AA831769 | UL16 binding protein 2 |
| 238795_at | AA424537 | chromosome 10 open reading frame 18 |
| 213713_s_at | R48779 | hypothetical protein BC008326 |
| 219703_at | NM_018365 | meiosis-specific nuclear structural 1 |
| 205186_at | NM_003462 | dynein, axonemal, light intermediate chain 1 |
| 225294_s_at | BG340967 | trafficking protein particle complex 1 |
| 224505_s_at | BC006355 | phospholipase C, delta 4 |
| 203626_s_at | NM_005983 | S-phase kinase-associated protein 2 (p45) |
| 217448_s_at | AL117508 | TOX high mobility group box family member 4 /// similar to Epidermal Langerhans cell protein LCP1 |
| 237206_at | AI452798 | myocardin |
| 210413_x_at | U19557 | serpin peptidase inhibitor, clade B (ovalbumin), member 4 |
| 214190_x_at | AI799984 | golgi associated, gamma adaptin ear containing, ARF binding protein 2 |
| 205924_at | BC005035 | RAB3B, member RAS oncogene family |
| 242660_at | AA846789 | chromosome 10 open reading frame 112 |
| 1555197_a_at | AY039243 | chromosome 21 open reading frame 58 |
| 225369_at | AL573851 | endothelial cell adhesion molecule |
| 238025_at | AA706818 | mixed lineage kinase domain-like |
| 235358_at | AW961205 | hypothetical protein LOC728485 |
| 1554628_at | BC028974 | zinc finger protein 57 |
| 1565347_s_at | AY034078 | transcription factor binding to IGHM enhancer 3 |
| 219168_s_at | NM_017701 | proline rich 5 (renal) |
| 212154_at | AI380298 | syndecan 2 |
| 1569486_at | BC035176 | CDNA clone IMAGE: 5266012 |
| 206847_s_at | AF026397 | homeobox A7 |
| 218260_at | NM_024050 | chromosome 19 open reading frame 58 |
| 1554466_a_at | BC007207 | chromosome 16 open reading frame 13 |
| 241611_s_at | BE675600 | fibronectin type III domain containing 3A |
| 215876_at | AK022254 | CDNA FLJ12192 fis, clone MAMMA1000851 |
| 200756_x_at | U67280 | calumenin |
| 237211_x_at | AA860341 | MORN repeat containing 3 |
| 216501_at | U25801 | Vac14 homolog (S. cerevisiae) |
| 207664_at | NM_001464 | ADAM metallopeptidase domain 2 (fertilin beta) |
| 217465_at | AK001291 | NCK-associated protein 1 |
| 235136_at | BF337528 | ORM1-like 3 (S. cerevisiae) |
| 201171_at | NM_003945 | ATPase, H+ transporting, lysosomal 9 kDa, V0 subunit e1 |
| 203892_at | NM_006103 | WAP four-disulfide core domain 2 |
| 218810_at | NM_025079 | zinc finger CCCH-type containing 12A |
| 241574_s_at | H93038 | Insulin-like growth factor 2 mRNA binding protein 1 |
| 211811_s_at | AF152484 | protocadherin alpha 6 |
| 210457_x_at | AF176039 | high mobility group AT-hook 1 |
| 208430_s_at | NM_001390 | dystrobrevin, alpha |
| AFFX-HUMISGF3A/M97935_5_at | AFFX-HUMISGF3A/M97935_5 | signal transducer and activator of transcription 1, 91 kDa |
| 223631_s_at | AF213678 | chromosome 19 open reading frame 33 |
| 1555733_s_at | AF393369 | adaptor-related protein complex 1, sigma 3 subunit |
| 209208_at | AF059752 | mannose-P-dolichol utilization defect 1 |
| 206917_at | NM_006572 | guanine nucleotide binding protein (G protein), alpha 13 |
| 213160_at | D86964 | dedicator of cytokinesis 2 |
| 236058_at | AA573775 | chromosome 1 open reading frame 172 |
| 217270_s_at | AC005393 | dual-specificity tyrosine-(Y)-phosphorylation regulated kinase 1B |
| 1558015_s_at | BU175810 | ARP2 actin-related protein 2 homolog (yeast) |
| 227971_at | AI653107 | Nik related kinase |
| 204284_at | N26005 | protein phosphatase 1, regulatory (inhibitor) subunit 3C |
| 210421_s_at | AB014602 | solute carrier family 24 (sodium/potassium/calcium exchanger), member 1 |
| 220892_s_at | NM_021154 | phosphoserine aminotransferase 1 |

TABLE 13-continued (DEAH peptide disclosed as SEQ ID NO: 64; DEAD peptide disclosed as SEQ ID NO: 65)

| Systematic Name | Genbank | Description |
|---|---|---|
| 221762_s_at | AL162458 | chromosome 20 open reading frame 67 |
| 230926_s_at | AW452022 | outer dense fiber of sperm tails 2-like |
| 210079_x_at | U16953 | potassium voltage-gated channel, shaker-related subfamily, beta member 1 |
| 202859_x_at | NM_000584 | interleukin 8 |
| 37549_g_at | U87408 | Bardet-Biedl syndrome 9 |
| 224321_at | AB004064 | transmembrane protein with EGF-like and two follistatin-like domains 2 |
| 210828_s_at | AF001307 | aryl hydrocarbon receptor nuclear translocator |
| 222406_s_at | AV738970 | proline-rich nuclear receptor coactivator 2 |
| 222419_x_at | AW205983 | ubiquitin-conjugating enzyme E2H (UBC8 homolog, yeast) |
| 207686_s_at | NM_001228 | caspase 8, apoptosis-related cysteine peptidase |
| 213597_s_at | BF002474 | CTD (carboxy-terminal domain, RNA polymerase II, polypeptide A) small phosphatase-like |
| 202226_s_at | NM_016823 | v-crk sarcoma virus CT10 oncogene homolog (avian) |
| 221048_x_at | NM_017941 | chromosome 17 open reading frame 80 |
| 1553191_at | NM_020388 | dystonin |
| 213087_s_at | BF690020 | CDNA clone IMAGE: 4838699 |
| 1554327_a_at | AF328554 | calcium activated nucleotidase 1 |
| 233298_at | AL139377 | spermatogenesis and oogenesis specific basic helix-loop-helix 2 /// hypothetical protein LOC728591 |
| 223393_s_at | AL136805 | teashirt zinc finger homeobox 3 |
| 240983_a_at | AW292273 | cysteinyl-tRNA synthetase |
| 226905_at | BG036514 | family with sequence similarity 101, member B |
| 212797_at | BE742268 | sortilin 1 |
| 209719_x_at | U19556 | serpin peptidase inhibitor, clade B (ovalbumin), member 3 |
| 221364_at | NM_001510 | glutamate receptor, ionotropic, delta 2 |
| 1552641_s_at | NM_031921 | ATPase family, AAA domain containing 3A /// ATPase family, AAA domain containing 3B /// similar to ATPase family, AAA domain containing 3A /// similar to AAA-ATPase TOB3 |
| 222501_s_at | BE674760 | replication initiator 1 |
| 1552477_a_at | BC014852 | interferon regulatory factor 6 |
| 222711_s_at | AI761828 | rhomboid 5 homolog 1 (*Drosophila*) |
| 1552528_at | NM_058189 | chromosome 21 open reading frame 69 |
| 232498_at | AK023386 | hypothetical protein KIAA1833 |
| 226876_at | AI961778 | family with sequence similarity 101, member B |
| 230747_s_at | AA406435 | Chromosome 18 open reading frame 17 |
| 201979_s_at | NM_006247 | protein phosphatase 5, catalytic subunit |
| 210869_s_at | M29277 | melanoma cell adhesion molecule |
| 237911_at | BF057809 | Transcribed locus |
| 215037_s_at | U72398 | BCL2-like 1 |
| AFFX-DapX-5_at | AFFX-DapX-5 | — |
| 217211_at | D50604 | similar to cytoplasmic beta-actin |
| 214014_at | W81196 | CDC42 effector protein (Rho GTPase binding) 2 |
| 230517_at | AI416964 | similar to GLI-Kruppel family member HKR1 |
| 1563312_at | BI603681 | CDNA clone IMAGE: 5302682 |
| 206024_at | NM_002150 | 4-hydroxyphenylpyruvate dioxygenase |
| 1552610_a_at | NM_002227 | Janus kinase 1 (a protein tyrosine kinase) |
| 224279_s_at | AF295039 | calcium binding tyrosine-(Y)-phosphorylation regulated (fibrousheathin 2) |
| 220426_at | NM_024059 | chromosome 20 open reading frame 195 |
| 1553105_s_at | NM_001943 | desmoglein 2 |
| 234688_x_at | AF141344 | centrobin, centrosomal BRCA2 interacting protein |
| 210022_at | BC004952 | polycomb group ring finger 1 |
| 226306_at | BF984592 | chromosome 6 open reading frame 1 |
| 203771_s_at | AA740186 | biliverdin reductase A |
| 201465_s_at | BC002646 | jun oncogene |
| 216549_s_at | AL096712 | TBC1 domain family, member 22B |
| 1553229_at | NM_152412 | zinc finger protein 572 |
| 205065_at | AU130282 | — |
| 224301_x_at | BC003602 | H2A histone family, member J |
| 223616_at | BC005368 | zinc finger protein 649 |
| 209629_s_at | AF201942 | nuclear transport factor 2-like export factor 2 |
| 224037_at | AF132198 | — |
| 91826_at | AI219073 | EPS8-like 1 |
| 227841_at | BG260181 | Cementum protein 1 |
| 216641_s_at | U58994 | ladinin 1 |
| 217300_at | U80771 | — |
| 1552649_a_at | NM_057178 | ring finger and FYVE-like domain containing 1 |
| 221220_s_at | NM_017988 | SCY1-like 2 (*S. cerevisiae*) |
| 229296_at | AI659477 | CDNA FLJ34873 fis, clone NT2NE2014950 |
| 212003_at | BG171020 | chromosome 1 open reading frame 144 |
| 218922_s_at | NM_024552 | LAG1 homolog, ceramide synthase 4 |
| 237872_at | AI026919 | Transcribed locus |
| 209373_at | BC003179 | mal, T-cell differentiation protein-like |
| 224795_x_at | AW575927 | immunoglobulin kappa constant /// immunoglobulin kappa variable 1-5 /// immunoglobulin kappa variable 2-24 |
| 203065_s_at | NM_001753 | caveolin 1, caveolae protein, 22 kDa |
| 239623_at | N93197 | hypothetical gene supported by AK126569 |

TABLE 13-continued (DEAH peptide disclosed as SEQ ID NO: 64; DEAD peptide disclosed as SEQ ID NO: 65)

| Systematic Name | Genbank | Description |
| --- | --- | --- |
| 231243_s_at | R93946 | basic helix-loop-helix domain containing, class B, 3 |
| 234730_s_at | AP001743 | receptor-interacting serine-threonine kinase 4 |
| 228881_at | N30347 | presenilin associated, rhomboid-like |
| 231723_at | NM_013346 | sorting nexin 12 |
| 205462_s_at | NM_002149 | hippocalcin-like 1 |
| 200628_s_at | M61715 | tryptophanyl-tRNA synthetase |
| 230404_at | AI418538 | — |
| 1563809_a_at | AK094768 | MCF.2 cell line derived transforming sequence-like |
| 204470_at | NM_001511 | chemokine (C—X—C motif) ligand 1 (melanoma growth stimulating activity, alpha) |
| 205210_at | NM_004257 | transforming growth factor, beta receptor associated protein 1 |
| 228634_s_at | BF195718 | Cold shock domain protein A |
| 210971_s_at | AB000815 | aryl hydrocarbon receptor nuclear translocator-like |
| 243358_at | BF347362 | insulin-like growth factor 1 receptor |
| 1561039_a_at | BC039609 | zinc finger protein 81 |
| 222509_s_at | BG490634 | zinc finger protein 672 |
| 1552717_s_at | NM_153243 | centrosomal protein 170 kDa /// centrosomal protein 170 kDa-like |
| 221754_s_at | AI341234 | coronin, actin binding protein, 1B |
| 234920_at | AK022466 | Zinc finger protein 7 |
| 242571_at | AW962020 | RALBP1 associated Eps domain containing 2 |
| 222085_at | AW452357 | Hypothetical gene supported by AK075564; BC060873 |
| 1553697_at | NM_145257 | chromosome 1 open reading frame 96 |
| 1555830_s_at | BC001224 | family with sequence similarity 62 (C2 domain containing) member B |
| 217010_s_at | AF277724 | cell division cycle 25 homolog C (*S. pombe*) |
| 214845_s_at | AF257659 | calumenin |
| 218537_at | NM_017885 | host cell factor C1 regulator 1 (XPO1 dependent) |
| 202790_at | NM_001307 | claudin 7 |
| 1559528_at | BC040652 | Polycomb group ring finger 3 |
| 1567105_at | AF362887 | — |
| 211772_x_at | BC006114 | cholinergic receptor, nicotinic, alpha 3 |
| 219270_at | NM_024111 | ChaC, cation transport regulator homolog 1 (*E. coli*) |
| 207087_x_at | NM_020478 | ankyrin 1, erythrocytic |
| 213714_at | AI040163 | calcium channel, voltage-dependent, beta 2 subunit |
| 215649_s_at | AF217536 | mevalonate kinase (mevalonic aciduria) |
| 204638_at | NM_001611 | acid phosphatase 5, tartrate resistant |
| 228208_x_at | AL134573 | Hypothetical LOC645944 |
| 239664_at | H18857 | Transcribed locus |
| 215585_at | AK024081 | KIAA0174 |
| 211613_s_at | U79250 | glycerol-3-phosphate dehydrogenase 2 (mitochondrial) |
| 214903_at | AF070580 | synaptotagmin II |
| 1566472_s_at | AK098125 | retinol saturase (all-trans-retinol 13,14-reductase) |
| 234155_at | AK024928 | CDNA: FLJ21275 fis, clone COL01827 |
| 243952_at | BF000009 | TPTE pseudogene |
| 210994_x_at | AF230398 | tripartite motif-containing 23 |
| 205810_s_at | NM_003941 | Wiskott-Aldrich syndrome-like |
| 210455_at | AF050198 | chromosome 10 open reading frame 28 |
| 211672_s_at | AF019888 | actin related protein 2/3 complex, subunit 4, 20 kDa |
| 233827_s_at | AK024072 | suppressor of Ty 16 homolog (*S. cerevisiae*) |
| 201621_at | NM_005380 | neuroblastoma, suppression of tumorigenicity 1 |
| 1560020_at | BC043583 | DnaJ (Hsp40) homolog, subfamily C, member 13 |
| 202290_at | NM_014891 | PDGFA associated protein 1 |
| 216271_x_at | AC004794 | synapse defective 1, Rho GTPase, homolog 1 (*C. elegans*) |
| 210933_s_at | BC004908 | fascin homolog 1, actin-bundling protein (Strongylocentrotus purpuratus) |
| 1555569_a_at | BC042482 | potassium channel tetramerisation domain containing 7 |
| 221889_at | AW026481 | potassium channel tetramerisation domain containing 13 |
| 37547_at | U85995 | Bardet-Biedl syndrome 9 |
| 205117_at | X59065 | fibroblast growth factor 1 (acidic) |
| 201122_x_at | BC000751 | eukaryotic translation initiation factor 5A |
| 233638_s_at | AK026430 | protein O-linked mannose beta1,2-N-acetylglucosaminyltransferase |
| 221035_s_at | NM_031272 | testis expressed 14 |
| 223318_s_at | BC004393 | alkB, alkylation repair homolog 7 (*E. coli*) |
| 1555609_a_at | AF355465 | zinc finger, matrin type 3 |
| 232675_s_at | BG149850 | uridine-cytidine kinase 1-like 1 |
| 1555220_a_at | AB040820 | aldo-keto reductase family 1, member C-like 2 |
| 220246_at | NM_020397 | calcium/calmodulin-dependent protein kinase ID |
| 206943_at | NM_004612 | transforming growth factor, beta receptor I (activin A receptor type II-like kinase, 53 kDa) |
| 202779_s_at | NM_014501 | ubiquitin-conjugating enzyme E2S /// similar to Ubiquitin-conjugating enzyme E2S (Ubiquitin-conjugating enzyme E2-24 kDa) (Ubiquitin-protein ligase) (Ubiquitin carrier protein) (E2-EPF5) |
| 206336_at | NM_002993 | chemokine (C—X—C motif) ligand 6 (granulocyte chemotactic protein 2) |
| 210405_x_at | AF153687 | tumor necrosis factor receptor superfamily, member 10b |
| 1554339_a_at | BC038953 | component of oligomeric golgi complex 3 |
| 209062_x_at | AF010227 | nuclear receptor coactivator 3 |
| 234992_x_at | BG170335 | epithelial cell transforming sequence 2 oncogene |
| 1557637_at | BC038734 | CDNA clone IMAGE: 5267718 |
| 217711_at | BF594294 | TEK tyrosine kinase, endothelial (venous malformations, multiple cutaneous and |

TABLE 13-continued (DEAH peptide disclosed as SEQ ID NO: 64; DEAD peptide disclosed as SEQ ID NO: 65)

| Systematic Name | Genbank | Description |
|---|---|---|
| | | mucosal) |
| 1553351_at | NM_130901 | OTU domain containing 7A |
| 61734_at | AI797684 | reticulocalbin 3, EF-hand calcium binding domain |
| 203994_s_at | U84569 | chromosome 21 open reading frame 2 |
| 1565162_s_at | D16947 | microsomal glutathione S-transferase 1 |
| 231011_at | AI339785 | La ribonucleoprotein domain family, member 2 |
| 206209_s_at | NM_000717 | carbonic anhydrase IV |
| 209722_s_at | L40378 | serpin peptidase inhibitor, clade B (ovalbumin), member 9 |
| 214369_at | AI688812 | RAS guanyl releasing protein 2 (calcium and DAG-regulated) |
| 205390_s_at | NM_000037 | ankyrin 1, erythrocytic |
| 204188_s_at | M57707 | retinoic acid receptor, gamma |
| 232132_at | AB043635 | par-6 partitioning defective 6 homolog gamma (*C. elegans*) |
| 1552389_at | NM_173549 | chromosome 8 open reading frame 47 |
| 211911_x_at | L07950 | major histocompatibility complex, class I, B |
| 231402_at | AI830201 | Transcribed locus, strongly similar to XP_531081.2 hypothetical protein [Pantroglodytes] |
| 215913_s_at | AK023668 | GULP, engulfment adaptor PTB domain containing 1 |
| 213426_s_at | AA150110 | Caveolin 2 |
| 233543_s_at | AK021582 | coiled-coil domain containing 98 |
| 201559_s_at | AF109196 | chloride intracellular channel 4 |
| 241168_at | AV651242 | Transcribed locus |
| 216710_x_at | AL359578 | zinc finger protein 287 |
| 1555006_at | BC036233 | WD repeat domain 66 |
| 207453_s_at | NM_012266 | DnaJ (Hsp40) homolog, subfamily B, member 5 |
| 217234_s_at | AF199015 | villin 2 (ezrin) |
| 214446_at | NM_012081 | elongation factor, RNA polymerase II, 2 |
| 209372_x_at | BF971587 | tubulin, beta 2A /// tubulin, beta 2B |
| 218261_at | NM_005498 | adaptor-related protein complex 1, mu 2 subunit |
| 217445_s_at | AF008655 | phosphoribosylglycinamide formyltransferase, phosphoribosylglycinamide synthetase, phosphoribosylaminoimidazole synthetase |
| 205595_at | NM_001944 | desmoglein 3 (pemphigus vulgaris antigen) |
| 233669_s_at | AA868267 | tripartite motif-containing 54 |
| 1559028_at | BC037172 | chromosome 21 open reading frame 15 |
| 1561330_at | BC039098 | desmoglein 4 |
| 1562080_at | AK057351 | CDNA FLJ32789 fis, clone TESTI2002326 |
| 234976_x_at | BG324504 | Solute carrier family 4, sodium bicarbonate cotransporter, member 5 |
| 234085_at | AL139377 | spermatogenesis and oogenesis specific basic helix-loop-helix 2 /// hypothetical protein LOC728591 |
| 208067_x_at | NM_007125 | ubiquitously transcribed tetratricopeptide repeat gene, Y-linked |
| 231957_s_at | AC005594 | dipeptidyl-peptidase 9 |
| 1562244_at | AL833487 | MRNA; cDNA DKFZp686H1629 (from clone DKFZp686H1629) |
| 227488_at | AV728999 | hypothetical protein MGC16121 |
| 239407_at | AI793248 | CDNA clone IMAGE: 4837199 |
| 207540_s_at | NM_003177 | spleen tyrosine kinase |
| 1557984_s_at | BI464019 | RNA polymerase II associated protein 3 |
| 208608_s_at | NM_021021 | syntrophin, beta 1 (dystrophin-associated protein A1, 59 kDa, basic component 1) |
| 1554795_a_at | BC019895 | filamin binding LIM protein 1 |
| 209950_s_at | BC004300 | villin-like |
| 1558809_s_at | AK094324 | hypothetical protein LOC284408 |
| 225333_at | AI218383 | zinc finger protein 496 |
| 204522_at | NM_005510 | dom-3 homolog Z (*C. elegans*) |
| 218154_at | NM_024736 | gasdermin domain containing 1 |
| 201060_x_at | AI537887 | stomatin |
| 201012_at | NM_000700 | annexin A1 |
| 220889_s_at | NM_020178 | carbonic anhydrase X |
| 217729_s_at | NM_001130 | amino-terminal enhancer of split |
| 211187_at | AF118079 | — |
| 231396_s_at | AA776721 | family with sequence similarity 126, member A |
| AFFX-LysX-M_at | AFFX-LysX-5 | — |
| 222678_at | BF057821 | DCN1, defective in cullin neddylation 1, domain containing 1 (*S. cerevisiae*) |
| 220234_at | NM_004056 | carbonic anhydrase VIII |
| 1553962_s_at | BI668074 | ras homolog gene family, member B |
| 207950_s_at | NM_001149 | ankyrin 3, node of Ranvier (ankyrin G) |
| 221981_at | AA702154 | WD repeat domain 59 |
| 1568593_a_at | CA431328 | nudix (nucleoside diphosphate linked moiety X)-type motif 16 pseudogene |
| 223321_s_at | AF312678 | fibroblast growth factor receptor-like 1 |
| 206042_x_at | NM_022804 | small nuclear ribonucleoprotein polypeptide N /// SNRPN upstream reading frame |
| 210334_x_at | AB028869 | baculoviral IAP repeat-containing 5 (survivin) |
| 216591_s_at | AF080579 | succinate dehydrogenase complex, subunit C, integral membrane protein, 15 kDa /// hCG1776980 |
| 210206_s_at | U33833 | DEAD/H (Asp-Glu-Ala-Asp/His) box polypeptide 11 (CHL1-like helicase homolog, *S. cerevisiae*) |
| 226786_at | BF507952 | regulatory factor X, 1 (influences HLA class II expression) |
| 211561_x_at | L35253 | mitogen-activated protein kinase 14 |
| 211796_s_at | AF043179 | T cell receptor beta variable 19 /// T cell receptor beta variable 7-2 /// T cell receptor beta variable 5-4 /// T cell receptor beta variable 3-1 /// T cell receptor beta constant 1 |
| 216493_s_at | AL023775 | insulin-like growth factor 2 mRNA binding protein 3 /// similar to insulin-like growth factor 2 mRNA binding protein 3 /// similar to IGF-II mRNA-binding protein 3 |

TABLE 13-continued (DEAH peptide disclosed as SEQ ID NO: 64; DEAD peptide disclosed as SEQ ID NO: 65)

| Systematic Name | Genbank | Description |
| --- | --- | --- |
| 230309_at | BE876610 | Transcribed locus |
| 204806_x_at | NM_018950 | major histocompatibility complex, class I, F |
| 205369_x_at | J03208 | dihydrolipoamide branched chain transacylase E2 |
| 1556165_at | AK057525 | CDNA FLJ32963 fis, clone TESTI2008405 |
| 215047_at | AL080170 | tripartite motif-containing 58 |
| 225454_at | AW248770 | coiled-coil domain containing 124 |
| 1552480_s_at | NM_080923 | protein tyrosine phosphatase, receptor type, C |
| 205388_at | NM_003279 | troponin C type 2 (fast) |
| 218510_x_at | AI816291 | family with sequence similarity 134, member B |
| 1553685_s_at | NM_138473 | Sp1 transcription factor |
| 228672_at | AI971618 | inhibitor of growth family, member 5 |
| 205377_s_at | AI190022 | acetylcholinesterase (Yt blood group) |
| 230633_at | AI285730 | transmembrane protein 102 |
| 207704_s_at | NM_003644 | growth arrest-specific 7 |
| 215668_s_at | AJ011414 | plexin B1 |
| 212107_s_at | BE561014 | DEAH (Asp-Glu-Ala-His) box polypeptide 9 |
| 237282_s_at | AW137676 | A kinase (PRKA) anchor protein 14 |
| 220285_at | NM_016014 | family with sequence similarity 108, member B1 |
| 207979_s_at | NM_004931 | CD8b molecule |
| 226937_at | BF110844 | Cardiolipin synthase 1 |
| 226051_at | BF973568 | selenoprotein M |
| 212272_at | AA813260 | lipin 1 |
| 229881_at | R41200 | Kruppel-like factor 12 |
| 217524_x_at | AA018923 | Transcribed locus |
| 1559409_a_at | BE893129 | KIAA1345 protein |
| 238480_at | AI871745 | Chromosome 18 open reading frame 50 |
| 1553042_a_at | NM_032721 | T-cell activation NFKB-like protein |
| 221418_s_at | NM_005481 | mediator complex subunit 16 |
| 202465_at | NM_002593 | procollagen C-endopeptidase enhancer |
| 231004_s_at | BE219961 | H1 histone family, member X |
| 242552_x_at | AW274047 | zinc finger, BED-type containing 5 |
| 238699_s_at | AI659225 | calcium/calmodulin-dependent serine protein kinase (MAGUK family) |
| 242162_at | AA904430 | WD repeat domain 69 |
| 207379_at | NM_005711 | EGF-like repeats and discoidin I-like domains 3 |
| 211513_s_at | AF172449 | opioid growth factor receptor |
| 216981_x_at | X60502 | sialophorin (leukosialin, CD43) |
| 243938_x_at | AI872645 | dynein, axonemal, heavy chain 5 |
| 211027_s_at | BC006231 | inhibitor of kappa light polypeptide gene enhancer in B-cells, kinase beta |
| 231354_at | AW510748 | hypothetical LOC780529 |
| 232984_at | AL137259 | hydrocephalus inducing homolog (mouse) |
| 1554464_a_at | BC008745 | cartilage associated protein |
| 223661_at | AF130080 | — |
| 224282_s_at | AB040138 | 1-acylglycerol-3-phosphate O-acyltransferase 3 |
| 214520_at | NM_005251 | forkhead box C2 (MFH-1, mesenchyme forkhead 1) |
| 1569076_a_at | BE791720 | FLJ16287 protein |
| 210585_s_at | AF007748 | transportin 2 (importin 3, karyopherin beta 2b) |
| 211599_x_at | U19348 | met proto-oncogene (hepatocyte growth factor receptor) |
| 221051_s_at | NM_014446 | integrin beta 1 binding protein 3 |
| 217246_s_at | L22650 | diaphanous homolog 2 (*Drosophila*) |
| 221623_at | AF229053 | brevican |
| 238420_at | AV721958 | CDNA clone IMAGE: 5263531 |
| 1558643_s_at | AA297258 | EGF-like repeats and discoidin I-like domains 3 |
| 211266_s_at | U35399 | G protein-coupled receptor 4 |
| 208851_s_at | AL161958 | Thy-1 cell surface antigen |
| 220102_at | NM_023067 | forkhead box L2 |
| 214878_at | AU118165 | zinc finger protein 37A /// zinc finger protein 37B |
| 204480_s_at | NM_024112 | chromosome 9 open reading frame 16 |
| 1558247_s_at | BC021210 | hypothetical protein BC018697 |
| 206696_at | NM_000273 | G protein-coupled receptor 143 |
| 1560316_s_at | N32168 | glucocorticoid induced transcript 1 |
| 203990_s_at | AI140752 | ubiquitously transcribed tetratricopeptide repeat, X chromosome |
| 221638_s_at | AF008937 | syntaxin 16 |
| 230146_s_at | BF111850 | frequenin homolog (*Drosophila*) |
| 231151_at | AL122010 | discs, large (*Drosophila*) homolog-associated protein 3 |
| 233767_at | AU148706 | CDNA FLJ12557 fis, clone NT2RM4000783 |
| 211681_s_at | AF116705 | PDZ and LIM domain 5 |
| 225088_at | BG546917 | chromosome 16 open reading frame 63 |
| 203234_at | NM_003364 | uridine phosphorylase 1 |
| 202028_s_at | BC000603 | ribosomal protein L38 |
| 200954_at | NM_001694 | ATPase, H+ transporting, lysosomal 16 kDa, V0 subunit c |
| 211317_s_at | AF041461 | CASP8 and FADD-like apoptosis regulator |
| 208729_x_at | D83043 | major histocompatibility complex, class I, B |
| 206486_at | NM_002286 | lymphocyte-activation gene 3 |
| 1558093_s_at | BI832461 | matrin 3 /// similar to Matrin-3 (Nuclear scaffold protein P130/MAT3) |
| 204149_s_at | NM_000850 | glutathione S-transferase M4 |
| 1555942_a_at | AK091113 | NPC-A-5 |

TABLE 13-continued (DEAH peptide disclosed as SEQ ID NO: 64; DEAD peptide disclosed as SEQ ID NO: 65)

| Systematic Name | Genbank | Description |
|---|---|---|
| 1555202_a_at | BC010136 | hypothetical protein FLJ10656 |
| 231721_at | AF356518 | junctional adhesion molecule 3 |
| 224127_at | AF116660 | — |
| 224241_s_at | BC002350 | — |
| 216788_at | AK025564 | CDNA: FLJ21911 fis, clone HEP03855 |
| 228371_s_at | BF196007 | — |
| 221440_s_at | NM_006606 | retinoblastoma binding protein 9 |
| 220585_at | NM_025130 | hexokinase domain containing 1 |
| 229439_s_at | AI830823 | RNA-binding protein |
| 206026_s_at | NM_007115 | tumor necrosis factor, alpha-induced protein 6 |
| 209086_x_at | BE964361 | melanoma cell adhesion molecule |
| 229440_at | AI830823 | RNA-binding protein |
| 221875_x_at | AW514210 | major histocompatibility complex, class I, F |
| 1557918_s_at | AU131482 | solute carrier family 16, member 1 (monocarboxylic acid transporter 1) |
| 244735_at | AI377758 | coiled-coil domain containing 54 |
| 227358_at | Z39566 | zinc finger and BTB domain containing 46 |
| 224252_s_at | AF177940 | FXYD domain containing ion transport regulator 5 |
| 206025_s_at | AW188198 | tumor necrosis factor, alpha-induced protein 6 |
| 203953_s_at | BE791251 | claudin 3 |
| 231341_at | BE670584 | solute carrier family 35, member D3 |
| 213211_s_at | AI005317 | TAF6-like RNA polymerase II, p300/CBP-associated factor (PCAF)-associated factor, 65 kDa |
| 226988_s_at | AI709055 | myosin, heavy chain 14 |
| 208677_s_at | AL550657 | basigin (Ok blood group) |
| 234625_at | AK025055 | CDNA: FLJ21402 fis, clone COL03734 |
| 206769_at | NM_004202 | thymosin, beta 4, Y-linked |
| 229432_at | AV696264 | N-acetylglutamate synthase |
| 242338_at | BG535396 | transmembrane protein 64 |
| 1554029_a_at | BC030966 | KIAA0372 |
| 202793_at | NM_005768 | membrane bound O-acyltransferase domain containing 5 |
| 210449_x_at | AF100544 | mitogen-activated protein kinase 14 |
| 244171_at | AW505004 | muskelin 1, intracellular mediator containing kelch motifs |
| 238848_at | BF750565 | OTU domain containing 4 |
| 221354_s_at | NM_005297 | melanin-concentrating hormone receptor 1 |
| 204431_at | NM_003260 | transducin-like enhancer of split 2 (E(sp1) homolog, *Drosophila*) |
| 206491_s_at | NM_003827 | N-ethylmaleimide-sensitive factor attachment protein, alpha |
| 217371_s_at | Y09908 | interleukin 15 |
| 204891_s_at | NM_005356 | lymphocyte-specific protein tyrosine kinase |
| 200948_at | NM_005439 | myeloid leukemia factor 2 |
| 237806_s_at | AI684717 | Hypothetical protein LOC729296 |
| 203849_s_at | BG473130 | kinesin family member 1A |
| 211514_at | AF068286 | receptor interacting protein kinase 5 |
| 234724_x_at | AF152528 | protocadherin beta 18 pseudogene |
| 213665_at | AI989477 | SRY (sex determining region Y)-box 4 |
| 1552736_a_at | NM_138966 | neuropilin (NRP) and tolloid (TLL)-like 1 |
| 211088_s_at | Z25433 | polo-like kinase 4 (*Drosophila*) |
| 1554576_a_at | BC007242 | ets variant gene 4 (E1A enhancer binding protein, E1AF) |
| 243323_s_at | AI872979 | AT-binding transcription factor 1 |
| 220354_at | NM_025266 | hypothetical protein MGC2780 |
| 223821_s_at | BC004888 | sushi domain containing 4 |
| 200824_at | NM_000852 | glutathione S-transferase pi |
| 227619_at | BF195628 | Werner helicase interacting protein 1 |
| 201428_at | NM_001305 | claudin 4 |
| 215984_s_at | AL121845 | ADP-ribosylation factor related protein 1 |
| 206396_at | NM_004170 | solute carrier family 1 (neuronal/epithelial high affinity glutamate transporter, system Xag), member 1 |
| 229406_at | AI674243 | hypothetical protein LOC146713 |
| 243936_x_at | T85061 | — |
| 215495_s_at | AL117523 | sterile alpha motif domain containing 4A |
| 224003_at | AF332243 | testis-specific transcript, Y-linked 14 |
| 230102_at | AW206458 | Ets variant gene 5 (ets-related molecule) |
| 203267_s_at | BF223206 | developmentally regulated GTP binding protein 2 |
| 236940_at | W60647 | Transcribed locus, weakly similar to NP_066953.1 isomerase A isoform 1 [*Homo sapiens*] |
| 202002_at | AW072302 | acetyl-Coenzyme A acyltransferase 2 (mitochondrial 3-oxoacyl-Coenzyme A thiolase) |
| 1560228_at | BC041461 | snail homolog 3 (*Drosophila*) |
| 221317_x_at | NM_018939 | protocadherin beta 6 |
| 217552_x_at | AI432713 | complement component (3b/4b) receptor 1 (Knops blood group) |
| 214279_s_at | W74452 | NDRG family member 2 |
| 208629_s_at | BG472176 | hydroxyacyl-Coenzyme A dehydrogenase/3-ketoacyl-Coenzyme A thiolase/enoyl-Coenzyme A hydratase (trifunctional protein), alpha subunit |

TABLE 14

Table 14: Genes Expressed at a 2 fold or Greater Level in hES Cell Lines versus iPS Cell Lines (p ≤ 0.01)

| Systematic Name | Genbank | Description |
| --- | --- | --- |
| 234626_at | AF137396 | olfactory receptor, family 51, subfamily I, member 1 |
| 211006_s_at | L02840 | potassium voltage-gated channel, Shab-related subfamily, member 1 |
| 228239_at | AA148789 | chromosome 21 open reading frame 51 |
| 233583_at | AA608889 | Transcribed locus |
| 205911_at | NM_000316 | parathyroid hormone receptor 1 |
| 217715_x_at | BE045142 | — |
| 1566477_at | AL832530 | MRNA; cDNA DKFZp547F1316 (from clone DKFZp547F1316) |
| 205693_at | NM_006757 | troponin T type 3 (skeletal, fast) |
| 215406_at | AK024860 | CDNA: FLJ21207 fis, clone COL00362 |
| 1564121_at | AK026788 | CDNA: FLJ23135 fis, clone LNG08666 |
| 220002_at | NM_018012 | kinesin family member 26B |
| 233939_at | AL117522 | REX1, RNA exonuclease 1 homolog (*S. cerevisiae*) |
| 210382_at | U13989 | secretin receptor |
| 220596_at | NM_015590 | G patch domain containing 4 |
| 208448_x_at | NM_002173 | interferon, alpha 16 |
| 231670_at | AA057519 | — |
| 223472_at | AF071594 | Wolf-Hirschhorn syndrome candidate 1 |
| 1554542_at | BC025747 | similar to CG4995 gene product |
| 1559623_at | CA446227 | Chromosome 11 open reading frame 54 |
| 1562036_at | BC043279 | CDNA clone IMAGE: 5297259 |
| 229817_at | AI452715 | zinc finger protein 608 |
| 234674_at | AK027027 | CDNA: FLJ23374 fis, clone HEP16126 |
| 242628_at | AA194956 | Transcribed locus |
| 243081_at | AA824282 | CDNA clone IMAGE: 5296106 |
| 1553721_at | NM_173557 | ring finger protein 152 |
| 239200_at | BE503484 | Transcribed locus |
| 226286_at | AI686411 | RNA binding motif and ELMO/CED-12 domain 1 |
| 1558570_at | AK096657 | hypothetical protein LOC145783 |
| 1566204_at | AL589610 | CDNA FLJ35929 fis, clone TESTI2010833 |
| 233608_at | AU146417 | CDNA FLJ11929 fis, clone HEMBB1000434 |
| 217070_at | AJ249275 | 5,10-methylenetetrahydrofolate reductase (NADPH) |
| 220577_at | NM_025006 | GTPase, very large interferon inducible 1 |
| 220491_at | NM_021175 | hepcidin antimicrobial peptide |
| 242398_x_at | AA605121 | Transcribed locus |
| 237168_at | AA708016 | Transcribed locus |
| 1556638_at | AI250939 | hypothetical protein LOC284530 |
| 216928_at | X51990 | T-cell acute lymphocytic leukemia 1 |
| 209639_s_at | AF030111 | regulator of G-protein signaling 12 |
| 1561255_at | BC040329 | CDNA clone IMAGE: 4827712 |
| 233164_x_at | AK026955 | rhomboid domain containing 1 |
| 236038_at | N50714 | Transcribed locus |
| 238126_at | AA886236 | CDNA clone IMAGE: 4791585 |
| 243942_at | AI400012 | Transcribed locus |
| 1568978_s_at | BM547346 | chromosome 11 open reading frame 21 |
| 1566672_at | AK093656 | CDNA FLJ36337 fis, clone THYMU2006324 |
| 237663_at | AI681941 | Transcribed locus |
| 237151_s_at | BF433885 | similar to hypothetical protein |
| 212616_at | BF668950 | chromodomain helicase DNA binding protein 9 |
| 231792_at | AF325549 | myosin light chain kinase 2, skeletal muscle |
| 1555554_at | AY180924 | breast cancer and salivary gland expression gene |
| 1553512_at | NM_173860 | homeobox C12 |
| 211483_x_at | AF081924 | calcium/calmodulin-dependent protein kinase (CaM kinase) II beta |
| 1565588_at | BG708117 | SP140 nuclear body protein |
| 1559240_at | AA811339 | — |
| 230802_at | AI761947 | Rho GTPase activating protein 24 |
| 213369_at | AI825832 | protocadherin 21 |
| 235724_at | AW513684 | Acyl-CoA synthetase short-chain family member 1 |
| 238279_x_at | BF062155 | — |
| 1569167_at | BC013250 | *Homo sapiens*, clone IMAGE: 3867502, mRNA |
| 208559_at | NM_013311 | pancreatic and duodenal homeobox 1 |
| 217122_s_at | AL031282 | solute carrier family 35, member E2 /// similar to solute carrier family 35, member E2 |
| 234108_at | AF264628 | taste receptor, type 2, member 45 |
| 229480_at | AI341053 | MRNA; cDNA DKFZp686I18116 (from clone DKFZp686I18116) |
| 240623_at | BF589421 | Transcribed locus |
| 224519_at | BC006438 | CDNA clone MGC: 13162 IMAGE: 3010103 |
| 221456_at | NM_016943 | taste receptor, type 2, member 3 |
| 236728_at | AW070437 | leucyl/cystinyl aminopeptidase |
| 219839_x_at | NM_012468 | T-cell leukemia/lymphoma 6 |
| 238894_at | AW665144 | Transcribed locus |
| 231276_at | BF591245 | Phosphodiesterase 3B, cGMP-inhibited |
| 1552732_at | AL832152 | actin-binding Rho activating protein |
| 210292_s_at | AF332218 | protocadherin 11 X-linked /// protocadherin 11 Y-linked |
| 230354_at | BG236273 | Transcribed locus |
| 1557208_at | AA609739 | hypothetical protein LOC219731 |
| 240305_at | AI291536 | CDNA clone IMAGE: 5285563 |

TABLE 14-continued

Table 14: Genes Expressed at a 2 fold or Greater Level in hES Cell Lines versus iPS Cell Lines (p ≦ 0.01)

| Systematic Name | Genbank | Description |
| --- | --- | --- |
| 233075_at | AF071178 | hect domain and RLD 2 pseudogene 7 |
| 226134_s_at | AI978754 | Transcribed locus |
| 235796_at | AI927957 | Transcribed locus |
| 1567375_at | AJ011596 | Trapped 3' terminal exon, clone B2E8 |
| 232140_at | BF056548 | CDNA FLJ13474 fis, clone PLACE1003593 |
| 216707_at | AL162044 | MRNA; cDNA DKFZp761L0812 (from clone DKFZp761L0812); partial cds |
| 1557395_at | AW243434 | hypothetical LOC255130 |
| 1554629_at | BC027940 | EPH receptor A7 |
| 215488_at | AF052095 | Clone 23911 mRNA sequence |
| 211004_s_at | BC002553 | aldehyde dehydrogenase 3 family, member B1 |
| 244847_at | AA988223 | Transcribed locus |
| 222079_at | BF739971 | — |
| 237996_at | AV650867 | — |
| 216644_at | AK000185 | CDNA FLJ20178 fis, clone COL09990 |
| 238588_at | AI623295 | CDNA clone IMAGE: 5265193 |
| 222061_at | AA700015 | CD58 molecule |
| 211315_s_at | AB012043 | calcium channel, voltage-dependent, T type, alpha 1G subunit |
| 210037_s_at | L24553 | nitric oxide synthase 2A (inducible, hepatocytes) |
| 209957_s_at | M30262 | natriuretic peptide precursor A |
| 206449_s_at | NM_001879 | mannan-binding lectin serine peptidase 1 (C4/C2 activating component of Ra-reactive factor) |
| 1569064_at | BC027487 | hypothetical LOC643338 |
| 209747_at | J03241 | transforming growth factor, beta 3 |
| 224220_x_at | AF063824 | transient receptor potential cation channel, subfamily C, member 4 |
| 244711_at | BF512863 | Transcribed locus |
| 239452_at | AI088640 | Transcribed locus |
| 243281_at | AW188311 | Transcribed locus |
| 1560346_at | AL080057 | MRNA; cDNA DKFZp564D032 (from clone DKFZp564D032) |
| 1566623_at | AL050263 | DKFZP547J0410 protein |
| 222381_at | AI907083 | Programmed cell death 6 /// CDNA FLJ37304 fis, clone BRAMY2016070 |
| 227504_s_at | N64630 | MRNA; cDNA DKFZp686F09227 (from clone DKFZp686F09227) |
| 235164_at | BG433539 | zinc finger protein 25 |
| 1559159_at | AK094069 | centrosomal protein 68 kDa |
| 1570128_at | BC025771 | DEAD (Asp-Glu-Ala-As) box polypeptide 19A |
| 231055_at | BF432941 | Transcribed locus |
| 1557453_at | BM662646 | Full length insert cDNA clone ZD77B03 |
| 1564996_at | AK000024 | CDNA FLJ20017 fis, clone ADSE00552 |
| 243107_at | AI910590 | — |
| 204914_s_at | AW157202 | SRY (sex determining region Y)-box 11 |
| 1564855_at | AK058056 | hypothetical protein LOC727924 |
| 1564559_at | AL833395 | hypothetical protein LOC728073 |
| 204556_s_at | AL568422 | DAZ interacting protein 1 |
| 1562372_at | AK094917 | synaptic vesicle glycoprotein 2C |
| 205777_at | NM_001395 | dual specificity phosphatase 9 |
| 231475_at | BE671790 | TBC1 domain family, member 21 |
| 224239_at | AF301470 | defensin, beta 103B |
| 238228_at | AI732206 | — |
| 230763_at | AA905508 | spermatogenesis associated 17 |
| 229508_at | BF434828 | U2 small nuclear RNA auxiliary factor 2 |
| 236479_at | BF513986 | — |
| 205183_at | NM_002138 | heterogeneous nuclear ribonucleoprotein D (AU-rich element RNA binding protein 1, 37 kDa) |
| 216135_at | AK000122 | IQ motif containing K |
| 1553207_at | NM_173664 | ADP-ribosylation factor-like 10 |
| 217162_at | M94893 | testis specific protein, Y-linked 1 |
| 244328_x_at | T86832 | — |
| 1566003_x_at | AK096064 | CDNA FLJ38745 fis, clone KIDNE2012291 |
| 236736_at | AW274301 | Transcribed locus |
| 238532_at | AI125562 | D4, zinc and double PHD fingers, family 3 |
| 223781_x_at | M15943 | alcohol dehydrogenase 4 (class II), pi polypeptide |
| 222940_at | U55764 | sulfotransferase family 1E, estrogen-preferring, member 1 |
| 213953_at | AI732381 | keratin 20 |
| 241033_at | AI821633 | Transcribed locus |
| 1569332_at | BC022563 | chromosome 3 open reading frame 66 |
| 214049_x_at | AI829961 | CD7 molecule |
| 233165_at | AJ242655 | NCK interacting protein with SH3 domain |
| 241555_at | AI032090 | Transcribed locus |
| 1553405_a_at | NM_033225 | CUB and Sushi multiple domains 1 |
| 238406_x_at | AI734001 | seizure related 6 homolog (mouse)-like 2 |
| 203084_at | NM_000660 | transforming growth factor, beta 1 |
| 232182_at | AI142853 | hypothetical protein LOC286272 |
| 1559821_at | BC025328 | *Homo sapiens*, clone IMAGE: 3944699, mRNA |
| 206660_at | NM_020070 | immunoglobulin lambda-like polypeptide 1 |
| 1564658_at | BC037583 | Chromosome 7 open reading frame 52 |
| 220095_at | NM_017738 | chromosome 9 open reading frame 39 |
| 230694_at | AI340341 | — |

TABLE 14-continued

Table 14: Genes Expressed at a 2 fold or Greater Level in hES Cell Lines versus iPS Cell Lines (p ≤ 0.01)

| Systematic Name | Genbank | Description |
|---|---|---|
| 202341_s_at | AA149745 | tripartite motif-containing 2 |
| 1566577_at | AL831879 | MRNA; cDNA DKFZp547I1410 (from clone DKFZp547I1410) |
| 237587_at | AI733359 | Transcribed locus, weakly similar to NP_001041360.1 protein LOC317588 [Rattus norvegicus] |
| 1553868_a_at | NM_173665 | chromosome 5 open reading frame 36 |
| 238731_at | AW977837 | SET domain, bifurcated 2 |
| 235055_x_at | BF913667 | Mucin 4, cell surface associated |
| 230189_x_at | BF434897 | Transcribed locus |
| 1562656_at | BC043591 | CDNA clone IMAGE: 5248626 |
| 219898_at | NM_018970 | G protein-coupled receptor 85 |
| 217585_at | BE502910 | nebulette |
| 1554147_s_at | AB063297 | chromosome 3 open reading frame 15 |
| 231047_at | R56808 | Transcribed locus |
| 213525_at | AC002310 | CDNA clone IMAGE: 4906981 |
| 1553872_at | NM_152914 | transcript expressed during hematopoiesis 2 |
| 1557452_at | AF088024 | Full length insert cDNA clone ZC19A03 |
| 211618_s_at | M31008 | alkaline phosphatase, intestinal |
| 227121_at | BF476076 | MRNA; cDNA DKFZp586K1922 (from clone DKFZp586K1922) |
| 244364_at | AA443280 | myosin IIIA |
| 243797_at | AW070323 | serine/threonine kinase 17b |
| 1561396_at | AK092565 | EPH receptor A6 |
| 241071_at | BF432757 | — |
| 1554739_at | BC032544 | intracisternal A particle-promoted polypeptide |
| 237015_at | AI097501 | CDNA FLJ37017 fis, clone BRACE2010642 |
| 243825_at | T79768 | B-cell CLL/lymphoma 6, member B (zinc finger protein) |
| 232934_at | AA526468 | CDNA FLJ13422 fis, clone PLACE1002213 |
| 1561669_at | BC018424 | Homo sapiens, clone IMAGE: 4508536, mRNA |
| 244545_at | AI769647 | CDNA clone IMAGE: 5296106 |
| 1561200_at | BM981856 | von Willebrand factor A domain containing 3B |
| 244291_x_at | BE348646 | Transcribed locus |
| 1564854_at | AK058061 | CDNA FLJ25332 fis, clone TST00642 |
| 229962_at | W68731 | leucine rich repeat containing 37, member A3 |
| 225491_at | AL157452 | solute carrier family 1 (glial high affinity glutamate transporter), member 2 |
| 205713_s_at | NM_000095 | cartilage oligomeric matrix protein |
| 240692_at | AI809153 | SPR pseudogene |
| 1553894_at | NM_144974 | coiled-coil domain containing 122 |
| 217530_at | AW295295 | solute carrier family 34 (sodium phosphate), member 1 |
| 228376_at | AI972498 | glycoprotein, alpha-galactosyltransferase 1 /// similar to glycoprotein galactosyltransferase alpha 1, 3 |
| 244204_at | W87300 | — |
| 206128_at | AI264306 | adrenergic, alpha-2C-, receptor |
| 221275_s_at | NM_030896 | — |
| 233701_at | AK024580 | CDNA: FLJ20927 fis, clone ADSE01007 |
| 240588_at | AI821798 | — |
| 217233_at | Z97206 | — |
| 236719_at | AI042187 | Transcribed locus, moderately similar to XP_001086437.1 hypothetical protein [Macaca mulatta] |
| 1561205_at | BC036409 | CDNA clone IMAGE: 5266702 |
| 216129_at | AL117659 | ATPase, Class II, type 9A |
| 214428_x_at | K02403 | complement component 4A (Rodgers blood group) /// complement component 4B (Childo blood group) |
| 211579_at | U95204 | integrin, beta 3 (platelet glycoprotein IIIa, antigen CD61) |
| 209354_at | BC002794 | tumor necrosis factor receptor superfamily, member 14 (herpesvirus entry mediator) |
| 207896_s_at | NM_007337 | deleted in lung and esophageal cancer 1 |
| 1561319_at | BC041486 | CDNA clone IMAGE: 5492202 |
| 1569454_a_at | BG475827 | hypothetical protein LOC283352 |
| 240568_at | AW206555 | — |
| 1552872_at | NM_025091 | chromosome X and Y open reading frame 2 |
| 233734_s_at | AW271225 | oxysterol binding protein-like 5 |
| 214347_s_at | AW772056 | dopa decarboxylase (aromatic L-amino acid decarboxylase) |
| 1556803_at | BC033542 | polymerase (RNA) III (DNA directed) polypeptide B |
| 236154_at | R41907 | Quaking homolog, KH domain RNA binding (mouse) |
| 205623_at | NM_000691 | aldehyde dehydrogenase 3 family, member A1 |
| 220818_s_at | NM_016179 | transient receptor potential cation channel, subfamily C, member 4 |
| 1555043_at | BC028630 | lipoma HMGIC fusion partner-like 5 |
| 1568977_at | BC019871 | ribonuclease T2 |
| 235600_at | N63890 | Transcribed locus |
| 220150_s_at | NM_024581 | chromosome 6 open reading frame 60 |
| 210381_s_at | BC000740 | cholecystokinin B receptor |
| 1558397_at | BF976693 | CDNA FLJ34100 fis, clone FCBBF3007597 |
| 216214_at | AF070602 | Clone 24504 mRNA sequence |
| 221990_at | AI948472 | paired box 8 |
| 243817_at | AI874267 | — |
| 241380_at | BF508325 | FLJ41603 protein |
| 237604_at | AA906413 | BC038740 |
| 243708_at | AI678145 | transmembrane protein 132E |

TABLE 14-continued

Table 14: Genes Expressed at a 2 fold or Greater Level in hES Cell Lines versus iPS Cell Lines (p ≦ 0.01)

| Systematic Name | Genbank | Description |
| --- | --- | --- |
| 233876_at | AK000677 | — |
| 240858_at | AA680403 | Transcribed locus |
| 1560806_at | BC037249 | hypothetical protein LOC150527 |
| 239480_at | AA608964 | Transcribed locus |
| 1559580_at | AL832694 | leucine rich repeat containing 39 |
| 230610_at | AW008915 | Transcribed locus, moderately similar to XP_001087523.1 similar to Mid-1-related chloride channel 1 isoform 4 [*Macaca mulatta*] |
| 221022_s_at | NM_031293 | polyamine modulated factor 1 binding protein 1 |
| 239178_at | AL583692 | fibroblast growth factor 9 (glia-activating factor) |
| 237365_at | AI798981 | CDNA clone IMAGE: 5269899 |
| 1568870_at | BC034805 | CDNA clone IMAGE: 4818211 |
| 214411_x_at | AW584011 | chymotrypsinogen B2 |
| 244035_at | BF003032 | Full length insert cDNA clone YZ11B11 |
| 237094_at | AI953086 | family with sequence similarity 19 (chemokine (C-C motif)-like), member A5 |
| 239312_at | AW419032 | — |
| 207640_x_at | NM_006181 | netrin 2-like (chicken) |
| 242171_at | AA693730 | — |
| 1553248_at | NM_152675 | coiled-coil domain containing 57 |
| 234480_at | AL137340 | Hypothetical protein DKFZp761C1711 |
| 1555474_at | BC009479 | tubulin tyrosine ligase-like family, member 3 |
| 234261_at | AL137313 | MRNA; cDNA DKFZp761M10121 (from clone DKFZp761M10121) |
| 243459_x_at | AW300077 | — |
| 237676_at | AW274369 | Transcribed locus |
| 206819_at | NM_014549 | POM121-like protein |
| 1556125_at | BM668595 | G patch domain containing 2 |
| 1556065_at | BG828817 | Hypothetical protein LOC284926 |
| 232120_at | AA678124 | CDNA FLJ14259 fis, clone PLACE1001076 |
| 1553562_at | NM_172100 | CD8b molecule |
| 217016_x_at | AK026825 | hypothetical LOC389177 |
| 232807_at | AU158601 | family with sequence similarity 131, member A |
| 227389_x_at | AA058858 | — |
| 237528_at | D80212 | Transcribed locus |
| 242714_at | AW500340 | — |
| 205050_s_at | NM_012324 | mitogen-activated protein kinase 8 interacting protein 2 |
| 240159_at | AA836116 | solute carrier family 15 (H+/peptide transporter), member 2 |
| 240887_at | AI017957 | Transcribed locus |
| 1562577_at | BC025331 | *Homo sapiens*, clone IMAGE: 4546564, mRNA |
| 244715_at | R39803 | Transcribed locus |
| 1561500_at | AW575915 | Hypothetical protein LOC348180 |
| 239627_at | BG034114 | Transmembrane emp24 protein transport domain containing 9 |
| 222901_s_at | AF153815 | potassium inwardly-rectifying channel, subfamily J, member 16 |
| 233351_at | AF339776 | Clone IMAGE: 1542282, mRNA sequence |
| 1566898_at | X53943 | succinate dehydrogenase flavoprotein subunit |
| 228136_s_at | AI280446 | Chromosome 17 open reading frame 70 |
| 233387_s_at | AK024009 | pericentrin (kendrin) |
| 231911_at | AA736604 | KIAA1189 |
| 240402_at | H05918 | kin of IRRE like 3 (*Drosophila*) |
| 244840_x_at | AW452588 | dedicator of cytokinesis 4 |
| 1556172_at | AL832916 | MRNA; cDNA DKFZp762I0915 (from clone DKFZp762I0915) |
| 232833_at | AF070565 | Clone 24425 mRNA sequence |
| 1558797_at | BC017743 | *Homo sapiens*, clone IMAGE: 4391558, mRNA |
| 243542_at | BF445273 | prolyl endopeptidase-like |
| 223717_s_at | AB051833 | acrosin binding protein |
| 231324_at | AW452134 | Transcribed locus |
| 1556713_at | AK022031 | CDNA FLJ11969 fis, clone HEMBB1001142 |
| 232186_at | AK027041 | chromosome 20 open reading frame 142 |
| 231158_x_at | AI380289 | Polypyrimidine tract binding protein 1 |
| 228816_at | AK022625 | hypothetical protein LOC92270 |
| 1567390_x_at | AJ011600 | Trapped 3' terminal exon, clone C2B5 |
| 1565732_at | BI254450 | MRNA; cDNA DKFZp761B0218 (from clone DKFZp761B0218) |
| 230228_at | W94546 | hypothetical LOC284297 |
| 217462_at | AC004770 | chromosome 11 open reading frame 9 |
| 1561759_at | AF085995 | Similar to septin 7 |
| 211225_at | U27329 | fucosyltransferase 5 (alpha (1,3) fucosyltransferase) |
| 210565_at | U03469 | glucagon receptor |
| 237523_at | AI939584 | Transcribed locus |
| 221921_s_at | AI951798 | cell adhesion molecule 3 |
| 234764_x_at | U96394 | Immunoglobulin lambda variable 1-44 /// Immunoglobulin anti-HBsAg lambda light chain (LM25) /// Immunoglobulin lambda locus |

TABLE 15

Table 15: Genes Expressed at a 5 fold or Greater Level in iPS Cell Lines versus both hES Cell Lines and Parental Fibroblasts (p ≦ 0.01)

| Systematic Name | Genbank | Description |
| --- | --- | --- |
| AFFX-r2-Ec-bioD-5_at | BF057809 | Transcribed locus |
| 239206_at | AF268617 | POU class 5 homeobox 1 pseudogene 3 |
| 239205_s_at | AW003929 | claudin 6 |
| 215101_s_at | NM_004360 | cadherin 1, type 1, E-cadherin (epithelial) |
| 210697_at | NM_017697 | RNA binding motif protein 35A |
| 223551_at | NM_003212 | teratocarcinoma-derived growth factor 1 /// teratocarcinoma-derived growth factor 3, pseudogene |
| 214974_x_at | AK022821 | developmental pluripotency associated 4 |
| 237552_at | AF268615 | POU class 5 homeobox 1 /// POU class 5 homeobox 1 pseudogene 1 /// POU class 5 homeobox 1 pseudogene 3 /// POU class 5 homeobox 1 pseudogene 4 |
| 231120_x_at | AI554075 | Transcribed locus |
| 235075_at | NM_024674 | lin-28 homolog (*C. elegans*) |
| 211906_s_at | AY072911 | coxsackie virus and adenovirus receptor |
| 217230_at | NM_005356 | lymphocyte-specific protein tyrosine kinase |
| 225908_at | BF001941 | RNA binding motif protein 35A |
| 232881_at | BC028721 | solute carrier family 1 (high affinity aspartate/glutamate transporter), member 6 |
| 239951_at | L08599 | cadherin 1, type 1, E-cadherin (epithelial) |
| 1553276_at | BG166705 | chemokine (C—X—C motif) ligand 5 |
| 219837_s_at | NM_001100 | actin, alpha 1, skeletal muscle |
| 208542_x_at | NM_014474 | sphingomyelin phosphodiesterase, acid-like 3B |
| 239319_at | BI092935 | zinc finger protein 42 homolog (mouse) |
| 235779_at | AL117612 | mal, T-cell differentiation protein 2 |
| 220638_s_at | M83248 | secreted phosphoprotein 1 (osteopontin, bone sialoprotein I, early T-lymphocyte activation 1) |
| 214336_s_at | AU148706 | CDNA FLJ12557 fis, clone NT2RM4000783 |
| 219807_x_at | NM_003413 | Zic family member 3 heterotaxy 1 (odd-paired homolog, *Drosophila*) |
| 1559503_a_at | AL515381 | coronin, actin binding protein, 2A |
| 209040_s_at | AF450454 | zinc finger protein 42 homolog (mouse) |
| 214090_at | BG327863 | CD24 molecule |
| 223629_at | NM_020436 | sal-like 4 (*Drosophila*) |
| 1559051_s_at | NM_014446 | integrin beta 1 binding protein 3 |
| 212105_s_at | AI674565 | family with sequence similarity 110, member C |
| 203872_at | BE974098 | tumor protein D52 |
| 222935_x_at | AL136825 | ubiquitin specific peptidase 44 |
| 243195_s_at | W92748 | sema domain, transmembrane domain (TM), and cytoplasmic domain, (semaphorin) 6A |
| 220179_at | AL556409 | galanin |
| 222898_s_at | AL533416 | kinesin family member 1A |
| 229332_at | AU143918 | hypothetical gene supported by AJ002784 |
| 1555731_a_at | X69397 | CD24 molecule |
| 1553873_at | NM_024939 | RNA binding motif protein 35B |
| 235942_at | NM_005755 | Epstein-Barr virus induced gene 3 |
| 244178_at | NM_173553 | hypothetical protein FLJ25801 |
| 224463_s_at | AF493872 | guanine nucleotide binding protein (G protein), gamma 4 |
| 206797_at | NM_002196 | insulinoma-associated 1 |
| 212278_x_at | NM_021195 | claudin 6 |
| 211107_s_at | AA594937 | cordon-bleu homolog (mouse) |
| 214519_s_at | AK000168 | CD24 molecule |
| 216469_at | BE552138 | complement component (3b/4b) receptor 1-like |
| 221123_x_at | AI963203 | solute carrier family 7 (cationic amino acid transporter, y+ system), member 3 |
| 1568574_x_at | NM_006892 | DNA (cytosine-5-)-methyltransferase 3 beta |
| 1554777_at | AB020630 | protein phosphatase 1, regulatory (inhibitor) subunit 16B |
| 211214_s_at | AF154005 | F11 receptor |
| 205920_at | BE542563 | Hypothetical protein LOC728342 |
| 232771_at | NM_001943 | desmoglein 2 |
| 1555765_a_at | AB019562 | Secreted phosphoprotein 1 (osteopontin, bone sialoprotein I, early T-lymphocyte activation 1) |
| 206220_s_at | AF027205 | serine peptidase inhibitor, Kunitz type, 2 |
| 201130_s_at | AF225513 | protein kinase (cAMP-dependent, catalytic) inhibitor beta |
| 219911_s_at | NM_024749 | vasohibin 2 |
| 226654_at | NM_003991 | endothelin receptor type B |
| 1559361_at | NM_000273 | G protein-coupled receptor 143 |
| 209260_at | AL359055 | MRNA full length insert cDNA clone EUROIMAGE 2344436 |
| 1552399_a_at | NM_001038 | sodium channel, nonvoltage-gated 1 alpha |
| 205910_s_at | BE552138 | complement component (3b/4b) receptor 1 (Knops blood group) /// complement component (3b/4b) receptor 1-like /// similar to complement component (3b/4b) receptor 1 isoform F precursor |
| 206232_s_at | AK057525 | CDNA FLJ32963 fis, clone TESTI2008405 |
| 212009_s_at | AB020630 | protein phosphatase 1, regulatory (inhibitor) subunit 16B |
| 204815_s_at | AI935915 | SH3-binding domain kinase 1 |
| 1554776_at | BG389015 | tumor protein D52 |
| 242070_at | NM_005397 | podocalyxin-like |
| 1554508_at | AK026546 | chemokine (C—X—C motif) ligand 5 |
| 236741_at | AA761181 | CD24 molecule |

TABLE 15-continued

Table 15: Genes Expressed at a 5 fold or Greater Level in iPS Cell Lines versus both hES Cell Lines and Parental Fibroblasts (p ≦ 0.01)

| Systematic Name | Genbank | Description |
| --- | --- | --- |
| 206604_at | NM_003182 | tachykinin, precursor 1 (substance K, substance P, neurokinin 1, neurokinin 2, neuromedin L, neurokinin alpha, neuropeptide K, neuropeptide gamma) |
| 1555829_at | NM_014392 | DNA segment on chromosome 4 (unique) 234 expressed sequence |
| 1555434_a_at | AF070651 | zinc finger protein 257 |
| 1564706_s_at | BF056473 | CDNA clone IMAGE: 4667929 |
| 242519_at | AF225425 | sema domain, transmembrane domain (TM), and cytoplasmic domain, (semaphorin) 6A |
| 205344_at | AI653107 | Nik related kinase |
| 201123_s_at | AA074145 | proline dehydrogenase (oxidase) 1 |
| 1564339_a_at | AL569326 | protein kinase (cAMP-dependent, catalytic) inhibitor beta |
| 216031_x_at | NM_004929 | calbindin 1, 28 kDa |
| 223285_s_at | AI824954 | SRY (sex determining region Y)-box 3 |
| 1555800_at | AF110329 | glutaminase 2 (liver, mitochondrial) |
| 1557910_at | AW014927 | calbindin 1, 28 kDa |
| 204823_at | BC038422 | zinc finger protein 533 |
| 1553852_at | BC028721 | solute carrier family 1 (high affinity aspartate/glutamate transporter), member 6 |
| 1557924_s_at | NM_006984 | claudin 10 |
| 1552995_at | AI492376 | killer cell lectin-like receptor subfamily G, member 2 |
| 216360_x_at | AI830823 | RNA-binding protein |
| 232751_at | L19659 | glucosaminyl (N-acetyl) transferase 2, I-branching enzyme (I blood group) |
| 231452_at | NM_031272 | testis expressed 14 |
| 213171_s_at | N23258 | Transcribed locus |
| 209756_s_at | NM_013267 | glutaminase 2 (liver, mitochondrial) |
| 1556670_at | AI014470 | hypothetical protein LOC728485 |
| 227759_at | NM_003007 | semenogelin I |
| 208621_s_at | NM_012116 | Cas-Br-M (murine) ecotropic retroviral transforming sequence c |
| 229289_at | NM_004775 | UDP-Gal:betaGlcNAc beta 1,4-galactosyltransferase, polypeptide 6 |
| 1553698_a_at | R61322 | coiled-coil domain containing 64 |
| 207532_at | NM_004485 | guanine nucleotide binding protein (G protein), gamma 4 |
| 219424_at | AW193600 | hypothetical gene supported by AY007155 |
| 214154_s_at | AW007161 | SRY (sex determining region Y)-box 2 |
| 221213_s_at | AI056483 | zinc finger protein 488 |
| 1556834_at | M74921 | endothelin receptor type B |
| 227757_at | NM_005498 | adaptor-related protein complex 1, mu 2 subunit |
| 208504_x_at | Z83838 | Rho GTPase activating protein 8 /// PRR5-ARHGAP8 fusion |
| 214008_at | AB037776 | immunoglobulin superfamily, member 9 |
| 209875_s_at | AI989477 | SRY (sex determining region Y)-box 4 |
| 1555821_a_at | NM_000224 | keratin 18 |
| 216915_s_at | W58601 | Transcribed locus |
| 239239_at | NM_152332 | tandem C2 domains, nuclear |
| 221408_at | U07236 | lymphocyte-specific protein tyrosine kinase |
| 212016_s_at | NM_153270 | kelch-like 34 (Drosophila) |
| 214828_s_at | AI193252 | leucine rich repeat and Ig domain containing 1 |
| 233305_at | AF335278 | cytochrome P450, family 2, subfamily S, polypeptide 1 |
| 216985_at | BF527050 | SRY (sex determining region Y)-box 8 |
| 231789_at | AA205873 | chromosome 9 open reading frame 58 |
| 211363_s_at | H93038 | Insulin-like growth factor 2 mRNA binding protein 1 |
| 217294_s_at | AA573775 | chromosome 1 open reading frame 172 |
| 211922_s_at | AL566906 | Transcribed locus |
| 204018_x_at | AI669212 | protein phosphatase 2 (formerly 2A), regulatory subunit B, gamma isoform |
| 243347_at | AIF191495 | F11 receptor |
| 206595_at | BF791631 | kelch domain containing 8A |
| 238125_at | NM_003822 | nuclear receptor subfamily 5, group A, member 2 |
| 209958_s_at | NM_007267 | transmembrane channel-like 6 |
| 238692_at | BC007230 | coagulation factor C homolog, cochlin (Limulus polyphemus) |
| 206390_x_at | NM_024794 | abhydrolase domain containing 9 |
| 210572_at | BG479856 | family with sequence similarity 60, member A /// similar to teratocarcinoma expressed, serine rich /// similar to Protein FAM60A (Tera protein) |
| 1555034_at | NM_003385 | visinin-like 1 |
| 210587_at | AL137763 | grainyhead-like 3 (Drosophila) |
| 231013_at | AI420156 | MARVEL domain containing 3 |
| 206665_s_at | AW139759 | solute carrier family 39 (zinc transporter), member 8 |
| 206882_at | BC041633 | chromosome 1 open reading frame 210 |
| 1555716_a_at | AB046400 | serpin peptidase inhibitor, clade B (ovalbumin), member 4 |
| 217051_s_at | NM_022449 | RAB17, member RAS oncogene family |
| 222508_s_at | AF193756 | EF-hand calcium binding protein 1 |
| 211529_x_at | BC039098 | desmoglein 4 |
| 220108_at | BC015108 | Homo sapiens, Similar to otoconin 90, clone IMAGE: 4044247, mRNA |
| 1561367_a_at | AW299463 | WD repeat domain 72 |
| 211022_s_at | AL537457 | neurofilament, light polypeptide 68 kDa |
| 218931_at | BE791251 | claudin 3 |
| 213363_at | AF039555 | visinin-like 1 |
| 230112_at | AV706971 | polycystic kidney and hepatic disease 1 (autosomal recessive)-like 1 |
| 209136_s_at | AA888057 | plakophilin 2 |
| 212125_at | AI268404 | protocadherin alpha 9 /// protocadherin alpha subfamily C, 2 /// protocadherin alpha |

TABLE 15-continued

Table 15: Genes Expressed at a 5 fold or Greater Level in iPS Cell Lines versus both hES Cell Lines and Parental Fibroblasts (p ≦ 0.01)

| Systematic Name | Genbank | Description |
|---|---|---|
| | | subfamily C, 1 /// protocadherin alpha 13 /// protocadherin alpha 12 /// protocadherin alpha 11 /// protocadherin alpha 10 /// protocadherin alpha 8 /// protocadherin alpha 7 /// protocadherin alpha 6 /// protocadherin alpha 5 /// protocadherin alpha 4 /// protocadherin alpha 3 /// protocadherin alpha 2 /// protocadherin alpha 1 |
| 217370_x_at | BG473130 | kinesin family member 1A |
| 211016_x_at | BC001745 | DNA segment on chromosome 4 (unique) 234 expressed sequence |
| 241661_at | NM_000814 | gamma-aminobutyric acid (GABA) A receptor, beta 3 |
| 222611_s_at | AI792670 | Full-length cDNA clone CS0DC002YA18 of Neuroblastoma Cot 25-normalized of *Homo sapiens* (human) |
| 213722_at | U46745 | dystrobrevin, alpha |
| 212574_x_at | NM_014289 | calpain 6 |
| 219928_s_at | AF152474 | protocadherin alpha subfamily C, 2 |
| 204895_x_at | BC029917 | phosphoinositide-3-kinase adaptor protein 1 |
| 208275_x_at | NM_001877 | complement component (3d/Epstein Barr virus) receptor 2 |
| 232001_at | BC000181 | G protein-coupled receptor 160 |
| 223828_s_at | AI871354 | v-myc myelocytomatosis viral related oncogene, neuroblastoma derived (avian) |
| 210654_at | NM_006465 | AT rich interactive domain 3B (BRIGHT-like) |
| 206208_at | BF905445 | Proline rich Gla (G-carboxyglutamic acid) 4 (transmembrane) |
| 1553535_a_at | BC000329 | stratifin |
| 222936_s_at | BC014155 | Ras homolog enriched in brain like 1 |
| 1566764_at | NM_016354 | solute carrier organic anion transporter family, member 4A1 |
| 226913_s_at | NM_001307 | claudin 7 |
| 208478_s_at | AB032179 | erythrocyte membrane protein band 4.1 like 4B |
| 202662_s_at | AF152528 | protocadherin beta 18 pseudogene |
| 228851_s_at | U53823 | occludin /// occludin pseudogene |
| 206552_s_at | NM_003389 | coronin, actin binding protein, 2A |
| 213943_at | AA565499 | NLR family, pyrin domain containing 7 |
| 209198_s_at | AF232238 | hairy/enhancer-of-split related with YRPW motif 2 |
| 211699_x_at | AF213678 | chromosome 19 open reading frame 33 |
| 207402_at | NM_004297 | guanine nucleotide binding protein (G protein), alpha 14 |
| 224539_s_at | BF732462 | PRKC, apoptosis, WT1, regulator |
| 229566_at | AV681807 | v-erb-b2 erythroblastic leukemia viral oncogene homolog 3 (avian) |
| 238742_x_at | BC007242 | ets variant gene 4 (E1A enhancer binding protein, E1AF) |
| 1555639_a_at | AI768894 | cingulin |
| 211899_s_at | NM_004968 | islet cell autoantigen 1, 69 kDa |
| 1553694_a_at | AA565509 | Transcribed locus, strongly similar to XP_531332.1 hypothetical protein XP_531332 [Pantroglodytes] |
| 213926_s_at | AW961205 | hypothetical protein LOC728485 |
| 214000_s_at | NM_005562 | laminin, gamma 2 |
| 203729_at | BC001186 | protocadherin beta 5 |
| 203085_s_at | BE350882 | delta-like 3 (*Drosophila*) |
| 207118_s_at | NM_000015 | N-acetyltransferase 2 (arylamine N-acetyltransferase) |
| 232591_s_at | BE080109 | similar to embigin homolog |
| 236158_at | AL359055 | MRNA full length insert cDNA clone EUROIMAGE 2344436 |
| 229901_at | BF057784 | G protein-coupled receptor 114 |
| 211051_s_at | U58994 | ladinin 1 |
| 222458_s_at | NM_024306 | fatty acid 2-hydroxylase |
| 230809_at | NM_007153 | zinc finger protein 208 |
| 221279_at | BC000568 | transmembrane protein 108 |
| 224169_at | AB018009 | solute carrier family 7 (cationic amino acid transporter, y+ system), member 5 |
| 233297_s_at | U53470 | inositol polyphosphate-5-phosphatase, 145 kDa |
| 221665_s_at | NM_002773 | protease, serine, 8 |
| 205391_x_at | AA702685 | organic solute transporter alpha |
| 215728_s_at | BC004907 | EPS8-like 1 |
| 208474_at | NM_021209 | NLR family, CARD domain containing 4 |
| 223567_at | AA910946 | adaptor-related protein complex 1, mu 2 subunit |
| 1558662_s_at | BC011672 | G protein regulated inducer of neurite outgrowth 2 |
| 210620_s_at | U73844 | E74-like factor 3 (ets domain transcription factor, epithelial-specific) |
| 211020_at | AI740544 | ADAM metallopeptidase with thrombospondin type 1 motif, 16 |
| 231698_at | AI434443 | Zinc finger protein 81 |
| 227316_at | R99562 | forkhead box A3 |
| 1555814_a_at | AI694320 | zinc finger protein 533 |
| 235728_at | NM_003121 | Spi-B transcription factor (Spi-1/PU.1 related) |
| 213713_s_at | NM_025266 | hypothetical protein MGC2780 |
| 237206_at | BC035960 | protein tyrosine phosphatase, receptor type, O |
| 210413_x_at | NM_006467 | polymerase (RNA) III (DNA directed) polypeptide G (32 kD) |
| 242660_at | NM_003577 | undifferentiated embryonic cell transcription factor 1 |
| 225369_at | AV709406 | transmembrane protein 125 |
| 235358_at | AI653169 | adenylate kinase 3-like 2 |
| 1554628_at | BC035104 | CDNA clone IMAGE: 5262438 |
| 212154_at | NM_004659 | matrix metallopeptidase 23B /// matrix metallopeptidase 23A (pseudogene) |
| 218260_at | AI928513 | — |
| 207664_at | NM_005477 | hyperpolarization activated cyclic nucleotide-gated potassium channel 4 |
| 201171_at | NM_004973 | jumonji, AT rich interactive domain 2 |

TABLE 15-continued

Table 15: Genes Expressed at a 5 fold or Greater Level in iPS Cell Lines versus both hES Cell Lines and Parental Fibroblasts (p ≤ 0.01)

| Systematic Name | Genbank | Description |
| --- | --- | --- |
| 203892_at | BF739767 | homolog of rat pragma of Rnd2 |
| 241574_s_at | AF059274 | chondroitin sulfate proteoglycan 5 (neuroglycan C) |
| 210457_x_at | NM_018593 | solute carrier family 16, member 10 (aromatic amino acid transporter) |
| 223631_s_at | AA531023 | family with sequence similarity 46, member B |
| 1555733_s_at | AI566130 | adenylate kinase 3-like 2 |
| 206917_at | NM_002045 | growth associated protein 43 |
| 236058_at | AW173071 | UDP glycosyltransferase 3 family, polypeptide A1 |
| 1558015_s_at | AI885670 | selenophosphate synthetase 1 |
| 227971_at | AF257210 | neuropeptide FF receptor 2 |
| 220892_s_at | AI653050 | 4-hydroxyphenylpyruvate dioxygenase-like |
| 230926_s_at | AK026966 | adenylate kinase 3-like 2 |
| 37549_g_at | NM_003364 | uridine phosphorylase 1 |
| 210828_s_at | H23979 | CD200 molecule |
| 222406_s_at | R45446 | Transcribed locus |
| 1553191_at | NM_022357 | dipeptidase 3 |
| 1554327_a_at | AF147790 | mucin 12, cell surface associated |
| 240983_s_at | NM_024645 | zinc finger, matrin type 4 |
| 212797_at | L40378 | serpin peptidase inhibitor, clade B (ovalbumin), member 9 |
| 209719_x_at | AL139377 | hypothetical protein LOC728591 |
| 1552641_s_at | NM_001464 | ADAM metallopeptidase domain 2 (fertilin beta) |
| 222501_s_at | NM_002119 | major histocompatibility complex, class II, DO alpha |
| 1552477_a_at | AB055704 | LIM homeobox 4 |
| 226876_at | AI936724 | Transcribed locus, weakly similar to XP_001114804.1 spectrin, beta, non-erythrocytic 1 isoform 4 [*Macaca mulatta*] |
| 210869_s_at | NM_002286 | lymphocyte-activation gene 3 |
| 237911_at | U19557 | serpin peptidase inhibitor, clade B (ovalbumin), member 4 |
| 215037_s_at | BC000740 | cholecystokinin B receptor |
| 206024_at | AL137145 | protein kinase C, theta |
| 224279_s_at | AL080170 | tripartite motif-containing 58 |
| 1553105_s_at | NM_003177 | spleen tyrosine kinase |
| 210022_at | BC005368 | zinc finger protein 649 |
| 223616_at | AC006539 | zinc finger protein 682 |
| 209629_s_at | NM_005712 | HERV-H LTR-associating 1 |
| 224037_at | NM_001944 | desmoglein 3 (pemphigus vulgaris antigen) |
| 91826_at | AL832535 | hypothetical protein LOC157627 |
| 216641_s_at | AI807681 | SH3 domain containing ring finger 2 |
| 218922_s_at | NM_006574 | chondroitin sulfate proteoglycan 5 (neuroglycan C) |
| 237872_at | R38389 | olfactomedin 1 |
| 203065_s_at | AF279779 | cholinergic receptor, muscarinic 3 /// similar to cholinergic receptor, muscarinic 3 |
| 228634_s_at | AW242668 | hypothetical LOC645321 |
| 234920_at | AK057525 | CDNA FLJ32963 fis, clone TESTI2008405 |
| 1553697_at | NM_022307 | islet cell autoantigen 1, 69 kDa |
| 217010_s_at | AV682679 | selenophosphate synthetase 1 |
| 202790_at | AB045118 | frequently rearranged in advanced T-cell lymphomas 2 |
| 211772_x_at | AW302207 | Transcribed locus |
| 219270_at | AW510925 | HRAS-like suppressor family, member 5 |
| 207087_x_at | BC013944 | spermatogenesis and oogenesis specific basic helix-loop-helix 2 |
| 213714_at | NM_005242 | coagulation factor II (thrombin) receptor-like 1 |
| 215649_s_at | NM_004615 | tetraspanin 7 |
| 214903_at | AF052167 | MRS2-like, magnesium homeostasis factor (*S. cerevisiae*) |
| 210455_at | NM_152476 | zinc finger protein 560 |
| 233827_s_at | AW268880 | Solute carrier family 25, member 13 (citrin) |
| 37547_at | NM_018931 | protocadherin beta 11 |
| 233638_s_at | AW166283 | protein phosphatase 2 (formerly 2A), regulatory subunit B, gamma isoform |
| 221035_s_at | Z39566 | zinc finger and BTB domain containing 46 |
| 1555609_a_at | R83905 | IBR domain containing 2 |
| 202779_s_at | NM_004532 | mucin 4, cell surface associated |
| 206336_at | AW139719 | Transcribed locus |
| 1554339_a_at | BF059512 | delta/notch-like EGF repeat containing |
| 217711_at | AK023446 | aminoadipate-semialdehyde synthase |
| 231011_at | NM_003027 | SH3-domain GRB2-like 3 |
| 206209_s_at | NM_013410 | adenylate kinase 3-like 1 /// adenylate kinase 3-like 2 /// similar to Adenylate kinase isoenzyme 4, mitochondrial (ATP-AMP transphosphorylase) |
| 209722_s_at | AK093656 | CDNA FLJ36337 fis, clone THYMU2006324 |
| 214369_s_at | NM_020662 | MRS2-like, magnesium homeostasis factor (*S. cerevisiae*) |
| 1552389_at | AF086401 | Full length insert cDNA clone ZD75H06 |
| 215913_s_at | L01087 | protein kinase C, theta |
| 201559_s_at | AA868267 | tripartite motif-containing 54 |
| 217234_s_at | W25881 | CDNA: FLJ21041 fis, clone CAE10652 |
| 209372_x_at | AI807356 | — |
| 218261_at | BF063271 | UDP-N-acetyl-alpha-D-galactosamine:polypeptide N-acetylgalactosaminyltransferase 3 (GalNAc-T3) |
| 217445_s_at | AW006735 | CD8a molecule |
| 205595_at | NM_023940 | RAS-like, family 11, member B |
| 233669_s_at | AF222694 | lectin, galactoside-binding, soluble, 12 (galectin 12) |

TABLE 15-continued

Table 15: Genes Expressed at a 5 fold or Greater Level in iPS Cell Lines versus both hES Cell Lines and Parental Fibroblasts (p ≦ 0.01)

| Systematic Name | Genbank | Description |
| --- | --- | --- |
| 1561330_at | U92817 | — |
| 234976_x_at | AW440392 | Hypothetical protein LOC342892 |
| 234085_at | AA824282 | CDNA clone IMAGE: 5296106 |
| 207540_s_at | NM_014901 | ring finger protein 44 |
| 208608_s_at | AF061785 | gamma-aminobutyric acid (GABA) A receptor, alpha 5 /// similar to gamma-aminobutyric acid (GABA) A receptor, alpha 5 |
| 207950_s_at | AF229180 | aminoadipate-semialdehyde synthase |
| 221981_s_at | AV723167 | synaptotagmin I |
| 206042_x_at | NM_000366 | tropomyosin 1 (alpha) |
| 210334_x_at | BI825302 | transmembrane protein 37 |
| 210206_s_at | AI554106 | polyhomeotic homolog 1 (Drosophila) |
| 226786_at | M61870 | zinc finger protein 90 |
| 211796_s_at | BC027940 | EPH receptor A7 |
| 216493_s_at | AY026481 | galactose-3-O-sulfotransferase 3 |
| 204806_x_at | BF438028 | Transcribed locus |
| 1556165_at | AI830823 | RNA-binding protein |
| 215047_at | AF115765 | artemin |
| 1552480_s_at | NM_000363 | troponin I type 3 (cardiac) |
| 205388_at | AB019490 | RAB GTPase activating protein 1-like |
| 228672_at | BF195936 | hypothetical LOC342979 |
| 205377_s_at | BC005161 | inhibin, beta E |
| 230633_at | BC014852 | interferon regulatory factor 6 |
| 207704_s_at | BF060667 | gap junction protein, beta 3, 31 kDa |
| 215668_s_at | U26744 | dystrobrevin, alpha |
| 212107_s_at | NM_021978 | suppression of tumorigenicity 14 (colon carcinoma) |
| 237282_s_at | NM_006103 | WAP four-disulfide core domain 2 |
| 220285_at | NM_002993 | chemokine (C—X—C motif) ligand 6 (granulocyte chemotactic protein 2) |
| 207979_s_at | AI208292 | chromosome 5 open reading frame 35 |
| 229881_at | BC003574 | T-cell leukemia/lymphoma 1A |
| 242162_at | NM_005490 | SH2 domain containing 3A |
| 207379_at | NM_004202 | thymosin, beta 4, Y-linked |
| 216981_x_at | AI452798 | myocardin |
| 224282_s_at | AY116207 | NLR family, pyrin domain containing 12 |
| 221051_s_at | NM_003260 | transducin-like enhancer of split 2 (E(sp1) homolog, Drosophila) |
| 221623_at | NM_000810 | gamma-aminobutyric acid (GABA) A receptor, alpha 5 |
| 206696_at | T15991 | — |
| 203990_s_at | AV731490 | synaptotagmin I |
| 233767_at | NM_001902 | cystathionase (cystathionine gamma-lyase) |
| 211681_s_at | Z83850 | Nik related kinase |
| 203234_at | AF243527 | kallikrein-related peptidase 5 |
| 208729_x_at | U63824 | TEA domain family member 4 |
| 206486_at | AF070580 | synaptotagmin II |
| 1558093_s_at | BC001606 | neutrophil cytosolic factor 2 (65 kDa, chronic granulomatous disease, autosomal 2) |
| 1555942_a_at | AI857639 | phorbol-12-myristate-13-acetate-induced protein 1 |
| 1555202_a_at | AB022433 | sema domain, transmembrane domain (TM), and cytoplasmic domain, (semaphorin) 6B |
| 229439_s_at | AI862542 | CDNA clone IMAGE: 4837650 |
| 209086_x_at | AL517395 | hypothetical protein BC004941 |
| 229440_at | BC002693 | spermatid perinuclear RNA binding protein |
| 1557918_s_at | U19556 | serpin peptidase inhibitor, clade B (ovalbumin), member 3 |
| 227358_at | NM_052836 | cadherin-like 23 |
| 203953_s_at | NM_003054 | solute carrier family 18 (vesicular monoamine), member 2 |
| 206769_at | H58488 | Transcribed locus |
| 242338_at | AA174083 | Clone IMAGE: 609847, mRNA sequence |
| 1554029_a_at | NM_003963 | transmembrane 4 L six family member 5 |
| 244171_at | AK000794 | — |
| 204431_at | AK025747 | fidgetin |
| 204891_s_at | NM_057162 | kelch-like 4 (Drosophila) |
| 203849_s_at | BG289314 | cadherin-like 26 |
| 234724_x_at | AF060924 | mitochondrial protein 18 kDa |
| 213665_at | AA608964 | Transcribed locus |
| 1552736_a_at | AI733281 | Transcribed locus |
| 211088_s_at | AK022644 | dysbindin (dystrobrevin binding protein 1) domain containing 1 |
| 1554576_a_at | BC001387 | HRAS-like suppressor 3 |
| 220354_at | NM_004426 | polyhomeotic homolog 1 (Drosophila) /// similar to polyhomeotic 1-like |
| 223821_s_at | NM_016323 | hect domain and RLD 5 |
| 227619_at | AL121753 | matrix metallopeptidase 24 (membrane-inserted) |
| 215984_s_at | AA401492 | GNAS complex locus |
| 1560228_at | NM_004432 | ELAV (embryonic lethal, abnormal vision, Drosophila)-like 2 (Hu antigen B) |
| 217552_s_at | NM_005071 | solute carrier family 1 (high affinity aspartate/glutamate transporter), member 6 |
| 214279_s_at | NM_018283 | nudix (nucleoside diphosphate linked moiety X)-type motif 15 |
| 1554952_s_at | NM_002235 | potassium voltage-gated channel, shaker-related subfamily, member 6 |
| 215313_x_at | NM_002090 | chemokine (C—X—C motif) ligand 3 |
| 237145_at | AF043179 | T cell receptor beta variable 19 /// T cell receptor beta variable 7-2 /// T cell receptor beta variable 5-4 /// T cell receptor beta variable 3-1 /// T cell receptor beta constant 1 |

TABLE 15-continued

Table 15: Genes Expressed at a 5 fold or Greater Level in iPS Cell Lines versus both hES Cell Lines and Parental Fibroblasts (p ≤ 0.01)

| Systematic Name | Genbank | Description |
|---|---|---|
| 1556348_at | AI613010 | F-box and leucine-rich repeat protein 16 |
| 201140_s_at | AA350425 | Similar to zinc finger protein 91 |
| 1556128_a_at | W48843 | sprouty homolog 4 (*Drosophila*) |
| 213810_s_at | NM_001149 | ankyrin 3, node of Ranvier (ankyrin G) |
| 226857_at | NM_002583 | PRKC, apoptosis, WT1, regulator |
| 1553257_at | BC009701 | peptidyl arginine deiminase, type II |
| 1559880_at | NM_001275 | chromogranin A (parathyroid secretory protein 1) |
| 1552849_at | NM_014289 | calpain 6 |
| 1552804_a_at | AF279774 | growth associated protein 43 |
| 1554689_a_at | NM_016510 | selenocysteine lyase |
| 1552580_at | AF482697 | clarin 1 |
| 237461_at | NM_002744 | protein kinase C, zeta |
| 1559954_s_at | NM_173549 | chromosome 8 open reading frame 47 |
| 219367_s_at | AW003107 | — |
| 207419_s_at | AK023059 | CDNA FLJ12997 fis, clone NT2RP3000247 |
| 201750_s_at | AU132789 | zinc finger protein 273 |
| 206907_at | AL139377 | spermatogenesis and oogenesis specific basic helix-loop-helix 2 /// hypothetical protein LOC728591 |
| 220756_s_at | AF097159 | UDP-Gal: betaGlcNAc beta 1,4-galactosyltransferase, polypeptide 6 |
| 223510_at | NM_022552 | DNA (cytosine-5-)-methyltransferase 3 alpha |
| 214671_s_at | AU131482 | solute carrier family 16, member 1 (monocarboxylic acid transporter 1) |
| 208750_s_at | AI738919 | ligand of numb-protein X 1 |
| 1554052_at | NM_012282 | KCNE1-like |
| 222234_s_at | NM_024037 | chromosome 1 open reading frame 135 |
| 221423_s_at | AF277724 | cell division cycle 25 homolog C (*S. pombe*) |
| 205528_s_at | NM_002450 | metallothionein 1X |
| 205531_s_at | BC037211 | hypothetical protein LOC283432 |
| 221162_at | NM_022154 | solute carrier family 39 (zinc transporter), member 8 |
| 203381_s_at | AF307451 | cat eye syndrome chromosome region, candidate 6 |
| 210001_s_at | AJ011414 | plexin B1 |
| 215509_s_at | AA522514 | KIAA0746 protein |
| 205174_s_at | NM_003740 | potassium channel, subfamily K, member 5 |
| 41037_at | NM_015894 | stathmin-like 3 |
| 206701_x_at | AA527080 | KIAA1727 protein |
| 205121_at | U87408 | Bardet-Biedl syndrome 9 |
| 1555106_a_at | AV722990 | protocadherin beta 15 |
| 214414_x_at | AK091113 | NPC-A-5 |
| 214390_s_at | AA894574 | FK506 binding protein 4, 59 kDa |
| 237810_at | NM_016365 | nebulette |
| 217441_at | BF971587 | tubulin, beta 2A /// tubulin, beta 2B |
| 1562022_s_at | NM_000573 | complement component (3b/4b) receptor 1 (Knops blood group) |
| 207279_s_at | AF096296 | chemokine (C-C motif) ligand 26 |
| 202400_s_at | AA825563 | Transcribed locus |
| 203798_s_at | BC006117 | L-2-hydroxyglutarate dehydrogenase |
| 230641_at | AI979334 | chromosome 12 open reading frame 35 |
| 221539_at | NM_017894 | zinc finger and SCAN domain containing 2 |
| 238716_at | NM_005059 | relaxin 2 |
| 223402_at | BC023610 | CDNA clone IMAGE: 4638753 |
| 209619_at | NM_003914 | cyclin A1 |
| 209949_at | AA329676 | CDNA FLJ45742 fis, clone KIDNE2016327 |
| 243354_at | NM_004720 | endothelial differentiation, lysophosphatidic acid G-protein-coupled receptor, 4 |
| 212953_x_at | AW450586 | family with sequence similarity 124A |
| 208949_s_at | NM_005110 | glutamine-fructose-6-phosphate transaminase 2 |
| 212647_at | AF136972 | protein phosphatase 1B (formerly 2C), magnesium-dependent, beta isoform |
| 231195_at | NM_006334 | olfactomedin 1 |
| 209995_s_at | AF393369 | adaptor-related protein complex 1, sigma 3 subunit |
| 242422_at | AI758697 | zinc finger protein 493 |
| 209569_x_at | AA524029 | chromosome 9 open reading frame 61 |
| 235235_s_at | NM_012099 | CD3e molecule, epsilon associated protein |
| 207043_s_at | AL043927 | tubulin tyrosine ligase-like family, member 4 |
| 228530_at | AI272059 | LOC401629 /// LOC401630 |
| 205184_at | NM_005314 | gastrin-releasing peptide receptor |
| 222871_at | NM_016089 | zinc finger protein 589 |
| 209772_s_at | R48779 | hypothetical protein BC008326 |
| 228570_at | AF007143 | Clone 23738 mRNA sequence |
| 1554751_at | AK098715 | CDNA FLJ25849 fis, clone TST08968 |
| 211392_s_at | D53659 | myotubularin related protein 7 |
| 213869_x_at | NM_000717 | carbonic anhydrase IV |
| 1555659_a_at | N33009 | apolipoprotein E |
| 1553156_at | AW451792 | COMM domain containing 7 |
| 227429_at | BC010432 | CDNA clone IMAGE: 3528357 |
| 212720_at | NM_001392 | dystrobrevin, alpha |
| 206442_at | BG328998 | glutamic pyruvate transaminase (alanine aminotransferase) 2 |
| 238959_at | AL040935 | BTB (POZ) domain containing 11 |
| 226281_at | AW292273 | cysteinyl-tRNA synthetase |

TABLE 15-continued

Table 15: Genes Expressed at a 5 fold or Greater Level in iPS Cell Lines versus both hES Cell Lines and Parental Fibroblasts (p ≤ 0.01)

| Systematic Name | Genbank | Description |
|---|---|---|
| 223385_at | AF393369 | adaptor-related protein complex 1, sigma 3 subunit |
| 217996_at | NM_018932 | protocadherin beta 12 |
| 220010_at | AI683694 | EF-hand calcium binding domain 4A |
| 237217_at | NM_002915 | replication factor C (activator 1) 3, 38 kDa |
| 1556854_at | AW139618 | synapsin II |
| 239012_at | NM_003213 | TEA domain family member 4 |
| 1555618_s_at | NM_145019 | family with sequence similarity 124A |
| 218707_at | AI971618 | inhibitor of growth family, member 5 |
| 1564494_s_at | NM_005958 | melatonin receptor 1A |
| 205262_at | AF095784 | gamma-aminobutyric acid (GABA) B receptor, 2 |
| 208352_x_at | AW268880 | solute carrier family 25, member 13 (citrin) |
| 204326_x_at | AB040903 | regulator of chromosome condensation 2 |
| 201201_at | H90656 | nicotinamide nucleotide adenylyltransferase 2 |
| 219885_at | NM_004561 | ovo-like 1 (*Drosophila*) |
| 236070_at | BF663141 | villin 2 (ezrin) |
| 212142_at | AW966474 | sushi domain containing 3 |
| 204452_s_at | NM_024595 | chromosome 1 open reading frame 108 |
| 1553328_a_at | NM_022804 | small nuclear ribonucleoprotein polypeptide N /// SNRPN upstream reading frame |
| 205899_at | NM_004346 | caspase 3, apoptosis-related cysteine peptidase |
| 234842_at | NM_003236 | transforming growth factor, alpha |
| 1570253_a_at | NM_012168 | F-box protein 2 |
| 1559057_at | NM_016941 | delta-like 3 (*Drosophila*) |
| 207850_at | AI219073 | EPS8-like 1 |
| 205204_at | NM_001254 | cell division cycle 6 homolog (*S. cerevisiae*) |
| 218075_at | BE896137 | DCP2 decapping enzyme homolog (*S. cerevisiae*) |
| 213022_s_at | AA928939 | transmembrane protein 63C |
| 210039_s_at | NM_004931 | CD8b molecule |
| 215758_x_at | AL136179 | SRY (sex determining region Y)-box 4 |
| 1554397_s_at | NM_000148 | fucosyltransferase 1 (galactoside 2-alpha-L-fucosyltransferase, H blood group) |
| 219165_at | AB012043 | calcium channel, voltage-dependent, T type, alpha 1G subunit |
| 217110_s_at | AA588400 | ovo-like 1 (*Drosophila*) |
| 203879_at | BF438407 | zinc finger protein 551 |
| 221098_x_at | AL163202 | similar to zinc finger protein 43 (HTF6) |
| 218533_s_at | M98528 | DNA segment on chromosome 4 (unique) 234 expressed sequence |
| 218178_s_at | NM_012261 | chromosome 20 open reading frame 103 |
| 208980_s_at | M28880 | ankyrin 1, erythrocytic |
| 206961_at | AF199015 | villin 2 (ezrin) |
| 202307_s_at | NM_032785 | ATP/GTP binding protein-like 4 |
| 219735_s_at | NM_022006 | FXYD domain containing ion transport regulator 7 |
| 228800_x_at | U77949 | cell division cycle 6 homolog (*S. cerevisiae*) |
| 225103_at | NM_173549 | chromosome 8 open reading frame 47 |
| 223074_s_at | AF277724 | cell division cycle 25 homolog C (*S. pombe*) |
| 233348_at | AC003682 | zinc finger protein interacting with K protein 1 homolog (mouse) |
| 220158_at | AF498927 | Rho GDP dissociation inhibitor (GDI) beta |
| 1559701_s_at | BF594294 | TEK tyrosine kinase, endothelial (venous malformations, multiple cutaneous and mucosal) |
| 223392_s_at | NM_013447 | egf-like module containing, mucin-like, hormone receptor-like 2 |
| 203331_s_at | AE000659 | T-cell receptor alpha-chain pseudogene mRNA, clone HAP60 (V-alpha-1.1 family) |
| 1569022_a_at | NM_018093 | WD repeat domain 74 |
| 1555467_a_at | AF255647 | transmembrane protein 163 |
| 225868_at | AA906413 | BC038740 |
| 240982_at | NM_003097 | small nuclear ribonucleoprotein polypeptide N /// SNRPN upstream reading frame |
| 238315_s_at | NM_005738 | ADP-ribosylation factor-like 4A |
| 215708_at | AF231021 | NLR family, pyrin domain containing 12 |
| 205007_s_at | BF446578 | RasGEF domain family, member 1A |
| 201742_x_at | NM_017965 | solute carrier family 7, (neutral amino acid transporter, y+ system) member 10 |
| 1554374_at | BC004940 | naked cuticle homolog 2 (*Drosophila*) |
| 1560303_at | AI813438 | desmoglein 3 (pemphigus vulgaris antigen) |
| 219468_s_at | AA496034 | BAI1-associated protein 2-like 1 |
| 219875_s_at | NM_000558 | hemoglobin, alpha 1 /// hemoglobin, alpha 2 |
| 225608_at | NM_006426 | dihydropyrimidinase-like 4 |
| 200806_s_at | AB017332 | aurora kinase C |
| 201309_x_at | AK094809 | Ras protein-specific guanine nucleotide-releasing factor 2 |
| 241013_at | BG291649 | OCIA domain containing 2 |
| 1554586_a_at | AF332218 | protocadherin 11 X-linked /// protocadherin 11 Y-linked |
| 1553430_a_at | AF279900 | minichromosome maintenance complex component 7 |
| 205019_s_at | NM_025243 | solute carrier family 19, member 3 |
| 226955_at | AB011446 | aurora kinase B |
| 216458_at | AF136381 | sorbin and SH3 domain containing 1 |
| 204347_at | AF229053 | brevican |
| 214240_at | AF336127 | solute carrier family 4, sodium borate transporter, member 11 |
| 211656_x_at | BC006114 | cholinergic receptor, nicotinic, alpha 3 |
| 204395_s_at | AI205764 | chromosome 1 open reading frame 108 |
| 1554593_s_at | W92036 | proprotein convertase subtilisin/kexin type 9 |
| 224097_s_at | AF199015 | villin 2 (ezrin) |

TABLE 15-continued

Table 15: Genes Expressed at a 5 fold or Greater Level in iPS Cell Lines versus both hES Cell Lines and Parental Fibroblasts (p ≦ 0.01)

| Systematic Name | Genbank | Description |
|---|---|---|
| 204890_s_at | NM_006891 | crystallin, gamma D |
| 219121_s_at | S76738 | alkaline phosphatase, liver/bone/kidney |
| 225063_at | BC038538 | *Homo sapiens*, clone IMAGE: 5172739, mRNA |
| 202874_s_at | NM_004994 | matrix metallopeptidase 9 (gelatinase B, 92 kDa gelatinase, 92 kDa type IV collagenase) |
| 1554199_at | AC007204 | zinc finger protein 93 |
| 208206_s_at | BF509686 | chromosome 8 open reading frame 42 |
| 1554261_at | AI939470 | glutamate receptor, ionotropic, AMPA 2 |
| 1554752_a_at | BE671925 | Transcribed locus |
| 208868_s_at | NM_004252 | solute carrier family 9 (sodium/hydrogen exchanger), member 3 regulator 1 |
| 234238_at | D88357 | cell division cycle 2, G1 to S and G2 to M |
| 235149_at | AC005587 | similar to CTAGE family, member 5 |
| 215362_at | NM_018944 | chromosome 21 open reading frame 45 |
| 212529_at | AI333651 | frizzled homolog 7 (*Drosophila*) |
| 1570266_x_at | AI830073 | chromosome 1 open reading frame 88 |
| 202660_at | AI692696 | Transcribed locus |
| 202284_s_at | AL080057 | MRNA; cDNA DKFZp564D032 (from clone DKFZp564D032) |
| 209197_at | M29277 | melanoma cell adhesion molecule |
| 219463_at | NM_018891 | laminin, gamma 2 |
| 219513_s_at | AF114817 | zinc finger protein 589 |
| 202129_s_at | AL573851 | endothelial cell adhesion molecule |
| 223038_s_at | NM_002150 | 4-hydroxyphenylpyruvate dioxygenase |
| 229230_at | N64686 | chromosome 1 open reading frame 96 |
| 204281_at | NM_080923 | protein tyrosine phosphatase, receptor type, C |
| 219869_s_at | AW138134 | PHD finger protein 17 |
| 210357_s_at | BG255416 | KIAA0114 |
| 206119_at | AA921835 | hypothetical protein LOC283501 |
| 206445_s_at | NM_004595 | spermine synthase |
| 201812_s_at | NM_000041 | apolipoprotein E |
| 206946_at | BC042986 | CDNA clone IMAGE: 5296106 |
| 209774_x_at | NM_018139 | chromosome 14 open reading frame 104 |
| 1554384_at | NM_000238 | potassium voltage-gated channel, subfamily H (eag-related), member 2 |
| 209346_s_at | NM_024081 | proline rich Gla (G-carboxyglutamic acid) 4 (transmembrane) |
| 227641_at | NM_016629 | tumor necrosis factor receptor superfamily, member 21 |
| 205748_s_at | AB020676 | WW and C2 domain containing 1 |
| 208646_at | BF510581 | BTB (POZ) domain containing 11 |
| 205861_at | BG164358 | DEAD (Asp-Glu-Ala-Asp) box polypeptide 21 |
| 1557067_s_at | BC000729 | A kinase (PRKA) anchor protein 1 |
| 227171_at | NM_018087 | transmembrane protein 48 |
| 1558212_at | NM_018182 | chromosome 17 open reading frame 63 |
| 227733_at | AV753544 | phosphoglucomutase 2-like 1 |
| 231420_at | U85995 | Bardet-Biedl syndrome 9 |
| 201538_s_at | NM_001444 | fatty acid binding protein 5 (psoriasis-associated) /// similar to Fatty acid-binding protein, epidermal (E-FABP) (Psoriasis-associated fatty acid-binding protein homolog) (PA-FABP) |
| 212457_at | AF095771 | Bardet-Biedl syndrome 9 |
| 203163_at | NM_001786 | cell division cycle 2, G1 to S and G2 to M |
| 224334_s_at | AB055703 | LIM homeobox 4 |
| 201946_s_at | AI829603 | chromosome 13 open reading frame 3 |
| 205845_at | NM_018351 | FYVE, RhoGEF and PH domain containing 6 |
| 210038_at | NM_025151 | RAB11 family interacting protein 1 (class I) |
| 213932_x_at | NM_025047 | ADP-ribosylation factor-like 14 |
| 1562378_s_at | AI140752 | ubiquitously transcribed tetratricopeptide repeat, X chromosome |
| 214532_x_at | NM_017791 | feline leukemia virus subgroup C cellular receptor family, member 2 |
| 1555788_a_at | NM_007196 | kallikrein-related peptidase 8 |
| 242329_at | BE542381 | methionyl-tRNA synthetase 2, mitochondrial |
| 242387_at | NM_024785 | family with sequence similarity 124B |
| 222283_at | NM_021154 | phosphoserine aminotransferase 1 |
| 226094_at | BE645821 | cell adhesion molecule 4 |
| 239303_at | AI026919 | Transcribed locus |
| 227248_at | AI343600 | Transcribed locus |
| 206116_s_at | AK024583 | keratin, hair, basic, 5 |
| 209464_at | AF289220 | BCL2-like 12 (proline rich) |
| 222701_s_at | BF513674 | MRNA; cDNA DKFZp779C0742 (from clone DKFZp779C0742) |
| 210091_s_at | BC002652 | crumbs homolog 3 (*Drosophila*) |
| 231715_s_at | NM_004741 | nucleolar and coiled-body phosphoprotein 1 |
| 241172_at | NM_006086 | tubulin, beta 3 |
| 210008_s_at | NM_002394 | solute carrier family 3 (activators of dibasic and neutral amino acid transport), member 2 |
| 217644_s_at | AF426267 | chromosome 21 open reading frame 88 |
| 230675_at | U49396 | purinergic receptor P2X, ligand-gated ion channel, 5 |
| 65517_at | NM_005504 | branched chain aminotransferase 1, cytosolic |
| 222841_s_at | BC000258 | tubulin, delta 1 |

TABLE 15-continued

Table 15: Genes Expressed at a 5 fold or Greater Level in iPS Cell Lines versus both hES Cell Lines and Parental Fibroblasts ($p \leq 0.01$)

| Systematic Name | Genbank | Description |
| --- | --- | --- |
| 210291_s_at | NM_014285 | exosome component 2 |
| 239492_at | AI476267 | zinc finger protein 195 |
| 200894_s_at | AI761824 | zinc finger protein 398 |

TABLE 16

Table 16: Genes Expressed at a 5 fold or Greater Level in iPS Cell Lines versus hES Cell Lines ($p \leq 0.01$), but not Significantly Different from Parental Fibroblasts ($p \geq 0.05$)

| Systematic Name | Genbank | Description |
| --- | --- | --- |
| 217211_at | D50604 | similar to cytoplasmic beta-actin |
| 231723_at | NM_013346 | sorting nexin 12 |
| 228371_s_at | BF196007 | — |
| 215172_at | AL050040 | protein tyrosine phosphatase, non-receptor type 20B /// protein tyrosine phosphatase, non-receptor type 20A |
| 225088_at | BG546917 | chromosome 16 open reading frame 63 |
| 223994_s_at | BC000154 | solute carrier family 12 (potassium/chloride transporters), member 9 |
| 1554660_a_at | BC036200 | chromosome 1 open reading frame 71 |
| 1554334_a_at | BC031044 | DnaJ (Hsp40) homolog, subfamily A, member 4 |
| 1555197_a_at | AY039243 | chromosome 21 open reading frame 58 |
| 220472_at | NM_014150 | zinc finger, CCHC domain containing 4 |
| 213014_at | BG222394 | mitogen-activated protein kinase 8 interacting protein 1 |
| 1554795_a_at | BC019895 | filamin binding LIM protein 1 |
| 232132_at | AB043635 | par-6 partitioning defective 6 homolog gamma (*C. elegans*) |
| 206749_at | NM_001764 | CD1b molecule |
| 213426_s_at | AA150110 | Caveolin 2 |
| 223318_s_at | BC004393 | alkB, alkylation repair homolog 7 (*E. coli*) |
| 221310_at | NM_004115 | fibroblast growth factor 14 |
| 211513_s_at | AF172449 | opioid growth factor receptor |
| 211527_x_at | M27281 | vascular endothelial growth factor A |
| 1560154_a_at | AK026500 | CDNA: FLJ22847 fis, clone KAIA686 |
| 205196_s_at | NM_001283 | adaptor-related protein complex 1, sigma 1 subunit |
| 200954_at | NM_001694 | ATPase, H+ transporting, lysosomal 16 kDa, V0 subunit c |
| 208067_x_at | NM_007125 | ubiquitously transcribed tetratricopeptide repeat gene, Y-linked |
| 224241_s_at | BC002350 | — |
| 200621_at | NM_004078 | cysteine and glycine-rich protein 1 |
| 205095_s_at | NM_005177 | ATPase, H+ transporting, lysosomal V0 subunit a1 |
| 222546_s_at | AW204755 | EPS8-like 2 |
| 206832_s_at | NM_004186 | sema domain, immunoglobulin domain (Ig), short basic domain, secreted, (semaphorin) 3F |
| 1552470_a_at | NM_148914 | abhydrolase domain containing 11 |
| 220259_at | NM_024927 | pleckstrin homology domain containing, family H (with MyTH4 domain) member 3 |
| 220426_at | NM_024059 | chromosome 20 open reading frame 195 |
| 213597_s_at | BF002474 | CTD (carboxy-terminal domain, RNA polymerase II, polypeptide A) small phosphatase-like |
| 1555220_a_at | AB040820 | aldo-keto reductase family 1, member C-like 2 |
| 219430_at | NM_020155 | G protein-coupled receptor 137 |
| 233492_s_at | AC005587 | olfactory receptor, family 2, subfamily A, member 4 /// olfactory receptor, family 2, subfamily A, member 7 /// similar to rho guanine nucleotide exchange factor 5 |
| 231146_at | AI300541 | family with sequence similarity 24, member B |
| 243936_x_at | T85061 | — |
| 232498_at | AK023386 | hypothetical protein KIAA1833 |
| 211823_s_at | D86862 | paxillin |
| 231243_s_at | R93946 | basic helix-loop-helix domain containing, class B, 3 |
| 235854_x_at | AA167669 | Rho-associated, coiled-coil containing protein kinase 1 |
| 215634_at | AF007137 | Clone 23618 mRNA sequence |
| 226983_at | AA626717 | zinc finger protein 777 |
| 1569076_a_at | BE791720 | FLJ16287 protein |
| 208894_at | M60334 | major histocompatibility complex, class II, DR alpha |
| 208430_s_at | NM_001390 | dystrobrevin, alpha |
| 210171_s_at | S68134 | cAMP responsive element modulator |
| 1552528_at | NM_058189 | chromosome 21 open reading frame 69 |
| 1568905_at | BC030750 | CDNA clone IMAGE: 4795773 |
| 214520_at | NM_005251 | forkhead box C2 (MFH-1, mesenchyme forkhead 1) |
| 217248_s_at | AL365343 | solute carrier family 7 (cationic amino acid transporter, y+ system), member 8 |
| 1558214_s_at | BG330076 | catenin (cadherin-associated protein), alpha 1, 102 kDa |
| 213160_at | D86964 | dedicator of cytokinesis 2 |
| 210978_s_at | BC002616 | transgelin 2 |
| 214878_at | AU118165 | zinc finger protein 37A /// zinc finger protein 37B |
| 240703_s_at | AW591969 | hect (homologous to the E6-AP (UBE3A) carboxyl terminus) domain and RCC1 (CHC1)-like domain (RLD) 1 |

TABLE 16-continued

Table 16: Genes Expressed at a 5 fold or Greater Level in iPS Cell Lines versus hES Cell Lines (p ≦ 0.01), but not Significantly Different from Parental Fibroblasts (p ≧ 0.05)

| Systematic Name | Genbank | Description |
| --- | --- | --- |
| 204698_at | NM_002201 | interferon stimulated exonuclease gene 20 kDa |
| 205822_s_at | NM_002130 | 3-hydroxy-3-methylglutaryl-Coenzyme A synthase 1 (soluble) |
| 1558809_s_at | AK094324 | hypothetical protein LOC284408 |
| 1569486_at | BC035176 | CDNA clone IMAGE: 5266012 |
| 241168_at | AV651242 | Transcribed locus |
| 216205_s_at | AK021947 | mitofusin 2 |
| 205810_s_at | NM_003941 | Wiskott-Aldrich syndrome-like |
| 206396_at | NM_004170 | solute carrier family 1 (neuronal/epithelial high affinity glutamate transporter, system Xag), member 1 |
| 216710_x_at | AL359578 | zinc finger protein 287 |
| 243323_s_at | AI872979 | AT-binding transcription factor 1 |
| 229284_at | R60683 | Methionine adenosyltransferase II, beta |
| 238699_s_at | AI659225 | calcium/calmodulin-dependent serine protein kinase (MAGUK family) |
| 217767_at | NM_000064 | similar to Complement C3 precursor |
| 205924_at | BC005035 | RAB3B, member RAS oncogene family |
| 224301_x_at | BC003602 | H2A histone family, member J |
| 206932_at | NM_003956 | cholesterol 25-hydroxylase |
| 222419_x_at | AW205983 | ubiquitin-conjugating enzyme E2H (UBC8 homolog, yeast) |
| 216501_at | U25801 | Vac14 homolog (*S. cerevisiae*) |
| 233421_s_at | AU146738 | nucleoporin 133 kDa |
| 202627_s_at | AL574210 | serpin peptidase inhibitor, clade E (nexin, plasminogen activator inhibitor type 1), member 1 |
| 205867_at | NM_002834 | protein tyrosine phosphatase, non-receptor type 11 (Noonan syndrome 1) |
| 204480_s_at | NM_024112 | chromosome 9 open reading frame 16 |
| 206026_at | NM_007115 | tumor necrosis factor, alpha-induced protein 6 |
| 222678_s_at | BF057821 | DCN1, defective in cullin neddylation 1, domain containing 1 (*S. cerevisiae*) |
| 220246_at | NM_020397 | calcium/calmodulin-dependent protein kinase ID |
| 208677_s_at | AL550657 | basigin (Ok blood group) |
| 206997_s_at | NM_004807 | heparan sulfate 6-O-sulfotransferase 1 /// similar to Heparan-sulfate 6-O-sulfotransferase 1 (HS6ST-1) |
| 213807_x_at | BE870509 | met proto-oncogene (hepatocyte growth factor receptor) |
| 211187_at | AF118079 | — |
| 236940_at | W60647 | Transcribed locus, weakly similar to NP_066953.1 isomerase A isoform 1 [*Homo sapiens*] |
| 224505_s_at | BC006355 | phospholipase C, delta 4 |
| 205210_at | NM_004257 | transforming growth factor, beta receptor associated protein 1 |
| 206025_s_at | AW188198 | tumor necrosis factor, alpha-induced protein 6 |
| 238461_at | AA228031 | eukaryotic translation initiation factor 4E family member 3 |
| 224003_at | AF332243 | testis-specific transcript, Y-linked 14 |
| 1553685_s_at | NM_138473 | Sp1 transcription factor |
| 1561039_a_at | BC039609 | zinc finger protein 81 |
| 235136_at | BF337528 | ORM1-like 3 (*S. cerevisiae*) |
| 205117_at | X59065 | fibroblast growth factor 1 (acidic) |
| 213643_s_at | AK022846 | inositol polyphosphate-5-phosphatase, 75 kDa |
| 225322_s_at | AL514147 | chromosome 17 open reading frame 70 |
| 232506_s_at | AK026504 | chromosome 15 open reading frame 41 |
| AFFX-r2-P1-cre-3_at | AFFX-TrpnX-5 | — |
| 221220_s_at | NM_017988 | SCY1-like 2 (*S. cerevisiae*) |
| 224127_at | AF116660 | — |
| 215876_at | AK022254 | CDNA FLJ12192 fis, clone MAMMA1000851 |
| 205195_at | NM_001283 | adaptor-related protein complex 1, sigma 1 subunit |
| 1563809_a_at | AK094768 | MCF.2 cell line derived transforming sequence-like |
| 238480_at | AI871745 | Chromosome 18 open reading frame 50 |
| 206673_at | NM_007223 | G protein-coupled receptor 176 |
| 206100_at | NM_001874 | carboxypeptidase M |
| 231299_at | AI494590 | centaurin, gamma 3 |
| 202793_at | NM_005768 | membrane bound O-acyltransferase domain containing 5 |
| 205925_s_at | NM_002867 | RAB3B, member RAS oncogene family |
| 204522_at | NM_005510 | dom-3 homolog Z (*C. elegans*) |
| 233543_s_at | AK021582 | coiled-coil domain containing 98 |
| 233573_s_at | AK001080 | WD repeat domain 6 |
| 242552_x_at | AW274047 | zinc finger, BED-type containing 5 |
| 232566_at | AK026258 | nucleolar protein family 6 (RNA-associated) |
| 202859_x_at | NM_000584 | interleukin 8 |
| 231396_s_at | AA776721 | family with sequence similarity 126, member A |
| 1557787_at | BC038734 | CDNA clone IMAGE: 5267718 |
| 232343_at | AK022200 | CDNA FLJ12138 fis, clone MAMMA1000331 |
| 238025_at | AA706818 | mixed lineage kinase domain-like |
| 210256_s_at | U78576 | phosphatidylinositol-4-phosphate 5-kinase, type I, alpha |
| 239959_x_at | AI147520 | — |
| 227175_at | AI806486 | Myeloid cell leukemia sequence 1 (BCL2-related) |
| 223708_at | AF329838 | C1q and tumor necrosis factor related protein 4 |
| 1554417_s_at | AY113699 | anterior pharynx defective 1 homolog A (*C. elegans*) |
| 217300_at | U80771 | — |
| 234688_x_at | AF141344 | centrobin, centrosomal BRCA2 interacting protein |

TABLE 16-continued

Table 16: Genes Expressed at a 5 fold or Greater Level in iPS Cell Lines versus hES Cell Lines (p ≦ 0.01), but not Significantly Different from Parental Fibroblasts (p ≧ 0.05)

| Systematic Name | Genbank | Description |
| --- | --- | --- |
| 210935_s_at | AF274954 | WD repeat domain 1 |
| 201048_x_at | NM_002869 | RAB6A, member RAS oncogene family |
| 209208_s_at | AF059752 | mannose-P-dolichol utilization defect 1 |
| 219168_s_at | NM_017701 | proline rich 5 (renal) |
| 201045_s_at | BF513857 | RAB6A, member RAS oncogene family /// RAB6C-like |
| 219878_s_at | NM_015995 | Kruppel-like factor 13 |
| 223143_s_at | AI742378 | chromosome 6 open reading frame 166 |
| 212575_at | BF966155 | chromosome 19 open reading frame 6 |
| 210930_s_at | AF177761 | v-erb-b2 erythroblastic leukemia viral oncogene homolog 2, neuro/glioblastoma derived oncogene homolog (avian) |
| 217270_s_at | AC005393 | dual-specificity tyrosine-(Y)-phosphorylation regulated kinase 1B |
| AFFX-r2-Ec-bioD-3_at | AFFX-ThrX-M | — |
| 210994_x_at | AF230398 | tripartite motif-containing 23 |
| 222511_x_at | AW140098 | Fas (TNFRSF6) associated factor 1 |
| 208262_x_at | NM_000243 | Mediterranean fever |
| AFFX-HSAC07/X00351_5_at | AFFX-HSAC07/X00351_5 | actin, beta |
| AFFX-hum_alu_at | AFFX-r2-Bs-lys-M | — |
| 237806_at | AI684717 | Hypothetical protein LOC729296 |
| 211599_x_at | U19348 | met proto-oncogene (hepatocyte growth factor receptor) |
| 1554544_a_at | L18865 | myelin basic protein |
| 235913_at | AI285722 | zinc finger-like |
| 231957_s_at | AC005594 | dipeptidyl-peptidase 9 |
| 210421_s_at | AB014602 | solute carrier family 24 (sodium/potassium/calcium exchanger), member 1 |
| 243319_at | AI274981 | Transcribed locus |
| 220825_s_at | NM_018240 | kin of IRRE like (*Drosophila*) |
| 1563719_a_at | AK024924 | CDNA: FLJ21271 fis, clone COL01751 |
| 234155_at | AK024928 | CDNA: FLJ21275 fis, clone COL01827 |
| 213210_at | AI005317 | TAF6-like RNA polymerase II, p300/CBP-associated factor (PCAF)-associated factor, 65 kDa |
| 230257_s_at | AI264325 | chromosome 1 open reading frame 19 |
| 236657_at | AW014647 | Full length insert cDNA YI37C01 |
| 236771_at | AW511485 | chromosome 6 open reading frame 159 |
| 1552649_a_at | NM_057178 | ring finger and FYVE-like domain containing 1 |
| 225245_x_at | BG386566 | H2A histone family, member J |
| 228261_at | BE045549 | mindbomb homolog 2 (*Drosophila*) |
| 1566666_at | AK074225 | CDNA FLJ23645 fis, clone COL02691 |
| 207686_s_at | NM_001228 | caspase 8, apoptosis-related cysteine peptidase |
| 224321_at | AB004064 | transmembrane protein with EGF-like and two follistatin-like domains 2 |
| 201169_s_at | BG326045 | basic helix-loop-helix domain containing, class B, 2 |
| 207678_s_at | NM_007017 | SRY (sex determining region Y)-box 30 |
| 1555724_s_at | BC010946 | transgelin |
| 228901_at | AI040910 | Cyclin-dependent kinase 9 (CDC2-related kinase) |
| 223083_s_at | AW057545 | egl nine homolog 2 (*C. elegans*) |
| 1562080_at | AK057351 | CDNA FLJ32789 fis, clone TESTI2002326 |
| AFFX-r2-P1-cre-5_at | AFFX-TrpnX-M | — |
| 210971_s_at | AB000815 | aryl hydrocarbon receptor nuclear translocator-like |
| 219298_at | NM_024693 | enoyl Coenzyme A hydratase domain containing 3 |
| 222814_s_at | AI916361 | zinc finger, HIT type 2 |
| 217246_s_at | L22650 | diaphanous homolog 2 (*Drosophila*) |
| 1560224_at | BF327463 | AT hook containing transcription factor 1 |
| 217448_s_at | AL117508 | TOX high mobility group box family member 4 /// similar to Epidermal Langerhans cell protein LCP1 |
| 200841_s_at | AI142677 | glutamyl-prolyl-tRNA synthetase |
| 211087_x_at | Z25432 | mitogen-activated protein kinase 14 |
| 1552717_s_at | NM_153243 | centrosomal protein 170 kDa /// centrosomal protein 170 kDa-like |
| 241084_x_at | BF062339 | dynein, cytoplasmic 1, heavy chain 1 |
| 1555559_s_at | AF419247 | ubiquitin specific peptidase 25 |
| 203890_s_at | BF686824 | death-associated protein kinase 3 |
| 223393_s_at | AL136805 | teashirt zinc finger homeobox 3 |
| 224805_s_at | BF508824 | chromosome 15 open reading frame 17 |
| AFFX-LysX-M_at | AFFX-LysX-5 | — |
| 227071_at | AI762558 | zinc finger protein 414 |
| 216788_at | AK025564 | CDNA: FLJ21911 fis, clone HEP03855 |
| 205081_at | NM_001311 | cysteine-rich protein 1 (intestinal) |
| 203626_s_at | NM_005983 | S-phase kinase-associated protein 2 (p45) |
| 211613_s_at | U79250 | glycerol-3-phosphate dehydrogenase 2 (mitochondrial) |
| 219703_at | NM_018365 | meiosis-specific nuclear structural 1 |
| 238420_at | AV721958 | CDNA clone IMAGE: 5263531 |
| 205186_at | NM_003462 | dynein, axonemal, light intermediate chain 1 |
| 214975_s_at | AK001816 | myotubularin related protein 1 |
| 215585_at | AK024081 | KIAA0174 |
| 204994_at | NM_002463 | myxovirus (influenza virus) resistance 2 (mouse) |
| 202017_at | NM_000120 | epoxide hydrolase 1, microsomal (xenobiotic) |

TABLE 16-continued

Table 16: Genes Expressed at a 5 fold or Greater Level in iPS Cell Lines versus hES Cell Lines (p ≦ 0.01), but not Significantly Different from Parental Fibroblasts (p ≧ 0.05)

| Systematic Name | Genbank | Description |
| --- | --- | --- |
| 222509_s_at | BG490634 | zinc finger protein 672 |
| 228683_s_at | AI925361 | potassium channel tetramerisation domain containing 15 |
| 208978_at | U36190 | cysteine-rich protein 2 |
| 243952_at | BF000009 | TPTE pseudogene |
| 235940_at | AW983691 | chromosome 9 open reading frame 64 |
| 222085_at | AW452357 | Hypothetical gene supported by AK075564; BC060873 |
| 229746_x_at | BF439451 | *Homo sapiens*, clone IMAGE: 3885733, mRNA |
| 1553219_a_at | NM_015365 | Alport syndrome, mental retardation, midface hypoplasia and elliptocytosis chromosomal region, gene 1 |
| 1559028_at | BC037172 | chromosome 21 open reading frame 15 |
| 205390_s_at | NM_000037 | ankyrin 1, erythrocytic |
| 1554988_at | BC042592 | solute carrier family 9, member 11 |
| 205065_at | AU130282 | — |
| 1555569_a_at | BC042482 | potassium channel tetramerisation domain containing 7 |
| 226632_at | AL513673 | cytoglobin |
| 210732_s_at | AF342816 | lectin, galactoside-binding, soluble, 8 (galectin 8) |
| AFFX-r2-Bs-dap-3_at | AFFX-r2-Bs-phe-3 | — |
| 213087_s_at | BF690020 | CDNA clone IMAGE: 4838699 |
| 221638_s_at | AF008937 | syntaxin 16 |
| 213211_s_at | AI005317 | TAF6-like RNA polymerase II, p300/CBP-associated factor (PCAF)-associated factor, 65 kDa |
| 238848_at | BF750565 | OTU domain containing 4 |
| 229328_at | T90358 | Zinc finger protein 540 |
| 1553962_s_at | BI668074 | ras homolog gene family, member B |
| 238013_at | BF347859 | pleckstrin homology domain containing, family A (phosphoinositide binding specific) member 2 |
| 205382_s_at | NM_001928 | complement factor D (adipsin) |
| 222711_s_at | AI761828 | rhomboid 5 homolog 1 (*Drosophila*) |
| 1567274_at | Z36814 | — |
| 224346_at | AF116671 | — |
| 219058_x_at | NM_022164 | tubulointerstitial nephritis antigen-like 1 |
| 234939_s_at | AL161953 | PHD finger protein 12 |
| 217524_x_at | AA018923 | Transcribed locus |
| 214190_x_at | AI799984 | golgi associated, gamma adaptin ear containing, ARF binding protein 2 |
| 228208_x_at | AL134573 | Hypothetical LOC645944 |
| 239664_at | H18857 | Transcribed locus |
| 237211_x_at | AA860341 | MORN repeat containing 3 |
| 203402_at | AL520102 | potassium voltage-gated channel, shaker-related subfamily, beta member 2 |
| 1555766_a_at | AF493870 | guanine nucleotide binding protein (G protein), gamma 2 |
| 202873_at | BF034973 | ATPase, H+ transporting, lysosomal 42 kDa, V1 subunit C1 |
| 205577_at | NM_005609 | phosphorylase, glycogen; muscle (McArdle syndrome, glycogen storage disease type V) |
| 213928_s_at | AI742626 | HIV-1 Rev binding protein |
| 200601_at | U48734 | actinin, alpha 4 |
| 216549_s_at | AL096712 | TBC1 domain family, member 22B |
| 211564_s_at | BC003096 | PDZ and LIM domain 4 |
| 221418_s_at | NM_005481 | mediator complex subunit 16 |
| 210933_at | BC004908 | fascin homolog 1, actin-bundling protein (*Strongylocentrotus purpuratus*) |
| 210585_s_at | AF007748 | transportin 2 (importin 3, karyopherin beta 2b) |
| 203726_s_at | NM_000227 | laminin, alpha 3 |
| 224795_x_at | AW575927 | immunoglobulin kappa constant /// immunoglobulin kappa variable 1-5 /// immunoglobulin kappa variable 2-24 |
| 231354_at | AW510748 | hypothetical LOC780529 |
| AFFX-r2-Ec-bioC-5_at | AFFX-ThrX-5 | — |
| 1552367_a_at | AF276507 | scinderin |
| 201796_s_at | BE790854 | valyl-tRNA synthetase |
| 206847_s_at | AF026397 | homeobox A7 |
| 225333_at | AI218383 | zinc finger protein 496 |
| 211514_at | AF068286 | receptor interacting protein kinase 5 |
| 1560316_s_at | N32168 | glucocorticoid induced transcript 1 |
| 232315_at | AU149712 | Zinc finger-like |
| 221628_s_at | AF326966 | cytokine-like nuclear factor n-pac |
| 239623_at | N93197 | hypothetical gene supported by AK126569 |
| AFFX-DapX-5_at | AFFX-DapX-5 | — |
| 238542_at | AA831769 | UL16 binding protein 2 |
| 200628_s_at | M61715 | tryptophanyl-tRNA synthetase |
| 231881_at | AU145225 | caldesmon 1 |
| 233754_x_at | AC007228 | zinc finger protein 71 |
| 61734_at | AI797684 | reticulocalbin 3, EF-hand calcium binding domain |
| 215955_x_at | Y10388 | Rho GTPase activating protein 26 |
| 201979_s_at | NM_006247 | protein phosphatase 5, catalytic subunit |
| 213767_at | U43586 | kinase suppressor of ras 1 |
| 87100_at | AI832249 | abhydrolase domain containing 2 |
| 1562234_a_at | AF397731 | neuron navigator 3 /// similar to neuron navigator 3 |

TABLE 16-continued

Table 16: Genes Expressed at a 5 fold or Greater Level in iPS Cell Lines versus hES Cell Lines (p ≤ 0.01), but not Significantly Different from Parental Fibroblasts (p ≥ 0.05)

| Systematic Name | Genbank | Description |
| --- | --- | --- |
| 230309_at | BE876610 | Transcribed locus |
| 1558247_s_at | BC021210 | hypothetical protein BC018697 |
| 205462_s_at | NM_002149 | hippocalcin-like 1 |
| 221440_s_at | NM_006606 | retinoblastoma binding protein 9 |
| 206488_s_at | NM_000072 | CD36 molecule (thrombospondin receptor) |
| 223661_at | AF130080 | — |
| 211019_s_at | D63807 | lanosterol synthase (2,3-oxidosqualene-lanosterol cyclase) |
| 211811_s_at | AF152484 | protocadherin alpha 6 |
| 1562527_at | AF519622 | hypothetical protein LOC283027 |
| 1569895_at | BC016994 | Homo sapiens, clone IMAGE: 4401848, mRNA |
| 231402_at | AI830201 | Transcribed locus, strongly similar to XP_531081.2 hypothetical protein [Pan troglodytes] |
| 1567105_at | AF362887 | — |
| 209555_s_at | M98399 | CD36 molecule (thrombospondin receptor) |
| 227137_at | N25937 | Chromosome 10 open reading frame 46 |
| 212937_s_at | M20776 | collagen, type VI, alpha 1 |
| 1560090_at | BC043583 | DnaJ (Hsp40) homolog, subfamily C, member 13 |
| 214040_s_at | BE675337 | gelsolin (amyloidosis, Finnish type) |
| 201465_s_at | BC002646 | jun oncogene |
| 234625_at | AK025055 | CDNA: FLJ21402 fis, clone COL03734 |
| 1554466_a_at | BC007207 | chromosome 16 open reading frame 13 |
| 208721_s_at | BF967271 | anaphase promoting complex subunit 5 |
| 213667_at | AB002307 | Snf2-related CBP activator protein |
| 231151_at | AL122010 | discs, large (Drosophila) homolog-associated protein 3 |
| 1552610_a_at | NM_002227 | Janus kinase 1 (a protein tyrosine kinase) |
| 1565347_s_at | AY034078 | transcription factor binding to IGHM enhancer 3 |
| 209261_s_at | BF000629 | nuclear receptor subfamily 2, group F, member 6 |
| AFFX-r2-Bs-dap-M_at | AFFX-r2-Bs-phe-M | — |
| 242948_x_at | T97602 | Transcribed locus |
| 214300_s_at | AI676092 | topoisomerase (DNA) III alpha |
| 1556748_x_at | AI476341 | CDNA FLJ39784 fis, clone SPLEN2002314 |
| 1562244_at | AL833487 | MRNA; cDNA DKFZp686H1629 (from clone DKFZp686H1629) |
| 244735_at | AI377758 | coiled-coil domain containing 54 |
| 215581_s_at | AK022303 | minichromosome maintenance complex component 3 associated protein |
| 1555240_s_at | AF493879 | guanine nucleotide binding protein (G protein), gamma 12 |
| 216971_s_at | Z54367 | plectin 1, intermediate filament binding protein 500 kDa |
| 234971_x_at | AI521584 | phospholipase C, delta 3 |
| 212938_at | M20776 | collagen, type VI, alpha 1 |
| 230404_at | AI418538 | — |
| 210298_x_at | AF098518 | four and a half LIM domains 1 |
| 204952_at | NM_014400 | LY6/PLAUR domain containing 3 |
| 232915_at | AW571715 | DEAD (Asp-Glu-Ala-Asp) box polypeptide 49 |
| 243358_at | BF347362 | insulin-like growth factor 1 receptor |
| 225061_at | N45231 | DnaJ (Hsp40) homolog, subfamily A, member 4 |
| 218154_at | NM_024736 | gasdermin domain containing 1 |
| 203324_s_at | NM_001233 | caveolin 2 |
| 1554757_a_at | AF273055 | inositol polyphosphate-5-phosphatase, 40 kDa |
| 242676_at | AA401733 | Transcribed locus |
| 1569039_s_at | BC029855 | zinc finger protein 677 |
| 221048_x_at | NM_017941 | chromosome 17 open reading frame 80 |
| 1553042_a_at | NM_032721 | T-cell activation NFKB-like protein |
| 218944_at | NM_023078 | pyrroline-5-carboxylate reductase-like |
| 204638_at | NM_001611 | acid phosphatase 5, tartrate resistant |
| 241611_s_at | BE675600 | fibronectin type III domain containing 3A |
| 222363_at | AW979018 | Transcribed locus |
| 201008_s_at | AA812232 | thioredoxin interacting protein |
| 224252_s_at | AF177940 | FXYD domain containing ion transport regulator 5 |
| 225800_at | AI990891 | JAZF zinc finger 1 |
| 240407_at | AW450035 | Homo sapiens, clone IMAGE: 5171705, mRNA |
| 200796_s_at | BF594446 | myeloid cell leukemia sequence 1 (BCL2-related) |
| 214992_s_at | AD000092 | deoxyribonuclease II, lysosomal |
| 209373_at | BC003179 | mal, T-cell differentiation protein-like |
| 212272_at | AA813260 | lipin 1 |
| 242571_at | AW962020 | RALBP1 associated Eps domain containing 2 |
| 215019_x_at | AW474158 | zinc finger protein 528 |
| 211668_s_at | K03226 | plasminogen activator, urokinase |
| 204876_at | NM_014699 | zinc finger protein 646 |
| 201167_x_at | D13989 | Rho GDP dissociation inhibitor (GDI) alpha |
| 211672_s_at | AF019888 | actin related protein 2/3 complex, subunit 4, 20 kDa |
| 212003_at | BG171020 | chromosome 1 open reading frame 144 |
| 217465_at | AK001291 | NCK-associated protein 1 |
| 236340_at | AI769947 | Transcribed locus, strongly similar to XP_001146557.1 hypothetical protein [Pan troglodytes] |
| 226504_at | AA522720 | family with sequence similarity 109, member B |
| 219899_x_at | NM_014434 | NADPH dependent diflavin oxidoreductase 1 |

TABLE 16-continued

Table 16: Genes Expressed at a 5 fold or Greater Level in iPS Cell Lines versus hES Cell Lines (p ≦ 0.01), but not Significantly Different from Parental Fibroblasts (p ≧ 0.05)

| Systematic Name | Genbank | Description |
| --- | --- | --- |
| 1567013_at | AF323119 | nuclear factor (erythroid-derived 2)-like 2 |
| 203348_s_at | BF060791 | ets variant gene 5 (ets-related molecule) |
| 215315_at | AC003682 | zinc finger protein 549 |
| 209062_x_at | AF010227 | nuclear receptor coactivator 3 |
| 1555229_a_at | BC007010 | complement component 1, s subcomponent |
| 203508_at | NM_001066 | tumor necrosis factor receptor superfamily, member 1B |
| 217494_s_at | AF023139 | phosphatase and tensin homolog (mutated in multiple advanced cancers 1), pseudogene 1 |
| 210362_x_at | AF230409 | promyelocytic leukemia |
| 201060_x_at | AI537887 | stomatin |
| 204560_at | NM_004117 | FK506 binding protein 5 |
| 236574_at | AI304870 | Hypothetical protein LOC284373 |
| 222542_x_at | BF724826 | chaperone, ABC1 activity of bc1 complex homolog (*S. pombe*) |
| 211162_x_at | AF116616 | stearoyl-CoA desaturase (delta-9-desaturase) |
| 203771_s_at | AA740186 | biliverdin reductase A |
| 217569_x_at | AA017093 | — |
| 240397_x_at | AI801626 | Transcribed locus |
| 207080_s_at | NM_004160 | peptide YY |
| 213695_at | L48516 | paraoxonase 3 |
| 216591_s_at | AF080579 | succinate dehydrogenase complex, subunit C, integral membrane protein, 15 kDa /// hCG1776980 |
| 1554464_a_at | BC008745 | cartilage associated protein |
| 201971_s_at | NM_001690 | ATPase, H+ transporting, lysosomal 70 kDa, V1 subunit A |
| AFFX-r2-Bs-dap-5_at | AFFX-r2-Bs-phe-5 | — |
| 215337_at | AK022508 | mediator complex subunit 24 |
| 227806_at | BG285710 | chromosome 16 open reading frame 74 |
| 216271_x_at | AC004794 | synapse defective 1, Rho GTPase, homolog 1 (*C. elegans*) |
| 212113_at | AI927479 | hypothetical LOC552889 |
| 230517_at | AI416964 | similar to GLI-Kruppel family member HKR1 |
| 214123_s_at | AI126492 | chromosome 4 open reading frame 10 |
| 219360_s_at | NM_017636 | transient receptor potential cation channel, subfamily M, member 4 |
| 205715_at | NM_004334 | bone marrow stromal cell antigen 1 |
| 1558775_s_at | AU142380 | neutral sphingomyelinase (N-SMase) activation associated factor |
| 1558423_at | BE715671 | hypothetical LOC349114 |
| 218510_x_at | AI816291 | family with sequence similarity 134, member B |
| 205457_at | NM_024294 | chromosome 6 open reading frame 106 |
| 214446_at | NM_012081 | elongation factor, RNA polymerase II, 2 |
| 210449_x_at | AF100544 | mitogen-activated protein kinase 14 |
| 1552667_a_at | NM_005489 | SH2 domain containing 3C |
| 205827_at | NM_000729 | cholecystokinin |
| 231004_s_at | BE219961 | H1 histone family, member X |
| 220102_at | NM_023067 | forkhead box L2 |
| 222387_s_at | BG476669 | vacuolar protein sorting 35 homolog (*S. cerevisiae*) |
| 211708_s_at | BC005807 | stearoyl-CoA desaturase (delta-9-desaturase) |
| 207453_s_at | NM_012266 | DnaJ (Hsp40) homolog, subfamily B, member 5 |
| 1568646_x_at | BC038199 | zinc finger protein 208 |
| 210932_s_at | AF293342 | ring finger protein (C3H2C3 type) 6 |
| 1559528_at | BC040652 | Polycomb group ring finger 3 |
| 225454_at | AW248770 | coiled-coil domain containing 124 |
| 230747_s_at | AA406435 | Chromosome 18 open reading frame 17 |
| 202226_s_at | NM_016823 | v-crk sarcoma virus CT10 oncogene homolog (avian) |
| 228881_at | N30347 | presenilin associated, rhomboid-like |
| 238969_at | BF512162 | chromosome 3 open reading frame 55 |
| 235234_at | AA359612 | FLJ36874 protein |
| 243409_at | AI005407 | forkhead box L1 |
| 202465_at | NM_002593 | procollagen C-endopeptidase enhancer |
| 211124_s_at | AF119835 | KIT ligand |
| 200948_at | NM_005439 | myeloid leukemia factor 2 |
| 204149_s_at | NM_000850 | glutathione S-transferase M4 |
| 217371_s_at | Y09908 | interleukin 15 |
| 218000_s_at | NM_007350 | pleckstrin homology-like domain, family A, member 1 |
| 211272_s_at | AF064771 | diacylglycerol kinase, alpha 80 kDa |
| 211266_s_at | U35399 | G protein-coupled receptor 4 |
| 205384_at | NM_005031 | FXYD domain containing ion transport regulator 1 (phospholemman) |
| 1553970_s_at | BC042510 | carboxyl ester lipase (bile salt-stimulated lipase) |
| 230146_s_at | BF111850 | frequenin homolog (*Drosophila*) |
| 1559409_a_at | BE893129 | KIAA1345 protein |
| 211561_x_at | L35253 | mitogen-activated protein kinase 14 |
| 220585_at | NM_025130 | hexokinase domain containing 1 |
| 234237_s_at | AL137611 | hypothetical protein FLJ20294 |
| 243110_x_at | AI868441 | neuropeptide W |
| 214014_at | W81196 | CDC42 effector protein (Rho GTPase binding) 2 |
| 215774_s_at | AV650470 | — |
| 203994_s_at | U84569 | chromosome 21 open reading frame 2 |
| 227419_x_at | AW964972 | placenta-specific 9 |

TABLE 16-continued

Table 16: Genes Expressed at a 5 fold or Greater Level in iPS Cell Lines versus hES Cell Lines (p ≦ 0.01), but not Significantly Different from Parental Fibroblasts (p ≧ 0.05)

| Systematic Name | Genbank | Description |
| --- | --- | --- |
| 206531_at | NM_004647 | D4, zinc and double PHD fingers family 1 |
| 208851_s_at | AL161958 | Thy-1 cell surface antigen |
| 201621_at | NM_005380 | neuroblastoma, suppression of tumorigenicity 1 |
| 231341_at | BE670584 | solute carrier family 35, member D3 |
| 214505_s_at | AF220153 | four and a half LIM domains 1 |
| 211027_s_at | BC006231 | inhibitor of kappa light polypeptide gene enhancer in B-cells, kinase beta |
| 201428_at | NM_001305 | claudin 4 |
| 211317_s_at | AF041461 | CASP8 and FADD-like apoptosis regulator |
| 216926_s_at | AC003030 | KIAA0892 |
| 221875_x_at | AW514210 | major histocompatibility complex, class I, F |
| 209213_at | BC002511 | carbonyl reductase 1 |
| 1552914_a_at | NM_025240 | CD276 molecule |
| 211530_x_at | M90686 | HLA-G histocompatibility antigen, class I, G |
| 1558697_a_at | BI600341 | KIAA0430 |
| 244852_at | AU119545 | dermatan sulfate epimerase-like |
| 226306_at | BF984592 | chromosome 6 open reading frame 1 |
| 221943_x_at | AW303136 | Ribosomal protein L38 |
| 204470_at | NM_001511 | chemokine (C—X—C motif) ligand 1 (melanoma growth stimulating activity, alpha) |
| 1552611_a_at | AL555086 | Janus kinase 1 (a protein tyrosine kinase) |
| 208879_x_at | BG469030 | PRP6 pre-mRNA processing factor 6 homolog (S. cerevisiae) |
| 209427_at | AF064238 | smoothelin |
| 1565162_s_at | D16947 | microsomal glutathione S-transferase 1 |
| 227841_at | BG260181 | Cementum protein 1 |
| 234773_x_at | AL442080 | MRNA; cDNA DKFZp434A0226 (from clone DKFZp434A0226) |
| 238750_at | AW083576 | chemokine (C-C motif) ligand 28 |
| 228251_at | BE467577 | UBX domain containing 1 |
| 206943_at | NM_004612 | transforming growth factor, beta receptor I (activin A receptor type II-like kinase, 53 kDa) |
| 226051_at | BF973568 | selenoprotein M |
| 202639_s_at | AI689052 | RAN binding protein 3 |
| 200756_x_at | U67280 | calumenin |
| 217399_s_at | AF032887 | forkhead box O3 |
| 1555730_a_at | D00682 | cofilin 1 (non-muscle) |
| 216831_s_at | AF018283 | runt-related transcription factor 1; translocated to, 1 (cyclin D-related) |
| 215719_x_at | X83493 | Fas (TNF receptor superfamily, member 6) |
| 233298_at | AL139377 | spermatogenesis and oogenesis specific basic helix-loop-helix 2 /// hypothetical protein LOC728591 |
| 215495_s_at | AL117523 | sterile alpha motif domain containing 4A |
| 218537_at | NM_017885 | host cell factor C1 regulator 1 (XPO1 dependent) |
| 201367_s_at | AI356398 | zinc finger protein 36, C3H type-like 2 |
| 223321_s_at | AF312678 | fibroblast growth factor receptor-like 1 |
| 203676_at | NM_002076 | glucosamine (N-acetyl)-6-sulfatase (Sanfilippo disease IIID) |
| AFFX-HUMISGF3A/M97935_5_at | AFFX-HUMISGF3A/M97935_5 | signal transducer and activator of transcription 1, 91 kDa |
| 232984_at | AL137259 | hydrocephalus inducing homolog (mouse) |
| 217601_at | AL523184 | nucleoporin 188 kDa |
| 238795_at | AA424537 | chromosome 10 open reading frame 18 |
| 222385_x_at | AF346602 | Sec61 alpha 1 subunit (S. cerevisiae) |
| 214971_s_at | AV695711 | ST6 beta-galactosamide alpha-2,6-sialyltranferase 1 |
| 202002_at | AW072302 | acetyl-Coenzyme A acyltransferase 2 (mitochondrial 3-oxoacyl-Coenzyme A thiolase) |
| 236491_at | AI813346 | BCL2-like 10 (apoptosis facilitator) |
| 231721_at | AF356518 | junctional adhesion molecule 3 |
| 220234_at | NM_004056 | carbonic anhydrase VIII |
| 213548_s_at | BG257762 | CDV3 homolog (mouse) |
| 1554321_a_at | BC018471 | NFS1 nitrogen fixation 1 homolog (S. cerevisiae) |
| 231805_at | AL563031 | prolactin releasing hormone receptor |
| 1555006_at | BC036233 | WD repeat domain 66 |
| 221889_at | AW026481 | potassium channel tetramerisation domain containing 13 |
| 201156_s_at | AF141304 | RAB5C, member RAS oncogene family |
| 1554383_a_at | BC028121 | translocation associated membrane protein 2 |
| 210079_x_at | U16953 | potassium voltage-gated channel, shaker-related subfamily, beta member 1 |
| 219558_at | NM_024524 | ATPase type 13A3 |
| 220889_s_at | NM_020178 | carbonic anhydrase X |
| 227488_at | AV728999 | hypothetical protein MGC16121 |
| 221762_s_at | AL162458 | chromosome 20 open reading frame 67 |
| 209727_at | M76477 | GM2 ganglioside activator |
| 76897_s_at | AA628140 | FK506 binding protein 15, 133 kDa |

TABLE 17

Human Oct3/4 Amino Acid Substitution Matrix
(Predictions Based on PMUT Analysis)
(Sequences disclosed as SEQ ID NO: 66)

| WT Position | | Sequence | Number of Predicted Deleterious Mutations | Number of Predicted Neutral Mutations |
|---|---|---|---|---|
| M | 1 | M G A P V I L F S C T N Q H Y W D E K R | 4 | 16 |
| A | 2 | M G A P V I L F S C T N Q H Y W D E K R | 9 | 11 |
| G | 3 | M G A P V I L F S C T N Q H Y W D E K R | 7 | 13 |
| H | 4 | M G A P V I L F S C T N Q H Y W D E K R | 5 | 15 |
| L | 5 | M G A P V I L F S C T N Q H Y W D E K R | 6 | 14 |
| A | 6 | M G A P V I L F S C T N Q H Y W D E K R | 15 | 5 |
| S | 7 | M G A P V I L F S C T N Q H Y W D E K R | 4 | 16 |
| D | 8 | M G A P V I L F S C T N Q H Y W D E K R | 5 | 15 |
| F | 9 | M G A P V I L F S C T N Q H Y W D E K R | 15 | 5 |
| A | 10 | M G A P V I L F S C T N Q H Y W D E K R | 11 | 9 |
| F | 11 | M G A P V I L F S C T N Q H Y W D E K R | 5 | 15 |
| S | 12 | M G A P V I L F S C T N Q H Y W D E K R | 7 | 13 |
| P | 13 | M G A P V I L F S C T N Q H Y W D E K R | 5 | 15 |
| P | 14 | M G A P V I L F S C T N Q H Y W D E K R | 6 | 14 |
| P | 15 | M G A P V I L F S C T N Q H Y W D E K R | 2 | 18 |
| G | 16 | M G A P V I L F S C T N Q H Y W D E K R | 10 | 10 |
| G | 17 | M G A P V I L F S C T N Q H Y W D E K R | 6 | 14 |
| G | 18 | M G A P V I L F S C T N Q H Y W D E K R | 15 | 5 |
| G | 19 | M G A P V I L F S C T N Q H Y W D E K R | 6 | 14 |
| D | 20 | M G A P V I L F S C T N Q H Y W D E K R | 6 | 14 |
| G | 21 | M G A P V I L F S C T N Q H Y W D E K R | 14 | 6 |
| P | 22 | M G A P V I L F S C T N Q H Y W D E K R | 5 | 15 |
| G | 23 | M G A P V I L F S C T N Q H Y W D E K R | 4 | 16 |
| G | 24 | M G A P V I L F S C T N Q H Y W D E K R | 13 | 7 |
| P | 25 | M G A P V I L F S C T N Q H Y W D E K R | 5 | 15 |
| E | 26 | M G A P V I L F S C T N Q H Y W D E K R | 8 | 12 |
| P | 27 | M G A P V I L F S C T N Q H Y W D E K R | 6 | 14 |
| G | 28 | M G A P V I L F S C T N Q H Y W D E K R | 7 | 13 |
| W | 29 | M G A P V I L F S C T N Q H Y W D E K R | 14 | 6 |
| V | 30 | M G A P V I L F S C T N Q H Y W D E K R | 6 | 14 |
| D | 31 | M G A P V I L F S C T N Q H Y W D E K R | 13 | 7 |
| P | 32 | M G A P V I L F S C T N Q H Y W D E K R | 2 | 18 |
| R | 33 | M G A P V I L F S C T N Q H Y W D E K R | 15 | 5 |
| T | 34 | M G A P V I L F S C T N Q H Y W D E K R | 7 | 13 |
| W | 35 | M G A P V I L F S C T N Q H Y W D E K R | 15 | 5 |
| L | 36 | M G A P V I L F S C T N Q H Y W D E K R | 5 | 15 |

TABLE 17-continued

Human Oct3/4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| S | 37 | M G A P V I L F S C T N Q H Y W D E K R | 11 | 9 |
| F | 38 | M G A P V I L F S C T N Q H Y W D E K R | 3 | 17 |
| Q | 39 | M G A P V I L F S C T N Q H Y W D E K R | 11 | 9 |
| G | 40 | M G A P V I L F S C T N Q H Y W D E K R | 12 | 8 |
| P | 41 | M G A P V I L F S C T N Q H Y W D E K R | 10 | 10 |
| P | 42 | M G A P V I L F S C T N Q H Y W D E K R | 10 | 10 |
| G | 43 | M G A P V I L F S C T N Q H Y W D E K R | 10 | 10 |
| G | 44 | M G A P V I L F S C T N Q H Y W D E K R | 5 | 15 |
| P | 45 | M G A P V I L F S C T N Q H Y W D E K R | 11 | 9 |
| G | 46 | M G A P V I L F S C T N Q H Y W D E K R | 8 | 12 |
| I | 47 | M G A P V I L F S C T N Q H Y W D E K R | 5 | 15 |
| G | 48 | M G A P V I L F S C T N Q H Y W D E K R | 4 | 16 |
| P | 49 | M G A P V I L F S C T N Q H Y W D E K R | 4 | 16 |
| G | 50 | M G A P V I L F S C T N Q H Y W D E K R | 10 | 10 |
| V | 51 | M G A P V I L F S C T N Q H Y W D E K R | 2 | 18 |
| G | 52 | M G A P V I L F S C T N Q H Y W D E K R | 2 | 18 |
| P | 53 | M G A P V I L F S C T N Q H Y W D E K R | 5 | 15 |
| G | 54 | M G A P V I L F S C T N Q H Y W D E K R | 7 | 13 |
| S | 55 | M G A P V I L F S C T N Q H Y W D E K R | 8 | 12 |
| E | 56 | M G A P V I L F S C T N Q H Y W D E K R | 8 | 12 |
| V | 57 | M G A P V I L F S C T N Q H Y W D E K R | 5 | 15 |
| W | 58 | M G A P V I L F S C T N Q H Y W D E K R | 14 | 6 |
| G | 59 | M G A P V I L F S C T N Q H Y W D E K R | 14 | 6 |
| I | 60 | M G A P V I L F S C T N Q H Y W D E K R | 3 | 17 |
| P | 61 | M G A P V I L F S C T N Q H Y W D E K R | 5 | 15 |
| P | 62 | M G A P V I L F S C T N Q H Y W D E K R | 3 | 17 |
| C | 63 | M G A P V I L F S C T N Q H Y W D E K R | 5 | 15 |
| P | 64 | M G A P V I L F S C T N Q H Y W D E K R | 6 | 14 |
| P | 65 | M G A P V I L F S C T N Q Y W D E K R | 4 | 16 |
| P | 66 | M G A P V I L F S C T N Q Y W D E K R | 6 | 14 |
| Y | 67 | M G A P V I L F S C T N Q H Y W D E K R | 5 | 15 |
| E | 68 | M G A P V I L F S C T N Q H Y W D E K R | 7 | 13 |
| F | 69 | M G A P V I L F S C T N Q H Y W D E K R | 4 | 16 |
| C | 70 | M G A P V I L F S C T N Q H Y W D E K R | 6 | 14 |
| G | 71 | M G A P V I L F S C T N Q H Y W D E K R | 2 | 18 |

TABLE 17-continued

Human Oct3/4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| G | 72 | M G A P V I L F S C T N Q H Y W D E K R | 15 | 5 |
| M | 73 | M G A P V I L F S C T N Q H Y W D E K R | 8 | 12 |
| A | 74 | M G A P V I L F S C T N Q H Y W D E K R | 13 | 7 |
| Y | 75 | M G A P V I L F S C T N Q H Y W D E K R | 0 | 20 |
| C | 76 | M G A V I L F S C T N Q H Y W D E K R | 6 | 14 |
| G | 77 | M G A P V I L F S C T N Q H Y W D E K R | 8 | 12 |
| P | 78 | M G A P V I L F S C T N Q H Y W D E K R | 3 | 17 |
| Q | 79 | M G A P V I L F S C T N Q H Y W D E K R | 1 | 19 |
| V | 80 | M G A P V I L F S C T N Q H Y W D E K R | 6 | 14 |
| G | 81 | M G A P V I L F S C T N Q H Y W D E K R | 5 | 15 |
| V | 82 | M G A P V I L F S C T N Q H Y W D E K R | 4 | 16 |
| G | 83 | M G A P V I L F S C T N Q H Y W D E K R | 15 | 5 |
| L | 84 | M G A P V I L F S C T N Q H Y W D E K R | 1 | 19 |
| V | 85 | M G A P V I L F S C T N Q H Y W D E K R | 4 | 16 |
| P | 86 | M G A P V I L F S C T N Q H Y W D E K R | 6 | 14 |
| Q | 87 | M G A P V I L F S C T N Q H Y W D E K R | 2 | 18 |
| G | 88 | M G A P V I L F S C T N Q H Y W D E K R | 11 | 9 |
| G | 89 | M G A P V I L F S C T N Q H Y W D E K R | 7 | 13 |
| L | 90 | M G A P V I L F S C T N Q H Y W D E K R | 0 | 20 |
| E | 91 | M G A P V I L F S C T N Q H Y W D E K R | 5 | 15 |
| T | 92 | M G A P V I L F S C T N Q H Y W D E K R | 10 | 10 |
| S | 93 | M G A P V I L F S C T N Q H Y W D E K R | 12 | 8 |
| Q | 94 | M G A P V I L F S C T N Q H Y W D E K R | 5 | 15 |
| P | 95 | M G A P V I L F S C T N Q H Y W D E K R | 5 | 15 |
| E | 96 | M G A P V I L F S C T N Q H Y W D E K R | 8 | 12 |
| G | 97 | M G A P V I L F S C T N Q H Y W D E K R | 8 | 12 |
| E | 98 | M G A P V I L F S C T N Q H Y W D E K R | 10 | 10 |
| A | 99 | M G A P V I L F S C T N Q H Y W D E K R | 11 | 9 |
| G | 100 | M G A P V I L F S C T N Q H Y W D E K R | 7 | 13 |
| V | 101 | M G A P V I L F S C T N Q H Y W D E K R | 0 | 20 |
| G | 102 | M G A P V I L F S C T N Q H Y W D E K R | 8 | 12 |
| V | 103 | M G A P V I L F S C T N Q H Y W D E K R | 6 | 14 |
| E | 104 | M G A P V I L F S C T N Q H Y W D E K R | 8 | 12 |
| S | 105 | M G A P V I L F S C T N Q H Y W D E K R | 10 | 10 |
| N | 106 | M G A P V I L F S C T N Q H Y W D E K R | 6 | 14 |
| S | 107 | M G A P V I L F S C T N Q H Y W D E K R | 15 | 5 |

TABLE 17-continued

Human Oct3/4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| D | 108 | M G A P V I L F S C T N Q H Y W D E K R | 4 | 16 |
| G | 109 | M G A P V I L F S C T N Q H Y W D E K R | 1 | 19 |
| A | 110 | M G A P V I L F S C T N Q H Y W D E K R | 11 | 9 |
| S | 111 | M G A P V I L F S C T N Q H Y W D E K R | 5 | 15 |
| P | 112 | M G A P V I L F S C T N Q H Y W D E K R | 2 | 18 |
| E | 113 | M G A P V I L F S C T N Q H Y Y W D E K R | 6 | 14 |
| P | 114 | M G A P V I L F S C T N Q H Y W D E K R | 6 | 14 |
| C | 115 | M G A P V I L F S C T N Q H Y W D E K R | 9 | 11 |
| T | 116 | M G A P V I L F S C T N Q H Y W D E K R | 6 | 14 |
| V | 117 | M G A P V I L F S C T N Q H Y W D E K R | 4 | 16 |
| T | 118 | M G A P V I L F S C T N Q H Y Y W D E K R | 7 | 13 |
| P | 119 | M G A P V I L F S C T N Q H Y W D E K R | 4 | 16 |
| G | 120 | M G A P V I L F S C T N Q H Y W D E K R | 12 | 8 |
| A | 121 | M G A P V I L F S C T N Q H Y W D E K R | 14 | 6 |
| V | 122 | M G A P V I L F S C T N Q H Y W D E K R | 5 | 15 |
| K | 123 | M G A P V I L F S C T N Q H Y W D E K R | 13 | 7 |
| L | 124 | M G A P V I L F S C T N Q H Y W D E K R | 8 | 12 |
| E | 125 | M G A P V I L F S C T N Q H Y W D E K R | 4 | 16 |
| K | 126 | M G A P V I L F S C T N Q H Y W D E K R | 10 | 10 |
| E | 127 | M G A P V I L F S C T N Q H Y W D E K R | 8 | 12 |
| K | 128 | M G A P V I L F S C T N Q H Y W D E K R | 12 | 8 |
| L | 129 | M G A P V I L F S C T N Q H Y W D E K R | 3 | 17 |
| E | 130 | M G A P V I L F S C T N Q H Y W D E K R | 8 | 12 |
| Q | 131 | M G A P V I L F S C T N Q H Y W D E K R | 10 | 10 |
| N | 132 | M G A P V I L F S C T N Q H Y W D E K R | 5 | 15 |
| P | 133 | M G A P V I L F S C T N Q H Y W D E K R | 7 | 13 |
| E | 134 | M G A P V I L F S C T N Q H Y W D E K R | 9 | 11 |
| E | 135 | M G A P V I L F S C T N Q H Y W D E K R | 10 | 10 |
| S | 136 | M G A P V I L F S C T N Q H Y W D E K R | 11 | 9 |
| Q | 137 | M G A P V I L F S C T N Q H Y W D E K R | 7 | 13 |
| D | 138 | M G A P V I L F S C T N Q H Y W D E K R | 4 | 16 |
| I | 139 | M G A P V I L F S C T N Q H Y W D E K R | 4 | 16 |
| K | 140 | M G A P V I L F S C T N Q H Y W D E K R | 13 | 7 |
| A | 141 | M G A P V I L F S C T N Q H Y W D E K R | 9 | 11 |
| L | 142 | M G A P V I L F S C T N Q H Y W D E K R | 2 | 18 |

TABLE 17-continued

Human Oct3/4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| Q | 143 | M G A P V I L F S C T N Q H Y W D E K R | 9 | 11 |
| K | 144 | M G A P V I L F S C T N Q H Y W D E K R | 12 | 8 |
| E | 145 | M G A P V I L F S C T N Q H Y W D E K R | 9 | 11 |
| L | 146 | M G A P V I L F S C T N Q H Y W D E K R | 2 | 18 |
| E | 147 | M G A P V I L F S C T N Q H Y W D E K R | 9 | 11 |
| Q | 148 | M G A P V I L F S C T N Q H Y W D E K R | 12 | 8 |
| F | 149 | M G A P V I L F S C T N Q H Y W D E K R | 8 | 12 |
| A | 150 | M G A P V I L F S C T N Q H Y W D E K R | 13 | 7 |
| K | 151 | M G A P V I L F S C T N Q H Y W D E K R | 16 | 4 |
| L | 152 | M G A P V I L F S C T N Q H Y W D E K R | 5 | 15 |
| L | 153 | M G A P V I L F S C T N Q H Y W D E K R | 5 | 15 |
| K | 154 | M G A P V I L F S C T N Q H Y W D E K R | 17 | 3 |
| Q | 155 | M G A P V I L F S C T N Q H Y W D E K R | 9 | 11 |
| K | 156 | M G A P V I L F S C T N Q H Y W D E K R | 16 | 4 |
| R | 157 | M G A P V I L F S C T N Q H Y W D E K R | 16 | 4 |
| I | 158 | M G A P V I L F S C T N Q H Y W D E K R | 7 | 13 |
| T | 159 | M G A P V I L F S C T N Q H Y W D E K R | 8 | 12 |
| L | 160 | M G A P V I L F S C T N Q H Y W D E K R | 3 | 17 |
| G | 161 | M G A P V I L F S C T N Q H Y W D E K R | 3 | 17 |
| Y | 162 | M G A P V I L F S C T N Q H Y W D E K R | 9 | 11 |
| T | 163 | M G A P V I L F S C T N Q H Y W D E K R | 11 | 9 |
| Q | 164 | M G A P V I L F S C T N Q H Y W D E K R | 13 | 7 |
| A | 165 | M G A P V I L F S C T N Q H Y W D E K R | 6 | 14 |
| D | 166 | M G A P V I L F S C T N Q H Y W D E K R | 6 | 14 |
| V | 167 | M G A P V I L F S C T N Q H Y W D E K R | 13 | 7 |
| G | 168 | M G A P V I L F S C T N Q H Y W D E K R | 17 | 3 |
| L | 169 | M G A P V I L F S C T N Q H Y W D E K R | 1 | 19 |
| T | 170 | M G A P V I L F S C T N Q H Y W D E K R | 11 | 9 |
| L | 171 | M G A P V I L F S C T N Q H Y W D E K R | 1 | 19 |
| G | 172 | M G A P V I L F S C T N Q H Y W D E K R | 8 | 12 |
| V | 173 | M G A P V I L F S C T N Q H Y W D E K R | 4 | 16 |
| L | 174 | M G A P V I L F S C T N Q H Y W D E K R | 2 | 18 |
| F | 175 | M G A P V I L F S C T N Q H Y W D E K R | 5 | 15 |
| G | 176 | M G A P V I L F S C T N Q H Y W D E K R | 13 | 7 |
| K | 177 | M G A P V I L F S C T N Q H Y W D E K R | 15 | 5 |
| V | 178 | M G A P V I L F S C T N Q H Y W D E K R | 7 | 13 |

TABLE 17-continued

Human Oct3/4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| F | 179 | M G A P V I L F S C T N Q H Y W D E K R | 8 | 12 |
| S | 180 | M G A P V I L F S C T N Q H Y W D E K R | 12 | 8 |
| Q | 181 | M G A P V I L F S C T N Q H Y W D E K R | 14 | 6 |
| T | 182 | M G A P V I L F S C T N Q H Y W D E K R | 11 | 9 |
| T | 183 | M G A P V I L F S C T N Q H Y W D E K R | 9 | 11 |
| I | 184 | M G A P V I L F S C T N Q H Y W D E K R | 9 | 11 |
| C | 185 | M G A P V I L F S C T N Q H Y W D E K R | 17 | 3 |
| R | 186 | M G A P V I L F S C T N Q H Y W D E K R | 17 | 3 |
| F | 187 | M G A P V I L F S C T N Q H Y W D E K R | 13 | 7 |
| E | 188 | M G A P V I L F S C T N Q H Y W D E K R | 13 | 7 |
| A | 189 | M G A P V I L F S C T N Q H Y W D E K R | 11 | 9 |
| L | 190 | M G A P V I L F S C T N Q H Y W D E K R | 2 | 18 |
| Q | 191 | M G A P V I L F S C T N Q H Y W D E K R | 13 | 7 |
| L | 192 | M G A P V I L F S C T N Q H Y W D E K R | 4 | 16 |
| S | 193 | M G A P V I L F S C T N Q H Y W D E K R | 10 | 10 |
| F | 194 | M G A P V I L F S C T N Q H Y W D E K R | 7 | 13 |
| K | 195 | M G A P V I L F S C T N Q H Y W D E K R | 15 | 5 |
| N | 196 | M G A P V I L F S C T N Q H Y W D E K R | 16 | 4 |
| M | 197 | M G A P V I L F S C T N Q H Y W D E K R | 12 | 8 |
| C | 198 | M G A P V I L F S C T N Q H Y W D E K R | 14 | 6 |
| K | 199 | M G A P V I L F S C T N Q H Y Y W D E K R | 9 | 11 |
| L | 200 | M G A P V I L F S C T N Q H Y W D E K R | 12 | 8 |
| R | 201 | M G A P V I L F S C T N Q H Y W D E K R | 18 | 2 |
| P | 202 | M G A P V I L F S C T N Q H Y W D E K R | 16 | 4 |
| L | 203 | M G A P V I L F S C T N Q H Y W D E K R | 8 | 12 |
| L | 204 | M G A P V I L F S C T N Q H Y W D E K R | 9 | 11 |
| Q | 205 | M G A P V I L F S C T N Q H Y W D E K R | 6 | 14 |
| K | 206 | M G A P V I L F S C T N Q H Y W D E K R | 15 | 5 |
| W | 207 | M G A P V I L F S C T N Q H Y W D E K R | 18 | 2 |
| V | 208 | M G A P V I L F S C T N Q H Y W D E K R | 13 | 7 |
| E | 209 | M G A P V I L F S C T N Q H Y W D E K R | 12 | 8 |
| E | 210 | M G A P V I L F S C T N Q H Y W D E K R | 16 | 4 |
| A | 211 | M G A P V I L F S C T N Q H Y W D E K R | 17 | 3 |
| D | 212 | M G A P V I L F S C T N Q H Y W D E K R | 12 | 8 |
| N | 213 | M G A P V I L F S C T N Q H Y W D E K R | 15 | 5 |

TABLE 17-continued

Human Oct3/4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| N | 214 | M G A P V I L F S C T N Q H Y W D E K R | 8 | 12 |
| E | 215 | M G A P V I L F S C T N Q H Y W D E K R | 5 | 15 |
| N | 216 | M G A P V I L F S C T N Q H Y W D E K R | 18 | 2 |
| L | 217 | M G A P V I L F S C T N Q H Y W D E K R | 10 | 10 |
| Q | 218 | M G A P V I L F S C T N Q H Y W D E K R | 12 | 8 |
| E | 219 | M G A P V I L F S C T N Q H Y W D E K R | 5 | 15 |
| I | 220 | M G A P V I L F S C T N Q H Y W D E K R | 12 | 8 |
| C | 221 | M G A P V I L F S C T N Q H Y W D E K R | 17 | 3 |
| K | 222 | M G A P V I L F S C T N Q H Y W D E K R | 13 | 7 |
| A | 223 | M G A P V I L F S C T N Q H Y W D E K R | 6 | 14 |
| E | 224 | M G A P V I L F S C T N Q H Y W D E K R | 13 | 7 |
| T | 225 | M G A P V I L F S C T N Q H Y W D E K R | 11 | 9 |
| L | 226 | M G A P V I L F S C T N Q H Y W D E K R | 7 | 13 |
| V | 227 | M G A P V I L F S C T N Q H Y W D E K R | 6 | 14 |
| Q | 228 | M G A P V I L F S C T N Q H Y W D E K R | 18 | 2 |
| A | 229 | M G A P V I L F S C T N Q H Y W D E K R | 15 | 5 |
| R | 230 | M G A P V I L F S C T N Q H Y W D E K R | 18 | 2 |
| K | 231 | M G A P V I L F S C T N Q H Y W D E K R | 14 | 6 |
| R | 232 | M G A P V I L F S C T N Q H Y W D E K R | 18 | 2 |
| K | 233 | M G A P V I L F S C T N Q H Y W D E K R | 8 | 12 |
| R | 234 | M G A P V I L F S C T N Q H Y W D E K R | 18 | 2 |
| T | 235 | M G A P V I L F S C T N Q H Y W D E K R | 11 | 9 |
| S | 236 | M G A P V I L F S C T N Q H Y W D E K R | 15 | 5 |
| I | 237 | M G A P V I L F S C T N Q H Y W D E K R | 13 | 7 |
| E | 238 | M G A P V I L F S C T N Q H Y W D E K R | 9 | 11 |
| N | 239 | M G A P V I L F S C T N Q H Y W D E K R | 14 | 6 |
| R | 240 | M G A P V I L F S C T N Q H Y W D E K R | 18 | 2 |
| V | 241 | M G A P V I L F S C T N Q H Y W D E K R | 11 | 9 |
| R | 242 | M G A P V I L F S C T N Q H Y W D E K R | 18 | 2 |
| G | 243 | M G A P V I L F S C T N Q H Y W D E K R | 15 | 5 |
| N | 244 | M G A P V I L F S C T N Q H Y W D E K R | 19 | 1 |
| L | 245 | M G A P V I L F S C T N Q H Y W D E K R | 10 | 10 |
| E | 246 | M G A P V I L F S C T N Q H Y W D E K R | 13 | 7 |
| N | 247 | M G A P V I L F S C T N Q H Y W D E K R | 16 | 4 |
| L | 248 | M G A P V I L F S C T N Q H Y W D E K R | 9 | 11 |
| F | 249 | M G A P V I L F S C T N Q H Y W D E K R | 16 | 4 |

TABLE 17-continued

Human Oct3/4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| L | 250 | M G A P V I L F S C T N Q H Y W D E K R | 16 | 4 |
| Q | 251 | M G A P V I L F S C T N Q H Y W D E K R | 18 | 2 |
| C | 252 | M G A P V I L F S C T N Q H Y W D E K R | 16 | 4 |
| P | 253 | M G A P V I L F S C T N Q H Y W D E K R | 17 | 3 |
| K | 254 | M G A P V I L F S C T N Q H Y W D E K R | 11 | 9 |
| P | 255 | M G A P V I L F S C T N Q H Y W D E K R | 16 | 4 |
| T | 256 | M G A P V I L F S C T N Q H Y W D E K R | 15 | 5 |
| L | 257 | M G A P V I L F S C T N Q H Y W D E K R | 9 | 11 |
| Q | 258 | M G A P V I L F S C T N Q H Y W D E K R | 18 | 2 |
| Q | 259 | M G A P V I L F S C T N Q H Y W D E K R | 15 | 5 |
| I | 260 | M G A P V I L F S C T N Q H Y W D E K R | 14 | 6 |
| S | 261 | M G A P V I L F S C T N Q H Y W D E K R | 15 | 5 |
| H | 262 | M G A P V I L F S C T N Q H Y W D E K R | 18 | 2 |
| I | 263 | M G A P V I L F S C T N Q H Y W D E K R | 13 | 7 |
| A | 264 | M G A P V I L F S C T N Q H Y W D E K R | 15 | 5 |
| Q | 265 | M G A P V I L F S C T N Q H Y W D E K R | 9 | 11 |
| Q | 266 | M G A P V I L F S C T N Q H Y W D E K R | 18 | 2 |
| L | 267 | M G A P V I L F S C T N Q H Y W D E K R | 14 | 6 |
| G | 268 | M G A P V I L F S C T N Q H Y W D E K R | 17 | 3 |
| L | 269 | M G A P V I L F S C T N Q H Y W D E K R | 11 | 9 |
| E | 270 | M G A P V I L F S C T N Q H Y W D E K R | 16 | 4 |
| K | 271 | M G A P V I L F S C T N Q H Y W D E K R | 14 | 6 |
| D | 272 | M G A P V I L F S C T N Q H Y W D E K R | 15 | 5 |
| V | 273 | M G A P V I L F S C T N Q H Y W D E K R | 15 | 5 |
| V | 274 | M G A P V I L F S C T N Q H Y W D E K R | 16 | 4 |
| R | 275 | M G A P V I L F S C T N Q H Y W D E K R | 18 | 2 |
| V | 276 | M G A P V I L F S C T N Q H Y W D E K R | 17 | 3 |
| W | 277 | M G A P V I L F S C T N Q H Y W D E K R | 19 | 1 |
| F | 278 | M G A P V I L F S C T N Q H Y W D E K R | 18 | 2 |
| C | 279 | M G A P V I L F S C T N Q H Y W D E K R | 19 | 1 |
| N | 280 | M G A P V I L F S C T N Q H Y W D E K R | 18 | 2 |
| R | 281 | M G A P V I L F S C T N Q H Y W D E K R | 18 | 2 |
| R | 282 | M G A P V I L F S C T N Q H Y W D E K R | 13 | 7 |
| Q | 283 | M G A P V I L F S C T N Q H Y W D E K R | 18 | 2 |
| K | 284 | M G A P V I L F S C T N Q H Y W D E K R | 11 | 9 |

TABLE 17-continued

Human Oct3/4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| G | 285 | M G A P V I L F S C T N Q H Y W D E K R | 18 | 2 |
| K | 286 | M G A P V I L F S C T N Q H Y W D E K R | 12 | 8 |
| R | 287 | M G A P V I L F S C T N Q H Y W D E K R | 18 | 2 |
| S | 288 | M G A P V I L F S C T N Q H Y W D E K R | 15 | 5 |
| S | 289 | M G A P V I L F S C T N Q H Y W D E K R | 13 | 7 |
| S | 290 | M G A P V I L F S C T N Q H Y W D E K R | 15 | 5 |
| D | 291 | M G A P V I L F S C T N Q H Y W D E K R | 13 | 7 |
| Y | 292 | M G A P V I L F S C T N Q H Y W D E K R | 17 | 3 |
| A | 293 | M G A P V I L F S C T N Q H Y W D E K R | 16 | 4 |
| Q | 294 | M G A P V I L F S C T N Q H Y W D E K R | 18 | 2 |
| R | 295 | M G A P V I L F S C T N Q H Y W D E K R | 18 | 2 |
| E | 296 | M G A P V I L F S C T N Q H Y W D E K R | 17 | 3 |
| D | 297 | M G A P V I L F S C T N Q H Y W D E K R | 15 | 5 |
| F | 298 | M G A P V I L F S C T N Q H Y W D E K R | 14 | 6 |
| E | 299 | M G A P V I L F S C T N Q H Y W D E K R | 7 | 13 |
| A | 300 | M G A P V I L F S C T N Q H Y W D E K R | 16 | 4 |
| A | 301 | M G A P V I L F S C T N Q H Y W D E K R | 15 | 5 |
| G | 302 | M G A P V I L F S C T N Q H Y W D E K R | 19 | 1 |
| S | 303 | M G A P V I L F S C T N Q H Y W D E K R | 15 | 5 |
| P | 304 | M G A P V I L F S C T N Q H Y W D E K R | 14 | 6 |
| F | 305 | M G A P V I L F S C T N Q H Y W D E K R | 16 | 4 |
| S | 306 | M G A P V I L F S C T N Q H Y W D E K R | 7 | 13 |
| G | 307 | M G A P V I L F S C T N Q H Y W D E K R | 18 | 2 |
| G | 308 | M G A P V I L F S C T N Q H Y W D E K R | 19 | 1 |
| P | 309 | M G A P V I L F S C T N Q H Y W D E K R | 17 | 3 |
| V | 310 | M G A P V I L F S C T N Q H Y W D E K R | 16 | 4 |
| S | 311 | M G A P V I L F S C T N Q H Y W D E K R | 14 | 6 |
| F | 312 | M G A P V I L F S C T N Q H Y W D E K R | 18 | 2 |
| P | 313 | M G A P V I L F S C T N Q H Y W D E K R | 18 | 2 |
| L | 314 | M G A P V I L F S C T N Q H Y W D E K R | 12 | 8 |
| A | 315 | M G A P V I L F S C T N Q H Y W D E K R | 17 | 3 |
| P | 316 | M G A P V I L F S C T N Q H Y W D E K R | 18 | 2 |
| G | 317 | M G A P V I L F S C T N Q H Y W D E K R | 19 | 1 |
| P | 318 | M G A P V I L F S C T N Q H Y W D E K R | 18 | 2. |
| H | 319 | M G A P V I L F S C T N Q H Y W D E K R | 18 | 2 |
| F | 320 | M G A P V I L F S C T N Q H Y W D E K R | 18 | 2 |

TABLE 17-continued

Human Oct3/4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| G | 321 | M G A P V I L F S C T N Q H Y W D E K R | 18 | 2 |
| T | 322 | M G A P V I L F S C T N Q H Y W D E K R | 14 | 6 |
| P | 323 | M G A P V I L F S C T N Q H Y W D E K R | 18 | 2 |
| G | 324 | M G A P V I L F S C T N Q H Y W D E K R | 17 | 3 |
| Y | 325 | M G A P V I L F S C T N Q H Y W D E K R | 16 | 4 |
| G | 326 | M G A P V I L F S C T N Q H Y W D E K R | 19 | 1 |
| S | 327 | M G A P V I L F S C T N Q H Y W D E K R | 15 | 5 |
| P | 328 | M G A P V I L F S C T N Q H Y W D E K R | 18 | 2 |
| H | 329 | M G A P V I L F S C T N Q H Y W D E K R | 18 | 2 |
| F | 330 | M G A P V I L F S C T N Q H Y W D E K R | 16 | 4 |
| T | 331 | M G A P V I L F S C T N Q H Y W D E K R | 17 | 3 |
| A | 332 | M G A P V I L F S C T N Q H Y W D E K R | 14 | 6 |
| L | 333 | M G A P V I L F S C T N Q H Y W D E K R | 14 | 6 |
| Y | 334 | M G A P V I L F S C T N Q H Y W D E K R | 16 | 4 |
| S | 335 | M G A P V I L F S C T N Q H Y W D E K R | 16 | 4 |
| S | 336 | M G A P V I L F S C T N Q H Y W D E K R | 16 | 4 |
| V | 337 | M G A P V I L F S C T N Q H Y W D E K R | 15 | 5 |
| P | 338 | M G A P V I L F S C T N Q H Y W D E K R | 18 | 2 |
| F | 339 | M G A P V I L F S C T N Q H Y W D E K R | 18 | 2 |
| P | 340 | M G A P V I L F S C T N Q H Y W D E K R | 18 | 2 |
| E | 341 | M G A P V I L F S C T N Q H Y W D E K R | 15 | 5 |
| G | 342 | M G A P V I L F S C T N Q H Y W D E K R | 19 | 1 |
| E | 343 | M G A P V I L F S C T N Q H Y W D E K R | 7 | 13 |
| A | 344 | M G A P V I L F S C T N Q H Y W D E K R | 17 | 3 |
| F | 345 | M G A P V I L F S C T N Q H Y W D E K R | 17 | 3 |
| P | 346 | M G A P V I L F S C T N Q H Y W D E K R | 17 | 3 |
| P | 347 | M G A P V I L F S C T N Q H Y W D E K R | 10 | 10 |
| V | 348 | M G A P V I L F S C T N Q H Y W D E K R | 15 | 5 |
| S | 349 | M G A P V I L F S C T N Q H Y W D E K R | 13 | 3 |
| V | 350 | M G A P V I L F S C T N Q H Y W D E K R | 16 | 4 |
| T | 351 | M G A P V I L F S C T N Q H Y W D E K R | 15 | 5 |
| T | 352 | M G A P V I L F S C T N Q H Y W D E K R | 15 | 5 |
| L | 353 | M G A P V I L F S C T N Q H Y W D E K R | 14 | 6 |
| G | 354 | M G A P V I L F S C T N Q H Y W D E K R | 19 | 1 |
| S | 355 | M G A P V I L F S C T N Q H Y W D E K R | 14 | 6 |

TABLE 17-continued

Human Oct3/4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| P | 356 | M G A P V I L F S C T N Q H Y W D E K R | 18 | 2 |
| M | 357 | M G A P V I L F S C T N Q H Y W D E K R | 18 | 2 |
| H | 358 | M G A P V I L F S C T N Q H Y W D E K R | 18 | 2 |
| S | 359 | M G A P V I L F S C T N Q H Y W D E K R | 15 | 5 |
| N | 360 | M G A P V I L F S C T N Q H Y W D E K R | 13 | 3 |

TABLE 18

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| M | 1 | M G A P V I L F S C T N Q H Y W D E K R | 12 | 8 |
| Y | 2 | M G A P V I L F S C T N Q H Y W D E K R | 8 | 12 |
| N | 3 | M G A P V I L F S C T N Q H Y W D E K R | 15 | 5 |
| M | 4 | M G A P V I L F S C T N Q H Y W D E K R | 14 | 6 |
| M | 5 | M G A P V I L F S C T N Q H Y W D E K R | 8 | 12 |
| E | 6 | M G A P V I L F S C T N Q H Y W D E K R | 13 | 7 |
| T | 7 | M G A P V I L F S C T N Q H Y W D E K R | 10 | 10 |
| E | 8 | M G A P V I L F S C T N Q H Y W D E K R | 10 | 10 |
| L | 9 | M G A P V I L F S C T N Q H Y W D E K R | 0 | 20 |
| K | 10 | M G A P V I L F S C T N Q H Y W D E K R | 9 | 11 |
| P | 11 | M G A P V I L F S C T N Q H Y W D E K R | 11 | 9 |
| P | 12 | M G A P V I L F S C T N Q H Y W D E K R | 11 | 9 |
| G | 13 | M G A P V I L F S C T N Q H Y W D E K R | 19 | 1 |
| P | 14 | M G A P V I L F S C T N Q H Y W D E K R | 9 | 11 |
| Q | 15 | M G A P V I L F S C T N Q H Y W D E K R | 7 | 13 |
| Q | 16 | M G A P V I L F S C T N Q H Y W D E K R | 5 | 15 |
| T | 17 | M G A P V I L F S C T N Q H Y W D E K R | 7 | 13 |
| S | 18 | M G A P V I L F S C T N Q H Y W D E K R | 1 | 19 |
| G | 19 | M G A P V I L F S C T N Q H Y W D E K R | 11 | 9 |
| G | 20 | M G A P V I L F S C T N Q H Y W D E K R | 17 | 3 |
| G | 21 | M G A P V I L F S C T N Q H Y W D E K R | 7 | 13 |
| C | 22 | M G A P V I L F S C T N Q H Y W D E K R | 13 | 7 |
| C | 23 | M G A P V I L F S C T N Q H Y W D E K R | 15 | 5 |
| N | 24 | M G A P V I L F S C T N Q H Y W D E K R | 5 | 15 |

TABLE 18-continued

Human Sox2 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| S | 25 | M G A P V I L F S C T N Q H Y W D E K R | 6 | 14 |
| T | 26 | M G A P V I L F S C T N Q H Y W D E K R | 5 | 15 |
| A | 27 | M G A P V I L F S C T N Q H Y W D E K R | 14 | 6 |
| A | 28 | M G A P V I L F S C T N Q H Y W D E K R | 3 | 17 |
| A | 29 | M G A P V I L F S C T N Q H Y W D E K R | 10 | 10 |
| A | 30 | M G A P V I L F S C T N Q H Y W D E K R | 14 | 6 |
| G | 31 | M G A P V I L F S C T N Q H Y W D E K R | 4 | 16 |
| G | 32 | M G A P V I L F S C T N Q H Y W D E K R | 6 | 14 |
| N | 33 | M G A P V I L F S C T N Q H Y W D E K R | 13 | 7 |
| Q | 34 | M G A P V I L F S C T N Q H Y W D E K R | 5 | 15 |
| K | 35 | M G A P V I L F S C T N Q H Y W D E K R | 12 | 8 |
| N | 36 | M G A P V I L F S C T N Q H Y W D E K R | 11 | 9 |
| S | 37 | M G A P V I L F S C T N Q H Y W D E K R | 5 | 15 |
| P | 38 | M G A P V I L F S C T N Q H Y W D E K R | 1 | 19 |
| D | 39 | M G A P V I L F S C T N Q H Y W D E K R | 12 | 8 |
| R | 40 | M G A P V I L F S C T N Q H Y W D E K R | 18 | 2 |
| V | 41 | M G A P V I L F S C T N Q H Y W D E K R | 10 | 10 |
| K | 42 | M G A P V I L F S C T N Q H Y W D E K R | 18 | 2 |
| R | 43 | M G A P V I L F S C T N Q H Y W D E K R | 18 | 2 |
| P | 44 | M G A P V I L F S C T N Q H Y W D E K R | 18 | 2 |
| M | 45 | M G A P V I L F S C T N Q H Y W D E K R | 15 | 5 |
| N | 46 | M G A P V I L F S C T N Q H Y W D E K R | 17 | 3 |
| A | 47 | M G A P V I L F S C T N Q H Y W D E K R | 17 | 3 |
| F | 48 | M G A P V I L F S C T N Q H Y W D E K R | 16 | 4 |
| M | 49 | M G A P V I L F S C T N Q H Y W D E K R | 13 | 7 |
| V | 50 | M G A P V I L F S C T N Q H Y W D E K R | 18 | 2 |
| W | 51 | M G A P V I L F S C T N Q H Y W D E K R | 19 | 1 |
| S | 52 | M G A P V I L F S C T N Q H Y W D E K R | 16 | 4 |
| R | 53 | M G A P V I L F S C T N Q H Y W D E K R | 18 | 2 |
| G | 54 | M G A P V I L F S C T N Q H Y W D E K R | 14 | 6 |
| Q | 55 | M G A P V I L F S C T N Q H Y W D E K R | 18 | 2 |
| R | 56 | M G A P V I L F S C T N Q H Y W D E K R | 17 | 3 |
| R | 57 | M G A P V I L F S C T N Q H Y W D E K R | 18 | 2 |
| K | 58 | M G A P V I L F S C T N Q H Y W D E K R | 18 | 2 |
| M | 59 | M G A P V I L F S C T N Q H Y W D E K R | 15 | 5 |

TABLE 18-continued

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| A | 60 | M G A P V I L F S C T N Q H Y W D E K R | 17 | 3 |
| Q | 61 | M G A P V I L F S C T N Q H Y W D E K R | 18 | 2 |
| E | 62 | M G A P V I L F S C T N Q H Y W D E K R | 16 | 4 |
| N | 63 | M G A P V I L F S C T N Q H Y W D E K R | 17 | 3 |
| P | 64 | M G A P V I L F S C T N Q H Y W D E K R | 16 | 4 |
| K | 65 | M G A P V I L F S C T N Q H Y W D E K R | 16 | 4 |
| M | 66 | M G A P V I L F S C T N Q H Y W D E K R | 13 | 7 |
| H | 67 | M G A P V I L F S C T N Q H Y W D E K R | 18 | 2 |
| N | 68 | M G A P V I L F S C T N Q H Y W D E K R | 18 | 2 |
| S | 69 | M G A P V I L F S C T N Q H Y W D E K R | 13 | 7 |
| E | 70 | M G A P V I L F S C T N Q H Y W D E K R | 12 | 8 |
| 4 I | 71 | M G A P V I L F S C T N Q H Y W D E K R | 15 | 5 |
| S | 72 | M G A P V I L F S C T N Q H Y W D E K R | 16 | 4 |
| K | 73 | M G A P V I L F S C T N Q H Y W D E K R | 16 | 4 |
| R | 74 | M G A P V I L F S C T N Q H Y W D E K R | 16 | 4 |
| L | 75 | M G A P V I L F S C T N Q H Y W D E K R | 12 | 8 |
| G | 76 | M G A P V I L F S C T N Q H Y W D E K R | 17 | 3 |
| A | 77 | M G A P V I L F S C T N Q H Y W D E K R | 18 | 2 |
| E | 78 | M G A P V I L F S C T N Q H Y W D E K R | 9 | 11 |
| W | 79 | M G A P V I L F S C T N Q H Y W D E K R | 19 | 1 |
| K | 80 | M G A P V I L F S C T N Q H Y W D E K R | 16 | 4 |
| L | 81 | M G A P V I L F S C T N Q H Y W D E K R | 12 | 8 |
| L | 82 | M G A P V I L F S C T N Q H Y W D E K R | 10 | 10 |
| S | 83 | M G A P V I L F S C T N Q H Y W D E K R | 2 | 18 |
| E | 84 | M G A P V I L F S C T N Q H Y W D E K R | 10 | 10 |
| T | 85 | M G A P V I L F S C T N Q H Y W D E K R | 0 | 20 |
| E | 86 | M G A P V I L F S C T N Q H Y W D E K R | 11 | 9 |
| K | 87 | M G A P V I L F S C T N Q H Y W D E K R | 15 | 5 |
| R | 88 | M G A P V I L F S C T N Q H Y W D E K R | 17 | 3 |
| P | 89 | M G A P V I L F S C T N Q H Y W D E K R | 17 | 3 |
| F | 90 | M G A P V I L F S C T N Q H Y W D E K R | 18 | 2 |
| I | 91 | M G A P V I L F S C T N Q H Y W D E K R | 10 | 10 |
| D | 92 | M G A P V I L F S C T N Q H Y W D E K R | 11 | 9 |
| E | 93 | M G A P V I L F S C T N Q H Y W D E K R | 12 | 8 |
| A | 94 | M G A P V I L F S C T N Q H Y W D E K R | 17 | 3 |
| K | 95 | M G A P V I L F S C T N Q H Y W D E K R | 15 | 5 |

TABLE 18-continued

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| R | 96 | M G A P V I L F S C T N Q H Y W D E K R | 18 | 2 |
| L | 97 | M G A P V I L F S C T N Q H Y W D E K R | 14 | 6 |
| R | 98 | M G A P V I L F S C T N Q H Y W D E K R | 18 | 2 |
| A | 99 | M G A P V I L F S C T N Q H Y W D E K R | 16 | 4 |
| L | 100 | M G A P V I L F S C T N Q H Y W D E K R | 5 | 15 |
| H | 101 | M G A P V I L F S C T N Q H Y W D E K R | 18 | 2 |
| M | 102 | M G A P V I L F S C T N Q H Y W D E K R | 13 | 7 |
| K | 103 | M G A P V I L F S C T N Q H Y W D E K R | 14 | 6 |
| E | 104 | M G A P V I L F S C T N Q H Y W D E K R | 11 | 9 |
| H | 105 | M G A P V I L F S C T N Q H Y W D E K R | 14 | 6 |
| P | 106 | M G A P V I L F S C T N Q H Y W D E K R | 15 | 5 |
| D | 107 | M G A P V I L F S C T N Q H Y W D E K R | 12 | 8 |
| Y | 108 | M G A P V I L F S C T N Q H Y W D E K R | 17 | 3 |
| K | 109 | M G A P V I L F S C T N Q H Y W D E K R | 14 | 6 |
| Y | 110 | M G A P V I L F S C T N Q H Y W D E K R | 16 | 4 |
| R | 111 | M G A P V I L F S C T N Q H Y W D E K R | 18 | 2 |
| P | 112 | M G A P V I L F S C T N Q H Y W D E K R | 17 | 3 |
| R | 113 | M G A P V I L F S C T N Q H Y W D E K R | 17 | 3 |
| R | 114 | M G A P V I L F S C T N Q H Y W D E K R | 18 | 2 |
| K | 115 | M G A P V I L F S C T N Q H Y W D E K R | 14 | 6 |
| T | 116 | M G A P V I L F S C T N Q H Y W D E K R | 15 | 5 |
| K | 117 | M G A P V I L F S C T N Q H Y W D E K R | 16 | 4 |
| T | 118 | M G A P V I L F S C T N Q H Y W D E K R | 11 | 9 |
| L | 119 | M G A P V I L F S C T N Q H Y W D E K R | 12 | 8 |
| M | 120 | M G A P V I L F S C T N Q H Y W D E K R | 10 | 10 |
| K | 121 | M G A P V I L F S C T N Q H Y W D E K R | 14 | 6 |
| K | 122 | M G A P V I L F S C T N Q H Y W D E K R | 17 | 3 |
| Q | 123 | M G A P V I L F S C T N Q H Y W D E K R | 13 | 7 |
| K | 124 | M G A P V I L F S C T N Q H Y W D E K R | 16 | 4 |
| Y | 125 | M G A P V I L F S C T N Q H Y W D E K R | 14 | 6 |
| T | 126 | M G A P V I L F S C T N Q H Y W D E K R | 9 | 11 |
| L | 127 | M G A P V I L F S C T N Q H Y W D E K R | 9 | 11 |
| P | 128 | M G A P V I L F S C T N Q H Y W D E K R | 15 | 5 |
| G | 129 | M G A P V I L F S C T N Q H Y W D E K R | 18 | 2 |
| G | 130 | M G A P V I L F S C T N Q H Y W D E K R | 19 | 1 |

TABLE 18-continued

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| L | 131 | M G A P V I L F S C T N Q H Y W D E K R | 8 | 12 |
| L | 132 | M G A P V I L F S C T N Q H Y W D E K R | 6 | 14 |
| A | 133 | M G A P V I L F S C T N Q H Y W D E K R | 13 | 7 |
| P | 134 | M G A P V I L F S C T N Q H Y W D E K R | 10 | 10 |
| G | 135 | M G A P V I L F S C T N Q H Y W D E K R | 12 | 8 |
| G | 136 | M G A P V I L F S C T N Q H Y W D E K R | 6 | 14 |
| N | 137 | M G A P V I L F S C T N Q H Y W D E K R | 12 | 8 |
| S | 138 | M G A P V I L F S C T N Q H Y W D E K R | 7 | 13 |
| M | 139 | M G A P V I L F S C T N Q H Y W D E K R | 9 | 11 |
| A | 140 | M G A P V I L F S C T N Q H Y W D E K R | 9 | 11 |
| S | 141 | M G A P V I L F S C T N Q H Y W D E K R | 8 | 12 |
| G | 142 | M G A P V I L F S C T N Q H Y W D E K R | 14 | 6 |
| V | 143 | M G A P V I L F S C T N Q H Y W D E K R | 7 | 13 |
| G | 144 | M G A P V I L F S C T N Q H Y W D E K R | 10 | 10 |
| V | 145 | M G A P V I L F S C T N Q H Y W D E K R | 6 | 14 |
| G | 146 | M G A P V I L F S C T N Q H Y W D E K R | 7 | 13 |
| A | 147 | M G A P V I L F S C T N Q H Y W D E K R | 14 | 6 |
| G | 148 | M G A P V I L F S C T N Q H Y W D E K R | 10 | 10 |
| L | 149 | M G A P V I L F S C T N Q H Y W D E K R | 3 | 17 |
| G | 150 | M G A P V I L F S C T N Q H Y W D E K R | 15 | 5 |
| A | 151 | M G A P V I L F S C T N Q H Y W D E K R | 1 | 19 |
| G | 152 | M G A P V I L F S C T N Q H Y W D E K R | 17 | 3 |
| V | 153 | M G A P V I L F S C T N Q H Y W D E K R | 7 | 13 |
| N | 154 | M G A P V I L F S C T N Q H Y W D E K R | 10 | 10 |
| Q | 155 | M G A P V I L F S C T N Q H Y W D E K R | 15 | 5 |
| R | 156 | M G A P V I L F S C T N Q H Y W D E K R | 18 | 2 |
| M | 157 | M G A P V I L F S C T N Q H Y W D E K R | 13 | 7 |
| D | 158 | M G A P V I L F S C T N Q H Y W D E K R | 16 | 4 |
| S | 159 | M G A P V I L F S C T N Q H Y W D E K R | 14 | 6 |
| Y | 160 | M G A P V I L F S C T N Q H Y W D E K R | 13 | 7 |
| A | 161 | M G A P V I L F S C T N Q H Y W D E K R | 12 | 8 |
| H | 162 | M G A P V I L F S C T N Q H Y W D E K R | 14 | 6 |
| M | 163 | M G A P V I L F S C T N Q H Y W D E K R | 11 | 9 |
| N | 164 | M G A P V I L F S C T N Q H Y W D E K R | 16 | 4 |
| G | 165 | M G A P V I L F S C T N Q H Y W D E K R | 12 | 8 |
| W | 166 | M G A P V I L F S C T N Q H Y W D E K R | 16 | 4 |

TABLE 18-continued

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| S | 167 | M G A P V I L F S C T N Q H Y W D E K R | 6 | 14 |
| N | 168 | M G A P V I L F S C T N Q H Y W D E K R | 11 | 9 |
| G | 169 | M G A P V I L F S C T N Q H Y W D E K R | 15 | 5 |
| S | 170 | M G A P V I L F S C T N Q H Y W D E K R | 7 | 13 |
| Y | 171 | M G A P V I L F S C T N Q H Y W D E K R | 11 | 9 |
| S | 172 | M G A P V I L F S C T N Q H Y W D E K R | 13 | 7 |
| M | 173 | M G A P V I L F S C T N Q H Y W D E K R | 11 | 9 |
| M | 174 | M G A P V I L F S C T N Q H Y W D E K R | 13 | 7 |
| Q | 175 | M G A P V I L F S C T N Q H Y W D E K R | 15 | 5 |
| D | 176 | M G A P V I L F S C T N Q H Y W D E K R | 13 | 7 |
| Q | 177 | M G A P V I L F S C T N Q H Y W D E K R | 14 | 6 |
| L | 178 | M G A P V I L F S C T N Q H Y W D E K R | 7 | 13 |
| G | 179 | M G A P V I L F S C T N Q H Y W D E K R | 16 | 4 |
| Y | 180 | M G A P V I L F S C T N Q H Y W D E K R | 17 | 3 |
| P | 181 | M G A P V I L F S C T N Q H Y W D E K R | 13 | 7 |
| Q | 182 | M G A P V I L F S C T N Q H Y W D E K R | 16 | 4 |
| H | 183 | M A P V I L F S C T N Q H Y W D E K R | 14 | 6 |
| P | 184 | M G A P V I L F S C T N Q H Y W D E K R | 15 | 5 |
| G | 185 | M G A P V I L F S C T N Q H Y W D E K R | 10 | 10 |
| L | 186 | M G A P V I L F S C T N Q H Y W D E K R | 4 | 16 |
| N | 187 | M G A P V I L F S C T N Q H Y W D E K R | 17 | 3 |
| A | 188 | M G A P V I L F S C T N Q H Y W D E K R | 5 | 15 |
| H | 189 | M G A P V I L F S C T N Q H Y W D E K R | 11 | 9 |
| G | 190 | M G A P V I L F S C T N Q H Y W D E K R | 10 | 10 |
| A | 191 | M G A P V I L F S C T N Q H Y W D E K R | 8 | 12 |
| A | 192 | M G A P V I L F S C T N Q H Y W D E K R | 9 | 11 |
| Q | 193 | M G A P V I L F S C T N Q H Y W D E K R | 9 | 11 |
| M | 194 | M G A P V I L F S C T N Q H Y W D E K R | 10 | 10 |
| Q | 195 | M G A P V I L F S C T N Q H Y W D E K R | 12 | 8 |
| P | 196 | M G A P V I L F S C T N Q H Y W D E K R | 9 | 11 |
| M | 197 | M G A P V I L F S C T N Q H Y W D E K R | 14 | 6 |
| H | 198 | M G A P V I L F S C T N Q H Y W D E K R | 16 | 4 |
| R | 199 | M G A P V I L F S C T N Q H Y W D E K R | 18 | 2 |
| Y | 200 | M G A P V I L F S C T N Q H Y W D E K R | 14 | 6 |
| D | 201 | M G A P V I L F S C T N Q H Y W D E K R | 15 | 5 |

TABLE 18-continued

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| V | 202 | M G A P V I L F S C T N Q H Y W D E K R | 3 | 17 |
| S | 203 | M G A P V I L F S C T N Q H Y W D E K R | 11 | 9 |
| A | 204 | M G A P V I L F S C T N Q H Y W D E K R | 13 | 7 |
| L | 205 | M G A P V I L F S C T N Q H Y W D E K R | 12 | 8 |
| Q | 206 | M G A P V I L F S C T N Q H Y W D E K R | 18 | 2 |
| Y | 207 | M G A P V I L F S C T N Q H Y W D E K R | 16 | 4 |
| N | 208 | M G A P V I L F S C T N Q H Y W D E K R | 10 | 10 |
| S | 209 | M G A P V I L F S C T N Q H Y W D E K R | 13 | 7 |
| M | 210 | M G A P V I L F S C T N Q H Y W D E K R | 13 | 7 |
| T | 211 | M G A P V I L F S C T N Q H Y W D E K R | 8 | 12 |
| S | 212 | M G A P V I L F S C T N Q H Y W D E K R | 13 | 7 |
| S | 213 | M G A P V I L F S C T N Q H Y W D E K R | 13 | 7 |
| Q | 214 | M G A P V I L F S C T N Q H Y W D E K R | 16 | 4 |
| T | 215 | M G A P V I L F S C T N Q H Y W D E K R | 14 | 6 |
| Y | 216 | M G A P V I L F S C T N Q H Y W D E K R | 17 | 3 |
| M | 217 | M G A P V I L F S C T N Q H Y W D E K R | 14 | 6 |
| N | 218 | M G A P V I L F S C T N Q H Y W D E K R | 13 | 7 |
| G | 219 | M G A P V I L F S C T N Q H Y W D E K R | 18 | 2 |
| S | 220 | M G A P V I L F S C T N Q H Y W D E K R | 12 | 8 |
| P | 221 | M G A P V I L F S C T N Q H Y W D E K R | 13 | 7 |
| T | 222 | M G A P V I L F S C T N Q H Y W D E K R | 10 | 10 |
| Y | 223 | M G A P V I L F S C T N Q H Y W D E K R | 14 | 6 |
| S | 224 | M G A P V I L F S C T N Q H Y W D E K R | 13 | 7 |
| M | 225 | M G A P V I L F S C T N Q H Y W D E K R | 12 | 8 |
| S | 226 | M G A P V I L F S C T N Q H Y W D E K R | 11 | 9 |
| Y | 227 | M G A P V I L F S C T N Q H Y W D E K R | 15 | 5 |
| S | 228 | M G A P V I L F S C T N Q H Y W D E K R | 13 | 7 |
| Q | 229 | M G A P V I L F S C T N Q H Y W D E K R | 13 | 7 |
| Q | 230 | M G A P V I L F S C T N Q H Y W D E K R | 12 | 8 |
| G | 231 | M G A P V I L F S C T N Q H Y W D E K R | 14 | 6 |
| T | 232 | M G A P V I L F S C T N Q H Y W D E K R | 3 | 17 |
| P | 233 | M G A P V I L F S C T N Q H Y W D E K R | 15 | 5 |
| G | 234 | M G A P V I L F S C T N Q H Y W D E K R | 14 | 6 |
| M | 235 | M G A P V I L F S C T N Q H Y W D E K R | 14 | 6 |
| A | 236 | M G A P V I L F S C T N Q H Y W D E K R | 12 | 8 |
| L | 237 | M G A P V I L F S C T N Q H Y W D E K R | 12 | 8 |

TABLE 18-continued

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| G | 238 | M G A P V I L F S C T N Q H Y W D E K R | 19 | 1 |
| S | 239 | M G A P V I L F S C T N Q H Y W D E K R | 15 | 5 |
| M | 240 | M G A P V I L F S C T N Q H Y W D E K R | 14 | 6 |
| G | 241 | M G A P V I L F S C T N Q H Y W D E K R | 19 | 1 |
| S | 242 | M G A P V I L F S C T N Q H Y W D E K R | 15 | 5 |
| V | 243 | M G A P V I L F S C T N Q H Y W D E K R | 13 | 7 |
| V | 244 | M G A P V I L F S C T N Q H Y W D E K R | 13 | 7 |
| K | 245 | M G A P V I L F S C T N Q H Y W D E K R | 14 | 6 |
| S | 246 | M G A P V I L F S C T N Q H Y W D E K R | 15 | 5 |
| E | 247 | M G A P V I L F S C T N Q H Y W D E K R | 12 | 8 |
| A | 248 | M G A P V I L F S C T N Q H Y W D E K R | 3 | 17 |
| S | 249 | M G A P V I L F S C T N Q H Y W D E K R | 10 | 10 |
| S | 250 | M G A P V I L F S C T N Q H Y W D E K R | 10 | 10 |
| S | 251 | M G A P V I L F S C T N Q H Y W D E K R | 14 | 6 |
| P | 252 | M G A P V I L F S C T N Q H Y W D E K R | 16 | 4 |
| P | 253 | M G A P V I L F S C T N Q H Y W D E K R | 18 | 2 |
| V | 254 | M G A P V I L F S C T N Q H Y W D E K R | 12 | 8 |
| V | 255 | M G A P V I L F S C T N Q H Y W D E K R | 7 | 13 |
| T | 256 | M G A P V I L F S C T N Q H Y W D E K R | 13 | 7 |
| S | 257 | M G A P V I L F S C T N Q H Y W D E K R | 10 | 10 |
| S | 258 | M G A P V I L F S C T N Q H Y W D E K R | 14 | 6 |
| S | 259 | M G A P V I L F S C T N Q H Y W D E K R | 12 | 8 |
| H | 260 | M G A P V I L F S C T N Q H Y W D E K R | 18 | 2 |
| S | 261 | M G A P V I L F S C T N Q H Y W D E K R | 14 | 6 |
| R | 262 | M G A P V I L F S C T N Q H Y W D E K R | 18 | 2 |
| A | 263 | M G A P V I L F S C T N Q H Y W D E K R | 16 | 4 |
| P | 264 | M G A P V I L F S C T N Q H Y W D E K R | 17 | 3 |
| C | 265 | M G A P V I L F S C T N Q H Y W D E K R | 17 | 3 |
| Q | 266 | M G A P V I L F S C T N Q H Y W D E K R | 18 | 2 |
| A | 267 | M G A P V I L F S C T N Q H Y W D E K R | 10 | 10 |
| G | 268 | M G A P V I L F S C T N Q H Y W D E K R | 19 | 1 |
| D | 269 | M G A P V I L F S C T N Q H Y W D E K R | 17 | 3 |
| L | 270 | M G A P V I L F S C T N Q H Y W D E K R | 14 | 6 |
| R | 271 | M G A P V I L F S C T N Q H Y W D E K R | 18 | 2 |
| D | 272 | M G A P V I L F S C T N Q H Y W D E K R | 16 | 4 |

TABLE 18-continued

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| M | 273 | M G A P V I L F S C T N Q H Y W D E K R | 17 | 3 |
| I | 274 | M G A P V I L F S C T N Q H Y W D E K R | 16 | 4 |
| S | 275 | M G A P V I L F S C T N Q H Y W D E K R | 16 | 4 |
| M | 276 | M G A P V I L F S C T N Q H Y W D E K R | 16 | 4 |
| Y | 277 | M G A P V I L F S C T N Q H Y W D E K R | 18 | 2 |
| L | 278 | M G A P V I L F S C T N Q H Y W D E K R | 11 | 9 |
| P | 279 | M G A P V I L F S C T N Q H Y W D E K R | 18 | 2 |
| G | 280 | M G A P V I L F S C T N Q H Y W D E K R | 19 | 1 |
| A | 281 | M G A P V I L F S C T N Q H Y W D E K R | 15 | 5 |
| E | 282 | M G A P V I L F S C T N Q H Y W D E K R | 16 | 4 |
| V | 283 | M G A P V I L F S C T N Q H Y W D E K R | 10 | 10 |
| P | 284 | M G A P V I L F S C T N Q H Y W D E K R | 10 | 10 |
| E | 285 | M G A P V I L F S C T N Q H Y W D E K R | 10 | 10 |
| P | 286 | M G A P V I L F S C T N Q H Y W D E K R | 14 | 6 |
| A | 287 | M G A P V I L F S C T N Q H Y W D E K R | 15 | 5 |
| A | 288 | M G A P V I L F S C T N Q H Y W D E K R | 16 | 4 |
| P | 289 | M G A P V I L F S C T N Q H Y W D E K R | 3 | 17 |
| S | 290 | M G A P V I L F S C T N Q H Y W D E K R | 15 | 5 |
| R | 291 | M G A P V I L F S C T N Q H Y W D E K R | 18 | 2 |
| L | 292 | M G A P V I L F S C T N Q H Y W D E K R | 13 | 7 |
| H | 293 | M G A P V I L F S C T N Q H Y W D E K R | 19 | 1 |
| M | 294 | M G A P V I L F S C T N Q H Y W D E K R | 13 | 7 |
| S | 295 | M G A P V I L F S C T N Q H Y W D E K R | 12 | 8 |
| Q | 296 | M G A P V I L F S C T N Q H Y W D E K R | 18 | 2 |
| H | 297 | M G A P V I L F S C T N Q H Y W D E K R | 18 | 2 |
| Y | 298 | M G A P V I L F S C T N Q H Y W D E K R | 17 | 3 |
| Q | 299 | M G A P V I L F S C T N Q H Y W D E K R | 17 | 3 |
| S | 300 | M G A P V I L F S C T N Q H Y W D E K R | 16 | 4 |
| G | 301 | M G A P V I L F S C T N Q H Y W D E K R | 17 | 3 |
| P | 302 | M G A P V I L F S C T N Q Q H Y W D E K R | 8 | 12 |
| V | 303 | M G A P V I L F S C T N Q H Y W D E K R | 16 | 4 |
| P | 304 | M G A P V I L F S C T N Q H Y W D E K R | 18 | 2 |
| G | 305 | M G A P V I L F S C T N Q H Y W D E K R | 19 | 1 |
| T | 306 | M G A P V I L F S C T N Q H Y W D E K R | 15 | 5 |
| A | 307 | M G A P V I L F S C T N Q H Y W D E K R | 15 | 5 |
| I | 308 | M G A P V I L F S C T N Q H Y W D E K R | 14 | 6 |

TABLE 18-continued

Human Sox2 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| N | 309 | M G A P V I L F S C T N Q H Y W D E K R | 18 | 2 |
| G | 310 | M G A P V I L F S C T N Q H Y W D E K R | 19 | 1 |
| T | 311 | M G A P V I L F S C T N Q H Y W D E K R | 17 | 3 |
| L | 312 | M G A P V I L F S C T N Q H Y W D E K R | 11 | 9 |
| P | 313 | M G A P V I L F S C T N Q H Y W D E K R | 18 | 2 |
| L | 314 | M G A P V I L F S C T N Q H Y W D E K R | 15 | 5 |
| S | 315 | M G A P V I L F S C T N Q H Y W D E K R | 12 | 8 |
| H | 316 | M G A P V I L F S C T N Q H Y W D E K R | 18 | 2 |
| M | 317 | M G A P V I L F S C T N Q H Y W D E K R | 16 | 4 |

TABLE 19

Human Klf4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| M | 1 | M G A P V I L F S C T N Q H Y W D E K R | 3 | 17 |
| A | 2 | M G A P V I L F S C T N Q H Y W D E K R | 4 | 16 |
| V | 3 | M G A P V I L F S C T N Q H Y W D E K R | 0 | 20 |
| S | 4 | M G A P V I L F S C T N Q H Y W D E K R | 3 | 17 |
| D | 5 | M G A P V I L F S C T N Q H Y W D E K R | 3 | 17 |
| A | 6 | M G A P V I L F S C T N Q H Y W D E K R | 1 | 19 |
| L | 7 | M G A P V I L F S C T N Q H Y W D E K R | 0 | 20 |
| L | 8 | M G A P V I L F S C T N Q H Y W D E K R | 0 | 20 |
| P | 9 | M G A P V I L F S C T N Q H Y W D E K R | 0 | 20 |
| S | 10 | M G A P V I L F S C T N Q H Y W D E K R | 1 | 19 |
| F | 11 | M G A P V I L F S C T N Q H Y W D E K R | 13 | 7 |
| S | 12 | M G A P V I L F S C T N Q H Y W D E K R | 2 | 18 |
| T | 13 | M G A P V I L F S C T N Q H Y W D E K R | 3 | 17 |
| F | 14 | M G A P V I L F S C T N Q H Y W D E K R | 0 | 20 |
| A | 15 | M G A P V I L F S C T N Q H Y W D E K R | 0 | 20 |
| S | 16 | M G A P V I L F S C T N Q H Y W D E K R | 1 | 19 |
| G | 17 | M G A P V I L F S C T N Q H Y W D E K R | 5 | 15 |
| P | 18 | M G A P V I L F S C T N Q H Y W D E K R | 1 | 19 |
| A | 19 | M G A P V I L F S C T N Q H Y W D E K R | 3 | 17 |

TABLE 19-continued

Human Klf4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| G | 20 | M G A P V I L F S C T N Q H Y W D E K R | 10 | 10 |
| R | 21 | M G A P V I L F S C T N Q H Y W D E K R | 4 | 16 |
| E | 22 | M G A P V I L F S C T N Q H Y W D E K R | 1 | 19 |
| K | 23 | M G A P V I L F S C T N Q H Y W D E K R | 1 | 19 |
| T | 24 | M G A P V I L F S C T N Q H Y W D E K R | 0 | 20 |
| L | 25 | M G A P V I L F S C T N Q H Y W D E K R | 0 | 20 |
| R | 26 | M G A P V I L F S C T N Q H Y W D E K R | 5 | 15 |
| Q | 27 | M G A P V I L F S C T N Q H Y W D E K R | 5 | 15 |
| A | 28 | M G A P V I L F S C T N Q H Y W D E K R | 5 | 15 |
| G | 29 | M G A P V I L F S C T N Q H Y W D E K R | 1 | 19 |
| A | 30 | M G A P V I L F S C T N Q H Y W D E K R | 4 | 16 |
| P | 31 | M G A P V I L F S C T N Q H Y W D E K R | 0 | 20 |
| N | 32 | M G A P V I L F S C T N Q H Y W D E K R | 2 | 18 |
| N | 33 | M G A P V I L F S C T N Q H Y W D E K R | 1 | 19 |
| R | 34 | M G A P V I L F S C T N Q H Y W D E K R | 7 | 13 |
| W | 35 | M G A P V I L F S C T N Q H Y W D E K R | 3 | 17 |
| R | 36 | M G A P V I L F S C T N Q H Y W D E K R | 6 | 14 |
| E | 37 | M G A P V I L F S C T N Q H Y W D E K R | 7 | 13 |
| E | 38 | M G A P V I L F S C T N Q H Y W D E K R | 0 | 20 |
| L | 39 | M G A P V I L F S C T N Q H Y W D E K R | 0 | 20 |
| S | 40 | M G A P V I L F S C T N Q H Y W D E K R | 5 | 15 |
| H | 41 | M G A P V I L F S C T N Q H Y W D E K R | 10 | 10 |
| M | 42 | M G A P V I L F S C T N Q H Y W D E K R | 1 | 19 |
| K | 43 | M G A P V I L F S C T N Q H Y W D E K R | 12 | 8 |
| R | 44 | M G A P V I L F S C T N Q H Y W D E K R | 12 | 8 |
| L | 45 | M G A P V I L F S C T N Q H Y W D E K R | 3 | 17 |
| P | 46 | M G A P V I L F S C T N Q H Y W D E K R | 5 | 15 |
| P | 47 | M G A P V I L F S C T N Q H Y W D E K R | 0 | 20 |
| V | 48 | M G A P V I L F S C T N Q H Y W D E K R | 0 | 20 |
| L | 49 | M G A P V I L F S C T N Q H Y W D E K R | 0 | 20 |
| P | 50 | M G A P V I L F S C T N Q H Y W D E K R | 4 | 16 |
| C | 51 | M G A P V I L F S C T N Q H Y W D E K R | 0 | 20 |
| R | 52 | M G A P V I L F S C T N Q H Y W D E K R | 11 | 9 |
| P | 53 | M G A P V I L F S C T N Q H Y W D E K R | 2 | 18 |
| Y | 54 | M G A P V I L F S C T N Q H Y W D E K R | 1 | 19 |
| D | 55 | M G A P V I L F S C T N Q H Y W D E K R | 4 | 16 |

TABLE 19-continued

Human Klf4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| L | 56 | M G A P V I L F S C T N Q H Y W D E K R | 0 | 20 |
| A | 57 | M G A P V I L F S C T N Q H Y W D E K R | 1 | 19 |
| A | 58 | M G A P V I L F S C T N Q H Y W D E K R | 2 | 18 |
| A | 59 | M G A P V I L F S C T N Q H Y W D E K R | 0 | 20 |
| T | 60 | M G A P V I L F S C T N Q H Y W D E K R | 5 | 15 |
| V | 61 | M G A P V I L F S C T N Q H Y W D E K R | 0 | 20 |
| A | 62 | M G A P V I L F S C T N Q H Y W D E K R | 0 | 20 |
| T | 63 | M G A P V I L F S C T N Q H Y W D E K R | 7 | 13 |
| D | 64 | M G A P V I L F S C T N Q H Y W D E K R | 3 | 17 |
| L | 65 | M G A P V I L F S C T N Q H Y W D E K R | 0 | 20 |
| E | 66 | M G A P V I L F S C T N Q H Y W D E K R | 2 | 18 |
| S | 67 | M G A P V I L F S C T N Q H Y W D E K R | 6 | 14 |
| G | 68 | M G A P V I L F S C T N Q H Y W D E K R | 6 | 14 |
| G | 69 | M G A P V I L F S C T N Q H Y W D E K R | 6 | 14 |
| A | 70 | M G A P V I L F S C T N Q H Y W D E K R | 5 | 15 |
| G | 71 | M G A P V I L F S C T N Q H Y W D E K R | 14 | 6 |
| A | 72 | M G A P V I L F S C T N Q H Y W D E K R | 1 | 19 |
| A | 73 | M G A P V I L F S C T N Q H Y W D E K R | 7 | 13 |
| C | 74 | M G A P V I L F S C T N Q H Y W D E K R | 6 | 14 |
| G | 75 | M G A P V I L F S C T N Q H Y W D E K R | 7 | 13 |
| G | 76 | M G A P V I L F S C T N Q H Y D E K R | 9 | 11 |
| S | 77 | M G A P V I L F S C T N Q H Y W D E K R | 4 | 16 |
| N | 78 | M G A P V I L F S C T N Q H Y W D E K R | 7 | 13 |
| L | 79 | M G A P V I L F S C T N Q H Y W D E K R | 0 | 20 |
| A | 80 | M G A P V I L F S C T N Q H Y W D E K R | 8 | 12 |
| P | 81 | M G A P V I L F S C T N Q H Y W D E K R | 0 | 20 |
| L | 82 | M G A P V I L F S C T N Q H Y W D E K R | 0 | 20 |
| P | 83 | M G A P V I L F S C T N Q H Y W D E K R | 0 | 20 |
| R | 84 | M G A P V I L F S C T N Q H Y W D E K R | 11 | 9 |
| R | 85 | M G A P V I L F S C T N Q H Y W D E K R | 17 | 3 |
| E | 86 | M G A P V I L F S C T N Q H Y W D E K R | 3 | 17 |
| T | 87 | M G A P V I L F S C T N Q H Y W D E K R | 0 | 20 |
| E | 88 | M G A P V I L F S C T N Q H Y W D E K R | 9 | 11 |
| E | 89 | M G A P V I L F S C T N Q H Y W D E K R | 1 | 19 |
| F | 90 | M G A P V I L F S C T N Q H Y W D E K R | 0 | 20 |

TABLE 19-continued

Human Klf4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| N | 91 | M G A P V I L F S C T N Q H Y W D E K R | 2 | 18 |
| D | 92 | M G A P V I L F S C T N Q H Y W D E K R | 3 | 17 |
| L | 93 | M G A P V I L F S C T N Q H Y W D E K R | 0 | 20 |
| L | 94 | M G A P V I L F S C T N Q H Y W D E K R | 0 | 20 |
| D | 95 | M G A P V I L F S C T N Q H Y W D E K R | 6 | 14 |
| L | 96 | M G A P V I L F S C T N Q H Y W D E K R | 0 | 20 |
| D | 97 | M G A P V I L F S C T N Q H Y W D E K R | 2 | 18 |
| F | 98 | M G A P V I L F S C T N Q H Y W D E K R | 0 | 20 |
| I | 99 | M G A P V I L F S C T N Q H Y W D E K R | 3 | 17 |
| L | 100 | M G A P V I L F S C T N Q H Y W D E K R | 0 | 20 |
| S | 101 | M G A P V I L F S C T N Q H Y W D E K R | 13 | 7 |
| N | 102 | M G A P V I L F S C T N Q H Y W D E K R | 7 | 13 |
| S | 103 | M G A P V I L F S C T N Q H Y W D E K R | 1 | 19 |
| L | 104 | M G A P V I L F S C T N Q H Y W D E K R | 1 | 19 |
| T | 105 | M G A P V I L F S C T N Q H Y W D E K R | 9 | 11 |
| H | 106 | M G A P V I L F S C T N Q H Y W D E K R | 15 | 5 |
| P | 107 | M G A P V I L F S C T N Q H Y W D E K R | 2 | 18 |
| P | 108 | M G A P V I L F S C T N Q H Y W D E K R | 3 | 17 |
| E | 109 | M G A P V I L F S C T N Q H Y W D E K R | 4 | 16 |
| S | 110 | M G A P V I L F S C T N Q H Y W D E K R | 1 | 19 |
| V | 111 | M G A P V I L F S C T N Q H Y W D E K R | 1 | 19 |
| A | 112 | M G A P V I L F S C T N Q H Y W D E R | 9 | 11 |
| A | 113 | M G A P V I L F S C T N Q H Y W D E K R | 6 | 14 |
| T | 114 | M G A P V I L F S C T N Q H Y W D E K R | 9 | 11 |
| V | 115 | M G A P V I L F S C T N Q H Y W D E K R | 2 | 18 |
| S | 116 | M G A P V I L F S C T N Q H Y W D E K R | 11 | 9 |
| S | 117 | M G A P V I L F S C T N Q H Y W D E K R | 4 | 16 |
| S | 118 | M G A P V I L F S C T N Q H Y W D E K R | 6 | 14 |
| A | 119 | M G A P V I L F S C T N Q H Y W D E K R | 8 | 12 |
| S | 120 | M G A P V I L F S C T N Q H Y W D E K R | 13 | 7 |
| A | 121 | M G A P V I L F S C T N Q H Y W D E K R | 5 | 15 |
| S | 122 | M G A P V I L F S C T N Q H Y W D E K R | 10 | 10 |
| S | 123 | M G A P V I L F S C T N Q H Y W D E K R | 10 | 10 |
| S | 124 | M G A P V I L F S C T N Q H Y W D E K R | 2 | 18 |
| S | 125 | M G A P V I L F S C T N Q H Y W D E K R | 12 | 8 |
| S | 126 | M G A P V I L F S C T N Q H Y W D E K R | 5 | 15 |

TABLE 19-continued

Human Klf4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| P | 127 | M G A P V I L F S C T N Q H Y W D E K R | 6 | 14 |
| S | 128 | M G A P V I L F S C T N Q H Y W D E K R | 3 | 17 |
| S | 129 | M G A P V I L F S C T N Q H Y W D E K R | 9 | 11 |
| S | 130 | M G A P V I L F S C T N Q H Y W D E K R | 11 | 9 |
| G | 131 | M G A P V I L F S C T N Q H Y W D E K R | 16 | 4 |
| P | 132 | M G A P V I L F S C T N Q Y W D E K R | 11 | 9 |
| A | 133 | M G A P V I L F S C T N Q H Y W D E K R | 4 | 16 |
| S | 134 | M G A P V I L F S C T N Q H Y W D E K R | 11 | 9 |
| A | 135 | M G A P V I L F S C T N Q H Y W D E K R | 12 | 8 |
| P | 136 | M G A P V I L F S C T N Q H Y W D E K R | 14 | 6 |
| S | 137 | M G A P V I L F S C T N Q H Y W D E K R | 9 | 11 |
| T | 138 | M G A P V I L F S C T N Q H Y W D E K R | 7 | 13 |
| A | 139 | M G A P V I L F S C T N Q H Y W D E K R | 14 | 6 |
| S | 140 | M G A P V I L F S C T N Q H Y W D E K R | 8 | 12 |
| F | 141 | M G A P V I L F S C T N Q H Y W D E K R | 11 | 9 |
| T | 142 | M G A P V I L F S C T N Q H Y W D E K R | 1 | 19 |
| Y | 143 | M G A P V I L F S C T N Q H Y W D E K R | 13 | 7 |
| P | 144 | M G A P V I L F S C T N Q H Y W D E K R | 6 | 14 |
| I | 145 | M G A P V I L F S C T N Q H Y W D E K R | 7 | 13 |
| R | 146 | M G A P V I L F S C T N Q H Y W D E K R | 7 | 13 |
| A | 147 | M G A P V I L F S C T N Q H Y W D E K R | 10 | 10 |
| G | 148 | M G A P V I L F S C T N Q H Y W D E K R | 6 | 14 |
| N | 149 | M G A P V I L F S C T N Q H Y W D E K R | 3 | 17 |
| D | 150 | M G A P V I L F S C T N Q H Y W D E K R | 12 | 8 |
| P | 151 | M G A P V I L F S C T N Q H Y W D E K R | 16 | 4 |
| G | 152 | M G A P V I L F S C T N Q H Y W D E K R | 5 | 15 |
| V | 153 | M G A P V I L F S C T N Q H Y W D E K R | 6 | 14 |
| A | 154 | M G A P V I L F S C T N Q H Y W D E K R | 10 | 10 |
| P | 155 | M G A P V I L F S C T N Q H Y W D E K R | 11 | 9 |
| G | 156 | M G A P V I L F S C T N Q H Y W D E K R | 5 | 15 |
| G | 157 | M G A P V I L F S C T N Q H Y W D E K R | 18 | 2 |
| T | 158 | M G A P V I L F S C T N Q H Y W D E K R | 4 | 16 |
| G | 159 | M G A P V I L F S C T N Q H Y W D E K R | 12 | 8 |
| G | 160 | M G A P V I L F S C T N Q H Y W D E K R | 12 | 8 |
| G | 161 | M G A P V I L F S C T N Q H Y W D E K R | 8 | 12 |

TABLE 19-continued

Human Klf4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| L | 162 | M G A P V I L F S C T N Q H Y W D E K R | 5 | 15 |
| L | 163 | M G A P V I L F S C T N Q H Y W D E K R | 2 | 18 |
| Y | 164 | M G A P V I L F S C T N Q H Y W D E K R | 7 | 13 |
| G | 165 | M G A P V I L F S C T N Q H Y W D E K R | 17 | 3 |
| R | 166 | M G A P V I L F S C T N Q H Y W D E K R | 7 | 13 |
| E | 167 | M G A P V I L F S C T N Q H Y W D E K R | 6 | 14 |
| S | 168 | M G A P V I L F S C T N Q H Y W D E K R | 8 | 12 |
| A | 169 | M G A P V I L F S C T N Q H Y W D E K R | 14 | 6 |
| P | 170 | M G A P V I L F S C T N Q H Y W D E K R | 13 | 7 |
| P | 171 | M G A P V I L F S C T N Q H Y W D E K R | 5 | 15 |
| P | 172 | M G A P V I L F S C T N Q H Y W D E K R | 5 | 15 |
| T | 173 | M G A P V I L F S C T N Q H Y W D E K R | 3 | 17 |
| A | 174 | M G A P V I L F S C T N Q H Y W D E K R | 14 | 6 |
| P | 175 | M G A P V I L F S C T N Q H Y W D E K R | 11 | 9 |
| F | 176 | M G A P V I L F S C T N Q H Y W D E K R | 15 | 5 |
| N | 177 | M G A P V I L F S C T N Q H Y W D E K R | 11 | 9 |
| L | 178 | M G A P V I L F S C T N Q H Y W D E K R | 5 | 15 |
| A | 179 | M G A P V I L F S C T N Q H Y W D E K R | 5 | 15 |
| D | 180 | M G A P V I L F S C T N Q H Y W D E K R | 13 | 7 |
| I | 181 | M G A P V I L F S C T N Q H Y W D E K R | 8 | 12 |
| N | 182 | M G A P V I L F S C T N Q H Y W D E K R | 7 | 13 |
| D | 183 | M G A P V I L F S C T N Q H Y W D E K R | 8 | 12 |
| V | 184 | M G A P V I L F S C T N Q H Y W D E K R | 9 | 11 |
| S | 185 | M G A P V I L F S C T N Q H Y W D E K R | 7 | 13 |
| P | 186 | M G A P V I L F S C T N Q H Y W D E K R | 8 | 12 |
| S | 187 | M G A P V I L F S C T N Q H Y W D E K R | 6 | 14 |
| G | 188 | M G A P V I L F S C T N Q H Y W D E K R | 13 | 7 |
| G | 189 | M G A P V I L F S C T N Q H Y W D E K R | 14 | 6 |
| F | 190 | M G A P V I L F S C T N Q H Y W D E K R | 12 | 8 |
| V | 191 | M G A P V I L F S C T N Q H Y W D E K R | 8 | 12 |
| A | 192 | M G A P V I L F S C T N Q H Y W D E K R | 13 | 7 |
| E | 193 | M G A P V I L F S C T N Q H Y W D E K R | 6 | 14 |
| L | 194 | M G A P V I L F S C T N Q H Y W D E K R | 5 | 15 |
| L | 195 | M G A P V I L F S C T N Q H Y W D E K R | 6 | 14 |
| R | 196 | M G A P V I L F S C T N Q H Y W D E K R | 11 | 9 |
| P | 197 | M G A P V I L F S C T N Q H Y W D E K R | 7 | 13 |

TABLE 19-continued

Human Klf4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| E | 198 | M G A P V I L F S C T N Q H Y W D E K R | 4 | 16 |
| L | 199 | M G A P V I L F S C T N Q H Y W D E K R | 8 | 12 |
| D | 200 | M G A P V I L F S C T N Q H Y W D E K R | 12 | 8 |
| P | 201 | M G A P V I L F S C T N Q H Y W D E K R | 5 | 15 |
| V | 202 | M G A P V I L F S C T N Q H Y W D E K R | 4 | 16 |
| Y | 203 | M G A P V I L F S C T N Q H Y W D E K R | 13 | 7 |
| I | 204 | M G A P V I L F S C T N Q H Y W D E K R | 12 | 8 |
| P | 205 | M G A P V I L F S C T N Q H Y W D E K R | 13 | 7 |
| P | 206 | M G A P V I L F S C T N Q H Y W D E K R | 4 | 16 |
| Q | 207 | M G A P V I L F S C T N Q H Y W D E K R | 7 | 13 |
| Q | 208 | M G A P V I L F S C T N Q H Y W D E K R | 12 | 8 |
| P | 209 | M G A P V I L F S C T N Q H Y W D E K R | 4 | 16 |
| Q | 210 | M G A P V I L F S C T N Q H Y W D E K R | 4 | 16 |
| P | 211 | M G A P V I L F S C T N Q H Y W D E K R | 6 | 14 |
| P | 212 | M G A P V I L F S C T N Q H Y W D E K R | 10 | 10 |
| G | 213 | M G A P V I L F S C T N Q H Y W D E K R | 16 | 4 |
| G | 214 | M G A P V I L F S C T N Q H Y W D E K R | 11 | 9 |
| G | 215 | M G A P V I L F S C T N Q H Y W D E K R | 14 | 6 |
| L | 216 | M G A P V I L F S C T N Q H Y W D E K R | 3 | 17 |
| M | 217 | M G A P V I L F S C T N Q H Y W D E K R | 8 | 12 |
| G | 218 | M G A P V I L F S C T N Q H Y W D E K R | 11 | 9 |
| K | 219 | M G A P V I L F S C T N Q H Y W D E K R | 13 | 7 |
| F | 220 | M G A P V I L F S C T N Q H Y W D E K R | 13 | 7 |
| V | 221 | M G A P V I L F S C T N Q H Y W D E K R | 10 | 10 |
| L | 222 | M G A P V I L F S C T N Q H Y W D E K R | 8 | 12 |
| K | 223 | M G A P V I L F S C T N Q H Y W D E K R | 12 | 8 |
| A | 224 | M G A P V I L F S C T N Q H Y W D E K R | 12 | 8 |
| S | 225 | M G A P V I L F S C T N Q H Y W D E K R | 3 | 17 |
| L | 226 | M G A P V I L F S C T N Q H Y W D E K R | 6 | 14 |
| S | 227 | M G A P V I L F S C T N Q H Y W D E K R | 3 | 17 |
| A | 228 | M G A P V I L F S C T N Q H Y W D E K R | 11 | 9 |
| P | 229 | M G A P V I L F S C T N Q H Y W D E K R | 14 | 6 |
| G | 230 | M G A P V I L F S C T N Q H Y W D E K R | 17 | 3 |
| S | 231 | M G A P V I L F S C T N Q H Y W D E K R | 13 | 7 |
| E | 232 | M G A P V I L F S C T N Q H Y W D E K R | 4 | 16 |

TABLE 19-continued

Human Klf4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| Y | 233 | M G A P V I L F S C T N Q H Y W D E K R | 12 | 8 |
| G | 234 | M G A P V I L F S C T N Q H Y W D E K R | 14 | 6 |
| S | 235 | M G A P V I L F S C T N Q H Y W D E K R | 6 | 14 |
| P | 236 | M G A P V I L F S C T N Q H Y W D E K R | 6 | 14 |
| S | 237 | M G A P V I L F S C T N Q H Y W D E K R | 4 | 16 |
| V | 238 | M G A P V I L F S C T N Q H Y W D E K R | 6 | 14 |
| I | 239 | M G A P V I L F S C T N Q H Y W D E K R | 11 | 9 |
| S | 240 | M G A P V I L F S C T N Q H Y W D E K R | 4 | 16 |
| V | 241 | M G A P V I L F S C T N Q H Y W D E K R | 10 | 10 |
| S | 242 | M G A P V I L F S C T N Q H Y W D E K R | 13 | 7 |
| K | 243 | M G A P V I L F S C T N Q H Y W D E K R | 4 | 16 |
| G | 244 | M G A P V I L F S C T N Q H Y W D E K R | 13 | 7 |
| S | 245 | M G A P V I L F S C T N Q H Y W D E K R | 12 | 8 |
| P | 246 | M G A P V I L F S C T N Q H Y W D E K R | 6 | 14 |
| D | 247 | M G A P V I L F S C T N Q H Y W D E K R | 10 | 10 |
| G | 248 | M G A P V I L F S C T N Q H Y W D E K R | 13 | 7 |
| S | 249 | M G A P V I L F S C T N Q H Y W D E K R | 4 | 16 |
| H | 250 | M G A P V I L F S C T N Q H Y W D E K R | 17 | 3 |
| P | 251 | M G A P V I L F S C T N Q H Y W D E K R | 11 | 9 |
| V | 252 | M G A P V I L F S C T N Q H Y W D E K R | 11 | 9 |
| V | 253 | M G A P V I L F S C T N Q H Y W D E K R | 7 | 13 |
| V | 254 | M G A P V I L F S C T N Q H Y W D E K R | 12 | 8 |
| A | 255 | M G A P V I L F S C T N Q H Y W D E K R | 12 | 8 |
| P | 256 | M G A P V I L F S C T N Q H Y W D E K R | 11 | 9 |
| Y | 257 | M G A P V I L F S C T N Q H Y W D E K R | 11 | 9 |
| N | 258 | M G A P V I L F S C T N Q H Y W D E K R | 2 | 18 |
| G | 259 | M G A P V I L F S C T N Q H Y W D E K R | 13 | 7 |
| G | 260 | M G A P V I L F S C T N Q H Y W D E K R | 16 | 4 |
| P | 261 | M G A P V I L F S C T N Q H Y W D E K R | 13 | 7 |
| P | 262 | M G A P V I L F S C T N Q H Y W D E K R | 7 | 13 |
| R | 263 | M G A P V I L F S C T N Q H Y W D E K R | 15 | 5 |
| T | 264 | M G A P V I L F S C T N Q H Y W D E K R | 5 | 15 |
| C | 265 | M G A P V I L F S C T N Q H Y W D E K R | 16 | 4 |
| P | 266 | M G A P V I L F S C T N Q H Y W D E K R | 7 | 13 |
| K | 267 | M G A P V I L F S C T N Q H Y W D E K R | 5 | 15 |
| I | 268 | M G A P V I L F S C T N Q H Y W D E K R | 12 | 8 |

TABLE 19-continued

Human Klf4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| K | 269 | M G A P V I L F S C T N Q H Y W D E K R | 4 | 16 |
| Q | 270 | M G A P V I L F S C T N Q H Y W D E K R | 8 | 12 |
| E | 271 | M G A P V I L F S C T N Q H Y W D E K R | 10 | 10 |
| A | 272 | M G A P V I L F S C T N Q H Y W D E K R | 11 | 9 |
| V | 273 | M G A P V I L F S C T N Q H Y W D E K R | 6 | 14 |
| S | 274 | M G A P V I L F S C T N Q H Y Y D E K R | 4 | 16 |
| S | 275 | M G A P V I L F S C T N Q H Y Y D E K R | 4 | 16 |
| C | 276 | M G A P V I L F S C T N Q H Y W D E K R | 13 | 7 |
| T | 277 | M G A P V I L F S C T N Q H Y W D E K R | 14 | 6 |
| H | 278 | M G A P V I L F S C T N Q H Y W D E K R | 15 | 5 |
| L | 279 | M G A P V I L F S C T N Q H Y W D E K R | 1 | 19 |
| G | 280 | M G A P V I L F S C T N Q H Y W D E K R | 15 | 5 |
| A | 281 | M G A P V I L F S C T N Q H Y W D E K R | 7 | 13 |
| G | 282 | M G A P V I L F S C T N Q H Y W D E K R | 13 | 7 |
| P | 283 | M G A P V I L F S C T N Q H Y W D E K R | 16 | 4 |
| P | 284 | M G A P V I L F S C T N Q H Y W D E K R | 9 | 11 |
| L | 285 | M G A P V I L F S C T N Q H Y W D E K R | 3 | 17 |
| S | 286 | M G A P V I L F S C T N Q H Y W D E K R | 4 | 16 |
| N | 287 | M G A P V I L F S C T N Q H Y W D E K R | 8 | 12 |
| G | 288 | M G A P V I L F S C T N Q H Y W D E K R | 12 | 8 |
| H | 289 | M G A P V I L F S C T N Q H Y W D E K R | 12 | 8 |
| R | 290 | M G A P V I L F S C T N Q H Y W D E K R | 12 | 8 |
| P | 291 | M G A P V I L F S C T N Q H Y W D E K R | 11 | 9 |
| A | 292 | M G A P V I L F S C T N Q H Y W D E K R | 6 | 14 |
| A | 293 | M G A P V I L F S C T N Q H Y W D E K R | 11 | 9 |
| H | 294 | M G A P V I L F S C T N Q H Y W D E K R | 15 | 5 |
| D | 295 | M G A P V I L F S C T N Q H Y W D E K R | 10 | 10 |
| F | 296 | M G A P V I L F S C T N Q H Y W D E K R | 12 | 8 |
| P | 297 | M G A P V I L F S C T N Q H Y W D E K R | 7 | 13 |
| L | 298 | M G A P V I L F S C T N Q H Y W D E K R | 7 | 13 |
| G | 299 | M G A P V I L F S C T N Q H Y W D E K R | 15 | 5 |
| R | 300 | M G A P V I L F S C T N Q H Y W D E K R | 19 | 1 |
| Q | 301 | M G A P V I L F S C T N Q H Y W D E K R | 5 | 15 |
| L | 302 | M G A P V I L F S C T N Q H Y W D E K R | 5 | 15 |
| P | 303 | M G A P V I L F S C T N Q H Y W D E K R | 11 | 9 |

TABLE 19-continued

Human Klf4 Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| S | 304 | M G A P V I L F S C T N Q H Y W D E K R | 8 | 12 |
| R | 305 | M G A P V I L F S C T N Q H Y W D E K R | 14 | 6 |
| T | 306 | M G A P V I L F S C T N Q H Y W D E K R | 8 | 12 |
| T | 307 | M G A P V I L F S C T N Q H Y W D E K R | 6 | 14 |
| P | 308 | M G A P V I L F S C T N Q H Y W D E K R | 13 | 7 |
| T | 309 | M G A P V I L F S C T N Q H Y W D E K R | 5 | 15 |
| L | 310 | M G A P V I L F S C T N Q H Y W D E K R | 2 | 18 |
| G | 311 | M G A P V I L F S C T N Q H Y W D E K R | 17 | 3 |
| L | 312 | M G A P V I L F S C T N Q H Y W D E K R | 1 | 19 |
| E | 313 | M G A P V I L F S C T N Q H Y W D E K R | 4 | 16 |
| E | 314 | M G A P V I L F S C T N Q H Y W D E K R | 4 | 16 |
| V | 315 | M G A P V I L F S C T N Q H Y W D E K R | 8 | 12 |
| L | 316 | M G A P V I L F S C T N Q H Y W D E K R | 6 | 14 |
| S | 317 | M G A P V I L F S C T N Q H Y W D E K R | 10 | 10 |
| S | 318 | M G A P V I L F S C T N Q H Y W D E K R | 13 | 7 |
| R | 319 | M G A P V I L F S C T N Q H Y W D E K R | 15 | 5 |
| D | 320 | M G A P V I L F S C T N Q H Y W D E K R | 9 | 11 |
| C | 321 | M G A P V I L F S C T N Q H Y W D E K R | 14 | 6 |
| H | 322 | M G A P V I L F S C T N Q H Y W D E K R | 15 | 5 |
| P | 323 | M G A P V I L F S C T N Q H Y W D E K R | 10 | 10 |
| A | 324 | M G A P V I L F S C T N Q H Y W D E K R | 10 | 10 |
| L | 325 | M G A P V I L F S C T N Q H Y W D E K R | 6 | 14 |
| P | 326 | M G A P V I L F S C T N Q H Y W D E K R | 15 | 5 |
| L | 327 | M G A P V I L F S C T N Q H Y W D E K R | 6 | 14 |
| P | 328 | M G A P V I L F S C T N Q H Y W D E K R | 14 | 6 |
| P | 329 | M G A P V I L F S C T N Q H Y W D E K R | 9 | 11 |
| G | 330 | M G A P V I L F S C T N Q H Y W D E K R | 17 | 3 |
| F | 331 | M G A P V I L F S T N Q H Y W D E K R | 6 | 14 |
| H | 332 | M G A P V I L F S C T N Q H Y W D E K R | 16 | 4 |
| P | 333 | M G A P V I L F S C T N Q H Y W D E K R | 18 | 2 |
| H | 334 | M G A P V I L F S C T N Q H Y W D E K R | 16 | 4 |
| P | 335 | M G A P V I L F S C T N Q H Y W D E K R | 6 | 14 |
| G | 336 | M G A P V I L F S C T N Q H Y W D E K R | 16 | 4 |
| P | 337 | M G A P V I L F S C T N Q H Y W D E K R | 6 | 14 |
| N | 338 | M G A P V I L F S C T N Q H Y W D E K R | 8 | 12 |
| Y | 339 | M G A P V I L F S C T N Q H Y W D E K R | 12 | 8 |

TABLE 19-continued

Human Klf4 Amino Acid Substitution Matrix
(Predictions Based on PMUT Analysis)
(Sequences disclosed as SEQ ID NO: 66)

| WT | Position | Substitution Matrix | Number of Predicted Deleterious Mutations | Number of Predicted Neutral Mutations |
|---|---|---|---|---|
| P | 340 | M G A P V I L F S C T N Q H Y W D E K R | 8 | 12 |
| S | 341 | M G A P V I L F S C T N Q H Y W D E K R | 7 | 13 |
| F | 342 | M G A P V I L F S C T N Q H Y W D E K R | 12 | 8 |
| L | 343 | M G A P V I L F S C T N Q H Y W D E K R | 5 | 15 |
| P | 344 | M G A P V I L F S C T N Q H Y W D E K R | 7 | 13 |
| D | 345 | M G A P V I L F S C T N Q H Y W D E K R | 12 | 8 |
| Q | 346 | M G A P V I L F S C T N Q H Y W D E K R | 7 | 13 |
| M | 347 | M G A P V I L F S C T N Q H Y W D E K R | 12 | 8 |
| Q | 348 | M G A P V I L F S C T N Q H Y W D E K R | 12 | 8 |
| P | 349 | M G A P V I L F S C T N Q H Y W D E K R | 5 | 15 |
| Q | 350 | M G A P V I L F S C T N Q H Y W D E K R | 4 | 16 |
| V | 351 | M G A P V I L F S C T N Q H Y W D E K R | 7 | 13 |
| P | 352 | M G A P V I L F S C T N Q H Y W D E K R | 11 | 9 |
| P | 353 | M G A P V I L F S C T N Q H Y W D E K R | 8 | 12 |
| L | 354 | M G A P V I L F S C T N Q H Y W D E K R | 8 | 12 |
| H | 355 | M G A P V I L F S C T N Q H Y W D E K R | 13 | 7 |
| Y | 356 | M G A P V I L F S C T N Q H Y W D E K R | 14 | 6 |
| Q | 357 | M G A P V I L F S C T N Q H Y W D E K R | 5 | 15 |
| E | 358 | M G A P V I L F S C T N Q H Y W D E K R | 7 | 13 |
| L | 359 | M G A P V I L F S C T N Q H Y W D E K R | 6 | 14 |
| M | 360 | M G A P V I L F S C T N Q H Y W D E K R | 7 | 13 |
| P | 361 | M G A P V I L F S C T N Q H Y W D E K R | 16 | 4 |
| P | 362 | M G A P V I L F S C T N Q H Y W D E K R | 17 | 3 |
| G | 363 | M G A P V I L F S C T N Q H Y W D E K R | 12 | 8 |
| S | 364 | M G A P V I L F S C T N Q H Y W D E K R | 9 | 11 |
| C | 365 | M G A P V I L F S C T N Q H Y W D E K R | 15 | 5 |
| M | 366 | M G A P V I L F S C T N Q H Y W D E K R | 10 | 10 |
| P | 367 | M G A P V I L F S C T N Q H Y W D E K R | 14 | 6 |
| E | 368 | M G A P V I L F S C T N Q H Y W D E K R | 5 | 15 |
| E | 369 | M G A P V I L F S C T N Q H Y W D E K R | 9 | 11 |
| P | 370 | M G A P V I L F S C T N Q H Y W D E K R | 6 | 14 |
| K | 371 | M G A P V I L F S C T N Q H Y W D E K R | 14 | 6 |
| P | 372 | M G A P V I L F S C T N Q H Y W D E K R | 10 | 10 |
| K | 373 | M G A P V I L F S C T N Q H Y W D E K R | 6 | 14 |
| R | 374 | M G A P V I L F S C T N Q H Y W D E K R | 10 | 10 |

TABLE 19-continued

Human Klf4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| G | 375 | M G A P V I L F S C T N Q H Y W D E K R | 17 | 3 |
| R | 376 | M G A P V I L F S C T N Q H Y W D E K R | 11 | 9 |
| R | 377 | M G A P V I L F S C T N Q H Y W D E K R | 17 | 3 |
| S | 378 | M G A P V I L F S C T N Q H Y W D E K R | 9 | 11 |
| W | 379 | M G A P V I L F S C T N Q H Y W D E K R | 2 | 18 |
| P | 380 | M G A P V I L F S C T N Q H Y W D E K R | 13 | 7 |
| R | 381 | M G A P V I L F S C T N Q H Y W D E K R | 18 | 2 |
| K | 382 | M G A P V I L F S C T N Q H Y W D E K R | 6 | 14 |
| R | 383 | M G A P V I L F S C T N Q H Y W D E K R | 18 | 2 |
| T | 384 | M G A P V I L F S C T N Q H Y W D E K R | 5 | 15 |
| A | 385 | M G A P V I L F S C T N Q H Y W D E K R | 14 | 6 |
| T | 386 | M G A P V I L F S C T N Q H Y W D E K R | 11 | 9 |
| H | 387 | M G A P V I L F S C T N Q H Y W D E K R | 14 | 6 |
| T | 388 | M G A P V I L F S C T N Q H Y W D E K R | 10 | 10 |
| C | 389 | M G A P V I L F S C T N Q H Y W D E K R | 17 | 3 |
| D | 390 | M G A P V I L F S C T N Q H Y W D E K R | 14 | 6 |
| Y | 391 | M G A P V I L F S C T N Q H Y W D E K R | 11 | 9 |
| A | 392 | M G A P V I L F S C T N Q H Y W D E K R | 14 | 6 |
| G | 393 | M G A P V I L F S C T N Q H Y W D E K R | 16 | 4 |
| C | 394 | M G A P V I L F S C T N Q H Y W D E K R | 18 | 2 |
| G | 395 | M G A P V I L F S C T N Q H Y W D E K R | 16 | 4 |
| K | 396 | M G A P V I L F S C T N Q H Y W D E K R | 15 | 5 |
| T | 397 | M G A P V I L F S C T N Q H Y W D E K R | 12 | 8 |
| Y | 398 | M G A P V I L F S C T N Q H Y W D E K R | 13 | 7 |
| T | 399 | M G A P V I L F S C T N Q H Y W D E K R | 12 | 8 |
| K | 400 | M G A P V I L F S C T N Q H Y W D E K R | 14 | 6 |
| S | 401 | M G A P V I L F S C T N Q H Y W D E K R | 14 | 6 |
| S | 402 | M G A P V I L F S C T N Q H Y W D E K R | 14 | 6 |
| H | 403 | M G A P V I L F S C T N Q H Y W D E K R | 18 | 2 |
| L | 404 | M G A P V I L F S C T N Q H Y W D E K R | 10 | 10 |
| K | 405 | M G A P V I L F S C T N Q H Y W D E K R | 14 | 6 |
| A | 406 | M G A P V I L F S C T N Q H Y W D E K R | 15 | 5 |
| H | 407 | M G A P V I L F S C T N Q H Y W D E K R | 18 | 2 |
| L | 408 | M G A P V I L F S C T N Q H Y W D E K R | 7 | 13 |
| R | 409 | M G A P V I L F S C T N Q H Y W D E K R | 18 | 2 |
| T | 410 | M G A P V I L F S C T N Q H Y W D E K R | 14 | 6 |

TABLE 19-continued

Human Klf4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| H | 411 | M G A P V I L F S C T N Q H Y W D E K R | 15 | 5 |
| T | 412 | M G A P V I L F S C T N Q H Y W D E K R | 12 | 8 |
| G | 413 | M G A P V I L F S C T N Q H Y W D E K R | 16 | 4 |
| E | 414 | M G A P V I L F S C T N Q H Y W D E K R | 13 | 7 |
| K | 415 | M G A P V I L F S C T N Q H Y W D E K R | 14 | 6 |
| P | 416 | M G A P V I L F S C T N Q H Y W D E K R | 15 | 5 |
| Y | 417 | M G A P V I L F S C T N Q H Y W D E K R | 13 | 7 |
| H | 418 | M G A P V I L F S C T N Q H Y W D E K R | 15 | 5 |
| C | 419 | M G A P V I L F S C T N Q H Y W D E K R | 18 | 2 |
| D | 420 | M G A P V I L F S C T N Q H Y W D E K R | 13 | 7 |
| W | 421 | M G A P V I L F S C T N Q H Y W D E K R | 18 | 2 |
| D | 422 | M G A P V I L F S C T N Q H Y W D E K R | 10 | 10 |
| G | 423 | M G A P V I L F S C T N Q H Y W D E K R | 16 | 4 |
| C | 424 | M G A P V I L F S C T N Q H Y W D E K R | 18 | 2 |
| G | 425 | M G A P V I L F S C T N Q H Y W D E K R | 16 | 4 |
| W | 426 | M G A P V I L F S C T N Q H Y W D E K R | 18 | 2 |
| K | 427 | M G A P V I L F S C T N Q H Y W D E K R | 14 | 6 |
| F | 428 | M G A P V I L F S C T N Q H Y W D E K R | 15 | 5 |
| A | 429 | M G A P V I L F S C T N Q H Y W D E K R | 14 | 6 |
| R | 430 | M G A P V I L F S C T N Q H Y W D E K R | 18 | 2 |
| S | 431 | M G A P V I L F S C T N Q H Y W D E K R | 12 | 8 |
| D | 432 | M G A P V I L F S C T N Q H Y W D E K R | 17 | 3 |
| E | 433 | M G A P V I L F S C T N Q H Y W D E K R | 16 | 4 |
| L | 434 | M G A P V I L F S C T N Q H Y W D E K R | 10 | 10 |
| T | 435 | M G A P V I L F S C T N Q H Y W D E K R | 14 | 6 |
| R | 436 | M G A P V I L F S C T N Q H Y W D E K R | 18 | 2 |
| H | 437 | M G A P V I L F S C T N Q H Y W D E K R | 18 | 2 |
| Y | 438 | M G A P V I L F S C T N Q H Y W D E K R | 13 | 7 |
| R | 439 | M G A P V I L F S C T N Q H Y W D E K R | 18 | 2 |
| K | 440 | M G A P V I L F S C T N Q H Y W D E K R | 16 | 4 |
| H | 441 | M G A P V I L F S C T N Q H Y W D E K R | 18 | 2 |
| T | 442 | M G A P V I L F S C T N Q H Y W D E K R | 12 | 8 |
| G | 443 | M G A P V I L F S C T N Q H Y W D E K R | 16 | 4 |
| H | 444 | M G A P V I L F S C T N Q H Y W D E K R | 15 | 5 |
| R | 445 | M G A P V I L F S C T N Q H Y W D E K R | 16 | 4 |

TABLE 19-continued

Human Klf4 Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| P | 446 | M G A P V I L F S C T N Q H Y W D E K R | 16 | 4 |
| F | 447 | M G A P V I L F S C T N Q H Y W D E K R | 14 | 6 |
| Q | 448 | M G A P V I L F S C T N Q H Y W D E K R | 11 | 9 |
| C | 449 | M G A P V I L F S C T N Q H Y W D E K R | 17 | 3 |
| Q | 450 | M G A P V I L F S C T N Q H Y W D E K R | 12 | 8 |
| K | 451 | M G A P V I L F S C T N Q H Y W D E K R | 12 | 8 |
| C | 452 | M G A P V I L F S C T N Q H Y W D E K R | 17 | 3 |
| D | 453 | M G A P V I L F S C T N Q H Y W D E K R | 15 | 5 |
| R | 454 | M G A P V I L F S C T N Q H Y W D E K R | 18 | 2 |
| A | 455 | M G A P V I L F S C T N Q H Y W D E K R | 14 | 6 |
| F | 456 | M G A P V I L F S C T N Q H Y W D E K R | 13 | 7 |
| S | 457 | M G A P V I L F S C T N Q H Y W D E K R | 12 | 8 |
| R | 458 | M G A P V I L F S C T N Q H Y W D E K R | 18 | 2 |
| S | 459 | M G A P V I L F S C T N Q H Y W D E K R | 14 | 6 |
| D | 460 | M G A P V I L F S C T N Q H Y W D E K R | 15 | 5 |
| H | 461 | M G A P V I L F S C T N Q H Y W D E K R | 18 | 2 |
| L | 462 | M G A P V I L F S C T N Q H Y W D E K R | 10 | 10 |
| A | 463 | M G A P V I L F S C T N Q H Y W D E K R | 15 | 5 |
| L | 464 | M G A P V I L F S C T N Q H Y W D E K R | 10 | 10 |
| H | 465 | M G A P V I L F S C T N Q H Y W D E K R | 18 | 2 |
| M | 466 | M G A P V I L F S C T N Q H Y W D E K R | 17 | 3 |
| K | 467 | M G A P V I L F S C T N Q H Y W D E K R | 16 | 4 |
| R | 468 | M G A P V I L F S C T N Q H Y W D E K R | 18 | 2 |
| H | 469 | M G A P V I L F S C T N Q H Y W D E K R | 15 | 5 |
| F | 470 | M G A P V I L F S C T N Q H Y W D E K R | 11 | 9 |

TABLE 20

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| M | 1 | M G A P V I L F S C T N Q H Y W D E K R | 13 | 7 |
| P | 2 | M G A P V I L F S C T N Q H Y W D E K R | 14 | 6 |
| L | 3 | M G A P V I L F S C T N Q H Y W D E K R | 12 | 8 |
| N | 4 | M G A P V I L F S C T N Q H Y W D E K R | 11 | 9 |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| V | 5  | M G A P V I L F S C T N Q H Y W D E K R | 7  | 13 |
| S | 6  | M G A P V I L F S C T N Q H Y W D E K R | 10 | 10 |
| F | 7  | M G A P V I L F S C T N Q H Y W D E K R | 13 | 7  |
| T | 8  | M G A P V I L F S C T N Q H Y W D E K R | 0  | 20 |
| N | 9  | M G A P V I L F S C T N Q H Y W D E K R | 8  | 12 |
| R | 10 | M G A P V I L F S C T N Q H Y W D E K R | 9  | 11 |
| N | 11 | M G A P V I L F S C T N Q H Y W D E K R | 13 | 7  |
| Y | 12 | M G A P V I L F S C T N Q H Y W D E K R | 10 | 10 |
| D | 13 | M G A P V I L F S C T N Q H Y W D E K R | 16 | 4  |
| L | 14 | M G A P V I L F S C T N Q H Y W D E K R | 6  | 14 |
| D | 15 | M G A P V I L F S C T N Q H Y W D E K R | 11 | 9  |
| Y | 16 | M G A P V I L F S C T N Q H Y W D E K R | 14 | 6  |
| D | 17 | M G A P V I L F S C T N Q H Y W D E K R | 15 | 5  |
| S | 18 | M G A P V I L F S C T N Q H Y W D E K R | 16 | 4  |
| V | 19 | M G A P V I L F S C T N Q H Y W D E K R | 5  | 15 |
| Q | 20 | M G A P V I L F S C T N Q H Y W D E K R | 18 | 2  |
| P | 21 | M G A P V I L F S C T N Q H Y W D E K R | 17 | 3  |
| Y | 22 | M G A P V I L F S C T N Q H Y W D E K R | 14 | 6  |
| F | 23 | M G A P V I L F S C T N Q H Y W D E K R | 18 | 2  |
| Y | 24 | M G A P V I L F S C T N Q H Y W D E K R | 10 | 10 |
| C | 25 | M G A P V I L F S C T N Q H Y W D E K R | 7  | 13 |
| D | 26 | M G A P V I L F S C T N Q H Y W D E K R | 12 | 8  |
| E | 27 | M G A P V I L F S C T N Q H Y W D E K R | 11 | 9  |
| E | 28 | M G A P V I L F S C T N Q H Y W D E K R | 8  | 12 |
| E | 29 | M G A P V I L F S C T N Q H Y W D E K R | 10 | 10 |
| N | 30 | M G A P V I L F S C T N Q H Y W D E K R | 10 | 10 |
| F | 31 | M G A P V I L F S C T N Q H Y W D E K R | 6  | 14 |
| Y | 32 | M G A P V I L F S C T N Q H Y W D E K R | 14 | 6  |
| Q | 33 | M G A P V I L F S C T N Q H Y W D E K R | 4  | 16 |
| Q | 34 | M G A P V I L F S C T N Q H Y W D E K R | 15 | 5  |
| Q | 35 | M G A P V I L F S C T N Q H Y W D E K R | 12 | 8  |
| Q | 36 | M G A P V I L F S C T N Q H Y W D E K R | 5  | 15 |
| Q | 37 | M G A P V I L F S C T N Q H Y W D E K R | 11 | 9  |
| S | 38 | M G A P V I L F S C T N Q H Y W D E K R | 9  | 11 |
| E | 39 | M G A P V I L F S C T N Q H Y W D E K R | 13 | 7  |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| L | 40 | M G A P V I L F S C T N Q H Y W D E K R | 10 | 10 |
| Q | 41 | M G A P V I L F S C T N Q H Y W D E K R | 16 | 4 |
| P | 42 | M G A P V I L F S C T N Q H Y W D E K R | 11 | 9 |
| P | 43 | M G A P V I L F S C T N Q H Y W D E K R | 12 | 8 |
| A | 44 | M G A P V I L F S C T N Q H Y W D E K R | 16 | 4 |
| P | 45 | M G A P V I L F S C T N Q H Y W D E K R | 18 | 2 |
| S | 46 | M G A P V I L F S C T N Q H Y W D E K R | 9 | 11 |
| E | 47 | M G A P V I L F S C T N Q H Y W D E K R | 11 | 9 |
| D | 48 | M G A P V I L F S C T N Q H Y W D E K R | 14 | 6 |
| I | 49 | M G A P V I L F S C T N Q H Y W D E K R | 12 | 8 |
| W | 50 | M G A P V I L F S C T N Q H Y W D E K R | 18 | 2 |
| K | 51 | M G A P V I L F S C T N Q H Y W D E K R | 16 | 4 |
| K | 52 | M G A P V I L F S C T N Q H Y W D E K R | 16 | 4 |
| F | 53 | M G A P V I L F S C T N Q H Y W D E K R | 18 | 2 |
| E | 54 | M G A P V I L F S C T N Q H Y W D E K R | 11 | 9 |
| L | 55 | M G A P V I L F S C T N Q H Y W D E K R | 7 | 13 |
| L | 56 | M G A P V I L F S C T N Q H Y W D E K R | 11 | 9 |
| P | 57 | M G A P V I L F S C T N Q H Y W D E K R | 14 | 6 |
| T | 58 | M G A P V I L F S C T N Q H Y W D E K R | 15 | 5 |
| P | 59 | M G A P V I L F S C T N Q H Y W D E K R | 16 | 4 |
| P | 60 | M G A P V I L F S C T N Q H Y W D E K R | 15 | 5 |
| L | 61 | M G A P V I L F S C T N Q H Y W D E K R | 7 | 13 |
| S | 62 | M G A P V I L F S C T N Q H Y W D E K R | 17 | 3 |
| P | 63 | M G A P V I L F S C T N Q H Y W D E K R | 14 | 6 |
| S | 64 | M G A P V I L F S C T N Q H Y W D E K R | 15 | 5 |
| R | 65 | M G A P V I L F S C T N Q H Y W D E K R | 17 | 3 |
| R | 66 | M G A P V I L F S C T N Q H Y W D E K R | 15 | 5 |
| S | 67 | M G A P V I L F S C T N Q H Y W D E K R | 14 | 6 |
| G | 68 | M G A P V I L F S C T N Q H Y W D E K R | 13 | 7 |
| L | 69 | M G A P V I L F S C T N Q H Y W D E K R | 3 | 17 |
| C | 70 | M G A P V I L F S C T N Q H Y W D E K R | 14 | 6 |
| S | 71 | M G A P V I L F S C T N Q H Y W D E K R | 13 | 7 |
| P | 72 | M G A P V I L F S C T N Q H Y W D E K R | 15 | 5 |
| S | 73 | M G A P V I L F S C T N Q H Y W D E K R | 7 | 13 |
| Y | 74 | M G A P V I L F S C T N Q H Y W D E K R | 8 | 12 |
| V | 75 | M G A P V I L F S C T N Q H Y W D E K R | 9 | 11 |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| A | 76  | M G A P V I L F S C T N Q H Y W D E K R | 9  | 11 |
| V | 77  | M G A P V I L F S C T N Q H Y W D E K R | 2  | 18 |
| T | 78  | M G A P V I L F S C T N Q H Y W D E K R | 19 | 1  |
| P | 79  | M G A P V I L F S C T N Q H Y W D E K R | 3  | 17 |
| F | 80  | M G A P V I L F S C T N Q H Y W D E K R | 8  | 12 |
| S | 81  | M G A P V I L F S C T N Q H Y W D E K R | 14 | 6  |
| L | 82  | M G A P V I L F S C T N Q H Y W D E K R | 1  | 19 |
| R | 83  | M G A P V I L F S C T N Q H Y W D E K R | 12 | 8  |
| G | 84  | M G A P V I L F S C T N Q H Y W D E K R | 11 | 9  |
| D | 85  | M G A P V I L F S C T N Q H Y W D E K R | 9  | 11 |
| N | 86  | M G A P V I L F S C T N Q H Y W D E K R | 3  | 17 |
| D | 87  | M G A P V I L F S C T N Q H Y W D E K R | 13 | 7  |
| G | 88  | M G A P V I L F S C T N Q H Y W D E K R | 10 | 10 |
| G | 89  | M G A P V I L F S C T N Q H Y W D E K R | 8  | 12 |
| G | 90  | M G A P V I L F S C T N Q H Y W D E K R | 11 | 9  |
| G | 91  | M G A P V I L F S C T N Q H Y W D E K R | 8  | 12 |
| S | 92  | M G A P V I L F S C T N Q H Y W D E K R | 13 | 7  |
| F | 93  | M G A P V I L F S C T N Q H Y W D E K R | 4  | 16 |
| S | 94  | M G A P V I L F S C T N Q H Y W D E K R | 12 | 8  |
| T | 95  | M G A P V I L F S C T N Q H Y W D E K R | 16 | 4  |
| A | 96  | M G A P V I L F S C T N Q H Y W D E K R | 16 | 4  |
| D | 97  | M G A P V I L F S C T N Q H Y W D E K R | 12 | 8  |
| Q | 98  | M G A P V I L F S C T N Q H Y W D E K R | 16 | 4  |
| L | 99  | M G A P V I L F S C T N Q H Y W D E K R | 12 | 8  |
| E | 100 | M G A P V I L F S C T N Q H Y W D E K R | 14 | 6  |
| M | 101 | M G A P V I L F S C T N Q H Y W D E K R | 14 | 6  |
| V | 102 | M G A P V I L F S C T N Q H Y W D E K R | 15 | 5  |
| T | 103 | M G A P V I L F S C T N Q H Y W D E K R | 10 | 10 |
| E | 104 | M G A P V I L F S C T N Q H Y W D E K R | 15 | 5  |
| L | 105 | M G A P V I L F S C T N Q H Y W D E K R | 9  | 11 |
| L | 106 | M G A P V I L F S C T N Q H Y W D E K R | 10 | 10 |
| G | 107 | M G A P V I L F S C T N Q H Y W D E K R | 17 | 3  |
| G | 108 | M G A P V I L F S C T N Q H Y W D E K R | 10 | 10 |
| D | 109 | M G A P V I L F S C T N Q H Y W D E K R | 17 | 3  |
| M | 110 | M G A P V I L F S C T N Q H Y W D E K R | 13 | 7  |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| V | 111 | M G A P V I L F S C T N Q H Y W D E K R | 14 | 6 |
| N | 112 | M G A P V I L F S C T N Q H Y W D E K R | 16 | 4 |
| Q | 113 | M G A P V I L F S C T N Q H Y W D E K R | 15 | 5 |
| S | 114 | M G A P V I L F S C T N Q H Y W D E K R | 15 | 5 |
| F | 115 | M G A P V I L F S C T N Q H Y W D E K R | 13 | 7 |
| I | 116 | M G A P V I L F S C T N Q H Y W D E K R | 14 | 6 |
| C | 117 | M G A P V I L F S C T N Q H Y W D E K R | 16 | 4 |
| D | 118 | M G A P V I L F S C T N Q H Y W D E K R | 14 | 6 |
| P | 119 | M G A P V I L F S C T N Q H Y W D E K R | 13 | 7 |
| D | 120 | M G A P V I L F S C T N Q H Y W D E K R | 14 | 6 |
| D | 121 | M G A P V I L F S C T N Q H Y W D E K R | 10 | 10 |
| E | 122 | M G A P V I L F S C T N Q H Y W D E K R | 12 | 8 |
| T | 123 | M G A P V I L F S C T N Q H Y Y W D E K R | 9 | 11 |
| F | 124 | M G A P V I L F S C T N Q H Y W D E K R | 16 | 4 |
| I | 125 | M G A P V I L F S C T N Q H Y W D E K R | 9 | 11 |
| K | 126 | M G A P V I L F S C T N Q H Y W D E K R | 17 | 3 |
| N | 127 | M G A P V I L F S C T N Q H Y W D E K R | 6 | 14 |
| I | 128 | M G A P V I L F S C T N Q H Y W D E K R | 14 | 6 |
| I | 129 | M G A P V I L F S C T N Q H Y W D E K R | 13 | 7 |
| I | 130 | M G A P V I L F S C T N Q H Y W D E K R | 12 | 8 |
| Q | 131 | M G A P V I L F S C T N Q H Y W D E K R | 16 | 4 |
| D | 132 | M G A P V I L F S C T N Q H Y W D E K R | 17 | 3 |
| C | 133 | M G A P V I L F S C T N Q H Y W D E K R | 17 | 3 |
| M | 134 | M G A P V I L F S C T N Q H Y W D E K R | 14 | 6 |
| W | 135 | M G A P V I L F S C T N Q H Y W D E K R | 19 | 1 |
| S | 136 | M G A P V I L F S C T N Q H Y W D E K R | 15 | 5 |
| G | 137 | M G A P V I L F S C T N Q H Y W D E K R | 18 | 2 |
| F | 138 | M G A P V I L F S C T N Q H Y W D E K R | 17 | 3 |
| S | 139 | M G A P V I L F S C T N Q H Y W D E K R | 16 | 4 |
| A | 140 | M G A P V I L F S C T N Q H Y W D E K R | 17 | 3 |
| A | 141 | M G A P V I L F S C T N Q H Y W D E K R | 16 | 4 |
| A | 142 | M G A P V I L F S C T N Q H Y W D E K R | 17 | 3 |
| K | 143 | M G A P V I L F S C T N Q H Y W D E K R | 18 | 2 |
| L | 144 | M G A P V I L F S C T N Q H Y W D E K R | 12 | 8 |
| V | 145 | M G A P V I L F S C T N Q H Y W D E K R | 15 | 5 |
| S | 146 | M G A P V I L F S C T N Q H Y W D E K R | 14 | 6 |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| E | 147 | M G A P V I L F S C T N Q H Y W D E K R | 14 | 6 |
| K | 148 | M G A P V I L F S C T N Q H Y W D E K R | 17 | 3 |
| L | 149 | M G A P V I L F S C T N Q H Y W D E K R | 14 | 6 |
| A | 150 | M G A P V I L F S C T N Q H Y W D E K R | 16 | 4 |
| S | 151 | M G A P V I L F S C T N Q H Y W D E K R | 11 | 9 |
| Y | 152 | M G A P V I L F S C T N Q H Y W D E K R | 15 | 5 |
| Q | 153 | M G A P V I L F S C T N Q H Y W D E K R | 17 | 3 |
| A | 154 | M G A P V I L F S C T N Q H Y W D E K R | 17 | 3 |
| A | 155 | M G A P V I L F S C T N Q H Y W D E K R | 12 | 8 |
| R | 156 | M G A P V I L F S C T N Q H Y W D E K R | 17 | 3 |
| K | 157 | M G A P V I L F S C T N Q H Y W D E K R | 11 | 9 |
| D | 158 | M G A P V I L F S C T N Q H Y W D E K R | 8 | 12 |
| S | 159 | M G A P V I L F S C T N Q H Y W D E K R | 9 | 11 |
| G | 160 | M G A P V I L F S C T N Q H Y W D E K R | 10 | 10 |
| S | 161 | M G A P V I L F S C T N Q H Y W D E K R | 7 | 13 |
| P | 162 | M G A P V I L F S C T N Q H Y W D E K R | 13 | 7 |
| N | 163 | M G A P V I L F S C T N Q H Y W D E K R | 2 | 18 |
| P | 164 | M G A P V I L F S C T N H Y W D E K R | 8 | 12 |
| A | 165 | M G A P V I L F S C T N Q H Y W D E K R | 8 | 12 |
| R | 166 | M G A P V I L F S C T N Q H Y W D E K R | 16 | 4 |
| G | 167 | M G A P V I L F S C T N Q H Y W D E K R | 11 | 9 |
| H | 168 | M G A P V I L F S C T N Q H Y W D E K R | 14 | 6 |
| S | 169 | M G A P V I L F S C T N Q H Y W D E K R | 4 | 16 |
| V | 170 | M G A P V I L F S C T N Q H Y W D E K R | 10 | 10 |
| C | 171 | M G A P V I L F S C T N Q H Y W D E K R | 10 | 10 |
| S | 172 | M G A P V I L F S C T N Q H Y W D E K R | 10 | 10 |
| T | 173 | M G A P V I L F S C T N Q H Y W D E K R | 10 | 10 |
| S | 174 | M G A P V I L F S C T N Q H Y W D E K R | 13 | 7 |
| S | 175 | M G A P V I L F S C T N Q H Y W D E K R | 10 | 10 |
| L | 176 | M G A P V I L F S C T N Q H Y W D E K R | 6 | 14 |
| Y | 177 | M G A P V I L F S C T N Q H Y W D E K R | 11 | 9 |
| L | 178 | M G A P V I L F S C T N Q H Y W D E K R | 9 | 11 |
| Q | 179 | M G A P V I L F S C T N Q H Y W D E K R | 13 | 7 |
| D | 180 | M G A P V I L F S C T N Q H Y W D E K R | 15 | 5 |
| L | 181 | M G A P V I L F S C T N Q H Y W D E K R | 10 | 10 |

TABLE 20-continued

Human c-Myc Amino Acid Substitution Matrix
(Predictions Based on PMUT Analysis)
(Sequences disclosed as SEQ ID NO: 66)

| WT | Position | Sequence | Number of Predicted Deleterious Mutations | Number of Predicted Neutral Mutations |
|---|---|---|---|---|
| S | 182 | M G A P V I L F S C T N Q H Y W D E K R | 9 | 11 |
| A | 183 | M G A P V I L F S C T N Q H Y W D E K R | 11 | 9 |
| A | 184 | M G A P V I L F S C T N Q H Y W D E K R | 14 | 6 |
| A | 185 | M G A P V I L F S C T N Q H Y W D E K R | 15 | 5 |
| S | 186 | M G A P V I L F S C T N Q H Y W D E K R | 15 | 5 |
| E | 187 | M G A P V I L F S C T N Q H Y W D E K R | 9 | 11 |
| C | 188 | M G A P V I L F S C T N Q H Y W D E K R | 18 | 2 |
| I | 189 | M G A P V I L F S C T N Q H Y W D E K R | 14 | 6 |
| D | 190 | M G A P V I L F S C T N Q H Y W D E K R | 16 | 4 |
| P | 191 | M G A P V I L F S C T N Q H Y W D E K R | 16 | 4 |
| S | 192 | M G A P V I L F S C T N Q H Y W D E K R | 15 | 5 |
| V | 193 | M G A P V I L F S C T N Q H Y W D E K R | 17 | 3 |
| V | 194 | M G A P V I L F S C T N Q H Y W D E K R | 15 | 5 |
| F | 195 | M G A P V I L F S C T N Q H Y W D E K R | 17 | 3 |
| P | 196 | M G A P V I L F S C T N Q H Y W D E K R | 18 | 2 |
| Y | 197 | M G A P V I L F S C T N Q H Y W D E K R | 17 | 3 |
| P | 198 | M G A P V I L F S C T N Q H Y W D E K R | 18 | 2 |
| L | 199 | M G A P V I L F S C T N Q H Y W D E K R | 14 | 6 |
| N | 200 | M G A P V I L F S C T N Q H Y W D E K R | 11 | 9 |
| D | 201 | M G A P V I L F S C T N Q H Y W D E K R | 12 | 8 |
| S | 202 | M G A P V I L F S C T N Q H Y W D E K R | 11 | 9 |
| S | 203 | M G A P V I L F S C T N Q H Y W D E K R | 9 | 11 |
| S | 204 | M G A P V I L F S C T N Q H Y W D E K R | 13 | 7 |
| P | 205 | M G A P V I L F S C T N Q H Y W D E K R | 13 | 7 |
| K | 206 | M G A P V I L F S C T N Q H Y W D E K R | 10 | 10 |
| S | 207 | M G A P V I L F S C T N Q H Y W D E K R | 6 | 14 |
| C | 208 | M G A P V I L F S C T N Q H Y W D E K R | 12 | 8 |
| A | 209 | M G A P V I L F S C T N Q H Y W D E K R | 11 | 9 |
| S | 210 | M G A P V I L F S C T N Q H Y W D E K R | 11 | 9 |
| Q | 211 | M G A P V I L F S C T N Q H Y W D E K R | 1 | 19 |
| D | 212 | M G A P V I L F S C T N Q H Y W D E K R | 14 | 6 |
| S | 213 | M G A P V I L F S C T N Q H Y W D E K R | 13 | 7 |
| S | 214 | M G A P V I L F S C T N Q H Y W D E K R | 7 | 13 |
| A | 215 | M G A P V I L F S C T N Q H Y W D E K R | 16 | 4 |
| F | 216 | M G A P V I L F S C T N Q H Y W D E K R | 6 | 14 |
| S | 217 | M G A P V I L F S C T N Q H Y W D E K R | 16 | 4 |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| P | 218 | M G A P V I L F S C T N Q H Y W D E K R | 15 | 5 |
| S | 219 | M G A P V I L F S C T N Q H Y W D E K R | 11 | 9 |
| S | 220 | M G A P V I L F S C T N Q H Y W D E K R | 10 | 10 |
| D | 221 | M G A P V I L F S C T N Q H Y W D E K R | 9 | 11 |
| S | 222 | M G A P V I L F S C T N Q H Y W D E K R | 14 | 6 |
| L | 223 | M G A P V I L F S C T N Q H Y W D E K R | 6 | 14 |
| L | 224 | M G A P V I L F S C T N Q H Y W D E K R | 9 | 11 |
| S | 225 | M G A P V I L F S C T N Q H Y W D E K R | 10 | 10 |
| S | 226 | M G A P V I L F S C T N Q H Y W D E K R | 10 | 10 |
| T | 227 | M G A P V I L F S C T N Q H Y W D E K R | 8 | 12 |
| E | 228 | M G A P V I L F S C T N Q H Y W D E K R | 10 | 10 |
| S | 229 | M G A P V I L F S C T N Q H Y W D E K R | 8 | 12 |
| S | 230 | M G A P V I L F S C T N Q H Y W D E K R | 11 | 9 |
| P | 231 | M G A P V I L F S C T N Q H Y W D E K R | 14 | 6 |
| Q | 232 | M G A P V I L F S C T N Q H Y W D E K R | 2 | 18 |
| G | 233 | M G A P V I L F S C T N Q H Y W D E K R | 11 | 9 |
| S | 234 | M G A P V I L F S C T N Q H Y W D E K R | 13 | 7 |
| P | 235 | M G A P V I L F S C T N Q H Y W D E K R | 15 | 5 |
| E | 236 | M G A P V I L F S C T N Q H Y W D E K R | 10 | 10 |
| P | 237 | M G A P V I L F S C T N Q H Y W D E K R | 14 | 6 |
| L | 238 | M G A P V I L F S C T N Q H Y W D E K R | 5 | 15 |
| V | 239 | M G A P V I L F S C T N Q H Y W D E K R | 10 | 10 |
| L | 240 | M G A P V I L F S C T N Q H Y W D E K R | 8 | 12 |
| H | 241 | M G G A P V I L F S C T N Q H Y W D E K R | 14 | 6 |
| E | 242 | M G A P V I L F S C T N Q H Y Y D E K R | 11 | 9 |
| E | 243 | M G A P V I L F S C T N Q H Y W D E K R | 14 | 6 |
| T | 244 | M G A P V I L F S C T N Q H Y W D E K R | 12 | 8 |
| P | 245 | M G A P V I L F S C T N Q H Y W D E K R | 14 | 6 |
| P | 246 | M G A P V I L F S C T N Q H Y W D E K R | 15 | 5 |
| T | 247 | M G A P V I L F S C T N Q H Y W D E K R | 11 | 9 |
| Y | 248 | M G A P V I L F S C T N Q H Y W D E K R | 11 | 9 |
| S | 249 | M G A P V I L F S C T N Q H Y W D E K R | 10 | 10 |
| S | 250 | M G A P V I L F S C T N Q H Y W D E K R | 11 | 9 |
| D | 251 | M G A P V I L F S C T N Q H Y W D E K R | 16 | 4 |
| S | 252 | M G A P V I L F S C T N Q H Y W D E K R | 10 | 10 |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| E | 253 | M G A P V I L F S C T N Q H Y W D E K R | 14 | 6 |
| E | 254 | M G A P V I L F S C T N Q H Y W D E K R | 15 | 5 |
| E | 255 | M G A P V I L F S C T N Q H Y W D E K R | 15 | 5 |
| Q | 256 | M G A P V I L F S C T N Q H Y W D E K R | 15 | 5 |
| E | 257 | M G A P V I L F S C T N Q H Y W D E K R | 13 | 7 |
| D | 258 | M G A P V I L F S C T N Q H Y W D E K R | 13 | 7 |
| E | 259 | M G A P V I L F S C T N Q H Y W D E K R | 13 | 7 |
| E | 260 | M G A P V I L F S C T N Q H Y W D E K R | 14 | 6 |
| E | 261 | M G A P V I L F S C T N Q H Y W D E K R | 16 | 4 |
| I | 262 | M G A P V I L F S C T N Q H Y W D E K R | 16 | 4 |
| D | 263 | M G A P V I L F S C T N Q H Y W D E K R | 17 | 3 |
| V | 264 | M G A P V I L F S C T N Q H Y W D E K R | 17 | 3 |
| V | 265 | M G A P V I L F S C T N Q H Y W D E K R | 17 | 3 |
| S | 266 | M G A P V I L F S C T N Q H Y W D E K R | 12 | 8 |
| V | 267 | M G A P V I L F S C T N Q H Y W D E K R | 16 | 4 |
| E | 268 | M G A P V I L F S C T N Q H Y W D E K R | 16 | 4 |
| K | 269 | M G A P V I L F S C T N Q H Y W D E K R | 15 | 5 |
| R | 270 | M G A P V I L F S C T N Q H Y W D E K R | 18 | 2 |
| Q | 271 | M G A P V I L F S C T N Q H Y W D E K R | 18 | 2 |
| A | 272 | M G A P V I L F S C T N Q H Y W D E K R | 8 | 12 |
| P | 273 | M G A P V I L F S C T N Q H Y W D E K R | 13 | 7 |
| G | 274 | M G A P V I L F S C T N Q H Y W D E K R | 7 | 13 |
| K | 275 | M G A P V I L F S C T N Q H Y W D E K R | 15 | 5 |
| R | 276 | M G A P V I L F S C T N Q H Y W D E K R | 18 | 2 |
| S | 277 | M G A P V I L F S C T N Q H Y W D E K R | 12 | 8 |
| E | 278 | M G A P V I L F S C T N Q H Y W D E K R | 12 | 8 |
| S | 279 | M G A P V I L F S C T N Q H Y W D E K R | 13 | 7 |
| G | 280 | M G A P V I L F S C T N Q H Y W D E K R | 15 | 5 |
| S | 281 | M G A P V I L F S C T N Q H Y W D E K R | 11 | 9 |
| P | 282 | M G A P V I L F S C T N Q H Y W D E K R | 9 | 11 |
| S | 283 | M G A P V I L F S C T N Q H Y W D E K R | 14 | 6 |
| A | 284 | M G A P V I L F S C T N Q H Y W D E K R | 13 | 7 |
| G | 285 | M G A P V I L F S C T N Q H Y W D E K R | 9 | 11 |
| G | 286 | M G A P V I L F S C T N Q H Y W D E K R | 15 | 5 |
| H | 287 | M G A P V I L F S C T N Q H Y W D E K R | 15 | 5 |
| S | 288 | M G A P V I L F S C T N Q H Y W D E K R | 12 | 8 |

TABLE 20-continued

Human c-Myc Amino Acid Substitution Matrix
(Predictions Based on PMUT Analysis)
(Sequences disclosed as SEQ ID NO: 66)

| WT | Position | Substitutions | Number of Predicted Deleterious Mutations | Number of Predicted Neutral Mutations |
|---|---|---|---|---|
| K | 289 | M G A P V I L F S C T N Q H Y W D E K R | 17 | 3 |
| P | 290 | M G A P V I L F S C T N Q H Y W D E K R | 14 | 6 |
| P | 291 | M G A P V I L F S C T N Q H Y W D E K R | 11 | 9 |
| H | 292 | M G A P V I L F S C T N Q H Y W D E K R | 15 | 5 |
| S | 293 | M G A P V I L F S C T N Q H Y W D E K R | 16 | 4 |
| P | 294 | M G A P V I L F S C T N Q H Y W D E K R | 17 | 3 |
| L | 295 | M G A P V I L F S C T N Q H Y W D E K R | 15 | 5 |
| V | 296 | M G A P V I L F S C T N Q H Y W D E K R | 15 | 5 |
| L | 297 | M G A P V I L F S C T N Q H Y W D E K R | 16 | 4 |
| K | 298 | M G A P V I L F S C T N Q H Y W D E K R | 18 | 2 |
| R | 299 | M G A P V I L F S C T N Q H Y W D E K R | 19 | 1 |
| C | 300 | M G A P V I L F S C T N Q H Y W D E K R | 18 | 2 |
| H | 301 | M G A P V I L F S C T N Q H Y W D E K R | 17 | 3 |
| V | 302 | M G A P V I L F S C T N Q H Y W D E K R | 16 | 4 |
| S | 303 | M G A P V I L F S C T N Q H Y W D E K R | 12 | 8 |
| T | 304 | M G A P V I L F S C T N Q H Y W D E K R | 11 | 9 |
| H | 305 | M G A P V I L F S C T N Q H Y W D E K R | 15 | 5 |
| Q | 306 | M G A P V I L F S C T N Q H Y W D E K R | 18 | 2 |
| H | 307 | M G A P V I L F S C T N Q H Y W D E K R | 18 | 2 |
| N | 308 | M G A P V I L F S C T N Q H Y W D E K R | 18 | 2 |
| Y | 309 | M G A P V I L F S C T N Q H Y W D E K R | 18 | 2 |
| A | 310 | M G A P V I L F S C T N Q H Y W D E K R | 17 | 3 |
| A | 311 | M G A P V I L F S C T N Q H Y W D E K R | 18 | 2 |
| P | 312 | M G A P V I L F S C T N Q H Y W D E K R | 19 | 1 |
| P | 313 | M G A P V I L F S C T N Q H Y W D E K R | 17 | 3 |
| S | 314 | M G A P V I L F S C T N Q H Y W D E K R | 15 | 5 |
| T | 315 | M G A P V I L F S C T N Q H Y W D E K R | 12 | 8 |
| R | 316 | M G A P V I L F S C T N Q H Y W D E K R | 17 | 3 |
| K | 317 | M G A P V I L F S C T N Q H Y W D E K R | 12 | 8 |
| D | 318 | M G A P V I L F S C T N Q H Y W D E K R | 15 | 5 |
| Y | 319 | M G A P V I L F S C T N Q H Y W D E K R | 16 | 4 |
| P | 320 | M G A P V I L F S C T N Q H Y W D E K R | 17 | 3 |
| A | 321 | M G A P V I L F S C T N Q H Y W D E K R | 15 | 5 |
| A | 322 | M G A P V I L F S C T N Q H Y W D E K R | 11 | 9 |
| K | 323 | M G A P V I L F S C T N Q H Y W D E K R | 17 | 3 |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| P | 324 | M G A P V I L F S C T N Q H Y W D E K R | 18 | 2 |
| V | 325 | M G A P V I L F S C T N Q H Y W D E K R | 4 | 16 |
| K | 326 | M G A P V I L F S C T N Q H Y W D E K R | 16 | 4 |
| L | 327 | M G A P V I L F S C T N Q H Y W D E K R | 14 | 6 |
| D | 328 | M G A P V I L F S C T N Q H Y W D E K R | 14 | 6 |
| S | 329 | M G A P V I L F S C T N Q H Y W D E K R | 15 | 5 |
| V | 330 | M G A P V I L F S C T N Q H Y W D E K R | 5 | 15 |
| R | 331 | M G A P V I L F S C T N Q H Y W D E K R | 18 | 2 |
| V | 332 | M G A P V I L F S C T N Q H Y W D E K R | 16 | 4 |
| L | 333 | M G A P V I L F S C T N Q H Y W D E K R | 11 | 9 |
| R | 334 | M G A P V I L F S C T N Q H Y W D E K R | 15 | 5 |
| Q | 335 | M G A P V I L F S C T N Q H Y W D E K R | 14 | 6 |
| I | 336 | M G A P V I L F S C T N Q H Y W D E K R | 14 | 6 |
| S | 337 | M G A P V I L F S C T N Q H Y W D E K R | 16 | 4 |
| N | 338 | M G A P V I L F S C T N Q H Y W D E K R | 13 | 7 |
| N | 339 | M G A P V I L F S C T N Q H Y W D E K R | 12 | 8 |
| R | 340 | M G A P V I L F S C T N Q H Y W D E K R | 18 | 2 |
| K | 341 | M G A P V I L F S C T N Q H Y W D E K R | 18 | 2 |
| C | 342 | M G A P V I L F S C T N Q H Y W D E K R | 18 | 2 |
| T | 343 | M G A P V I L F S C T N Q H Y W D E K R | 5 | 15 |
| S | 344 | M G A P V I L F S C T N Q H Y W D E K R | 14 | 6 |
| P | 345 | M G A P V I L F S C T N Q H Y W D E K R | 17 | 3 |
| R | 346 | M G A P V I L F S C T N Q H Y W D E K R | 19 | 1 |
| S | 347 | M G A P V I L F S C T N Q H Y W D E K R | 16 | 4 |
| S | 348 | M G A P V I L F S C T N Q H Y W D E K R | 17 | 3 |
| D | 349 | M G A P V I L F S C T N Q H Y W D E K R | 16 | 4 |
| T | 350 | M G A P V I L F S C T N Q H Y W D E K R | 11 | 9 |
| E | 351 | M G A P V I L F S C T N Q H Y W D E K R | 15 | 5 |
| E | 352 | M G A P V I L F S C T N Q H Y W D E K R | 15 | 5 |
| N | 353 | M G A P V I L F S C T N Q H Y W D E K R | 17 | 3 |
| V | 354 | M G A P V I L F S C T N Q H Y W D E K R | 1 | 19 |
| K | 355 | M G A P V I L F S C T N Q H Y W D E K R | 16 | 4 |
| R | 356 | M G A P V I L F S C T N Q H Y W D E K R | 18 | 2 |
| R | 357 | M G A P V I L F S C T N Q H Y W D E K R | 18 | 2 |
| T | 358 | M G A P V I L F S C T N Q H Y W D E K R | 16 | 4 |
| H | 359 | M G A P V I L F S C T N Q H Y W D E K R | 18 | 2 |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| N | 360 | M G A P V I L F S C T N Q H Y W D E K R | 18 | 2 |
| V | 361 | M G A P V I L F S C T N Q H Y W D E K R | 16 | 4 |
| L | 362 | M G A P V I L F S C T N Q H Y W D E K R | 16 | 4 |
| E | 363 | M G A P V I L F S C T N Q H Y W D E K R | 17 | 3 |
| R | 364 | M G A P V I L F S C T N Q H Y W D E K R | 18 | 2 |
| Q | 365 | M G A P V I L F S C T N Q H Y W D E K R | 18 | 2 |
| R | 366 | M G A P V I L F S C T N Q H Y W D E K R | 18 | 2 |
| R | 367 | M G A P V I L F S C T N Q H Y W D E K R | 18 | 2 |
| N | 368 | M G A P V I L F S C T N Q H Y W D E K R | 15 | 5 |
| E | 369 | M G A P V I L F S C T N Q H Y W D E K R | 15 | 5 |
| L | 370 | M G A P V I L F S C T N Q H Y W D E K R | 16 | 4 |
| K | 371 | M G A P V I L F S C T N Q H Y W D E K R | 18 | 2 |
| R | 372 | M G A P V I L F S C T N Q H Y W D E K R | 18 | 2 |
| S | 373 | M G A P V I L F S C T N Q H Y W D E K R | 17 | 3 |
| F | 374 | M G A P V I L F S C T N Q H Y W D E K R | 18 | 2 |
| F | 375 | M G A P V I L F S C T N Q H Y W D E K R | 18 | 2 |
| A | 376 | M G A P V I L F S C T N Q H Y W D E K R | 17 | 3 |
| L | 377 | M G A P V I L F S C T N Q H Y W D E K R | 16 | 4 |
| R | 378 | M G A P V I L F S C T N Q H Y W D E K R | 19 | 1 |
| D | 379 | M G A P V I L F S C T N Q H Y W D E K R | 15 | 5 |
| Q | 380 | M G A P V I L F S C T N Q H Y W D E K R | 18 | 2 |
| I | 381 | M G A P V I L F S C T N Q H Y W D E K R | 15 | 5 |
| P | 382 | M G A P V I L F S C T N Q H Y W D E K R | 18 | 2 |
| E | 383 | M G A P V I L F S C T N Q H Y W D E K R | 15 | 5 |
| L | 384 | M G A P V I L F S C T N Q H Y W D E K R | 13 | 7 |
| E | 385 | M G A P V I L F S C T N Q H Y W D E K R | 13 | 7 |
| N | 386 | M G A P V I L F S C T N Q H Y W D E K R | 15 | 5 |
| N | 387 | M G A P V I L F S C T N Q H Y W D E K R | 15 | 5 |
| E | 388 | M G A P V I L F S C T N Q H Y W D E K R | 14 | 6 |
| K | 389 | M G A P V I L F S C T N Q H Y W D E K R | 18 | 2 |
| A | 390 | M G A P V I L F S C T N Q H Y W D E K R | 17 | 3 |
| P | 391 | M G A P V I L F S C T N Q H Y W D E K R | 17 | 3 |
| K | 392 | M G A P V I L F S C T N Q H Y W D E K R | 18 | 2 |
| V | 393 | M G A P V I L F S C T N Q H Y W D E K R | 18 | 2 |
| V | 394 | M G A P V I L F S C T N Q H Y W D E K R | 18 | 2 |

TABLE 20-continued

Human c-Myc Amino Acid Substitution Matrix
(Predictions Based on PMUT Analysis)
(Sequences disclosed as SEQ ID NO: 66)

| WT Position | | | Number of Predicted Deleterious Mutations | Number of Predicted Neutral Mutations |
|---|---|---|---|---|
| I | 395 | M G A P V I L F S C T N Q H Y W D E K R | 16 | 4 |
| L | 396 | M G A P V I L F S C T N Q H Y W D E K R | 16 | 4 |
| K | 397 | M G A P V I L F S C T N Q H Y W D E K R | 18 | 2 |
| K | 398 | M G A P V I L F S C T N Q H Y W D E K R | 18 | 2 |
| A | 399 | M G A P V I L F S C T N Q H Y W D E K R | 17 | 3 |
| T | 400 | M G A P V I L F S C T N Q H Y W D E K R | 16 | 4 |
| A | 401 | M G A P V I L F S C T N Q H Y W D E K R | 13 | 7 |
| Y | 402 | M G A P V I L F S C T N Q H Y W D E K R | 16 | 4 |
| I | 403 | M G A P V I L F S C T N Q H Y W D E K R | 15 | 5 |
| L | 404 | M G A P V I L F S C T N Q H Y W D E K R | 14 | 6 |
| S | 405 | M G A P V I L F S C T N Q H Y W D E K R | 16 | 4 |
| V | 406 | M G A P V I L F S C T N Q H Y W D E K R | 12 | 8 |
| Q | 407 | M G A P V I L F S C T N Q H Y W D E K R | 18 | 2 |
| A | 408 | M G A P V I L F S C T N Q H Y W D E K R | 16 | 4 |
| E | 409 | M G A P V I L F S C T N Q H Y W D E K R | 10 | 10 |
| E | 410 | M G A P V I L F S C T N Q H Y W D E K R | 17 | 3 |
| Q | 411 | M G A P V I L F S C T N Q H Y W D E K R | 16 | 4 |
| K | 412 | M G A P V I L F S C T N Q H Y W D E K R | 18 | 2 |
| L | 413 | M G A P V I L F S C T N Q H Y W D E K R | 16 | 4 |
| I | 414 | M G A P V I L F S C T N Q H Y W D E K R | 16 | 4 |
| S | 415 | M G A P V I L F S C T N Q H Y W D E K R | 15 | 5 |
| E | 416 | M G A P V I L F S C T N Q H Y W D E K R | 17 | 3 |
| E | 417 | M G A P V I L F S C T N Q H Y W D E K R | 10 | 10 |
| D | 418 | M G A P V I L F S C T N Q H Y W D E K R | 17 | 3 |
| L | 419 | M G A P V I L F S C T N Q H Y W D E K R | 13 | 7 |
| L | 420 | M G A P V I L F S C T N Q H Y W D E K R | 16 | 4 |
| R | 421 | M G A P V I L F S C T N Q H Y W D E K R | 18 | 2 |
| K | 422 | M G A P V I L F S C T N Q H Y W D E K R | 15 | 5 |
| R | 423 | M G A P V I L F S C T N Q H Y W D E K R | 18 | 2 |
| R | 424 | M G A P V I L F S C T N Q H Y W D E K R | 18 | 2 |
| E | 425 | M G A P V I L F S C T N Q H Y W D E K R | 16 | 4 |
| Q | 426 | M G A P V I L F S C T N Q H Y W D E K R | 18 | 2 |
| L | 427 | M G A P V I L F S C T N Q H Y W D E K R | 17 | 3 |
| K | 428 | M G A P V I L F S C T N Q H Y W D E K R | 18 | 2 |
| H | 429 | M G A P V I L F S C T N Q H Y W D E K R | 18 | 2 |
| K | 430 | M G A P V I L F S C T N Q H Y W D E K R | 18 | 2 |

TABLE 20-continued

Human c-Myc Amino Acid Substitution Matrix
(Predictions Based on PMUT Analysis)
(Sequences disclosed as SEQ ID NO: 66)

| WT | Position | | Number of Predicted Deleterious Mutations | Number of Predicted Neutral Mutations |
|---|---|---|---|---|
| L | 431 | M G A P V I L F S C T N Q H Y W D E K R | 17 | 3 |
| E | 432 | M G A P V I L F S C T N Q H Y W D E K R | 17 | 3 |
| Q | 433 | M G A P V I L F S C T N Q H Y W D E K R | 18 | 2 |
| L | 434 | M G A P V I L F S C T N Q H Y W D E K R | 17 | 3 |
| R | 435 | M G A P V I L F S C T N Q H Y W D E K R | 19 | 1 |
| N | 436 | M G A P V I L F S C T N Q H Y W D E K R | 18 | 2 |
| S | 437 | M G A P V I L F S C T N Q H Y W D E K R | 16 | 4 |
| C | 438 | M G A P V I L F S C T N Q H Y W D E K R | 19 | 1 |
| A | 439 | M G A P V I L F S C T N Q H Y W D E K R | 18 | 2 |

TABLE 21

Probe Sets ID, Gene Name, and Gene Description for Hierarchical Clustering Analysis (The International Stem Cell Initiative)
(DEAD peptide disclosed as SEQ ID NO: 65)
(DEAD peptide disclosed as SEQ ID NO: 65)

| Probe Set ID | Gene Name | Gene Description |
|---|---|---|
| AFFX-HUMGAPDH/M33197_M_at | GAPDH | glyceraldehyde-3-phosphate dehydrogenase |
| AFFX-HUMGAPDH/M33197_5_at | GAPDH | glyceraldehyde-3-phosphate dehydrogenase |
| AFFX-HUMGAPDH/M33197_3_at | GAPDH | glyceraldehyde-3-phosphate dehydrogenase |
| 40284_at | FOXA2 | forkhead box A2 |
| 244849_at | SEMA3A | sema domain, immunoglobulin domain (Ig), short basicdomain, secreted, (semaphorin) 3A |
| 244163_at | SEMA3A | sema domain, immunoglobulin domain (Ig), short basicdomain, secreted, (semaphorin) 3A |
| 243712_at | XIST | X (inactive)-specific transcript |
| 243692_at | GATA4 | GATA binding protein 4 |
| 243161_x_at | ZFP42 | zinc finger protein 42 homolog (mouse) |
| 242622_x_at | PTEN | Phosphatase and tensin homolog (mutated in multipleadvanced cancers 1) |
| 241861_at | SYCP3 | Synaptonemal complex protein 3 |
| 241609_at | FOXD3 | Forkhead box D3 |
| 237896_at | NODAL | nodal homolog (mouse) |
| 236930_at | NUMB | Numb homolog (*Drosophila*) |
| 236859_at | RUNX2 | runt-related transcription factor 2 |
| 235795_at | PAX6 | paired box gene 6 (aniridia, keratitis) |
| 234967_at | IL6ST | interleukin 6 signal transducer (gp130, oncostatin Mreceptor) |
| 234474_x_at | IL6ST | interleukin 6 signal transducer (gp130, oncostatin Mreceptor) |
| 233322_at | CD9 | CD9 molecule |
| 233317_at | CD9 | CD9 molecule |
| 233314_at | PTEN | phosphatase and tensin homolog (mutated in multipleadvanced cancers 1) |
| 233254_x_at | PTEN | phosphatase and tensin homolog (mutated in multipleadvanced cancers 1) |
| 232809_s_at | FLT1 | Fms-related tyrosine kinase 1 (vascular endothelialgrowth factor/vascular permeability factor receptor) |
| 232231_at | RUNX2 | runt-related transcription factor 2 |
| 231798_at | NOG | Noggin |
| 231776_at | EOMES | eomesodermin homolog (*Xenopus laevis*) |
| 231592_at | XIST | X (inactive)-specific transcript |
| 230916_at | NODAL | nodal homolog (mouse) |
| 230855_at | GATA4 | GATA binding protein 4 |
| 230462_at | NUMB | numb homolog (*Drosophila*) |
| 230318_at | SERPINA1 | Serpin peptidase inhibitor, clade A (alpha-1antiproteinase, antitrypsin), member 1 |

TABLE 21-continued

Probe Sets ID, Gene Name, and Gene Description for Hierarchical Clustering Analysis (The International Stem Cell Initiative)
(DEAD peptide disclosed as SEQ ID NO: 65)
(DEAD peptide disclosed as SEQ ID NO: 65)

| Probe Set ID | Gene Name | Gene Description |
| --- | --- | --- |
| 229724_at | GABRB3 | gamma-aminobutyric acid (GABA) A receptor, beta 3 |
| 229346_at | NES | nestin |
| 229341_at | TFCP2L1 | Transcription factor CP2-like 1 |
| 229282_at | GATA6 | GATA binding protein 6 |
| 229259_at | GFAP | glial fibrillary acidic protein |
| 228038_at | SOX2 | SRY sex determining region Y)-box 2 |
| 227830_at | GABRB3 | gamma-aminobutyric acid (GABA) A receptor, beta 3 |
| 227771_at | LIFR | leukemia inhibitory factor receptor alpha |
| 227690_at | GABRB3 | gamma-aminobutyric acid (GABA) A receptor, beta 3 |
| 227671_at | XIST | X (inactive)-specific transcript |
| 227642_at | TFCP2L1 | Transcription factor CP2-like 1 |
| 227469_at | PTEN | Phosphatase and tensin homolog (mutated in multipleadvanced cancers 1) |
| 227048_at | LAMA1 | laminin, alpha 1 |
| 225575_at | LIFR | leukemia inhibitory factor receptor alpha |
| 225571_at | LIFR | leukemia inhibitory factor receptor alpha |
| 225363_at | PTEN | phosphatase and tensin homolog (mutated in multipleadvanced cancers 1) |
| 224590_at | XIST | X (inactive)-specific transcript |
| 224589_at | XIST | X (inactive)-specific transcript |
| 224588_at | XIST | X (inactive)-specific transcript |
| 223963_s_at | IGF2BP2 | insulin-like growth factor 2 mRNA binding protein 2 |
| 223679_a | CTNNB1 | catenin (cadherin-associated protein), beta 1, 88 kDa |
| 223122_s_at | SFRP2 | secreted frizzled-related protein 2 |
| 223121_s_at | SFRP2 | secreted frizzled-related protein 2 |
| 222346_at | LAMA1 | laminin, alpha 1 |
| 222176_at | PTEN | phosphatase and tensin homolog (mutated in multipleadvanced cancers 1) |
| 222033_s_at | FLT1 | Fms-related tyrosine kinase 1 (vascular endothelialgrowth factor/vascular permeability factor receptor) |
| 221728_x_at | XIST | X (inactive)-specific transcript |
| 221630_s_at | DDX4 | DEAD (Asp-Glu-Ala-Asp) box polypeptide 4 |
| 221283_at | RUNX2 | runt-related transcription factor 2 |
| 221282_x_at | RUNX2 | runt-related transcription factor 2 |
| 220668_s_at | DNMT3B | DNA (cytosine-5-)-methyltransferase 3 beta |
| 220184_at | NANOG | Nanog homeobox |
| 220053_at | GDF3 | growth differentiation factor 3 |
| 219993_at | SOX17 | SRY (sex determining region Y)-box 17 |
| 219823_at | LIN28 | lin-28 homolog (*C. elegans*) |
| 219735_s_at | TFCP2L1 | transcription factor CP2-like 1 |
| 219177_at | BXDC2 | brix domain containing 2 |
| 218847_at | IGF2BP2 | insulin-like growth factor 2 mRNA binding protein 2 |
| 218678_at | NES | nestin |
| 218048_at | COMMD3 | COMM domain containing 3 |
| 217430_x_at | COL1A1 | collagen, type I, alpha 1 |
| 217404_s_at | COL2A1 | collagen, type II, alpha 1 (primary osteoarthritis, spondyloepiphyseal dysplasia, congenital) |
| 217398_x_at | GAPDH | glyceraldehyde-3-phosphate dehydrogenase |
| 217246_s_at | DIAPH2 | diaphanous homolog 2 (*Drosophila*) |
| 217232_x_at | HBB | hemoglobin, beta |
| 216994_s_at | RUNX2 | runt-related transcription factor 2 |
| 216953_s_at | WT1 | Wilms tumor 1 |
| 216947_at | DES | desmin |
| 216442_x_at | FN1 | fibronectin 1 |
| 214702_at | FN1 | fibronectin 1 |
| 214701_s_at | FN1 | fibronectin 1 |
| 214614_at | HLXB9 | homeobox HB9 |
| 214532_x_at | LOC642559///LOC645682///POU5F1 /// | POU domain, class 5, transcription factor 1 /// POU domain, class 5, transcription factor 1 pseudogene 1/// POU domain, class 5, transcription factor 1 pseudogene |
| 214413_at | TAT | Tyrosine aminotransferase |
| 214312_at | FOXA2 | forkhead box A2 |
| 214240_at | GAL | galanin |
| 214218_s_at | XIST | X (inactive)-specific transcript |
| 214178_s_at | SOX2 | SRY (sex determining region Y)-box 2 |
| 214022_s_at | IFITM1 | interferon induced transmembrane protein 1 (9-27) |
| 213921_at | SST | somatostatin |
| 213825_at | OLIG2 | oligodendrocyte lineage transcription factor 2 |
| 213824_at | OLIG2 | oligodendrocyte lineage transcription factor 2 |
| 213722_at | SOX2 | SRY (sex determining region Y)-box 2 |
| 213721_at | SOX2 | SRY (sex determining region Y)-box 2 |
| 213492_at | COL2A1 | collagen, type II, alpha 1 (primary osteoarthritis, spondyloepiphyseal dysplasia, congenital) |

TABLE 21-continued

Probe Sets ID, Gene Name, and Gene Description for Hierarchical Clustering Analysis (The International Stem Cell Initiative)
(DEAD peptide disclosed as SEQ ID NO: 65)
(DEAD peptide disclosed as SEQ ID NO: 65)

| Probe Set ID | Gene Name | Gene Description |
| --- | --- | --- |
| 213453_x_at | GAPDH | glyceraldehyde-3-phosphate dehydrogenase |
| 213200_at | SYP | synaptophysin |
| 212581_x_at | GAPDH | glyceraldehyde-3-phosphate dehydrogenase |
| 212464_s_at | FN1 | fibronectin 1 |
| 212196_at | IL6ST | Interleukin 6 signal transducer (gp130, oncostatin M receptor) |
| 212195_at | IL6ST | Interleukin 6 signal transducer (gp130, oncostatin M receptor) |
| 211719_x_at | FN1 | fibronectin 1 |
| 211711_s_at | PTEN | phosphatase and tensin homolog (mutated in multiple advanced cancers 1) |
| 211696_x_at | HBB | hemoglobin, beta |
| 211651_s_at | LAMB1 | laminin, beta 1 |
| 211429_s_at | SERPINA1 | serpin peptidase inhibitor, clade A (alpha-1 antiproteinase, antitrypsin), member 1 |
| 211428_at | SERPINA1 | serpin peptidase inhibitor, clade A (alpha-1 antiproteinase, antitrypsin), member 1 |
| 211402_x_at | NR6A1 | nuclear receptor subfamily 6, group A, member 1 |
| 211176_s_at | PAX4 | paired box gene 4 |
| 211000_s_at | IL6ST | interleukin 6 signal transducer (gp130, oncostatin M receptor) |
| 210938_at | PDX1 | pancreatic and duodenal homeobox 1 |
| 210937_s_at | PDX1 | pancreatic and duodenal homeobox 1 |
| 210761_s_at | GRB7 | growth factor receptor-bound protein 7 |
| 210560_at | GBX2 | gastrulation brain homeobox 2 |
| 210495_x_at | FN1 | fibronectin 1 |
| 210392_x_at | NR6A1 | nuclear receptor subfamily 6, group A, member 1 |
| 210391_at | NR6A1 | nuclear receptor subfamily 6, group A, member 1 |
| 210311_at | FGF5 | fibroblast growth factor 5 |
| 210310_s_at | FGF5 | fibroblast growth factor 5 |
| 210287_s_at | FLT1 | fms-related tyrosine kinase 1 (vascular endothelial growth factor/vascular permeability factor receptor) |
| 210174_at | NR5A2 | nuclear receptor subfamily 5, group A, member 2 |
| 210103_s_at | FOXA2 | forkhead box A2 |
| 210002_at | GATA6 | GATA binding protein 6 |
| 209957_s_at | NPPA | natriuretic peptide precursor A |
| 209543_s_at | CD34 | CD34 molecule |
| 209116_x_at | HBB | hemoglobin, beta |
| 209073_s_at | NUMB | numb homolog (*Drosophila*) |
| 208983_s_at | PECAM1 | platelet/endothelial cell adhesion molecule (CD31 |
| 208982_at | PECAM1 | platelet/endothelial cell adhesion molecule (CD31 |
| 208981_at | PECAM1 | platelet/endothelial cell adhesion molecule (CD31 |
| 208559_at | PDX1 | pancreatic and duodenal homeobox 1 |
| 208500_x_at | FOXD3 | forkhead box D3 |
| 208378_x_at | FGF5 | fibroblast growth factor 5 |
| 208343_s_at | NR5A2 | nuclear receptor subfamily 5, group A, member 2 |
| 208337_s_at | NR5A2 | nuclear receptor subfamily 5, group A, member 2 |
| 208291_s_at | TH | tyrosine hydroxylase |
| 208286_x_at | LOC642559///LOC645682///POU5F1/// | POU domain, class 5, transcription factor 1 /// POU domain, class 5, transcription factor 1 pseudogene 1/// POU domain, class 5, transcription factor 1 pseudogene |
| 208275_x_at | UTF1 | undifferentiated embryonic cell transcription factor 1 |
| 207867_at | PAX4 | paired box gene 4 |
| 207742_s_at | NR6A1 | nuclear receptor subfamily 6, group A, member 1 |
| 207545_s_at | NUMB | numb homolog (*Drosophila*) |
| 207466_at | GAL | galanin |
| 207424_at | MYF5 | myogenic factor 5 |
| 207199_at | TERT | telomerase reverse transcriptase |
| 207062_at | IAPP | islet amyloid polypeptide |
| 206916_x_at | TAT | tyrosine aminotransferase |
| 206805_at | SEMA3A | sema domain, immunoglobulin domain (Ig), short basic domain, secreted, (semaphorin) 3A |
| 206783_at | FGF4 | fibroblast growth factor 4 (heparin secretory transforming protein 1, Kaposi sarcoma oncogene) |
| 206701_x_at | EDNRB | endothelin receptor type B |
| 206657_s_at | MYOD1 | myogenic differentiation 1 |
| 206647_at | HBZ | hemoglobin, zeta |
| 206598_at | INS | insulin |
| 206524_at | T | T, brachyury homolog (mouse) |
| 206422_at | GCG | glucagon |
| 206387_at | CDX2 | caudal type homeobox transcription factor 2 |
| 206286_s_at | TDGF1 ///TDGF3 | teratocarcinoma-derived growth factor 1 ///teratocarcinoma-derived growth factor 3, pseudogene |
| 206282_at | NEUROD1 | neurogenic differentiation 1 |
| 206269_at | GCM1 | glial cells missing homolog 1 (*Drosophila*) |
| 206268_at | LEFTY1 | left-right determination factor 1 |
| 206104_at | ISL1 | ISL1 transcription factor, LIM/homeodomain, (islet-1) |

TABLE 21-continued

Probe Sets ID, Gene Name, and Gene Description for Hierarchical Clustering Analysis (The International Stem Cell Initiative)
(DEAD peptide disclosed as SEQ ID NO: 65)
(DEAD peptide disclosed as SEQ ID NO: 65)

| Probe Set ID | Gene Name | Gene Description |
| --- | --- | --- |
| 206067_s_at | WT1 | Wilms tumor 1 |
| 206012_at | LEFTY2 | left-right determination factor 2 |
| 205900_at | KRT1 | keratin 1 (epidermolytic hyperkeratosis) |
| 205876_at | LIFR | leukemia inhibitory factor receptor alpha |
| 205850_s_at | GABRB3 | gamma-aminobutyric acid (GABA) A receptor, beta 3 |
| 205726_at | DIAPH2 | diaphanous homolog 2 (*Drosophila*) |
| 205646_s_at | PAX6 | paired box gene 6 (aniridia, keratitis) |
| 205603_s_at | DIAPH2 | diaphanous homolog 2 (*Drosophila*) |
| 205517_at | GATA4 | GATA binding protein 4 |
| 205387_s_at | CGB ///CGB5 ///CGB7 | chorionic gonadotropin, beta polypeptide /// chorionicgonadotropin, beta polypeptide 5 /// chorionicgonadotropin, beta polypeptide 7 |
| 205132_at | ACTC1 | actin, alpha, cardiac muscle 1 |
| 205051_s_at | KIT | v-kit Hardy-Zuckerman 4 feline sarcoma viral oncogene homolog |
| 204864_s_at | IL6ST | interleukin 6 signal transducer (gp130, oncostatin Mreceptor) |
| 204863_s_at | IL6ST | interleukin 6 signal transducer (gp130, oncostatin Mreceptor) |
| 204694_at | AFP | alpha-fetoprotein |
| 204677_at | CDH5 | cadherin 5, type 2, VE-cadherin (vascular epithelium) |
| 204535_s_at | REST | RE1-silencing transcription factor |
| 204406_at | FLT1 | fms-related tyrosine kinase 1 (vascular endothelial growth factor/vascular permeability factor receptor) |
| 204273_at | EDNRB | endothelin receptor type B |
| 204271_s_at | EDNRB | endothelin receptor type B |
| 204054_at | PTEN | phosphatase and tensin homolog (mutated in multiple advanced cancers 1) |
| 204053_x_at | PTEN | phosphatase and tensin homolog (mutated in multiple advanced cancers 1) |
| 203540_at | GFAP | glial fibrillary acidic protein |
| 202833_s_at | SERPINA1 | serpin peptidase inhibitor, clade A (alpha-1 antiproteinase, antitrypsin), member 1 |
| 202575_at | CRABP2 | cellular retinoic acid binding protein 2 |
| 202312_s_at | COL1A1 | collagen, type I, alpha 1 |
| 202311_s_at | COL1A1 | collagen, type I, alpha 1 |
| 202310_s_at | COL1A1 | collagen, type I, alpha 1 |
| 202222_s_at | DES | desmin |
| 201601_x_at | IFITM1 | interferon induced transmembrane protein 1 (9-27) |
| 201578_at | PODXL | podocalyxin-like |
| 201533_at | CTNNB1 | catenin (cadherin-associated protein), beta 1, 88 kDa |
| 201505_at | LAMB1 | laminin, beta 1 |
| 201315_x_at | IFITM2 | interferon induced transmembrane protein 2 (1-8D) |
| 201005_at | CD9 | CD9 molecule |
| 200771_at | LAMC1 | laminin, gamma 1 (formerly LAMB2) |
| 200770_s_at | LAMC1 | laminin, gamma 1 (formerly LAMB2) |
| 1570276_a_at | GATA4 | GATA binding protein 4 |
| 1562981_at | HBB | Hemoglobin, beta |
| 1561316_at | GABRB3 | Gamma-aminobutyric acid (GABA) A receptor, beta 3 |
| 1560469_at | NR5A2 | nuclear receptor subfamily 5, group A, member 2 |
| 1559921_at | PECAM1 | platelet/endothelial cell adhesion molecule (CD31 |
| 1558199_at | FN1 | fibronectin 1 |
| 1556499_s_at | COL1A1 | collagen, type I, alpha 1 |
| 1556057_s_at | NEUROD1 | neurogenic differentiation 1 |
| 1555271_a_at | TERT | telomerase reverse transcriptase |
| 1554777_at | ZFP42 | zinc finger protein 42 homolog (mouse) |
| 1554776_at | ZFP42 | zinc finger protein 42 homolog (mouse) |
| 1554411_at | CTNNB1 | catenin (cadherin-associated protein), beta 1, 88 kDa |
| 1553599_a_at | SYCP3 | synaptonemal complex protein 3 |
| 1553131_a_at | GATA4 | GATA binding protein 4 |
| 1552982_a_at | FGF4 | fibroblast growth factor 4 (heparin secretory transforming protein 1, Kaposi sarcoma oncogene) |

While preferred embodiments have been described herein, such embodiments are provided by way of example only. Numerous variations, changes, and substitutions are feasible. It should be understood that various alternatives to the embodiments of the methods and compositions described herein may be employed in practicing the invention. It is intended that the following claims define the scope of the invention and that methods and compositions within the scope of these claims and their equivalents be covered thereby.

What is claimed is:

1. A method for generating a human stem cell, comprising the steps of:
   (i) culturing human post-natal cells;
   (ii) introducing into the cultured human post-natal cells one or more retroviral vectors encoding Oct 3/4, Sox2, and Klf4; and
   (iii) culturing the human post-natal cells from step (ii) in a culture medium suitable for culturing human ES cells, in the presence of an inhibitor of Rho kinase and exogenous FGF-2, on fibroblast feeder cells or on an extracellular matrix;
   wherein the culturing is performed under conditions that maintain pluripotency and self-renewal, and wherein exogenous c-Myc is not introduced into the human post-natal cells.

2. The method of claim 1, wherein the inhibitor of Rho kinase is Y-27632 or HA-1077.

3. A method for generating a human stem cell, comprising the steps of:
   (i) culturing human post-natal cells;
   (ii) introducing into the cultured human post-natal cells one or more retroviral vectors encoding Oct 3/4, Sox2, and Klf4 and contacting the human post-natal cells with a histone deacetylase inhibitor; and
   (iii) culturing the human post-natal cells from step (ii) in a culture medium suitable for culturing human ES cells, in the presence of exogenous FGF-2, on fibroblast feeder cells or on an extracellular matrix;
   wherein the culturing is performed under conditions that maintain pluripotency and self-renewal, and wherein exogenous c-Myc is not introduced into the human post-natal cells.

* * * * *

UNITED STATES PATENT AND TRADEMARK OFFICE
CERTIFICATE OF CORRECTION

PATENT NO. : 8,211,697 B2
APPLICATION NO. : 12/157967
DATED : July 3, 2012
INVENTOR(S) : Sakurada et al.

It is certified that error appears in the above-identified patent and that said Letters Patent is hereby corrected as shown below:

In column 1 (page 5 item 56) at line 23, Under Other Publications, change "Maintencance" to --Maintenance--.

In column 1 (page 7 item 56) at line 5, Under Other Publications, change "'sternness'" to --'stemness'--.

In column 2 (page 7 item 56) at line 12, Under Other Publications, change "Es" to --ES--.

In column 2 at line 27, Change "TDGF 1," to --TDGF1,--.

In column 3 at line 2, Change "zfp42," to --Zfp42,--.

In column 3 at line 10, Change "zfp42," to --Zfp42,--.

In column 6 at line 43, Change "pluripotency," to --pluripotent,--.

In column 9 at line 43, Change ""24 m TeSr"" to --"2-4 m TeSR"--.

In column 9 at line 43, After "clone" change "24" to --2-4--.

In column 9 at line 44, Change ""24MEF"" to --"2-4MEF"--.

In column 9 at line 44, After "clone" change "24" to --2-4--.

In column 11 at line 37 (approx.), Change "cMyc" to --c Myc--.

In column 17 at line 61, Change "gentamycin" to --gentamycin.--.

In column 18 at line 6, Change "0.45-1M" to --0.45-µM--.

In column 18 at line 62, Change "mTeSR1" to --mTeSR1™--.

In column 23 at line 7, Change "[(2E)-5[3-[(" to --[(2E)-5-[3-[(--.

In column 25 at line 12, Change "Oct314" to --Oct3/4--.

In column 25 at line 21, Change "Mal." to --Mol.--.

In column 25 at line 30, Change "Oct314" to --Oct3/4--.

In column 25 at line 60, Change "KIF4" to --Klf4--.

In column 30 at line 35, Change "13(34)" to --13(3-4)--.

Signed and Sealed this
Nineteenth Day of March, 2013

Teresa Stanek Rea
*Acting Director of the United States Patent and Trademark Office*

CERTIFICATE OF CORRECTION (continued)
U.S. Pat. No. 8,211,697 B2

In column 31 at line 27, Change "iF-PTD" to --IF-PTD--.

In column 32 at line 2, Change "3/4Oct3/4" to --Oct3/4--.

In column 32 at line 42, Change "Nat'l" to --Natl.--.

In column 36 at line 1, Change "(POU/DNA BindinG Domain of Human Oct3/4) SEQ ID NO:7" to --SEQ ID NO:7 (POU/DNA Binding Domain of Human Oct 3/4)--.

In column 37 at line 45, Change "FDEAKRLRALHMKEHPDYKYRPRRK" to --FIDEAKRLRALHMKEHPDYKYRPRRK--.

In column 38 at line 45 (approx.), Change "PVYWPPQQPQPPGGGLMKGFVLKASLSAPGSEKGSPDGSH" to --PVYIPPQQPQPPGGGLMGKFVLKASLSAPGSEYSPDGSH--.

In column 38 at line 52 (approx.), Change "SSHLKAHLRTHTGEKPYHCDWDGCGWKFARSDELTRHYRKHTGHRPFQGQ" to --SSHLKAHLRTHTGEKPYHCDWDGCGWKFARSDELTRHYRKHTGHRPFQCQ--.

In column 38 at line 54 (approx.), Change "KGDRAFSRSDHLALHMKRHF" to --KCDRAFSRSDHLALHMKRHF--.

In column 41 at line 19, Change "3/4Oct3/4" to --Oct3/4--.

In column 41 at line 21, Change "3/4Oct3/4" to --Oct3/4--.

In column 43 at line 37, Change "Indolyphosphate" to --Indolyophosphate--.

In column 43 at line 46, Change "Sal14," to --Sall4,--.

In column 44 at line 30, Change "Thy l" to --Thy-l--.

In column 45 at line 24, Change "karotype" to --karyotype--.

In column 47 at line 18, Change "SSEA4," to --SSEA-4,--.

In column 48 at line 13, Change "Genes." to --Genes--.

In column 48 at line 57, Change "24" to --2-4--.

In column 51 at line 6, Change "3140" to --31-40--.

In column 51 at line 9, After "679" insert --.--.

In column 52 at line 28, Change "BMP4" to --BMP-4--.

In column 57 at line 13, Change "Md.)/" to --Md.).--.

In column 59 at line 66, Change "I step" to --1 step--.

In column 60 at line 22, Change "m l," to --ml,--.

In column 60 at line 22, Change "g l," to --gl,--.

In column 60 at line 23, Change "m l," to --ml,--.

In column 60 at line 23, Change "m l," to --ml,--.

In column 60 at line 24, Change "s l." to --sl.--.

In column 71 at line 38, Change "I step" to --1 step--.

CERTIFICATE OF CORRECTION (continued)
U.S. Pat. No. 8,211,697 B2

In column 73 at line 33, Change "24" to --2-4--.

In column 74 at line 1, Change "I step" to --1 step--.

In column 74 at line 20, Change "SSEA4," to --SSEA-4,--.

In column 74 at line 26, Change "SSEA4" to --SSEA-4--.

In column 74 at line 40, After "expression" insert --.--.

In column 74 at line 42, Change "Sal14," to --Sall4,--.

In column 74 at line 51, Change "CYP26 µl" to --CYP26Al--.

In column 75 at line 55, Change "24" to --2-4--.

In column 75 at line 56, Change ""24MEF"" to --"2-4MEF"--.

In column 75 at line 56, Change "24" to --2-4--.

In column 76 at line 44, Change "24" to --2-4--.

In column 77 at line 1, Change "24" to --2-4--.

In column 77 at line 65, Change "KIF4" to --Klf4--.

In column 79 at line 8, Change "SSEA4," to --SSEA-4,--.

In column 81 at line 43, Change "iPS-24" to --iPS-2-4--.

In column 81 at line 53, Change "iPS-24" to --iPS-2-4--.

In column 82 at line 14, Change "g l," to --gl,--.

In column 82 at line 15, Change "m l," to --ml,--.

In column 82 at line 15, Change "s l," to --sl,--.

In column 82 at line 16, Change "s l," to --sl,--.

In column 82 at line 16, Change "g l," to --gl,--.

In column 82 at line 17, Change "m l," to --ml,--.

In column 82 at line 17, Change "m l," to --ml,--.

In column 82 at line 18, Change "m l," to --ml,--.

In column 82 at line 18, Change "m l )" to --ml)--.

In column 82 at line 23, Change "24" to --2-4--.

In column 82 at line 24, Change "24" to --2-4--.

In column 83 at line 29, Change "g l," to --gl,--.

In column 83 at line 30, Change "m l," to --ml,--.

In column 83 at line 30, Change "s l," to --sl,--.

In column 83 at line 31, Change "s l," to --sl,--.

In column 83 at line 31, Change "g l," to --gl,--.

In column 83 at line 32, Change "m l," to --ml,--.

In column 83 at line 32, Change "m l," to --ml,--.

In column 83 at line 33, Change "m l," to --ml,--.

CERTIFICATE OF CORRECTION (continued)
U.S. Pat. No. 8,211,697 B2

In column 83 at line 33, Change "m 1 )" to --ml)--.

In column 90 at line 34, Change "GGRRARRRRR" to --GGRRARRRRRR--.

In column 92 at line 6, Change "l g/mL" to --lg/mL--.

In column 93 at line 1, Change "(Oct314," to --(Oct3/4,--.

In column 93 at line 24, Change "Example 28" to --Example 30--.

In column 94 at line 59, Change "Table I" to --Table 1--.

In column 97-98 at line 30 (Table 4), Change "CGGGACTATGGTTGCTGAGT" to --CGGGACTATGGTTGCTGACT--.

In column 99 at line 2, Change "24" to --2-4--.

In column 103 at line 3, Change "5-249," to --5-2-49,--.

In column 103 at line 52, Change "24" to --2-4--.

In column 103 at line 52, Change "24" to --2-4--.

In column 103 at line 54, Change "24" to --2-4--.

In column 111-112 at line 35, Change "[Pantroglodytes]" to --[Pan troglodytes]--.

In column 125-126 at line 18, Change "[Pantroglodytes]" to --[Pan troglodytes]--.

In column 143-144 at line 42, Change "[Pantroglodytes]" to --[Pan troglodytes]--.

In column 259-260 (Table 21) at line 3, Below "(DEAD peptide disclosed as SEQ 10 NO:65)" delete ""(DEAD peptide disclosed as SEQ 10 NO: 65)".

In column 261-262 (Table 21) at line 3, Below "(DEAD peptide disclosed as SEQ 10 NO:65)" delete ""(DEAD peptide disclosed as SEQ 10 NO: 65)".

In column 261-262 (Table 21) at line 10, Change "sex" to --(sex--.

In column 263-264 (Table 21) at line 3, Below "(DEAD peptide disclosed as SEQ 10 NO:65)" delete ""(DEAD peptide disclosed as SEQ 10 NO: 65)".

In column 265-266 (Table 21) at line 3, Below "(DEAD peptide disclosed as SEQ 10 NO:65)" delete ""(DEAD peptide disclosed as SEQ 10 NO: 65)".

```
                        SEQUENCE LISTING

<160> NUMBER OF SEQ ID NOS: 67

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Gly Arg Lys Lys Arg Arg Gln Arg Arg Arg
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Lys Lys Arg Arg Gln Arg Arg
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ala Arg Ala Ala Ala Arg Gln Ala Arg Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr His Arg Leu Pro Arg Arg Arg Arg Arg Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Arg Arg Ala Arg Arg Arg Arg Arg Arg
1               5                   10
```

```
<210> SEQ ID NO 6
<211> LENGTH: 360
<212> TYPE: PRT
<213> ORGANISM: Homo sapiens

<400> SEQUENCE: 6

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 7
```

```
<211> LENGTH: 153
<212> TYPE: PRT
<213> ORGANISM: Homo sapiens

<400> SEQUENCE: 7

Asp Ile Lys Ala Leu Gln Lys Glu Leu Glu Gln Phe Ala Lys Leu Leu
1               5                   10                  15

Lys Gln Lys Arg Ile Thr Leu Gly Tyr Thr Gln Ala Asp Val Gly Leu
            20                  25                  30

Thr Leu Gly Val Leu Phe Gly Lys Val Phe Ser Gln Thr Thr Ile Cys
        35                  40                  45

Arg Phe Glu Ala Leu Gln Leu Ser Phe Lys Asn Met Cys Lys Leu Arg
50                  55                  60

Pro Leu Leu Gln Lys Trp Val Glu Glu Ala Asp Asn Asn Glu Asn Leu
65                  70                  75                  80

Gln Glu Ile Cys Lys Ala Glu Thr Leu Val Gln Ala Arg Lys Arg Lys
                85                  90                  95

Arg Thr Ser Ile Glu Asn Arg Val Arg Gly Asn Leu Glu Asn Leu Phe
            100                 105                 110

Leu Gln Cys Pro Lys Pro Thr Leu Gln Gln Ile Ser His Ile Ala Gln
        115                 120                 125

Gln Leu Gly Leu Glu Lys Asp Val Val Arg Val Trp Phe Cys Asn Arg
130                 135                 140

Arg Gln Lys Gly Lys Arg Ser Ser Ser
145                 150

<210> SEQ ID NO 8
<211> LENGTH: 317
<212> TYPE: PRT
<213> ORGANISM: Homo sapiens

<400> SEQUENCE: 8

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190
```

```
Gln Met Gln Pro Met His Arg Tyr Asp Val Ser Ala Leu Gln Tyr Asn
    195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
                260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315

<210> SEQ ID NO 9
<211> LENGTH: 76
<212> TYPE: PRT
<213> ORGANISM: Homo sapiens

<400> SEQUENCE: 9

Arg Val Lys Arg Pro Met Asn Ala Phe Met Val Trp Ser Arg Gly Gln
1               5                   10                  15

Arg Arg Lys Met Ala Gln Glu Asn Pro Lys Met His Asn Ser Glu Ile
            20                  25                  30

Ser Lys Arg Leu Gly Ala Glu Trp Lys Leu Leu Ser Glu Thr Glu Lys
        35                  40                  45

Arg Pro Phe Ile Asp Glu Ala Lys Arg Leu Arg Ala Leu His Met Lys
    50                  55                  60

Glu His Pro Asp Tyr Lys Tyr Arg Pro Arg Arg Lys
65                  70                  75

<210> SEQ ID NO 10
<211> LENGTH: 470
<212> TYPE: PRT
<213> ORGANISM: Homo sapiens

<400> SEQUENCE: 10

Met Ala Val Ser Asp Ala Leu Leu Pro Ser Phe Ser Thr Phe Ala Ser
1               5                   10                  15

Gly Pro Ala Gly Arg Glu Lys Thr Leu Arg Gln Ala Gly Ala Pro Asn
            20                  25                  30

Asn Arg Trp Arg Glu Glu Leu Ser His Met Lys Arg Leu Pro Pro Val
        35                  40                  45

Leu Pro Gly Arg Pro Tyr Asp Leu Ala Ala Thr Val Ala Thr Asp
    50                  55                  60

Leu Glu Ser Gly Gly Ala Gly Ala Ala Cys Gly Gly Ser Asn Leu Ala
65                  70                  75                  80

Pro Leu Pro Arg Arg Glu Thr Glu Glu Phe Asn Asp Leu Leu Asp Leu
            85                  90                  95

Asp Phe Ile Leu Ser Asn Ser Leu Thr His Pro Pro Glu Ser Val Ala
            100                 105                 110

Ala Thr Val Ser Ser Ser Ala Ser Ala Ser Ser Ser Ser Pro Ser
        115                 120                 125

Ser Ser Gly Pro Ala Ser Ala Pro Ser Thr Cys Ser Phe Thr Tyr Pro
```

```
                130             135             140
Ile Arg Ala Gly Asn Asp Pro Gly Val Ala Pro Gly Gly Thr Gly Gly
145                 150                 155                 160

Gly Leu Leu Tyr Gly Arg Glu Ser Ala Pro Pro Thr Ala Pro Phe
                165                 170                 175

Asn Leu Ala Asp Ile Asn Asp Val Ser Pro Gly Gly Phe Val Ala
            180                 185                 190

Glu Leu Leu Arg Pro Glu Leu Asp Pro Val Tyr Ile Pro Gln Gln
                195                 200                 205

Pro Gln Pro Pro Gly Gly Leu Met Gly Lys Phe Val Leu Lys Ala
        210                 215                 220

Ser Leu Ser Ala Pro Gly Ser Glu Tyr Gly Ser Pro Ser Val Ile Ser
225                 230                 235                 240

Val Ser Lys Gly Ser Pro Asp Gly Ser His Pro Val Val Ala Pro
                    245                 250                 255

Tyr Asn Gly Gly Pro Pro Arg Thr Cys Pro Lys Ile Lys Gln Glu Ala
                260                 265                 270

Val Ser Ser Cys Thr His Leu Gly Ala Gly Pro Pro Leu Ser Asn Gly
            275                 280                 285

His Arg Pro Ala Ala His Asp Phe Pro Leu Gly Arg Gln Leu Pro Ser
            290                 295                 300

Arg Thr Thr Pro Thr Leu Gly Leu Glu Glu Val Leu Ser Ser Arg Asp
305                 310                 315                 320

Cys His Pro Ala Leu Pro Leu Pro Pro Gly Phe His Pro His Pro Gly
                    325                 330                 335

Pro Asn Tyr Pro Ser Phe Leu Pro Asp Gln Met Gln Pro Gln Val Pro
                340                 345                 350

Pro Leu His Tyr Gln Glu Leu Met Pro Pro Gly Ser Cys Met Pro Glu
            355                 360                 365

Glu Pro Lys Pro Lys Arg Gly Arg Arg Ser Trp Pro Arg Lys Arg Thr
370                 375                 380

Ala Thr His Thr Cys Asp Tyr Ala Gly Cys Gly Lys Thr Tyr Thr Lys
385                 390                 395                 400

Ser Ser His Leu Lys Ala His Leu Arg Thr His Thr Gly Glu Lys Pro
                405                 410                 415

Tyr His Cys Asp Trp Asp Gly Cys Gly Trp Lys Phe Ala Arg Ser Asp
                420                 425                 430

Glu Leu Thr Arg His Tyr Arg Lys His Thr Gly His Arg Pro Phe Gln
            435                 440                 445

Cys Gln Lys Cys Asp Arg Ala Phe Ser Arg Ser Asp His Leu Ala Leu
450                 455                 460

His Met Lys Arg His Phe
465                 470

<210> SEQ ID NO 11
<211> LENGTH: 88
<212> TYPE: PRT
<213> ORGANISM: Homo sapiens

<400> SEQUENCE: 11

Lys Arg Thr Ala Thr His Thr Cys Asp Tyr Ala Gly Cys Gly Lys Thr
1               5                   10                  15

Tyr Thr Lys Ser Ser His Leu Lys Ala His Leu Arg Thr His Thr Gly
                20                  25                  30

Glu Lys Pro Tyr His Cys Asp Trp Asp Gly Cys Gly Trp Lys Phe Ala
```

```
                35                  40                  45
Arg Ser Asp Glu Leu Thr Arg His Tyr Arg Lys His Thr Gly His Arg
 50                  55                  60

Pro Phe Gln Cys Gln Lys Cys Asp Arg Ala Phe Ser Arg Ser Asp His
 65                  70                  75                  80

Leu Ala Leu His Met Lys Arg His
                 85

<210> SEQ ID NO 12
<211> LENGTH: 454
<212> TYPE: PRT
<213> ORGANISM: Homo sapiens

<400> SEQUENCE: 12

Met Asp Phe Phe Arg Val Val Glu Asn Gln Gln Pro Pro Ala Thr Met
 1               5                  10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
                35                  40                  45

Gln Gln Gln Gln Ser Glu Leu Gln Pro Pro Ala Pro Ser Glu Asp Ile
 50                  55                  60

Trp Lys Lys Phe Glu Leu Leu Pro Thr Pro Pro Leu Ser Pro Ser Arg
 65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
                115                 120                 125

Ser Phe Ile Cys Asp Pro Asp Asp Glu Thr Phe Ile Lys Asn Ile Ile
130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
                180                 185                 190

Leu Gln Asp Leu Ser Ala Ala Ala Ser Glu Cys Ile Asp Pro Ser Val
                195                 200                 205

Val Phe Pro Tyr Pro Leu Asn Asp Ser Ser Ser Pro Lys Ser Cys Ala
210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
                260                 265                 270

Asp Glu Glu Glu Ile Asp Val Val Ser Val Glu Lys Arg Gln Ala Pro
                275                 280                 285

Gly Lys Arg Ser Glu Ser Gly Ser Pro Ser Ala Gly Gly His Ser Lys
                290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
```

```
                    325                 330                 335
Ala Lys Arg Val Lys Leu Asp Ser Val Arg Val Leu Arg Gln Ile Ser
                340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
        370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 13
<211> LENGTH: 85
<212> TYPE: PRT
<213> ORGANISM: Homo sapiens

<400> SEQUENCE: 13

Lys Arg Arg Thr His Asn Val Leu Glu Arg Gln Arg Arg Asn Glu Leu
1               5                   10                  15

Lys Arg Ser Phe Phe Ala Leu Arg Asp Gln Ile Pro Glu Leu Glu Asn
            20                  25                  30

Asn Glu Lys Ala Pro Lys Val Val Ile Leu Lys Lys Ala Thr Ala Tyr
        35                  40                  45

Ile Leu Ser Val Gln Ala Glu Glu Gln Lys Leu Ile Ser Glu Glu Asp
    50                  55                  60

Leu Leu Arg Lys Arg Arg Glu Gln Leu Lys His Lys Leu Glu Gln Leu
65                  70                  75                  80

Arg Asn Ser Cys Ala
                85

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcagccctgg gtctccagat ctggccagc                                   29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtggccggg gccagggcta gccacgtgc                                   29

<210> SEQ ID NO 16
```

```
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
                35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
            115                 120                 125

Gly Gly Leu Leu Ala Pro Gly Gly Asn Ser Met Ala Ser Gly Val Gly
130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Ser Thr Thr Ala Pro Ile Thr Asp Val
            180                 185                 190

Ser Leu Gly Asp Glu Leu Arg Leu Asp Gly Glu Val Asp Met Thr
        195                 200                 205

Pro Ala Asp Ala Leu Asp Asp Phe Asp Leu Glu Met Leu Gly Asp Val
    210                 215                 220

Glu Ser Pro Ser Pro Gly Met Thr His Asp Pro Val Ser Tyr Gly Ala
225                 230                 235                 240

Leu Asp Val Asp Asp Phe Glu Phe Glu Gln Met Phe Thr Asp Ala Leu
                245                 250                 255

Gly Ile Asp Asp Phe Gly Gly
            260

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Lys Lys Lys Lys Lys Lys Lys
1               5

<210> SEQ ID NO 18
<211> LENGTH: 12
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 18
saccacgtgg ts                                                              12

<210> SEQ ID NO 19
<211> LENGTH: 148
<212> TYPE: PRT
<213> ORGANISM: Human herpesvirus 2

<400> SEQUENCE: 19

Thr Lys Thr Leu Met Lys Lys Asp Lys Tyr Thr Leu Pro Gly Gly Leu
1               5                   10                  15

Leu Ala Pro Gly Gly Asn Ser Met Ala Ser Gly Val Gly Val Gly Ala
            20                  25                  30

Gly Leu Gly Ala Gly Val Asn Gln Arg Met Asp Ser Tyr Ala His Met
        35                  40                  45

Asn Gly Trp Ser Asn Gly Ser Tyr Ser Met Met Gln Asp Gln Leu Gly
    50                  55                  60

Tyr Pro Gln His Ser Thr Thr Ala Pro Ile Thr Asp Val Ser Leu Gly
65                  70                  75                  80

Asp Glu Leu Arg Leu Asp Gly Glu Val Asp Met Thr Pro Ala Asp
                85                  90                  95

Ala Leu Asp Asp Phe Asp Leu Glu Met Leu Gly Asp Val Glu Ser Pro
            100                 105                 110

Ser Pro Gly Met Thr His Asp Pro Val Ser Tyr Gly Ala Leu Asp Val
        115                 120                 125

Asp Asp Phe Glu Phe Glu Gln Met Phe Thr Asp Ala Leu Gly Ile Asp
    130                 135                 140

Asp Phe Gly Gly
145

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agtctggctt atatccaaca cttcg                                                25

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gactttgctt tccttggtca gg                                                   22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 22
tacctcagcc tccagcagat                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgcgtcacac cattgctatt                                              20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agccagtctc accttcaacc gc                                           22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggagtagcag agggaggccg                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 aaacccagc acatcaactc                                               20

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtcattccct gggtggttc                                               19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
```

-continued ttggagtgca atggtgtgat                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tctgttcaca caggctccag                                              20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggcgtccgcg ggaatgtact tc                                           22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tggcttaggg gtggtctggc c                                            21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcagcgacca gtcctccgac t                                            21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aacgtgggga aggcctgtgc                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acagaacctg ctgcctgaat                                              20

```
<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agaaatgcct gaggaaagca                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cttgacaatc gagtggctga                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcatccgtgg tgtagccata                                                    20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aacctgcacg actcctcgca ca                                                 22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aggatgcgca tggcgattcg                                                    20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gagaaggaga agctggagca                                                    20

<210> SEQ ID NO 41
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aatagaaccc ccagggtgag                                                    20

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agtagacggc atcgcagctt gg                                                 22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggaagcttag ccaggtccga gg                                                 22

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caggagaacc ccaagatgc                                                     19

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gcagccgctt agcctcg                                                       17

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acactgcccc tctcacacat                                                    20

<210> SEQ ID NO 47
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 47
cgggactatg gttgctgact                                                    20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
accctgggtc ttgaggaagt                                                    20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgatcgtct tcccctcttt                                                    20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50 ctcacccetta ccgagtcggc g                                                 21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcagctgggg cacctgaacc                                                    20

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tccagcttgt acctgcagga tctga                                              25

<210> SEQ ID NO 53
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 53
cctccagcag aaggtgatcc agact                                          25

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agtagacggc atcgcagctt gg                                             22

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cctccagcag aaggtgatcc agact                                          25

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aggaagagag ggaatttaag gtgtatgtat tttttatttt                          40

<210> SEQ ID NO 57
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cagtaatacg actcactata gggagaaggc tataacccac ccctataatc ccaata        56

<210> SEQ ID NO 58
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aggaagagag gttaggttgg ttttaaattt ttgat                               35

<210> SEQ ID NO 59
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 59
cagtaatacg actcactata gggagaaggc ttttataata aaaactctat caccttaaac    60
c                                                                   61

<210> SEQ ID NO 60
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aggaagagag tagtagggat tttttggatt ggttt                               35

<210> SEQ ID NO 61
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagtaatacg actcactata gggagaaggc taaaactttt cccccactct tatattac     58

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aggaagagag ggtaataaag tgagattttg ttttaaaaa                           39

<210> SEQ ID NO 63
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cagtaatacg actcactata gggagaaggc tccacccact aaccttaacc tctaa        55

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Glu Ala His
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 65

Asp Glu Ala Asp
1

<210> SEQ ID NO 66
<211> LENGTH: 20
<212> TYPE: PRT
<213> ORGANISM: Homo sapiens

<400> SEQUENCE: 66

Met Gly Ala Pro Val Ile Leu Phe Ser Cys Thr Asn Gln His Tyr Trp
1               5                   10                  15

Asp Glu Lys Arg
            20

<210> SEQ ID NO 67
<211> LENGTH: 16
<212> TYPE: DNA
<213> ORGANISM: Homo sapiens

<400> SEQUENCE: 67
cttttgcatt acaatg                                                   16
```